United States Patent
Xu et al.

(10) Patent No.: US 10,035,790 B2
(45) Date of Patent: Jul. 31, 2018

(54) RORγ MODULATORS

(71) Applicants: BRISTOL-MYERS SQUIBB COMPANY, Princeton, NJ (US); EXELIXIS, INC., South San Francisco, CA (US)

(72) Inventors: Wei Xu, Danville, CA (US); Yong Wang, Foster City, CA (US); Sunghoon Ma, Foster City, CA (US); Elena S. Koltun, Foster City, CA (US); Byung Gyu Kim, Daejeon (KR); Joon Won Jeong, Belmont, CA (US); T. G. Murali Dhar, Princeton, NJ (US); Lynne Canne Bannen, Pacifica, CA (US)

(73) Assignees: Exelixis, Inc., Alameda, CA (US); Bristol-Myers Squibb Co., New York, NY (US)

( * ) Notice: Subject to any disclaimer, the term of this patent is extended or adjusted under 35 U.S.C. 154(b) by 0 days.

(21) Appl. No.: 14/436,355

(22) PCT Filed: Oct. 17, 2013

(86) PCT No.: PCT/US2013/065480
§ 371 (c)(1),
(2) Date: Apr. 16, 2015

(87) PCT Pub. No.: WO2014/062938
PCT Pub. Date: Apr. 24, 2014

(65) Prior Publication Data
US 2015/0266856 A1    Sep. 24, 2015

Related U.S. Application Data

(60) Provisional application No. 61/716,244, filed on Oct. 19, 2012, provisional application No. 61/716,233, filed on Oct. 19, 2012.

(51) Int. Cl.
| | | |
|---|---|---|
| C07D 403/04 | (2006.01) | |
| C07D 403/14 | (2006.01) | |
| C07D 401/04 | (2006.01) | |
| C07D 401/14 | (2006.01) | |
| C07D 413/14 | (2006.01) | |
| C07D 405/14 | (2006.01) | |
| C07D 417/14 | (2006.01) | |

(52) U.S. Cl.
CPC ......... *C07D 403/04* (2013.01); *C07D 401/04* (2013.01); *C07D 401/14* (2013.01); *C07D 403/14* (2013.01); *C07D 405/14* (2013.01); *C07D 413/14* (2013.01); *C07D 417/14* (2013.01)

(58) Field of Classification Search
CPC .. C07D 403/04; C07D 403/14; C07D 401/04; C07D 401/14; C07D 413/14; C07D 405/14; C07D 417/14
See application file for complete search history.

(56) References Cited

FOREIGN PATENT DOCUMENTS

| EP | 2 511 263 A1 | 10/2012 |
|---|---|---|
| WO | 2011/018415 * | 2/2011 |
| WO | WO 2011112263 A1 | 9/2011 |
| WO | WO 2012028100 A1 | 3/2012 |
| WO | WO 2012100732 A1 | 8/2012 |
| WO | WO 2012100734 A1 | 8/2012 |

OTHER PUBLICATIONS

International Search Report of PCT/US2013/065480, dated Dec. 20, 2013.

* cited by examiner

*Primary Examiner* — Alexander R Pagano
*Assistant Examiner* — Ebenezer O Sackey
(74) *Attorney, Agent, or Firm* — Honigman Miller Schwartz & Cohn LLP; Heidi M. Berven; Jonathan P. O'Brien

(57) ABSTRACT

Described are RORy modulators of the formula (I), and N-oxides thereof, and pharmaceutically acceptable salts thereof, and solvates and hydrates thereof, wherein $R^1$, $R^2$, $R^3$, $R^4$, $R^5$, $R^6$, $R^a$, x, y, L, G, Z, the bond denoted by "q", the ring system denoted by "A" and the ring system denoted by "B" are defined herein. Also provided are pharmaceutical compositions comprising the same. Such compounds and compositions are useful in methods for modulating RORy activity in a cell and methods for treating a subject suffering from a disease or disorder in which the subject would therapeutically benefit from modulation of RORy activity, for example, autoimmune and/or inflammatory disorders.

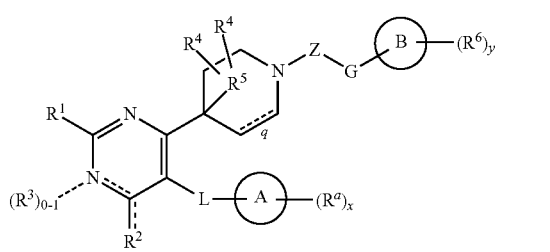

13 Claims, No Drawings

RORγ MODULATORS

CROSS-REFERENCE TO RELATED APPLICATIONS

This application is a 35 U.S.C. §371(c) U.S. National Phase filing of International Application Serial No. PCT/US2013/065480, filed Oct. 17, 2013, which claims the benefit of priority of U.S. Provisional Application Serial No. 61/716,244, filed Oct. 19, 2012, and U.S. Provisional Application Serial No. 61/716,233, filed Oct. 19, 2012, the entire contents of each of the aforementioned disclosures are incorporated herein by reference in their entirety.

BACKGROUND OF THE INVENTION

Field of the Invention

This invention relates to modulators of the retinoid-related orphan receptor RORγ and methods for using such modulators. The compounds described herein can be particularly useful for diagnosing, preventing, or treating a variety of diseases and disorders in humans and animals. Exemplary disorders include psoriasis, arthritis, asthma, inflammatory bowel disease and multiple sclerosis.

Summary of the Related Art

The retinoid-related orphan receptors RORα, RORβ, and RORγ play an important role in numerous biological processes including organ development, immunity, metabolism, and circadian rhythms. See, for example, Dussault et al. in *Mech. Dev.* (1998) vol. 70, 147-153; Andre et al. in *EMBO J.* (1998) vol. 17, 3867-3877; Sun et al. in *Science* (2000) vol. 288, 2369-2373; and Jetten in *Nucl. Recept. Signal.* (2009) vol. 7, 1-32.

RORγ is expressed in several tissues including the thymus, kidney, liver, and muscle. Two isoforms of RORγ have been identified: RORγ1 and RORγ2 (also known, respectively, as RORγ and RORγt). See, for example, Hirose et al. in *Biochem. Biophys. Res. Commun.* (1994) vol. 205, 1976-1983; Oritz et al. in *Mol. Endocrinol.* (1995) vol. 9, 1679-1691; and He et al. in *Immunity* (1998) vol. 9, 797-806. Expression of RORγt is restricted to lymphoid cell types including CD4$^+$CD8$^+$ thymocytes, IL-17 producing T helper (Th17) cells, lymphoid tissue inducer (LTi) cells, and γδ cells. RORγt is essential for the development of lymph nodes and Peyer's patches and for the normal differentiation of Th17, γδ, and LTi cells. See, for example, Sun et al. in *Science* (2000) vol. 288, 2369-2373; Ivanov et al. in *Cell* (2006) vol. 126, 1121-1133; Eberl et al. in *Nat. Immunol.* (2004) vol. 5, 64-73; Ivanov et al. in *Semin. Immunol.* (2007) vol. 19, 409-417; and Cua and Tato in *Nat. Rev. Immunol.* (2010) vol. 10, 479-489.

Proinflammatory cytokines such as IL-17A (also referred to as IL-17), IL-17F, and IL-22 produced by Th17 cells and other RORγ+ lymphocytes activate and direct the immune response to extracelluar pathogens. See, for example, Ivanov et al. in *Semin. Immunol.* (2007) vol. 19: 409-417; and Marks and Craft in *Semin. Immunol.* (2009) vol. 21, 164-171. RORγ directly regulates IL-17 transcription and disruption of RORγ in mice attenuates IL-17 production. See, for example, Ivanov et al. in *Cell* (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), and asthma. See, for example, Lock et al. in *Nat. Med.* (2002) vol. 8, 500-508; Tzartos et al. in *Am. J. Pathol.* (2008) vol. 172, 146-155; Kotake et al. in *J. Clin. Invest.* (1999) vol. 103, 1345-1352; Kirkham et al. in *Arthritis Rheum.* (2006) vol. 54, 1122-1131; Lowes et al. in *J. Invest. Dermatol.* (2008) vol. 128, 1207-1211; Leonardi et al. in *N. Engl. J. Med.* (2012) vol. 366, 1190-1199; Fujino et al. in *Gut* (2003) vol. 52, 65-70; Seiderer et al. in *Inflamm. Bowel Dis.* (2008) vol. 14, 437-445; Wong et al. in *Clin. Exp. Immunol.* (2001) vol. 125, 177-183; and Agache et al. in *Respir. Med.* (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in *Ann. N.Y. Acad. Sci.* (2011) vol. 1217, 60-76.

Disruption of RORγ in mice also attenuates disease progression or severity in animal models of autoimmunity and inflammation including experimental autoimmune encephalomyelitis (EAE), imiquimod induced psoriasis, colitis, and allergic airway disease. See, for example, Ivanov et al. in *Cell* (2006) vol. 126, 1121-1133; Yang et al. in *Immunity* (2008) vol. 28, 29-39; Pantelyushin et al. in *J. Clin. Invest.* (2012) vol. 122, 2252-2256; Leppkes et al. in *Gastroenterology* (2009) vol. 136, 257-267; and Tilley et al. in *J. Immunol.* (2007) vol. 178, 3208-3218.

Each of the references in this Background section is hereby incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

SUMMARY OF THE INVENTION

In one aspect, the invention comprises compounds of the formula (I),

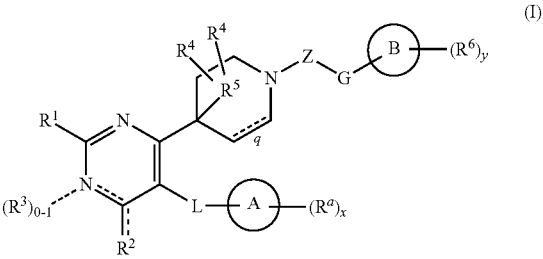

or N-oxides, pharmaceutically acceptable salts, solvates and/or hydrates thereof, wherein $R^1$, $R^2$, $R^3$, $R^4$, $R^5$, $R^6$, $R^a$, x, y, G, L, Z, the bond denoted by "q", the ring system denoted by "A" and the ring system denoted by "B" are defined herein. The invention includes stereoisomeric forms of the compounds of formula I, including stereoisomerically-pure, scalemic and racemic forms.

In another aspect, the invention comprises pharmaceutical compositions comprising a compound according to formula (I), stereoisomeric form, N-oxide, pharmaceutically acceptable salt, solvate or hydrate as described herein, and a pharmaceutically acceptable carrier, excipient, or diluent.

In another aspect, the invention comprises methods for antagonizing RORγ in a cell comprising contacting the cell with an effective amount of a compound according to formula (I), stereoisomeric form, N-oxide, pharmaceutically acceptable salt, solvate or hydrate as described herein. This aspect may be conducted in vitro or in vivo.

In another aspect, the invention comprises methods for treating a subject suffering from a disease or disorder modulated by RORγ, the method comprising administering to a subject a therapeutically effective amount of compound according to formula (I), stereoisomeric form, N-oxide, pharmaceutically acceptable salt, solvate, hydrate or pharmaceutical composition as described herein.

In another aspect, the invention comprises a method for treating a disease or disorder selected from an inflammatory disease or disorder, an autoimmune disease or disorder, an allergic disease or disorder, a metabolic disease or disorder, and/or cancer in a subject, the method comprising administering to the subject a therapeutically effective amount of compound according to formula (I), or a stereoisomeric form, N-oxide, pharmaceutically acceptable salt, solvate, hydrate or pharmaceutical composition thereof as described herein.

DETAILED DESCRIPTION OF THE INVENTION

In one aspect, the invention comprises compounds of formula (I),

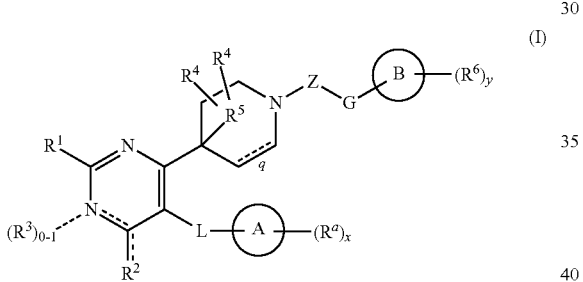

(I)

and stereoisomeric forms thereof, and N-oxides thereof, and pharmaceutically acceptable salts thereof, and solvates and hydrates thereof, wherein $R^1$ is selected from the group consisting of —H, -halogen, —CN, —NO$_2$, —OH, —O—(C$_1$-C$_4$)alkyl, —O—(C$_1$-C$_4$)fluoroalkyl, —SH, —S—(C$_1$-C$_4$)alkyl, —NH$_2$, —NH—(C$_1$-C$_4$)alkyl, —NH—(C$_1$-C$_4$)fluoroalkyl, —N((C$_1$-C$_4$)alkyl)$_2$, —N((C$_1$-C$_4$)fluoroalkyl)$_2$, —NH—(C$_3$-C$_6$)cycloalkyl, —O—C(O)—(C$_1$-C$_4$)alkyl, —S—C(O)—(C$_1$-C$_4$)alkyl, —NH—C(O)—(C$_1$-C$_4$)alkyl, —N((C$_1$-C$_4$)alkyl)-C(O)—(C$_1$-C$_4$)alkyl, —S(O)$_{1-2}$H, —S(O)$_{1-2}$(C$_1$-C$_4$)alkyl, —S(O)$_{1-2}$OH, —S(O)$_{1-2}$O(C$_1$-C$_4$)alkyl, —S(O)$_{1-2}$NH$_2$, —S(O)$_{1-2}$NH(C$_1$-C$_4$)alkyl, —S(O)$_{1-2}$N((C$_1$-C$_4$)alkyl)$_2$, —(C$_1$-C$_6$)alkyl, —(C$_1$-C$_6$)fluoroalkyl, —(C$_3$-C$_6$)cycloalkyl, —(C$_3$-C$_6$)heterocycloalkyl, —C(O)OH, —C(O)—(C$_1$-C$_4$)alkyl, —C(O)N H$_2$, —C(O)NH(C$_1$-C$_4$)alkyl, —C(O)N((C$_1$-C$_4$)alkyl)$_2$, —NH—CH$_2$-phenyl and phenyl, wherein each phenyl is optionally substituted by 1, 2 or 3 substituents selected from -halogen, —CN, —NO$_2$, —O—R$^{30}$, —N(R$^{31}$)$_2$ and —S(R$^{30}$), in which each R$^{30}$ is independently selected from the group consisting of —H, —CH$_3$, —CH$_2$CH$_3$ and —CF$_3$, and each R$^{31}$ is independently selected from the group consisting of —H, —CH$_3$ and —CH$_2$CH$_3$;

the

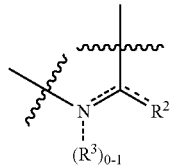

moiety has the structure (a)

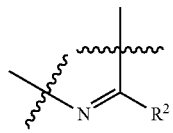

in which $R^2$ is selected from the group consisting of —H, -halogen, —CN, —NO$_2$, —N$_3$, —OH, —O—(C$_1$-C$_4$)alkyl, —O—(C$_1$-C$_4$)fluoroalkyl, —SH, —S—(C$_1$-C$_4$)alkyl, —NH$_2$, —NH—(C$_1$-C$_4$)alkyl, —N((C$_1$-C$_4$)alkyl)$_2$, —O—C(O)—(C$_1$-C$_4$)alkyl, —S—C(O)—(C$_1$-C$_4$)alkyl, —NH—C(O)—(C$_1$-C$_4$)alkyl, —N((C$_1$-C$_4$)alkyl)-C(O)—(C$_1$-C$_4$)alkyl, —S(O)$_{1-2}$H, —S(O)$_{1-2}$(C$_1$-C$_4$)alkyl, —S(O)$_{1-2}$OH, —S(O)$_{1-2}$O(C$_1$-C$_4$)alkyl, —S(O)$_{1-2}$NH$_2$, —S(O)$_{1-2}$NH(C$_1$-C$_4$)alkyl, —S(O)$_{1-2}$N((C$_1$-C$_4$)alkyl)$_2$, —(C$_1$-C$_6$)alkyl, —(C$_1$-C$_6$)fluoroalkyl, —(C$_3$-C$_6$)cycloalkyl, —(C$_3$-C$_6$)heterocycloalkyl, —C(O)OH, —C(O)—(C$_1$-C$_4$)alkyl, —C(O)NH$_2$, —C(O)NH(C$_1$-C$_4$)alkyl and —C(O)N((C$_1$-C$_4$)alkyl)$_2$, and when L is —C(O)—NH—CH$_2$—, $R^2$ is optionally the same

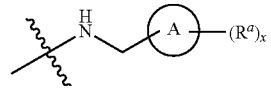

as defined below; or (b)

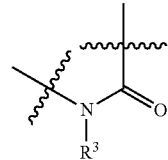

in which $R^3$ is —H, —(C$_1$-C$_4$)alkyl or —(C$_1$-C$_4$)fluoroalkyl;

each $R^4$ is independently —H, —CH$_3$ or —F;

$R^5$ is —H, —F or —CH$_3$;

the bond denoted by "q" is a single bond or a double bond;

Z is —C(O)—, —C(S)—, —S(O)$_2$— or —CH$_2$—;

G is a single bond, —CH$_2$—, —CHD-, —CD$_2$-, —CHF—, —CF$_2$—, —CH(R$^{14}$)—, —C(R$^{14}$)$_2$—, (C$_3$-C$_5$)cycloalkan-1,1-diyl, —NH—, —O— or —N(R$^{14}$)— in which each R$^{14}$ is independently methyl, ethyl, isopropyl or n-propyl;

the ring system denoted by "B" is phenyl, pyridyl, naphthyl, thiazolyl or pyrimidinyl;

y is 0, 1, 2, 3;

each $R^6$ is independently -halogen, —CN, —NO$_2$, —N$_3$, —OH, —O—(C$_1$-C$_4$)alkyl, —O—(C$_1$-C$_4$)fluoroalkyl, —SH, —S—(C$_1$-C$_4$)alkyl, —NH$_2$, —NH—(C$_1$-C$_4$)alkyl, —N((C$_1$-C$_4$)alkyl)$_2$, —O—C(O)—(C$_1$-C$_4$)alkyl, —S—C(O)—(C$_1$-C$_4$)alkyl, —NH—C(O)—(C$_1$-C$_4$)alkyl, —N((C$_1$-C$_4$)alkyl)-C(O)—(C$_1$-C$_4$)alkyl, —S(O)$_{1-2}$H, —S(O)$_{1-2}$(C$_1$-C$_4$)alkyl, —S(O)$_{1-2}$OH, —S(O)$_{1-2}$O(C$_1$-C$_4$)alkyl, —S(O)$_{1-2}$NH$_2$, —S(O)$_{1-2}$NH(C$_1$-C$_4$)alkyl, —S(O)$_{1-2}$N((C$_1$-C$_4$)alkyl)$_2$, —(C$_1$-C$_6$)alkyl, —(C$_1$-C$_6$)fluoroalkyl, —(C$_3$-C$_6$)cycloalkyl, —(C$_3$-C$_6$)heterocycloalkyl, —C(O)OH, —C(O)—(C$_1$-C$_4$)alkyl, —C(O)NH$_2$, —C(O)NH(C$_1$-C$_4$)alkyl or —C(O)N((C$_1$-C$_4$)alkyl)$_2$;

L is selected from the group consisting of —C(O)—NH—CH$_2$—, —C(O)—NH$_2$—CH$_2$—CH$_2$—O—, —C(O)—NH—CH—(CO$_2$R$^{15}$)—, —C(O)—NH—CH(R$^{15}$)—; C(O)—NH—CH(CH$_2$OH)—,

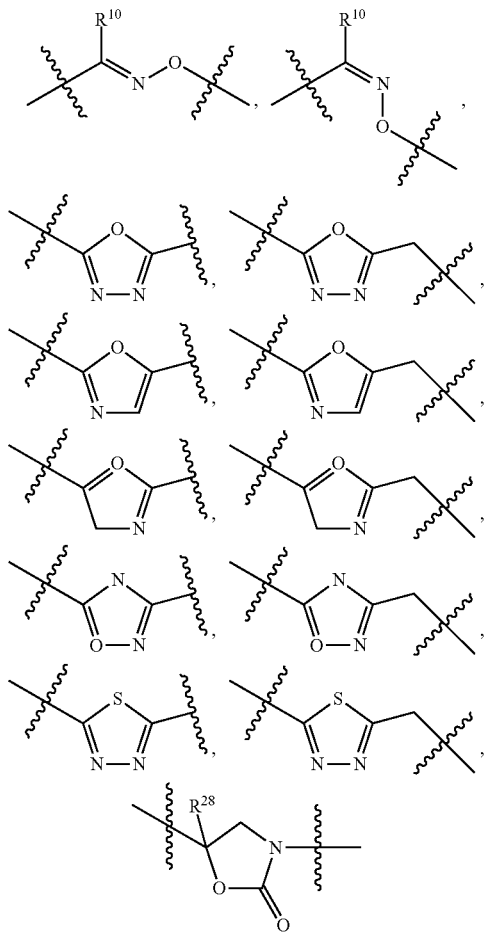

—C(OR$^{22}$)(R$^{16}$)—CH$_2$—NH—, —C(OR$^{22}$)(R$^{16}$)—CH$_2$—N(C$_1$-C$_4$)alkyl-, —C(OR$^{22}$)(R$^{16}$)—CH$_2$—O—, —C(OR$^{22}$)(R$^{24}$)—CH$_2$—O—, —C(OR$^{22}$)(R$^{25}$)—CH$_2$—O—, —C(OR$^{22}$)(R$^{16}$)—CH$_2$—CH$_2$—, —CH(NH$_2$)—CH$_2$—O—, —CH(NH(R$^{23}$))—CH$_2$—O—, —C(NH2)(R$^{27}$)—CH$_2$—O—, —C(=NHOH)—CH$_2$—O—, —C(OR$^{22}$)(R$^{26}$)—CH$_2$—O—, —C(R$^{11}$)(R$^{16}$)—CH$_2$—O—CH$_2$—, —C(R$^{12}$)(R$^{13}$)—CH$_2$—NH—CH$_2$—, —C(R$^{12}$)(R$^{13}$)—CH$_2$—NH—, —C(R$^{12}$)(R$^{13}$)—CH$_2$—O—, —C(R$^{12}$)(R$^{13}$)—CH$_2$—, —C(R$^{12}$)(R$^{13}$)—CH$_2$—S(O)$_{0-2}$—, —C(O)—NH—NH—, —C(O)—NH—O—, —CH$_2$—CH$_2$—CH$_2$—, —C(O)—CH$_2$—O—, —C(O)—CH$_2$—NH—, —CH=CH—CH$_2$—, —C(S)—NH—CH$_2$, and —CH$_2$—CH=CH—, in which $R^{10}$ is —H, —R$^{15}$, —CH$_2$OH or —CH$_2$F, $R^{11}$ is —H, —R$^{15}$, —CH$_2$OH, —CH$_2$OCH$_3$ or —CH$_2$—O—CH$_2$—CH(OH)—CH$_2$OH, $R^{12}$ is —H, —F, or —R$^{15}$ $R^{13}$ is —H, —F, —R$^{15}$, —CF$_3$, CH$_2$OH or CO$_2$R$^{15}$, or $R^{12}$ and $R^{13}$ come together to form a 4-6 membered heterocycloalkyl;

$R^{22}$ is H or —C(O)(C$_1$-C$_4$)alkyl;

$R^{24}$ is (C$_1$-C$_4$)alkyl, —C(O)(C$_1$-C$_4$)alkyl, —C(O)—NH—(C$_1$-C$_4$)alkyl, —(C$_1$-C$_4$)alkyl-NH—C(O)(C$_1$-C$_4$)alkyl, —C(O)—(C$_1$-C$_4$)alkyl-NH—C(O)—(C$_1$-C$_4$)alkyl, —C(O)—(C$_1$-C$_4$)alkyl-OH, piperidinyl, piperazinyl or pyrrolidinyl optionally substituted at a nitrogen position with —C(O)(C$_1$-C$_4$)alkyl or (C$_1$-C$_4$)alkyl $R^{25}$ is piperidinyl, piperazinyl or pyrrolidinyl optionally substituted at a nitrogen position with —C(O)(C$_1$-C$_4$)alkyl or (C$_1$-C$_4$)alkyl;

$R^{26}$ is —COOH, —COO(C$_1$-C$_4$)alkyl, —CN, —CONH$_2$, CONH(C$_1$-C$_4$)alkyl, —(C$_1$-C$_4$)alkyl, —(C$_1$-C$_4$)alkyl-OH, —(C$_1$-C$_4$)alkyl-NH$_2$, —(C$_1$-C$_4$)alkyl-N$_3$, —(C$_1$-C$_4$)alkyl-NHR$^{24}$, —CH$_2$—R$^{23}$ in which R$^{23}$ is piperazinyl, piperidinyl or pyrrolidinyl optionally substituted at a nitrogen position with —C(O)(C$_1$-C$_4$)alkyl or (C$_1$-C$_4$)alkyl;

$R^{27}$ is —CN, —CONH$_2$, —CONH(C$_1$-C$_4$)alkyl, —(C$_1$-C$_4$)alkyl, —(C$_1$-C$_4$)alkyl-OH, —(C$_1$-C$_4$)alkyl-NH$_2$, —(C$_1$-C$_4$)alkyl-N$_3$, —(C$_1$-C$_4$)alkyl-NHR$^{24}$, —CH$_2$—R$^{23}$ in which R$^{23}$ is piperazinyl, piperidinyl or pyrrolidinyl optionally substituted at a nitrogen position with —C(O)(C$_1$-C$_4$)alkyl or (C$_1$-C$_4$)alkyl; $R^{28}$ is H or (C$_1$-C$_4$)alkyl wherein each $R^{15}$ is independently methyl, ethyl, isopropyl or n-propyl, and each $R^{16}$ is independently —H, methyl, ethyl, isopropyl or n-propyl;

the ring system denoted by "A" is phenyl, pyridyl, pyrimidyl, thiazolyl, pyrazolyl or pyrazinyl;

x is 0, 1, 2 or 3; and each $R^a$ is independently —H, -halogen, —CN, —NO$_2$, —N$_3$, —OH, —O—(C$_1$-C$_4$)alkyl, —O—(C$_1$-C$_4$)fluoroalkyl, —SH, —S—(C$_1$-C$_4$)alkyl, —NH$_2$, —NH(C$_1$-C$_4$)alkyl, —N((C$_1$-C$_4$)alkyl)$_2$, —O—C(O)—(C$_1$-C$_4$)alkyl, —S—C(O)—(C$_1$-C$_4$)alkyl, —NH—C(O)—(C$_1$-C$_4$)alkyl, —N((C$_1$-C$_4$)alkyl)-C(O)—(C$_1$-C$_4$)alkyl, —S(O)$_{1-2}$H, —S(O)$_{1-2}$(C$_1$-C$_4$)alkyl, —S(O)$_{1-2}$OH, —S(O)$_{1-2}$O(C$_1$-C$_4$)alkyl, S(O)$_{1-2}$NH$_2$, —S(O)$_{1-2}$NH(C$_1$-C$_4$)alkyl, —S(O)$_{1-2}$N((C$_1$-C$_4$)alkyl)$_2$, —(C$_1$-C$_6$)alkyl, —(C$_1$-C$_6$)fluoroalkyl, —(C$_3$-C$_6$)cycloalkyl, —(C$_3$-C$_6$)heterocycloalkyl, —C(O)OH, —C(O)—(C$_1$-C$_4$)alkyl, —C(O)NH$_2$, —C(O)NH(C$_1$-C$_4$)alkyl or —C(O)N((C$_1$-C$_4$)alkyl)$_2$, in which each alkyl is optionally substituted with one or more substituents selected from the group consisting of -D, -halogen, —CN, —NO$_2$, —O—R$^{20}$, —N(R$^{21}$)$_2$ and —S(R$^{20}$), in which each R$^{20}$ is independently selected from the group consisting of —H, —CH$_3$, —CH$_2$CH$_3$ and —CF3, and each R$^{21}$ is independently selected from the group consisting of —H, —CH$_3$ and —CH$_2$CH$_3$.

In another aspect, the invention comprises compounds of formula (I), and stereoisomeric forms thereof, and N-oxides thereof, and pharmaceutically acceptable salts thereof, and solvates and hydrates thereof, wherein $R^1$ is selected from the group consisting of —H, -halogen, —CN, —NO$_2$, —OH, —O—(C$_1$-C$_4$)alkyl, —O—(C$_1$-C$_4$)fluoroalkyl, —SH, —S—(C$_1$-C$_4$)alkyl, —NH$_2$, —NH—(C$_1$-C$_4$)alkyl, —N((C$_1$-C$_4$)alkyl)$_2$, —O—C(O)—(C$_1$-C$_4$)alkyl, —S—C(O)—(C$_1$-C$_4$)alkyl, —NH—C(O)—(C$_1$-C$_4$)alkyl, —N((C$_1$-C$_4$)alkyl)-C(O)—(C$_1$-C$_4$)alkyl, —S(O)$_{1-2}$H, —S(O)$_{1-2}$(C$_1$-C$_4$)alkyl, —S(O)$_{1-2}$OH, —S(O)$_{1-2}$O(C$_1$-C$_4$)alkyl, —S(O)$_{1-2}$NH$_2$, —S(O)$_{1-2}$NH(C$_1$-C$_4$)alkyl, —S(O)$_{1-2}$N((C$_1$-C$_4$)alkyl)$_2$, —(C$_1$-C$_6$)alkyl, —(C$_1$-C$_6$)fluoroalkyl, —(C$_3$-C$_6$)cycloalkyl, —(C$_3$-C$_6$)heterocycloalkyl, —C(O)OH, —C(O)—(C$_1$-C$_4$)alkyl, —C(O)NH$_2$, —C(O)NH(C$_1$-C$_4$)alkyl, —C(O)N((C$_1$-C$_4$)alkyl)$_2$ and phenyl optionally substituted by 1, 2 or 3 substituents selected from -halogen, —CN, —NO$_2$, —O—R$^{30}$, —N(R$^{31}$)$_2$ and —S(R$^{30}$), in which each R$^{30}$ is independently selected from the group consisting of —H, —CH$_3$, —CH$_2$CH$_3$ and —CF$_3$, and each R$^{31}$ is independently selected from the group consisting of —H, —CH$_3$ and —CH$_2$CH$_3$;

the

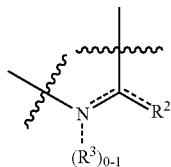

moiety has the structure (a)

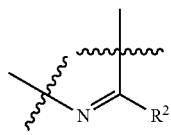

in which $R^2$ is selected from the group consisting of —H, -halogen, —CN, —NO$_2$, —N$_3$, —OH, —O—(C$_1$-C$_4$)alkyl, —O—(C$_1$-C$_4$)fluoroalkyl, —SH, —S—(C$_1$-C$_4$)alkyl, —NH$_2$, —NH—(C$_1$-C$_4$)alkyl, —N((C$_1$-C$_4$)alkyl)$_2$, —O—C(O)—(C$_1$-C$_4$)alkyl, —S—C(O)—(C$_1$-C$_4$)alkyl, —NH—C(O)—(C$_1$-C$_4$)alkyl, —N((C$_1$-C$_4$)alkyl)-C(O)—(C$_1$-C$_4$)alkyl, —S(O)$_{1-2}$H, —S(O)$_{1-2}$(C$_1$-C$_4$)alkyl, —S(O)$_{1-2}$OH, —S(O)$_{1-2}$O(C$_1$-C$_4$)alkyl, —S(O)$_{1-2}$NH$_2$, —S(O)$_{1-2}$NH(C$_1$-C$_4$)alkyl, —S(O)$_{1-2}$N((C$_1$-C$_4$)alkyl)$_2$, —(C$_1$-C$_6$)alkyl, —(C$_1$-C$_6$)fluoroalkyl, —(C$_3$-C$_6$)cycloalkyl, —(C$_3$-C$_6$)heterocycloalkyl, —C(O)OH, —C(O)—(C$_1$-C$_4$)alkyl, —C(O)NH$_2$, —C(O)NH(C$_1$-C$_4$)alkyl and —C(O)N((C$_1$-C$_4$)alkyl)$_2$, and when L is —C(O)—NH—CH$_2$—, $R^2$ is optionally the same

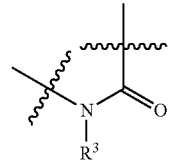

as defined below; or (b)

R$^3$ in which $R^3$ is —H, —(C$_1$-C$_4$)alkyl or —(C$_1$-C$_4$)fluoroalkyl;

each $R^4$ is independently —H, —CH$_3$ or —F;

$R^5$ is —H, —F or —CH$_3$;

the bond denoted by "q" is a single bond or a double bond;

Z is —C(O)—, —C(S)—, —S(O)$_2$— or —CH$_2$—;

G is a single bond, —CH$_2$—, —CHD-, —CD$_2$-, —CH(R$^{14}$)—, —C(R$^{14}$)$_2$—, —(C$_3$-C$_5$)cycloalkane-1,1-diyl, —NH— or —N(R$^{14}$)— in which each $R^{14}$ is independently methyl, ethyl, isopropyl or n-propyl;

the ring system denoted by "B" is phenyl, pyridyl, naphthyl, thiazolyl or pyrimidinyl;

y is 0, 1, 2, 3;

each $R^6$ is independently -halogen, —CN, —NO$_2$, —N$_3$, —OH, —O—(C$_1$-C$_4$)alkyl, —O—(C$_1$-C$_4$)fluoroalkyl, —SH, —S—(C$_1$-C$_4$)alkyl, —NH$_2$, —NH—(C$_1$-C$_4$)alkyl, —N((C$_1$-C$_4$)alkyl)$_2$, —O—C(O)—(C$_1$-C$_4$)alkyl, —S—C(O)—(C$_1$-C$_4$)alkyl, —NH—C(O)—(C$_1$-C$_4$)alkyl, —N((C$_1$-C$_4$)alkyl)-C(O)—(C$_1$-C$_4$)alkyl, —S(O)$_{1-2}$H, —S(O)$_{1-2}$(C$_1$-C$_4$)alkyl, —S(O)$_{1-2}$OH, —S(O)$_{1-2}$O(C$_1$-C$_4$)alkyl, —S(O)$_{1-2}$NH$_2$, —S(O)$_{1-2}$NH(C$_1$-C$_4$)alkyl, —S(O)$_{1-2}$N((C$_1$-C$_4$)alkyl)$_2$, —(C$_1$-C$_6$)alkyl, —(C$_1$-C$_6$)fluoroalkyl, —(C$_3$-C$_6$)cycloalkyl, —(C$_3$-C$_6$)heterocycloalkyl, —C(O)OH, —C(O)—(C$_1$-C$_4$)alkyl, —C(O)NH$_2$, —C(O)NH(C$_1$-C$_4$)alkyl or —C(O)N((C$_1$-C$_4$)alkyl)$_2$;

L is selected from the group consisting of —C(O)—NH—CH$_2$—, —C(O)—NH—CH$_2$—CH$_2$—O—, —C(O)—NH—CH—(CO$_2$R$^{15}$)—, —C(O)—NH—CH(R$^{15}$)—; C(O)—NH—CH(CH$_2$OH)—,

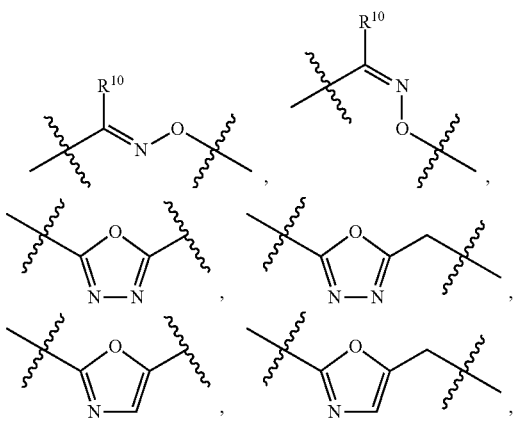

-continued

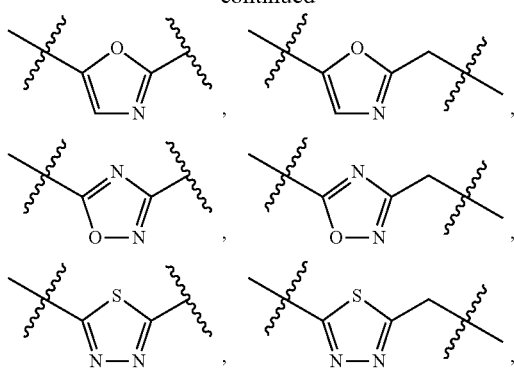

—C(OH)(R$^{16}$)—CH$_2$—NH—, —C(OH)(R$^{16}$)—CH$_2$—O—, —C(OH)(R$^{16}$)—CH$_2$—CH$_2$—, —C(R$^{11}$)(R$^{16}$)—CH$_2$—O—CH$_2$—, —C(R$^{12}$)(R$^{13}$)—CH$_2$—NH—CH$_2$—, —C(R$^{12}$)(R$^{13}$)—CH$_2$—NH—, —C(R$^{12}$)(R$^{13}$)—CH$_2$—O—, —C(R$^{12}$)(R$^{13}$)—CH$_2$—S(O)$_{0-2}$—, —C(O)—NH—NH—, —C(O)—NH—O—, —CH$_2$—CH$_2$—CH$_2$—, —C(O)—CH$_2$—O—, —CH═CH—CH$_2$—, —C(S)—NH—CH$_2$, and —CH$_2$—CH═CH—, in which R$^{10}$ is —H, —R$^{15}$, —CH$_2$OH or —CH$_2$F, R$^{11}$ is —H, —R$^{15}$, —CH$_2$OH, —CH$_2$OCH$_3$ or —CH$_2$—O—CH$_2$—CH(OH)—CH$_2$OH, R$^{12}$ is —H, —F, or —R$^{15}$, and R$^{13}$ is —H, —F, —R$^{15}$, —CF$_3$, CH$_2$OH or CO$_2$R$^{15}$, wherein each R$^{15}$ is independently methyl, ethyl, isopropyl or n-propyl, and each R$^{16}$ is independently —H, methyl, ethyl, isopropyl or n-propyl;

the ring system denoted by "A" is phenyl, pyridyl, pyrimidyl, thiazolyl, pyrazolyl or pyrazinyl;

x is 0, 1, 2 or 3; and each R$^a$ is independently —H, -halogen, —CN, —NO$_2$, —N$_3$, —OH, —O—(C$_1$-C$_4$)alkyl, —O—(C$_1$-C$_4$)fluoroalkyl, —SH, —S—(C$_1$-C$_4$)alkyl, —NH$_2$, —NH—(C$_1$-C$_4$)alkyl, —N((C$_1$-C$_4$)alkyl)$_2$, —O—C(O)—(C$_1$-C$_4$)alkyl, —S—C(O)—(C$_1$-C$_4$)alkyl, —NH—C(O)—(C$_1$-C$_4$)alkyl, —N((C$_1$-C$_4$)alkyl)-C(O)—(C$_1$-C$_4$)alkyl, —S(O)$_{1-2}$H, —S(O)$_{1-2}$(C$_1$-C$_4$)alkyl, —S(O)$_{1-2}$OH, —S(O)$_{1-2}$O(C$_1$-C$_4$)alkyl, S(O)$_{1-2}$NH$_2$, —S(O)$_{1-2}$NH(C$_1$-C$_4$)alkyl, —S(O)$_{1-2}$N((C$_1$-C$_4$)alkyl)$_2$, —(C$_1$-C$_6$)alkyl, —(C$_1$-C$_6$)fluoroalkyl, —(C$_3$-C$_6$)cycloalkyl, —(C$_3$-C$_6$)heterocycloalkyl, —C(O)OH, —C(O)—(C$_1$-C$_4$)alkyl, —C(O)NH$_2$, —C(O)NH(C$_1$-C$_4$)alkyl or —C(O)N((C$_1$-C$_4$)alkyl)$_2$, in which each alkyl is optionally substituted with one or more substituents selected from the group consisting of -D, -halogen, —CN, —NO$_2$, —O—R$^{20}$, —N(R$^{21}$)$_2$ and —S(R$^{20}$), in which each R$^{20}$ is independently selected from the group consisting of —H, —CH$_3$, —CH$_2$CH$_3$ and —CF$_3$, and each R$^{21}$ is independently selected from the group consisting of —H, —CH$_3$ and —CH$_2$CH$_3$.

In another aspect, the invention provides compounds of formula (Ia),

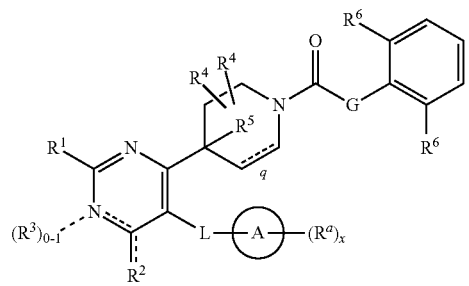

and stereoisomeric forms thereof, and N-oxides thereof, and pharmaceutically acceptable salts thereof, and solvates and hydrates thereof, wherein R$^1$ is selected from the group consisting of —H, —(C$_1$-C$_4$)alkyl, —(C$_1$-C$_4$)fluoroalkyl, —(C$_3$-C$_5$)cycloalkyl, —OH, —O—(C$_1$-C$_4$)alkyl, —SH, —S—(C$_1$-C$_4$)alkyl, —NH$_2$, —NH—(C$_1$-C$_4$)alkyl and —N((C$_1$-C$_4$)alkyl)$_2$;

the

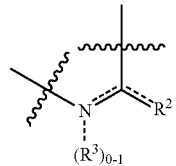

moiety has the structure (a)

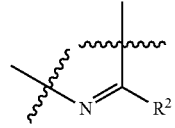

in which R$^2$ is selected from the group consisting of —H, —(C$_1$-C$_4$)alkyl, —(C$_1$-C$_4$)fluoroalkyl, —OH, —O—(C$_1$-C$_6$)alkyl, —NH$_2$, —NH—(C$_1$-C$_4$)alkyl and —N((C$_1$-C$_4$)alkyl)$_2$, or (b)

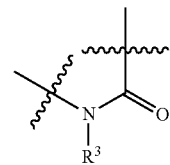

in which R$^3$ is —H;

each R$^4$ is independently H or F;

R$^5$ is —H, —CH$_3$, or —F;

the bond denoted by "q" is a single bond or a double bond;

G is a single bond, —CH$_2$—, —CHD-, —CD$_2$- or —NH—;

each R$^6$ is independently —H, -halogen, —(C$_1$-C$_4$ fluoroalkyl) or —O—(C$_1$-C$_4$ fluoroalkyl), provided that at least one R$^6$ is not —H;

L is selected from the group consisting of —C(O)—NH—CH$_2$—,

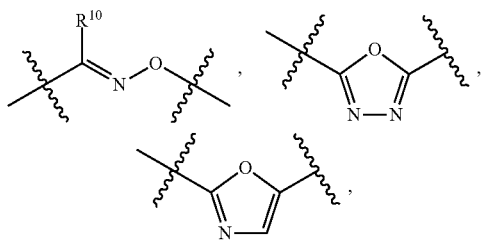

—C(OH)(CH$_3$)—CH$_2$—NH—, —C(OH)(CH$_3$)—CH$_2$—O—, —C(R$^{11}$)(CH$_3$)—CH$_2$—O—CH$_2$—, —C(R$^{12}$)(R$^{13}$)—CH$_2$—NH—CH$_2$—, —C(R$^{12}$)(R$^{13}$)—CH$_2$—NH—, —C(R$^{12}$)(R$^{13}$)—CH$_2$—O—, —C(R$^{12}$)(R$^{13}$)—CH$_2$—S(O)$_{0-2}$—, and —C(O)—NH—NH—, in which R$^{10}$ is —H, —CH$_3$, —CH$_2$OH or —CH$_2$F, R$^{11}$ is —H, —CH$_3$, —CH$_2$OH, —CH$_2$OCH$_3$ or —CH$_2$—O—CH$_2$—CH(OH)—CH$_2$OH, R$^{12}$ is —H, —F, or —CH$_3$, and R$^{13}$ is —H, —F, —CH$_3$ or —CF$_3$;

the ring system denoted by "A" is phenyl, pyridyl or pyrimidyl;

x is 1, 2 or 3; and each R$^a$ is independently -halogen, —(C$_1$-C$_4$)alkyl, —(C$_1$-C$_4$)fluoroalkyl, —O—(C$_1$-C$_4$)alkyl, —O—(C$_1$-C$_4$)fluoroalkyl, —CN or —NO$_2$, in which each alkyl is optionally substituted with one or more substituents selected from the group consisting of -D, -halogen, —CN, —NO$_2$, —O—R$^{20}$, —N(R$^{21}$)$_2$ and —S(R$^{20}$), in which each R$^{20}$ is independently selected from the group consisting of —H, —CH$_3$, —CH$_2$CH$_3$ and —CF$_3$, and each R$^{21}$ is independently selected from the group consisting of —H, —CH$_3$ and —CH$_2$CH$_3$.

The "L" moieties as described herein are presented with the connection to the central pyrimidine at the left, and the connection to the ring system denoted by "A" at the right.

The invention further comprises subgenera of formula (I) in which the substituents are selected as any and all combinations of one or more of R$^1$, R$^2$, R$^3$, R$^4$, R$^5$, R$^6$, R$^a$, x, y, G, L, Z, the bond denoted by "q", the ring system denoted by "A" and the ring system denoted by "B" as defined herein, including without limitation, the following:

In certain embodiments, the compound has one of the formulae (Ib)-(Ie):

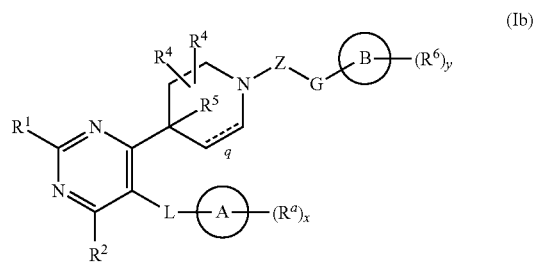
(Ib)

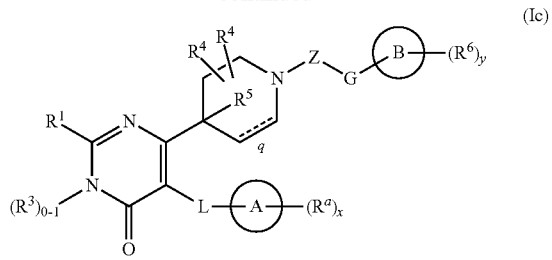
(Ic)

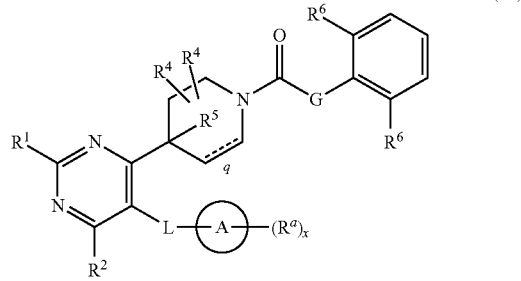
(Id)

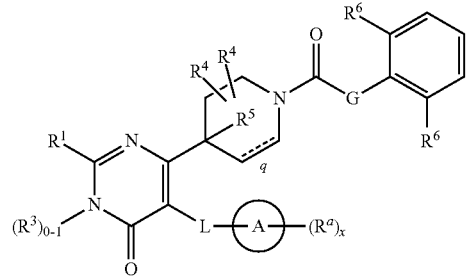
(Ie)

In certain embodiments of the compounds of any of formulae (I) and (Ia)-(Ie), R$^1$ is selected from one of the following groups (1a)-(1o):

(1a) R$^1$ is —H, —(C$_1$-C$_2$)alkyl, —(C$_1$-C$_2$)fluoroalkyl, —(C$_3$-C$_4$)cycloalkyl, —OH, —O—(C$_1$-C$_2$)alkyl, —SH, —S—(C$_1$-C$_2$)alkyl, —NH$_2$, —NH—(C$_1$-C$_2$)alkyl or —N((C$_1$-C$_2$)alkyl)$_2$.

(1b) R$^1$ is —H, —(C$_1$-C$_2$)alkyl, -cyclopropyl, —O—(C$_1$-C$_3$)alkyl, —S—(C$_1$-C$_2$)alkyl, —NH$_2$, —NH—(C$_1$-C$_3$)alkyl or —N((C$_1$-C$_2$)alkyl)$_2$.

(1c) R$^1$ is —H, —CH$_3$, —CH2CH$_3$, —CHD$_2$, -cyclopropyl, —OCH$_3$, —O—CH$_2$CH$_3$, —SCH$_3$, —NH$_2$, —NH(CH$_3$), —NH(CH$_2$CH$_3$), —NH—CH$_2$—CH$_2$—OH, —N(CH$_3$)$_2$ or —NH—CH(CH$_3$)$_2$.

(1d) R$^1$ is —H, —CH$_3$ or —CH$_2$CH$_3$.

(1e) R$^1$ is —CH$_3$.

(1f) R$^1$ is —H, —(C$_1$-C$_2$)alkyl, —(C$_1$-C$_2$)deuteroalkyl, —(C$_1$-C$_2$)fluoroalkyl, —(C$_3$-C$_4$)cycloalkyl, —OH, —O—(C$_1$-C$_2$)alkyl, —SH, —S—(C$_1$-C$_2$)alkyl, —NH$_2$, —NH—(C$_1$-C$_2$)alkyl, —NH—CH$_2$CH$_2$—OH, —NH—CH$_2$CH$_2$—NH$_2$, —NH—CH$_2$CH$_2$—NH(C$_1$-C$_2$)alkyl, —NH—CH$_2$CH$_2$—N((C$_1$-C$_2$)alkyl)$_2$, or —N((C$_1$-C$_2$)alkyl)$_2$, in which each alkyl is unsubstituted.

(1g) R$^1$ is —H, —(C$_1$-C$_4$)alkyl, —(C$_1$-C$_4$)fluoroalkyl, —(C$_3$-C$_5$)cycloalkyl, —OH, —O—(C$_1$-C$_4$)alkyl, —SH, —S—(C$_1$-C$_4$)alkyl, —NH$_2$, —NH—(C$_1$-C$_4$)alkyl or —N((C$_1$-C$_4$)alkyl)$_2$;

(1h) R$^1$ is —H, -halogen, —CN, —NO$_2$, —N$_3$, —OH, —O—(C$_1$-C$_4$)alkyl, —O—(C$_1$-C$_4$)fluoroalkyl, —SH, —S—(C$_1$-C$_4$)alkyl, —NH$_2$, —NH—(C$_1$-C$_4$)alkyl, —N((C$_1$-C$_4$)alkyl)$_2$, —O—C(O)—(C$_1$-C$_4$)alkyl, —S—C(O)—($C_1$-$C_4$)alkyl, —NH—C(O)—($C_1$-$C_4$)alkyl, —N(($C_1$-$C_4$)alkyl)-C(O)—($C_1$-$C_4$)alkyl, —S(O)$_{1-2}$H, —S(O)$_{1-2}$($C_1$-$C_4$)alkyl, —S(O)$_{1-2}$OH, —S(O)$_{1-2}$O($C_1$-$C_4$)alkyl, —S(O)$_{1-2}$NH$_2$, —S(O)$_{1-2}$NH($C_1$-$C_4$)alkyl, —S(O)$_{1-2}$N(($C_1$-$C_4$)alkyl)$_2$, —($C_1$-$C_6$)alkyl, —($C_1$-$C_6$)fluoroalkyl, —($C_3$-$C_6$)cycloalkyl, —($C_3$-$C_6$)heterocycloalkyl, —C(O)OH, —C(O)—($C_1$-$C_4$)alkyl, —C(O)NH$_2$, —C(O)NH($C_1$-$C_4$)alkyl, —C(O)N(($C_1$-$C_4$)alkyl)$_2$ or phenyl in which each alkyl and phenyl is unsubstituted.

(1i) $R^1$ is —H, -halogen, —CN, —NO$_2$, —N$_3$, —OH, —O—($C_1$-$C_2$)alkyl, —O—($C_1$-$C_2$)fluoroalkyl, —SH, —S—($C_1$-$C_2$)alkyl, —NH$_2$, —NH—($C_1$-$C_2$)alkyl, —N(($C_1$-$C_2$)alkyl)$_2$, —O—C(O)—($C_1$-$C_2$)alkyl, —S—C(O)—($C_1$-$C_2$)alkyl, —NH—C(O)—($C_1$-$C_2$)alkyl, —N(($C_1$-$C_2$)alkyl)-C(O)—($C_1$-$C_2$)alkyl, —S(O)$_{1-2}$H, —S(O)$_{1-2}$($C_1$-$C_2$)alkyl, —S(O)$_{1-2}$OH, —S(O)$_{1-2}$O($C_1$-$C_2$)alkyl, —S(O)$_{1-2}$NH$_2$, —S(O)$_{1-2}$NH($C_1$-$C_2$)alkyl, —S(O)$_{1-2}$N(($C_1$-$C_2$)alkyl)$_2$, —($C_1$-$C_2$)alkyl, —($C_1$-$C_2$)fluoroalkyl, —C(O)OH, —C(O)—($C_1$-$C_2$)alkyl, —C(O)NH$_2$, —C(O)NH($C_1$-$C_2$)alkyl or —C(O)N(($C_1$-$C_2$)alkyl)$_2$.

(1j) $R^1$ is —H, -halogen, —CN, —NO$_2$, —N$_3$, —O—($C_1$-$C_2$)alkyl, —O—($C_1$-$C_2$)fluoroalkyl, —S—($C_1$-$C_2$)alkyl, —NH$_2$, —NH—($C_1$-$C_2$)alkyl, —N(($C_1$-$C_2$)alkyl)$_2$, —O—C(O)—($C_1$-$C_2$)alkyl, —S—C(O)—($C_1$-$C_2$)alkyl, —NH—C(O)—($C_1$-$C_2$)alkyl, —N(($C_1$-$C_2$)alkyl)-C(O)—($C_1$-$C_2$)alkyl, —S(O)$_{1-2}$H, —S(O)$_{1-2}$($C_1$-$C_2$)alkyl, —S(O)$_{1-2}$OH, —S(O)$_{1-2}$O($C_1$-$C_2$)alkyl, —S(O)$_{1-2}$NH$_2$, —S(O)$_{1-2}$NH($C_1$-$C_2$)alkyl, —S(O)$_{1-2}$N(($C_1$-$C_2$)alkyl)$_2$, —($C_1$-$C_2$)alkyl, —($C_1$-$C_2$)fluoroalkyl, —C(O)OH, —C(O)—($C_1$-$C_2$)alkyl, —C(O)NH$_2$, —C(O)NH($C_1$-$C_2$)alkyl or —C(O)N(($C_1$-$C_2$)alkyl)$_2$.

(1k) $R^1$ is phenyl, optionally substituted by 1, 2 or 3 substituents selected from -halogen, —CN, —NO$_2$, —O—$R^{30}$, —N($R^{31}$)$_2$ and —S($R^{30}$), in which each $R^{30}$ is independently selected from the group consisting of —H, —CH$_3$, —CH$_2$CH$_3$ and —CF$_3$, and each $R^{31}$ is independently selected from the group consisting of —H, —CH$_3$ and —CH$_2$CH$_3$ (1l) $R^1$ is —NH—($C_1$-$C_4$)fluoroalkyl, —N(($C_1$-$C_4$)fluoroalkyl)$_2$, or —NH—($C_3$-$C_6$ cycloalkyl).

(1m) $R^1$ is —NH—CH$_2$-phenyl.

(1n) $R^1$ is —O—($C_1$-$C_4$)fluoroalkyl.

(1o) $R^1$ is selected from the group consisting of —H, -halogen, —CN, —NO$_2$, —OH, —O—($C_1$-$C_4$)alkyl, —O—($C_1$-$C_4$)fluoroalkyl, —SH, —S—($C_1$-$C_4$)alkyl, —NH$_2$, —NH—($C_1$-$C_4$)alkyl, —NH—($C_1$-$C_4$)fluoroalkyl, —N(($C_1$-$C_4$)alkyl)$_2$, —N(($C_1$-$C_4$)fluoroalkyl)$_2$, —NH—($C_3$-$C_6$)cycloalkyl, —O—C(O)—($C_1$-$C_4$)alkyl, —S—C(O)—($C_1$-$C_4$)alkyl, —NH—C(O)—($C_1$-$C_4$)alkyl, —N(($C_1$-$C_4$)alkyl)-C(O)—($C_1$-$C_4$)alkyl, —S(O)$_{1-2}$H, —S(O)$_{1-2}$($C_1$-$C_4$)alkyl, —S(O)$_{1-2}$OH, —S(O)$_{1-2}$O($C_1$-$C_4$)alkyl, —S(O)$_{1-2}$NH$_2$, —S(O)$_{1-2}$NH($C_1$-$C_4$)alkyl, —S(O)$_{1-2}$N(($C_1$-$C_4$)alkyl)$_2$, —($C_1$-$C_6$)alkyl, —($C_1$-$C_6$)fluoroalkyl, —($C_3$-$C_6$)cycloalkyl, —($C_3$-$C_6$)heterocycloalkyl, —C(O)OH, —C(O)—($C_1$-$C_4$)alkyl, —C(O)NH$_2$, —C(O)NH($C_1$-$C_4$)alkyl, —C(O)N(($C_1$-$C_4$)alkyl)$_2$, —NH—CH$_2$-phenyl and phenyl, wherein each phenyl is optionally substituted by 1, 2 or 3 substituents selected from -halogen, —CN, —NO$_2$, —O—$R^{30}$, —N($R^{31}$)$_2$ and —S($R^{30}$), in which each $R^{30}$ is independently selected from the group consisting of —H, —CH$_3$, —CH$_2$CH$_3$ and —CF$_3$, and each $R^{31}$ is independently selected from the group consisting of —H, —CH$_3$ and —CH$_2$CH$_3$.

In certain embodiments of the compounds of any of formulae (I), (Ia), (Ib) and (Id) as described above, $R^2$ is selected from one of the following groups (2a)-(2l):

(2a) $R^2$ is —H, —($C_1$-$C_2$)alkyl, —($C_1$-$C_2$)fluoroalkyl, —($C_3$-$C_4$)cycloalkyl, —OH, —O—($C_1$-$C_2$)alkyl, —SH, —S—($C_1$-$C_2$)alkyl, —NH$_2$, —NH—($C_1$-$C_2$)alkyl and —N(($C_1$-$C_2$)alkyl)$_2$.

(2b) $R^2$ is —H, —($C_1$-$C_2$)alkyl, —($C_1$-$C_2$)fluoroalkyl, —($C_3$-$C_4$)cycloalkyl, —O—($C_1$-$C_2$)alkyl, —S—($C_1$-$C_2$)alkyl, —NH—($C_1$-$C_2$)alkyl and —N(($C_1$-$C_2$)alkyl)$_2$.

(2c) $R^2$ is —H, —CH$_3$, —NH(CH$_3$), —OCH$_3$ or —CF$_3$.

(2d) $R^2$ is —H.

(2e) $R^2$ is —CH$_3$.

(2f) $R^2$ is —H, —($C_1$-$C_4$)alkyl, —($C_1$-$C_4$)fluoroalkyl, —OH, —O—($C_1$-$C_6$)alkyl, —NH$_2$, —NH—($C_1$-$C_4$)alkyl or —N(($C_1$-$C_4$)alkyl)$_2$.

(2g) $R^2$ is —H, —($C_1$-$C_2$)alkyl, —($C_1$-$C_2$)deuteroalkyl, —($C_1$-$C_2$)fluoroalkyl, —($C_3$-$C_4$)cycloalkyl, —OH, —O—($C_1$-$C_2$)alkyl, —SH, —S—($C_1$-$C_2$)alkyl, —NH$_2$, —NH—($C_1$-$C_2$)alkyl and —N(($C_1$-$C_2$)alkyl)$_2$, in which each alkyl is unsubstituted.

(2h) $R^2$ is —H, -halogen, —CN, —NO$_2$, —N$_3$, —OH, —O—($C_1$-$C_4$)alkyl, —O—($C_1$-$C_4$)fluoroalkyl, —SH, —S—($C_1$-$C_4$)alkyl, —NH$_2$, —NH—($C_1$-$C_4$)alkyl, —N(($C_1$-$C_4$)alkyl)$_2$, —O—C(O)—($C_1$-$C_4$)alkyl, —S—C(O)—($C_1$-$C_4$)alkyl, —NH—C(O)—($C_1$-$C_4$)alkyl, —N(($C_1$-$C_4$)alkyl)-C(O)—($C_1$-$C_4$)alkyl, —S(O)$_{1-2}$H, —S(O)$_{1-2}$($C_1$-$C_4$)alkyl, —S(O)$_{1-2}$OH, —S(O)$_{1-2}$O($C_1$-$C_4$)alkyl, —S(O)$_{1-2}$NH$_2$, —S(O)$_{1-2}$NH($C_1$-$C_4$)alkyl, —S(O)$_{1-2}$N(($C_1$-$C_4$)alkyl)$_2$, —($C_1$-$C_6$)alkyl, —($C_1$-$C_6$)fluoroalkyl, —($C_3$-$C_6$)cycloalkyl, —($C_3$-$C_6$)heterocycloalkyl, —C(O)OH, —C(O)—($C_1$-$C_4$)alkyl, —C(O)NH$_2$, —C(O)NH($C_1$-$C_4$)alkyl or —C(O)N(($C_1$-$C_4$)alkyl)$_2$ in which each alkyl is unsubstituted.

(2i) $R^2$ is —H, -halogen, —CN, —NO$_2$, —N$_3$, —OH, —O—($C_1$-$C_2$)alkyl, —O—($C_1$-$C_2$)fluoroalkyl, —SH, —S—($C_1$-$C_2$)alkyl, —NH$_2$, —NH—($C_1$-$C_2$)alkyl, —N(($C_1$-$C_2$)alkyl)$_2$, —O—C(O)—($C_1$-$C_2$)alkyl, —S—C(O)—($C_1$-$C_2$)alkyl, —NH—C(O)—($C_1$-$C_2$)alkyl, —N(($C_1$-$C_2$)alkyl)-C(O)—($C_1$-$C_2$)alkyl, —S(O)$_{1-2}$H, —S(O)$_{1-2}$($C_1$-$C_2$)alkyl, —S(O)$_{1-2}$OH, —S(O)$_{1-2}$O($C_1$-$C_2$)alkyl, —S(O)$_{1-2}$NH$_2$, —S(O)$_{1-2}$NH($C_1$-$C_2$)alkyl, —S(O)$_{1-2}$N(($C_1$-$C_2$)alkyl)$_2$, —($C_1$-$C_2$)alkyl, —($C_1$-$C_2$)fluoroalkyl, —C(O)OH, —C(O)—($C_1$-$C_2$)alkyl, —C(O)NH$_2$, —C(O)NH($C_1$-$C_2$)alkyl or —C(O)N(($C_1$-$C_2$)alkyl)$_2$.

(2j) $R^2$ is —H, -halogen, —CN, —NO$_2$, —N$_3$, —O—($C_1$-$C_2$)alkyl, —O—($C_1$-$C_2$)fluoroalkyl, —S—($C_1$-$C_2$)alkyl, —NH$_2$, —NH—($C_1$-$C_2$)alkyl, —N(($C_1$-$C_2$)alkyl)$_2$, —O—C(O)—($C_1$-$C_2$)alkyl, —S—C(O)—($C_1$-$C_2$)alkyl, —NH—C(O)—($C_1$-$C_2$)alkyl, —N(($C_1$-$C_2$)alkyl)-C(O)—($C_1$-$C_2$)alkyl, —S(O)$_{1-2}$H, —S(O)$_{1-2}$($C_1$-$C_2$)alkyl, —S(O)$_{1-2}$OH, —S(O)$_{1-2}$O($C_1$-$C_2$)alkyl, —S(O)$_{1-2}$NH$_2$, —S(O)$_{1-2}$NH($C_1$-$C_2$)alkyl, —S(O)$_{1-2}$N(($C_1$-$C_2$)alkyl)$_2$, —($C_1$-$C_2$)alkyl, —($C_1$-$C_2$)fluoroalkyl, —C(O)OH, —C(O)—($C_1$-$C_2$)alkyl, —C(O)NH$_2$, —C(O)NH($C_1$-$C_2$)alkyl or —C(O)N(($C_1$-$C_2$)alkyl)$_2$.

(2k) when L is —C(O)—NH—CH$_2$—, $R^2$ is optionally the same

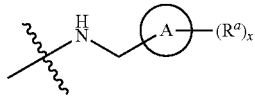

as defined above and in groups (Aa-Ai), (xa)-(xe) and (aa)-(ah) and (A-xa)-(A-xs) below.

(2l) $R^2$ is —H, -halogen, —CN, —NO$_2$, —N$_3$, —OH, —O—(C$_1$-C$_4$)alkyl, —O—(C$_1$-C$_4$)fluoroalkyl, —SH, —S—(C$_1$-C$_4$)alkyl, —NH$_2$, —NH—(C$_1$-C$_4$)alkyl, —N((C$_1$-C$_4$)alkyl)$_2$, —O—C(O)—(C$_1$-C$_4$)alkyl, —S—C(O)—(C$_1$-C$_4$)alkyl, —NH—C(O)—(C$_1$-C$_4$)alkyl, —N((C$_1$-C$_4$)alkyl)-C(O)—(C$_1$-C$_4$)alkyl, —S(O)$_{1-2}$H, —S(O)$_{1-2}$(C$_1$-C$_4$)alkyl, —S(O)$_{1-2}$OH, —S(O)$_{1-2}$O(C$_1$-C$_4$)alkyl, —S(O)$_{1-2}$NH$_2$, —S(O)$_{1-2}$NH(C$_1$-C$_4$)alkyl, —S(O)$_{1-2}$N((C$_1$-C$_4$)alkyl)$_2$, —(C$_1$-C$_6$)alkyl, —(C$_1$-C$_6$)fluoroalkyl, —(C$_3$-C$_6$)cycloalkyl, —(C$_3$-C$_6$)heterocycloalkyl, —C(O)OH, —C(O)—(C$_1$-C$_4$)alkyl, —C(O)NH$_2$, —C(O)NH(C$_1$-C$_4$)alkyl or —C(O)N((C$_1$-C$_4$)alkyl)$_2$, In certain embodiments of the compounds of any of formulae (I), (Ia), (Ic) and (Ie) as described above, $R^3$ is selected from one of the following groups (3a)-(3d):
(3a) $R^3$ is —H.
(3b) $R^3$ is —H, —(C$_1$-C$_4$)alkyl or —(C$_1$-C$_4$)fluoroalkyl in which the alkyl is unsubstituted;
(3c) $R^3$ is —CH$_3$ or —CH$_2$CH$_3$.
(3d) $R^3$ is —H, —(C$_1$-C$_4$)alkyl or —(C$_1$-C$_4$)fluoroalkyl.

In certain embodiments of the compounds of any of formulae (I) and (Ia)-(Ie) as described above, the $R^4$ are defined as in one of the following groups (4a)-(4f):
(4a) both $R^4$ are —H.
(4b) both $R^4$ are —F.
(4c) one $R^4$ is —H and the other is —F.
(4d) one $R^4$ is —H and the other is CH$_3$.
(4e) each $R^4$ is independently H, —CH$_3$ or —F.
(4f) each $R^4$ is H or F.

In certain embodiments of the compounds of any of formulae (I) and (Ia)-(Ie) as described herein, both $R^4$ are bound to the carbon in the alpha position relative to the carbon to which $R^5$ and the pyrimidine are bound (i.e., at the 3-position of the piperidine).

In certain embodiments of the compounds of any of formulae (I) and (Ia)-(Ie) as described above, $R^5$ is selected from one of the following groups (5a)-(5e):
(5a) $R^5$ is —H.
(5b) $R^5$ is —F.
(5c) $R^5$ is —H or —F.
(5d) $R^5$ is —CH$_3$.
(5e) $R^5$ is —H, —F or —CH$_3$.

In certain embodiments of the compounds of any of formulae (I) and (Ia)-(Ie) as described above, the bond denoted by "q" is selected from one of the following (q-1)-(q-2):
(q-1) the bond denoted by "q" is a single bond.
(q-2) the bond denoted by "q" is a double bond.

In certain embodiments of the compounds of any of formulae (I) and (Ia)-(Ie) as described above, the combination of the bond denoted by "q", the $R^4$ and $R^5$ is selected from one of the following groups (q-4-5a)-(q-4-5f):
(q-4-5a) the bond denoted by "q" is a single bond, both $R^4$ are H, and $R^5$ is H.
(q-4-5b) the bond denoted by "q" is a double bond, both $R^4$ are H, and $R^5$ is H.
(q-4-5c) the bond denoted by "q" is a single bond, both $R^4$ are H, and $R^5$ is F.
(q-4-5d) the bond denoted by "q" is a single bond, both $R^4$ are F, and $R^5$ is H.
(q-4-5e) the bond denoted by "q" is a single bond, both $R^4$ are H, and $R^5$ is —CH$_3$.
(q-4-5f) the bond denoted by "q" is a single bond or a double bond, each $R^4$ is independently H or F; and $R^5$ is —H, —CH$_3$, or —F.

In certain embodiments of the compounds of any of formulae (I), (Ib) and (Ic) as described above, Z is selected from one of the following groups (Za)-(Zd):
(Za) Z is —C(O)—.
(Zb) Z is —C(S)—.
(Zc) Z is —S(O)$_2$—.
(Zd) Z is —CH$_2$—.

In certain embodiments of the compounds of any of formulae (I) and (Ia)-(Ie) as described above, G is selected from one of the following groups (Ga)-(Gk):
(Ga) G is —CH$_2$—, —CHD- or —CD$_2$-.
(Gb) G is —NH—.
(Gc) G is —CH$_2$—.
(Gd) G is a single bond.
(Ge) G is —CH(R$^{14}$)—, —C(R$^{14}$)$_2$— in which each R$^{14}$ is independently methyl, ethyl, isopropyl or n-propyl. In certain such embodiments, each R$^{14}$ is methyl.
(Gf) G is (C$_3$-C$_5$)cycloalkan-1,1-diyl. In certain such embodiments, G is cyclopropan-1,1-diyl or cyclopentan-1,1-diyl.
(Gg) G is —N(R$^{14}$)— in which each R$^{14}$ is independently methyl, ethyl, isopropyl or n-propyl. In certain such embodiments, each R$^{14}$ is methyl.
(Gh) G is —CHF—, —CF$_2$— or —O—.
(Gh) G is —CF$_2$—.
(Gi) G is —O—.
(Gj) G is a single bond, —CH$_2$—, —CHD-, —CD$_2$-, —CH(R$^{14}$)—, —C(R$^{14}$)$_2$—, (C$_3$-C$_5$)cycloalkan-1,1-diyl, —NH— or —N(R$^{14}$)— in which each R$^{14}$ is independently methyl, ethyl, isopropyl or n-propyl.
(Gk) G is a single bond, —CH$_2$—, —CHD-, —CD$_2$- or —NH—.

In certain embodiments of the compounds of any of formula (I) and (Ia)-(Ie) as described above, the ring system denoted by "B" is selected from one of the following groups (Ba)-(Bg):
(Ba) the ring system denoted by "B" is phenyl.
(Bb) the ring system denoted by "B" is pyridyl.
(Bc) the ring system denoted by "B" is pyrid-2-yl.
(Bd) the ring system denoted by "B" is naphthyl.
(Be) the ring system denoted by "B" is naphth-1-yl.
(Bf) the ring system denoted by "B" is thiazolyl.
(Bg) the ring system denoted by "B" is pyrimidinyl.

In certain embodiments of the compounds of any of formula (I) and (Ia)-(Ie) as described above, y is selected from one of the following groups (ya)-(yc):
(ya) y is 1 or 2.
(yb) y is 1.
(yc) y is 2.
(yd) y is 0.

In certain embodiments of the compounds of any of formula (I) and (Ia)-(Ie) as described above, each $R^6$ is selected from one of the following groups (6a)-(6m):
(6a) each $R^6$ is independently —H, -halogen, —(C$_1$-C$_2$ fluoroalkyl) or —O—(C$_1$-C$_2$ fluoroalkyl), provided that y is at least 1.
(6b) each $R^6$ is independently —H, -halogen, —(C$_1$-C$_2$ fluoroalkyl) or —O—(C$_1$-C$_2$ fluoroalkyl), provided that y is at least 1.
(6c) each $R^6$ is independently -halogen, —(C$_1$-C$_2$ fluoroalkyl) or —O—(C$_1$-C$_2$ fluoroalkyl), provided that y is at least 1.
(6d) each $R^6$ is independently, —H, —F, —Cl, —CF$_3$ or —O—CF$_3$, provided that y is at least 1.

(6e) each $R^6$ is independently, —F, —Cl, —CF$_3$ or —O—CF$_3$, provided that y is at least 1.

(6f) each $R^6$ is independently —F, —Cl or —CF$_3$, provided that y is at least 1.

(6g) each $R^6$ is —F.

(6h) each $R^6$ is independently -halogen, —(C$_1$-C$_4$ fluoroalkyl) or —O—(C$_1$-C$_4$ fluoroalkyl), provided that y is at least 1.

(6i) each $R^6$ is independently -halogen, —CN, —NO$_2$, —N$_3$, —OH, —O—(C$_1$-C$_4$)alkyl, —O—(C$_1$-C$_4$)fluoroalkyl, —SH, —S—(C$_1$-C$_4$)alkyl, —NH$_2$, —NH—(C$_1$-C$_4$)alkyl, —N((C$_1$-C$_4$)alkyl)$_2$, —O—C(O)—(C$_1$-C$_4$)alkyl, —S—C(O)—(C$_1$-C$_4$)alkyl, —NH—C(O)—(C$_1$-C$_4$)alkyl, —N((C$_1$-C$_4$)alkyl)-C(O)—(C$_1$-C$_4$)alkyl, —S(O)$_{1-2}$H, —S(O)$_{1-2}$(C$_1$-C$_4$)alkyl, —S(O)$_{1-2}$OH, —S(O)$_{1-2}$O(C$_1$-C$_4$)alkyl, —S(O)$_{1-2}$NH$_2$, —S(O)$_{1-2}$NH(C$_1$-C$_4$)alkyl, —S(O)$_{1-2}$N((C$_1$-C$_4$)alkyl)$_2$, —(C$_1$-C$_6$)alkyl, —(C$_1$-C$_6$)fluoroalkyl, —(C$_3$-C$_6$)cycloalkyl, —(C$_3$-C$_6$)heterocycloalkyl, —C(O)OH, —C(O)—(C$_1$-C$_4$)alkyl, —C(O)NH$_2$, —C(O)NH(C$_1$-C$_4$)alkyl or —C(O)N((C$_1$-C$_4$)alkyl)$_2$ in which each alkyl is unsubstituted.

(6j) each $R^6$ is independently -halogen, —CN, —NO$_2$, —N$_3$, —OH, —O—(C$_1$-C$_2$)alkyl, —O—(C$_1$-C$_2$)fluoroalkyl, —SH, —S—(C$_1$-C$_2$)alkyl, —NH$_2$, —NH—(C$_1$-C$_2$)alkyl, —N((C$_1$-C$_2$)alkyl)$_2$, —O—C(O)—(C$_1$-C$_2$)alkyl, —S—C(O)—(C$_1$-C$_2$)alkyl, —NH—C(O)—(C$_1$-C$_2$)alkyl, —N((C$_1$-C$_2$)alkyl)-C(O)—(C$_1$-C$_2$)alkyl, —S(O)$_{1-2}$H, —S(O)$_{1-2}$(C$_1$-C$_2$)alkyl, —S(O)$_{1-2}$OH, —S(O)$_{1-2}$O(C$_1$-C$_2$)alkyl, —S(O)$_{1-2}$NH$_2$, —S(O)$_{1-2}$NH(C$_1$-C$_2$)alkyl, —S(O)$_{1-2}$N((C$_1$-C$_2$)alkyl)$_2$, —(C$_1$-C$_2$)alkyl, —(C$_1$-C$_2$)fluoroalkyl, —C(O)OH, —C(O)—(C$_1$-C$_2$)alkyl, —C(O)NH$_2$, —C(O)NH(C$_1$-C$_2$)alkyl or —C(O)N((C$_1$-C$_2$)alkyl)$_2$.

(6k) each $R^6$ is independently —H, -halogen, —(C$_1$-C$_4$ fluoroalkyl) or —O—(C$_1$-C$_4$ fluoroalkyl), provided that at least one $R^6$ is not —H.

(6l) each $R^6$ is independently -halogen, —CN, —NO$_2$, —N$_3$, —OH, —O—(C$_1$-C$_4$)alkyl, —O—(C$_1$-C$_4$)fluoroalkyl, —SH, —S—(C$_1$-C$_4$)alkyl, —NH$_2$, —NH—(C$_1$-C$_4$)alkyl, —N((C$_1$-C$_4$)alkyl)$_2$, —O—C(O)—(C$_1$-C$_4$)alkyl, —S—C(O)—(C$_1$-C$_4$)alkyl, —NH—C(O)—(C$_1$-C$_4$)alkyl, —N((C$_1$-C$_4$)alkyl)-C(O)—(C$_1$-C$_4$)alkyl, —S(O)$_{1-2}$H, —S(O)$_{1-2}$(C$_1$-C$_4$)alkyl, —S(O)$_{1-2}$OH, —S(O)$_{1-2}$O(C$_1$-C$_4$)alkyl, —S(O)$_{1-2}$NH$_2$, —S(O)$_{1-2}$NH(C$_1$-C$_4$)alkyl, —S(O)$_{1-2}$N((C$_1$-C$_4$)alkyl)$_2$, —(C$_1$-C$_6$)alkyl, —(C$_1$-C$_6$)fluoroalkyl, —(C$_3$-C$_6$)cycloalkyl, —(C$_3$-C$_6$)heterocycloalkyl, —C(O)OH, —C(O)—(C$_1$-C$_4$)alkyl, —C(O)NH$_2$, —C(O)NH(C$_1$-C$_4$)alkyl or —C(O)N((C$_1$-C$_4$)alkyl)$_2$.

(6m) As otherwise described herein, in which at least one $R^6$ is not H.

In certain embodiments of the compounds of any of formula (I), (Ib) and (Ic) as described above, the ring system denoted by "B" and y are selected such that the

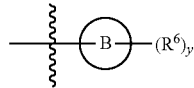

moiety has the structure (B-ya):

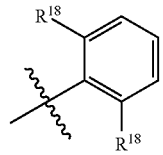

in which each $R^{18}$ is $R^6$ or H provided that at least one $R^{18}$ is not H.

In certain embodiments of the compounds of any of formula (I) and (Ia)-(Ie) as described above, L is selected from one of the following groups (La)-(Lv):

(La) L is —C(O)—NH—CH$_2$—, —C(O)—NH—CHD- or —C(O)—NH—CD$_2$-.

(Lb) L is

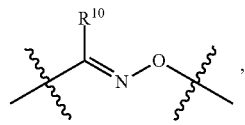

in which $R^{10}$ is —H, —CH$_3$, —CH$_2$OH or —CH$_2$F.

(Lc) L is

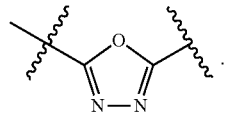 [SMILES: *c1nnc(*)o1]

(Ld) L is

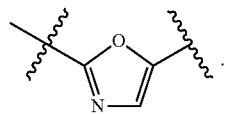 [SMILES: *c1cnc(*)o1]

(Le) L is —C(OH)(CH$_3$)—CH$_2$—NH— or —C(OH)(CH$_3$)—CH$_2$—O—.

(Lf) L is —C(R$^{11}$)(CH$_3$)—CH$_2$—O—CH$_2$—, in which R$^{11}$ is —H, —CH$_3$, —CH$_2$OH, —CH$_2$OCH$_3$ or —CH$_2$—O—CH$_2$—CH(OH)—CH$_2$OH.

(Lg) L is —C(R$^{12}$)(R$^{13}$)—CH$_2$—NH—CH$_2$— or —C(R$^{12}$)(R$^{13}$)—CH$_2$—NH—, in which R$^{12}$ is H, —F or CH$_3$, and R$^{13}$ is H, —FCH$_3$ or CF$_3$. In certain such embodiments, L is —C(CH$_3$)(CH$_3$)—CH$_2$—NH—, —CH(CF$_3$)—CH$_2$—NH—CH$_2$—, —CH(CH$_3$)—CH$_2$—NH—CH$_2$— or —CH$_2$—CH$_2$—NH—CH$_2$—.

(Lh) L is —C(R$^{12}$)(R$^{13}$)—CH$_2$—O— or —C(R$^{12}$)(R$^{13}$)—CH$_2$—S(O)$_{0-2}$—, in which R$^{12}$ is H or CH$_3$, and R$^{13}$ is H, CH$_3$ or CF$_3$. In certain such embodiments, L is —CH$_2$—CH$_2$—O—.

(Li) L is —C(O)—NH—NH—.

(Lj) L is —C(O)—NH$_2$—CH$_2$—CH$_2$—O—, —C(O)—NH—CH—(CO$_2$R$^{15}$)—, —C(O)—NH—CH(R$^{15}$)—; —C(O)—NH—CH(CH$_2$OH)—, in which each R$^{15}$ is independently methyl, ethyl, isopropyl or n-propyl. In certain such embodiments, each R$^{15}$ is methyl.

(Lk) L is

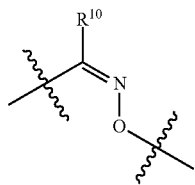

(Ll) L is

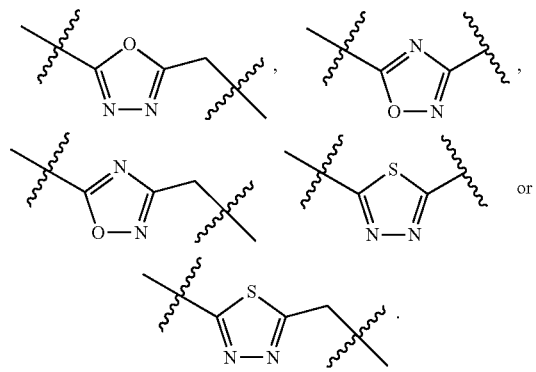

(Lm) L is —C(OH)(R$^{16}$)—CH$_2$—NH—, —C(OH)(R$^{16}$)—CH$_2$—O—, —C(OH)(R$^{16}$)—CH$_2$—CH$_2$—, in which each R$^{16}$ is independently —H, methyl, ethyl, isopropyl or n-propyl. In certain such embodiments, L is —C(OH)(CH$_3$)—CH$_2$—CH$_2$—.

(Ln) L is —C(R$^{11}$)(R$^{16}$)—CH$_2$—O—CH$_2$— in which R$^{11}$ is —H, —CH$_3$, —CH$_2$OH, —CH$_2$OCH$_3$ or —CH$_2$—O—CH$_2$—CH(OH)—CH$_2$OH and R$^{16}$ is —H, methyl, ethyl, isopropyl or n-propyl.

(Lo) L is —C(O)—NH—O—, —CH$_2$—CH$_2$—CH$_2$—, —C(O)—CH$_2$—O—, —CH=CH—CH$_2$—, —C(S)—NH—CH$_2$, or —CH$_2$—CH=CH—.

(Lp) L is —C(O)—NH—CH$_2$—, —C(O)—NH$_2$—CH$_2$—CH$_2$—O—, —C(O)—NH—CH—(CO$_2$R$^{15}$)—, —C(O)—NH—CH(R$^{15}$)—; C(O)—NH—CH(CH$_2$OH)—,

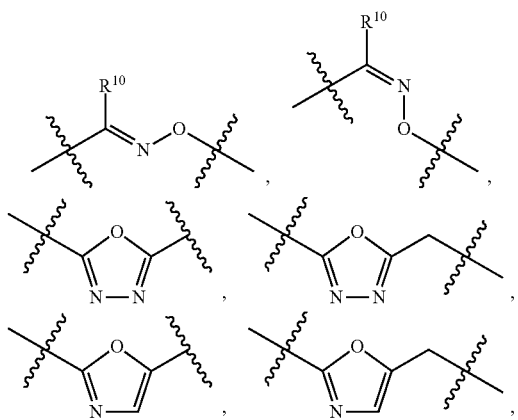

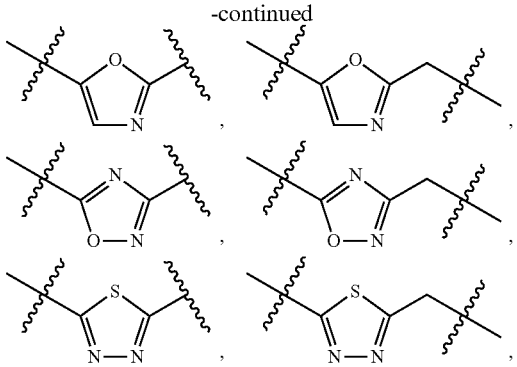

—C(OH)(R$^{16}$)—CH$_2$—NH—, —C(OH)(R$^{16}$)—CH$_2$—O—, —C(OH)(R$^{16}$)—CH$_2$—CH$_2$—, —C(R$^{11}$)(R$^{16}$)—CH$_2$—O—CH$_2$—, —C(R$^{12}$)(R$^{13}$)—CH$_2$—NH—CH$_2$—, —C(R$^{12}$)(R$^{13}$)—CH$_2$—NH—, —C(R$^{12}$)(R$^{13}$)—CH$_2$—O—, —C(R$^{12}$)(R$^{13}$)—CH$_2$—S(O)$_{0-2}$—, —C(O)—NH—NH—, —C(O)—NH—O—, —CH$_2$—CH$_2$—CH$_2$—, —C(O)—CH$_2$—O—, —CH=CH—CH$_2$—, —C(S)—NH—CH$_2$, or —CH$_2$—CH=CH—, in which R$^{10}$ is —H, —R$^{15}$, —CH$_2$OH or —CH$_2$F,
R$^{11}$ is —H, —R$^{15}$, —CH$_2$OH, —CH$_2$OCH$_3$ or —CH$_2$—O—CH$_2$—CH(OH)—CH$_2$OH,
R$^{12}$ is —H, —F, or —R$^{15}$, and
R$^{13}$ is —H, —F, —R$^{15}$, —CF$_3$, CH$_2$OH or CO$_2$R$^{15}$,
wherein each R$^{15}$ is independently methyl, ethyl, isopropyl or n-propyl, and each R$^{16}$ is independently —H, methyl, ethyl, isopropyl or n-propyl.

(Lp) L is —C(O)—NH—CH$_2$—,

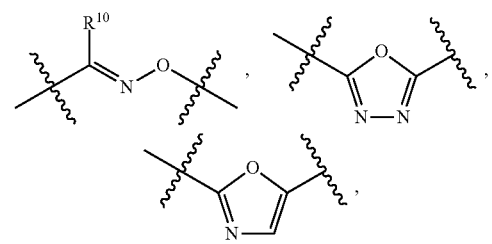

—C(OH)(CH$_3$)—CH$_2$—NH—, —C(OH)(CH$_3$)—CH$_2$—O—, —C(R$^{11}$)(CH$_3$)—CH$_2$—O—CH$_2$—, —C(R$^{12}$)(R$^{13}$)—CH$_2$—NH—CH$_2$—, —C(R$^{12}$)(R$^{13}$)—CH$_2$—NH—, —C(R$^{12}$)(R$^{13}$)—CH$_2$—O—, —C(R$^{12}$)(R$^{13}$)—CH$_2$—S(O)$_{0-2}$—, or —C(O)—NH—NH—, in which R$^{10}$ is —H, —CH$_3$, —CH$_2$OH or —CH$_2$F,
R$^{11}$ is —H, —CH$_3$, —CH$_2$OH, —CH$_2$OCH$_3$ or —CH$_2$—O—CH$_2$—CH(OH)—CH$_2$OH,
R$^{12}$ is —H, —F, or —CH$_3$, and
R$^{13}$ is —H, —F, —CH$_3$ or —CF$_3$.

(Lq) L is

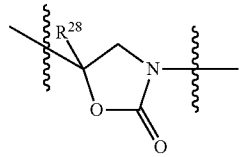

—C(OR$^{22}$)(R$^{16}$)—CH$_2$—NH—, —C(OR$^{22}$)(R$^{16}$)—CH$_2$—N(C$_1$-C$_4$)alkyl-, —C(OR$^{22}$)(R$^{16}$)—CH$_2$—O—, —C(OR$^{22}$)(R$^{24}$)—CH$_2$—O—, —C(OR$^{22}$)(R$^{25}$)—CH$_2$—O—, —C(OR$^{22}$)(R$^{16}$)—CH$_2$—CH$_2$—, —CH(NH$_2$)—CH$_2$—O—, —CH(NH(R$^{23}$))—CH$_2$—O—, —C(NH2)(R$^{27}$)—CH$_2$—O—, —C(=NHOH)—CH$_2$—O—, —C(OR$^{22}$)(R$^{26}$)—CH$_2$—O—, —C(R$^{12}$)(R$^{13}$)—CH$_2$— or —C(O)—CH$_2$—NH—.

(Lr) L is —C(CH$_3$)(OH)—CH$_2$—, —CH(OH)—CH$_2$—O—, —CH(OC(O)CH$_3$)—CH$_2$—O, —CHF—CH$_2$—O—, —CH(NH$_2$)—CH$_2$—O—, —C(=NHOH)—CH$_2$—O— or —CH(NHCH$_3$)—CH$_2$—O—.

(Ls) L is —CF$_2$—CH$_2$—O— or —CF$_2$—CH$_2$—NH—.

(Lt) L is —CH(NH(R$^{23}$))—CH$_2$—O— in which R$^{23}$ is 1-acetyl-piperidin-4-yl.

(Lu) L is —CH(OH)(R$^{26}$)—CH$_2$—O—, in which R$^{26}$ is —CH$_2$CH$_2$OH, —CH$_2$CH$_2$NH$_2$, —CH$_2$OH, —CH$_2$N$_3$, —CH$_2$NH$_2$, —CH2NHC(O)NHCH$_2$CH$_3$, —CH$_2$NHC(O)CH$_3$, —CH$_2$NHCH$_2$CH$_2$NHC(O)CH$_3$, —CH$_2$—(1-acetylpiperazin-4-yl), —CH$_2$—NH-(1-acetylpyrrolidin-3-yl), —CH$_2$NHC(O)CH$_2$CH$_2$NHC(O)CH$_3$, —CH$_2$NHC(O)CH$_2$CH$_2$OH, —CH$_2$NHC(O)CH$_3$, —COOH, —CONHCH$_3$.

(Lv) L is —C(NH$_2$)(R$^{27}$)—CH$_2$—O—, in which R$^{27}$ is —CN or —CONH$_2$.

In certain embodiments of the compounds of any of formula (I) and (Ia)-(Ie) as described above, the ring system denoted by "A" is selected from one of the following groups (Aa)-(Ai):

(Aa) the ring system denoted by "A" is phenyl.
(Ab) the ring system denoted by "A" is pyridyl.
(Ac) the ring system denoted by "A" is pyrid-2-yl or pyrid-4-yl.
(Ad) the ring system denoted by "A" is pyrimidyl.
(Ae) the ring system denoted by "A" is pyrimid-2-yl or pyrimid-4-yl.
(Af) the ring system denoted by "A" is thiazolyl, pyrazolyl or pyrazinyl.
(Ag) the ring system denoted by "A" is thiazol-5-yl, pyrazol-3-yl or pyrazin-2-yl.
(Ah) the ring system denoted by "A" is phenyl, pyridyl, pyrimidyl, thiazolyl, pyrazolyl or pyrazinyl.
(Ai) the ring system denoted by "A" is phenyl, pyridyl or pyrimidyl.

In certain embodiments of the compounds of any of formula (I) and (Ia)-(Ie) as described above, x is selected from one of the following groups (xa)-(xe):

(xa) x is 1 or 2.
(xb) x is 1.
(xc) x is 2.
(xd) x is 1, 2 or 3.
(xe) x is 0.

In certain embodiments of the compounds of any of formula (I) and (Ia)-(Ie) as described above, the ring system denoted by "A" and x are selected to form a residue selected from one of the following (A-xa)-(A-xs):

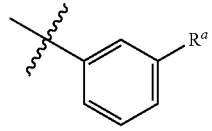

(A-xa)

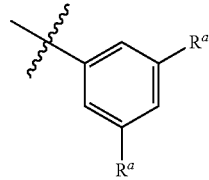

(A-xb)

(A-xc)

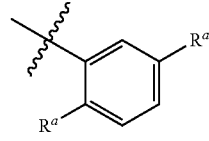

(A-xd)

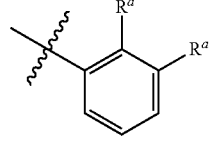

(A-xe)

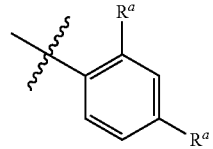

(A-xf)

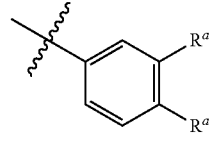

(A-xg)

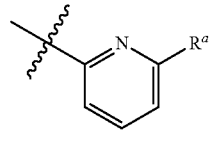

(A-xh)

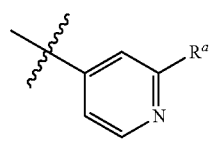

(A-xi)

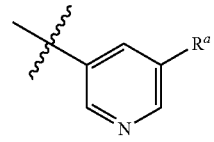

(A-xj)

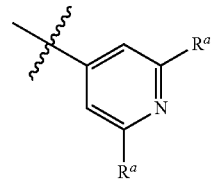

-continued

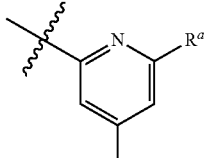
(A-xk)

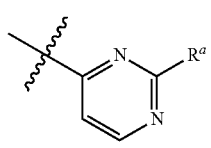
(A-xl)

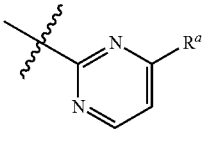
(A-xm)

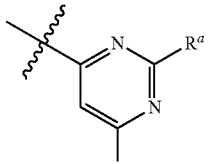
(A-xn)

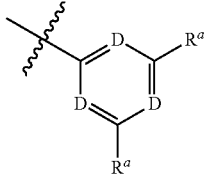
(A-xo)

in which 0, 1 or 2 D are N, and the others are CH

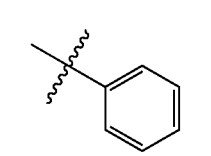
(A-xp)

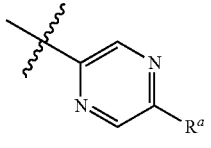
(A-xq)

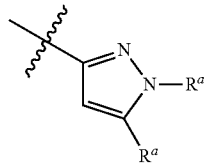
(A-xr)

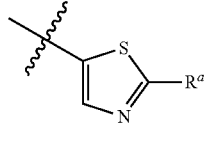
(A-xs)

In certain embodiments of the compounds of any of formula (I) and (Ia)-(Ie) as described above, each $R^a$ is selected from one of the following groups (aa)-(ah):

(aa) each $R^a$ is independently -halogen, —($C_1$-$C_2$)alkyl, —($C_1$-$C_2$)fluoroalkyl, —O—($C_1$-$C_2$)alkyl, —O—($C_1$-$C_2$)fluoroalkyl, —CN or —NO$_2$.

(ab) each $R^a$ is independently —F, —Cl, —CH$_3$, —CF$_3$, —CF$_2$CH$_3$, —OCH$_3$, —OCF$_3$ or —CN.

(ac) each $R^a$ is independently -halogen, —($C_1$-$C_4$)alkyl, —($C_1$-$C_4$)fluoroalkyl, —O—($C_1$-$C_4$)alkyl, —O—($C_1$-$C_4$)fluoroalkyl, —CN or —NO$_2$, in which each alkyl is unsubstituted.

(ad) each $R^a$ is independently -halogen, —($C_1$-$C_4$)alkyl, —($C_1$-$C_4$)fluoroalkyl, —O—($C_1$-$C_4$)alkyl, —O—($C_1$-$C_4$)fluoroalkyl, —CN or —NO$_2$.

(ae) each $R^a$ is independently —H, -halogen, —CN, —NO$_2$, —N$_3$, —OH, —O—($C_1$-$C_4$)alkyl, —O—($C_1$-$C_4$)fluoroalkyl, —SH, —S—($C_1$-$C_4$)alkyl, —NH$_2$, —NH—($C_1$-$C_4$)alkyl, —N(($C_1$-$C_4$)alkyl)$_2$, —O—C(O)—($C_1$-$C_4$)alkyl, —S—C(O)—($C_1$-$C_4$)alkyl, —NH—C(O)—($C_1$-$C_4$)alkyl, —N(($C_1$-$C_4$)alkyl)-C(O)—($C_1$-$C_4$)alkyl, —S(O)$_{1-2}$H, —S(O)$_{1-2}$($C_1$-$C_4$)alkyl, —S(O)$_{1-2}$OH, —S(O)$_{1-2}$O($C_1$-$C_4$)alkyl, —S(O)$_{1-2}$NH$_2$, —S(O)$_{1-2}$NH($C_1$-$C_4$)alkyl, —S(O)$_{1-2}$N(($C_1$-$C_4$)alkyl)$_2$, —($C_1$-$C_6$)alkyl, —($C_1$-$C_6$)fluoroalkyl, —($C_3$-$C_6$)cycloalkyl, —($C_3$-$C_6$)heterocycloalkyl, —C(O)OH, —C(O)—($C_1$-$C_4$)alkyl, —C(O)NH$_2$, —C(O)NH($C_1$-$C_4$)alkyl or —C(O)N(($C_1$-$C_4$)alkyl)$_2$ in which each alkyl is unsubstituted.

(af) each $R^a$ is independently —H, -halogen, —CN, —NO$_2$, —N$_3$, —OH, —O—($C_1$-$C_2$)alkyl, —O—($C_1$-$C_2$)fluoroalkyl, —SH, —S—($C_1$-$C_2$)alkyl, —NH$_2$, —NH—($C_1$-$C_2$)alkyl, —N(($C_1$-$C_2$)alkyl)$_2$, —O—C(O)—($C_1$-$C_2$)alkyl, —S—C(O)—($C_1$-$C_2$)alkyl, —NH—C(O)—($C_1$-$C_2$)alkyl, —N(($C_1$-$C_2$)alkyl)-C(O)—($C_1$-$C_2$)alkyl, —S(O)$_{1-2}$H, —S(O)$_{1-2}$($C_1$-$C_2$)alkyl, —S(O)$_{1-2}$OH, —S(O)$_{1-2}$O($C_1$-$C_2$)alkyl, —S(O)$_{1-2}$NH$_2$, —S(O)$_{1-2}$NH($C_1$-$C_2$)alkyl, —S(O)$_{1-2}$N(($C_1$-$C_2$)alkyl)$_2$, —($C_1$-$C_2$)alkyl, —($C_1$-$C_2$)fluoroalkyl, —C(O)OH, —C(O)—($C_1$-$C_2$)alkyl, —C(O)NH$_2$, —C(O)NH($C_1$-$C_2$)alkyl or —C(O)N(($C_1$-$C_2$)alkyl)$_2$.

(ag) each $R^a$ is independently —H, -halogen, —CN, —NO$_2$, —N$_3$, —OH, —O—($C_1$-$C_4$)alkyl, —O—($C_1$-$C_4$)fluoroalkyl, —SH, —S—($C_1$-$C_4$)alkyl, —NH$_2$, —NH—($C_1$-$C_4$)alkyl, —N(($C_1$-$C_4$)alkyl)$_2$, —O—C(O)—($C_1$-$C_4$)alkyl, —S—C(O)—($C_1$-$C_4$)alkyl, —NH—C(O)—($C_1$-$C_4$)alkyl, —N(($C_1$-$C_4$)alkyl)-C(O)—($C_1$-$C_4$)alkyl, —S(O)$_{1-2}$H, —S(O)$_{1-2}$($C_1$-$C_4$)alkyl, —S(O)$_{1-2}$OH, —S(O)$_{1-2}$O($C_1$-$C_4$)alkyl, S(O)$_{1-2}$NH$_2$, —S(O)$_{1-2}$NH($C_1$-$C_4$)alkyl, —S(O)$_{1-2}$N(($C_1$-$C_4$)alkyl)$_2$, —($C_1$-$C_6$)alkyl, —($C_1$-$C_6$)fluoroalkyl, —($C_3$-$C_6$)cycloalkyl, —($C_3$-$C_6$)heterocycloalkyl, —C(O)OH, —C(O)—($C_1$-$C_4$)alkyl, —C(O)NH$_2$, —C(O)NH($C_1$-$C_4$)alkyl or —C(O)N(($C_1$-$C_4$)alkyl)$_2$.

(ah) each $R^a$ is independently -halogen, —($C_1$-$C_4$)alkyl, —($C_1$-$C_4$)fluoroalkyl, —O—($C_1$-$C_4$)alkyl, —O—($C_1$-$C_4$)fluoroalkyl, —CN or —NO$_2$.

In certain embodiments of the compounds of any of formula (I) and (Ia)-(Ie) as described above, the combination of the ring system denoted by "A", x and all $R^a$ groups combine to form a residue selected from one of the following (A-x-aa)-(A-x-aad):

(A-x-aa) 3-chlorophenyl
(A-x-ab) 3,5-dimethylphenyl
(A-x-ac) 3-chloro-5-fluorophenyl
(A-x-ad) 5-chloro-2-fluorophenyl
(A-x-ae) 3-fluorophenyl (A-x-af) 6-(trifluoromethyl)pyridin-2-yl
(A-x-ag) 3-(trifluoromethyl)phenyl
(A-x-ah) 2-(trifluoromethyl)pyridin-4-yl
(A-x-ai) 3,4-dichlorophenyl
(A-x-aj) 3,5-dichloropyridin-4-yl
(A-x-ak) 3-cyanophenyl
(A-x-al) 3,5-dichlorophenyl
(A-x-am) 3-chloro-5-methoxypyridin-4-yl
(A-x-an) 3-(trifluoromethoxy)phenyl
(A-x-ao) 3-chloro-2-fluorophenyl
(A-x-ap) 2-cyanopyridin-4-yl
(A-x-aq) 2-chloropyridin-4-yl
(A-x-ar) 3-methoxyphenyl
(A-x-as) 4-chloro-2-methylphenyl
(A-x-at) 3-methylphenyl
(A-x-au) 5-fluoro-2-methylphenyl
(A-x-av) 2-(trifluoromethyl)pyrimidin-4-yl
(A-x-aw) 2,5-dimethylphenyl
(A-x-ax) 2-(1,1-difluoroethyl)pyrimidin-4-yl
(A-x-ay) 6-chloropyridin-2-yl
(A-x-az) 4,6-dimethylpyridin-2-yl
(A-x-aaa) 4-(trifluoromethyl)pyrimidin-2-yl
(A-x-aab) 6-methyl-2-(trifluoromethyl)pyrimidin-4-yl
(A-x-aac) 2-chloro-6-(trifluoromethyl)pyridin-4-yl
(A-x-aad) 2,6-difluoropyridin-4-yl Particular embodiments according to this aspect of the invention include compounds of Formula (I) as defined in each of the following rows, in which each entry is a group number as defined above (e.g., (1e) indicates that $R^1$ is —$CH_3$), and a dash "-" indicates that the variable is as defined for formula (I) or is defined according to any applicable variable definition above (e.g., when the $R^1$ column is "-", $R^1$ can be defined as for Formula (I) or any one of definitions (1a)-(1o)).

| Form. (I)* | $R^1$ | $R^2/R^3$ | $R^4$-$R^5$-"q" bond | Z | G | B-y | $R^6$ | L | "A" | x | $R^a$ |
|---|---|---|---|---|---|---|---|---|---|---|---|
| (Ia) | (1a) | (2a) | (q-4-5a) | (Za) | (Ga) | (B-ya) | (6a) | (La) | (Aa)-(Ae) | (xd) | (ad) |
| (Ia) | (1a) | (2a) | (q-4-5a) | (Za) | (Ga) | (B-ya) | (6a) | (Lb) | (Aa)-(Ae) | (xd) | (ad) |
| (Ia) | (1a) | (2a) | (q-4-5a) | (Za) | (Ga) | (B-ya) | (6a) | (Lc) | (Aa)-(Ae) | (xd) | (ad) |
| (Ia) | (1a) | (2a) | (q-4-5a) | (Za) | (Ga) | (B-ya) | (6a) | (Le) | (Aa)-(Ae) | (xd) | (ad) |
| (Ia) | (1a) | (2a) | (q-4-5a) | (Za) | (Ga) | (B-ya) | (6a) | (Lf) | (Aa)-(Ae) | (xd) | (ad) |
| (Ia) | (1a) | (2a) | (q-4-5a) | (Za) | (Ga) | (B-ya) | (6a) | (Lg) | (Aa)-(Ae) | (xd) | (ad) |
| (Ia) | (1a) | (2a) | (q-4-5a) | (Za) | (Ga) | (B-ya) | (6a) | (Li) | (Aa)-(Ae) | (xd) | (ad) |
| (Ia) | (1a) | (2a) | (q-4-5a)-(q-4-5d) | (Za) | (Ga) | (B-ya) | (6a) | (La) | (Aa) | (xa) | (ad) |
| (Ia) | (1a) | (2a) | (q-4-5a)-(q-4-5d) | (Za) | (Ga) | (B-ya) | (6a) | (La) | (Ab) | (xa) | (ad) |
| (Ia) | (1a) | (2a) | (q-4-5a)-(q-4-5d) | (Za) | (Ga) | (B-ya) | (6a) | (Lb) | (Aa) | (xa) | (ad) |
| (Ia) | (1a) | (2a) | (q-4-5a)-(q-4-5d) | (Za) | (Ga) | (B-ya) | (6a) | (Lb) | (Ab) | (xa) | (ad) |
| (Ia) | (1a) | (2a) | (q-4-5a)-(q-4-5d) | (Za) | (Ga) | (B-ya) | (6a) | (Lb) | (Ad) | (xa) | (ad) |
| (Ia) | (1a) | (2a) | (q-4-5a)-(q-4-5d) | (Za) | (Ga) | (B-ya) | (6a) | (Lc) | (Aa) | (xa) | (ad) |
| (Ia) | (1a) | (2a) | (q-4-5a)-(q-4-5d) | (Za) | (Ga) | (B-ya) | (6a) | (Lc) | (Ab) | (xa) | (ad) |
| (Ia) | (1a) | (2a) | (q-4-5a)-(q-4-5d) | (Za) | (Ga) | (B-ya) | (6a) | (Lc) | (Ad) | (xa) | (ad) |
| (Ia) | (1a) | (2a) | (q-4-5a)-(q-4-5d) | (Za) | (Ga) | (B-ya) | (6a) | (Le) | (Aa) | (xa) | (ad) |
| (Ia) | (1a) | (2a) | (q-4-5a)-(q-4-5d) | (Za) | (Ga) | (B-ya) | (6a) | (Le) | (Ab) | (xa) | (ad) |
| (Ia) | (1a) | (2a) | (q-4-5a)-(q-4-5d) | (Za) | (Ga) | (B-ya) | (6a) | (Le) | (Ad) | (xa) | (ad) |
| (Ia) | (1a) | (2a) | (q-4-5a)-(q-4-5d) | (Za) | (Ga) | (B-ya) | (6a) | (Lf) | (Aa) | (xa) | (ad) |
| (Ia) | (1a) | (2a) | (q-4-5a)-(q-4-5d) | (Za) | (Ga) | (B-ya) | (6a) | (Lg) | (Aa) | (xa) | (ad) |
| (Ia) | (1a) | (2a) | (q-4-5a)-(q-4-5d) | (Za) | (Ga) | (B-ya) | (6a) | (Lg) | (Ad) | (xa) | (ad) |
| (Ia) | (1a) | (2a) | (q-4-5a)-(q-4-5d) | (Za) | (Ga) | (B-ya) | (6a) | (Li) | (Aa) | (xa) | (ad) |
| (Ib) | (1a) | (3a) | (q-4-5a)-(q-4-5d) | (Za) | (Ga) | (B-ya) | (6a) | (La) | (Aa) | (xa) | (ad) |
| (Ib) | (1a) | (3a) | (q-4-5a)-(q-4-5d) | (Za) | (Ga) | (B-ya) | (6a) | (La) | (Ab) | (xa) | (ad) |
| (Ib) | (1a) | (3a) | (q-4-5a)-(q-4-5d) | (Za) | (Ga) | (B-ya) | (6a) | (Lb) | (Aa) | (xa) | (ad) |
| (Ib) | (1a) | (3a) | (q-4-5a)-(q-4-5d) | (Za) | (Ga) | (B-ya) | (6a) | (Lb) | (Ab) | (xa) | (ad) |
| (Ib) | (1a) | (3a) | (q-4-5a)-(q-4-5d) | (Za) | (Ga) | (B-ya) | (6a) | (Lb) | (Ad) | (xa) | (ad) |
| (Ia)-(Ib) | (1c) | (2c)/(3a) | (q-4-5a) | (Za) | (Ga)-(Gc) | (B-ya) | (6a) | (La)-(Li) | (Aa)-(Ae) | (xa) | (aa) |
| (Ia) | (1g) | (2f)/(3a) | (q-4-5-a) | (Za) | (Ga)-(Gc) | (B-ya) | (6f) | (La)-(Li) | (A-xo) | | (ad) |

*Both $R^4$ are bound at the 3-position of the piperidine.

Particular embodiments according to this aspect of the invention include compounds of Formula (I) as defined above, in which R$^1$ is selected from the group consisting of H, —(C$_1$-C$_4$)alkyl, —(C$_1$-C$_4$)fluoroalkyl, —(C$_3$-C$_5$)cycloalkyl, —OH, —O—(C$_1$-C$_4$)alkyl, —SH, —S—(C$_1$-C$_4$)alkyl, —NH$_2$, —NH—(C$_1$-C$_4$)alkyl, —N((C$_1$-C$_4$)alkyl)$_2$ and phenyl;

the

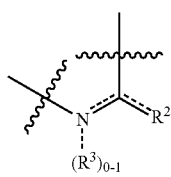

moiety has the structure (a)

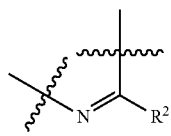

in which R$^2$ is selected from the group consisting of —H, —(C$_1$-C$_4$)alkyl, —(C$_1$-C$_4$)fluoroalkyl, —OH, —O—(C$_1$-C$_6$)alkyl, —NH$_2$, —NH—(C$_1$-C$_4$)alkyl and —N((C$_1$-C$_4$)alkyl)$_2$, and when L is —C(O)—NH—CH$_2$—, R$^2$ is optionally the same

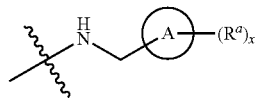

as defined below or (b)

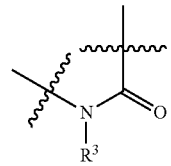

in which R$^3$ is —H, —(C$_1$-C$_4$)alkyl and —(C$_1$-C$_4$)fluoroalkyl;

each R$^4$ is independently H or F;

R$^5$ is —H, —F or —CH$_3$;

the bond denoted by "q" is a single bond or a double bond;

—Z-G- is —C(O)—CH$_2$—, —C(O)—CHD-, —C(O)—CD$_2$-, —C(O)—NH—, —C(O)—N(CH$_3$)—, —C(O)—C(CH$_3$)$_2$—, —C(O)—CH(CH$_3$)—, —C(O)—, —C(O)-cyclopentan-1,1-diyl-, —C(O)-cyclopropan-1,1-diyl-, —CH$_2$—CH$_2$—, —CH$_2$—CH(CH$_3$)—, —S(O)$_2$—, —S(O)$_2$—CH$_2$ or —C(S)—CH$_2$—;

the ring system denoted by "B" is phenyl, pyridyl or naphthyl;

y is 0, 1 or 2;

each R$^6$ is
independently -halogen, —(C$_1$-C$_4$)fluoroalkyl, —O—(C$_1$-C$_4$)fluoroalkyl, —(C$_1$-C$_4$)alkyl, —O—(C$_1$-C$_4$)alkyl, or NO$_2$;

L is selected from the group consisting of —C(O)—NH—CH$_2$—, —C(O)—NH—CH$_2$CH$_2$—O—, —C(O)—NH—CH(CO$_2$CH$_3$)—, —C(O)—NH—CH(CH$_3$)—, —C(O)—NH—CH(CH$_2$OH)—,

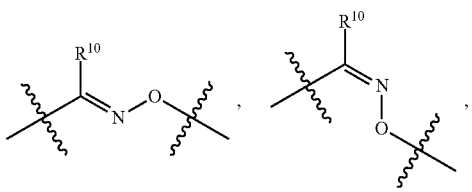

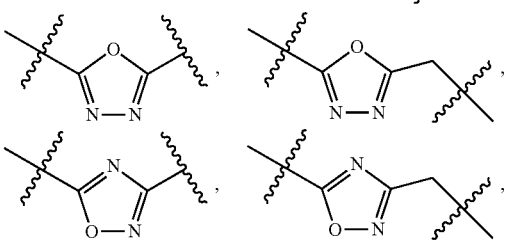

—C(OH)(CH$_3$)—CH$_2$—NH—, —C(OH)(CH$_3$)—CH$_2$—O—, —C(OH)(CH$_3$)—CH$_2$—CH$_2$—, —C(R$^{11}$)(CH$_3$)—CH$_2$—O—CH$_2$—, —C(R$^{12}$)(R$^{13}$)—CH$_2$—NH—CH$_2$—, —C(R$^{12}$)(R$^{13}$)—CH$_2$—NH—, —C(O)—NH—NH—, —C(O)—NH—O—, —CH$_2$—CH$_2$—CH$_2$—, —C(O)—CH$_2$—O—, —CH=CH—CH$_2$—, —C(S)—NH—CH$_2$, and —CH$_2$—CH=CH—, in which R$^{10}$ is —H, —CH$_3$, —CH$_2$OH, —CH$_2$F or CF$_3$, R$^{11}$ is —H, —CH$_3$, —CH$_2$OH, —CH$_2$OCH$_3$ or —CH$_2$—O—CH$_2$—CH(OH)—CH$_2$OH, R$^{12}$ is —H or —CH$_3$, and R$^{13}$ is —H, —CH$_3$, —CF$_3$, CH$_2$OH or CO$_2$CH$_3$;

the ring system denoted by "A" is phenyl, pyridyl, pyrimidyl, thiazolyl, pyrazolyl or pyrazinyl;

x is 0, 1, 2 or 3; and each R$^a$ is -halogen, —(C$_1$-C$_4$)alkyl, —(C$_1$-C$_4$)fluoroalkyl, —O—(C$_1$-C$_4$)alkyl, —O—(C$_1$-C$_4$)fluoroalkyl, —CN, —NO$_2$ or —C(O)N(R$^{17}$)$_2$ in which each R$^{17}$ is independently H, methyl, ethyl, isopropyl or n-propyl;

in which each alkyl is optionally substituted with one or more substituents selected from the group consisting of -D, -halogen, —CN, —NO$_2$, —O—R$^{20}$, —N(R$^{21}$)$_2$ and —S(R$^{20}$), in which each R$^{20}$ is independently selected from the group consisting of —H, —CH$_3$, —CH$_2$CH$_3$ and —CF$_3$, and each R$^{21}$ is independently selected from the group consisting of —H, —CH$_3$ and —CH$_2$CH$_3$.

The compounds according to such embodiments can be further defined as described above, as appropriate.

Other embodiments of the invention as described herein include compounds of formula (II)

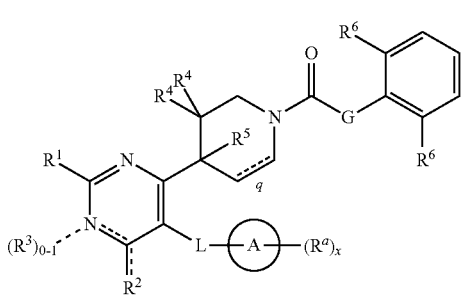

(II)

in which
R¹ is selected from the group consisting of —H, —(C₁-C₄)alkyl, —(C₁-C₄)fluoroalkyl, —(C₃-C₅)cycloalkyl, —OH, —O—(C₁-C₄)alkyl, —SH, —S—(C₁-C₄)alkyl, —NH₂, —NH—(C₁-C₄)alkyl and —N((C₁-C₄)alkyl)₂;
the

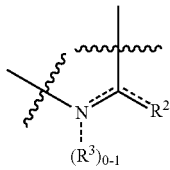

moiety has the structure
(a)

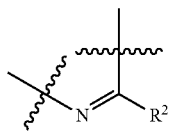

in which R² is selected from the group consisting of —H, —(C₁-C₄)alkyl, —(C₁-C₄)fluoroalkyl, —OH, —O—(C₁-C₆)alkyl, —NH₂, —NH—(C₁-C₄)alkyl and —N((C₁-C₄)alkyl)₂, or
(b)

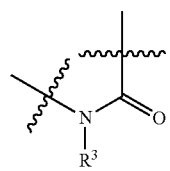

in which R³ is —H;
each R⁴ is independently H or F;
R⁵ is —H or —F;
the bond denoted by "q" is a single bond or a double bond;
G is —CH₂—, —CHD-, —CD₂- or —NH—; and
each R⁶ is independently —H, -halogen, —(C₁-C₄ fluoroalkyl) or —O—(C₁-C₄ fluoroalkyl), provided that at least one R⁶ is not —H.
L is selected from the group consisting of —C(O)—NH—CH₂—,

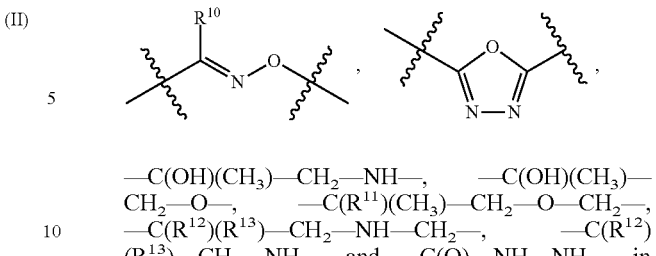

—C(OH)(CH₃)—CH₂—NH—, —C(OH)(CH₃)—CH₂—O—, —C(R¹¹)(CH₃)—CH₂—O—CH₂—, —C(R¹²)(R¹³)—CH₂—NH—CH₂—, —C(R¹²)(R¹³)—CH₂—NH—, and —C(O)—NH—NH—, in which
R¹⁰ is —H, —CH₃, —CH₂OH or —CH₂F,
R¹¹ is —H, —CH₃, —CH₂OH, —CH₂OCH₃ or —CH₂—O—CH₂—CH(OH)—CH₂OH,
R¹² is —H or —CH₃, and
R¹³ is —H, —CH₃ or —CF₃;
the ring system denoted by "A" is phenyl, pyridyl or pyrimidyl;
x is 1, 2 or 3; and
each Rᵃ is independently -halogen, —(C₁-C₄)alkyl, —(C₁-C₄) fluoroalkyl, —O—(C₁-C₄)alkyl, —O—(C₁-C₄)fluoroalkyl, —CN or —NO₂,
in which
each alkyl is optionally substituted with one or more substituents selected from the group consisting of -D, -halogen, —CN, —NO₂, —O—R²⁰, —N(R²¹)₂ and —S(R²⁰), in which each R²⁰ is independently selected from the group consisting of —H, —CH₃, —CH₂CH₃ and —CF₃, and each R²¹ is independently selected from the group consisting of —H, —CH₃ and —CH₂CH₃.

The compounds according to such embodiments can be further defined as described above, as appropriate.

As noted above, each alkyl moiety (i.e., defined as "alkyl") is optionally substituted with one or more substituents (e.g., in various embodiments, from 1-5, from 1-3, from 1-2 or one) selected from the group consisting of -D, -halogen, —CN, —NO₂, —O—R²⁰, —N(R²¹)₂ and —S(R²⁰), in which each R²⁰ is independently selected from the group consisting of —H, —CH₃, —CH₂CH₃ and —CF₃, and each R²¹ is independently selected from the group consisting of —H, —CH₃ and —CH₂CH₃. In certain embodiments of the invention as described herein, each alkyl is optionally substituted with one or more substituents selected from the group consisting of -D, -halogen, —O—R²⁰ and —N(R²¹)₂ and —S(R²⁰), in which each R²⁰ is independently selected from the group consisting of —H, and —CH₃, and each R²¹ is independently selected from the group consisting of —H and —CH₃. In other embodiments, each alkyl is optionally substituted with one or more substituents selected from the group consisting of -D, -halogen, —OH, —NH₂ and —SH. In other embodiments, each alkyl is unsubstituted.

As used herein, the "alkyl" groups are defined as having a given number of carbons. Accordingly, "(C₁-C₄)alkyl" is an alkyl group having from one to four carbons. An alkyl group can be branched or unbranched. Thus, "(C₁-C₄)alkyl" encompasses methyl, ethyl, n-propyl, isopropyl, n-butyl, sec-butyl and t-butyl, in unsubstituted and substituted forms as described above. In certain embodiments, each —(C₁-C₆)alkyl is a (C₁-C₄)alkyl. In certain embodiments, each —(C₁-C₆)alkyl and —(C₁-C₄)alkyl is a —(C₁-C₂)alkyl.

The term "fluoroalkyl" as used herein, means an alkyl group substituted with one or more fluorines and no other substituents. In certain embodiments, one or more carbons of the fluoroalkyl group is persubstituted with fluorine.

Examples of fluoroalkyl moieties include, without limitation, fluoromethyl, difluromethyl, trifluoromethyl, pentafluoroethyl, 2,2,2-trifluoroethyl, and 1,1,1,3,3,3-hexafluoroisopropyl. "Fluoroalkyl" is encompassed within optionally-substituted alkyl as described above. In certain embodiments, each —$(C_1-C_6)$fluoroalkyl is a $(C_1-C_4)$fluoroalkyl. In certain embodiments, each —$(C_1-C_6)$fluoroalkyl and —$(C_1-C_4)$fluoroalkyl is a —$(C_1-C_2)$fluoroalkyl.

The term "heterocycloalkyl" as used herein means a cyclic unsaturated or partially unsaturated group that includes one or more (e.g., 1, 2 or 3, for example, 1 or 2) heteroatoms selected from N, O and S in the ring. The heterocycloalkyl can be, for example, a $(C_3-C_6)$heterocycloalkyl (i.e., having 3-6 members in the ring, inclusive of heteroatoms). In certain embodiments, each heterocycloalkyl is selected from the group consisting of piperidine, piperazine and morpholine. In other embodiments, each heterocycloalkyl is selected from the group consisting of piperidine, piperazine, morpholine, 1H-tetrahydropyran, pyrrolidine and tetrahydrofuran. In other embodiments, each heterocycloalkyl is selected from the group consisting of piperidine, piperazine, morpholine, 1H-tetrahydropyran, pyrrolidine, tetrahydrofuran, azetidine, aziridine and oxetane.

In general, any hydrogen atom of the compounds described herein (whether described explicitly as "—H" or as part of another moiety such as an alkyl or a phenyl) can be provided as a protium, or a deuterium. Thus, while deuterium is often described herein as a "substituent," the person of skill in the art will understand that deuterium can be used as the hydrogen atom species at any position in the compound. However, in certain embodiments of the compounds described herein, every hydrogen atom, unless otherwise explicitly specified, is a protium.

The term "deuteroalkyl" as used herein means an alkyl group substituted with one or more deuteria and no other substituents. Examples of "deuteroalkyl" include deuteromethyl and dideuteromethyl.

Individual compounds of certain embodiments of the present invention are provided in Tables 1-15 below.

TABLE 1

| Cpd. | Q¹ | Q² | R¹ | R² | Chemical Name |
|---|---|---|---|---|---|
| A1 | 2,6-difluorobenzyl | 3,5-dimethylbenzyl | Me | H | 2-[(2-4-(1-(2-(2,6-difluorophenyl)acetyl)piperidin-4-yl)-N-(3,5-dimethylbenzyl)-2-methylpyrimidine-5-carboxamide |
| A2 | 2,6-difluorobenzyl | 3,4-dichlorobenzyl | Me | H | N-(3,4-dichlorobenzyl)-4-(1-(2-(2,6-difluorophenyl)acetyl)piperidin-4-yl)-2-methylpyrimidine-5-carboxamide |
| A3 | 2-chloro-6-fluorobenzyl | 3,5-dimethylbenzyl | Me | H | 4-(1-(2-(2-chloro-6-fluorophenyl)acetyl)piperidin-4-yl)-N-(3,5-dimethylbenzyl)-2-methylpyrimidine-5-carboxamide |
| A4 | 2-fluoro-6-(trifluoromethyl)benzyl | 3,5-dimethylbenzyl | Me | H | N-(3,5-dimethylbenzyl)-4-(1-(2-(2-fluoro-6-(trifluoromethyl)phenyl)acetyl)piperidin-4-yl)-2-methylpyrimidine-5-carboxamide |

TABLE 1-continued

| Cpd. | Q¹ | Q² | R¹ | R² | Chemical Name |
|---|---|---|---|---|---|
| A5 | 2-(trifluoromethyl)phenyl | 3,5-dimethylphenyl | Me | H | N-(3,5-dimethylbenzyl)-2-methyl-4-(1-(2-(2-(trifluoromethyl)phenyl)acetyl)piperidin-4-yl)pyrimidine-5-carboxamide |
| A6 | 2-chloro-6-fluorophenyl | 3,4-dichlorophenyl | H | H | 4-(1-(2-(2-chloro-6-fluorophenyl)acetyl)piperidin-4-yl)-N-(3,4-dichlorobenzyl)pyrimidine-5-carboxamide |
| A7 | 2-chlorophenyl | 3,5-dimethylphenyl | Me | H | 4-(1-(2-(2-chlorophenyl)acetyl)piperidin-4-yl)-N-(3,5-dimethylbenzyl)-2-methylpyrimidine-5-carboxamide |
| A8 | 2-chloro-6-fluorophenyl | 3,5-dimethylphenyl | Me | H | 4-(1-(2-chloro-6-fluorobenzoyl)piperidin-4-yl)-N-(3,5-dimethylbenzyl)-2-methylpyrimidine-5-carboxamide |
| A9 | 2-(trifluoromethoxy)phenyl | 3,5-dimethylphenyl | Me | H | N-(3,5-dimethylbenzyl)-2-methyl-4-(1-(2-(2-(trifluoromethoxy)phenyl)acetyl)piperidin-4-yl)pyrimidine-5-carboxamide |
| A10 | 2-methoxyphenyl | 3,5-dimethylphenyl | Me | H | N-(3,5-dimethylbenzyl)-4-(1-(2-(2-methoxyphenyl)acetyl)piperidin-4-yl)-2-methylpyrimidine-5-carboxamide |
| A11 | 2-methylphenyl | 3,5-dimethylphenyl | Me | H | N-(3,5-dimethylbenzyl)-2-methyl-4-(1-(2-(o-tolyl)acetyl)piperidin-4-yl)pyrimidine-5-carboxamide |

TABLE 1-continued

| Cpd. | Q¹ | Q² | R¹ | R² | Chemical Name |
|---|---|---|---|---|---|
| A12 | 2-fluorobenzyl | 3,5-dimethylbenzyl | Me | H | N-(3,5-dimethylbenzyl)-4-(1-(2-(2-fluorophenyl)acetyl)piperidin-4-yl)-2-methylpyrimidine-5-carboxamide |
| A13 | 2,3,6-trifluorobenzyl | 3,4-dichlorobenzyl | Me | H | N-(3,4-dichlorobenzyl)-2-methyl-4-(1-(2-(2,3,6-trifluorophenyl)acetyl)piperidin-4-yl)pyrimidine-5-carboxamide |
| A14 | 2,5-difluorobenzyl | 3,5-dimethylbenzyl | Me | H | 4-(1-(2-(2,5-difluorophenyl)acetyl)piperidin-4-yl)-N-(3,5-dimethylbenzyl)-2-methylpyrimidine-5-carboxamide |
| A15 | 2-nitrobenzyl | 3,5-dimethylbenzyl | Me | H | N-(3,5-dimethylbenzyl)-2-methyl-4-(1-(2-(2-nitrophenyl)acetyl)piperidin-4-yl)pyrimidine-5-carboxamide |
| A16 | (R)-1-(2-chlorophenyl)ethyl | 3,5-dimethylbenzyl | Me | H | (R)-N-(3,5-dimethylbenzyl)-2-methyl-4-(1-(2-phenylpropanoyl)piperidin-4-yl)pyrimidine-5-carboxamide |
| A17 | 2,4-difluorobenzyl | 3,5-dimethylbenzyl | Me | H | 4-(1-(2-(2,4-difluorophenyl)acetyl)piperidin-4-yl)-N-(3,5-dimethylbenzyl)-2-methylpyrimidine-5-carboxamide |
| A18 | 2,3-difluorobenzyl | 3,5-dimethylbenzyl | Me | H | 4-(1-(2-(2,3-difluorophenyl)acetyl)piperidin-4-yl)-N-(3,5-dimethylbenzyl)-2-methylpyrimidine-5-carboxamide |
| A19 | naphthalen-1-ylmethyl | 3,5-dimethylbenzyl | Me | H | N-(3,5-dimethylbenzyl)-2-methyl-4-(1-(2-(naphthalen-1-yl)acetyl)piperidin-4-yl)pyrimidine-5-carboxamide |

TABLE 1-continued

| Cpd. | Q¹ | Q² | R¹ | R² | Chemical Name |
|---|---|---|---|---|---|
| A20 | 2,6-difluorobenzyl | 2-phenoxyethyl | Me | H | 4-(1-(2-(2,6-difluorophenyl)acetyl)piperidin-4-yl)-2-methyl-N-(2-phenoxyethyl)pyrimidine-5-carboxamide |
| A21 | 2,6-difluorobenzyl | 3,4-dichlorobenzyl | $CF_3$ | H | N-(3,4-dichlorobenzyl)-4-(1-(2-(2,6-difluorophenyl)acetyl)piperidin-4-yl)-2-(trifluoromethyl)pyrimidine-5-carboxamide |
| A22 | 3-fluorobenzyl | 3,5-dimethylbenzyl | Me | H | N-(3,5-dimethylbenzyl)-4-(1-(2-(3-fluorophenyl)acetyl)piperidin-4-yl)-2-methylpyrimidine-5-carboxamide |
| A23 | 2-fluorophenyl (carbonyl) | 3,5-dimethylbenzyl | Me | H | N-(3,5-dimethylbenzyl)-4-(1-(2-fluorobenzoyl)piperidin-4-yl)-2-methylpyrimidine-5-carboxamide |
| A24 | 2-chlorophenyl (carbonyl) | 3,5-dimethylbenzyl | Me | H | 4-(1-(2-chlorobenzoyl)piperidin-4-yl)-N-(3,5-dimethylbenzyl)-2-methylpyrimidine-5-carboxamide |
| A25 | benzyl | 3,5-dimethylbenzyl | Me | H | N-(3,5-dimethylbenzyl)-2-methyl-4-(1-(2-phenylacetyl)piperidin-4-yl)pyrimidine-5-carboxamide |
| A26 | (S)-1-phenylethyl | 3,5-dimethylbenzyl | Me | H | (S)-N-(3,5-dimethylbenzyl)-2-methyl-4-(1-(2-phenylpropanoyl)piperidin-4-yl)pyrimidine-5-carboxamide |

TABLE 1-continued

| Cpd. | Q¹ | Q² | R¹ | R² | Chemical Name |
|---|---|---|---|---|---|
| A27 | 3,5-difluorobenzyl | 3,5-dimethylbenzyl | Me | H | 4-(1-(2-(3,5-difluorophenyl)acetyl)piperidin-4-yl)-N-(3,5-dimethylbenzyl)-2-methylpyrimidine-5-carboxamide |
| A28 | 2,6-difluorobenzyl | 3,4-dichlorobenzyl | —iPr | H | N-(3,4-dichlorobenzyl)-4-(1-(2-(2,6-difluorophenyl)acetyl)piperidin-4-yl)-2-isopropylpyrimidine-5-carboxamide |
| A29 | 4-fluorobenzyl | 3,5-dimethylbenzyl | Me | H | N-(3,5-dimethylbenzyl)-4-(1-(2-(4-fluorophenyl)acetyl)piperidin-4-yl)-2-methylpyrimidine-5-carboxamide |
| A30 | 3-methylbenzyl | 3,5-dimethylbenzyl | Me | H | N-(3,5-dimethylbenzyl)-2-methyl-4-(1-(2-(m-tolyl)acetyl)piperidin-4-yl)pyrimidine-5-carboxamide |
| A31 | 1-(2-fluorophenyl)cyclopentyl | 3,5-dimethylbenzyl | Me | H | N-(3,5-dimethylbenzyl)-4-(1-(1-2-fluorophenyl)cyclopentanecarbonyl)piperidin-4-yl)-2-methylpyrimidine-5-carboxamide |
| A32 | 1-phenylcyclopropyl | 3,5-dimethylbenzyl | Me | H | N-(3,5-dimethylbenzyl)-2-methyl-4-(1-(1-phenylcyclopropanecarbonyl)piperidin-4-yl)pyrimidine-5-carboxamide |
| A33 | 3-chloropyridin-2-yl | 3,5-dimethylbenzyl | Me | H | 4-(1-(3-chloropicolinoyl)piperidin-4-yl)-N-(3,5-dimethylbenzyl)-2-methylpyrimidine-5-carboxamide |

TABLE 1-continued

| Cpd. | Q¹ | Q² | R¹ | R² | Chemical Name |
|---|---|---|---|---|---|
| A34 | 3,4-difluorophenyl | 3,5-dimethylbenzyl | Me | H | 4-(1-(2-(3,4-difluorophenyl)acetyl)piperidin-4-yl)-N-(3,5-dimethylbenzyl)-2-methylpyrimidine-5-carboxamide |
| A35 | 2-methyl-2-phenylpropyl | 3,5-dimethylbenzyl | Me | H | N-(3,5-dimethylbenzyl)-2-methyl-4-(1-(2-methyl-2-phenylpropanoyl)piperidin-4-yl)pyrimidine-5-carboxamide |
| A36 | 2-fluorophenyl | 3,4-dichlorobenzyl | —iPr | H | N-(3,4-dichlorobenzyl)-4-(1-(2-(2-fluorophenyl)acetyl)piperidin-4-yl)-2-isopropylpyrimidine-5-carboxamide |
| A37 | 2,6-difluorophenyl | 3,4-dichlorobenzyl | Ph | H | N-(3,4-dichlorobenzyl)-4-(1-(2-(2,6-difluorophenyl)acetyl)piperidin-4-yl)-2-phenylpyrimidine-5-carboxamide |
| A38 | pyridin-2-yl | 3,5-dimethylbenzyl | Me | H | N-(3,5-dimethylbenzyl)-2-methyl-4-(1-(2-(pyridin-2-yl)acetyl)piperidin-4-yl)pyrimidine-5-carboxamide |
| A39 | 3-methoxyphenyl | 3,5-dimethylbenzyl | Me | H | N-(3,5-dimethylbenzyl)-4-(1-(2-(3-methoxyphenyl)acetyl)piperidin-4-yl)-2-methylpyrimidine-5-carboxamide |
| A40 | 2,6-difluorophenyl | 3-chlorobenzyl | Me | H | N-(3-chlorobenzyl)-4-(1-(2-(2,6-difluorophenyl)acetyl)piperidin-4-yl)-2-methylpyrimidine-5-carboxamide |

TABLE 1-continued

| Cpd. | Q¹ | Q² | R¹ | R² | Chemical Name |
|---|---|---|---|---|---|
| A41 | 2,6-difluorophenyl-CH< | 3-chloro-5-fluorobenzyl | Me | H | N-(3-chloro-5-fluorobenzyl)-4-(1-(2-(2,6-difluorophenyl)acetyl)piperidin-4-yl)-2-methylpyrimidine-5-carboxamide |
| A42 | 2,6-difluorophenyl-CH< | 5-chloro-2-fluorobenzyl | Me | H | N-(5-chloro-2-fluorobenzyl)-4-(1-(2-(2,6-difluorophenyl)acetyl)piperidin-4-yl)-2-methylpyrimidine-5-carboxamide |
| A43 | 2,6-difluorophenyl-CH< | 3,5-dimethylbenzyl | -cyclopropyl | H | 2-cyclopropyl-4-(1-(2-(2,6-difluorophenyl)acetyl)piperidin-4-yl)-N-(3,5-dimethylbenzyl)pyrimidine-5-carboxamide |
| A44 | 2,6-difluorophenyl-CH< | (6-(trifluoromethyl)pyridin-2-yl)methyl | Me | H | 4-(1-(2-(2,6-difluorophenyl)acetyl)piperidin-4-yl)-2-methyl-N-((6-(trifluoromethyl)pyridin-2-yl)methyl)pyrimidine-5-carboxamide |
| A45 | 2,6-difluorophenyl-CH< | 3-chlorobenzyl | -cyclopropyl | H | N-(3-chlorobenzyl)-2-cyclopropyl-4-(1-(2-(2,6-difluorophenyl)acetyl)piperidin-4-yl)pyrimidine-5-carboxamide |
| A46 | 2,6-difluorophenyl-CH< | 3-(trifluoromethyl)benzyl | Me | H | 4-(1-(2-(2,6-difluorophenyl)acetyl)piperidin-4-yl)-2-methyl-N-(3-(trifluoromethyl)benzyl)pyrimidine-5-carboxamide |
| A47 | 2,6-difluorophenyl-CH< | (2-(trifluoromethyl)pyridin-4-yl)methyl | Me | H | 4-(1-(2-(2,6-difluorophenyl)acetyl)piperidin-4-yl)-2-methyl-N-((2-(trifluoromethyl)pyridin-4-yl)methyl)pyrimidine-5-carboxamide |

TABLE 1-continued

| Cpd. | Q¹ | Q² | R¹ | R² | Chemical Name |
|---|---|---|---|---|---|
| A48 | 2,6-difluorobenzyl | 3-chlorobenzyl | Et | H | N-(3-chlorobenzyl)-4-(1-(2-(2,6-difluorophenyl)acetyl)piperidin-4-yl)-2-ethylpyrimidine-5-carboxamide |
| A49 | 2,6-difluorobenzyl | (2,6-dichloropyridin-4-yl)methyl | Me | H | N-((2,6-dichloropyridin-4-yl)methyl)-4-(1-(2-(2,6-difluorophenyl)acetyl)piperidin-4-yl)-2-methylpyrimidine-5-carboxamide |
| A50 | 2,6-difluorobenzyl | 3-cyanobenzyl | Me | H | N-(3-cyanobenzyl)-4-(1-(2-(2,6-difluorophenyl)acetyl)piperidin-4-yl)-2-methylpyrimidine-5-carboxamide |
| A51 | 2,6-difluorobenzyl | 3,5-dichlorobenzyl | Me | H | N-(3,5-dichlorobenzyl)-4-(1-(2-(2,6-difluorophonyl)acetyl)piperidin-4-yl)-2-methylpyrimidine-5-carboxamide |
| A52 | 2,6-difluorobenzyl | (2-chloro-6-methoxypyridin-4-yl)methyl | Me | H | N-((2-chloro-6-methoxypyridin-4-yl)methyl)-4-(1-(2-(2,6-difluorophenyl)acetyl)piperidin-4-yl)-2-methylpyrimidine-5-carboxamide |
| A53 | 2,6-difluorobenzyl | 3-(trifluoromethoxy)benzyl | Me | H | 4-(1-(2-(2,6-difluorophenyl)acetyl)piperidin-4-yl)-2-methyl-N-(3-(trifluoromethoxy)benzyl)pyrimidine-5-carboxamide |
| A54 | 2,6-difluorobenzyl | 3-chloro-2-fluorobenzyl | Me | H | N-(3-chloro-2-fluorobenzyl)-4-(1-(2-(2,6-difluorophenyl)acetyl)piperidin-4-yl)-2-methylpyrimidine-5-carboxamide |

TABLE 1-continued

| Cpd. | Q¹ | Q² | R¹ | R² | Chemical Name |
|---|---|---|---|---|---|
| A55 | 2,6-difluorophenyl-CH | (2-cyanopyridin-4-yl)methyl | Me | H | N-((2-cyanopyridin-4-yl)methyl)-4-(1-(2-(2,6-difluorophenyl)acetyl)piperidin-4-yl)-2-methylpyrimidine-5-carboxamide |
| A56 | 2,6-difluorophenyl-CH | (2-chloropyridin-4-yl)methyl | Me | H | N-((2-chloropyridin-4-yl)methyl)-4-(1-(2-(2,6-difluorophenyl)acetyl)piperidin-4-yl)-2-methylpyrimidine-5-carboxamide |
| A57 | 2,6-difluorophenyl-CH | (3,5-dimethylbenzyl) | H | H | 4-(1-(2-(2,6-difluorophenyl)acetyl)piperidin-4-yl)-N-(3,5-dimethylbenzyl)pyrimidine-5-carboxamide |
| A58 | 2,6-difluorophenyl-CH | (3-methoxybenzyl) | Me | H | 4-(1-(2-(2,6-difluorophenyl)acetyl)piperidin-4-yl)-N-(3-methoxybenzyl)-2-methylpyrimidine-5-carboxamide |
| A59 | 2,6-difluorophenyl-CH | (4-chloro-2-methylbenzyl) | Me | H | N-(4-chloro-2-methylbenzyl)-4-(1-(2-(2,6-difluorophenyl)acetyl)piperidin-4-yl)-2-methylpyrimidine-5-carboxamide |
| A60 | 2,6-difluorophenyl-CH | (3-methylbenzyl) | Me | H | 4-(1-(2-(2,6-difluorophenyl)acetyl)piperidin-4-yl)-2-methyl-N-(3-methylbenzyl)pyrimidine-5-carboxamide |
| A61 | 2,6-difluorophenyl-CH | (2-(trifluoromethyl)pyridin-4-yl)methyl | Me | Me | 4-(1-(2-(2,6-difluorophenyl)acetyl)piperidin-4-yl)-2,6-dimethyl-N-((2-(trifluoromethyl)pyridin-4-yl)methyl)pyrimidine-5-carboxamide |

TABLE 1-continued

| Cpd. | Q¹ | Q² | R¹ | R² | Chemical Name |
|---|---|---|---|---|---|
| A62 | 2,6-difluorobenzyl | 4-chlorobenzyl | Me | H | N-(4-chlorobenzyl)-4-(1-(2-(2,6-difluorophenyl)acetyl)piperidin-4-yl)-2-methylpyrimidine-5-carboxamide |
| A63 | 2,6-difluorobenzyl | 3-chloro-2-methylbenzyl | Me | H | N-(3-chloro-2-methylbenzyl)-4-(1-(2-(2,6-difluorophenyl)acetyl)piperidin-4-yl)-2-methylpyrimidine-5-carboxamide |
| A64 | 2,6-difluorobenzyl | 3,5-dimethylbenzyl | Et | H | 4-(1-(2-(2,6-difluorophenyl)acetyl)piperidin-4-yl)-N-(3,5-dimethylbenzyl)-2-ethylpyrimidine-5-carboxamide |
| A65 | 2,6-dichlorobenzyl | 3,4-dichlorobenzyl | H | H | N-(3,4-dichlorobenzyl)-4-(1-(2-(2,6-dichlorophenyl)acetyl)piperidin-4-yl)pyrimidine-5-carboxamide |
| A66 | 2,6-difluorobenzyl | (4-(trifluoromethyl)pyridin-2-yl)methyl | Me | H | 4-(1-(2-(2,6-difluorophenyl)acetyl)piperidin-4-yl)-2-methyl-N-((4-(trifluoromethyl)pyridin-2-yl)methyl)pyrimidine-5-carboxamide |
| A67 | 2,6-difluorobenzyl | (4-methyl-6-(trifluoromethyl)pyrimidin-2-yl)methyl | Me | H | 4-(1-(2-(2,6-difluorophenyl)acetyl)piperidin-4-yl)-2-methyl-N-((4-methyl-6-(trifluoromethyl)pyrimidin-2-yl)methyl)pyrimidine-5-carboxamide |
| A68 | 2,3,6-trifluorobenzyl | 3,4-dichlorobenzyl | H | H | N-(3,4-dichlorobenzyl)-4-(1-(2-(2,3,6-trifluorophenyl)acetyl)piperidin-4-yl)pyrimidine-5-carboxamide |

TABLE 1-continued

| Cpd. | Q¹ | Q² | R¹ | R² | Chemical Name |
|---|---|---|---|---|---|
| A69 | 2,6-difluorobenzyl | benzyl | Me | H | N-benzyl-4-(1-(2-(2,6-difluorophenyl)acetyl)piperidin-4-yl)-2-methylpyrimidine-5-carboxamide |
| A70 | 2,6-difluorobenzyl | (2-methylpyridin-4-yl)methyl | Me | H | 4-(1-(2-(2,6-difluorophenyl)acetyl)piperidin-4-yl)-2-methyl-N-((2-methylpyridin-4-yl)methyl)pyrimidine-5-carboxamide |
| A71 | 2,6-difluorobenzyl | (6-chloropyridin-3-yl)methyl | Me | H | N-((6-chloropyridin-3-yl)methyl)-4-(1-(2-(2,6-difluorophenyl)acetyl)piperidin-4-yl)-2-methylpyrimidine-5-carboxamide |
| A72 | 2,6-difluorobenzyl | (2-chlorothiazol-5-yl)methyl | Me | H | N-((2-chlorothiazol-5-yl)methyl)-4-(1-(2-(2,6-difluorophenyl)acetyl)piperidin-4-yl)-2-methylpyrimidine-5-carboxamide |
| A73 | 2,6-difluorobenzyl | (2,6-dimethylpyridin-4-yl)methyl | Me | H | 4-(1-(2-(2,6-difluorophenyl)acetyl)piperidin-4-yl)-N-((2,6-dimethylpyridin-4-yl)methyl)-2-methylpyrimidine-5-carboxamide |
| A74 | 2,6-difluorobenzyl | (6-(trifluoromethyl)pyridin-3-yl)methyl | Me | H | 4-(1-(2-(2,6-difluorophenyl)acetyl)piperidin-4-yl)-2-methyl-N-((6-(trifluoromethyl)pyridin-3-yl)methyl)pyrimidine-5-carboxamide |
| A75 | 2,6-difluorobenzyl | methyl 2-(3-chlorophenyl)acetate | Me | H | methyl 2-(3-chlorophenyl)-2-(4-(1-(2-(2,6-difluorophenyl)acetyl)piperidin-4-yl)-2-methylpyrimidine-5-carboxamido)acetate |

TABLE 1-continued

| Cpd. | Q¹ | Q² | R¹ | R² | Chemical Name |
|---|---|---|---|---|---|
| A76 | 2,6-difluorobenzyl | 1-(3-chlorophenyl)ethyl | Me | H | N-(1-(3-chlorophenyl)ethyl)-4-(1-(2-(2,6-difluorophenyl)acetyl)piperidin-4-yl)-2-methylpyrimidine-5-carboxamide |
| A77 | 2,6-difluorobenzyl | (4-ethyl-2-(ethylcarbamoyl)pyridin-... | Me | H | 4-(1-(2-(2,6-difluorophenyl)acetyl)piperidin-4-yl)-N-((2-(ethylcarbamoyl)pyridin-4-yl)methyl)-2-methylpyrimidine-5-carboxamide |
| A78 | 2,6-difluorobenzyl | (1,5-dimethyl-1H-pyrazol-3-yl)methyl | Me | H | 4-(1-(2-(2,6-difluorophenyl)acetyl)piperidin-4-yl)-N-((1,5-dimethyl-1H-pyrazol-3-yl)methyl)-2-methylpyrimidine-5-carboxamide |
| A79 | 2,6-difluorobenzyl | (5-methylpyrazin-2-yl)methyl | Me | H | 4-(1-(2-(2,6-difluorophenyl)acetyl)piperidin-4-yl)-2-methyl-N-((5-methylpyrazin-2-yl)methyl)pyrimidine-5-carboxamide |
| A80 | 2,6-difluorobenzyl | 3,5-dimethylbenzyl | Me | Me | 4-(1-(2-(2,6-difluorophenyl)acetyl)piperidin-4-yl)-N-(3,5-dimethylbenzyl)-2,6-dimethylpyrimidine-5-carboxamide |
| A81 | 2,6-difluorobenzyl | 3-chlorobenzyl | Me | Me | N-(3-chlorophenyl)-4-(1-(2-(2,6-difluorophenyl)acetyl)piperidin-4-yl)-2,6-dimethylpyrimidine-5-carboxamide |
| A82 | 2,6-difluorobenzyl | (6-(trifluoromethyl)pyridin-2-yl)methyl | Me | Me | 4-(1-(2-(2,6-difluorophenyl)acetyl)piperidin-4-yl)-2,6-dimethyl-N-((6-(trifluoromethyl)pyridin-2-yl)methyl)pyrimidine-5-carboxamide |

TABLE 1-continued

| Cpd. | Q¹ | Q² | R¹ | R² | Chemical Name |
|---|---|---|---|---|---|
| A83 | 2,6-difluorobenzyl | (2-cyanopyridin-4-yl)methyl | Me | Me | N-((2-cyanopyridin-4-yl)methyl)-4-(1-(2-(2,6-difluorophenyl)acetyl)piperidin-4-yl)-2,6-dimethylpyrimidine-5-carboxamide |
| A84 | 2,6-difluorobenzyl | 3,5-dimethylbenzyl | Me | —iPr | 4-(1-(2-(2,6-difluorophenyl)acetyl)piperidin-4-yl)-N-(3,5-dimethylbenzyl)-6-isopropyl-2-methylpyrimidine-5-carboxamide |
| A85 | 2,6-difluorobenzyl | 3,4-dichlorobenzyl | SMe | H | N-(3,4-dichlorobenzyl)-4-(1-(2-(2,6-difluorophenyl)acetyl)piperidin-4-yl)-2-(methylthio)pyrimidine-5-carboxamide |
| A86 | 2,6-difluorobenzyl | 3,4-dichlorobenzyl | OMe | H | N-(3,4-dichlorobenzyl)-4-(1-(2-(2,6-difluorophenyl)acetyl)piperidin-4-yl)-2-methoxypyrimidine-5-carboxamide |
| A87 | 2,6-difluorobenzyl | 3-chlorobenzyl | HOCH₂CH₂NH— | H | N-(3-chlorobenzyl)-4-(1-(2-(2,6-difluorophenyl)acetyl)piperidin-4-yl)-2-((2-hydroxyethyl)amino)pyrimidine-5-carboxamide |
| A88 | 2,6-difluorobenzyl | 3-chlorobenzyl | —N(Me)₂ | H | N-(3-chlorobenzl)-4-(1-(2-(2,6-difluorophenyl)acetyl)piperidin-4-yl)-2-(dimethylamino)pyrimidine-5-carboxamide |
| A89 | 2,6-difluorobenzyl | 3-chlorobenzyl | NH₂ | H | 2-amino-N-(3-chlorobenzyl)-4-(1-(2-(2,6-difluorophenyl)acetyl)piperidin-4-yl)pyrimidine-5-carboxamide |

TABLE 1-continued

| Cpd. | Q¹ | Q² | R¹ | R² | Chemical Name |
|---|---|---|---|---|---|
| A90 | 2,6-difluorobenzyl | 3-chlorobenzyl | NHMe | H | N-(3-chlorobenzyl)-4-(1-(2-(2,6-difluorophenyl)acetyl)piperidin-4-yl)-2-(methylamino)pyrimidine-5-carboxamide |
| A91 | 2,6-difluorobenzyl | 3-chlorobenzyl | NHEt | H | N-(3-chlorobenzyl)-4-(1-(2-(2,6-difluorophenyl)acetyl)piperidin-4-yl)-2-(ethylamino)pyrimidine-5-carboxamide |
| A92 | 2,6-difluorobenzyl | 3-chlorobenzyl | OMe | H | N-(3-chlorobenzyl)-4-(1-(2-(2,6-difluorophenyl)acetyl)piperidin-4-yl)-2-methoxypyrimidine-5-carboxamide |
| A93 | 2,6-difluorobenzyl | 3-chlorobenzyl | OEt | H | N-(3-chlorobenzyl)-4-(1-(2-(2,6-difluorophenyl)acetyl)piperidin-4-yl)-2-ethoxypyrimidine-5-carboxamide |
| A94 | 2,6-difluorobenzyl | 3-chlorobenzyl | —NHiPr | H | N-(3-chlorobenzyl)-4-(1-(2-(2,6-difluorophenyl)acetyl)piperidin-4-yl)-2-(isopropylamino)pyrimidine-5-carboxamide |
| A95 | 2,6-difluorobenzyl | 3-chlorobenzyl | OiPr | H | N-(3-chlorobenzyl)-4-(1-(2-(2,6-difluorophenyl)acetyl)piperidin-4-yl)-2-isopropoxypyrimidine-5-carboxamide |
| A96 | 2,6-difluorobenzyl | 3-chlorobenzyl | NH(CH$_2$)$_2$—NH$_2$ | H | 2-((2-aminoethyl)amino)-N-(3-chlorobenzyl)-4-(1-(2-(2,6-difluorophenyl)acetyl)piperidin-4-yl)pyrimidine-5-carboxamide |

TABLE 1-continued

| Cpd. | Q¹ | Q² | R¹ | R² | Chemical Name |
|---|---|---|---|---|---|
| A97 | 2,6-difluorobenzyl | 3-chlorobenzyl | NH(CH₂)₂—N(Me)₂ | H | N-(3-chlorobenzyl)-4-(1-(2-(2,6-difluorophenyl)acetyl)piperidin-4-yl)-2-((2-(dimethylamino)ethyl)amino)pyrimidine-5-carboxamide |
| A98 | 2,6-difluorobenzyl | 3-chlorobenzyl | OH | H | N-(3-chlorobenzyl)-4-(1-(2-(2,6-difluorophenyl)acetyl)piperidin-4-yl)-2-hydroxypyrimidine-5-carboxamide |
| A106 | 2-fluorophenyl | 3,5-dimethylbenzyl | Me | H | N-(3,5-dimethylbenzyl)-4-(1-((2-fluorophenyl)carbamoyl)piperidin-4-yl)-2-methylpyrimidine-5-carboxamide |
| A108 | 2,6-difluorobenzyl | 3,5-dimethylbenzyl | Me | NHMe | 4-(1-(2-(2,6-difluorophenyl)acetyl)piperidin-4-yl)-N-(3,5-dimethylbenzyl)-2-methyl-6-(methylamino)pyrimidine-5-carboxamide |
| A109 | 2,6-difluorobenzyl | 3-chlorobenzyl | Me | NHMe | N-(3-chlorobenzyl)-4-(1-(2-(2,6-difluorophenyl)acetyl)piperidin-4-yl)-2-methyl-6-(methylamino)pyrimidine-5-carboxamide |
| A110 | 2,6-difluorobenzyl | 1-(3-chlorophenyl)-2-hydroxyethyl | Me | H | N-(1-(3-chlorophenyl)-2-hydroxyethyl)-4-(1-(2-(2,6-difluorophenyl)acetyl)piperidin-4-yl)-2-methylpyrimidine-5-carboxamide |
| A111 | 2,6-difluorobenzyl | 3-chlorobenzyl | Me | OMe | N-(3-chlorobenzyl)-4-(1-(2-(2,6-difluorophenyl)acetyl)piperidin-4-yl)-6-methoxy-2-methylpyrimidine-5-carboxamide |

TABLE 1-continued

| Cpd. | Q¹ | Q² | R¹ | R² | Chemical Name |
|---|---|---|---|---|---|
| A112 | 2,6-difluorobenzyl | 3,5-dimethylbenzyl | Me | CF₃ | 4-(1-(2-(2,6-difluorophenyl)acetyl)piperidin-4-yl)-N-(3,5-dimethylbenzyl)-2-methyl-6-(trifluoromethyl)pyrimidine-5-carboxamide |
| A116 | (2,6-difluorophenyl)difluoromethyl | 3,5-dimethylbenzyl | Me | H | 4-{1-[(2,6-Difluorophenyl)(difluoro)acetyl]piperidin-4-yl}-N-[(3,5-dimethylphenyl)methyl]-2-methylpyrimidine-5-carboxamide |
| A117 | difluoro(phenyl)methyl | 3,5-dimethylbenzyl | Me | H | 4-{1-[Difluoro(phenyl)acetyl]piperidin-4-yl}-N-[(3,5-dimethylphenyl)methyl]-2-methylpyrimidine-5-carboxamide |
| A118 | (2-chlorophenyl)difluoromethyl | 3,5-dimethylbenzyl | Me | H | 4-{1-[Difluoro(2-fluorophenyl)acetyl]piperidin-4-yl}-N-[(3,5-dimethylphenyl)methyl]-2-methylpyrimidine-5-carboxamide |
| A119 | 2-chlorophenoxy | 3,5-dimethylbenzyl | Me | H | 2-Chlorophenyl 4-[5-({[(3,5-dimethylphenyl)methyl]amino}carbonyl)-2-methylpyrimidin-4-yl]piperidine-1-carboxylate |
| A120 | 2,6-difluorophenoxy | 3,5-dimethylbenzyl | Me | H | 2,6-Difluorophenyl 4-[5-({[(3,5-dimethylphenyl)methyl]amino}carbonyl)-2-methylpyrimidin-4-yl]piperidine-1-carboxylate |
| A121 | 2,6-difluorobenzyl | [2-(trifluoromethyl)pyrimidin-4-yl]methyl | Me | Me | 4-{1-[(2,6-Difluorophenyl)acetyl]piperidin-4-yl}-2,6-dimethyl-N-{[2-(trifluoromethyl)pyrimidin-4-yl]methyl}pyrimidine-5-carboxamide |

TABLE 1-continued

| Cpd. | Q¹ | Q² | R¹ | R² | Chemical Name |
|---|---|---|---|---|---|
| A122 | 2,6-difluorophenyl-NH- | -CH(CH₃)-[2-(trifluoromethyl)pyrimidin-4-yl] | Me | Me | 4-(1-{[(2,6-difluorophenyl)amino]carbonyl}piperidin-4-yl)-2,6-dimethyl-N-{[2-(trifluoromethyl)pyrimidin-4-yl]methyl}pyrimidine-5-carboxamide |
| A123 | 2,6-difluorophenyl-O- | -CH(CH₃)-[2-(trifluoromethyl)pyrimidin-4-yl] | Me | Me | 2,6-Difluorophenyl 4-{2,6-dimethyl-5-[({[2-(trifluoromethyl)pyrimidin-4-yl]methyl}amino)carbonyl]pyrimidin-4-yl}piperidine-1-carboxylate |
| A124 | 2-fluorophenyl-O- | -CH(CH₃)-[2-(trifluoromethyl)pyrimidin-4-yl] | Me | Me | 2-Fluorophenyl 4-{2,6-dimethyl-5-[({[2-(trifluoromethyl)pyrimidin-4-yl]methyl}amino)carbonyl]pyrimidin-4-yl}piperidine-1-carboxylate |
| A125 | phenyl-O- | -CH(CH₃)-[2-(trifluoromethyl)pyrimidin-4-yl] | Me | Me | Phenyl 4-{2,6-dimethyl-5-[({[2-(trifluoromethyl)pyrimidin-4-yl]methyl}amino)carbonyl]pyrimidin-4-yl}piperidine-1-carboxylate |
| A126 | 2-fluorophenyl-O- | -CH(CH₃)-[2-(trifluoromethyl)pyrimidin-4-yl] | NH₂ | Me | 2-Fluorophenyl 4-{2-amino-6-methyl-5-[({[2-(trifluoromethyl)pyrimidin-4-yl]methyl}amino)carbonyl]pyrimidin-4-yl}piperidine-1-carboxylate |
| I2 | 2,6-difluorophenyl-CH(CH₃)- | -CH(CH₃)-[2-(trifluoromethyl)pyridin-4-yl] | | Me | 4-(1-(2-(2,6-difluorophenyl)acetyl)piperidin-4-yl)-2-methyl-N-((2-(trifluoromethyl)pyridin-4-yl)methyl)-6-(((2-(trifluoromethyl)pyridin-4-yl)methyl)amino)pyrimidine-5-carboxamide |

TABLE 2

| Cpd | Q³ | Q⁴ | Chemical Name |
|---|---|---|---|
| A99 | 2,6-difluorophenethyl-piperidin-4-yl | N-(3,5-dimethylbenzyl)carboxamide | 4-(1-(2,6-difluorophenethyl)piperidin-4-yl)-N-(3,5-dimethylbenzyl)-2-methylpyrimidine-5-carboxamide |
| A100 | 2-chlorophenethyl-piperidin-4-yl | N-(3,5-dimethylbenzyl)carboxamide | 4-(1-(2-chlorophenethyl)piperidin-4-yl)-N-(3,5-dimethylbenzyl)-2-methylpyrimidine-5-carboxamide |
| A101 | phenethyl-piperidin-4-yl | N-(3,5-dimethylbenzyl)carboxamide | N-(3,5-dimethylbenzyl)-2-methyl-4-(1-phenethylpiperidin-4-yl)pyrimidine-5-carboxamide |

TABLE 2-continued
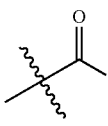
| Cpd | Q³ | Q⁴ | Chemical Name |
|---|---|---|---|
| A102 | 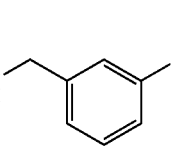 | 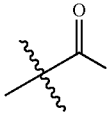 | N-(3-chlorobenzyl)-4-(1-(2-(2,6-difluorophenyl)acetyl)-4-methylpiperidin-4-yl)-2-methylpyrimidine-5-carboxamide |
| A103 | 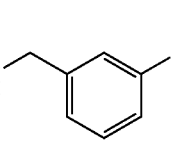 | 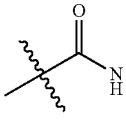 | N-(3-chlorobenzyl)-4-(1-(2-(2,6-difluorophenyl)acetyl)-4-fluoropiperidin-4-yl)-2-methylpyrimidine-5-carboxamide |
| A104 | 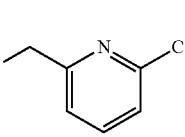 | | 4-(1-(2-(2,6-difluorophenyl)acetyl)-4-fluoropiperidin-4-yl)-2-methyl-N-((6-(trifluoromethyl)pyridin-2-yl)methyl)pyrimidine-5-carboxamide |

TABLE 2-continued
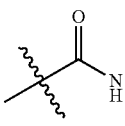
| Cpd | Q³ | Q⁴ | Chemical Name |
|---|---|---|---|
| A105 | 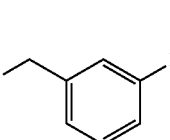 | 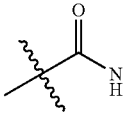 | 4-(1-(2-(2,6-difluorophenyl)acetyl)-4-fluoropiperidin-4-yl)-N-(3,5-dimethylbenzyl)-2-methylpyrimidine-5-carboxamide |
| A107 | 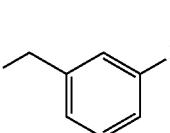 | 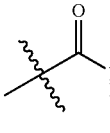 | 4-(1-((2,6-difluorophenyl)carbamoyl)piperidin-4-yl)-N-(3,5-dimethylbenzyl)-2-methylpyrimidine-5-carboxamide |
| A113 | 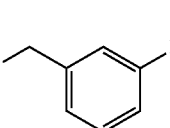 | | 4-(1-(2-(2,6-difluorophenyl)acetyl)piperidin-4-yl)-N-(3,5-dimethylbenzyl)-N,2-dimethylpyrimidine-5-carboxamide |

TABLE 2-continued
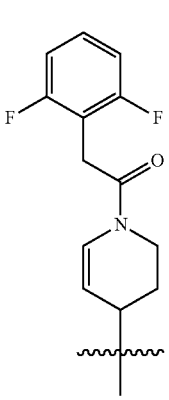 [SMILES: *C1C=CN(C(=O)Cc2c(F)cccc2F)CC1]
| Cpd | Q³ | Q⁴ | Chemical Name |
|---|---|---|---|
| A114 | 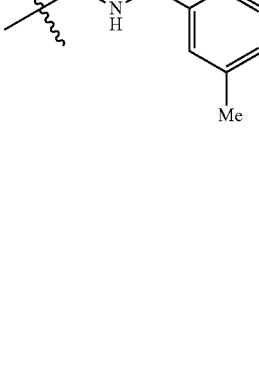 | 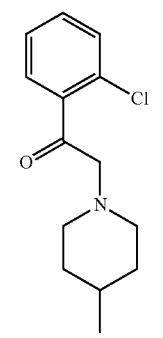 | 4-(1-(2-(2,6-difluorophenyl)acetyl)-1,2,3,4-tetrahydropyridin-4-yl)-N-(3,5-dimethylbenzyl)-2-methylpyrimidine-5-carboxamide |
| A115 | 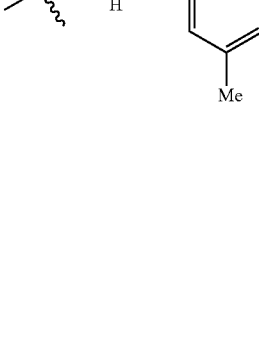 | 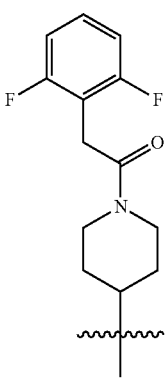 [SMILES: *C1CCN(C(=O)Cc2c(F)cccc2F)CC1] | 4-(1-(2-(2-chlorophenyl)-2-oxoethyl)piperidin-4-yl)-N-(3,5-dimethylbenzyl)-2-methylpyrimidine-5-carboxamide |
| K1 |  | | N-((4-(1-(2-(2,6-difluorophenyl)acetyl)piperidin-4-yl)-2-methylpyrimidin-5-yl)methyl)-3,5-dimethylbenzamide |

TABLE 3

| Cpd. | R¹ | R² | each R⁴ | R⁴ᵃ | R⁶ | R¹⁰ | G | Q⁵ | Chemical Name |
|---|---|---|---|---|---|---|---|---|---|
| B1 | Me | Me | H | H | F | Me | CH₂ | 3-(trifluoromethyl)phenyl | (E)-2-(2,6-difluorophenyl)-1-(4-(2,6-dimethyl-5-(1-((3-(trifluoromethyl)phenoxy)imino)ethyl)pyrimidin-4-yl)piperidin-1-yl)ethanone |
| B3 | Me | H | H | H | F | Me | CH₂ | 3-(trifluoromethyl)phenyl | (E)-2-(2,6-difluorophenyl)-1-(4-(2-methyl-5-(1-((3-(trifluoromethyl)phenoxy)imino)ethyl)pyrimidin-4-yl)piperidin-1-yl)ethanone |
| B5 | Me | H | H | H | F | Me | CH₂ | 3-chlorophenyl | (E)-1-(4-(5-(1-((3-chlorophenoxy)imino)ethyl)-2-methylpyrimidin-4-yl)piperidin-1-yl)-2-(2,6-difluorophenyl)ethanone |
| B7 | Me | H | H | H | F | Me | CH₂ | 3-(trifluoromethoxy)phenyl | (E)-2-(2,6-difluorophenyl)-1-(4-(2-methyl-5-(1-((3-(trifluoromethoxy)phenoxy)imino)ethyl)pyrimidin-4-yl)piperidin-1-yl)ethanone |
| B9 | Me | H | H | H | F | Me | CH₂ | 3,5-dimethylphenyl | (E)-2-(2,6-difluorophenyl)-1-(4-(5-(1-((3,5-dimethylphenoxy)imino)ethyl)-2-methylpyrimidin-4-yl)piperidin-1-yl)ethanone |
| B11 | Me | Me | H | H | F | Me | CH₂ | 3-methylphenyl | (E)-2-(2,6-difluorophenyl)-1-(4-(2-methyl-5-(1-((m-tolyloxy)imino)ethyl)pyrimidin-4-yl)piperidin-1-yl)ethanone |
| B12 | Me | H | H | H | F | Me | CH₂ | 3-chloro-5-fluorophenyl | (E)-1-(4-(5-(1-((3-chloro-5-fluorophenoxy)imino)ethyl)-2-methylpyrimidin-4-yl)piperidin-1-yl)-2-(2,6-difluorophenyl)ethanone |
| B13 | Me | H | H | H | F | Me | CH₂ | 2-cyanopyridin-4-yl | (E)-4-(((1-(4-(1-(2-(2,6-difluorophenyl)acetyl)piperidin-4-yl)-2-methylpyrimidin-5-yl)ethylidene)amino)oxy)picolinonitrile |

TABLE 3-continued

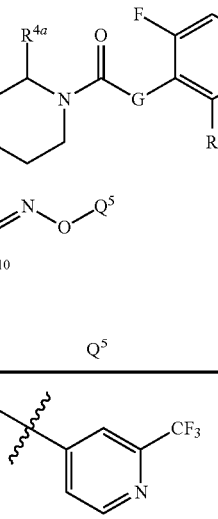

| Cpd. | R¹ | R² | each R⁴ | R⁴ᵃ | R⁶ | R¹⁰ | G | Q⁵ | Chemical Name |
|---|---|---|---|---|---|---|---|---|---|
| B14 | Me | H | H | H | F | Me | CH₂ | 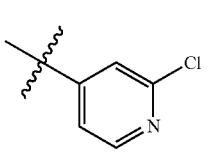 [SMILES: *c1ccnc(Cl)c1] | (E)-2-(2,6-difluorophenyl)-1-(4-(2-methyl-5-(1-(((2-(trifluoromethyl)pyridin-4-yl)oxy)imino)ethyl)pyrimidin-4-yl)piperidin-1-yl)ethanone |
| B15 | Me | H | H | H | F | Me | CH₂ | 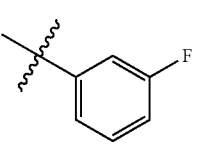 [SMILES: *c1cccc(F)c1] | (E)-1-(4-(5-(1-(((2-chloropyridin-4-yl)oxy)imino)ethyl)-2-methylpyrimidin-4-yl)piperidin-1-yl)-2-(2,6-difluorophenyl)ethanone |
| B16 | Me | H | H | H | F | Me | CH₂ | 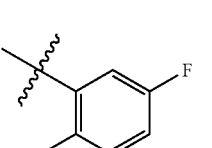 | (E)-2-(2,6-difluorophenyl)-1-(4-(5-(1-((3-fluorophenoxy)imino)ethyl)-2-methylpyrimidin-4-yl)piperidin-1-yl)ethanone |
| B17 | Me | H | H | H | F | Me | CH₂ | 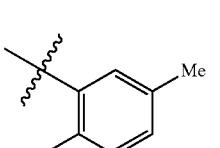 | (E)-2-(2,6-difluorophenyl)-1-(4-(5-(1-((5-fluoro-2-methylphenoxy)imino)ethyl)-2-methylpyrimidin-4-yl)piperidin-1-yl)ethanone |
| B18 | Me | H | H | H | F | Me | CH₂ | 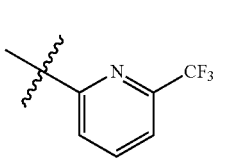 [SMILES: *c1cccc(C(F)(F)F)n1] | (E)-2-(2,6-difluorophenyl)-1-(4-(5-(1-((2,5-dimethylphenoxy)imino)ethyl)-2-methylpyrimidin-4-yl)piperidin-1-yl)ethanone |
| B19 | Me | H | H | H | F | Me | CH₂ | 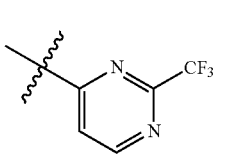 | (E)-2-(2,6-difluorophenyl)-1-(4-(2-methyl-5-(1-(((6-(trifluoromethyl)pyridin-2-yl)oxy)imino)ethyl)pyrimidin-4-yl)piperidin-1-yl)ethanone |
| B20 | Me | H | H | H | F | Me | CH₂ | 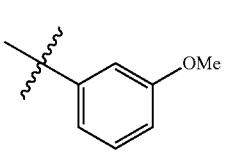 [SMILES: *c1cccc(OC)c1] | (E)-2-(2,6-difluorophenyl)-1-(4-(2-methyl-5-(1-(((2-(trifluoromethyl)pyrimidin-4-yl)oxy)imino)ethyl)pyrimidin-4-yl)piperidin-1-yl)ethanone |
| B21 | Me | H | H | H | F | Me | CH₂ | | (E)-2-(2,6-difluorophenyl)-1-(4-(5-(1-((3-methoxyphenoxy)imino)ethyl)-2-methylpyrimidin-4-yl)piperidin-1-yl)ethanone |

TABLE 3-continued

| Cpd. | R¹ | R² | each R⁴ | R⁴ᵃ | R⁶ | R¹⁰ | G | Q⁵ | Chemical Name |
|---|---|---|---|---|---|---|---|---|---|
| B22 | Me | H | H | H | F | Me | CH₂ | 2,3-dimethylphenyl | (E)-2-(2,6-difluorophenyl)-1-(4-(5-(1-((2,3-dimethylphenoxy)imino)ethyl)-2-methylpyrimidin-4-yl)piperidin-1-yl)ethanone |
| B23 | Me | H | H | H | F | —CH₂OH | CH₂ | 2-(trifluoromethyl)pyridin-4-yl | (Z)-2-(2,6-difluorophenyl)-1-(4-(5-(2-hydroxy-1-(((2-(trifluoromethyl)pyridin-4-yl)oxy)imino)ethyl)-2-methylpyrimidin-4-yl)piperidin-1-yl)ethanone |
| B24 | Me | H | H | H | F | —CH₂F | CH₂ | 2-(trifluoromethyl)pyridin-4-yl | (Z)-2-(2,6-difluorophenyl)-1-(4-(5-(2-fluoro-1-(((2-(trifluoromethyl)pyridin-4-yl)oxy)imino)ethyl)-2-methylpyrimidin-4-yl)piperidin-1-yl)ethanone |
| B25 | Me | H | H | H | F | —CH₂OH | CH₂ | 2-(trifluoromethyl)pyrimidin-4-yl | (Z)-2-(2,6-difluorophenyl)-1-(4-(5-(2-hydroxy-1-(((2-(trifluoromethyl)pyrimidin-4-yl)oxy)imino)ethyl)-2-methylpyrimidin-4-yl)piperidin-1-yl)ethanone |
| B27 | Me | H | H | H | F | —CH₂F | CH₂ | 2-(trifluoromethyl)pyrimidin-4-yl | (Z)-2-(2,6-difluorophenyl)-1-(4-(5-(2-fluoro-1-(((2-(trifluoromethyl)pyrimidin-4-yl)oxy)imino)ethyl)-2-methylpyrimidin-4-yl)piperidin-1-yl)ethanone |
| B28 | Me | H | H | H | F | —CH₂OH | CH₂ | 3-(trifluoromethyl)phenyl | (Z)-2-(2,6-difluorophenyl)-1-(4-(5-(2-hydroxy-1-((3-(trifluoromethyl)phenoxy)imino)ethyl)-2-methylpyrimidin-4-yl)piperidin-1-yl)ethanone |
| B29 | Me | H | H | H | F | CF₃ | CH₂ | 3-fluorophenyl | (Z)-2-(2,6-difluorophenyl)-1-(4-(2-methyl-5-(2,2,2-trifluoro-1-((3-fluorophenoxy)imino)ethyl)pyrimidin-4-yl)piperidin-1-yl)ethanone |
| B30 | Me | H | H | H | F | H | CH₂ | 3-(trifluoromethyl)phenyl | (E)-4-(1-(2-(2,6-difluorophenyl)acetyl)piperidin-4-yl)-2-methylpyrimidine-5-carbaldehyde O-(3-(trifluoromethyl)phenyl) oxime |

TABLE 3-continued

| Cpd. | R¹ | R² | each R⁴ | R⁴ᵃ | R⁶ | R¹⁰ | G | Q⁵ | Chemical Name |
|---|---|---|---|---|---|---|---|---|---|
| B31 | Me | Me | H | H | F | H | CH₂ | 3-(trifluoromethyl)phenyl | (E)-4-(1-(2-(2,6-difluorophenyl)acetyl)piperidin-4-yl)-2,6-dimethylpyrimidine-5-carbaldehyde O-(3-(trifluoromethyl)phenyl) oxime |
| B32 | Me | H | H | H | F | —CHF₂ | CH₂ | 2-(trifluoromethyl)pyridin-4-yl | (Z)-1-(4-(5-(2,2-difluoro-1-(((2-(trifluoromethyl)pyridin-4-yl)oxy)imino)ethyl)-2-methylpyrimidin-4-yl)piperidin-1-yl)-2-(2,6-difluorophenyl)ethanone |
| B33 | Me | H | F | H | F | H | CH₂ | 3-(trifluoromethyl)phenyl | (E)-4-(1-(2-(2,6-difluorophenyl)acetyl)-3,3-difluoropiperidin-4-yl)-2-methylpyrimidine-5-carbaldehyde O-(3-(trifluoromethyl)phenyl) oxime |
| B34 | Me | H | F | H | F | Me | CH₂ | 2-(trifluoromethyl)pyridin-4-yl | (E)-1-(3,3-difluoro-4-(2-methyl-5-(1-(((2-(trifluoromethyl)pyridin-4-yl)oxy)imino)ethyl)pyrimidin-4-yl)piperidin-1-yl)-2-(2,6-difluorophenyl)ethanone |
| B35 | Me | H | F | H | F | —CH₂F | CH₂ | 2-(trifluoromethyl)pyrimidin-4-yl | (Z)-1-(3,3-difluoro-4-(5-(2-fluoro-1-(((2-(trifluoromethyl)pyrimidin-4-yl)oxy)imino)ethyl)-2-methylpyrimidin-4-yl)piperidin-1-yl)-2-(2,6-difluorophenyl)ethanone |
| B36 | Me | H | H | H | F | Me | NH | 2-(trifluoromethyl)pyrimidin-4-yl | N-(2,6-Difluorophenyl)-4-{2-methyl-5-[(1E)-N-{[2-(trifluoromethyl)pyrimidin-4-yl]oxy}ethanimidoyl]pyrimidin-4-yl}piperidine-1-carboxamide |
| B37 | Me | H | H | H | F | Me | NH | 2-(trifluoromethyl)pyridin-4-yl | N-(2,6-Difluorophenyl)-4-{2-methyl-5-[(1E)-N-{[2-(trifluoromethyl)pyridin-4-yl]oxy}ethanimidoyl]pyrimidin-4-yl}piperidine-1-carboxamide |
| B38 | Me | H | H | H | F | Me | NH | 6-(trifluoromethyl)pyridin-2-yl | N-(2,6-Difluorophenyl)-4-{2-methyl-5-[(1E)-N-{[6-(trifluoromethyl)pyridin-2-yl]oxy}ethanimidoyl]pyrimidin-4-yl}piperidine-1-carboxamide |

TABLE 3-continued

| Cpd. | R¹ | R² | each R⁴ | R⁴ᵃ | R⁶ | R¹⁰ | G | Q⁵ | Chemical Name |
|---|---|---|---|---|---|---|---|---|---|
| B39 | Me | H | H | H | CF₃ | Me | NH | 2-(trifluoromethyl)pyrimidin-4-yl | N-[2-Fluoro-6-(trifluoromethyl)phenyl]-4-{2-methyl-5-[(1E)-N-{[2-(trifluoromethyl)pyrimidin-4-yl]oxy}ethanimidoyl]pyrimidin-4-yl}piperidine-1-carboxamide |
| B40 | Me | H | H | H | F | Me | NH | 2-chloro-6-(trifluoromethyl)pyridin-4-yl | 4-{5-[(1E)-N-{[2-chloro-6-(trifluoromethyl)pyridin-4-yl]oxy}ethanimidoyl]-2-methylpyrimidin-4-yl}-N-(2,6-difluorophenyl)piperidine-1-carboxamide |
| B42 | Me | H | H | H | F | Me | NH | 6-methyl-2-(trifluoromethyl)pyrimidin-4-yl | N-(2,6-difluorophenyl)-4-{2-methyl-5-[(1E)-N-{[6-methyl-2-(trifluoromethyl)pyrimidin-4-yl]oxy}ethanimidoyl]pyrimidin-4-yl}piperidine-1-carboxamide |
| B43 | Me | H | H | H | F | Me | NH | 3-(trifluoromethyl)phenyl | N-(2,6-Difluorophenyl)-4-{2-methyl-5-[(1E)-N-{[3-(trifluoromethyl)phenyl]oxy}ethanimidoyl]pyrimidin-4-yl}piperidine-1-carboxamide |
| B45 | Me | H | H | H | CF₃ | Me | NH | 3-(trifluoromethyl)phenyl | N-[2-fluoro-6-(trifluoromethyl)phenyl]-4-{2-methyl-5-[(1E)-N-{[3-(trifluoromethyl)phenyl]oxy}ethanimidoyl]pyrimidin-4-yl}piperidine-1-carboxamide |
| B46 | Me | Me | H | H | F | H | NH | 3-(trifluoromethyl)phenyl | N-(2,6-Difluorophenyl)-4-{2,6-dimethyl-5-[(E)-({[3-(trifluoromethyl)phenyl]oxy}imino)methyl]pyrimidin-4-yl}piperidine-1-carboxamide |
| B47 | Me | H | H | Me | F | Me | NH | 3-(trifluoromethyl)phenyl | N-(2,6-Difluorophenyl)-2-methyl-4-{2-methyl-5-[(1E)-N-{[3-(trifluoromethyl)phenyl]oxy}ethanimidoyl]pyrimidin-4-yl}piperidine-1-carboxamide |
| B48 | Me | Me | H | H | F | n-Pr | CH₂ | 3-(trifluoromethyl)phenyl | (1E)-1-(4-{1-[(2,6-difluorophenyl)acetyl]piperidin-4-yl}-2,6-dimethylpyrimidin-5-yl)butan-1-one O-[3-(trifluoromethyl)phenyl]oxime |

TABLE 3-continued

| Cpd. | R¹ | R² | each R⁴ | R⁴ᵃ | R⁶ | R¹⁰ | G | Q⁵ | Chemical Name |
|---|---|---|---|---|---|---|---|---|---|
| B50 | SMe | H | H | H | F | Me | NH | 3-(trifluoromethyl)phenyl | N-(2,6-Difluorophenyl)-4-{2-(methylthio)-5-[(1E)-N-{[3-(trifluoromethyl)phenyl]oxy}ethanimidoyl]pyrimidin-4-yl}piperidine-1-carboxamide |
| B51 | NH₂ | H | H | H | F | Me | NH | 3-(trifluoromethyl)phenyl | 4-{2-Amino-5-[(1E)-N-{[3-(trifluoromethyl)phenyl]oxy}ethanimidoyl]pyrimidin-4-yl}-N-(2,6-difluorophenyl)piperidine-1-carboxamide |
| B52 | SMe | H | H | H | F | Me | NH | 2-(trifluoromethyl)pyridin-4-yl | N-(2,6-Difluorophenyl)-4-{2-(methylthio)-5-[(1E)-N-{[2-(trifluoromethyl)pyridin-4-yl]oxy}ethanimidoyl]pyrimidin-4-yl}piperidine-1-carboxamide |
| B53 | NH₂ | H | H | H | F | Me | NH | 2-(trifluoromethyl)pyridin-4-yl | 4-{2-amino-5-[(1E)-N-{[2-(trifluoromethyl)pyridin-4-yl]oxy}ethanimidoyl]pyrimidin-4-yl}-N-(2,6-difluorophenyl)piperidine-1-carboxamide |
| B54 | NH₂ | H | H | H | F | Me | NH | 2-(trifluoromethyl)pyrimidin-4-yl | 4-{2-Amino-5-[(1E)-N-{[2-(trifluoromethyl)pyrimidin-4-yl]oxy}ethanimidoyl]pyrimidin-4-yl}-N-(2,6-difluorophenyl)piperidine-1-carboxamide |
| B55 | NH₂ | H | H | H | F | Me | NH | 2-chloro-6-(trifluoromethyl)pyridin-4-yl | 4-{2-Amino-5-[(1E)-N-{[2-chloro-6-(trifluoromethyl)pyridin-4-yl]oxy}ethanimidoyl]pyrimidin-4-yl}-N-(2,6-difluorophenyl)piperidine-1-carboxamide |
| B56 | NH₂ | H | H | H | F | Me | NH | 2,6-difluoropyridin-4-yl | 4-(2-Amino-5-{(1E)-N-[(2,6-difluoropyridin-4-yl)oxy]ethanimidoyl}pyrimidin-4-yl)-N-(2,6-difluorophenyl)piperidine-1-carboxamide |
| B58 | SMe | H | H | H | F | Me | NH | 2-chloropyridin-4-yl | 4-[5-{(1E)-N-[(2-Chloropyridin-4-yl)oxy]ethanimidoyl}-2-(methylthio)pyrimidin-4-yl]-N-(2,6-difluorophenyl)piperidine-1-carboxamide |

TABLE 3-continued

| Cpd. | R¹ | R² | each R⁴ | R⁴ᵃ | R⁶ | R¹⁰ | G | Q⁵ | Chemical Name |
|---|---|---|---|---|---|---|---|---|---|
| B59 | NH₂ | H | H | H | F | Me | NH | 2-chloropyridin-4-yl (4-position, Cl at 2) | 4-(2-Amino-5-{(1E)-N-[(2-chloropyridin-4-yl)oxy]ethanimidoyl}pyrimidin-4-yl)-N-(2,6-difluorophenyl)piperidine-1-carboxamide |
| B60 | NEt | H | H | H | F | Me | NH | 2-(trifluoromethyl)pyridin-4-yl | N-(2,6-Difluorophenyl)-4-{2-(ethylamino)-5-[(1E)-N-{[2-(trifluoromethyl)pyridin-4-yl]oxy}ethanimidoyl]pyrimidin-4-yl}piperidine-1-carboxamide |
| B61 | NMe₂ | H | H | H | F | Me | NH | 2-(trifluoromethyl)pyridin-4-yl | N-(2,6-Difluorophenyl)-4-{2-(dimethylamino)-5-[(1E)-N-{[2-(trifluoromethyl)pyridin-4-yl]oxy}ethanimidoyl]pyrimidin-4-yl}piperidine-1-carboxamide |

TABLE 4

| Cpd | R¹ | R² | R¹⁰ | G | Q⁶ | Chemical Name |
|---|---|---|---|---|---|---|
| B2 | Me | Me | Me | CH₂ | 2-(trifluoromethyl)pyridin-4-yl | (Z)-2-(2,6-difluorophenyl)-1-(4-(2,6-dimethyl-5-(1-(((2-(trifluoromethyl)pyridin-4-yl)oxy)imino)ethyl)pyrimidin-4-yl)piperidin-1-yl)ethanone |
| B4 | Me | H | Me | CH₂ | 3-(trifluoromethyl)phenyl | (Z)-2-(2,6-difluorophenyl)-1-(4-(2-methyl-5-(1-((3-(trifluoromethyl)phenoxy)imino)ethyl)pyrimidin-4-yl)piperidin-1-yl)ethanone |

TABLE 4-continued

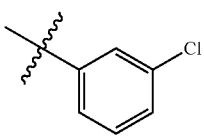 [SMILES: *c1cccc(Cl)c1]

| Cpd | R¹ | R² | R¹⁰ | G | Q⁶ | Chemical Name |
|---|---|---|---|---|---|---|
| B6 | Me | H | H | CH₂ | 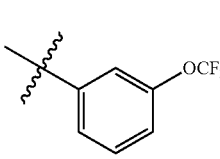 | (Z)-1-(4-(5-(1-(((3-chlorophenoxy)imino)ethyl)-2-methylpyrimidin-4-yl)piperidin-1-yl)-2-(2,6-difluorophenyl)ethanone |
| B8 | Me | H | Me | CH₂ | 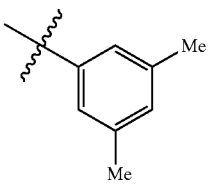 [SMILES: *c1cc(C)cc(C)c1] | (Z)-2-(2,6-difluorophenyl)-1-(4-(2-methyl-5-(1-((3-(trifluoromethoxy)phenoxy)imino)ethyl)pyrimidin-4-yl)piperidin-1-yl)ethanone |
| B10 | Me | H | Me | CH₂ | 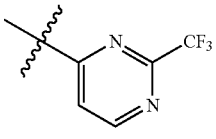 [SMILES: *c1ccnc(C(F)(F)F)n1] | (Z)-2-(2,6-difluorophenyl)-1-(4-(5-(1-(((3,5-dimethylphenoxy)imino)ethyl)-2-methylpyrimidin-4-yl)piperidin-1-yl)ethanone |
| B26 | Me | H | —CH₂OH | CH₂ | 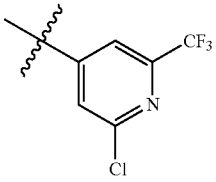 [SMILES: *c1cc(Cl)nc(C(F)(F)F)c1] | (E)-2-(2,6-difluorophenyl)-1-(4-(5-(2-hydroxy-1-(((2-(trifluoromethyl)pyrimidin-4-yl)oxy)imino)ethyl)-2-methylpyrimidin-4-yl)piperidin-1-yl)ethanone |
| B41 | Me | H | Me | NH | 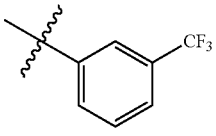 [SMILES: *c1cccc(C(F)(F)F)c1] | 4-{5-[(1Z)-N-{[2-chloro-6-(trifluoromethyl)pyridin-4-yl]oxy}ethanimidoyl]-2-methylpyrimidin-4-yl}-N-(2,6-difluorophenyl)piperidine-1-carboxamide |
| B44 | Me | H | Me | NH | 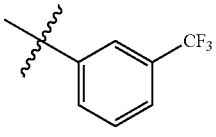 [SMILES: *c1cccc(C(F)(F)F)c1] | N-(2,6-Difluorophenyl)-4-{2-methyl-5-[(1Z)-N-{[3-(trifluoromethyl)phenyl]oxy}ethanimidoyl]pyrimidin-4-yl}piperidine-1-carboxamide |
| B49 | Me | Me | n-Pr | CH₂ | 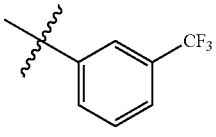 [SMILES: *c1cccc(C(F)(F)F)c1] | (1Z)-1-(4-{1-[(2,6-difluorophenyl)acetyl]piperidin-4-yl}-2,6-dimethylpyrimidin-5-yl)butan-1-one O-[3-(trifluoromethyl)phenyl]oxime |

TABLE 4-continued

| Cpd | R¹ | R² | R¹⁰ | G | Q⁶ | Chemical Name |
|---|---|---|---|---|---|---|
| B57 | NH₂ | H | Me | NH | (2,6-difluoropyridin-4-yl) | 4-(2-Amino-5-{(1Z)-N-[(2,6-difluoropyridin-4-yl)oxy]ethanimidoyl}pyrimidin-4-yl)-N-(2,6-difluorophenyl)piperidine-1-carboxamide |

TABLE 5

| Cpd | Structure | Chemical Name |
|---|---|---|
| C1 | 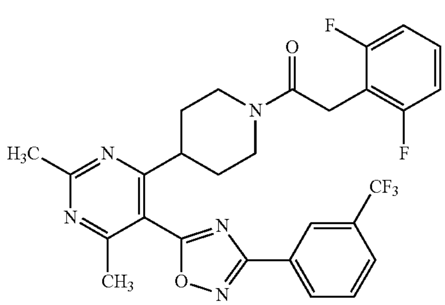 [SMILES: Cc1nc(C)c(-c2nc(-c3cccc(C(F)(F)F)c3)no2)c(C2CCN(C(=O)Cc3c(F)cccc3F)CC2)n1] | 2-(2,6-difluorophenyl)-1-(4-(2,6-dimethyl-5-(3-(3-(trifluoromethyl)phenyl)-1,2,4-oxadiazol-5-yl)pyrimidin-4-yl)piperidin-1-yl)ethanone |
| C2 | 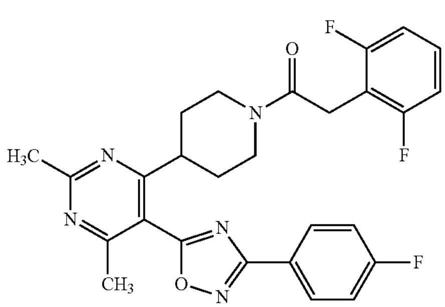 [SMILES: Cc1nc(C)c(-c2nc(-c3ccc(F)cc3)no2)c(C2CCN(C(=O)Cc3c(F)cccc3F)CC2)n1] | 2-(2,6-difluorophenyl)-1-(4-(5-(3-(4-fluorophenyl)-1,2,4-oxadiazol-5-yl)-2,6-dimethylpyrimidin-4-yl)piperidin-1-yl)ethanone |

TABLE 5-continued

| Cpd | Structure | Chemical Name |
|---|---|---|
| C3 | 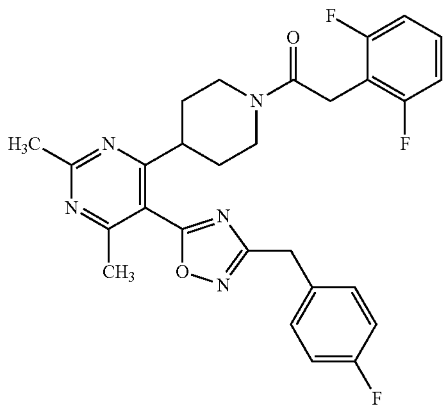 [SMILES: Cc1nc(C)c(-c2nc(Cc3ccc(F)cc3)no2)c(C2CCN(C(=O)Cc3c(F)cccc3F)CC2)n1] | 2-(2,6-difluorophenyl)-1-(4-(5-(3-(4-fluorobenzyl)-1,2,4-oxadiazol-5-yl)-2,6-dimethylpyrimidin-4-yl)piperidin-1-yl)ethanone |
| C4 | 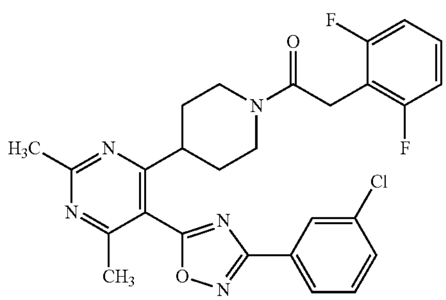 [SMILES: Cc1nc(C)c(-c2nc(-c3cccc(Cl)c3)no2)c(C2CCN(C(=O)Cc3c(F)cccc3F)CC2)n1] | 1-(4-(5-(3-(3-chlorophenyl)-1,2,4-oxadiazol-5-yl)-2,6-dimethylpyrimidin-4-yl)piperidin-1-yl)-2-(2,6-difluorophenyl)ethanone |
| C5 | 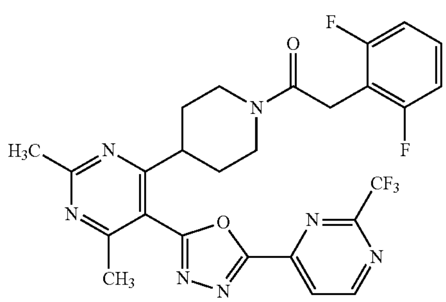 | 2-(2,6-difluorophenyl)-1-(4-(2,6-dimethyl-5-(5-(2-(trifluoromethyl)pyrimidin-4-yl)-1,3,4-oxadiazol-2-yl)pyrimidin-4-yl)piperidin-1-yl)ethanone |
| C6 | 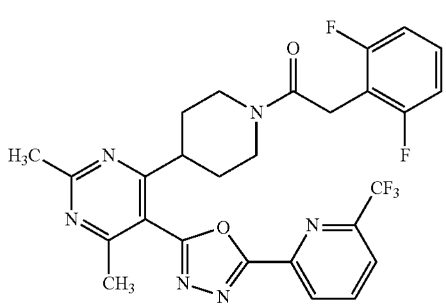 [SMILES: Cc1nc(C)c(-c2nnc(-c3cccc(C(F)(F)F)n3)o2)c(C2CCN(C(=O)Cc3c(F)cccc3F)CC2)n1] | 2-(2,6-difluorophenyl)-1-(4-(2,6-dimethyl-5-(5-(6-(trifluoromethyl)pyridin-2-yl)-1,3,4-ozadiazol-2-yl)pyrimidin-4-yl)piperidin-1-yl)ethanone |

TABLE 5-continued

| Cpd | Structure | Chemical Name |
|---|---|---|
| C7 | 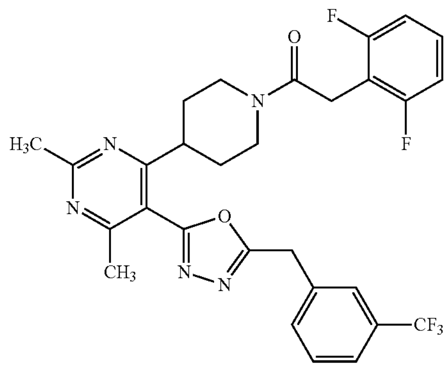 [SMILES: Cc1nc(C)c(-c2nnc(Cc3cccc(C(F)(F)F)c3)o2)c(C2CCN(C(=O)Cc3c(F)cccc3F)CC2)n1] | 2-(2,6-difluorophenyl)-1-(4-(2,6-dimethyl-5-(5-(3-(trifluoromethyl)benzyl)-1,3,4-oxadiazol-2-yl)pyrimidin-4-yl)piperidin-1-yl)ethanone |
| C8 | 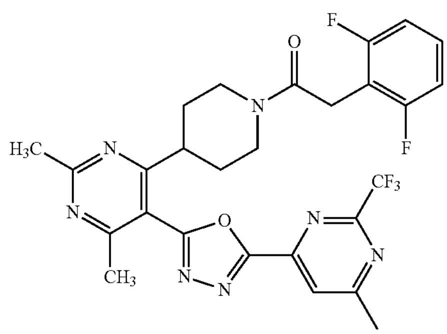 [SMILES: Cc1cc(-c2nnc(-c3c(C)nc(C)nc3C3CCN(C(=O)Cc4c(F)cccc4F)CC3)o2)nc(C(F)(F)F)n1] | 2-(2,6-difluorophenyl)-1-(4-(2,6-dimethyl-5-(5-(6-methyl-2-(trifluoromethyl)pyrimidin-4-yl)-1,3,4-oxadiazol-2-yl)pyrimidin-4-yl)piperidin-1-yl)ethanone |
| C9 | 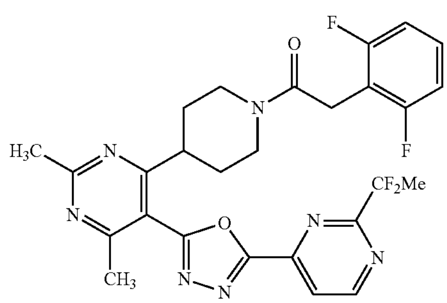 | 1-(4-(5-(5-(6-(1,1-difluoroethyl)pyridin-2-yl)-1,3,4-oxadiazol-2-yl)-2,6-dimethylpyrimidin-4-yl)piperidin-1-yl)-2,6-difluorophenyl)ethanone |
| C10 | 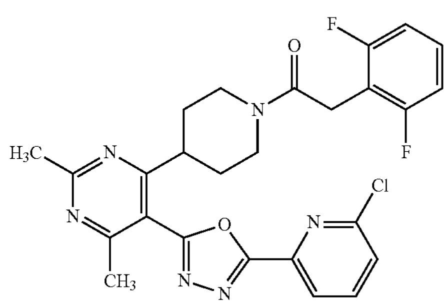 [SMILES: Cc1nc(C)c(-c2nnc(-c3cccc(Cl)n3)o2)c(C2CCN(C(=O)Cc3c(F)cccc3F)CC2)n1] | (1-(4-(5-(5-(6-chloropyridin-2-yl)-1,3,4-oxadiazol-2-yl)-2,6-dimethylpyrimidin-4-yl)piperidin-1-yl)-2-(2,6-difluorophenyl)ethanone |
| C11 | 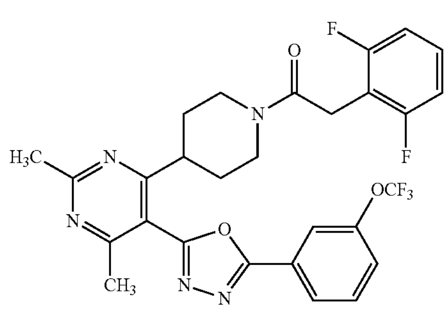 [SMILES: Cc1nc(C)c(-c2nnc(-c3cccc(OC(F)(F)F)c3)o2)c(C2CCN(C(=O)Cc3c(F)cccc3F)CC2)n1] | 2-(2,6-difluorophenyl)-1-(4-(2,6-dimethyl-5-(5-(3-(trifluoromethoxy)phenyl)-1,3,4-oxadiazol-2-yl)pyrimidin-4-yl)piperidin-1-yl)ethanone |

TABLE 5-continued

| Cpd | Structure | Chemical Name |
|---|---|---|
| C12 | 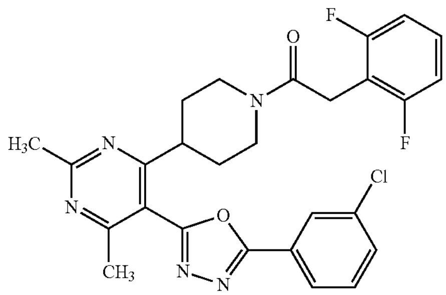 [SMILES: Cc1nc(C)c(-c2nnc(-c3cccc(Cl)c3)o2)c(C2CCN(C(=O)Cc3c(F)cccc3F)CC2)n1] | 1-(4-(5-(5-(3-chlorophenyl)-1,3,4-oxadiazol-2-yl)-2,6-dimethylpyrimidin-4-yl)piperidin-1-yl)-2-(2,6-difluorophenyl)ethanone |
| C13 | 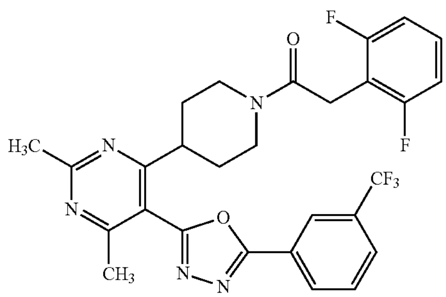 [SMILES: Cc1nc(C)c(-c2nnc(-c3cccc(C(F)(F)F)c3)o2)c(C2CCN(C(=O)Cc3c(F)cccc3F)CC2)n1] | 2-(2,6-difluorophenyl)-1-(4-(2,6-dimethyl-5-(5-(3-(trifluoromethyl)phenyl)-1,3,4-oxadiazol-2-yl)pyrimidin-4-yl)piperidin-1-yl)ethanone |
| C14 | 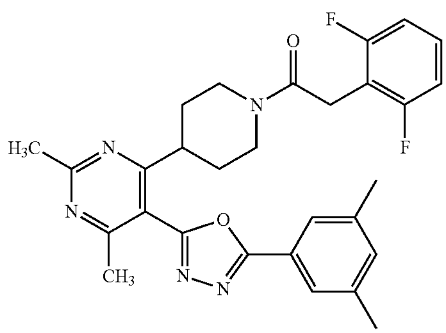 [SMILES: Cc1cc(C)cc(-c2nnc(-c3c(C)nc(C)nc3C3CCN(C(=O)Cc4c(F)cccc4F)CC3)o2)c1] | 2-(2,6-difluorophenyl)-1-(4-(5-(5-(3,5-dimethylphenyl)-1,3,4-oxadiazol-2-yl)-2,6-dimethylpyrimidin-4-yl)piperidin-1-yl)ethanone |
| C15 | 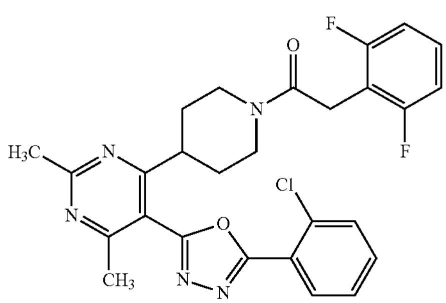 [SMILES: Cc1nc(C)c(-c2nnc(-c3ccccc3Cl)o2)c(C2CCN(C(=O)Cc3c(F)cccc3F)CC2)n1] | 1-(4-(5-(5-(2-chlorophenyl)-1,3,4-oxadiazol-2-yl)-2,6-dimethylpyrimidin-4-yl)piperidin-1-yl)-2-(2,6-difluorophenyl)ethanone |
| C16 | 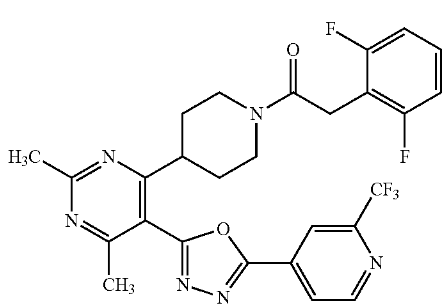 [SMILES: Cc1nc(C)c(-c2nnc(-c3ccnc(C(F)(F)F)c3)o2)c(C2CCN(C(=O)Cc3c(F)cccc3F)CC2)n1] | 2-(2,6-difluorophenyl)-1-(4-(2,6-dimethyl-5-(5-(2-(trifluoromethyl)pyridin-4-yl)-1,3,4-oxadiazol-2-yl)pyrimidin-4-yl)piperidin-1-yl)ethanone |

TABLE 5-continued

| Cpd | Structure | Chemical Name |
|---|---|---|
| C17 | 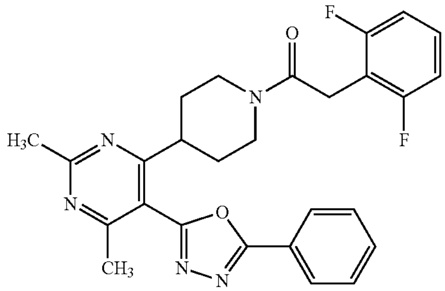 [SMILES: Cc1nc(C)c(-c2nnc(-c3ccccc3)o2)c(C2CCN(C(=O)Cc3c(F)cccc3F)CC2)n1] | 2-(2,6-difluorophenyl)-1-(4-(2,6-dimethyl-5-(5-phenyl-1,3,4-oxadiazol-2-yl)pyrimidin-4-yl)piperidin-1-yl)ethanone |
| C18 | 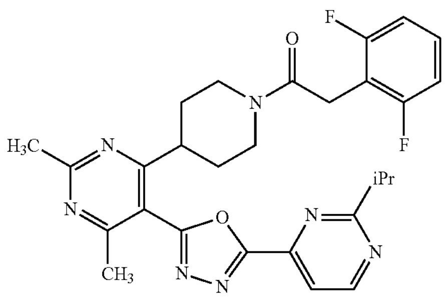 [SMILES: Cc1nc(C)c(-c2nnc(-c3ccnc(C(C)C)n3)o2)c(C2CCN(C(=O)Cc3c(F)cccc3F)CC2)n1] | 2-(2,6-difluorophenyl)-1-(4-(5-(5-(2-isopropylpyrimidin-4-yl)-1,3,4-oxadiazol-2-yl)-2,6-dimethylpyrimidin-4-yl)piperidin-1-yl)ethanone |
| C19 | 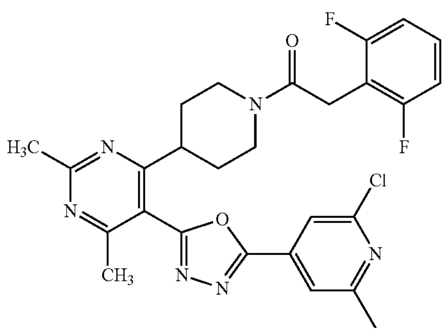 [SMILES: Cc1cc(-c2nnc(-c3c(C)nc(C)nc3C3CCN(C(=O)Cc4c(F)cccc4F)CC3)o2)cc(Cl)n1] | 1-(4-(5-(5-(2-chloro-6-methylpyridin-4-yl)-1,3,4-oxadiazol-2-yl)-2,6-dimethylpyrimidin-4-yl)piperidin-1-yl)-2-(2,6-difluorophenyl)ethanone |
| C20 | 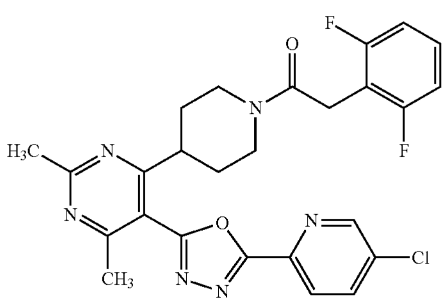 [SMILES: Cc1nc(C)c(-c2nnc(-c3ccc(Cl)cn3)o2)c(C2CCN(C(=O)Cc3c(F)cccc3F)CC2)n1] | 1-(4-(5-(5-(5-chloropyridin-2-yl)-1,3,4-oxadiazol-2-yl)-2,6-dimethylpyrimidin-4-yl)piperidin-1-yl)-2-(2,6-difluorophenyl)ethanone |
| C21 | 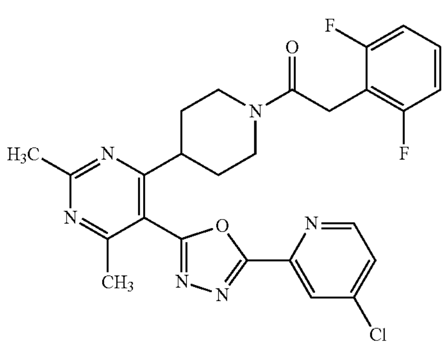 [SMILES: Cc1nc(C)c(-c2nnc(-c3cc(Cl)ccn3)o2)c(C2CCN(C(=O)Cc3c(F)cccc3F)CC2)n1] | 1-(4-(5-(5-(4-chloropyridin-2-yl)-1,3,4-oxadiazol-2-yl)-2,6-dimethylpyrimidin-4-yl)piperidin-1-yl)-2-(2,6-difluorophenyl)ethanone |

TABLE 5-continued

| Cpd | Structure | Chemical Name |
|---|---|---|
| C22 | 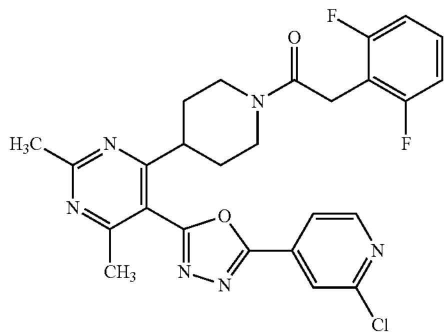 [SMILES: Cc1nc(C)c(-c2nnc(-c3ccnc(Cl)c3)o2)c(C2CCN(C(=O)Cc3c(F)cccc3F)CC2)n1] | 1-(4-(5-(5-(2-chloropyridin-4-yl)-1,3,4-oxadiazol-2-yl)-2,6-dimethylpyrimidin-4-yl)piperidin-1-yl)-2-(2,6-difluorophenyl)ethanone |
| C23 | 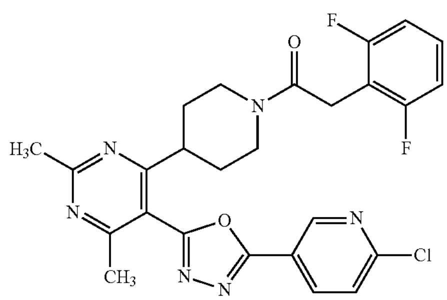 [SMILES: Cc1nc(C)c(-c2nnc(-c3ccc(Cl)nc3)o2)c(C2CCN(C(=O)Cc3c(F)cccc3F)CC2)n1] | 1-(4-(5-(5-(6-chloropyridin-3-yl)-1,3,4-oxadiazol-2-yl)-2,6-dimethylpyrimidin-4-yl)piperidin-1-yl)-2-(2,6-difluorophenyl)ethanone |
| C24 | 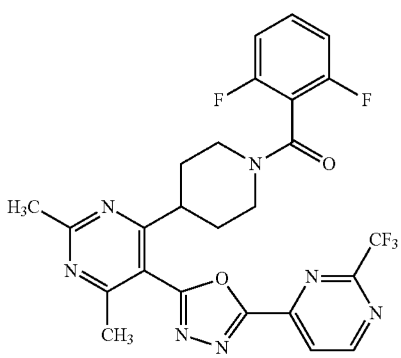 [SMILES: Cc1nc(C)c(-c2nnc(-c3ccnc(C(F)(F)F)n3)o2)c(C2CCN(C(=O)c3c(F)cccc3F)CC2)n1] | (2,6-difluorophenyl)(4-(2,6-dimethyl-5-(5-(2-(trifluoromethyl)pyrimidin-4-yl)-1,3,4-oxadiazol-2-yl)pyrimidin-4-yl)piperidin-1-yl)methanone |
| C25 | 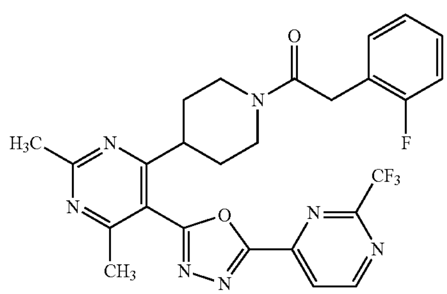 [SMILES: Cc1nc(C)c(-c2nnc(-c3ccnc(C(F)(F)F)n3)o2)c(C2CCN(C(=O)Cc3ccccc3F)CC2)n1] | 1-(4-(2,6-dimethyl-5-(5-(2-(trifluoromethyl)pyrimidin-4-yl)-1,3,4-oxadiazol-2-yl)pyrimidin-4-yl)piperidin-1-yl)-2-(2-fluorophenyl)ethanone |
| C26 | 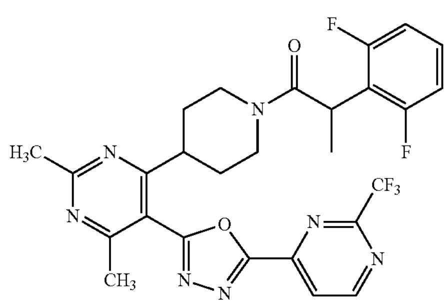 [SMILES: Cc1nc(C)c(-c2nnc(-c3ccnc(C(F)(F)F)n3)o2)c(C2CCN(C(=O)C(C)c3c(F)cccc3F)CC2)n1] | 2-(2,6-difluorophenyl)-1-(4-(2,6-dimethyl-5-(5-(2-(trifluoromethyl)pyrimidin-4-yl)-1,3,4-oxadiazol-2-yl)pyrimidin-4-yl)piperidin-1-yl)propan-1-one |

TABLE 5-continued

| Cpd | Structure | Chemical Name |
|---|---|---|
| C27 | 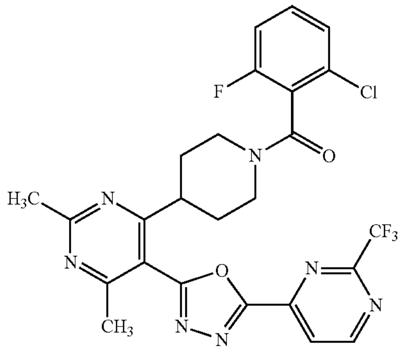 [SMILES: Cc1nc(C)c(-c2nnc(-c3ccnc(C(F)(F)F)n3)o2)c(C2CCN(C(=O)c3c(F)cccc3Cl)CC2)n1] | (2-chloro-6-fluorophenyl)(4-(2,6-dimethyl-5-(5-(2-(trifluoromethyl)pyrimidin-4-yl)-1,3,4-oxadiazol-2-yl)pyrimidin-4-yl)piperidin-1-yl)methanone |
| C28 | 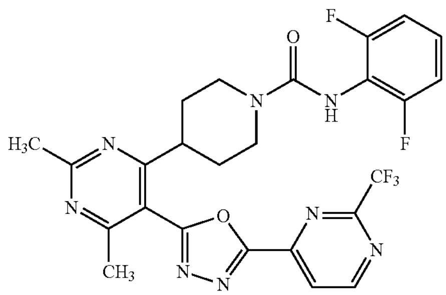 [SMILES: Cc1nc(C)c(-c2nnc(-c3ccnc(C(F)(F)F)n3)o2)c(C2CCN(C(=O)Nc3c(F)cccc3F)CC2)n1] | N-(2,6-difluorophenyl)-4-(2,6-dimethyl-5-(5-(2-(trifluoromethyl)pyrimidin-4-yl)-1,3,4-oxadiazol-2-yl)pyrimidin-4-yl)piperidine-1-carboxamide |
| C29 | 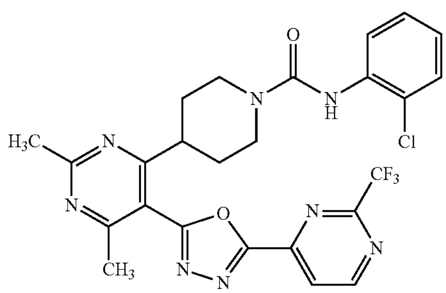 [SMILES: Cc1nc(C)c(-c2nnc(-c3ccnc(C(F)(F)F)n3)o2)c(C2CCN(C(=O)Nc3ccccc3Cl)CC2)n1] | N-(2-chlorophenyl)-4-(2,6-dimethyl-5-{5-[2-(trifluoromethyl)pyrimidin-4-yl]-1,3,4-oxadiazol-2-yl}pyrimidin-4-yl)piperidine-1-carboxamide |
| C30 | 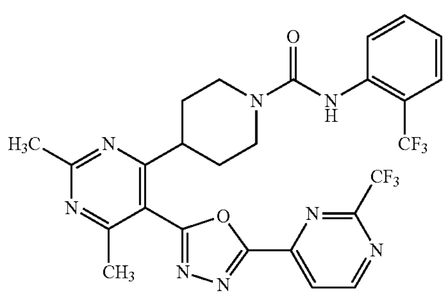 [SMILES: Cc1nc(C)c(-c2nnc(-c3ccnc(C(F)(F)F)n3)o2)c(C2CCN(C(=O)Nc3ccccc3C(F)(F)F)CC2)n1] | 4-(2,6-dimethyl-5-{5-[2-(trifluoromethyl)pyrimidin-4-yl]-1,3,4-oxadiazol-2-yl}pyrimidin-4-yl)-N-[2-(trifluoromethyl)phenyl]piperidine-1-carboxamide |
| C31 | 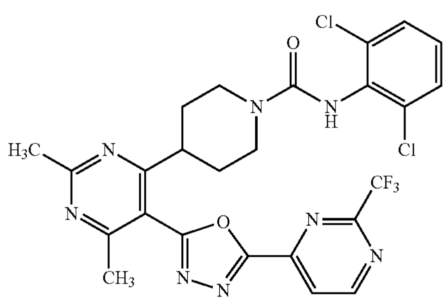 [SMILES: Cc1nc(C)c(-c2nnc(-c3ccnc(C(F)(F)F)n3)o2)c(C2CCN(C(=O)Nc3c(Cl)cccc3Cl)CC2)n1] | N-(2,6-dichlorophenyl)-4-(2,6-dimethyl-5-{5-[2-(trifluoromethyl)pyrimidin-4-yl]-1,3,4-oxadiazol-2-yl}pyrimidin-4-yl)piperidin-1-carboxamide |

TABLE 5-continued

| Cpd | Structure | Chemical Name |
| --- | --- | --- |
| C32 | 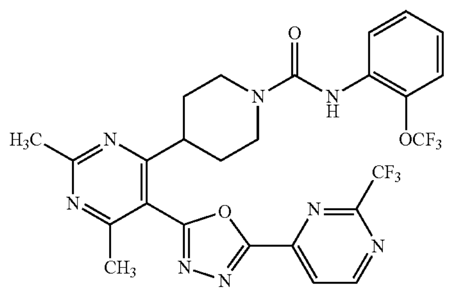 [SMILES: Cc1nc(C)c(-c2nnc(-c3ccnc(C(F)(F)F)n3)o2)c(C2CCN(C(=O)Nc3ccccc3OC(F)(F)F)CC2)n1] | 4-(2,6-dimethyl-5-{5-[2-(trifluoromethyl)pyrimidin-4-yl]-1,3,4-oxadiazol-2-yl}pyrimidin-4-yl)-N-{2-[(trifluoromethyl)oxy]phenyl}piperidine-1-carboxamide |
| C33 | 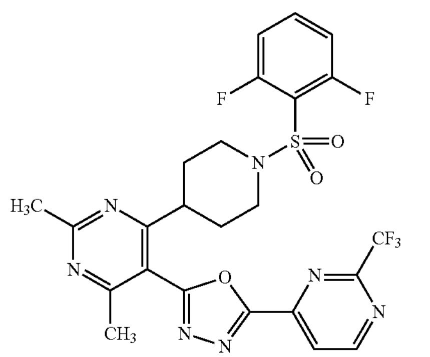 [SMILES: Cc1nc(C)c(-c2nnc(-c3ccnc(C(F)(F)F)n3)o2)c(C2CCN(S(=O)(=O)c3c(F)cccc3F)CC2)n1] | 2-(4-(1-((2,6-difluorophenyl)sulfonyl)piperidin-4-yl)-2,6-dimethylpyrimidin-5-yl)-5-(2-(trifluoromethyl)pyrimidin-4-yl)-1,3,4-oxadiazole |
| C34 | 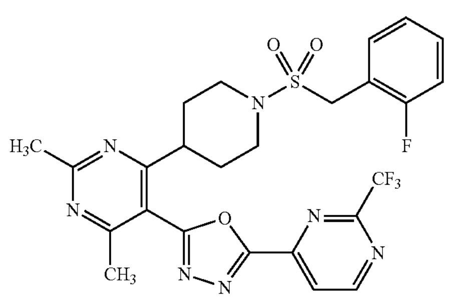 [SMILES: Cc1nc(C)c(-c2nnc(-c3ccnc(C(F)(F)F)n3)o2)c(C2CCN(S(=O)(=O)Cc3ccccc3F)CC2)n1] | 2-(4-(1-((2-fluorobenzyl)sulfonyl)piperidin-4-yl)-2,6-dimethylpyrimidin-5-yl)-5-(2-(trifluoromethyl)pyrimidin-4-yl)-1,3,4-oxadiazole |
| C35 | 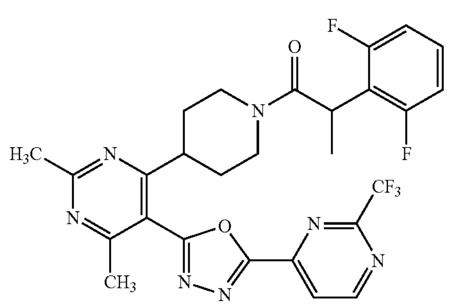 [SMILES: Cc1nc(C)c(-c2nnc(-c3ccnc(C(F)(F)F)n3)o2)c(C2CCN(C(=O)C(C)c3c(F)cccc3F)CC2)n1] | (R)-2-(2,6-Difluorophenyl)-1-(4-(2,6-dimethyl-5-(5-(2-(trifluoromethyl)pyrimidin-4-yl)-1,3,4-oxadiazol-2-yl)pyrimidin-4-yl)piperidin-1-yl)propan-1-one |
| C36 | 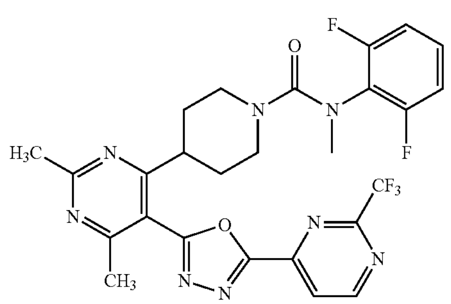 [SMILES: Cc1nc(C)c(-c2nnc(-c3ccnc(C(F)(F)F)n3)o2)c(C2CCN(C(=O)N(C)c3c(F)cccc3F)CC2)n1] | N-(2,6-Difluorophenyl)-4-(2,6-dimethyl-5-(5-(2-(trifluoromethyl)pyrimidin-4-yl)-1,3,4-oxadiazol-2-yl)pyrimidin-4-yl)-N-methylpiperidine-1-carboxamide |

TABLE 5-continued

| Cpd | Structure | Chemical Name |
|---|---|---|
| C37 | 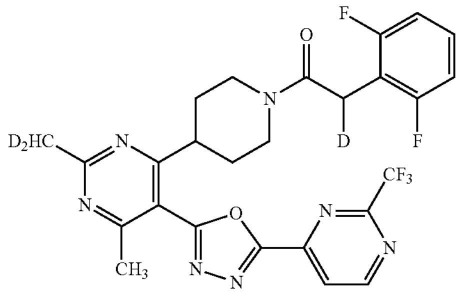 | 2-deutero-1-(4-(6-(dideuteromethyl)-2-methyl-5-(5-(2-(trifluoromethyl)pyrimidin-4-yl)-1,3,4-oxadiazol-2-yl)pyrimidin-4-yl)piperidin-1-yl)-2-(2,6-difluorophenyl)ethanone |
| C38 | 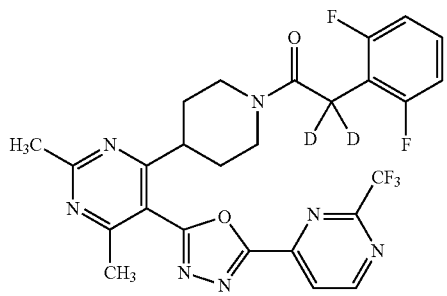 [SMILES: [2H]C([2H])(C(=O)N1CCC(c2nc(C)nc(C)c2-c2nnc(-c3ccnc(C(F)(F)F)n3)o2)CC1)c1c(F)cccc1F] | 2,2-dideutero-2-(2,6-difluorophenyl)-1-(4-(2,6-dimethyl-5-(5-(2-(trifluoromethyl)pyrimidin-4-yl)-1,3,4-oxadiazol-2-yl)pyrimidin-4-yl)piperidin-1-yl)ethanone |
| C39 | 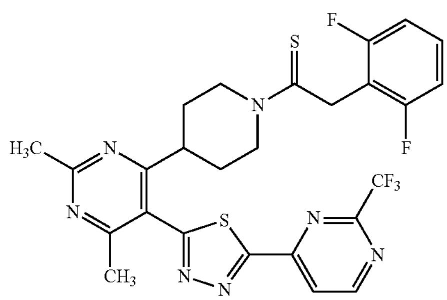 | 2-(2,6-difluorophenyl)-1-(4-(2,6-dimethyl-5-(5-(2-(trifluoromethyl)pyrimidin-4-yl)-1,3,4-thiadiazol-2-yl)pyrimidin-4-yl)piperidin-1-yl)ethanethione |
| C40 | 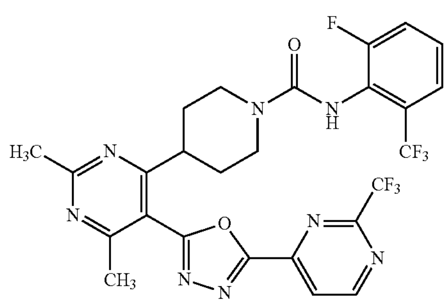 [SMILES: Cc1nc(C)c(-c2nnc(-c3ccnc(C(F)(F)F)n3)o2)c(C2CCN(C(=O)Nc3c(F)cccc3C(F)(F)F)CC2)n1] | 4-(2,6-dimethyl-5-(5-(2-(trifluoromethyl)pyrimidin-4-yl)-1,3,4-oxadiazol-2-yl)pyrimidin-4-yl)-N-(2-fluoro-6-(trifluoromethyl)phenyl)piperidine-1-carboxamide |
| C41 | 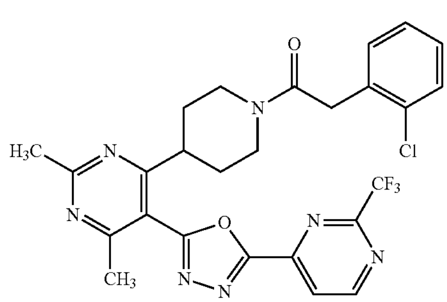 [SMILES: Cc1nc(C)c(-c2nnc(-c3ccnc(C(F)(F)F)n3)o2)c(C2CCN(C(=O)Cc3ccccc3Cl)CC2)n1] | 2-(2-chlorophenyl)-1-(4-(2,6-dimethyl-5-(5-(2-(trifluoromethyl)pyrimidin-4-yl)-1,3,4-oxadiazol-2-yl)pyrimidin-4-yl)piperidin-1-yl)ethanone |

TABLE 5-continued

| Cpd | Structure | Chemical Name |
|---|---|---|
| C42 | 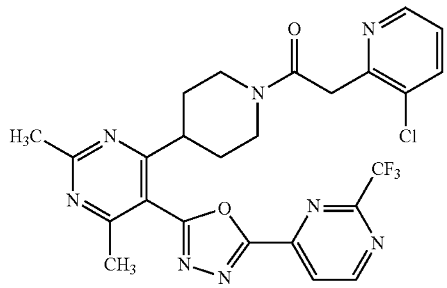 [SMILES: Cc1nc(C)c(-c2nnc(-c3ccnc(C(F)(F)F)n3)o2)c(C2CCN(C(=O)Cc3ncccc3Cl)CC2)n1] | 2-(3-chloropyridin-2-yl)-1-(4-(2,6-dimethyl-5-(5-(2-(trifluoromethyl)pyrimidin-4-yl)-1,3,4-oxadiazol-2-yl)pyrimidin-4-yl)piperidin-1-yl)ethanone |
| C43 | 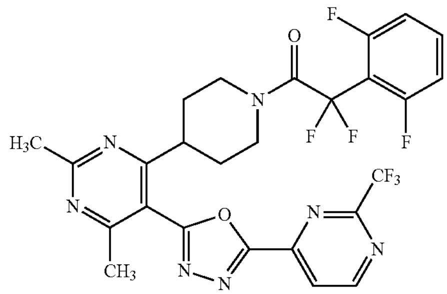 [SMILES: Cc1nc(C)c(-c2nnc(-c3ccnc(C(F)(F)F)n3)o2)c(C2CCN(C(=O)C(F)(F)c3c(F)cccc3F)CC2)n1] | 2-(2,6-difluorophenyl)-1-(4-(2,6-dimethyl-5-(5-(2-(trifluoromethyl)pyrimidin-4-yl)-1,3,4-oxadiazol-2-yl)pyrimidin-4-yl)piperidin-1-yl)-2,2-difluoroethanone |
| C44 | 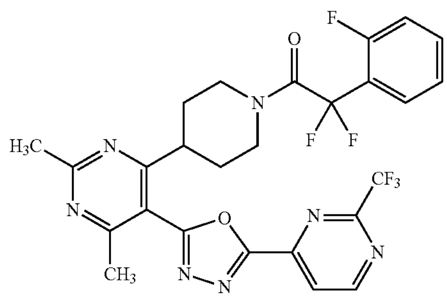 [SMILES: Cc1nc(C)c(-c2nnc(-c3ccnc(C(F)(F)F)n3)o2)c(C2CCN(C(=O)C(F)(F)c3ccccc3F)CC2)n1] | 1-(4-(2,6-dimethyl-5-(5-(2-(trifluoromethyl)pyrimidin-4-yl)-1,3,4-oxadiazol-2-yl)pyrimidin-4-yl)piperidin-1-yl)-2,2-difluoro-2-(2-fluorophenyl)ethanone |
| C45 | 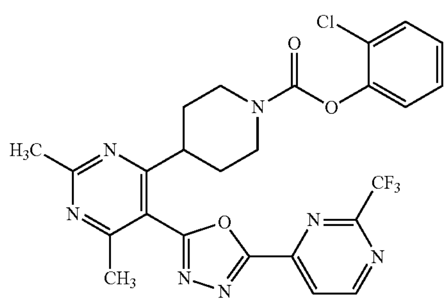 [SMILES: Cc1nc(C)c(-c2nnc(-c3ccnc(C(F)(F)F)n3)o2)c(C2CCN(C(=O)Oc3ccccc3Cl)CC2)n1] | 2-chlorophenyl 4-(2,6-dimethyl-5-(5-(2-(trifluoromethyl)pyrimidin-4-yl)-1,3,4-oxadiazol-2-yl)pyrimidin-4-yl)piperidine-1-carboxylate |
| C46 | 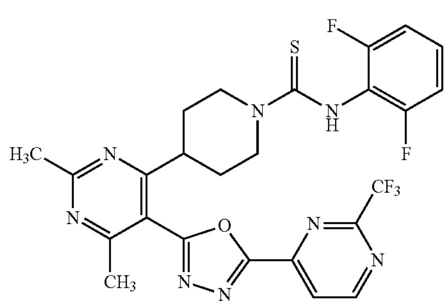 [SMILES: Cc1nc(C)c(-c2nnc(-c3ccnc(C(F)(F)F)n3)o2)c(C2CCN(C(=S)Nc3c(F)cccc3F)CC2)n1] | N-(2,6-difluorophenyl)-4-(2,6-dimethyl-5-(5-(2-(trifluoromethyl)pyrimidin-4-yl)-1,3,4-oxadiazol-2-yl)pyrimidin-4-yl)piperidine-1-carbothioamide |

TABLE 5-continued

| Cpd | Structure | Chemical Name |
|---|---|---|
| C47 | 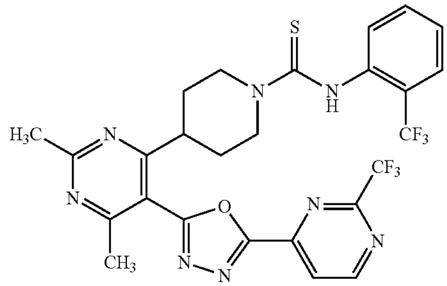 [SMILES: Cc1nc(C)c(-c2nnc(-c3ccnc(C(F)(F)F)n3)o2)c(C2CCN(C(=S)Nc3ccccc3C(F)(F)F)CC2)n1] | 4-(2,6-dimethyl-5-(5-(2-(trifluoromethyl)pyrimidin-4-yl)-1,3,4-oxadiazol-2-yl)pyrimidin-4-yl)-N-(2-(trifluoromethyl)phenyl)piperidine-1-carbothioamide |
| C48 | 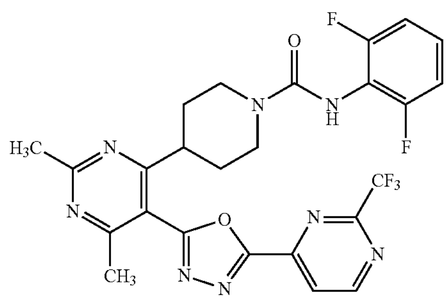 [SMILES: Cc1nc(C)c(-c2nnc(-c3ccnc(C(F)(F)F)n3)o2)c(C2CCN(C(=O)Nc3c(F)cccc3F)CC2)n1] | 4-(2-amino-6-methyl-5-(5-(2-(trifluoromethyl)pyrimidin-4-yl)-1,3,4-oxadiazol-2-yl)pyrimidin-4-yl)-N-(2,6-difluorophenyl)piperidine-1-carboxamide |
| C49 | 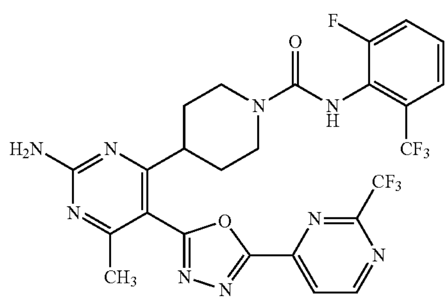 | 4-(2-amino-6-methyl-5-(5-(2-(trifluoromethyl)pyrimidin-4-yl)-1,3,4-oxadiazol-2-yl)pyrimidin-4-yl)-N-(2-fluoro-6-(trifluoromethyl)phenyl)piperidine-1-carboxamide |
| C50 | 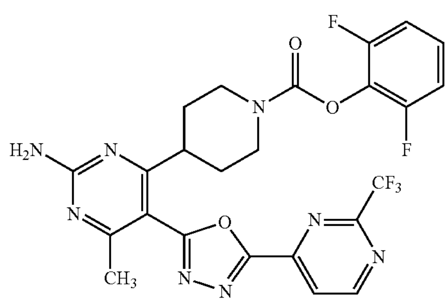 [SMILES: Cc1nc(N)nc(C2CCN(C(=O)Oc3c(F)cccc3F)CC2)c1-c1nnc(-c2ccnc(C(F)(F)F)n2)o1] | 2,6-difluorophenyl 4-(2-amino-6-methyl-5-(5-(2-(trifluoromethyl)pyrimidin-4-yl)-1,3,4-oxadiazol-2-yl)pyrimidin-4-yl)piperidine-1-carboxylate |
| C51 | 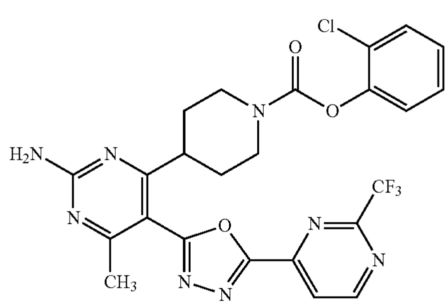 | 2-chlorophenyl 4-(2-amino-6-methyl-5-(5-(2-(trifluoromethyl)pyrimidin-4-yl)-1,3,4-oxadiazol-2-yl)pyrimidin-4-yl)piperidine-1-carboxylate |

TABLE 5-continued

| Cpd | Structure | Chemical Name |
|---|---|---|
| C52 | 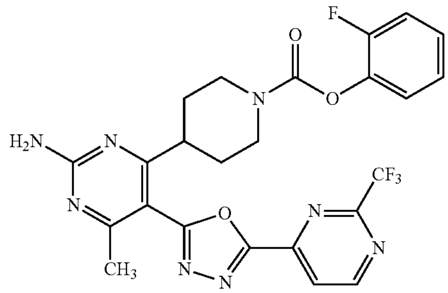 [SMILES: Cc1nc(N)nc(C2CCN(C(=O)Oc3ccccc3F)CC2)c1-c1nnc(-c2ccnc(C(F)(F)F)n2)o1] | 2-fluorophenyl 4-(2-amino-6-methyl-5-(5-(2-(trifluoromethyl)pyrimidin-4-yl)-1,3,4-oxadiazol-2-yl)pyrimidin-4-yl)piperidine-1-carboxylate |
| C53 | 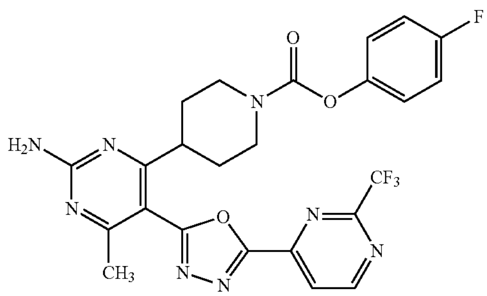 [SMILES: Cc1nc(N)nc(C2CCN(C(=O)Oc3ccc(F)cc3)CC2)c1-c1nnc(-c2ccnc(C(F)(F)F)n2)o1] | 4-fluorophenyl 4-(2-amino-6-methyl-5-(5-(2-(trifluoromethyl)pyrimidin-4-yl)-1,3,4-oxadiazol-2-yl)pyrimidin-4-yl)piperidine-1-carboxylate |
| C54 | 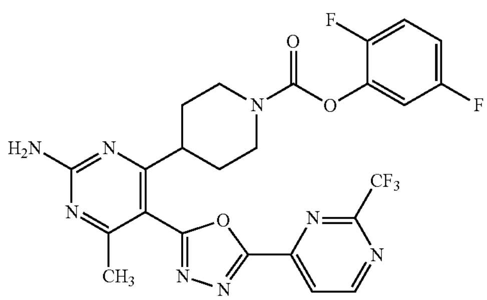 [SMILES: Cc1nc(N)nc(C2CCN(C(=O)Oc3cc(F)ccc3F)CC2)c1-c1nnc(-c2ccnc(C(F)(F)F)n2)o1] | 2,5-difluorophenyl 4-(2-amino-6-methyl-5-(5-(2-(trifluoromethyl)pyrimidin-4-yl)-1,3,4-oxadiazol-2-yl)pyrimidin-4-yl)piperidine-1-carboxylate |
| C55 | 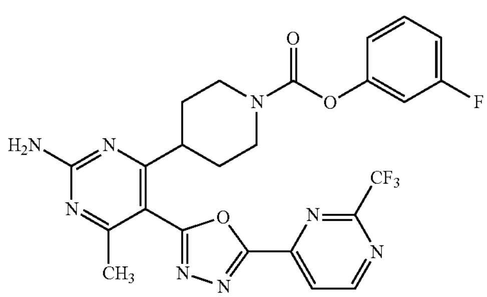 [SMILES: Cc1nc(N)nc(C2CCN(C(=O)Oc3cccc(F)c3)CC2)c1-c1nnc(-c2ccnc(C(F)(F)F)n2)o1] | 3-fluorophenyl 4-(2-amino-6-methyl-5-(5-(2-(trifluoromethyl)pyrimidin-4-yl)-1,3,4-oxadiazol-2-yl)pyrimidin-4-yl)piperidine-1-carboxylate |
| C56 | 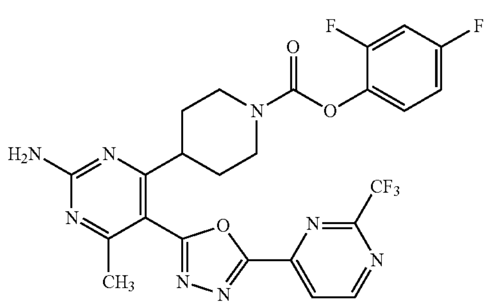 [SMILES: Cc1nc(N)nc(C2CCN(C(=O)Oc3ccc(F)cc3F)CC2)c1-c1nnc(-c2ccnc(C(F)(F)F)n2)o1] | 2,4-difluorophenyl 4-(2-amino-6-methyl-5-(5-(2-(trifluoromethyl)pyrimidin-4-yl)-1,3,4-oxadiazol-2-yl)pyrimidin-4-yl)piperidine-1-carboxylate |

TABLE 5-continued

| Cpd | Structure | Chemical Name |
|---|---|---|
| C57 | 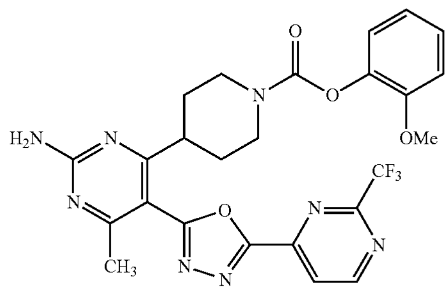 [SMILES: COc1ccccc1OC(=O)N1CCC(c2nc(N)nc(C)c2-c2nnc(-c3ccnc(C(F)(F)F)n3)o2)CC1] | 2-methoxyphenyl 4-(2-amino-6-methyl-5-(5-(2-(trifluoromethyl)pyrimidin-4-yl)-1,3,4-oxadiazol-2-yl)pyrimidin-4-yl)piperidine-1-carboxylate |
| C58 | 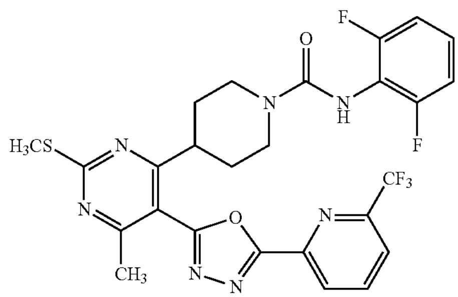 | N-(2,6-difluorophenyl)-4-(6-methyl-2-(methylthio)-5-(5-(6-(trifluoromethyl)pyridin-2-yl)-1,3,4-oxadiazol-2-yl)pyrimidin-4-yl)piperidine-1-carboxamide |
| C59 | 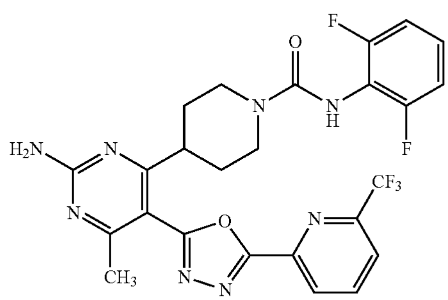 [SMILES: Cc1nc(N)nc(C2CCN(C(=O)Nc3c(F)cccc3F)CC2)c1-c1nnc(-c2cccc(C(F)(F)F)n2)o1] | 4-(2-amino-6-methyl-5-(5-(6-(trifluoromethyl)pyridin-2-yl)-1,3,4-oxadiazol-2-yl)pyrimidin-4-yl)-N-(2,6-difluorophenyl)piperidine-1-carboxamide |
| C60 | 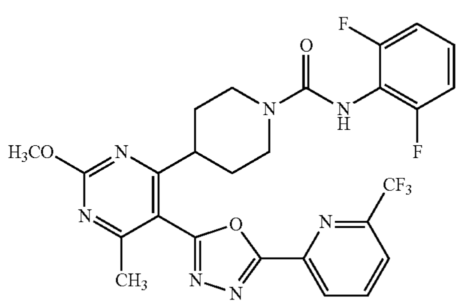 | N-(2,6-difluorophenyl)-4-(2-methoxy-6-methyl-5-(5-(6-(trifluoromethyl)pyridin-2-yl)-1,3,4-oxadiazol-2-yl)pyrimidin-4-yl)piperidine-1-carboxamide |
| C61 | 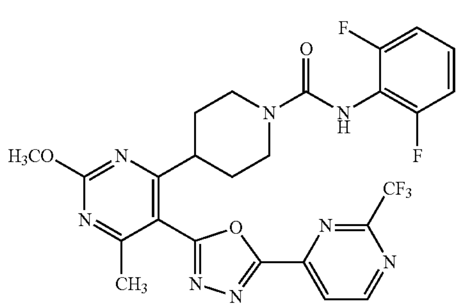 | N-(2,6-difluorophenyl)-4-(2-methoxy-6-methyl-5-(5-(2-(trifluoromethyl)pyrimidin-4-yl)-1,3,4-oxadiazol-2-yl)pyrimidin-4-yl)piperidine-1-carboxamide |

TABLE 5-continued

| Cpd | Structure | Chemical Name |
|---|---|---|
| C62 | 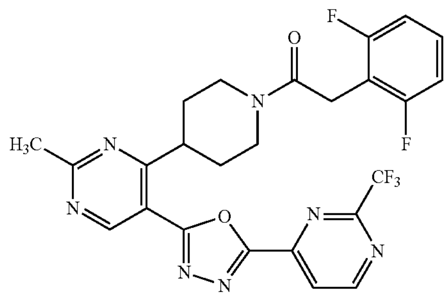 [SMILES: Cc1ncc(-c2nnc(-c3ccnc(C(F)(F)F)n3)o2)c(C2CCN(C(=O)Cc3c(F)cccc3F)CC2)n1] | 2-(2,6-difluorophenyl)-1-(4-(2-methyl-5-(5-(2-(trifluoromethyl)pyrimidin-4-yl)-1,3,4-oxadiazol-2-yl)pyrimidin-4-yl)piperidin-1-yl)ethanone |
| C63 | 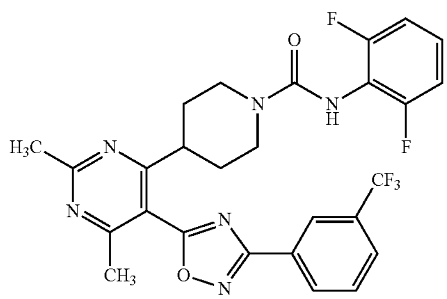 [SMILES: Cc1nc(C)c(-c2nc(-c3cccc(C(F)(F)F)c3)no2)c(C2CCN(C(=O)Nc3c(F)cccc3F)CC2)n1] | N-(2,6-difluorophenyl)-4-(2,6-dimethyl-5-(3-(3-(trifluoromethyl)phenyl)-1,2,4-oxadiazol-5-yl)pyrimidin-4-yl)piperidine-1-carboxamide |
| C64 | 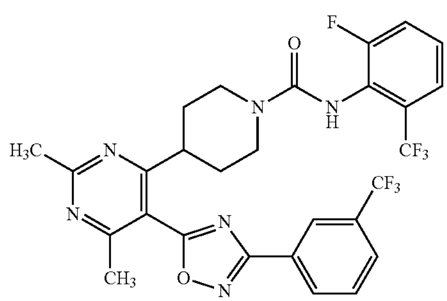 [SMILES: Cc1nc(C)c(-c2nc(-c3cccc(C(F)(F)F)c3)no2)c(C2CCN(C(=O)Nc3c(F)cccc3C(F)(F)F)CC2)n1] | 4-(2,6-dimethyl-5-(3-(3-(trifluoromethyl)phenyl)-1,2,4-oxadiazol-5-yl)pyrimidin-4-yl)-N-(2-fluoro-6-(trifluoromethyl)phenyl)piperidine-1-carboxamide |
| C65 | 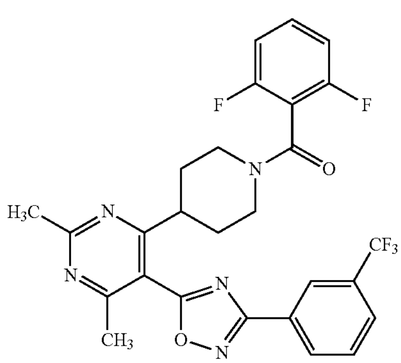 [SMILES: Cc1nc(C)c(-c2nc(-c3cccc(C(F)(F)F)c3)no2)c(C2CCN(C(=O)c3c(F)cccc3F)CC2)n1] | (2,6-difluorophenyl)(4-(2,6-dimethyl-5-(3-(3-(trifluoromethyl)phenyl)-1,2,4-oxadiazol-5-yl)pyrimidin-4-yl)piperidin-1-yl)methanone |
| C66 | 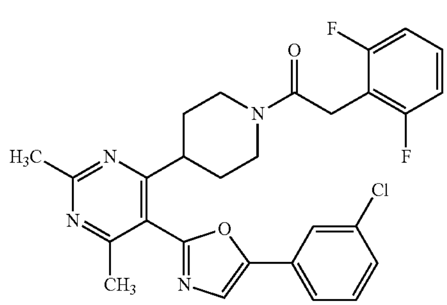 [SMILES: Cc1nc(C)c(-c2ncc(-c3cccc(Cl)c3)o2)c(C2CCN(C(=O)Cc3c(F)cccc3F)CC2)n1] | 1-(4-(5-(5-(3-chlorophenyl)oxazol-2-yl)-2,6-dimethylpyrimidin-4-yl)piperidin-1-yl)-2-(2,6-difluorophenyl)ethanone |

TABLE 5-continued

| Cpd | Structure | Chemical Name |
| --- | --- | --- |
| C67 | 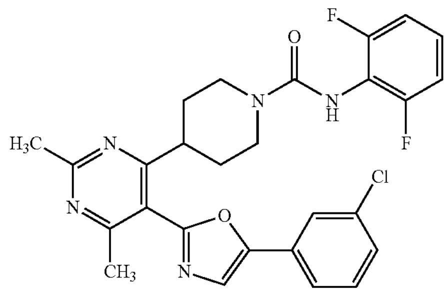 [SMILES: Cc1nc(C)c(-c2ncc(-c3cccc(Cl)c3)o2)c(C2CCN(C(=O)Nc3c(F)cccc3F)CC2)n1] | 4-(5-(5-(3-chlorophenyl)oxazol-2-yl)-2,6-dimethylpyrimidin-4-yl)-N-(2,6-difluorophenyl)piperidine-1-carboxamide |
| C68 | 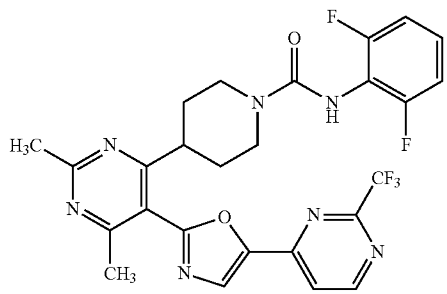 [SMILES: Cc1nc(C)c(-c2ncc(-c3ccnc(C(F)(F)F)n3)o2)c(C2CCN(C(=O)Nc3c(F)cccc3F)CC2)n1] | N-(2,6-difluorophenyl)-4-(2,6-dimethyl-5-(5-(2-(trifluoromethyl)pyrimidin-4-yl)oxazol-2-yl)pyrimidin-4-yl)piperidine-1-carboxamide |
| C69 | 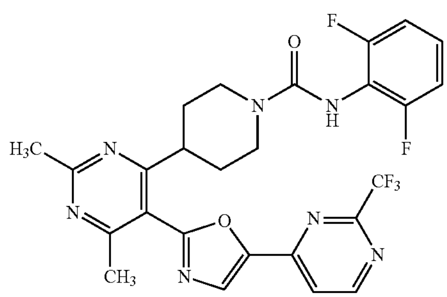 [SMILES: Cc1nc(C)c(-c2ncc(-c3ccnc(C(F)(F)F)n3)o2)c(C2CCN(C(=O)Nc3c(F)cccc3F)CC2)n1] | 4-(2-amino-6-methyl-5-(5-(2-(trifluoromethyl)pyrimidin-4-yl)oxazol-2-yl)pyrimidin-4-yl)-N-(2,6-difluorophenyl)piperidine-1-carboxamide |
| C70 | 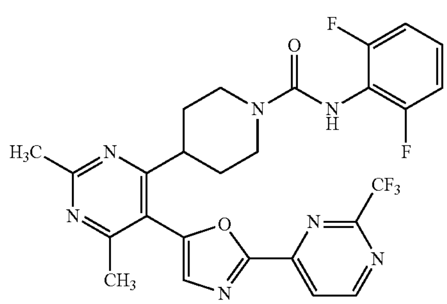 [SMILES: Cc1nc(C)c(-c2cnc(-c3ccnc(C(F)(F)F)n3)o2)c(C2CCN(C(=O)Nc3c(F)cccc3F)CC2)n1] | 4-(2-amino-6-methyl-5-(2-(2-(trifluoromethyl)pyrimidin-4-yl)oxazol-5-yl)pyrimidin-4-yl)-N-(2,6-difluorophenyl)piperidine-1-carboxamide |
| C71 | 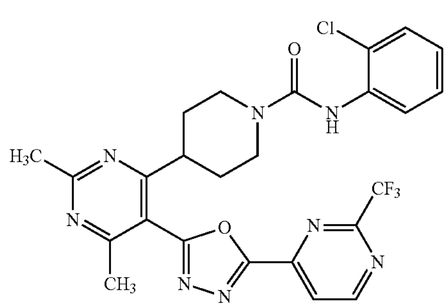 [SMILES: Cc1nc(C)c(-c2nnc(-c3ccnc(C(F)(F)F)n3)o2)c(C2CCN(C(=O)Nc3ccccc3Cl)CC2)n1] | 4-(2-amino-6-methyl-5-(5-(2-(trifluoromethyl)pyrimidin-4-yl)-1,3,4-oxadiazol-2-yl)pyrimidin-4-yl)-N-(2-chlorophenyl)piperidine-1-carboxamide |

TABLE 6

[Core structure: pyrimidine with R¹ at 2-position, 4-position bearing piperidine N-acylated with C(=O)-G-Q¹⁶; 5-position bearing C(OH)(CH₃)-CH₂-Q¹⁰]

| Cpd | R¹ | G | Q¹⁰ | Q¹⁶ | Chemical Name |
|---|---|---|---|---|---|
| D1 | Me | CH₂ | NH-(3-chlorophenyl) | 2,6-difluorophenyl | 1-(4-(5-(1-((3-chlorophenyl)amino)-2-hydroxypropan-2-yl)-2-methylpyrimidin-4-yl)piperidin-1-yl)-2-(2,6-difluorophenyl)ethanone |
| D2 | Me | CH₂ | NH-(6-(trifluoromethyl)pyridin-2-yl) | 2,6-difluorophenyl | 2-(2,6-difluorophenyl)-1-(4-(5-(2-hydroxy-1-((6-(trifluoromethyl)pyridin-2-yl)amino)propan-2-yl)-2-methylpyrimidin-4-yl)piperidin-1-yl)ethanone |
| D3 | Me | CH₂ | NH-(3,5-dimethylphenyl) | 2,6-difluorophenyl | 2-(2,6-difluorophenyl)-1-(4-(5-(1-((3,5-dimethylphenyl)amino)-2-hydroxypropan-2-yl)-2-methylpyrimidin-4-yl)piperidin-1-yl)ethanone |
| D4 | Me | CH₂ | NH-(3-(trifluoromethyl)phenyl) | 2,6-difluorophenyl | 2-(2,6-difluorophenyl)-1-(4-(5-(2-hydroxy-1-((3-(trifluoromethyl)phenyl)amino)propan-2-yl)-2-methylpyrimidin-4-yl)piperidin-1-yl)ethanone |
| D5 | Me | CH₂ | NH-(2-(trifluoromethyl)pyrimidin-4-yl) | 2,6-difluorophenyl | 2-(2,6-difluorophenyl)-1-(4-(5-(2-hydroxy-1-((2-(trifluoromethyl)pyrimidin-4-yl)amino)propan-2-yl)-2-methylpyrimidin-4-yl)piperidin-1-yl)ethanone |
| D6 | Me | CH₂ | NH-(4,6-dimethylpyridin-2-yl) | 2,6-difluorophenyl | 2-(2,6-difluorophenyl)-1-(4-(5-(1-((4,6-dimethylpyridin-2-yl)amino)-2-hydroxypropan-2-yl)-2-methylpyrimidin-4-yl)piperidin-1-yl)ethanone |
| D7 | Me | CH₂ | NH-(2-methylpyridin-4-yl) | 2,6-difluorophenyl | 1-(4-(5-(1-((2-chloropyridin-4-yl)amino)-2-hydroxypropan-2-yl)-2-methylpyrimidin-4-yl)piperidin-1-yl)-2-(2,6-difluorophenyl)ethanone |
| D8 | Me | CH₂ | NH-(4-(trifluoromethyl)pyridin-2-yl) | 2,6-difluorophenyl | 2-(2,6-difluorophenyl)-1-(4-(5-(2-hydroxy-1-((4-(trifluoromethyl)pyridin-2-yl)amino)propan-2-yl)-2-methylpyrimidin-4-yl)piperidin-1-yl)ethanone |

TABLE 6-continued

| Cpd | R¹ | G | Q¹⁰ | Q¹⁶ | Chemical Name |
|---|---|---|---|---|---|
| D9 | Me | CH₂ | 2-amino-4-methylpyridine linked via NH | 2,6-difluorophenyl | 2-(2,6-difluorophenyl)-1-(4-(5-(2-hydroxy-1-((4-methylpyridin-2-yl)amino)propan-2-yl)-2-methylpyrimidin-4-yl)piperidin-1-yl)ethanone |
| D10 | Me | CH₂ | 1-methyl-1H-pyrazol-3-yl linked via NH | 2,6-difluorophenyl | 2-(2,6-difluorophenyl)-1-(4-(5-(2-hydroxy-1-((1-methyl-1H-pyrazol-3-yl)amino)propan-2-yl)-2-methylpyrimidin-4-yl)piperidin-1-yl)ethanone |
| D11 | Me | CH₂ | 3,5-dimethylphenoxy | 2,6-difluorophenyl | 2-(2,6-difluorophenyl)-1-(4-(5-(1-(3,5-dimethylphenoxy)-2-hydroxypropan-2-yl)-2-methylpyrimidin-4-yl)piperidin-1-yl)ethanone |
| D12 | Me | CH₂ | 3-chlorophenoxy | 2,6-difluorophenyl | 1-(4-(5-(1-(3-chlorophenoxy)-2-hydroxypropan-2-yl)-2-methylpyrimidin-4-yl)piperidin-1-yl)-2-(2,6-difluorophenyl)ethanone |
| D13 | Me | CH₂ | (5-chloropyridin-3-yl)oxy | 2,6-difluorophenyl | 1-(4-(5-(1-((5-chloropyridin-3-yl)oxy)-2-hydroxypropan-2-yl)-2-methylpyrimidin-4-yl)piperidin-1-yl)-2-(2,6-difluorophenyl)ethanone |
| D14 | Me | CH₂ | pyridin-3-yloxy | 2,6-difluorophenyl | 2-(2,6-difluorophenyl)-1-(4-(5-(2-hydroxy-1-(pyridin-3-yloxy)propan-2-yl)-2-methylpyrimidin-4-yl)piperidin-1-yl)ethanone |
| D15 | Me | CH₂ | 3,5-dimethylphenyl (CH₂-linked) | 2,6-difluorophenyl | 2-(2,6-difluorophenyl)-1-(4-(5-(4-(3,5-dimethylphenyl)-2-hydroxybutan-2-yl)-2-methylpyrimidin-4-yl)piperidin-1-yl)ethanone |
| D16 | Me | NH | 6-(trifluoromethyl)pyridin-2-yl linked via NH | 2,6-difluorophenyl | N-(2,6-Difluorophenyl)-4-[5-(1-hydroxy-1-methyl-2-{[6-(trifluoromethyl)pyridin-2-yl]amino}ethyl)-2-methylpyrimidin-4-yl]piperidine-1-carboxamide |

TABLE 6-continued

| Cpd | R¹ | G | Q¹⁰ | Q¹⁶ | Chemical Name |
|---|---|---|---|---|---|
| D17 | Me | NH | (NH-pyrimidine-CF₃) | 2,6-difluorophenyl | N-(2,6-Difluorophenyl)-4-[5-(1-hydroxy-1-methyl-2-{[2-(trifluoromethyl)pyrimidin-4-yl]amino}ethyl)-2-methylpyrimidin-4-yl]piperidine-1-carboxamide |
| D18 | Me | NH | (NH-pyrimidine-CF₃) | 2-F-6-CF₃-phenyl | N-[2-Fluoro-6-(trifluoromethyl)phenyl]-4-[5-(1-hydroxy-1-methyl-2-{[2-(trifluoromethyl)pyrimidin-4-yl]amino}ethyl)-2-methylpyrimidin-4-yl]piperidine-1-carboxamide |
| D19 | Me | NH | (N(Me)-pyrimidine-CF₃) | 2,6-difluorophenyl | N-(2,6-Difluorophenyl)-4-[5-(1-hydroxy-1-methyl-2-{methyl[2-(trifluoromethyl)pyrimidin-4-yl]amino}ethyl)-2-methylpyrimidin-4-yl]piperidine-1-carboxamide |
| D20 | Me | CH₂ | (N(Me)-pyrimidine-CF₃) | 2,6-difluorophenyl | 2-(4-{1-[(2,6-Difluorophenyl)acetyl]piperidin-4-yl}-2-methylpyrimidin-5-yl)-1-{methyl[2-(trifluoromethyl)pyrimidin-4-yl]amino}propan-2-ol |
| D21 | Me | NH | (NH-pyrimidine-CF₃, 4-position) | 2,6-difluorophenyl | N-(2,6-Difluorophenyl)-4-[5-(1-hydroxy-1-methyl-2-{[4-(trifluoromethyl)pyrimidin-2-yl]amino}ethyl)-2-methylpyrimidin-4-yl]piperidine-1-carboxamide |
| D22 | Me | NH | (NH-pyrimidine-CF₃, 4-position) | 2-F-6-CF₃-phenyl | N-[2-Fluoro-6-(trifluoromethyl)phenyl]-4-[5-(1-hydroxy-1-methyl-2-{[4-(trifluoromethyl)pyrimidin-2-yl]amino}ethyl)-2-methylpyrimidin-4-yl]piperidine-1-carboxamide |
| D23 | Me | CH₂ | (NH-pyrimidine-CF₃, 4-position) | 2,6-difluorophenyl | 2-(4-{1-[(2,6-Difluorophenyl)acetyl]piperidin-4-yl}-2-methylpyrimidin-5-yl)-1-{[4-(trifluoromethyl)pyrimidin-2-yl]amino}propan-2-ol |
| D24 | Me | CH₂ | (O-pyridine-CF₃) | 2,6-difluorophenyl | 2-(4-{1-[(2,6-difluorophenyl)acetyl]piperidin-4-yl}-2-methylpyrimidin-5-yl)-1-{[6-(trifluoromethyl)pyridin-2-yl]oxy}propan-2-ol |

TABLE 6-continued

| Cpd | R¹ | G | Q¹⁰ | Q¹⁶ | Chemical Name |
|---|---|---|---|---|---|
| D25 | Me | NH | O-pyridine-CF₃ (6-trifluoromethylpyridin-2-yloxy) | 2,6-difluorophenyl | N-(2,6-difluorophenyl)-4-[5-(1-hydroxy-1-methyl-2-{[6-(trifluoromethyl)pyridin-2-yl]oxy}ethyl)-2-methylpyrimidin-4-yl]piperidine-1-carboxamide |
| D26 | SMe | NH | O-pyridine-CF₃ (6-trifluoromethylpyridin-2-yloxy) | 2,6-difluorophenyl | N-(2,6-Difluorophenyl)-4-[5-(1-hydroxy-1-methyl-2-{[6-(trifluoromethyl)pyridin-2-yl]oxy}ethyl)-2-(methylthio)pyrimidin-4-yl]piperidine-1-carboxamide |
| D27 | NH₂ | NH | O-pyridine-CF₃ (6-trifluoromethylpyridin-2-yloxy) | 2,6-difluorophenyl | 4-[2-Amino-5-(1-hydroxy-1-methyl-2-{[6-(trifluoromethyl)pyridin-2-yl]oxy}ethyl)pyrimidin-4-yl]-N-(2,6-difluorophenyl)piperidine-1-carboxamide |
| D28 | SMe | NH | O-pyrimidine-CF₃ (2-trifluoromethylpyrimidin-4-yloxy) | 2,6-difluorophenyl | N-(2,6-Difluorophenyl)-4-[5-(1-hydroxy-1-methyl-2-{[2-(trifluoromethyl)pyrimidin-4-yl]oxy}ethyl)-2-(methylthio)pyrimidin-4-yl]piperidine-1-carboxamide |
| D29 | NH₂ | NH | O-pyrimidine-CF₃ (2-trifluoromethylpyrimidin-4-yloxy) | 2,6-difluorophenyl | 4-[2-Amino-5-(1-hydroxy-1-methyl-2-{[2-(trifluoromethyl)pyrimidin-4-yl]oxy}ethyl)pyrimidin-4-yl]-N-(2,6-difluorophenyl)piperidine-1-carboxamide |
| D30 | NH₂ | CH₂ | O-pyrimidine-CF₃ (2-trifluoromethylpyrimidin-4-yloxy) | 2,6-difluorophenyl | 2-(2-Amino-4-{1-[(2,6-difluorophenyl)acetyl]piperidin-4-yl}pyrimidin-5-yl)-1-{[2-(trifluoromethyl)pyrimidin-4-yl]oxy}propan-2-ol |
| D31 | NHAc | NH | O-pyrimidine-CF₃ (2-trifluoromethylpyrimidin-4-yloxy) | 2,6-difluorophenyl | 4-[2-(Acetylamino)-5-(1-hydroxy-1-methyl-2-{[2-(trifluoromethyl)pyrimidin-4-yl]oxy}ethyl)pyrimidin-4-yl]-N-(2,6-difluorophenyl)piperidine-1-carboxamide |
| D32 | NHAc | NH | O-pyridine-CF₃ (6-trifluoromethylpyridin-2-yloxy) | 2,6-difluorophenyl | 4-[2-(Acetylamino)-5-(1-hydroxy-1-methyl-2-{[6-(trifluoromethyl)pyridin-2-yl]oxy}ethyl)pyrimidin-4-yl]-N-(2,6-difluorophenyl)piperidine-1-carboxamide |

TABLE 6-continued

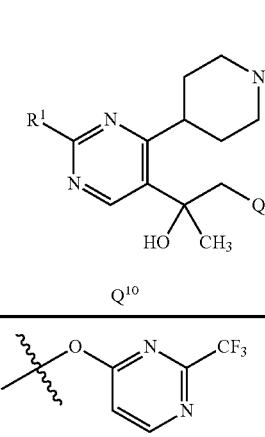

| Cpd | R¹ | G | Q¹⁰ | Q¹⁶ | Chemical Name |
|---|---|---|---|---|---|
| D33 | NHAc | CH₂ |  | 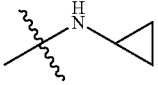 [SMILES: *NC1CC1] | N-[4-{1-[(2,6-Difluorophenyl)acetyl]piperidin-4-yl}-5-(1-hydroxy-1-methyl-2-{[2-(trifluoromethyl)pyrimidin-4-yl]oxy}ethyl)pyrimidin-2-yl]acetamide |
| D34 | 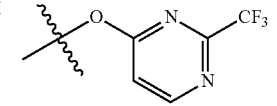 [SMILES: *Oc1ccnc(C(F)(F)F)n1] | NH | 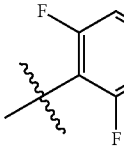 | 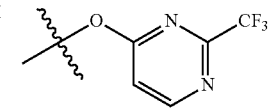 [SMILES: *Oc1ccnc(C(F)(F)F)n1] | 4-[2-(Cyclopropylamino)-5-(1-hydroxy-1-methyl-2-{[2-(trifluoromethyl)pyrimidin-4-yl]oxy}ethyl)pyrimidin-4-yl]-N-(2,6-difluorophenyl)piperidine-1-carboxamide |
| D35 | NHEt | NH | 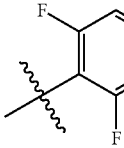 | 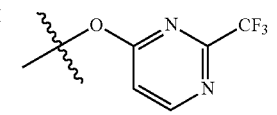 [SMILES: *Oc1ccnc(C(F)(F)F)n1] | N-(2,6-Difluorophenyl)-4-[2-(ethylamino)-5-(1-hydroxy-1-methyl-2-{[2-(trifluoromethyl)pyrimidin-4-yl]oxy}ethyl)pyrimidin-4-yl]piperidine-1-carboxamide |
| D36 | NHMe | NH | 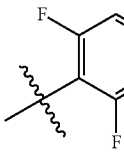 | 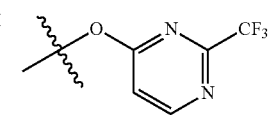 [SMILES: *Oc1ccnc(C(F)(F)F)n1] | N-(2,6-Difluorophenyl)-4-[5-(1-hydroxy-1-methyl-2-{[2-(trifluoromethyl)pyrimidin-4-yl]oxy}ethyl)-2-(methylamino)pyrimidin-4-yl]piperidine-1-carboxamide |
| D37 | 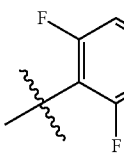 | NH | 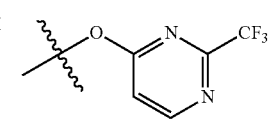 [SMILES: *Oc1ccnc(C(F)(F)F)n1] | 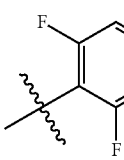 | 4-[2-({[2,4-Bis(methyloxy)phenyl]methyl}amino)-5-(1-hydroxy-1-methyl-2-{[2-(trifluoromethyl)pyrimidin-4-yl]oxy}ethyl)pyrimidin-4-yl]-N-(2,6-difluorophenyl)piperidine-1-carboxamide |
| D38 | NMe2 | NH | 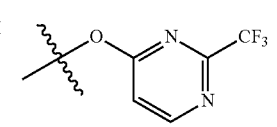 [SMILES: *Oc1ccnc(C(F)(F)F)n1] | | N-(2,6-Difluorophenyl)-4-[2-(dimethylamino)-5-(1-hydroxy-1-methyl-2-{[2-(trifluoromethyl)pyrimidin-4-yl]oxy}ethyl)pyrimidin-4-yl]piperidine-1-carboxamide |
| D39 | NHCH₂CHF₂ | NH | 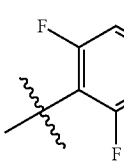 | 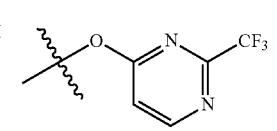 [SMILES: *Oc1ccnc(C(F)(F)F)n1] | 4-{2-[(2,2-Difluoroethyl)amino]-5-(1-hydroxy-1-methyl-2-{[2-(trifluoromethyl)pyrimidin-4-yl]oxy}ethyl)pyrimidin-4-yl}-N-(2,6-difluorophenyl)piperidine-1-carboxamide |
| D40 | OiPr | NH | 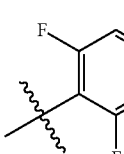 | | N-(2,6-Difluorophenyl)-4-{5-(1-hydroxy-1-methyl-2-{[2-(trifluoromethyl)pyrimidin-4-yl]oxy}ethyl)-2-[(1-methylethyl)oxy]pyrimidin-4-yl}piperidine-1-carboxamide |

TABLE 6-continued

| Cpd | R¹ | G | Q¹⁰ | Q¹⁶ | Chemical Name |
|---|---|---|---|---|---|
| D41 | OCH₂CHF₂ | NH | 4-oxy-2-(trifluoromethyl)pyrimidine | 2,6-difluorophenyl | 4-{2-[(2,2-Difluoroethyl)oxy]-5-(1-hydroxy-1-methyl-2-{[2-(trifluoromethyl)pyrimidin-4-yl]oxy}ethyl)pyrimidin-4-yl}-N-(2,6-difluorophenyl)piperidine-1-carboxamide |
| D42 | OCH(CH₂F)₂ | NH | 4-oxy-2-(trifluoromethyl)pyrimidine | 2,6-difluorophenyl | N-(2,6-Difluorophenyl)-4-[2-{[2-fluoro-1-(fluoromethyl)ethyl]oxy}-5-(1-hydroxy-1-methyl-2-{[2-(trifluoromethyl)pyrimidin-4-yl]oxy}ethyl)pyrimidin-4-yl]piperidine-1-carboxamide |
| D43 | OCH₂CH₂F | NH | 4-oxy-2-(trifluoromethyl)pyrimidine | 2,6-difluorophenyl | N-(2,6-Difluorophenyl)-4-{2-[(2-fluoroethyl)oxy]-5-(1-hydroxy-1-methyl-2-{[2-(trifluoromethyl)pyrimidin-4-yl]oxy}ethyl)pyrimidin-4-yl}piperidine-1-carboxamide |
| D44 | OMe | NH | 4-oxy-2-(trifluoromethyl)pyrimidine | 2,6-difluorophenyl | N-(2,6-Difluorophenyl)-4-[5-(1-hydroxy-1-methyl-2-{[2-(trifluoromethyl)pyrimidin-4-yl]oxy}ethyl)-2-(methyloxy)pyrimidin-4-yl]piperidine-1-carboxamide |
| D45 | OMe | NH | 2-oxy-6-(trifluoromethyl)pyridine | 2,6-difluorophenyl | N-(2,6-Difluorophenyl)-4-[5-(1-hydroxy-1-methyl-2-{[6-(trifluoromethyl)pyridin-2-yl]oxy}ethyl)-2-(methyloxy)pyrimidin-4-yl]piperidine-1-carboxamide |
| D46 | NH₂ | O | 4-oxy-2-(trifluoromethyl)pyrimidine | 2,6-difluorophenyl | 2,6-Difluorophenyl 4-[2-amino-5-(1-hydroxy-1-methyl-2-{[2-(trifluoromethyl)pyrimidin-4-yl]oxy}ethyl)pyrimidin-4-yl]piperidine-1-carboxylate |
| D47 | Me | NH | 2-oxy-6-(trifluoromethyl)pyridine | 2,6-difluorophenyl | N-(2,6-Difluorophenyl)-4-(5-{1-hydroxy-1-methyl-2-[6-(trifluoromethyl)pyridin-2-yl]ethyl}-2-methylpyrimidin-4-yl)piperidine-1-carboxamide |
| D48 | NH₂ | O | 2-oxy-6-(trifluoromethyl)pyridine | 2,6-difluorophenyl | 2,6-Difluorophenyl 4-[2-amino-5-(1-hydroxy-1-methyl-2-{[6-(trifluoromethyl)pyridin-2-yl]oxy}ethyl)pyrimidin-4-yl]piperidine-1-carboxylate |

TABLE 6-continued

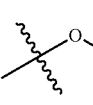

| Cpd | R¹ | G | Q¹⁰ | Q¹⁶ | Chemical Name |
|---|---|---|---|---|---|
| D49 | NH₂ | O | 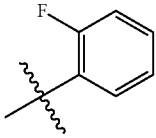 [SMILES: *c1ccccc1F] | 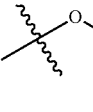 | 2-Fluorophenyl 4-[2-amino-5-(1-hydroxy-1-methyl-2-{[2-(trifluoromethyl)pyrimidin-4-yl]oxy}ethyl)pyrimidin-4-yl]piperidine-1-carboxylate |
| D50 | NH₂ | O | 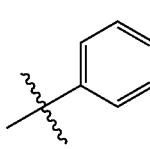 | 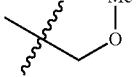 | 4-Fluorophenyl 4-[2-amino-5-(1-hydroxy-1-methyl-2-{[2-(trifluoromethyl)pyrimidin-4-yl]oxy}ethyl)pyrimidin-4-yl]piperidine-1-carboxylate |

TABLE 7

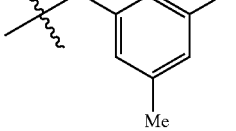

| Cpd | R¹¹ | Q¹¹ | Chemical Name |
|---|---|---|---|
| E1 | 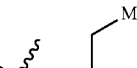 | 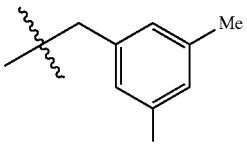 | 2-(2,6-difluorophenyl)-1-(4-(5-(2-((3,5-dimethylbenzyl)oxy)-1-methoxypropan-2-yl)-2-methylpyrimidin-4-yl)piperidin-1-yl)ethanone |
| E2 |  | | 2-(2,6-difluorophenyl)-1-(4-(5-(2-((3,5-dimethylbenzyl)oxy)-1-ethoxypropan-2-yl)-2-methylpyrimidin-4-yl)piperidin-1-yl)ethanone |
| E3 | 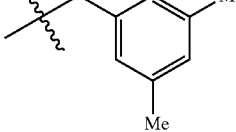 | | 2-(2,6-difluorophenyl)-1-(4-(5-(1-(2,3-dihydroxypropoxy)-2-((3,5-dimethylbenzyl)oxy)propan-2-yl)-2-methylpyrimidin-4-yl)piperidin-1-yl)ethanone |

TABLE 7-continued

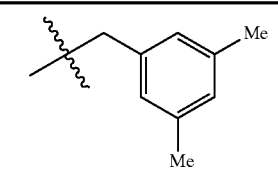

| Cpd | R[11] | Q[11] | Chemical Name |
|---|---|---|---|
| E4 | —CH₂OH | 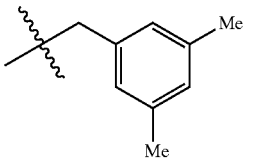 | 2-(2,6-difluorophenyl)-1-(4-(5-(2-((3,5-dimethylbenzyl)oxy)-1-hydroxypropan-2-yl)-2-methylpyrimidin-4-yl)piperidin-1-yl)ethanone |
| E5 | Me | 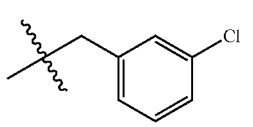 [SMILES: *Cc1cccc(Cl)c1] | 2-(2,6-difluorophenyl)-1-(4-(5-(2-((3,5-dimethylbenzyl)oxy)propan-2-yl)-2-methylpyrimidin-4-yl)piperidin-1-yl)ethanone |
| E6 | Me | 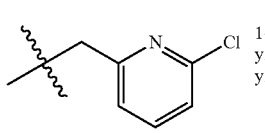 | 1-(4-(5-(2-((3-chlorobenzyl)oxy)propan-2-yl)-2-methylpyrimidin-4-yl)piperidin-1-yl)-2-(2,6-difluorophenyl)ethanone |
| E7 | Me | 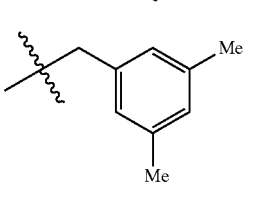 | 1-(4-(5-(2-((6-chloropyridin-2-yl)methoxy)propan-2-yl)-2-methylpyrimidin-4-yl)piperidin-1-yl)-2-(2,6-difluorophenyl)ethanone |
| E8 | 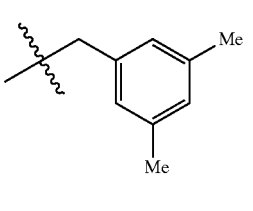 [SMILES: *Cc1cc(C)cc(C)c1] | | 2-(2,6-difluorophenyl)-1-(4-(5-(1-(2,3-dihydroxypropoxy)-2-((3,5-dimethylbenzyl)oxy)propan-2-yl)-2-methylpyrimidin-4-yl)piperidin-1-yl)ethanone |
| E9 | 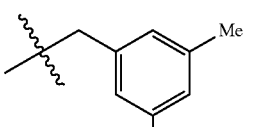 | | 2-(2,6-difluorophenyl)-1-(4-(5-(1-(2,3-dihydroxypropoxy)-2-((3,5-dimethylbenzyl)oxy)propan-2-yl)-2-methylpyrimidin-4-yl)piperidin-1-yl)ethanone |
| E10 | H | 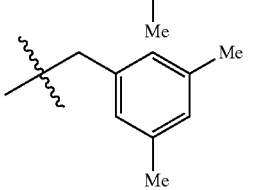 | 2-(2,6-difluorophenyl)-1-(4-(5-(((3,5-dimethylbenzyl)oxy)methyl)-2-methylpyrimidin-4-yl)piperidin-1-yl)ethanone |
| E11 | H | | 2-(2,6-difluorophenyl)-1-(4-(5-(1-((3,5-dimethylbenzyl)oxy)ethyl)-2-methylpyrimidin-4-yl)piperidin-1-yl)ethanone |

TABLE 8

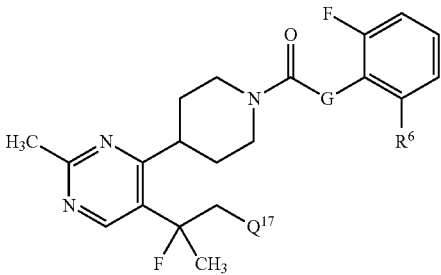

| Cpd | G | R⁶ | Q¹⁷ | Chemical Name |
|---|---|---|---|---|
| E12 | NH | F | 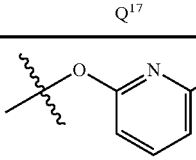 | N-(2,6-Difluorophenyl)-4-[5-(1-fluoro-1-methyl-2-{[6-(trifluoromethyl)pyridin-2-yl]oxy}ethyl)-2-methylpyrimidin-4-yl]piperidine-1-carboxamide |
| E13 | NH | CF₃ | 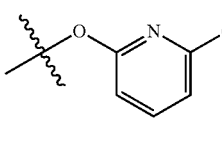 | 4-[5-(1-Fluoro-1-methyl-2-{[6-(trifluoromethyl)pyridin-2-yl]oxy}ethyl)-2-methylpyrimidin-4-yl]-N-[2-fluoro-6-(trifluoromethyl)phenyl]piperidine-1-carboxamide |
| E14 | CH₂ | F | 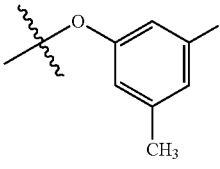 | 4-{1-[(2,6-Difluorophenyl)acetyl]piperidin-4-yl}-5-{2-[(3,5-dimethylphenyl)oxy]-1-fluoro-1-methylethyl}-2-methylpyrimidine |
| E15 | NH | F | 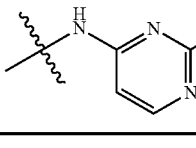 | N-(2,6-Difluorophenyl)-4-[5-(1-fluoro-1-methyl-2-{[2-(trifluoromethyl)pyrimidin-4-yl]amino}ethyl)-2-methylpyrimidin-4-yl]piperidine-1-carboxamide |

TABLE 9

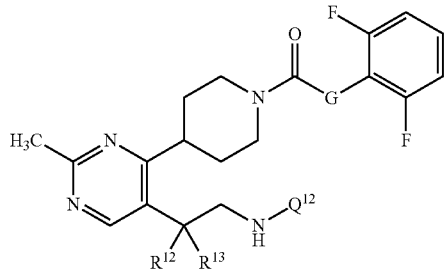

| Cpd | R¹² | R¹³ | Q¹² | G | Chemical Name |
|---|---|---|---|---|---|
| F1 | Me | Me | 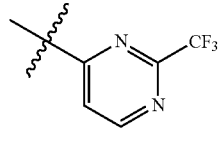 [SMILES: *c1ccnc(C(F)(F)F)n1] | CH₂ | 2-(2,6-difluorophenyl)-1-(4-(2-methyl-5-(2-methyl-1-((2-(trifluoromethyl)pyrimidin-4-yl)amino)propan-2-yl)pyrimidin-4-yl)piperidin-1-yl)ethanone |
| F2 | Me | Me | 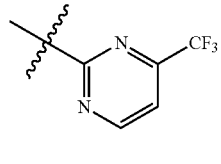 [SMILES: *c1nccc(C(F)(F)F)n1] | CH₂ | 2-(2,6-difluorophenyl)-1-(4-(2-methyl-5-(2-methyl-1-((4-(trifluoromethyl)pyrimidin-2-yl)amino)propan-2-yl)pyrimidin-4-yl)piperidin-1-yl)ethanone |

TABLE 9-continued

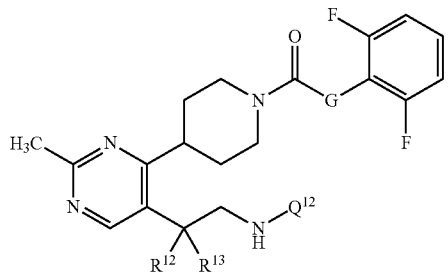

| Cpd | R¹² | R¹³ | Q¹² | G | Chemical Name |
|---|---|---|---|---|---|
| F3 | Me | Me | 6-(trifluoromethyl)pyridin-2-yl | CH₂ | N-[2-(4-{1-[(2,6-difluorophenyl)acetyl]piperidin-4-yl}-2-methylpyrimidin-5-yl)-2-methylpropyl]-6-(trifluoromethyl)pyridin-2-amine |
| F4 | Me | —CO₂Me | 2-(trifluoromethyl)pyrimidin-4-yl | CH₂ | methyl 2-(4-(1-(2-(2,6-difluorophenyl)acetyl)piperidin-4-yl)-2-methylpyrimidin-5-yl)-2-methyl-3-((2-(trifluoromethyl)pyrimidin-4-yl)amino)propanoate |
| F5 | Me | CH₂OH | 2-(trifluoromethyl)pyrimidin-4-yl | CH₂ | 2-(2,6-difluorophenyl)-1-(4-(5-(1-hydroxy-2-methyl-3-(2-(trifluoromethyl)pyrimidin-4-ylamino)propan-2-yl)-2-methylpyrimidin-4-yl)piperidin-1-yl)ethanone |
| F6 | H | H | 3,5-dimethylbenzyl | CH₂ | 2-(2,6-difluorophenyl)-1-(4-(5-(((3,5-dimethylbenzyl)amino)methyl)-2-methylpyrimidin-4-yl)piperidin-1-yl)ethanone |
| F7 | H | CF₃ | 3,5-dimethylbenzyl | CH₂ | 2-(2,6-difluorophenyl)-1-(4-(5-(1-((3,5-dimethylbenzyl)amino)-2,2,2-trifluoroethyl)-2-methylpyrimidin-4-yl)piperidin-1-yl)ethanone |
| F8 | Me | Me | 2-(trifluoromethyl)pyrimidin-4-yl | NH | N-(2,6-difluorophenyl)-4-(2-methyl-5-(2-methyl-1-((2-(trifluoromethyl)pyrimidin-4-yl)amino)propan-2-yl)pyrimidin-4-yl)piperidine-1-carboxamide |
| F9 | H | Me | 3,5-dimethylbenzyl | CH₂ | 2-(2,6-difluorophenyl)-1-(4-(5-(1-(((3,5-dimethylbenzyl)amino)ethyl)-2-methylpyrimidin-4-yl)piperidin-1-yl)ethanone |

TABLE 10

| Cpd | R¹ | R² | Chemical Name |
|---|---|---|---|
| G1 | Me | H | N'-(3-chlorophenyl)-4-(1-(2-(2,6-difluorophenyl)acetyl)piperidin-4-yl)-2-methylpyrimidine-5-carbohydrazide |
| G2 | Cyclopropyl | H | N'-(3-chlorophenyl)-2-cyclopropyl-4-(1-(2-(2,6-difluorophenyl)acetyl)piperidin-4-yl)pyrimidine-5-carbohydrazide |
| G3 | Et | H | N'-(3-chlorophenyl)-4-(1-(2-(2,6-difluorophenyl)acetyl)piperidin-4-yl)-2-ethylpyrimidine-5-carbohydrazide |
| G4 | Me | Me | N'-(3-chlorophenyl)-4-(1-(2-(2,6-difluorophenyl)acetyl)piperidin-4-yl)-2,6-dimethylpyrimidine-5-carbohydrazide |

TABLE 11

| Cpd | R¹ | R² | Q¹³ | Chemical Name |
|---|---|---|---|---|
| H1 | Me | H | 3-CF₃-phenyl | 4-(1-(2-(2,6-difluorophenyl)acetyl)piperidin-4-yl)-2-methyl-N-(3-(trifluoromethyl)phenoxy)pyrimidine-5-carboxamide |
| H2 | Me | H | 3,5-dimethylphenyl | 4-(1-(2-(2,6-difluorophenyl)acetyl)piperidin-4-yl)-N-(3,5-dimethylphenoxy)-2-methylpyrimidine-5-carboxamide |
| H3 | Me | H | 3-Cl-phenyl | N-(3-chlorophenoxy)-4-(1-(2-(2,6-difluorophenyl)acetyl)piperidin-4-yl)-2-methylpyrimidine-5-carboxamide |
| H4 | Me | H | 3-OCF₃-phenyl | 4-(1-(2-(2,6-difluorophenyl)acetyl)piperidin-4-yl)-2-methyl-N-(3-(trifluoromethoxy)phenoxy)pyrimidine-5-carboxamide |

TABLE 11-continued

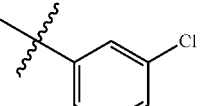

| Cpd | R¹ | R² | Q¹³ | Chemical Name |
|---|---|---|---|---|
| H5 | Me | Me | 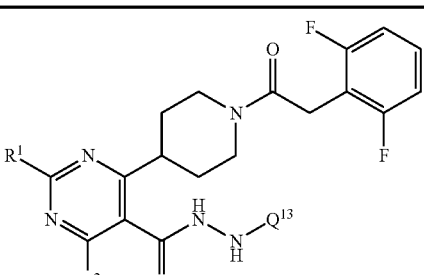 | N-(3-chlorophenoxy)-4-(1-(2-(2,6-difluorophenyl)acetyl)piperidin-4-yl)-2,6-dimethylpyrimidine-5-carboxamide |
| H6 | Me | H | 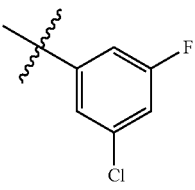 [SMILES: *c1cc(F)cc(Cl)c1] | N-(3-chloro-5-fluorophenoxy)-4-(1-(2-(2,6-difluorophenyl)acetyl)piperidin-4-yl)-2-methylpyrimidine-5-carboxamide |
| H7 | Me | H | 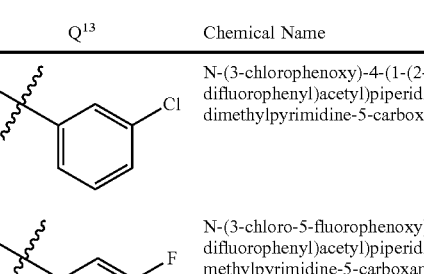 | 4-(1-(2-(2,6-difluorophenyl)acetyl)piperidin-4-yl)-2-methyl-N-phenoxypyrimidine-5-carboxamide |

TABLE 12

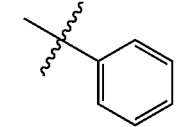 [SMILES: *c1ccccc1]

| Cpd | R¹ | R² | R⁶ | G | Q¹⁴ | Chemical Name |
|---|---|---|---|---|---|---|
| J1 | Me | H | F | CH₂ | 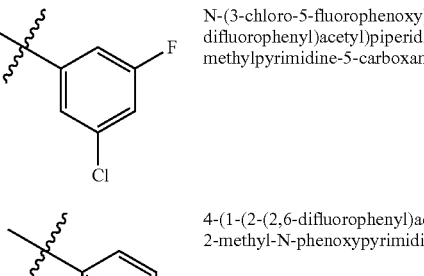 | (E)-2-(2,6-difluorophenyl)-1-(4-(5-(3-(3,5-dimethylphenyl)prop-1-en-1-yl)-2-methylpyrimidin-4-yl)piperidin-1-yl)ethanone |
| J2 | Me | H | F | CH₂ | 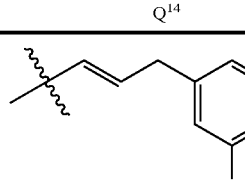 | (Z)-2-(2,6-difluorophenyl)-1-(4-(5-(3-(3,5-dimethylphenyl)prop-1-en-1-yl)-2-methylpyrimidin-4-yl)piperidin-1-yl)ethanone |

TABLE 12-continued

| Cpd | R¹ | R² | R⁶ | G | Q¹⁴ | Chemical Name |
|---|---|---|---|---|---|---|
| J3 | Me | H | F | CH₂ | (propyl-3,5-dimethylphenyl group) | 2-(2,6-difluorophenyl)-1-(4-(5-(3-(3,5-dimethylphenyl)propyl)-2-methylpyrimidin-4-yl)piperidin-1-yl)ethanone |
| L1 | H | H | F | CH₂ | (thioamide-N-CH₂-3,4-dichlorophenyl group) | N-(3,4-dichlorobenzyl)-4-(1-(2-(2,6-difluorophenyl)acetyl)piperidin-4-yl)pyrimidine-5-carbothioamide |
| M1 | Me | H | F | CH₂ | (–C(O)CH₂O-3,5-dimethylphenyl group) | 2-(3-chlorophenoxy)-1-(4-(1-(2-(2,6-difluorophenyl)acetyl)piperidin-4-yl)-2-methylpyrimidin-5-yl)ethanone |
| M2 | SMe | H | F | NH | (–C(O)CH₂O-[2-(trifluoromethyl)pyrimidin-4-yl] group) | N-(2,6-Difluorophenyl)-4-[2-(methylthio)-5-({[2-(trifluoromethyl)pyrimidin-4-yl]oxy}acetyl)pyrimidin-4-yl]piperidine-1-carboxamide |
| M3 | NH₂ | H | F | O | (–C(O)CH₂O-[2-(trifluoromethyl)pyrimidin-4-yl] group) | 2,6-Difluorophenyl 4-[2-amino-5-({[2-(trifluoromethyl)pyrimidin-4-yl]oxy}acetyl)pyrimidin-4-yl]piperidine-1-carboxylate |
| M4 | Me | H | F | NH | (–C(O)CH₂O-[6-(trifluoromethyl)pyridin-2-yl] group) | N-(2,6-Difluorophenyl)-4-[2-methyl-5-({[6-(trifluoromethyl)pyridin-2-yl]oxy}acetyl)pyrimidin-4-yl]piperidine-1-carboxamide |
| M5 | NH₂ | H | F | CH₂ | (–C(O)CH₂O-[2-(trifluoromethyl)pyrimidin-4-yl] group) | 1-(2-Amino-4-{1-[(2,6-difluorophenyl)acetyl]piperidin-4-yl}pyrimidin-5-yl)-2-{[2-(trifluoromethyl)pyrimidin-4-yl]oxy}ethanone |

TABLE 12-continued

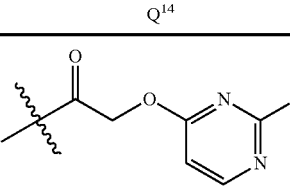

| Cpd | R¹ | R² | R⁶ | G | Q¹⁴ | Chemical Name |
|---|---|---|---|---|---|---|
| M6 | NH₂ | H | F | NH | 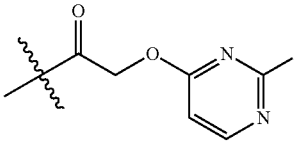 | 4-[2-Amino-5-({[2-(trifluoromethyl)pyrimidin-4-yl]oxy}acetyl)pyrimidin-4-yl]-N-(2,6-difluorophenyl)piperidine-1-carboxamide |
| M7 | NHCH₂CH₂F | H | F | NH | 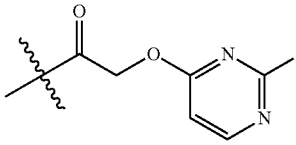 | N-(2,6-Difluorophenyl)-4-{2-[(2-fluoroethyl)amino]-5-({[2-(trifluoromethyl)pyrimidin-4-yl]oxy}acetyl)pyrimidin-4-yl}piperidine-1-carboxamide |
| M8 | Me | Me | F | NH | 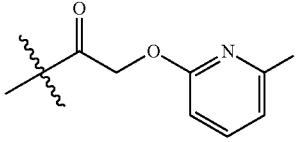 | N-(2,6-Difluorophenyl)-4-[2,6-dimethyl-5-({[2-(trifluoromethyl)pyrimidin-4-yl]oxy}acetyl)pyrimidin-4-yl]piperidine-1-carboxamide |
| M9 | Me | Me | F | NH | 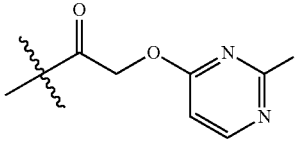 | N-(2,6-Difluorophenyl)-4-[5-(1-hydroxy-2-{[2-(trifluoromethyl)pyrimidin-4-yl]oxy}ethyl)-2,6-dimethylpyrimidin-4-yl]piperidine-1-carboxamide |
| M10 | NH₂ | Me | F | NH | 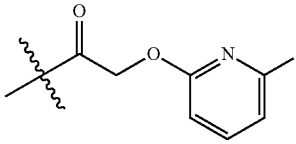 | 4-[2-Amino-6-methyl-5-({[2-(trifluoromethyl)pyrimidin-4-yl]oxy}acetyl)pyrimidin-4-yl]-N-(2,6-difluorophenyl)piperidine-1-carboxamide |
| M11 | NH₂ | Me | F | NH | 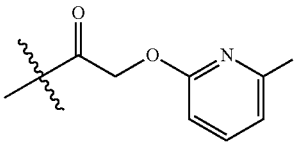 | 4-[2-Amino-6-methyl-5-({[6-(trifluoromethyl)pyridin-2-yl]oxy}acetyl)pyrimidin-4-yl]-N-(2,6-difluorophenyl)piperidine-1-carboxamide |
| M12 | NHAc | Me | F | NH | 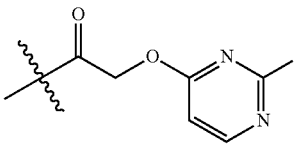 | 4-[2-(Acetylamino)-6-methyl-5-({[6-(trifluoromethyl)pyridin-2-yl]oxy}acetyl)pyrimidin-4-yl]-N-(2,6-difluorophenyl)piperidine-1-carboxamide |
| M13 | NH₂ | H | F | — |  | 1-(2-Amino-4-{1-[(2,6-difluorophenyl)carbonyl]piperidin-4-yl}pyrimidin-5-yl)-2-{[2-(trifluoromethyl)pyrimidin-4-yl]oxy}ethanone |

TABLE 12-continued

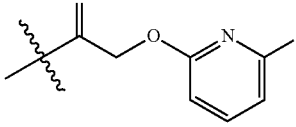

| Cpd | R¹ | R² | R⁶ | G | Q¹⁴ | Chemical Name |
|-----|-----|-----|-----|---|-----|---------------|
| M14 | NH₂ | H | H | O | (structure) | 2-Fluorophenyl 4-[2-amino-5-({[6-(trifluoromethyl)pyridin-2-yl]oxy}acetyl)pyrimidin-4-yl]piperidine-1-carboxylate |

TABLE 13

| Cpd | Q¹⁵ | Chemical Name |
|-----|-----|---------------|
| I1 | (structure) | 4-(1-(2-(2,6-difluorophenyl)acetyl)piperidin-4-yl)-2-methyl-6-oxo-N-((6-(trifluoromethyl)pyridin-2-yl)methyl)-1,6-dihydropyrimidine-5-carboxamide |
| I3 | (structure) | 4-(1-(2-(2,6-difluorophenyl)acetyl)piperidin-4-yl)-N-(3,5-dimethylbenzyl)-2-methyl-6-oxo-1,6-dihydropyrimidine-5-carboxamide |
| I4 | (structure) | N-(3-chlorobenzyl)-4-(1-(2-(2,6-difluorophenyl)acetyl)piperidin-4-yl)-2-methyl-6-oxo-1,6-dihydropyrimidine-5-carboxamide |
| I5 | (structure) | 4-(1-(2-(2,6-difluorophenyl)acetyl)piperidin-4-yl)-2-methyl-6-oxo-N-((2-(trifluoromethyl)pyridin-4-yl)methyl)-1,6-dihydropyrimidine-5-carboxamide |

TABLE 13-continued

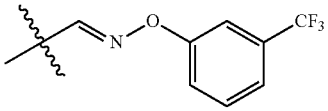 [SMILES: */C=N/Oc1cccc(C(F)(F)F)c1]

| Cpd | Q$^{15}$ | Chemical Name |
|---|---|---|
| I6 | | (E)-4-(1-(2-(2,6-difluorophenyl)acetyl)piperidin-4-yl)-2-methyl-6-oxo-1,6-dihydropyrimidine-5-carbaldehyde O-(3-(trifluoromethyl)phenyl) oxime |

TABLE 14

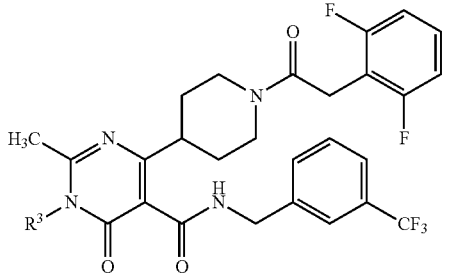

| Cpd | R$^3$ | Chemical Name |
|---|---|---|
| I7 | Me | 4-(1-(2-(2,6-difluorophenyl)acetyl)piperidin-4-yl)-1,2-dimethyl-6-oxo-N-((6-(trifluoromethyl)pyridin-2-yl)methyl)-1,6-dihydropyrimidine-5-carboxamide |
| I8 | Et | 4-(1-(2-(2,6-difluorophenyl)acetyl)piperidin-4-yl)-1-ethyl-2-methyl-6-oxo-N-((6-(trifluoromethyl)pyridin-2-yl)methyl)-1,6-dihydropyrimidine-5-carboxamide |

TABLE 15

| Cpd | Structure | Chemical Name |
|---|---|---|
| N1 | 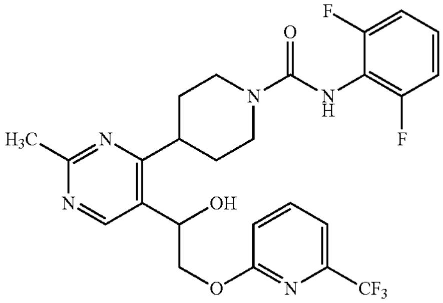 [SMILES: Cc1ncc(C(O)COc2cccc(C(F)(F)F)n2)c(C2CCN(C(=O)Nc3c(F)cccc3F)CC2)n1] | N-(2,6-difluorophenyl)-4-(5-(1-hydroxy-2-(6-(trifluoromethyl)pyridin-2-yloxy)ethyl)-2-methylpyrimidin-4-yl)piperidine-1-carboxamide |

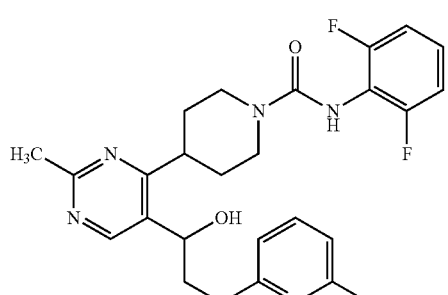

TABLE 15-continued

| Cpd | Structure | Chemical Name |
|---|---|---|
| N2 | 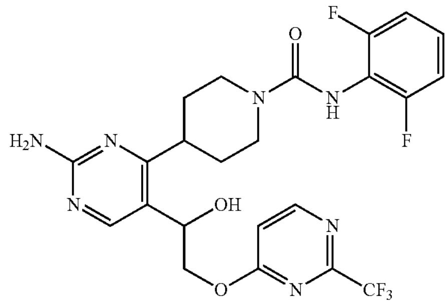 [SMILES: Nc1ncc(C(O)COc2ccnc(C(F)(F)F)n2)c(C2CCN(C(=O)Nc3c(F)cccc3F)CC2)n1] | 4-(2-amino-5-(1-hydroxy-2-(2-(trifluoromethyl)pyrimidin-4-yloxy)ethyl)pyrimidin-4-yl)-N-(2,6-difluorophenyl)piperidine-1-carboxamide |
| N3 | 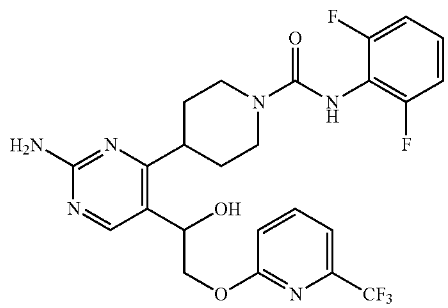 | 4-(2-amino-5-(1-hydroxy-2-(6-(trifluoromethyl)pyridin-2-yloxy)ethyl)pyrimidin-4-yl)-N-(2,6-difluorophenyl)piperidine-1-carboxamide |
| N4 | 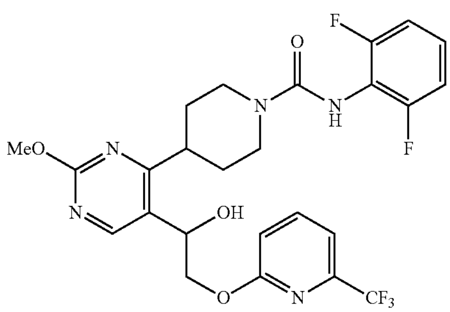 [SMILES: COc1ncc(C(O)COc2cccc(C(F)(F)F)n2)c(C2CCN(C(=O)Nc3c(F)cccc3F)CC2)n1] | N-(2,6-difluorophenyl)-4-(5-(1-hydroxy-2-(6-(trifluoromethyl)pyridin-2-yloxy)ethyl)-2-methoxypyrimidin-4-yl)piperidine-1-carboxamide |
| N5 | 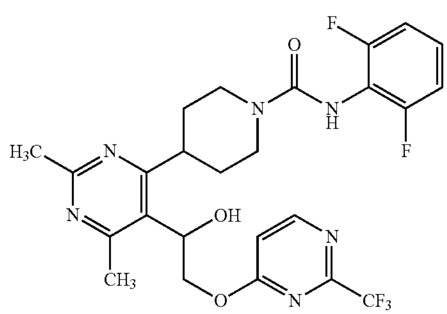 | N-(2,6-difluorophenyl)-4-(5-(1-hydroxy-2-(2-(trifluoromethyl)pyrimidin-4-yloxy)ethyl)-2,6-dimethylpyrimidin-4-yl)piperidine-1-carboxamide |
| N6 | 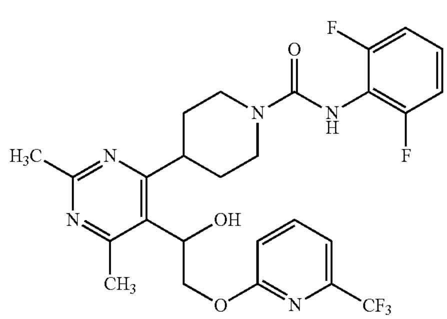 | N-(2,6-difluorophenyl)-4-(5-(1-hydroxy-2-(6-(trifluoromethyl)pyridin-2-yloxy)ethyl)-2,6-dimethylpyrimidin-4-yl)piperidine-1-carboxamide |

TABLE 15-continued

| Cpd | Structure | Chemical Name |
|---|---|---|
| N7 | 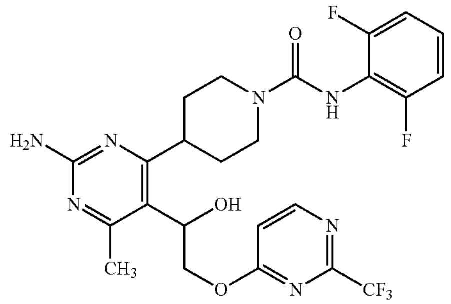 [SMILES: Cc1nc(C)c(C(O)COc2ccnc(C(F)(F)F)n2)c(C2CCN(C(=O)Nc3c(F)cccc3F)CC2)n1] | 4-(2-amino-5-(1-hydroxy-2-(2-(trifluoromethyl)pyrimidin-4-yloxy)ethyl)-6-methylpyrimidin-4-yl)-N-(2,6-difluorophenyl)piperidine-1-carboxamide |
| N8 | 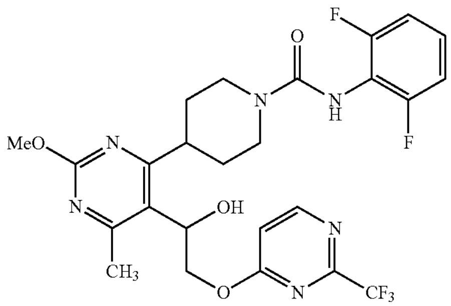 [SMILES: COc1nc(C)c(C(O)COc2ccnc(C(F)(F)F)n2)c(C2CCN(C(=O)Nc3c(F)cccc3F)CC2)n1] | N-(2,6-difluorophenyl)-4-(5-(1-hydroxy-2-(2-(trifluoromethyl)pyrimidin-4-yloxy)ethyl)-2-methoxy-6-methylpyrimidin-4-yl)piperidine-1-carboxamide |
| N9 | 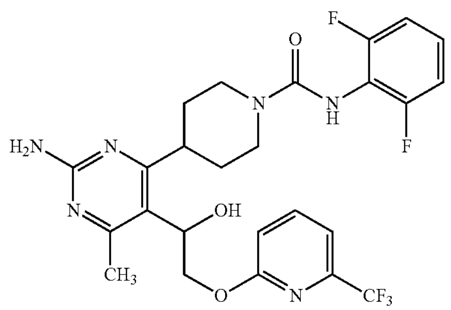 [SMILES: Cc1nc(N)nc(C2CCN(C(=O)Nc3c(F)cccc3F)CC2)c1C(O)COc1cccc(C(F)(F)F)n1] | 4-(2-amino-5-(1-hydroxy-2-(6-(trifluoromethyl)pyridin-2-yloxy)ethyl)-6-methylpyrimidin-4-yl)-N-(2,6-difluorophenyl)piperidine-1-carboxamide |
| N10 | 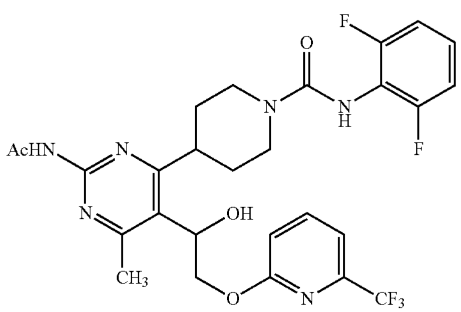 | 4-(2-acetamido-5-(1-hydroxy-2-(6-(trifluoromethyl)pyridin-2-yloxy)ethyl)-6-methylpyrimidin-4-yl)-N-(2,6-difluorophenyl)piperidine-1-carboxamide |
| N11 | 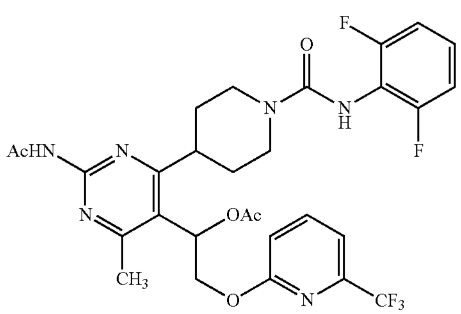 [SMILES: CC(=O)Nc1nc(C)c(C(COc2cccc(C(F)(F)F)n2)OC(C)=O)c(C2CCN(C(=O)Nc3c(F)cccc3F)CC2)n1] | 1-(2-acetamido-4-(1-(2,6-difluorophenylcarbamoyl)piperidin-4-yl)-6-methylpyrimidin-5-yl)-2-(6-(trifluoromethyl)pyridin-2-yloxy)ethyl acetate |

TABLE 15-continued

| Cpd | Structure | Chemical Name |
|---|---|---|
| N12 | 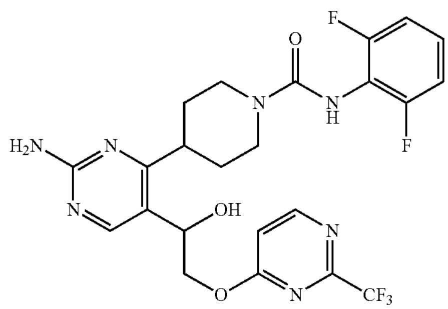 [SMILES: Nc1ncc(C(O)COc2ccnc(C(F)(F)F)n2)c(C2CCN(C(=O)Nc3c(F)cccc3F)CC2)n1] | 4-(2-amino-5-(1-hydroxy-2-(2-(trifluoromethyl)pyrimidin-4-ylamino)ethyl)pyrimidin-4-yl)-N-(2,6-difluorophenyl)piperidine-1-carboxamide |
| N13 | 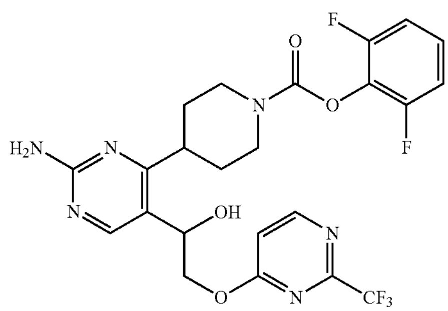 [SMILES: Nc1ncc(C(O)COc2ccnc(C(F)(F)F)n2)c(C2CCN(C(=O)Oc3c(F)cccc3F)CC2)n1] | 2,6-difluorophenyl 4-(2-amino-5-(1-hydroxy-2-(2-(trifluoromethyl)pyrimidin-4-yloxy)ethyl)pyrimidin-4-yl)piperidine-1-carboxylate |
| N14 | 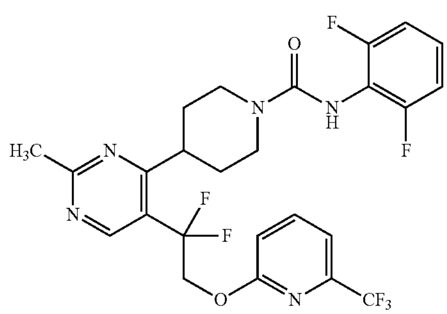 [SMILES: Cc1ncc(C(F)(F)COc2cccc(C(F)(F)F)n2)c(C2CCN(C(=O)Nc3c(F)cccc3F)CC2)n1] | 4-(5-(1,1-difluoro-2-(6-(trifluoromethyl)pyridin-2-yloxy)ethyl)-2-methylpyrimidin-4-yl)-N-(2,6-difluorophenyl)piperidine-1-carboxamide |
| N15 | 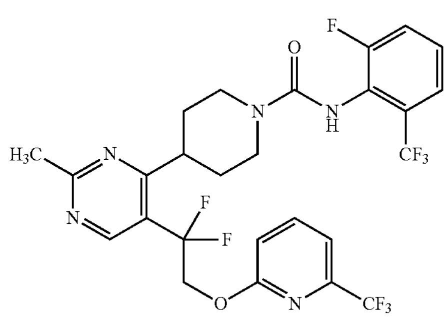 | 4-(5-(1,1-difluoro-2-(6-(trifluoromethyl)pyridin-2-yloxy)ethyl)-2-methylpyrimidin-4-yl)-N-(2-fluoro-6-(trifluoromethyl)phenyl)piperidine-1-carboxamide |
| N16 | 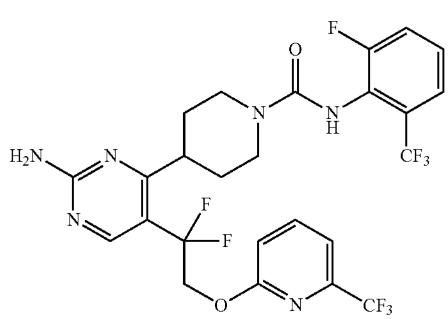 [SMILES: Nc1ncc(C(F)(F)COc2cccc(C(F)(F)F)n2)c(C2CCN(C(=O)Nc3c(F)cccc3C(F)(F)F)CC2)n1] | 4-(2-amino-5-(1,1-difluoro-2-(6-(trifluoromethyl)pyridin-2-yloxy)ethyl)pyrimidin-4-yl)-N-(2-fluoro-6-(trifluoromethyl)phenyl)piperidine-1-carboxamide |

TABLE 15-continued

| Cpd | Structure | Chemical Name |
| --- | --- | --- |
| N17 | 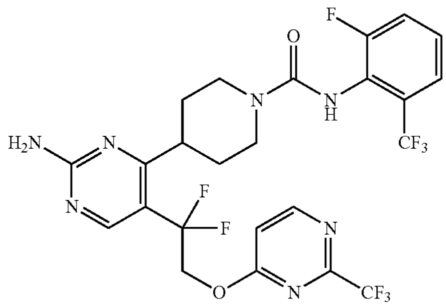 [SMILES: Nc1ncc(C(F)(F)COc2ccnc(C(F)(F)F)n2)c(C2CCN(C(=O)Nc3c(F)cccc3C(F)(F)F)CC2)n1] | 4-(2-amino-5-(1,1-difluoro-2-(2-(trifluoromethyl)pyrimidin-4-yloxy)ethyl)pyrimidin-4-yl)-N-(2-fluoro-6-(trifluoromethyl)phenyl)piperidine-1-carboxamide |
| N18 | 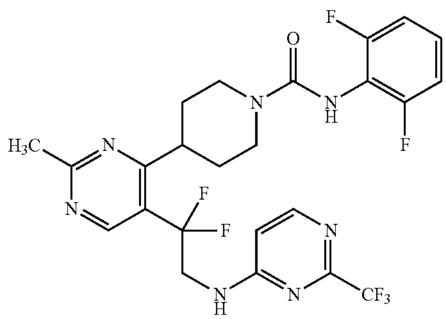 [SMILES: Cc1ncc(C(F)(F)CNc2ccnc(C(F)(F)F)n2)c(C2CCN(C(=O)Nc3c(F)cccc3F)CC2)n1] | 4-(5-(1,1-difluoro-2-(2-(trifluoromethyl)pyrimidin-4-ylamino)ethyl)-2-methylpyrimidin-4-yl)-N-(2,6-difluorophenyl)piperidine-1-carboxamide |
| N19 | 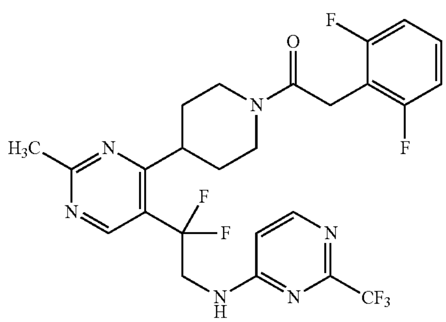 [SMILES: Cc1ncc(C(F)(F)CNc2ccnc(C(F)(F)F)n2)c(C2CCN(C(=O)Cc3c(F)cccc3F)CC2)n1] | 1-(4-(5-(1,1-difluoro-2-(2-(trifluoromethyl)pyrimidin-4-ylamino)ethyl)-2-methylpyrimidin-4-yl)piperidin-1-yl)-2-(2,6-difluorophenyl)ethanone |
| N20 | 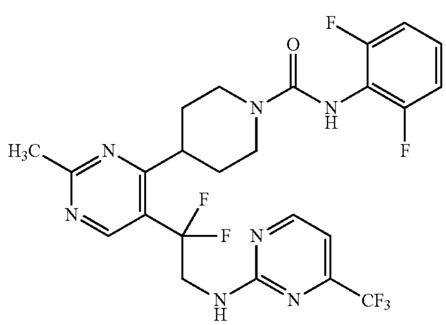 [SMILES: Cc1ncc(C(F)(F)CNc2nccc(C(F)(F)F)n2)c(C2CCN(C(=O)Nc3c(F)cccc3F)CC2)n1] | 4-(5-(1,1-difluoro-2-(4-(trifluoromethyl)pyrimidin-2-ylamino)ethyl)-2-methylpyrimidin-4-yl)-N-(2,6-difluorophenyl)piperidine-1-carboxamide |
| N21 | 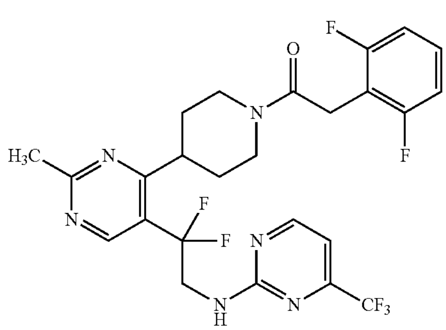 [SMILES: Cc1ncc(C(F)(F)CNc2nccc(C(F)(F)F)n2)c(C2CCN(C(=O)Cc3c(F)cccc3F)CC2)n1] | 1-(4-(5-(1,1-difluoro-2-(4-(trifluoromethyl)pyrimidin-2-ylamino)ethyl)-2-methylpyrimidin-4-yl)piperidin-1-yl)-2-(2,6-difluorophenyl)ethanone |

TABLE 15-continued

| Cpd | Structure | Chemical Name |
|---|---|---|
| N22 | 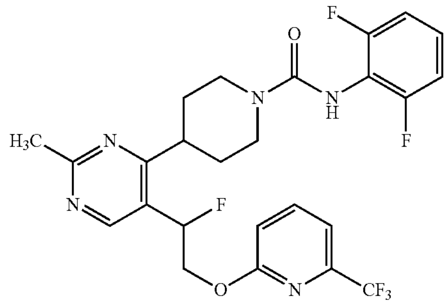 [SMILES: Cc1ncc(C(F)COc2cccc(C(F)(F)F)n2)c(C2CCN(C(=O)Nc3c(F)cccc3F)CC2)n1] | N-(2,6-difluorophenyl)-4-(5-(1-fluoro-2-(6-(trifluoromethyl)pyridin-2-yloxy)ethyl)-2-methylpyrimidin-4-yl)piperidine-1-carboxamide |
| N23 | 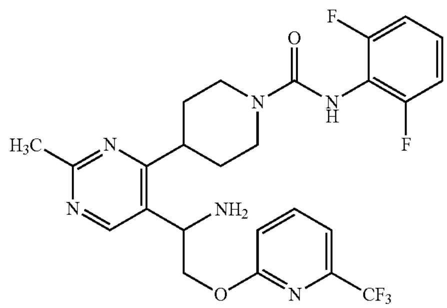 [SMILES: Cc1ncc(C(N)COc2cccc(C(F)(F)F)n2)c(C2CCN(C(=O)Nc3c(F)cccc3F)CC2)n1] | 4-(5-(1-amino-2-(6-(trifluoromethyl)pyridin-2-yloxy)ethyl)-2-methylpyrimidin-4-yl)-N-(2,6-difluorophenyl)piperidine-1-carboxamide |
| N24 | 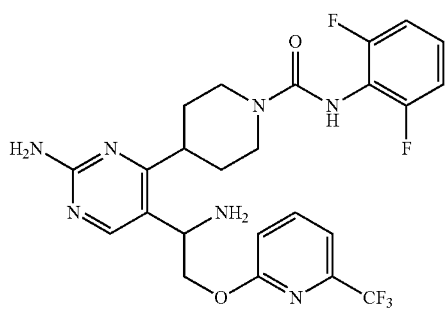 [SMILES: Nc1ncc(C(N)COc2cccc(C(F)(F)F)n2)c(C2CCN(C(=O)Nc3c(F)cccc3F)CC2)n1] | 4-(2-amino-5-(1-amino-2-(6-(trifluoromethyl)pyridin-2-yloxy)ethyl)pyrimidin-4-yl)-N-(2,6-difluorophenyl)piperidine-1-carboxamide |
| N25 | 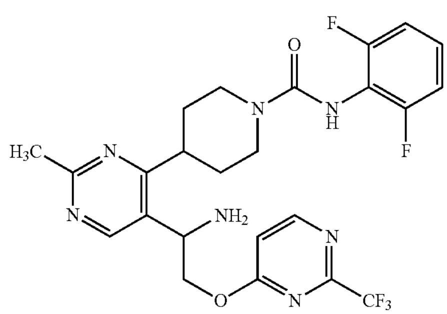 | 4-(5-(1-amino-2-(2-(trifluoromethyl)pyrimidin-4-yloxy)ethyl)-2-methylpyrimidin-4-yl)-N-(2,6-difluorophenyl)piperidine-1-carboxamide |
| N26 | 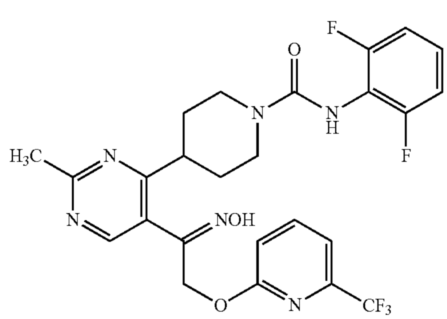 | N-(2,6-difluorophenyl)-4-(5-(1-(hydroxyimino)-2-(6-(trifluoromethyl)pyridin-2-yloxy)ethyl)-2-methylpyrimidin-4-yl)piperidine-1-carboxamide |

TABLE 15-continued

| Cpd | Structure | Chemical Name |
|---|---|---|
| N27 | 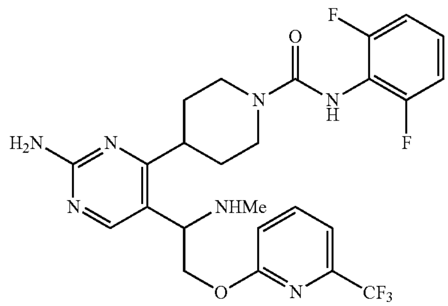 [SMILES: CNC(COc1cccc(C(F)(F)F)n1)c1cnc(N)nc1C1CCN(C(=O)Nc2c(F)cccc2F)CC1] | 4-(2-amino-5-(1-(methylamino)-2-(6-(trifluoromethyl)pyridin-2-yloxy)ethyl)pyrimidin-4-yl)-N-(2,6-difluorophenyl)piperidine-1-carboxamide |
| N28 | 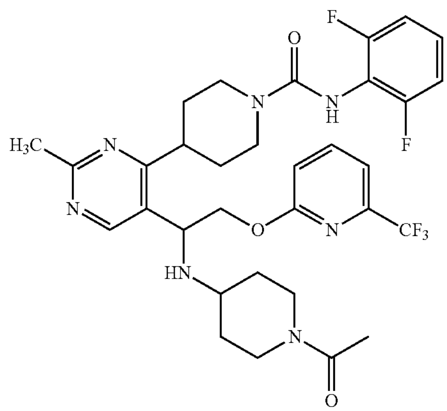 [SMILES: CC(=O)N1CCC(NC(COc2cccc(C(F)(F)F)n2)c2cnc(C)nc2C2CCN(C(=O)Nc3c(F)cccc3F)CC2)CC1] | 4-(5-(1-(1-acetylpiperidin-4-ylamino)-2-(6-(trifluoromethyl)pyridin-2-yloxy)ethyl)-2-methylpyrimidin-4-yl)-N-(2,6-difluorophenyl)piperidine-1-carboxamide |
| N29 | 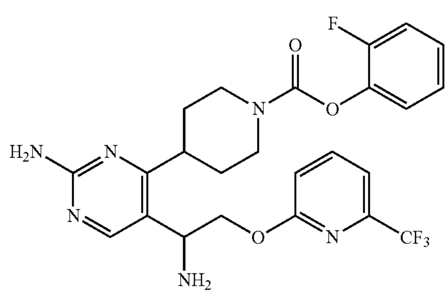 [SMILES: Nc1ncc(C(N)COc2cccc(C(F)(F)F)n2)c(C2CCN(C(=O)Oc3ccccc3F)CC2)n1] | 2-fluorophenyl 4-(2-amino-5-(1-amino-2-(6-(trifluoromethyl)pyridin-2-yloxy)ethyl)pyrimidin-4-yl)piperidine-1-carboxylate |
| N30 | 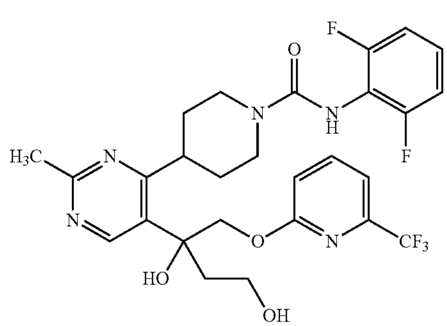 [SMILES: Cc1ncc(C(O)(CCO)COc2cccc(C(F)(F)F)n2)c(C2CCN(C(=O)Nc3c(F)cccc3F)CC2)n1] | N-(2,6-difluorophenyl)-4-(5-(2,4-dihydroxy-1-(6-(trifluoromethyl)pyridin-2-yloxy)butan-2-yl)-2-methylpyrimidin-4-yl)piperidine-1-carboxamide |

TABLE 15-continued

| Cpd | Structure | Chemical Name |
|---|---|---|
| N31 | 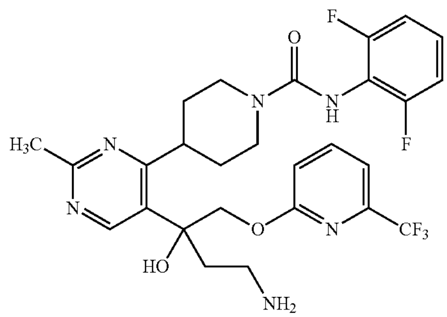 [SMILES: Cc1ncc(C(O)(CCN)COc2cccc(C(F)(F)F)n2)c(C2CCN(C(=O)Nc3c(F)cccc3F)CC2)n1] | 4-(5-(4-amino-2-hydroxy-1-(6-(trifluoromethyl)pyridin-2-yloxy)butan-2-yl)-2-methylpyrimidin-4-yl)-N-(2,6-difluorophenyl)piperidine-1-carboxamide |
| N32 | 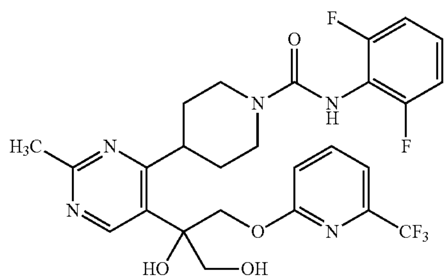 [SMILES: Cc1ncc(C(O)(CO)COc2cccc(C(F)(F)F)n2)c(C2CCN(C(=O)Nc3c(F)cccc3F)CC2)n1] | N-(2,6-difluorophenyl)-4-(5-(1,2-dihydroxy-3-(6-(trifluoromethyl)pyridin-2-yloxy)propan-2-yl)-2-methylpyrimidin-4-yl)piperidine-1-carboxamide |
| N33 | 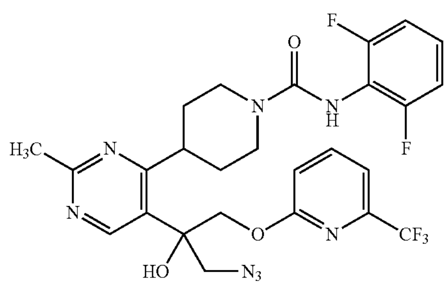 [SMILES: Cc1ncc(C(O)(CN=[N+]=[N-])COc2cccc(C(F)(F)F)n2)c(C2CCN(C(=O)Nc3c(F)cccc3F)CC2)n1] | 4-(5-(1-azido-2-hydroxy-3-(6-(trifluoromethyl)pyridin-2-yloxy)propan-2-yl)-2-methylpyrimidin-4-yl)-N-(2,6-difluorophenyl)piperidine-1-carboxamide |
| N34 | 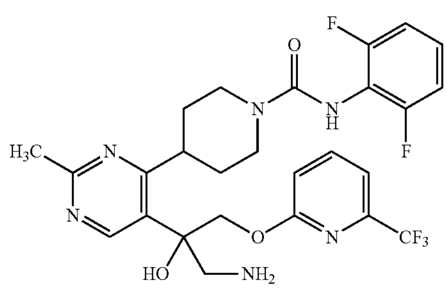 [SMILES: Cc1ncc(C(O)(CN)COc2cccc(C(F)(F)F)n2)c(C2CCN(C(=O)Nc3c(F)cccc3F)CC2)n1] | 4-(5-(1-amino-2-hydroxy-3-(6-(trifluoromethyl)pyridin-2-yloxy)propan-2-yl)-2-methylpyrimidin-4-yl)-N-(2,6-difluorophenyl)piperidine-1-carboxamide |
| N35 | 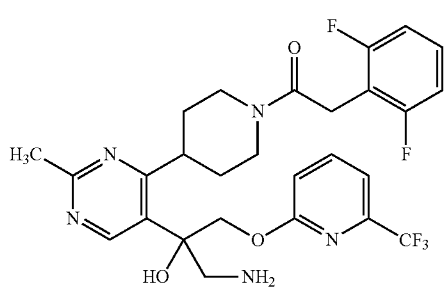 [SMILES: Cc1ncc(C(O)(CN)COc2cccc(C(F)(F)F)n2)c(C2CCN(C(=O)Cc3c(F)cccc3F)CC2)n1] | 1-(4-(5-(1-amino-2-hydroxy-3-(6-(trifluoromethyl)pyridin-2-yloxy)propan-2-yl)-2-methylpyrimidin-4-yl)piperidin-1-yl)-2-(2,6-difluorophenyl)ethanone |

TABLE 15-continued

| Cpd | Structure | Chemical Name |
|---|---|---|
| N36 | 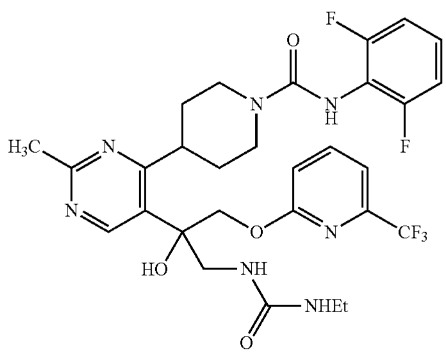 | N-(2,6-difluorophenyl)-4-(5-(1-(3-ethylureido)-2-hydroxy-3-(6-(trifluoromethyl)pyridin-2-yloxy)propan-2-yl)-2-methylpyrimidin-4-yl)piperidine-1-carboxamide |
| N37 | 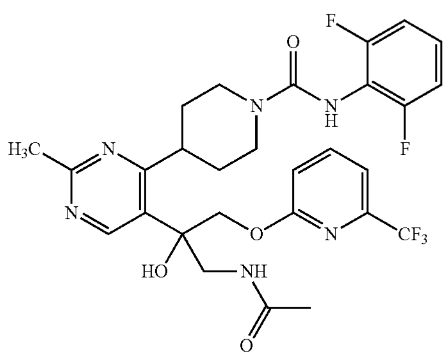 [SMILES: CC(=O)NCC(O)(COc1cccc(C(F)(F)F)n1)c1cnc(C)nc1C1CCN(C(=O)Nc2c(F)cccc2F)CC1] | 4-(5-(1-acetamido-2-hydroxy-3-(6-(trifluoromethyl)pyridin-2-yloxy)propan-2-yl)-2-methylpyrimidin-4-yl)-N-(2,6-difluorophenyl)piperidine-1-carboxamide |
| N38 | 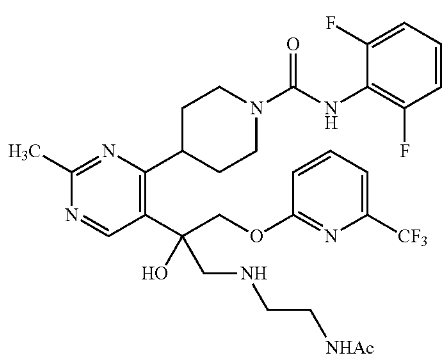 [SMILES: CC(=O)NCCNCC(O)(COc1cccc(C(F)(F)F)n1)c1cnc(C)nc1C1CCN(C(=O)Nc2c(F)cccc2F)CC1] | 4-(5-(1-(2-acetamidoethylamino)-2-hydroxy-3-(6-(trifluoromethyl)pyridin-2-yloxy)propan-2-yl)-2-methylpyrimidin-4-yl)-N-(2,6-difluorophenyl)piperidine-1-carboxamide |
| N39 | 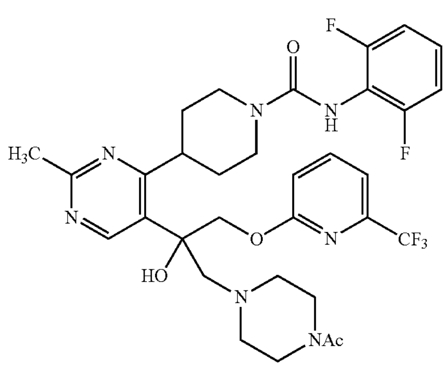 | 4-(5-(1-(4-acetylpiperazin-1-yl)-2-hydroxy-3-(6-(trifluoromethyl)pyridin-2-yloxy)propan-2-yl)-2-methylpyrimidin-4-yl)-N-(2,6-difluorophenyl)piperidine-1-carboxamide |

TABLE 15-continued

| Cpd | Structure | Chemical Name |
|---|---|---|
| N40 | 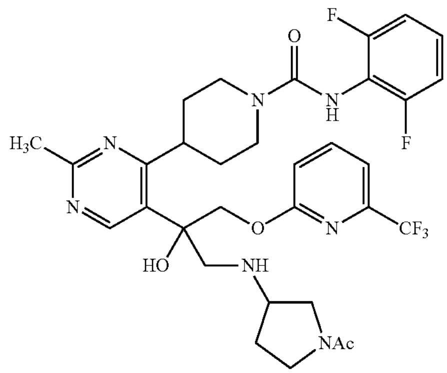 | 4-(5-(1-(1-acetylpyrrolidin-3-ylamino)-2-hydroxy-3-(6-(trifluoromethyl)pyridin-2-yloxy)propan-2-yl)-2-methylpyrimidin-4-yl)-N-(2,6-difluorophenyl)piperidine-1-carboxamide |
| N41 | 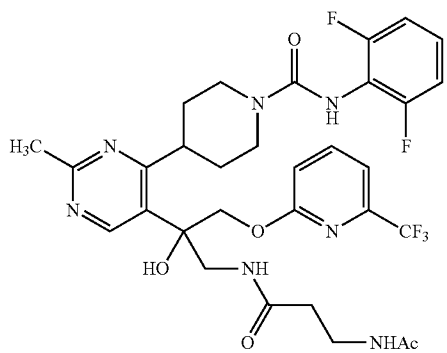 [SMILES: CC(=O)NCCC(=O)NCC(O)(COc1cccc(C(F)(F)F)n1)c1cnc(C)nc1C1CCN(C(=O)Nc2c(F)cccc2F)CC1] | 4-(5-(1-(3-acetamidopropanamido)-2-hydroxy-3-(6-(trifluoromethyl)pyridin-2-yloxy)propan-2-yl)-2-methylpyrimidin-4-yl)-N-(2,6-difluorophenyl)piperidine-1-carboxamide |
| N42 | 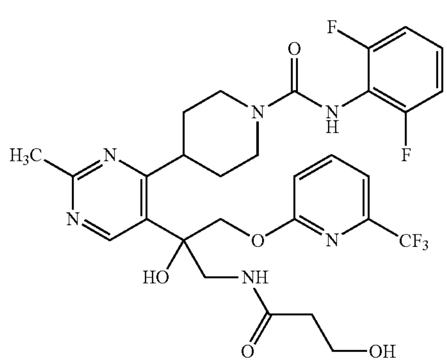 [SMILES: Cc1ncc(C(O)(CNC(=O)CCO)COc2cccc(C(F)(F)F)n2)c(C2CCN(C(=O)Nc3c(F)cccc3F)CC2)n1] | N-(2,6-difluorophenyl)-4-(5-(2-hydroxy-1-(3-hydroxypropanamido)-3-(6-(trifluoromethyl)pyridin-2-yloxy)propan-2-yl)-2-methylpyrimidin-4-yl)piperidine-1-carboxamide |
| N43 | 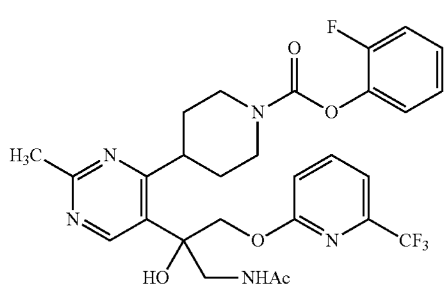 [SMILES: CC(=O)NCC(O)(COc1cccc(C(F)(F)F)n1)c1cnc(C)nc1C1CCN(C(=O)Oc2ccccc2F)CC1] | 2-fluorophenyl 4-(5-(1-acetamido-2-hydroxy-3-(6-(trifluoromethyl)pyridin-2-yloxy)propan-2-yl)-2-methylpyrimidin-4-yl)piperidine-1-carboxylate |

TABLE 15-continued

| Cpd | Structure | Chemical Name |
|---|---|---|
| N44 | 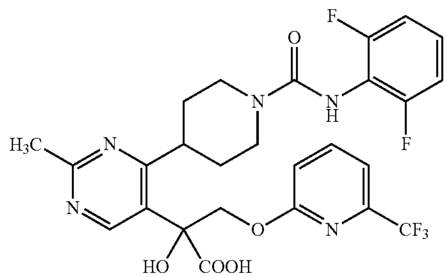 [SMILES: Cc1ncc(C(O)(COc2cccc(C(F)(F)F)n2)C(=O)O)c(C2CCN(C(=O)Nc3c(F)cccc3F)CC2)n1] | 2-(4-(1-(2,6-difluorophenylcarbamoyl)piperidin-4-yl)-2-methylpyrimidin-5-yl)-2-hydroxy-3-(6-(trifluoromethyl)pyridin-2-yloxy)propanoic acid |
| N45 | 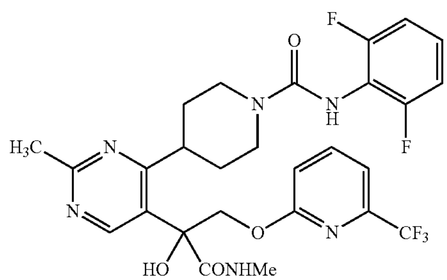 | N-(2,6-difluorophenyl)-4-(5-(2-hydroxy-1-(methylamino)-1-oxo-3-(6-(trifluoromethyl)pyridin-2-yloxy)propan-2-yl)-2-methylpyrimidin-4-yl)piperidine-1-carboxamide |
| N46 | 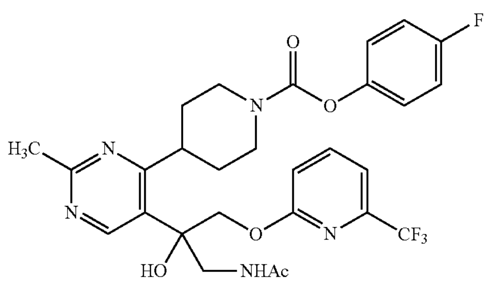 [SMILES: CC(=O)NCC(O)(COc1cccc(C(F)(F)F)n1)c1cnc(C)nc1C1CCN(C(=O)Oc2ccc(F)cc2)CC1] | 4-fluorophenyl 4-(5-(1-acetamido-2-hydroxy-3-(6-(trifluoromethyl)pyridin-2-yloxy)propan-2-yl)-2-methylpyrimidin-4-yl)piperidine-1-carboxylate |
| N47 | 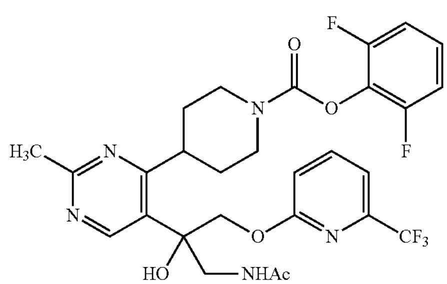 [SMILES: CC(=O)NCC(O)(COc1cccc(C(F)(F)F)n1)c1cnc(C)nc1C1CCN(C(=O)Oc2c(F)cccc2F)CC1] | 2,6-difluorophenyl 4-(5-(1-acetamido-2-hydroxy-3-(6-(trifluoromethyl)pyridin-2-yloxy)propan-2-yl)-2-methylpyrimidin-4-yl)piperidine-1-carboxylate |
| N48 | 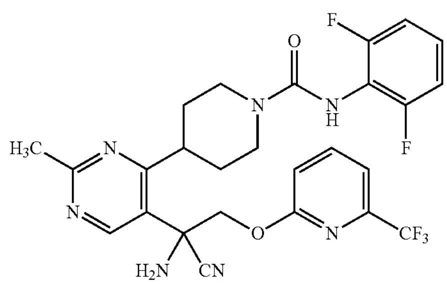 [SMILES: Cc1ncc(C(N)(C#N)COc2cccc(C(F)(F)F)n2)c(C2CCN(C(=O)Nc3c(F)cccc3F)CC2)n1] | 4-(5-(1-amino-1-cyano-2-(6-(trifluoromethyl)pyridin-2-yloxy)ethyl)-2-methylpyrimidin-4-yl)-N-(2,6-difluorophenyl)piperidine-1-carboxamide |

TABLE 15-continued

| Cpd | Structure | Chemical Name |
|---|---|---|
| N49 | 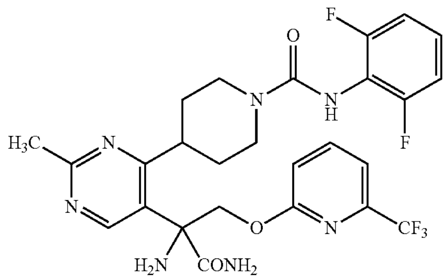 [SMILES: Cc1ncc(C(N)(COc2cccc(C(F)(F)F)n2)C(N)=O)c(C2CCN(C(=O)Nc3c(F)cccc3F)CC2)n1] | 4-(5-(1,2-diamino-1-oxo-3-(6-(trifluoromethyl)pyridin-2-yloxy)propan-2-yl)-2-methylpyrimidin-4-yl)-N-(2,6-difluorophenyl)piperidine-1-carboxamide |
| N50 | 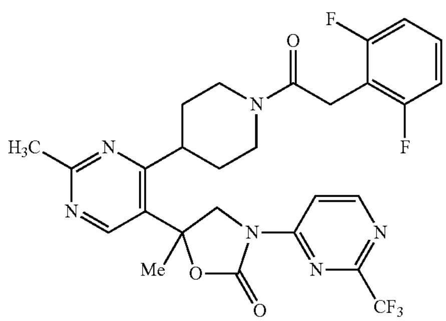 [SMILES: Cc1ncc(C2(C)CN(c3ccnc(C(F)(F)F)n3)C(=O)O2)c(C2CCN(C(=O)Cc3c(F)cccc3F)CC2)n1] | 5-(4-(1-(2-(2,6-difluorophenyl)acetyl)piperidin-4-yl)-2-methylpyrimidin-5-yl)-5-methyl-3-(2-(trifluoromethyl)pyrimidin-4-yl)oxazolidin-2-one |
| N51 | 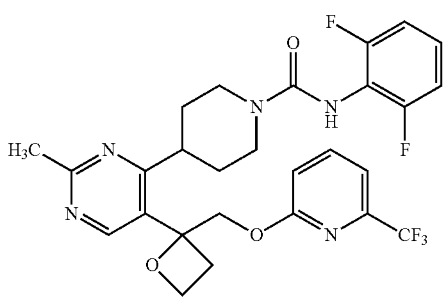 [SMILES: Cc1ncc(C2(COc3cccc(C(F)(F)F)n3)CCO2)c(C2CCN(C(=O)Nc3c(F)cccc3F)CC2)n1] | N-(2,6-difluorophenyl)-4-(2-methyl-5-(2-((6-(trifluoromethyl)pyridin-2-yloxy)methyl)oxetan-2-yl)pyrimidin-4-yl)piperidine-1-carboxamide |
| N52 | 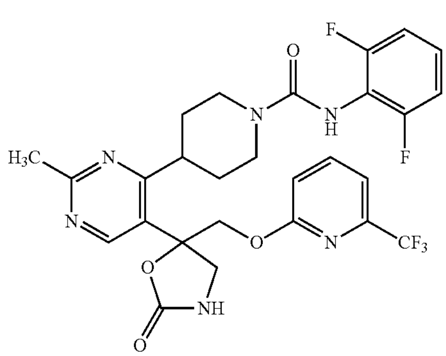 [SMILES: Cc1ncc(C2(COc3cccc(C(F)(F)F)n3)CNC(=O)O2)c(C2CCN(C(=O)Nc3c(F)cccc3F)CC2)n1] | N-(2,6-difluorophenyl)-4-(2-methyl-5-(2-oxo-5-((6-(trifluoromethyl)pyridin-2-yloxy)methyl)oxazolidin-5-yl)pyrimidin-4-yl)piperidine-1-carboxamide |

The compounds disclosed herein can be made using procedures familiar to the person of ordinary skill in the art and as described herein. For example, compounds of structural formula (I) can be prepared according to Schemes 1-50, below, or analogous synthetic schemes:
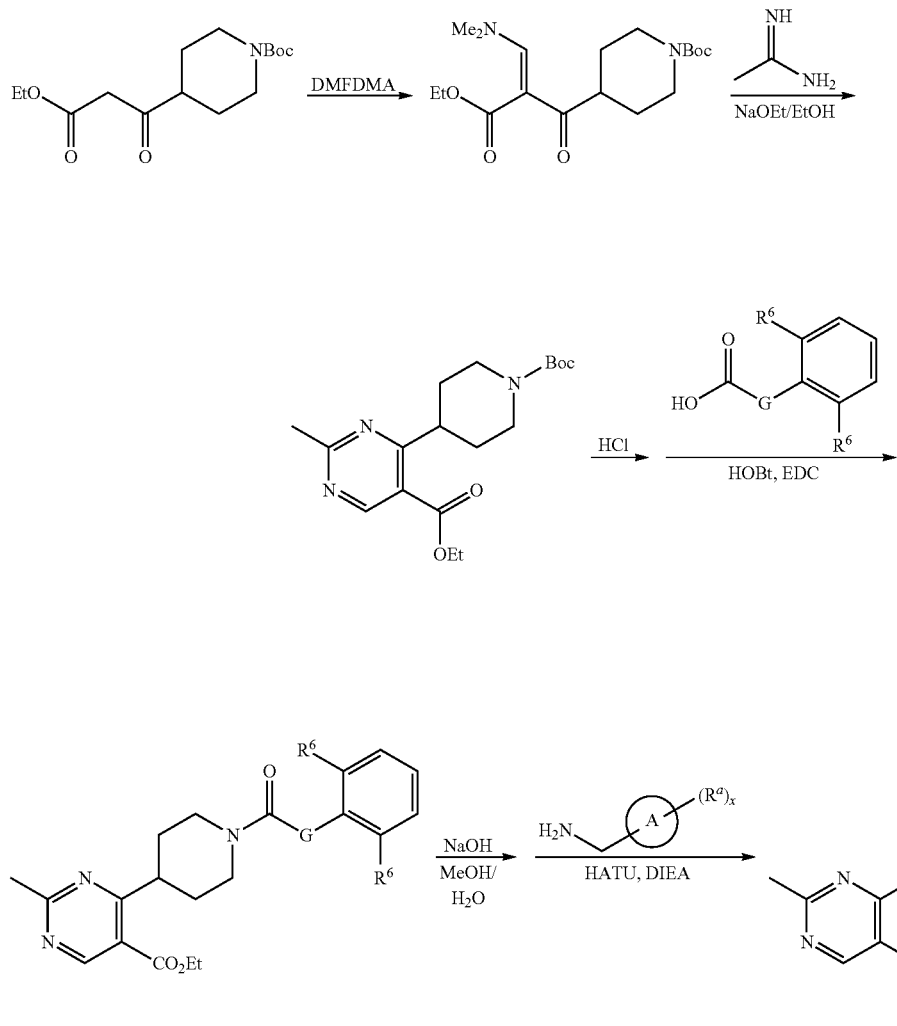
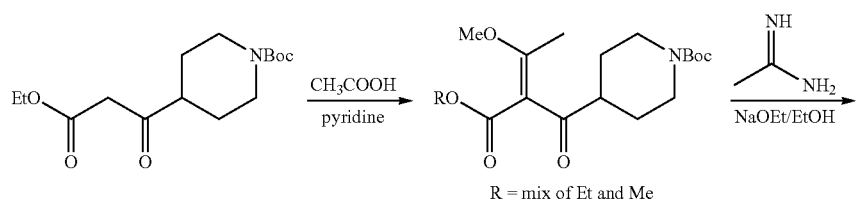
R = mix of Et and Me -continued
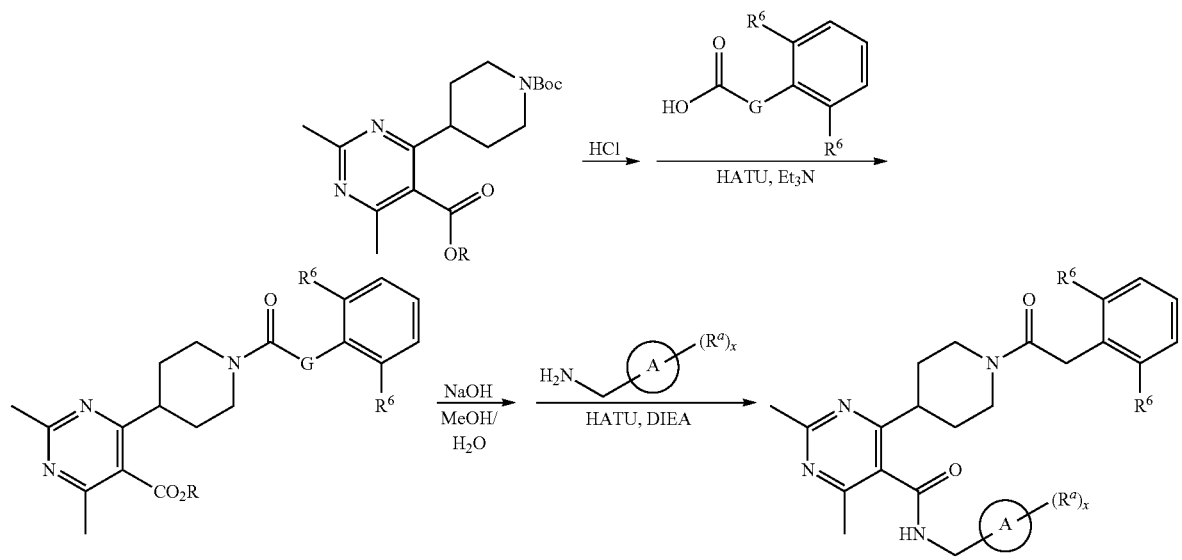
Scheme 3
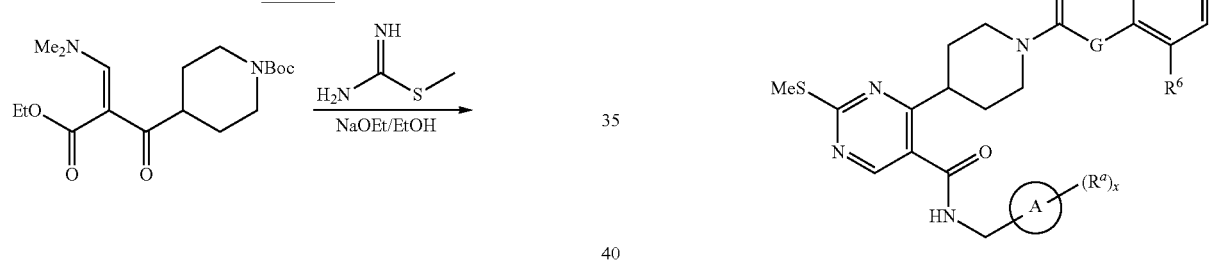
-continued
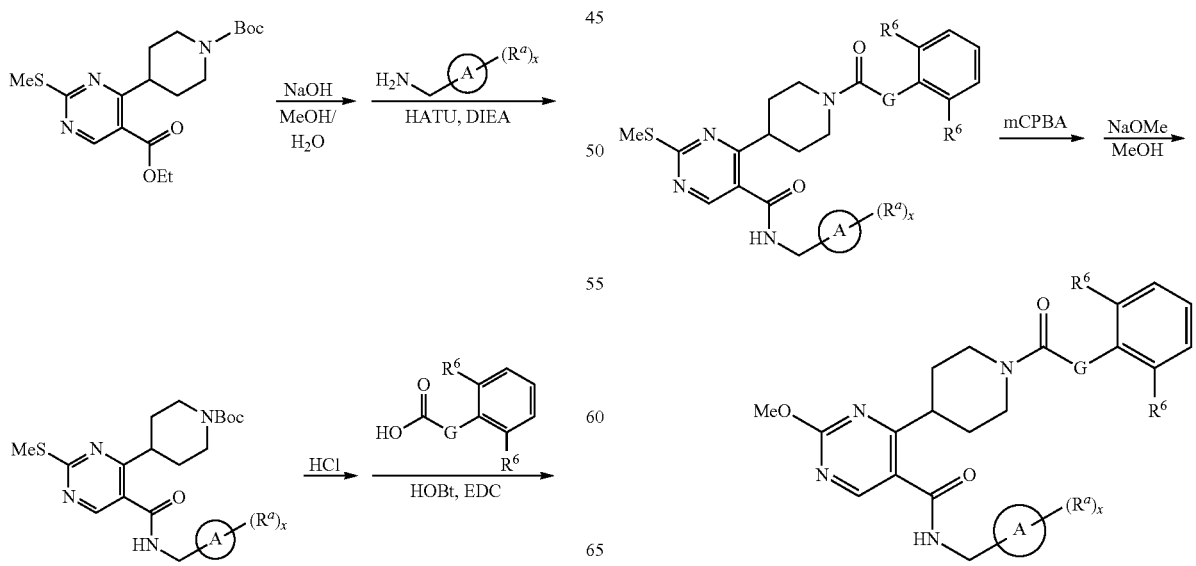
Scheme 4

Scheme 5
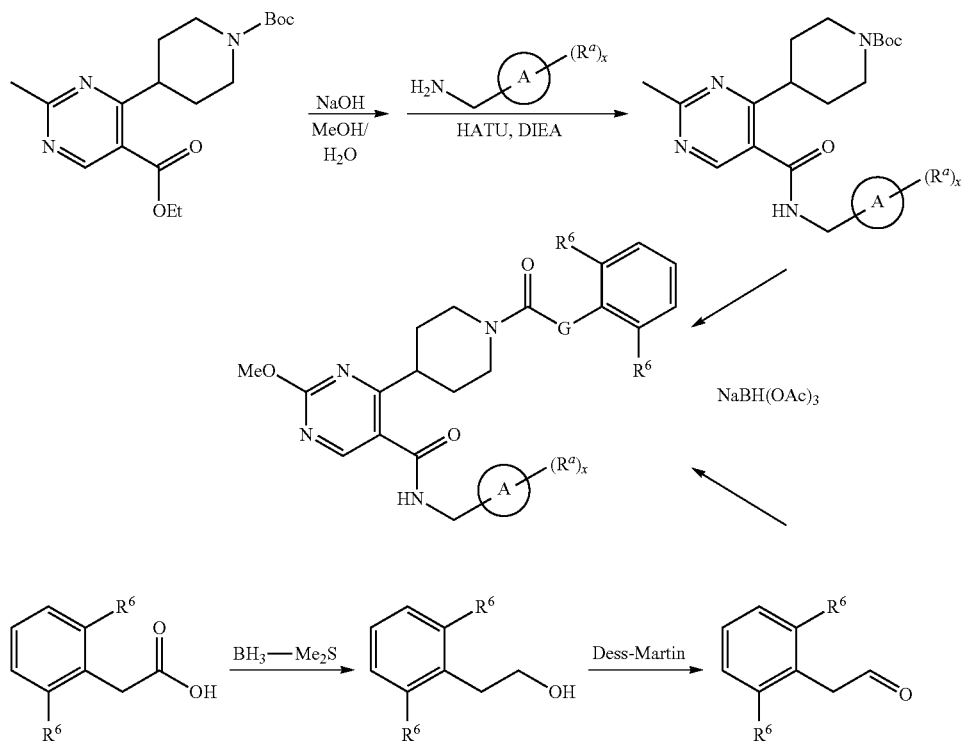
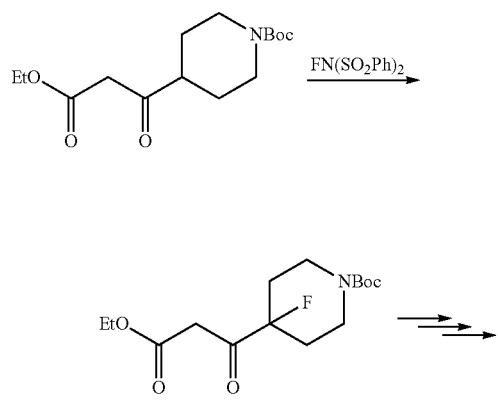
Scheme 6
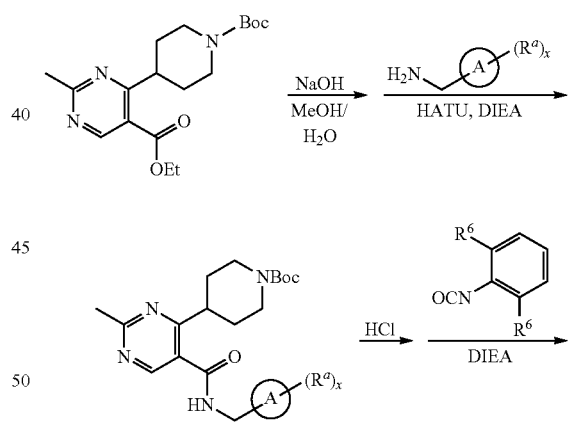
Scheme 7
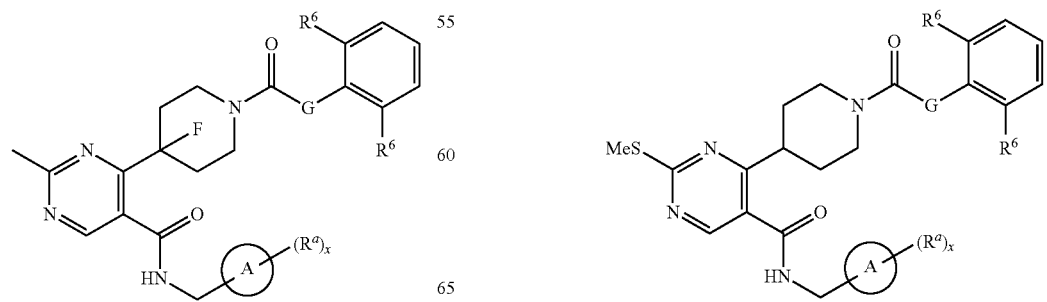

Scheme 8
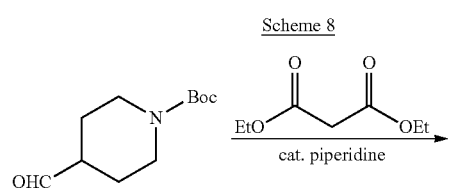
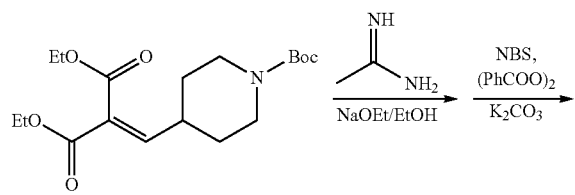
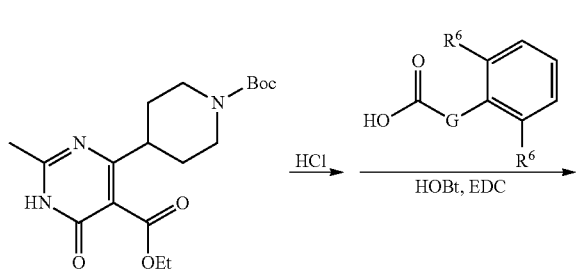
-continued
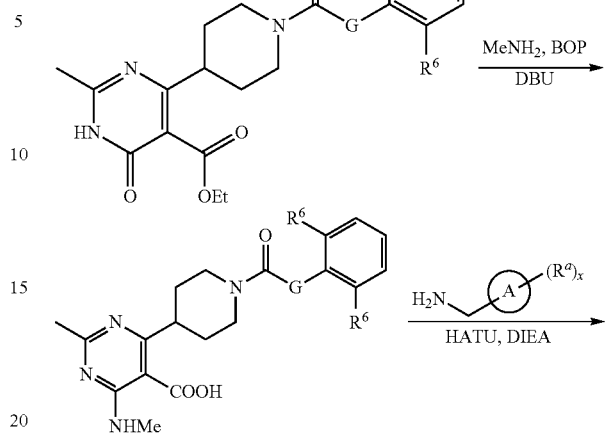
Scheme 9
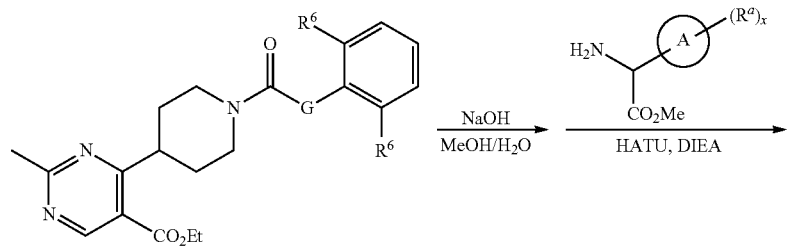
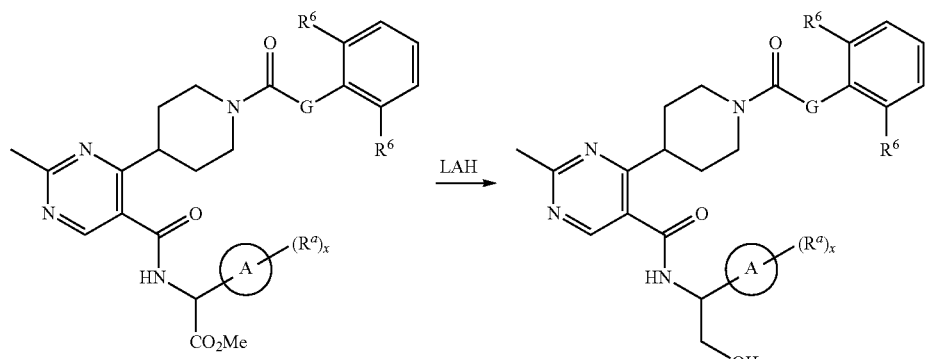
NOT IN NARROW Scheme 10
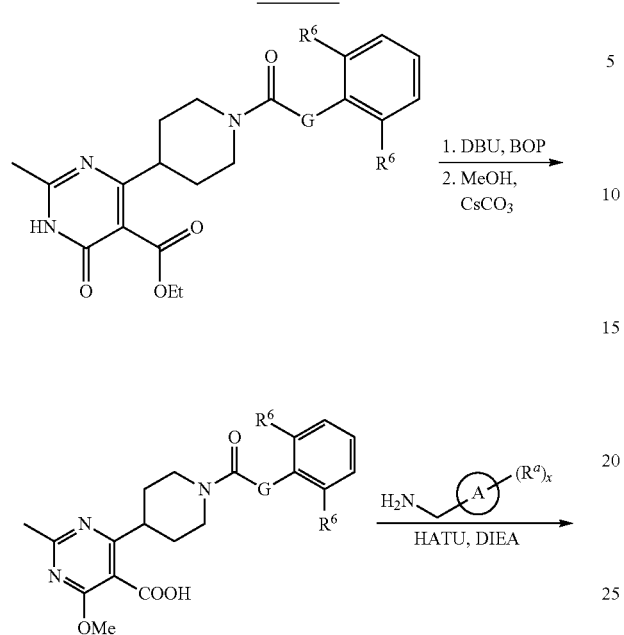
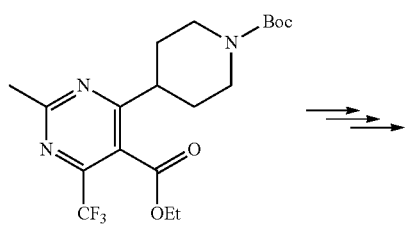
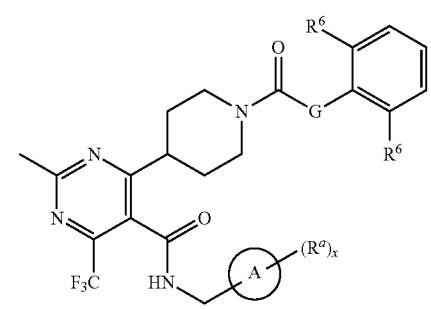
Scheme 11
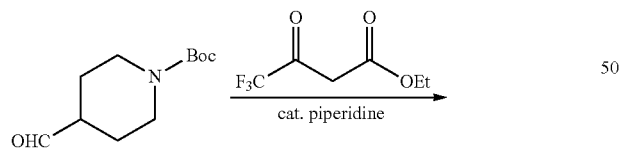
Scheme 12
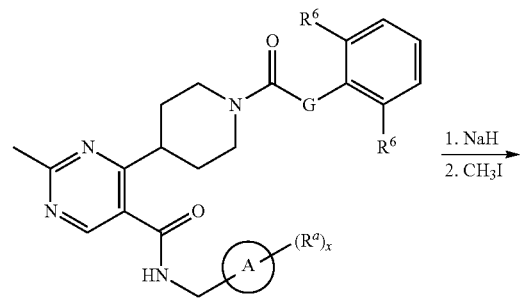
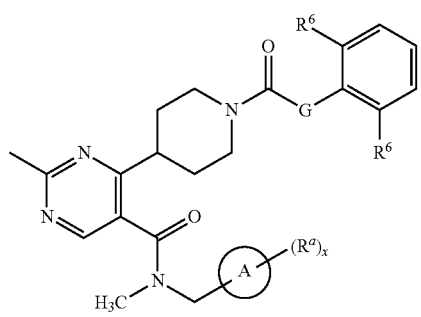
NOT IN NARROW Scheme 13
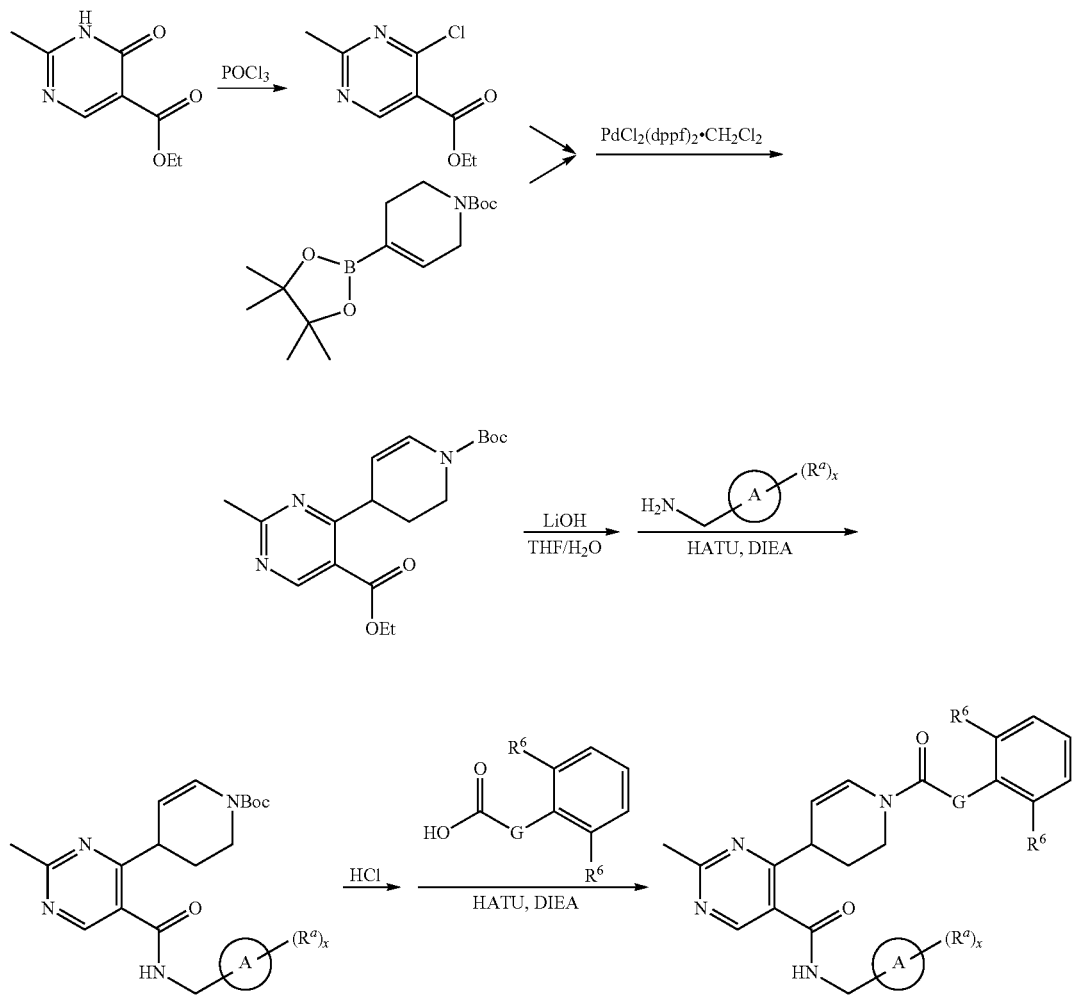
Scheme 14
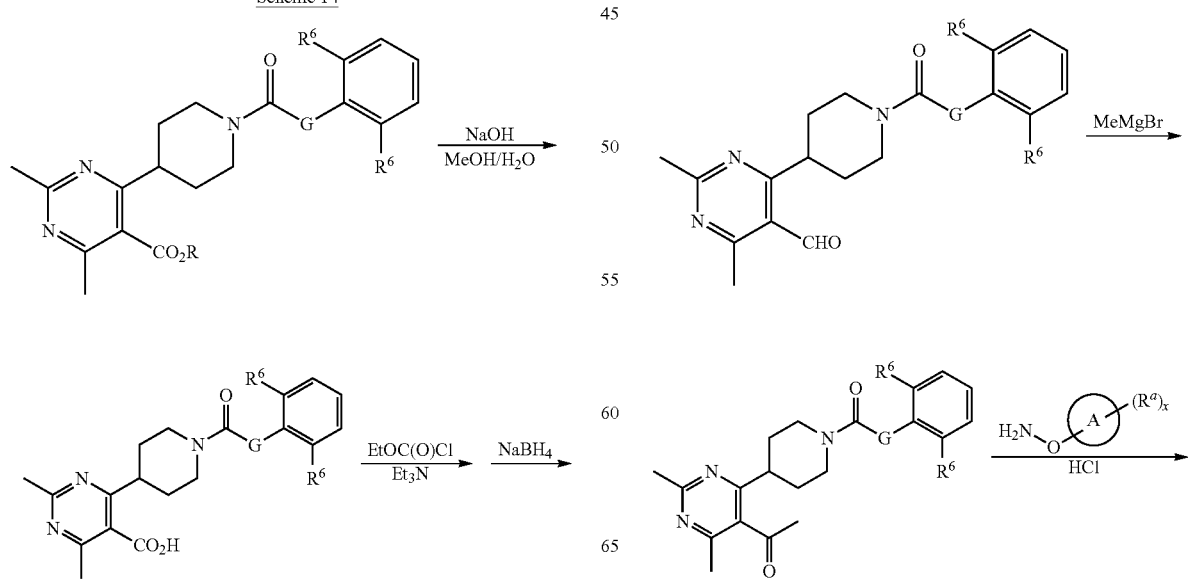

185
-continued
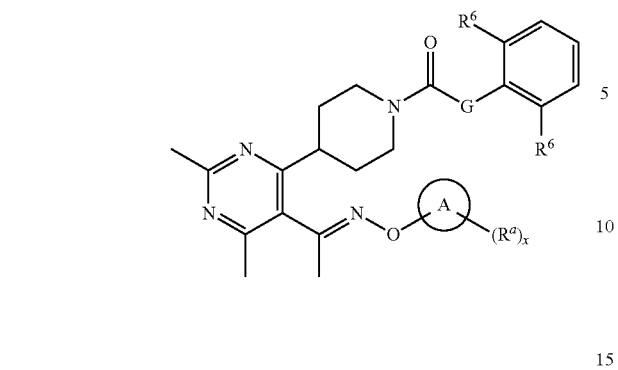
Scheme 15
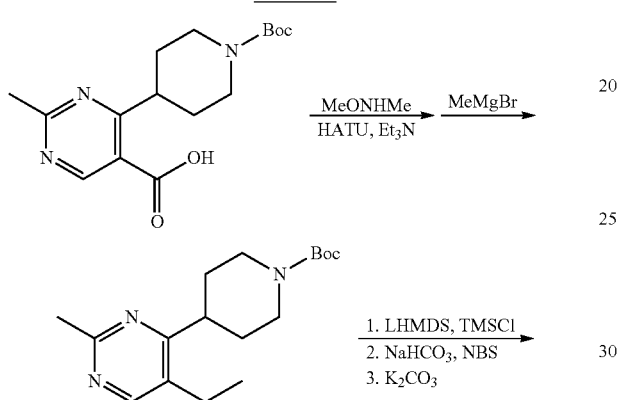
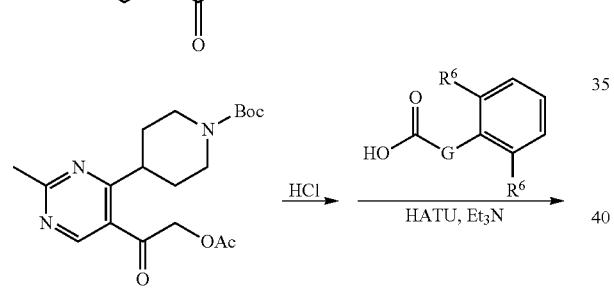
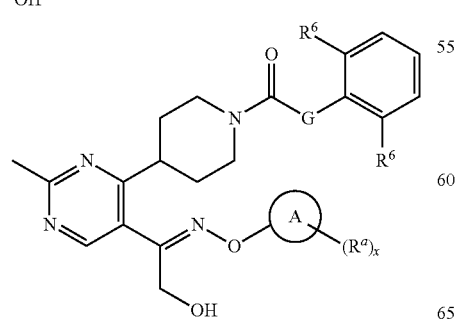
Scheme 16
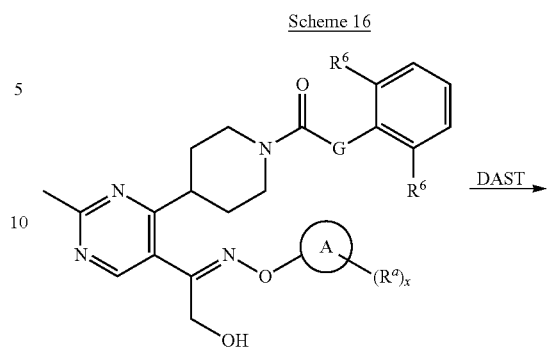
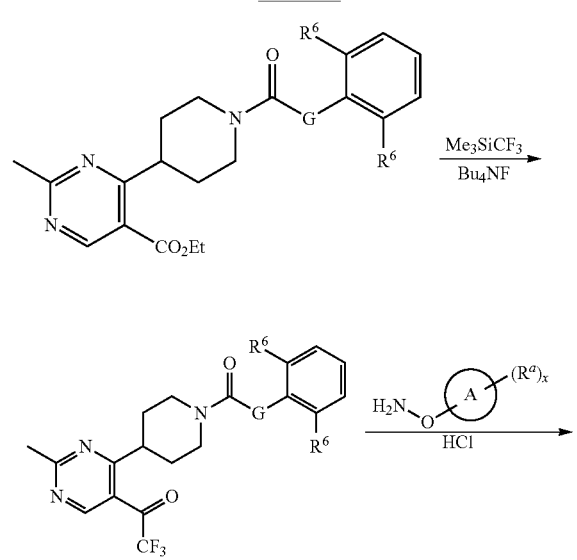
Scheme 17
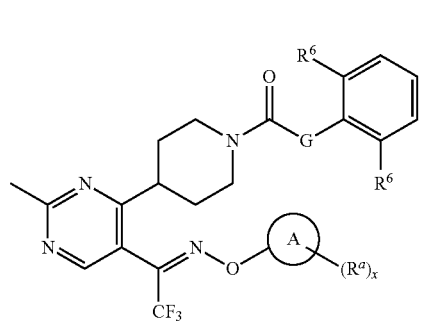

Scheme 18
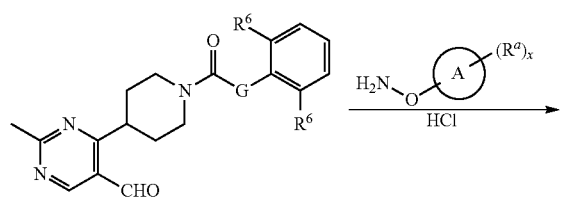
Scheme 19
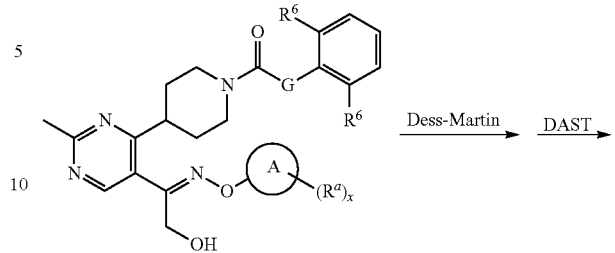
Scheme 20
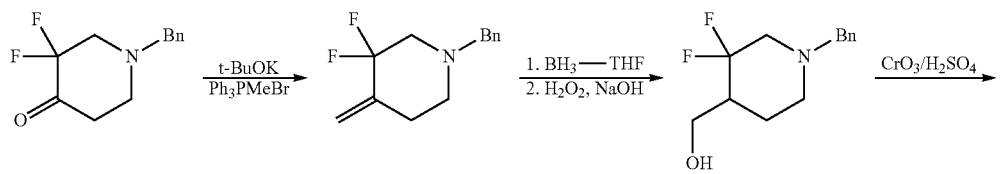

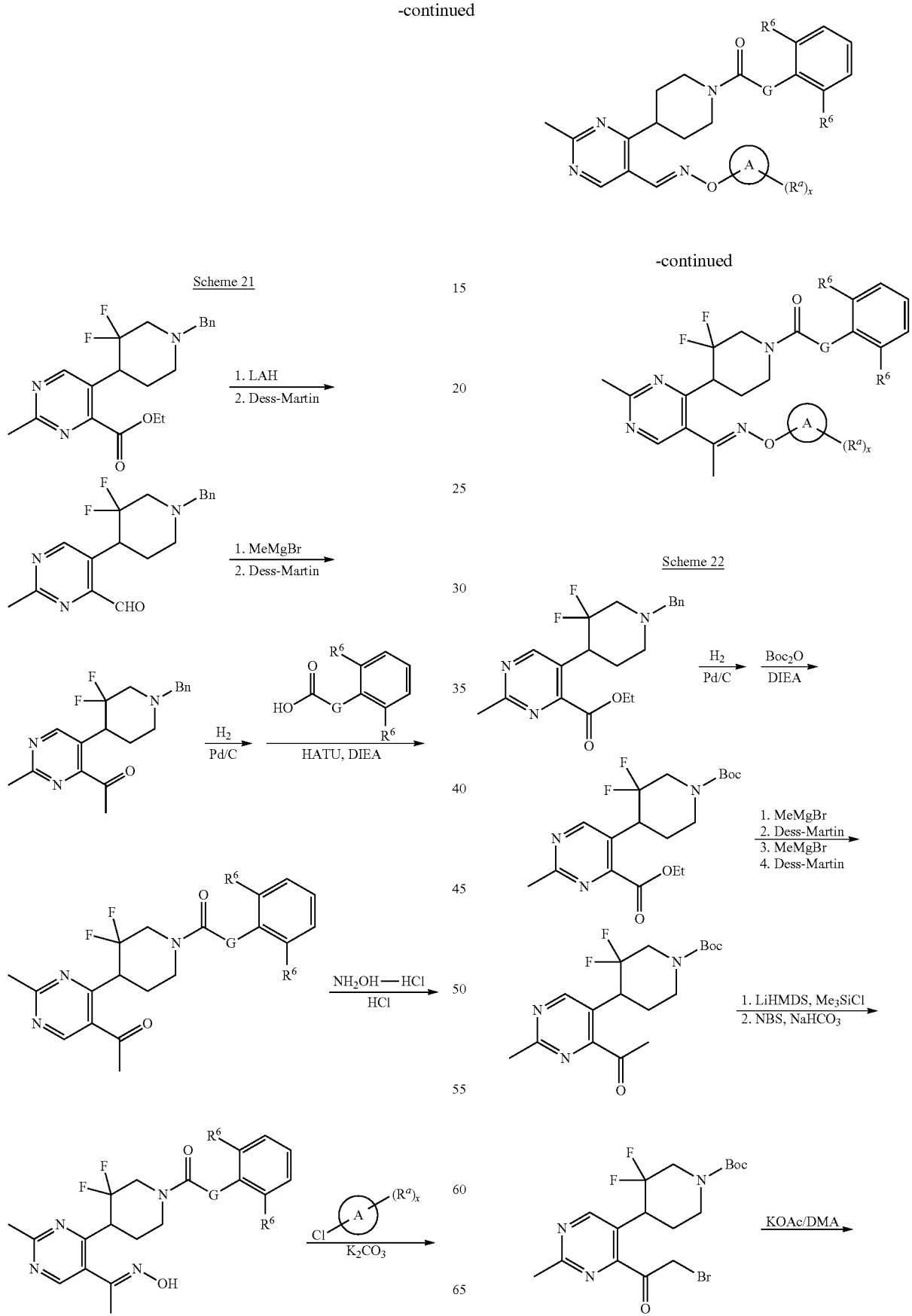

191
-continued
192
-continued
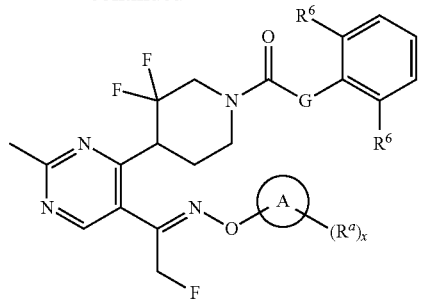
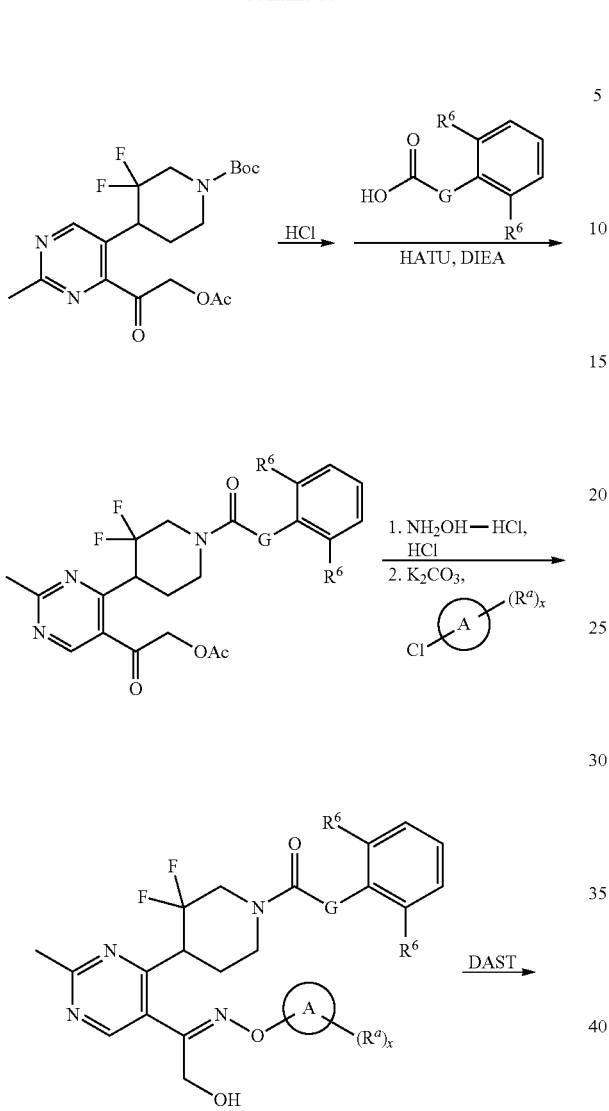
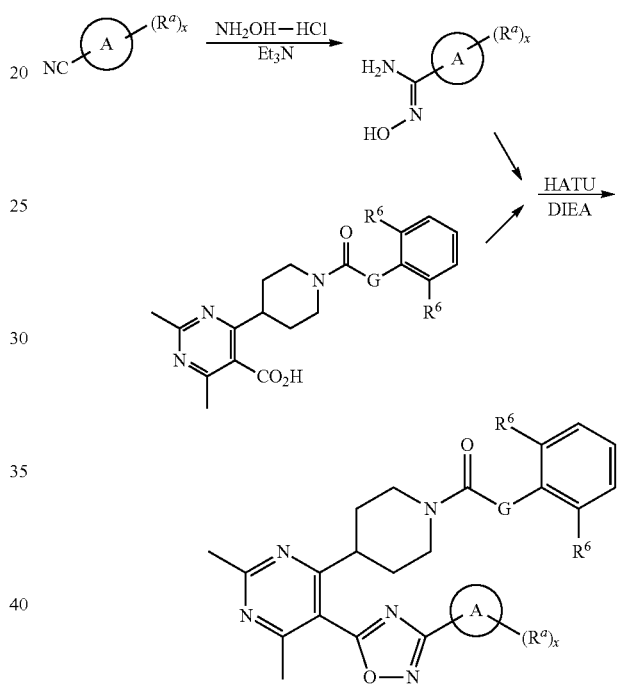
Scheme 23
Scheme 24
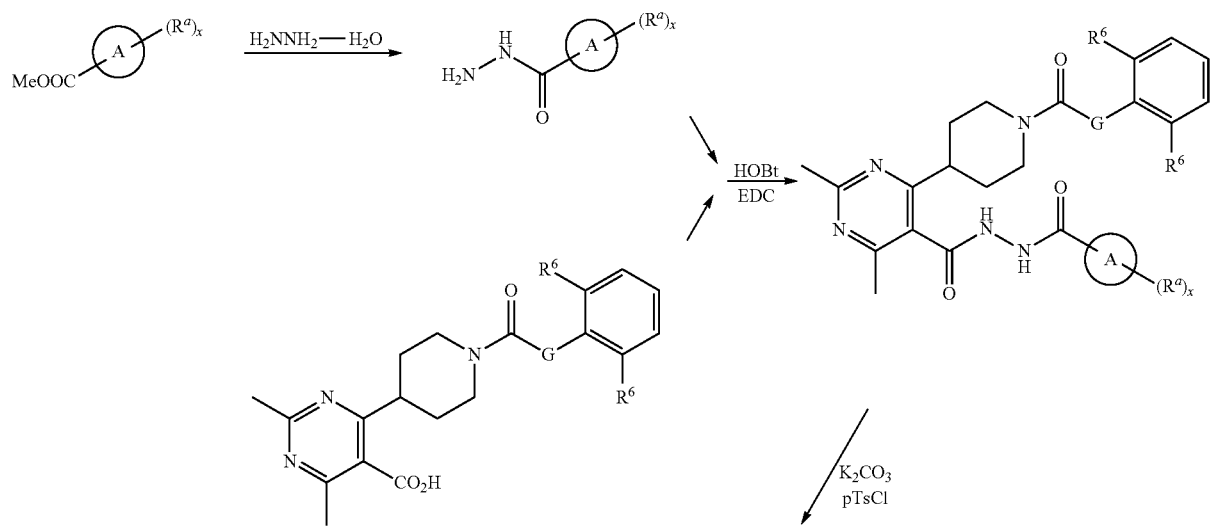

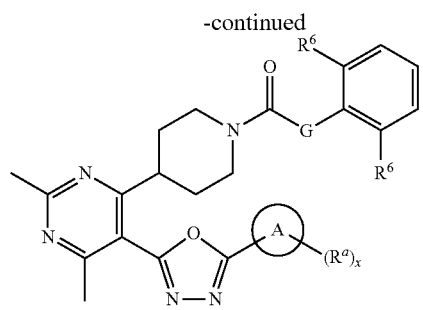
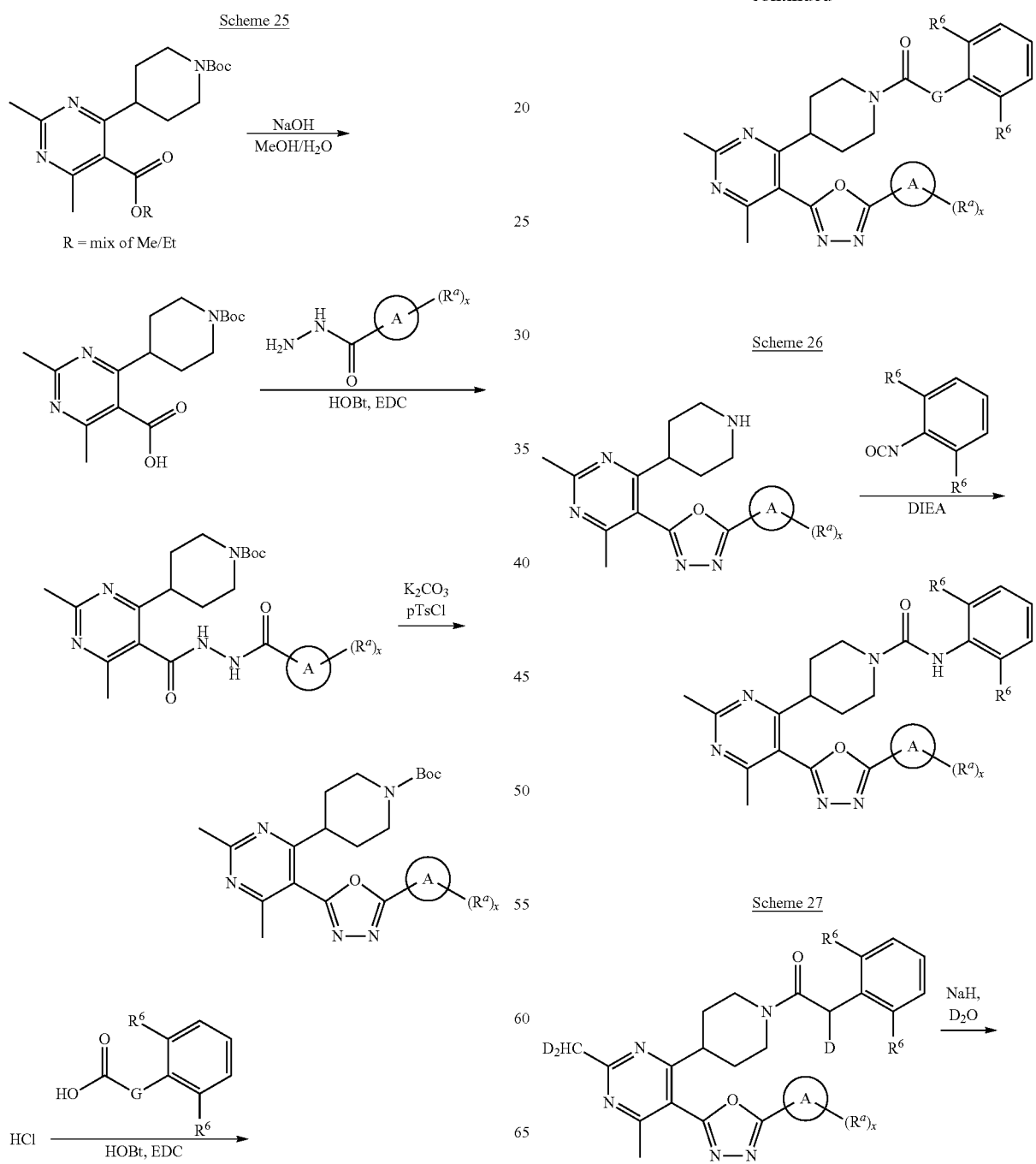

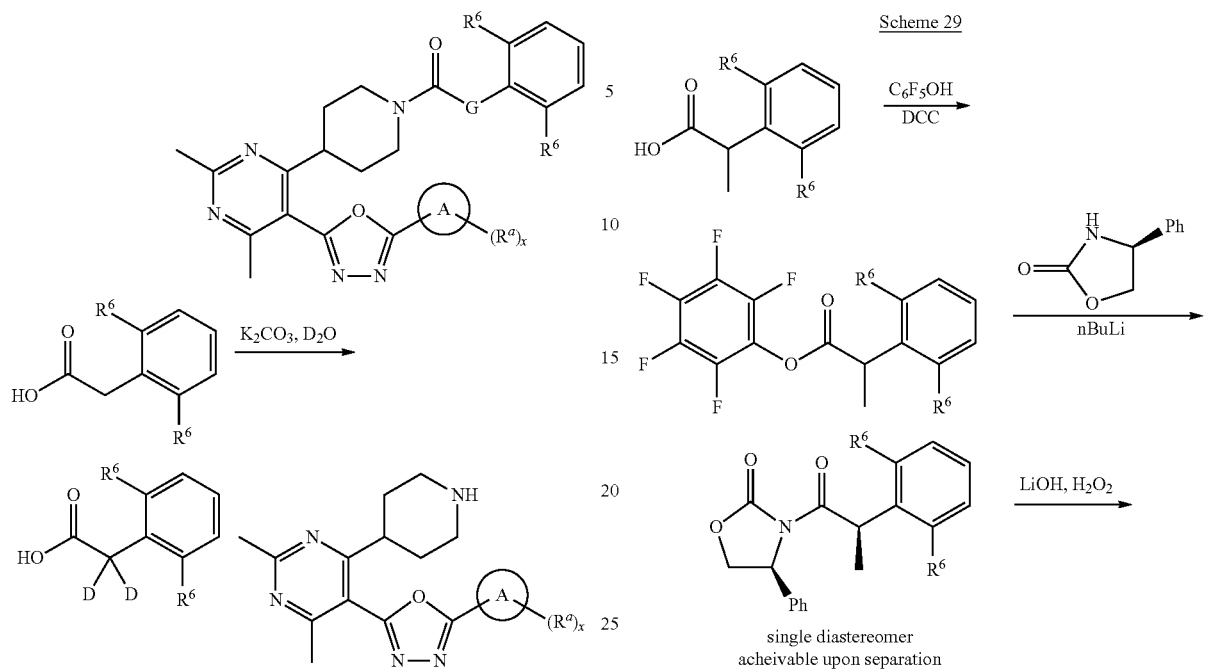
Scheme 28
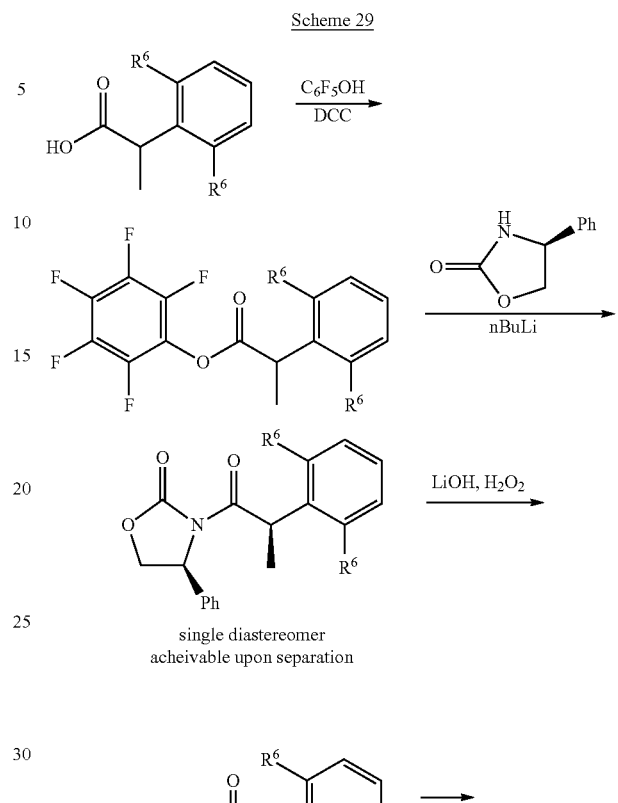
Scheme 29
Scheme 30
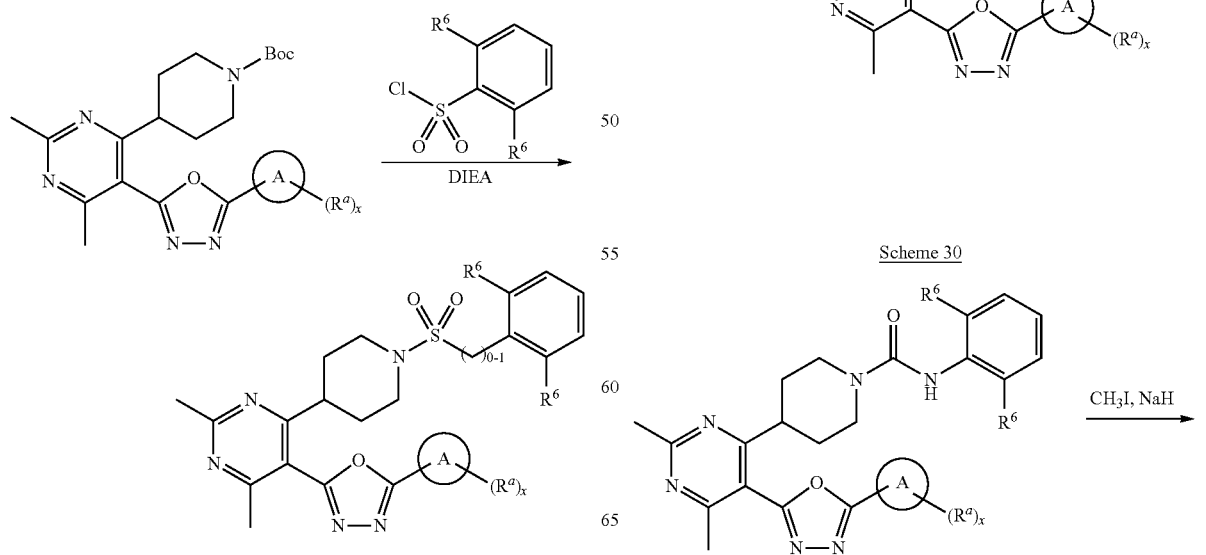

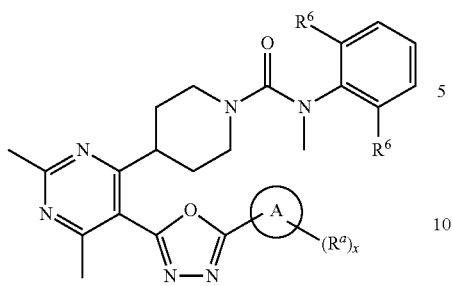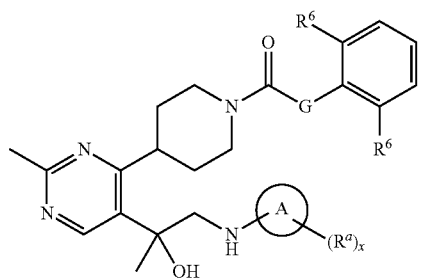
Scheme 31
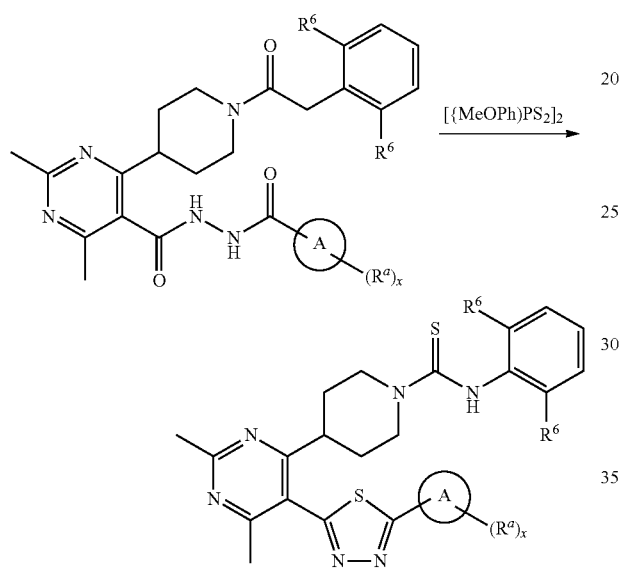
Scheme 32
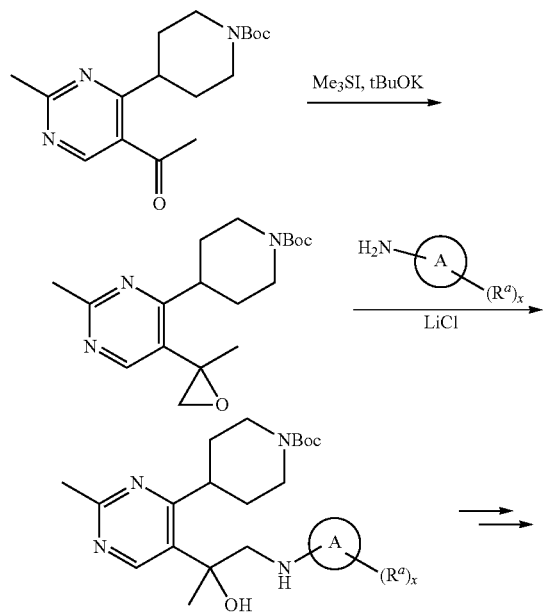
Scheme 33
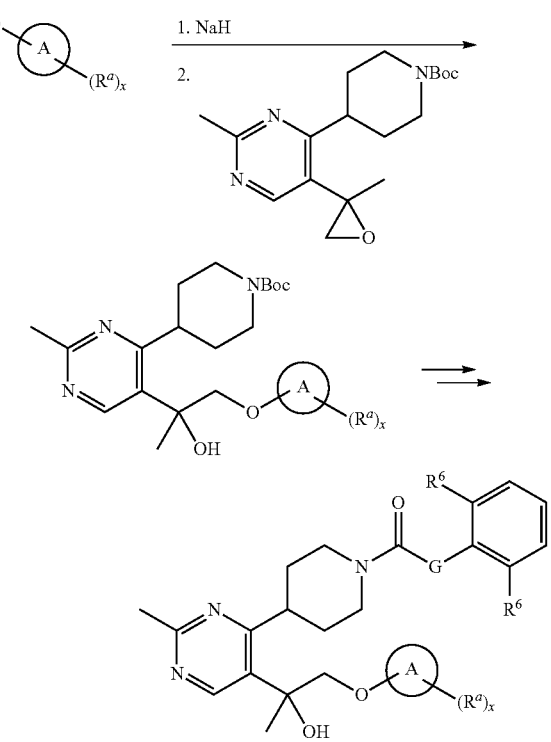
Scheme 34
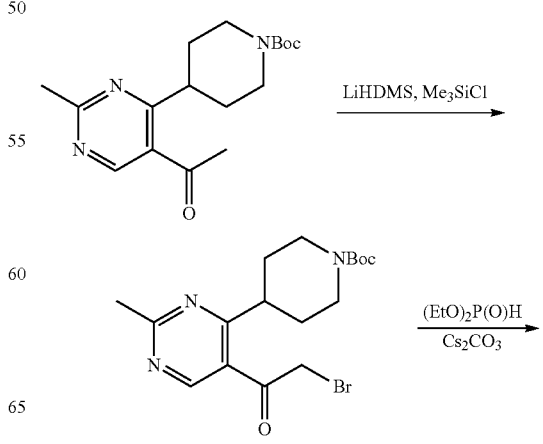

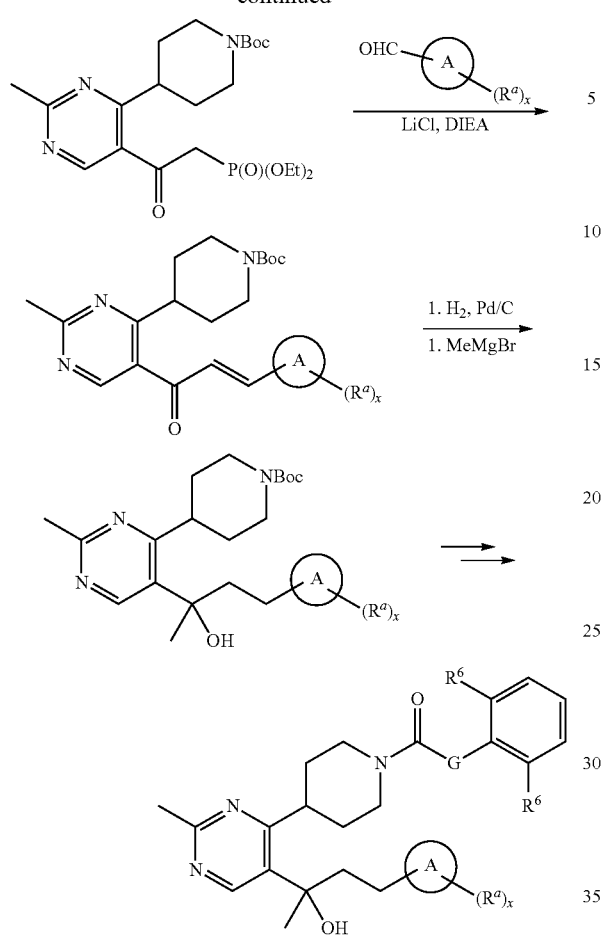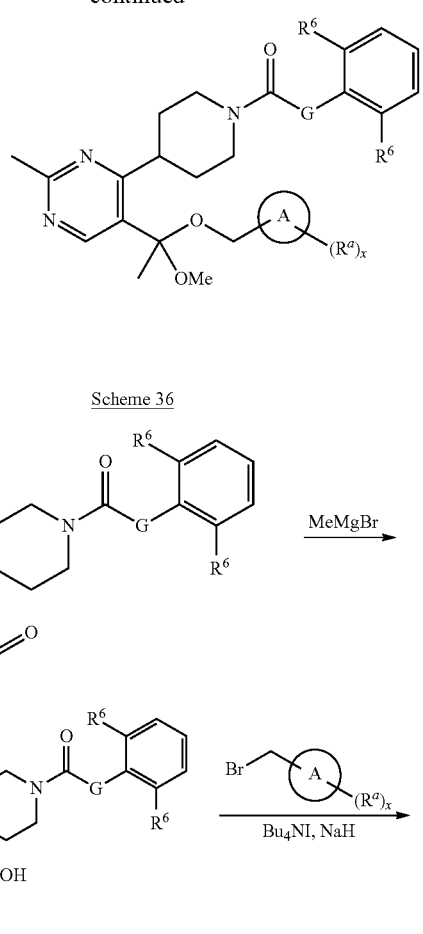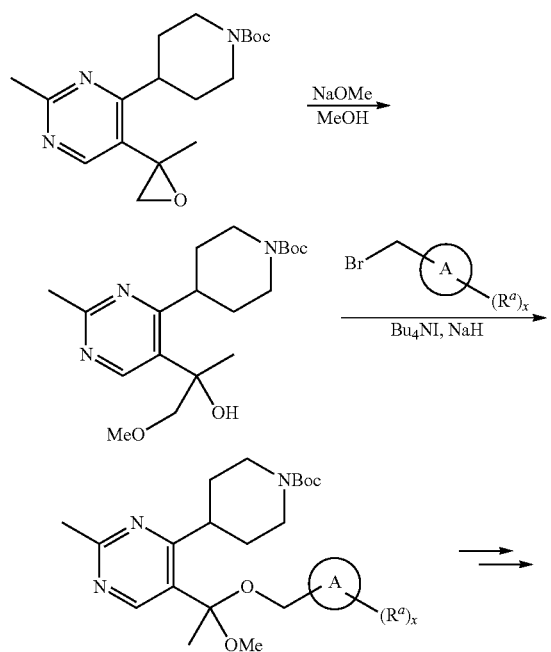
Scheme 35
Scheme 36
Scheme 37

201
-continued
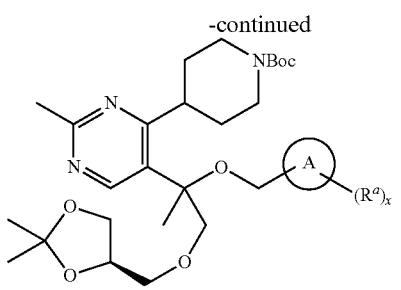
202
Scheme 38
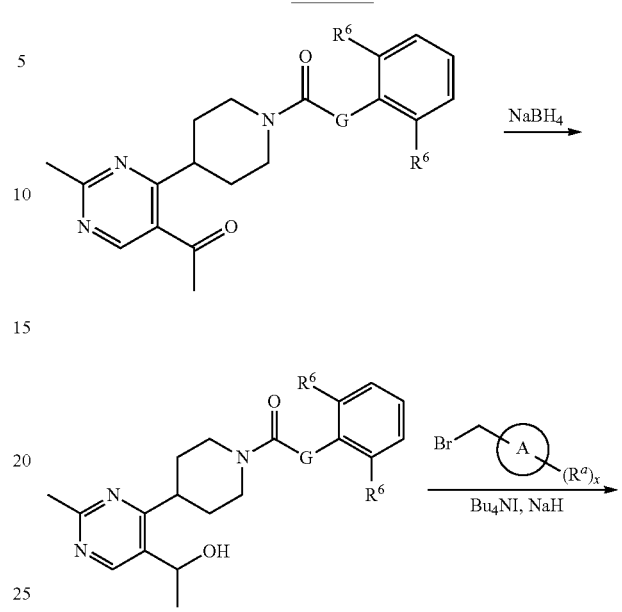
Scheme 38
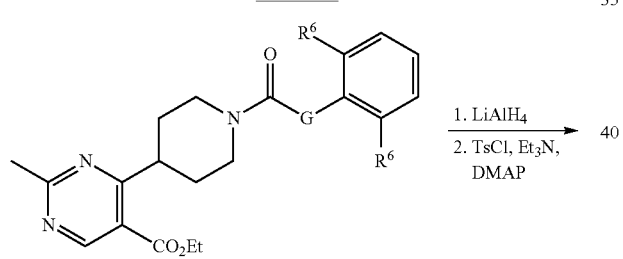
Scheme 39
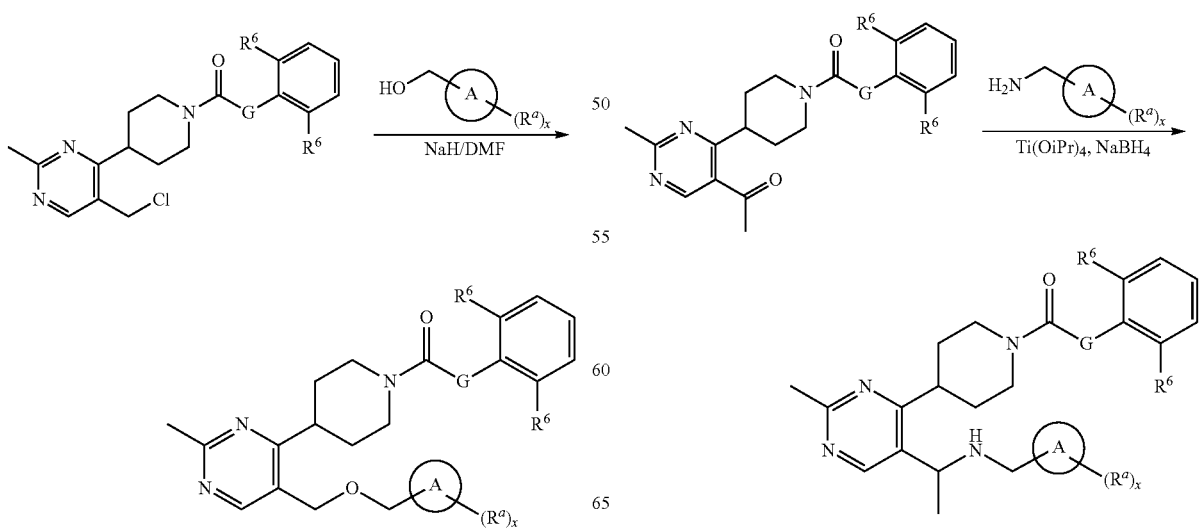

Scheme 40
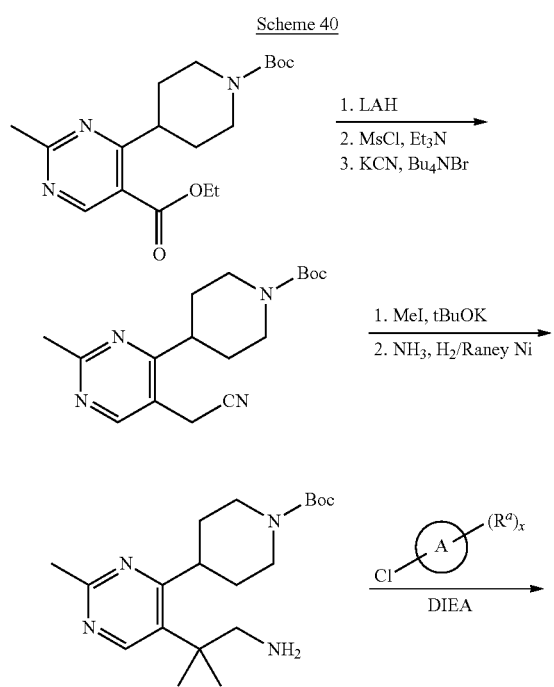
Scheme 41
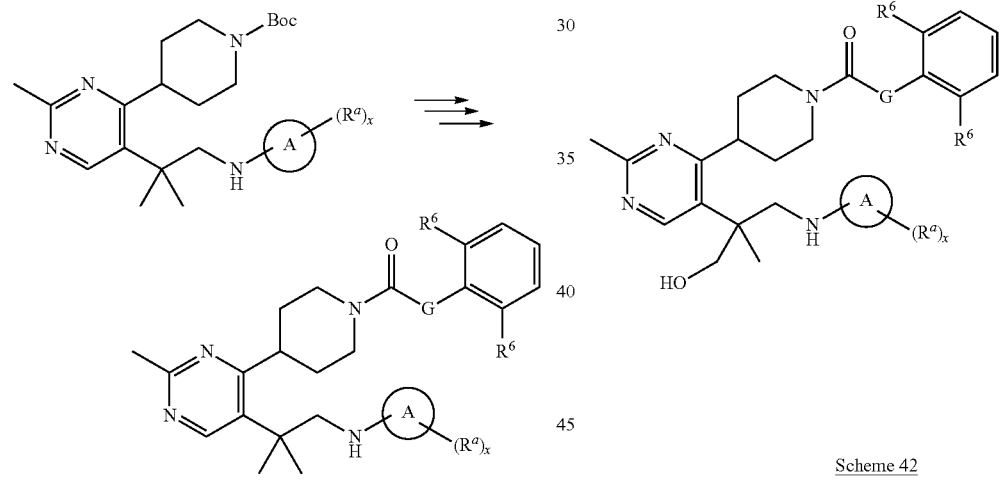
-continued
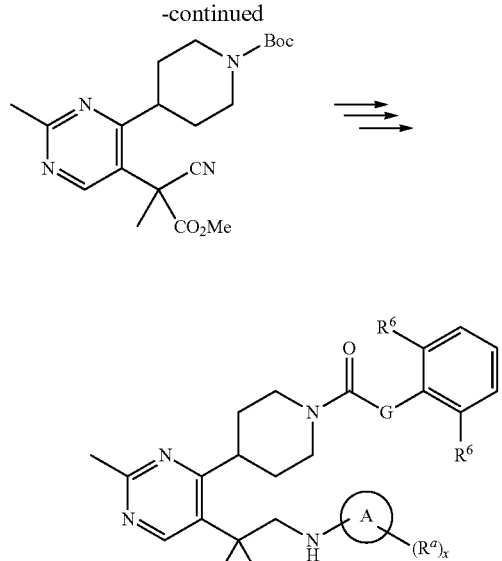
Scheme 42
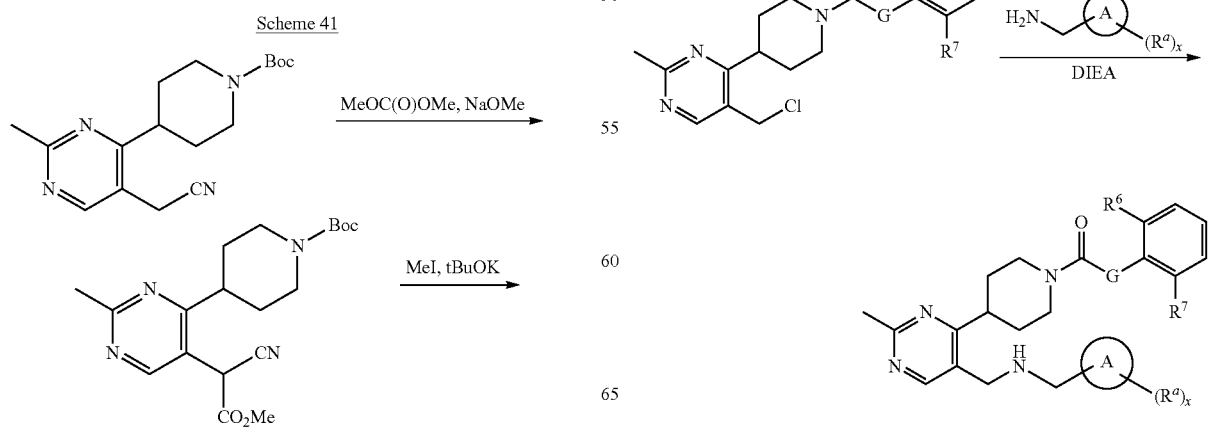

Scheme 43
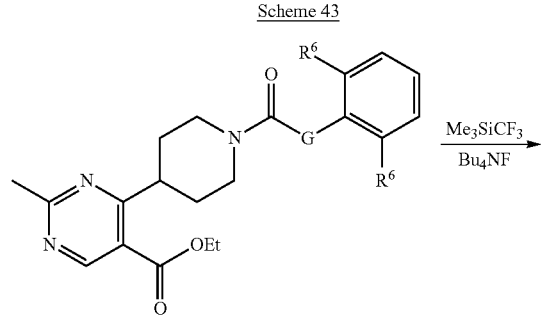
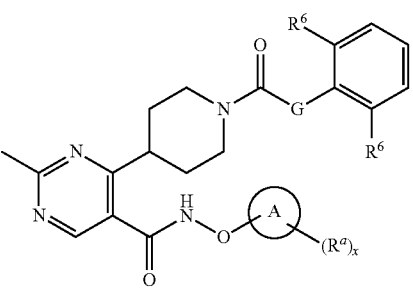
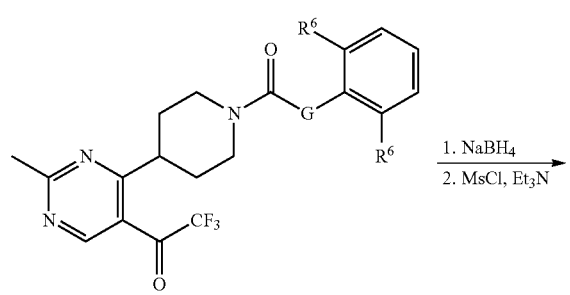
Scheme 44
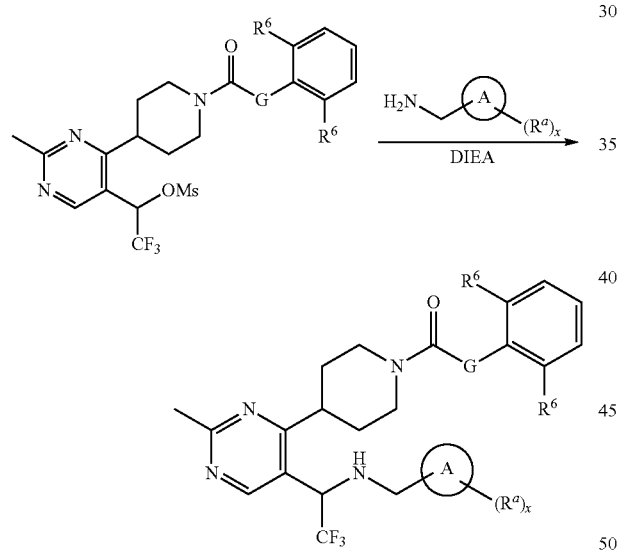
-continued
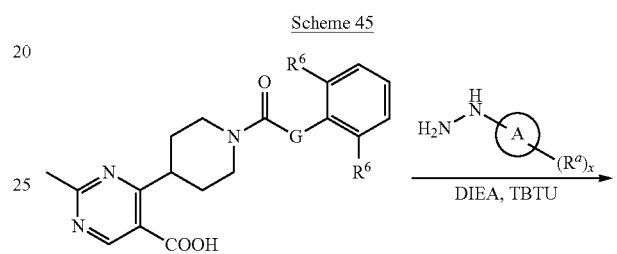
Scheme 45
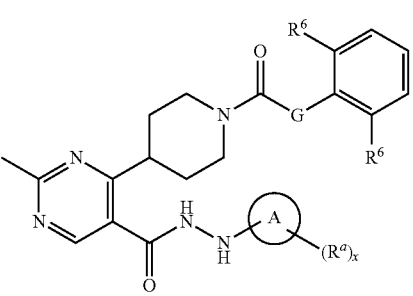
Scheme 46
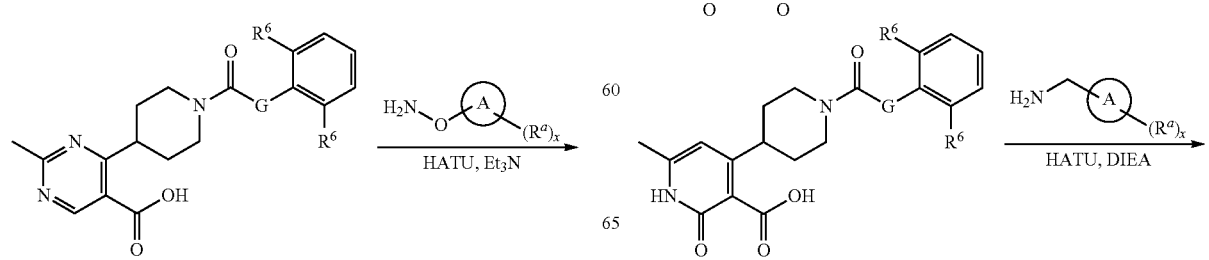

-continued
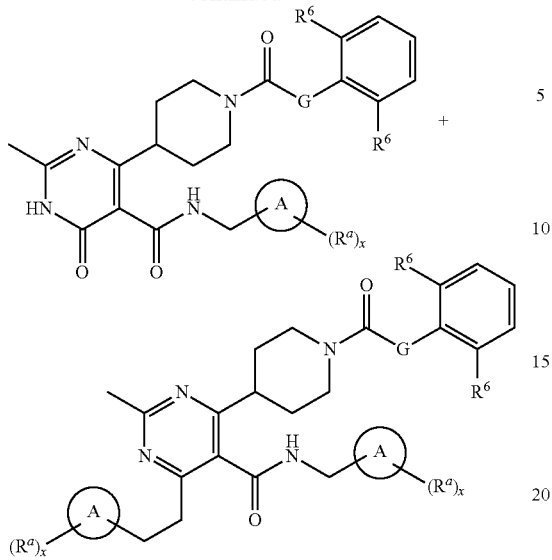
Scheme 47
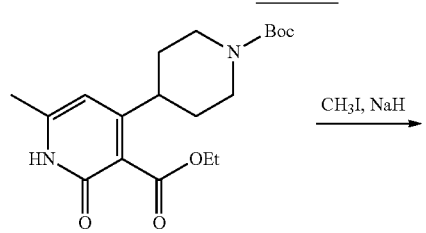
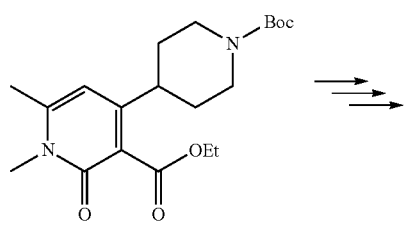
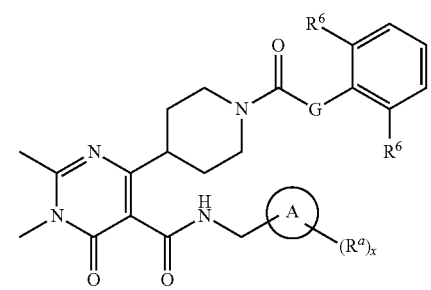
Scheme 48
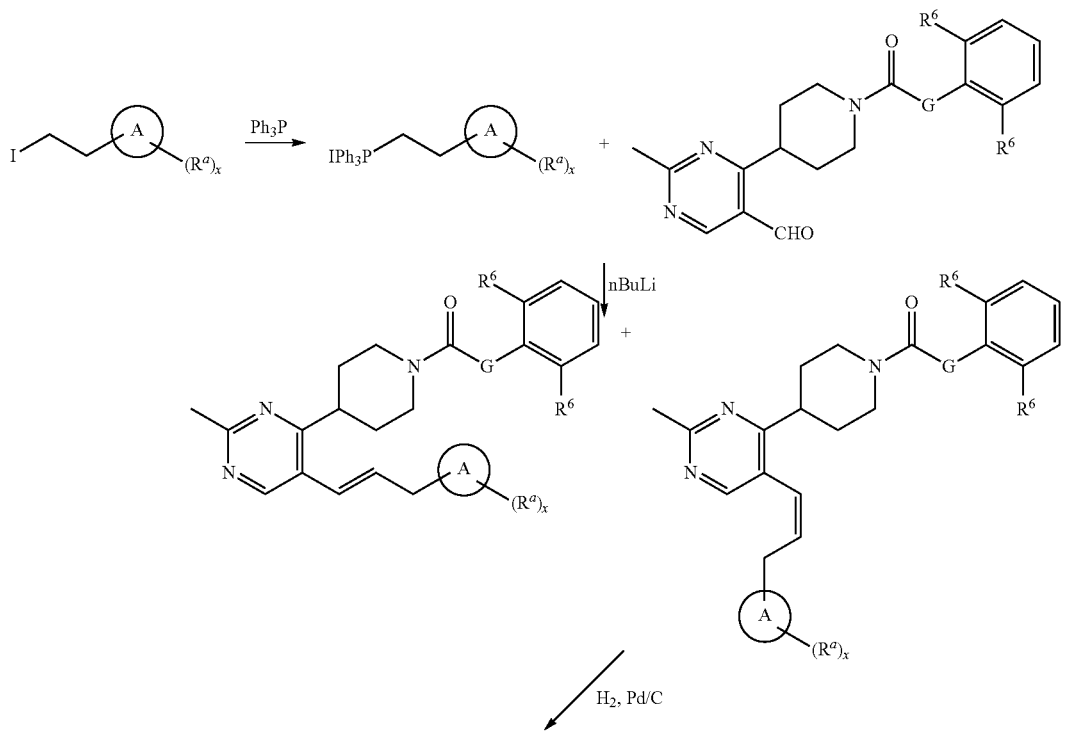

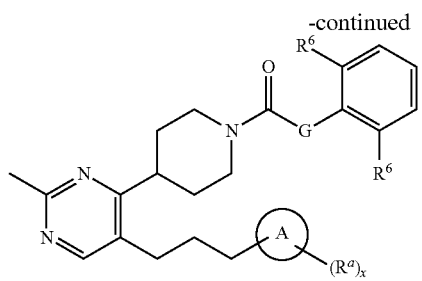

Scheme 49

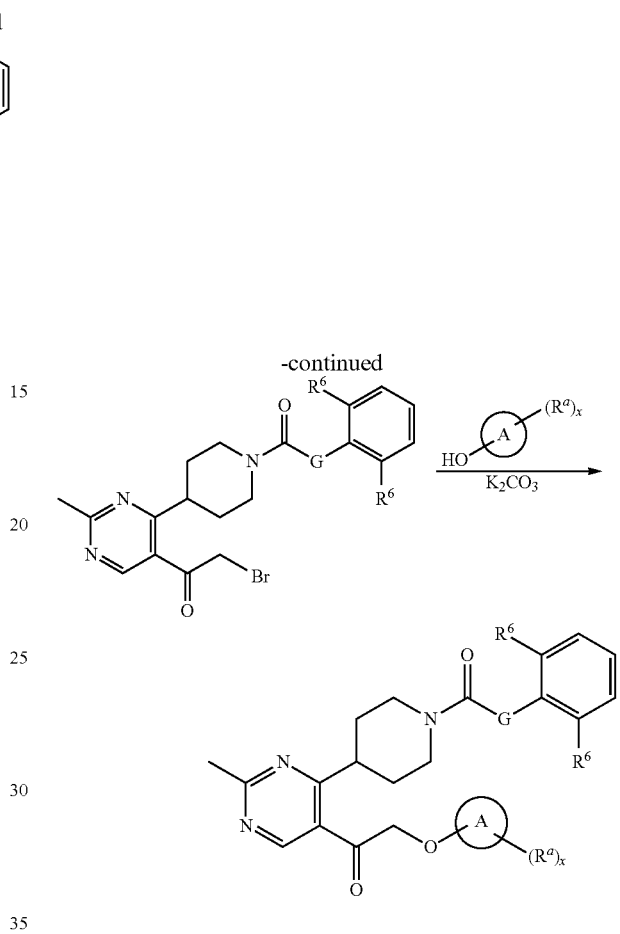

Scheme 50

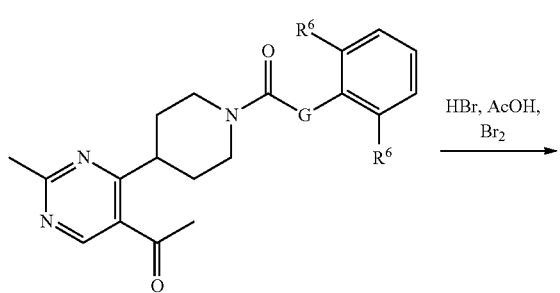

Additional schemes are provided in the Examples, below.

One of skill in the art can adapt the reaction sequences of Schemes 1-50 and of the Examples to fit the desired target molecule. For example, use of a 2-ethylpyrimidine will result in compounds in which $R^1$ is ethyl, instead of methyl as in many of the example compounds. Similarly, while the schemes generally depict the -("B" ring system)-$(R^b)_y$ moiety as ortho-disubstituted phenyl, the person of skill will appreciate that use of different starting materials will provide different rings and/or different patterns of substitution. Of course, in certain situations one of skill in the art will use different reagents to affect one or more of the individual steps or to use protected versions of certain of the substituents. Additionally, one skilled in the art would recognize that compounds of structural formula (I) can be synthesized using different routes altogether.

The compounds of the present invention can be provided in a number of stereoisomeric forms. Accordingly, another aspect of the invention is a stereoisomeric form of a compound as described herein. For example, a compound of the present invention can be provided in racemic form. In other embodiments, a compound of the present invention is provided in scalemic form, or in a stereoisomerically pure form (e.g., substantially as a single enantiomer).

Another aspect of the invention is an N-oxide of a compound or stereoisomeric form as described herein.

Another aspect of the invention is a pharmaceutically acceptable salt of a compound, stereoisomeric form, or N-oxide as described herein. As used herein, the phrase "pharmaceutically acceptable salt" refers to both pharmaceutically acceptable acid and base addition salts. Such pharmaceutically acceptable salts include salts of acids such as hydrochloric, phosphoric, hydrobromic, sulfuric, sulfinic, formic, trifluoroacetic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Another aspect of the invention is a solvate or hydrate of a compound, stereoisomeric form, N-oxide or pharmaceutically acceptable salt as described herein. The person of skill in the art can determine whether a particular compound will form a solvate or a hydrate.

Another aspect of the invention is a pharmaceutical composition including a compound, stereoisomeric form, N-oxide, pharmaceutical salt, solvate or hydrate as described herein The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μ/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the compound selected, formulation of the excipient, and its route of administration. Effective doses can be extrapolated from dose-response curves derived from in vitro or animal model test systems.

The compounds of the present invention are useful to prevent, diagnose, and treat various medical disorders in humans or animals. The compounds are used to inhibit or reduce one or more activities associated with RORγ receptors, relative to RORγ receptors in the absence of the same compounds. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of compound according to formula (I), stereoisomeric form, N-oxide, pharmaceutically acceptable salt, solvate, hydrate or pharmaceutical composition as described herein. See, e.g., L. A. Solt et al., "Action of RORs and their ligands in (patho)physiology," *Trends Endocrinol Metab.*, preprint available online Jul. 11, 2012 at http://www.sciencedirect.com/science/article/pii/S1043276012000926; M. S. Maddur et al., "Th17 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," *Nucl. Recept. Signal.* 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases and lupus. In certain embodiments, the allergic disease or disorder is selected from allergic rhinitis and dermatitis. In certain embodiments, the metabolic disease or disorder is selected from obesity, obesity-induced insulin resistance and type II diabetes.

In certain embodiments, the disease or disorder is rheumatoid arthritis. See, e.g., L. A. Solt et al., referenced above, as well as the references discussed in the Background section.

In other embodiments, the disease or disorder is multiple sclerosis. See, e.g., L. Codarri et al., "RORγt drives production of the cytokine GM-CSF in helper T cells, which is essential for the effector phase of autoimmune neuroinflammation," *Nat. Immunol.,* 2011 June; 12(6):560-7, which is hereby incorporated herein by reference in its entirety, as well as the references discussed in the Background section.

In other embodiments, the disease or disorder is ankylosing spondylitis. See, e.g., E. Toussirot, "The IL23/Th17 pathway as a therapeutic target in chronic inflammatory diseases," *Inflamm. Allergy Drug Targets,* 2012 April; 11(2):159-68, which is hereby incorporated herein by reference in its entirety, as well as the references discussed in the Background section.

In other embodiments, the disease or disorder is inflammatory bowel disease. See, e.g., M. Leppkes et al., "ROR-gamma-expressing Th17 cells induce murine chronic intestinal inflammation via redundant effects of IL-17A and IL-17F," *Gastroenterology,* 2009 January; 136(1):257-67, which is hereby incorporated herein by reference in its entirety, as well as the references discussed in the Background section.

In other embodiments, the disease or disorder is lupus. See, e.g., K. Yoh et al., "Overexpression of RORγt under control of the CD2 promoter induces polyclonal plasmacytosis and autoantibody production in transgenic mice," *Eur. J. Immunol.,* 2012 August; 42(8):1999-2009, which is hereby incorporated herein by reference in its entirety, as well as the references discussed in the Background section.

In other embodiments, the disease or disorder is psoriasis. See, e.g., S. Pantelyushin et al., "RORγt+ innate lymphocytes and γδ T cells initiate psoriasiform plaque formation in mice," *J. Clin. Invest.,* 2012 Jun. 1; 122(6):2252-6; and S. P. Raychaudhuri, "Role of IL-17 in Psoriasis and Psoriatic Arthritis," Clin. Rev. Allergy Immunol., preprint available online Feb. 24, 2012 at http://rd.springer.com/article/10.1007/s12016-012-8307-1 (PubMed PMID: 22362575), each of which is hereby incorporated herein by reference in its entirety, as well as the references discussed in the Background section.

In other embodiments, the disease or disorder is psoriatic arthritis. See, e.g., S. P. Raychaudhuri, referenced above, as well as the references discussed in the Background section.

In other embodiments, the disease or disorder is graft-vs.-host disease (GVHD). Y. Yu et al., "Prevention of GVHD while sparing GVL effect by targeting Th1 and Th17 transcription factorT-bet and RORγt in mice," *Blood,* 2011 Nov. 3; 118(18):5011-20, which is hereby incorporated herein by reference in its entirety, as well as the references discussed in the Background section.

In other embodiments, the disease or disorder is autoimmune uveitis. See, e.g., R. Horai et al., "Cytokines in autoimmune uveitis," *J. Interferon Cytokine Res.,* 2011 October; 31(10):733-44, which is hereby incorporated herein by reference in its entirety, as well as the references discussed in the Background section.

In other embodiments, the disease or disorder is obesity and/or insulin resistance. See, e.g., B. Meissburger et al., "Adipogenesis and insulin sensitivity in obesity are regulated by retinoid-related orphan receptor gamma," *EMBO Mol. Med.,* 2011 November; 3(11):637-51, which is hereby incorporated herein by reference in its entirety, as well as the references discussed in the Background section.

In other embodiments, the disease or disorder is melanoma. See, e.g., Purwar R, et al. Robust tumor immunity to melanoma mediated by interleukin-9-producing T cells. Nat. Med., 2012 July: 18:1248-53, which is hereby incorporated herein by reference in its entirety, as well as the references discussed in the Background section.

In certain aspects, the medical disorder being diagnosed, treated, or prevented by use of the presently disclosed compounds can be, for example, an autoimmune disorder. In other embodiments, the disorder being diagnosed, treated or prevented by use of the presently disclosed compounds can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, *H. pylori* infection and inflammatory bowel disease. In other embodiments, the disorder is selected from Crohn's disease, ulcerative colitis, sprue and food allergies. In other embodiments, the disorder is experimental autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

EXAMPLES

Example 1 Syntheses of Example Compounds

Compound A1—4-(1-(2-(2,6-Difluorophenyl)acetyl) piperidin-4-yl)-N-(3,5-dimethylbenzyl)-2-methylpyrimidine-5-carboxamide A1.1: tert-Butyl 4-(3-(dimethylamino)-2-(ethoxycarbonyl)acryloyl)piperidine-1-carboxylate tert-Butyl 4-(3-ethoxy-3-oxopropanoyl)piperidine-1-carboxylate (40 g, 133 mmol) and dimethylformamide dimethylacetal (DMFDMA) (19 g, 160 mmol) were dissolved in toluene (40 mL). The solution was stirred under reflux for 5 h and cooled to room temperature. The solution was concentrated and used as is in the next reaction.

A1.2: Ethyl 4-(1-(tert-butoxycarbonyl)piperidin-4-yl)-2-methylpyrimidine-5-carboxylate To a suspension of acetamidine hydrochloride (15.1 g, 160 mmol) in EtOH (100 mL) was added EtONa (11 g, 160 mmol). The resulting mixture was stirred for 15 min at room temperature. Crude enamine A1.1 was dissolved in EtOH (100 mL) and added to the acetamidine hydrochloride mixture. The mixture was heated to 70° C. with stirring for 2 h. The solvent was removed under reduced pressure. The residue was stirred in EtOAc (500 mL) and filtered. Concentration of the filtrate gave the crude product, which was further purified by flash column chromatography.

A1.3: Ethyl 2-methyl-4-(piperidin-4-yl)pyrimidine-5-carboxylate hydrochloride

To a solution of A1.2 (5 g, 13.7 mmol) in EtOH (20 mL) was added 4N HCl in dioxane (12 mL). The resulting solution was stirred for 12 h at room temperature. Ether (100 mL) was added with stirring. The solid was filtered and dried under vacuum. The crude product was used in the next step without further purification.

A1.4: Ethyl 4-(1-(2-(2,6-difluorophenyl)acetyl)piperidin-4-yl)-2-methylpyrimidine-5-carboxylate A1.3 was mixed with 2,6-difluorophenylacetic acid (3.13 g, 18 mmol), hydroxybenzotriazole (HOBt) (2.43 g, 18 mmol) and N,N-diisopropylethylamine (DIEA) (9 g, 70 mmol) in tetrahydrofuran (THF) (50 mL). To this solution was added ethyl(dimethylaminopropyl) carbodiimide (EDC) (3.43 g, 18 mmol). The resulting reaction mixture was stirred at room temperature for 5 h then diluted with aq. sat. $NaHCO_3$. The resulting mixture was extracted with EtOAc and the organic mixture was dried over sodium sulfate, filtered, and concentrated.

A1.5: 4-(1-(2-(2,6-Difluorophenyl)acetyl)piperidin-4-yl)-2-methylpyrimidine-5-carboxylic acid Crude A1.4 was stirred with NaOH (1.7 g, 42 mmol) in MeOH/water (40 mL/20 mL) at room temperature for 10 h. The solution was concentrated and the solid was dissolved in water (40 mL) and acidified with conc. HCl. The precipitated product was filtered and dried.

Compound A1

A1.5 (150 mg, 0.39 mmol) was mixed with 3,5-dimethylbenzylamine (62 mg, 0.45 mmol) and DIEA (0.5 mL) in THF (3 mL). To this solution was added 2-(1H-7-azabenzotriazol-1-yl)-1,1,3,3-tetramethyluronoium hexafluorphosphate (HATU) (217 mg, 0.58 mmol). The resulting reaction mixture was stirred at room temperature for 2 h then diluted with aq. sat. $NaHCO_3$. The mixture was extracted with $CH_2Cl_2$, dried over sodium sulfate, filtered, and concentrated. The crude mixture was purified by preparative HPLC to give Compound A1. $^1$H-NMR (400 MHz, DMSO-d6): δ 9.13 (t, 1H), 8.64 (s, 1H), 7.36 (m, 1H), 7.08 (t, 2H), 6.96 (s, 2H), 6.91 (s, 1H), 4.40 (m, 3H), 4.16 (d, 1H), 3.80 (d, 1H), 3.76 (d, 1H), 3.26 (m, 1H), 3.06 (m, 1H), 2.63 (s, 3H), 2.56 (m, 1H), 2.26 (s, 6H), 1.72 (m, 4H). MS (EI) for $C_{28}H_{30}F_2N_4O_2$, found: 493.0 (MH+). Analytical HPLC, ret. time=13.5 min, 93% purity.

Compounds A2-A79

Compounds A2 to A79 were prepared from methods analogous to those used to prepare Compound A1 utilizing appropriate reagent replacements at various steps.

| Cpd | Chemical Name | HPLC Retention Time (min) | MS Reported (MH+) |
|---|---|---|---|
| A2 | N-(3,4-dichlorobenzyl)-4-(1-(2-(2,6-difluorophenyl)acetyl)piperidin-4-yl)-2-methylpyrimidine-5-carboxamide | 4.92* | 533.1 |
| A3 | 4-(1-(2-(2-chloro-6-fluorophenyl)acetyl)piperidin-4-yl)-N-(3,5-dimethylbenzyl)-2-methylpyrimidine-5-carboxamide | 18.16 | 509.2 |
| A4 | N-(3,5-dimethylbenzyl)-4-(1-(2-(2-fluoro-6-(trifluoromethyl)phenyl)acetyl)piperidin-4-yl)-2-methylpyrimidine-5-carboxamide | 18.88 | 543.1 |
| A5 | N-(3,5-dimethylbenzyl)-2-methyl-4-(1-(2-(2-(trifluoromethyl)phenyl)acetyl)piperidin-4-yl)pyrimidine-5-carboxamide | 18.56 | 525.2 |
| A6 | 4-(1-(2-(2-chloro-6-fluorophenyl)acetyl)piperidin-4-yl)-N-(3,4-dichlorobenzyl)pyrimidine-5-carboxamide | 14.50 | 535.1 |
| A7 | 4-(1-(2-(2-chlorophenyl)acetyl)piperidin-4-yl)-N-(3,5-dimethylbenzyl)-2-methylpyrimidine-5-carboxamide | 17.79 | 491.2 |
| A8 | 4-(1-(2-chloro-6-fluorobenzoyl)piperidin-4-yl)-N-(3,5-dimethylbenzyl)-2-methylpyrimidine-5-carboxamide | 13.48 | 495.2 |
| A9 | N-(3,5-dimethylbenzyl)-2-methyl-4-(1-(2-(2-(trifluoromethoxy)phenyl)acetyl)piperidin-4-yl)pyrimidine-5-carboxamide | 18.99 | 541.2 |
| A10 | N-(3,5-dimethylbenzyl)-4-(1-(2-(2-methoxyphenyl)acetyl)piperidin-4-yl)-2-methylpyrimidine-5-carboxamide | 16.72 | 487.2 |
| A11 | N-(3,5-dimethylbenzyl)-2-methyl-4-(1-(2-(o-tolyl)acetyl)piperidin-4-yl)pyrimidine-5-carboxamide | 17.34 | 471.2 |
| A12 | N-(3,5-dimethylbenzyl)-4-(1-(2-(2-fluorophenyl)acetyl)piperidin-4-yl)-2-methylpyrimidine-5-carboxamide | 16.81 | 475.2 |
| A13 | N-(3,4-dichlorobenzyl)-2-methyl-4-(1-(2-(2,3,6-trifluorophenyl)acetyl)piperidin-4-yl)pyrimidine-5-carboxamide | 5.00* | 551.1 |
| A14 | 4-(1-(2-(2,5-difluorophenyl)acetyl)piperidin-4-yl)-N-(3,5-dimethylbenzyl)-2-methylpyrimidine-5-carboxamide | 17.16 | 493.2 |
| A15 | N-(3,5-dimethylbenzyl)-2-methyl-4-(1-(2-(2-nitrophenyl)acetyl)piperidin-4-yl)pyrimidine-5-carboxamide | 16.63 | 502.2 |
| A16 | (R)-N-(3,5-dimethylbenzyl)-2-methyl-4-(1-(2-phenylpropanoyl)piperidin-4-yl)pyrimidine-5-carboxamide | 17.59 | 471.2 |
| A17 | 4-(1-(2-(2,4-difluorophenyl)acetyl)piperidin-4-yl)-N-(3,5-dimethylbenzyl)-2-methylpyrimidine-5-carboxamide | 17.23 | 493.2 |
| A18 | 4-(1-(2-(2,3-difluorophenyl)acetyl)piperidin-4-yl)-N-(3,5-dimethylbenzyl)-2-methylpyrimidine-5-carboxamide | 17.21 | 493.2 |
| A19 | N-(3,5-dimethylbenzyl)-2-methyl-4-(1-(2-(naphthalen-1-yl)acetyl)piperidin-4-yl)pyrimidine-5-carboxamide | 18.63 | 507.2 |

-continued

| Cpd | Chemical Name | HPLC Retention Time (min) | MS Reported (MH+) |
|---|---|---|---|
| A20 | 4-(1-(2-(2,6-difluorophenyl)acetyl)piperidin-4-yl)-2-methyl-N-(2-phenoxyethyl)pyrimidine-5-carboxamide | 19.99** | 495.2 |
| A21 | N-(3,4-dichlorobenzyl)-4-(1-(2-(2,6-difluorophenyl)acetyl)piperidin-4-yl)-2-(trifluoromethyl)pyrimidine-5-carboxamide | 5.24* | 587.0 |
| A22 | N-(3,5-dimethylbenzyl)-4-(1-(2-(3-fluorophenyl)acetyl)piperidin-4-yl)-2-methylpyrimidine-5-carboxamide | 16.68 | 475.2 |
| A23 | N-(3,5-dimethylbenzyl)-4-(1-(2-fluorobenzoyl)piperidin-4-yl)-2-methylpyrimidine-5-carboxamide | 16.13 | 461.2 |
| A24 | 4-(1-(2-chlorobenzoyl)piperidin-4-yl)-N-(3,5-dimethylbenzyl)-2-methylpyrimidine-5-carboxamide | 16.64 | 477.2 |
| A25 | N-(3,5-dimethylbenzyl)-2-methyl-4-(1-(2-phenylacetyl)piperidin-4-yl)pyrimidine-5-carboxamide | 16.20 | 457.2 |
| A26 | (S)-N-(3,5-dimethylbenzyl)-2-methyl-4-(1-(2-phenylpropanoyl)piperidin-4-yl)pyrimidine-5-carboxamide | 17.66 | 471.2 |
| A27 | 4-(1-(2-(3,5-difluorophenyl)acetyl)piperidin-4-yl)-N-(3,5-dimethylbenzyl)-2-methylpyrimidine-5-carboxamide | 17.33 | 493.2 |
| A28 | N-(3,4-dichlorobenzyl)-4-(1-(2-(2,6-difluorophenyl)acetyl)piperidin-4-yl)-2-isopropylpyrimidine-5-carboxamide | 5.16* | 561.1 |
| A29 | N-(3,5-dimethylbenzyl)-4-(1-(2-(4-fluorophenyl)acetyl)piperidin-4-yl)-2-methylpyrimidine-5-carboxamide | 16.75 | 475.2 |
| A30 | N-(3,5-dimethylbenzyl)-2-methyl-4-(1-(2-(m-tolyl)acetyl)piperidin-4-yl)pyrimidine-5-carboxamide | 17.43 | 471.2 |
| A31 | N-(3,5-dimethylbenzyl)-4-(1-(1-(2-fluorophenyl)cyclopentanecarbonyl)piperidin-4-yl)-2-methylpyrimidine-5-carboxamide | 19.81 | 529.3 |
| A32 | N-(3,5-dimethylbenzyl)-2-methyl-4-(1-(1-phenylcyclopropanecarbonyl)piperidin-4-yl)pyrimidine-5-carboxamide | 17.19 | 483.2 |
| A33 | 4-(1-(3-chloropicolinoyl)piperidin-4-yl)-N-(3,5-dimethylbenzyl)-2-methylpyrimidine-5-carboxamide | 13.95 | 478.1 |
| A34 | 4-(1-(2-(3,4-difluorophenyl)acetyl)piperidin-4-yl)-N-(3,5-dimethylbenzyl)-2-methylpyrimidine-5-carboxamide | 17.16 | 493.2 |
| A35 | N-(3,5-dimethylbenzyl)-2-methyl-4-(1-(2-methyl-2-phenylpropanoyl)piperidin-4-yl)pyrimidine-5-carboxamide | 18.50 | 485.3 |
| A36 | N-(3,4-dichlorobenzyl)-4-(1-(2-(2-fluorophenyl)acetyl)piperidin-4-yl)-2-isopropylpyrimidine-5-carboxamide | 5.01* | 543.1 |
| A37 | N-(3,4-dichlorobenzyl)-4-(1-(2-(2,6-difluorophenyl)acetyl)piperidin-4-yl)-2-phenylpyrimidine-5-carboxamide | 5.24* | 595.9 |
| A38 | N-(3,5-dimethylbenzyl)-2-methyl-4-(1-(2-(pyridin-2-yl)acetyl)piperidin-4-yl)pyrimidine-5-carboxamide | 9.76 | 458.2 |
| A39 | N-(3,5-dimethylbenzyl)-4-(1-(2-(3-methoxyphenyl)acetyl)piperidin-4-yl)-2-methylpyrimidine-5-carboxamide | 16.14 | 487.2 |
| A40 | N-(3-chlorobenzyl)-4-(1-(2-(2,6-difluorophenyl)acetyl)piperidin-4-yl)-2-methylpyrimidine-5-carboxamide | 4.44* | 499.1 |
| A41 | N-(3-chloro-5-fluorobenzyl)-4-(1-(2-(2,6-difluorophenyl)acetyl)piperidin-4-yl)-2-methylpyrimidine-5-carboxamide | 17.38 | 517.0 |
| A42 | N-(5-chloro-2-fluorobenzyl)-4-(1-(2-(2,6-difluorophenyl)acetyl)piperidin-4-yl)-2-methylpyrimidine-5-carboxamide | 11.80 | 517.0 |
| A43 | 2-cyclopropyl-4-(1-(2-(2,6-difluorophenyl)acetyl)piperidin-4-yl)-N-(3,5-dimethylbenzyl)pyrimidine-5-carboxamide | 4.07* | 519.0 |
| A44 | 4-(1-(2-(2,6-difluorophenyl)acetyl)piperidin-4-yl)-2-methyl-N-((6-(trifluoromethyl)pyridin-2-yl)methyl)pyrimidine-5-carboxamide | 15.80 | 534.0 |
| A45 | N-(3-chlorobenzyl)-2-cyclopropyl-4-(1-(2-(2,6-difluorophenyl)acetyl)piperidin-4-yl)pyrimidine-5-carboxamide | 4.41* | 525.0 |
| A46 | 4-(1-(2-(2,6-difluorophenyl)acetyl)piperidin-4-yl)-2-methyl-N-(3-(trifluoromethyl)benzyl)pyrimidine-5-carboxamide | 17.44 | 533.0 |

-continued

| Cpd | Chemical Name | HPLC Retention Time (min) | MS Reported (MH+) |
|---|---|---|---|
| A47 | 4-(1-(2-(2,6-difluorophenyl)acetyl)piperidin-4-yl)-2-methyl-N-((2-(trifluoromethyl)pyridin-4-yl)methyl)pyrimidine-5-carboxamide | 10.88 | 534.0 |
| A48 | N-(3-chlorobenzyl)-4-(1-(2-(2,6-difluorophenyl)acetyl)piperidin-4-yl)-2-ethylpyrimidine-5-carboxamide | 4.30* | 513.0 |
| A49 | N-((2,6-dichloropyridin-4-yl)methyl)-4-(1-(2-(2,6-difluorophenyl)acetyl)piperidin-4-yl)-2-methylpyrimidine-5-carboxamide | 16.20 | 534.1 |
| A50 | N-(3-cyanobenzyl)-4-(1-(2-(2,6-difluorophenyl)acetyl)piperidin-4-yl)-2-methylpyrimidine-5-carboxamide | 14.47 | 490.0 |
| A51 | N-(3,5-dichlorobenzyl)-4-(1-(2-(2,6-difluorophenyl)acetyl)piperidin-4-yl)-2-methylpyrimidine-5-carboxamide | 18.66 | 532.9 |
| A52 | N-((2-chloro-6-methoxypyridin-4-yl)methyl)-4-(1-(2-(2,6-difluorophenyl)acetyl)piperidin-4-yl)-2-methylpyrimidine-5-carboxamide | 12.14 | 530.0 |
| A53 | 4-(1-(2-(2,6-difluorophenyl)acetyl)piperidin-4-yl)-2-methyl-N-(3-(trifluoromethoxy)benzyl)pyrimidine-5-carboxamide | 17.95 | 549.0 |
| A54 | N-(3-chloro-2-fluorobenzyl)-4-(1-(2-(2,6-difluorophenyl)acetyl)piperidin-4-yl)-2-methylpyrimidine-5-carboxamide | 12.97 | 517.0 |
| A55 | N-((2-cyanopyridin-4-yl)methyl)-4-(1-(2-(2,6-difluorophenyl)acetyl)piperidin-4-yl)-2-methylpyrimidine-5-carboxamide | 13.10 | 491.2 |
| A56 | N-((2-chloropyridin-4-yl)methyl)-4-(1-(2-(2,6-difluorophenyl)acetyl)piperidin-4-yl)-2-methylpyrimidine-5-carboxamide | 13.51 | 500.1 |
| A57 | 4-(1-(2-(2,6-difluorophenyl)acetyl)piperidin-4-yl)-N-(3,5-dimethylbenzyl)pyrimidine-5-carboxamide | 16.85 | 479.1 |
| A58 | 4-(1-(2-(2,6-difluorophenyl)acetyl)piperidin-4-yl)-N-(3-methoxybenzyl)-2-methylpyrimidine-5-carboxamide | 15.14 | 495.0 |
| A59 | N-(4-chloro-2-methylbenzyl)-4-(1-(2-(2,6-difluorophenyl)acetyl)piperidin-4-yl)-2-methylpyrimidine-5-carboxamide | 17.60 | 513.1 |
| A60 | 4-(1-(2-(2,6-difluorophenyl)acetyl)piperidin-4-yl)-2-methyl-N-(3-methylbenzyl)pyrimidine-5-carboxamide | 4.36* | 479.2 |
| A61 | 4-(1-(2-(2,6-difluorophenyl)acetyl)piperidin-4-yl)-2,6-dimethyl-N-((2-(trifluoromethyl)pyridin-4-yl)methyl)pyrimidine-5-carboxamide | 14.332 | 548.0 |
| A62 | N-(4-chlorobenzyl)-4-(1-(2-(2,6-difluorophenyl)acetyl)piperidin-4-yl)-2-methylpyrimidine-5-carboxamide | 4.54* | 499.1 |
| A63 | N-(3-chloro-2-methylbenzyl)-4-(1-(2-(2,6-difluorophenyl)acetyl)piperidin-4-yl)-2-methylpyrimidine-5-carboxamide | 17.792 | 513.0 |
| A64 | 4-(1-(2-(2,6-difluorophenyl)acetyl)piperidin-4-yl)-N-(3,5-dimethylbenzyl)-2-ethylpyrimidine-5-carboxamide | 4.41* | 507.0 |
| A65 | N-(3,4-dichlorobenzyl)-4-(1-(2-(2,6-dichlorophenyl)acetyl)piperidin-4-yl)pyrimidine-5-carboxamide | 4.94* | 553.1 |
| A66 | 4-(1-(2-(2,6-difluorophenyl)acetyl)piperidin-4-yl)-2-methyl-N-((4-(trifluoromethyl)pyridin-2-yl)methyl)pyrimidine-5-carboxamide | 14.87 | 534.0 |
| A67 | 4-(1-(2-(2,6-difluorophenyl)acetyl)piperidin-4-yl)-2-methyl-N-((4-methyl-6-(trifluoromethyl)pyridin-2-yl)methyl)pyrimidine-5-carboxamide | 15.16 | 549.0 |
| A68 | N-(3,4-dichlorobenzyl)-4-(1-(2-(2,3,6-trifluorophenyl)acetyl)piperidin-4-yl)pyrimidine-5-carboxamide | 4.94* | 537.1 |
| A69 | N-benzyl-4-(1-(2-(2,6-difluorophenyl)acetyl)piperidin-4-yl)-2-methylpyrimidine-5-carboxamide | 3.77* | 465.0 |
| A70 | 4-(1-(2-(2,6-difluorophenyl)acetyl)piperidin-4-yl)-2-methyl-N-((2-methylpyridin-4-yl)methyl)pyrimidine-5-carboxamide | 9.32 | 480.2 |
| A71 | N-((6-chloropyridin-3-yl)methyl)-4-(1-(2-(2,6-difluorophenyl)acetyl)piperidin-4-yl)-2-methylpyrimidine-5-carboxamide | 13.66 | 500.1 |
| A72 | N-((2-chlorothiazol-5-yl)methyl)-4-(1-(2-(2,6-difluorophenyl)acetyl)piperidin-4-yl)-2-methylpyrimidine-5-carboxamide | 14.22 | 505.9 |

-continued

| Cpd | Chemical Name | HPLC Retention Time (min) | MS Reported (MH+) |
|---|---|---|---|
| A73 | 4-(1-(2-(2,6-difluorophenyl)acetyl)piperidin-4-yl)-N-((2,6-dimethylpyridin-4-yl)methyl)-2-methylpyrimidine-5-carboxamide | 9.55 | 494.2 |
| A74 | 4-(1-(2-(2,6-difluorophenyl)acetyl)piperidin-4-yl)-2-methyl-N-((6-(trifluoromethyl)pyridin-3-yl)methyl)pyrimidine-5-carboxamide | 14.98 | 534.1 |
| A75 | methyl 2-(3-chlorophenyl)-2-(4-(1-(2-(2,6-difluorophenyl)acetyl)piperidin-4-yl)-2-methylpyrimidine-5-carboxamido)acetate | 4.19* | 557.0 |
| A76 | N-(1-(3-chlorophenyl)ethyl)-4-(1-(2-(2,6-difluorophenyl)acetyl)piperidin-4-yl)-2-methylpyrimidine-5-carboxamide | 13.52 | 513.0 |
| A77 | 4-(1-(2-(2,6-difluorophenyl)acetyl)piperidin-4-yl)-N-((2-(ethylcarbamoyl)pyridin-4-yl)methyl)-2-methylpyrimidine-5-carboxamide | 12.30 | 537.2 |
| A78 | 4-(1-(2-(2,6-difluorophenyl)acetyl)piperidin-4-yl)-N-((1,5-dimethyl-1H-pyrazol-3-yl)methyl)-2-methylpyrimidine-5-carboxamide | 11.25 | 483.2 |
| A79 | 4-(1-(2-(2,6-difluorophenyl)acetyl)piperidin-4-yl)-2-methyl-N-((5-methylpyrazin-2-yl)methyl)pyrimidine-5-carboxamide | 11.14 | 481.0 |

HPLC Conditions Used to Determine Retention Times:
Unless otherwise noted: YMC C18, 5µ 150×4.6 mm column, gradient 10% to 90% MeCN/water, in the presence of 0.1% TFA, 25 min gradient time, 27 min total run time at 1.5 mL/min flow rate, λ=254 nM
* Phenomenex, Gemini, 50×4.6 mm, 5µ column, gradient 10% to 90% MeCN/water, in the presence of 0.1% TFA, 5 min gradient time, 6 min total run time at 3.0 mL/min flow rate, λ=254 nM
**YMC C18, 5µ 150×4.6 mm column, gradient 10% to 100% MeCN/water, in the presence of 0.1% TFA, 25 min gradient time, 27 min total run time at 1.5 mL/min flow rate, λ=254 nM Compound A80—4-(1-(2-(2,6-Difluorophenyl) acetyl)piperidin-4-yl)-N-(3,5-dimethylbenzyl)-2,6-dimethylpyrimidine-5-carboxamide A80.1: Methyl/Ethyl 4-(1-(tert-butoxycarbonyl) piperidin-4-yl)-2,6-dimethylpyrimidine-5-carboxylate tert-Butyl-4-(3-ethoxy-3-oxopropanoyl)piperidine-1-carboxylate (6.0 g, 20.0 mmol), AcOH (57 µL, 1.0 mmol), pyridine (80 µL, 1.0 mmol), and toluene (100 mL) were charged into a 250 mL flask equipped with fractional distillation apparatus. The reaction mixture was stirred at 130° C. (bath temperature) and the solvent distilled at about the boiling point of the MeOH/toluene azeotrope for 48 h. The reaction mixture was cooled to room temperature and concentrated in vacuo to give tert-butyl 4-(2-(ethoxy(or methoxy)carbonyl)-3-methoxybut-2-enoyl)piperidine-1-carboxylate which was used directly in the next step. To a stirred suspension of acetamidine HCl (2.84 g, 30.0 mmol) in EtOH (60 mL) was added NaOEt (2.05 g, 30.0 mmol) and the reaction mixture was stirred at room temperature for 30 min. To this suspension was added the crude tert-butyl 4-(2-(ethoxy(or methoxy)carbonyl)-3-methoxybut-2-enoyl) piperidine-1-carboxylate in EtOH (20 mL) slowly at room temperature and the resulting mixture was stirred at reflux for 5 h. The reaction mixture was cooled down to room temperature, concentrated under reduced pressure, and the residue was partitioned between water and $CH_2Cl_2$. The separated aq. layer was extracted with $CH_2Cl_2$ (×2) and the combined organic layers were dried over sodium sulfate, concentrated in vacuo, and purified by flash chromatography to give a mixture of the methyl and ethyl esters of A80.1 (2.51 g, ca. 35%).

A80.2: Methyl/Ethyl 2,4-dimethyl-6-(piperidin-4-yl) pyrimidine-5-carboxylate

To a stirred solution of A80.1 (2.51 g, ca. 6.91 mmol) in 1,4-dioxane (20 mL) was added HCl (20 mL, 4M in 1,4-dioxane, 80 mmol) and the reaction mixture was stirred at room temperature overnight. The reaction mixture was concentrated in vacuo and the residue was used for the next step without further purification.

A80.3: Methyl/Ethyl 4-(1-(2-(2,6-difluorophenyl) acetyl)piperidin-4-yl)-2,6-dimethylpyrimidine-5-carboxylate A mixture of crude A80.2, 2,6-difluorophenylacetic acid (1.43 g, 8.31 mmol), $Et_3N$ (4.82 mL, 34.6 mmol) and DMF (20 mL) was treated with HATU (3.16 g, 8.31 mmol) and the resulting mixture was stirred at room temperature for 1 h. The reaction mixture was diluted with EtOAc, washed with aq. sodium bicarbonate, brine, dried over sodium sulfate, concentrated in vacuo and the residue purified by flash chromatography to afford a mixture of the methyl and ethyl esters of A80.3 (2.34 g, ca. 81%).

A80.4: 4-(1-(2-(2,6-Difluorophenyl)acetyl)piperidin-4-yl)-2,6-dimethylpyrimidine-5-carboxylic acid To a stirred solution of A80.3 (2.1 g, ca 5.0 mmol) in MeOH (30 mL) was added aq. 1N NaOH (20 mL) and the reaction mixture was stirred at room temperature overnight. MeOH was removed in vacuo and the residual aq. layer was acidified with 1N HCl to pH 4-5, and extracted with $CH_2Cl_2$ (×5). The combined organic layers were dried over sodium sulfate and concentrated in vacuo to give acid A80.4 (1.88 g, ca. 97%).

Compound A80

Compound A80 was synthesized from A80.4 and 3,5-dimethylbenzylamine in an identical manner to Compound A1. $^1$H-NMR (400 MHz, DMSO-d6): δ 9.07 (t, 1H), 7.36 (m, 1H), 7.07 (m, 2H), 6.97 (s, 2H), 6.92 (s, 1H), 4.41 (m, 3H), 4.12 (d, 1H), 3.82 (d, 1H), 3.73 (d, 1H), 2.93 (m, 1H), 2.81 (m, 1H), 2.56 (s, 3H), 2.44 (m, 1H), 2.34 (s, 3H), 2.27 (s, 6H), 1.70 (m, 4H). MS (EI) for $C_{29}H_{32}F_2N_4O_2$, found: 507.0 (MH+). Analytical HPLC, ret. time=3.46 min, 90% purity.

Compounds A81-A84

Compounds A81 to A84 were prepared from methods analogous to those used to prepare Compound A80 utilizing appropriate reagent replacements at various steps.

| Cpd | Chemical Name | HPLC Retention Time (min) | MS Reported (MH+) |
|---|---|---|---|
| A81 | 4-{1-[(2,6-difluorophenyl)acetyl]piperidin-4-yl}-N-[(3,5-dimethylphenyl)methyl]-N,2-dimethylpyrimidine-5-carboxamide | 3.86* | 513.0 |
| A82 | 4-(1-(2-(2,6-difluorophenyl)acetyl)piperidin-4-yl)-2,6-dimethyl-N-((6-(trifluoromethyl)pyridin-2-yl)methyl)pyrimidine-5-carboxamide | 14.44 | 548.0 |
| A83 | N-((2-cyanopyridin-4-yl)methyl)-4-(1-(2-(2,6-difluorophenyl)acetyl)piperidin-4-yl)-2,6-dimethylpyrimidine-5-carboxamide | 2.15* | 505.0 |
| A84 | 4-(1-(2-(2,6-difluorophenyl)acetyl)piperidin-4-yl)-N-(3,5-dimethylbenzyl)-6-isopropyl-2-methylpyrimidine-5-carboxamide | 3.96* | 535.1 |

HPLC Conditions Used to Determine Retention Times:

Unless otherwise noted: YMC C18, 5μ 150×4.6 mm column, gradient 10% to 90% MeCN/H2O, in the presence of 0.1% TFA, 25 min gradient time, 27 min total run time at 1.5 mL/min flow rate, λ=254 nM

* Phenomenex, Gemini, 50×4.6 mm, 5μ column, gradient 10% to 90% MeCN/H2O, in the presence of 0.1% TFA, 5 min gradient time, 6 min total run time at 3.0 mL/min flow rate, λ=254 nM Compound A85—N-(3,4-Dichlorobenzyl)-4-(1-(2-(2,6-difluorophenyl)acetyl)piperidin-4-yl)-2-(methylthio)pyrimidine-5-carboxamide A85.1: Ethyl 4-(1-(tert-butoxycarbonyl)piperidin-4-yl)-2-(methylthio)pyrimidine-5-carboxylate To a suspension of S-methyl thiourea sulfate (5.5 g, 39 mmol) in EtOH (50 mL) was added EtONa (2.7 g, 39 mmol). The resulting mixture was stirred for 15 min at room temperature. Crude enamine A1.1 in EtOH (30 mL) was added. The mixture was heated at 70° C. with stirring for 2 h. The solvent was removed under reduced pressure. The residue was stirred in EtOAc (500 mL) and filtered. Concentration of the filtrate gave the crude product, which was further purified by flash column chromatography.

A85.2: tert-Butyl 4-(5-(3,4-dichlorobenzylcarbamoyl)-2-(methylthio)pyrimidin-4-yl)piperidine-1-carboxylate To a solution of A85.1 (4.23 g, 11 mmol) in MeOH/water (50 mL/20 mL) was added NaOH (2.5 g, 55 mmol). The resulting mixture was stirred at room temperature for 10 h. MeOH was removed under reduced pressure. The aq. phase was acidified with conc. HCl. The precepited product was filtered and dried under vacuum. The resulting carboxylic acid (800 mg, 2.25 mmol) was mixed with 2,4-dichlorobenzylamine (475 mg, 2.7 mmol) and DIEA (0.5 mL) in $CH_2Cl_2$ (4 mL). To this solution was added HATU (1.0 g, 2.7 mmol). The resulting mixture was stirred at room temperature for 12 h then diluted with aq. sat. $NaHCO_3$. The mixture was extracted with EtOAc and the organic mixture was dried over sodium sulfate, filtered, and concentrated. The crude mixture was purified by flash column chromatography.

Compound A85

A85.2 (200 mg, 0.39 mmol) was treated with 4N HCl/dioxane (0.5 mL) in MeOH (3 mL) for 2 h. Ether (10 mL) was added. The precipitated HCl salt was filtered, dried and then mixed with 2,6-difluorophenylacetic acid (78 mg, 0.456 mmol), HOBt (62 mg, 0.456 mmol) and DIEA (193 mg, 1.5 mmol) in $CH_2Cl_2$ (3 mL). To this solution was added EDC (88 g, 0.456 mmol). The resulting reaction mixture was stirred at room temperature for 5 h then diluted with aq. sat. $NaHCO_3$. The resulting mixture was extracted with EtOAc and the organic phase was dried over sodium sulfate, filtered, and concentrated. The crude product was purified by flash column chromatography. $^1$H-NMR (400 MHz, DMSO-d6): δ 9.21 (s, 1H), 8.64 (s, 1H), 7.63 (m, 2H), 7.36 (m, 2H), 7.07 (m, 2H), 4.47 (m, 3H), 4.15 (d, 1H), 3.83 (d, 1H), 3.75 (d, 1H), 3.25 (m, 1H), 3.05 (m, 1H), 2.56 (m, 1H), 2.54 (s, 3H), 1.70 (m, 4H). MS (EI) for $C_{26}H_{24}Cl_2F_2N_4O_2S$, found: 564.9 (MH+). Analytical HPLC, ret. time=5.22 min, 95% purity Compound A86—N-(3,4-Dichlorobenzyl)-4-(1-(2-(2,6-difluorophenyl)acetyl)piperidin-4-yl)-2-methoxypyrimidine-5-carboxamide A86.1: N-(3,4-Dichlorobenzyl)-4-(1-(2-(2,6-difluorophenyl)acetyl)piperidin-4-yl)-2-(methylsulfonyl)pyrimidine-5-carboxamide To a 0° C. solution of A85.3 (50 mg, 0.088 mmol) in $CH_2Cl_2$ (3 mL) was added meta-chloroperoxybenzoic acid (mCPBA) (55 mg, 0.22 mmol, ~70%). The resulting mixture was stirred for 2 h while slowly warming to room temperature. Aq. sat. $NaHCO_3$ was added. The mixture was extracted with $CH_2Cl_2$ and the organic phase was washed with aq. $Na_2SO_3$ solution, dried over sodium sulfate, filtered, and concentrated. The crude product was purified by flash column chromatography.

Compound A86

A86.1 was treated with MeONa, which was freshly prepared from Na (23 mg, 1 mmol) in MeOH (2 mL). The mixture was stirred at room temperature for 2 h. Water was added to quench the reaction. The mixture was extracted with EtOAc, and the organic phase was dried over sodium sulfate, filtered, and concentrated. The crude product was purified by HPLC to give Compound A86. $^1$H-NMR (400 MHz, DMSO-d6): δ 9.18 (s, 1H), 8.64 (s, 1H), 7.63 (m, 2H), 7.37 (m, 2H), 7.07 (m, 2H), 4.47 (m, 3H), 4.15 (d, 1H), 3.95 (s, 3H), 3.83 (d, 1H), 3.75 (d, 1H), 3.28 (m, 1H), 3.10 (m, 1H), 2.56 (m, 1H), 1.70 (m, 4H). MS (EI) for $C_{26}H_{24}Cl_2F_2N_4O_3$, found: 549.1 (MH+). Analytical HPLC, ret. time=3.95 min, 95% purity.

Compounds A87-A98

Compounds A87 to A98 were prepared from methods analogous to those used to prepare Compounds A85 and A86 utilizing appropriate reagent replacements.

| Cpd | Chemical Name | HPLC Retention Time (min) | MS Reported (MH+) |
| --- | --- | --- | --- |
| A87 | N-(3-chlorobenzyl)-4-(1-(2-(2,6-difluorophenyl)acetyl)piperidin-4-yl)-2-((2-hydroxyethyl)amino)pyrimidine-5-carboxamide | 3.55 | 544.0 |
| A88 | N-(3-chlorobenzyl)-4-(1-(2-(2,6-difluorophenyl)acetyl)piperidin-4-yl)-2-(dimethylamino)pyrimidine-5-carboxamide | 3.58 | 528.0 |
| A89 | 2-amino-N-(3-chlorobenzyl)-4-(1-(2-(2,6-difluorophenyl)acetyl)piperidin-4-yl)pyrimidine-5-carboxamide | 3.57 | 500.0 |
| A90 | N-(3-chlorobenzyl)-4-(1-(2-(2,6-difluorophenyl)acetyl)piperidin-4-yl)-2-(methylamino)pyrimidine-5-carboxamide | 3.18 | 514.0 |
| A91 | N-(3-chlorobenzyl)-4-(1-(2-(2,6-difluorophenyl)acetyl)piperidin-4-yl)-2-(ethylamino)pyrimidine-5-carboxamide | 3.39 | 528.0 |
| A92 | N-(3-chlorobenzyl)-4-(1-(2-(2,6-difluorophenyl)acetyl)piperidin-4-yl)-2-methoxypyrimidine-5-carboxamide | 4.22 | 515.0 |
| A93 | N-(3-chlorobenzyl)-4-(1-(2-(2,6-difluorophenyl)acetyl)piperidin-4-yl)-2-ethoxypyrimidine-5-carboxamide | 4.41 | 529.0 |
| A94 | N-(3-chlorobenzyl)-4-(1-(2-(2,6-difluorophenyl)acetyl)piperidin-4-yl)-2-(isopropylamino)pyrimidine-5-carboxamide | 3.51 | 542.0 |
| A95 | N-(3-chlorobenzyl)-4-(1-(2-(2,6-difluorophenyl)acetyl)piperidin-4-yl)-2-isopropoxypyrimidine-5-carboxamide | 4.08 | 543.0 |
| A96 | 2-((2-aminoethyl)amino)-N-(3-chlorobenzyl)-4-(1-(2-(2,6-difluorophenyl)acetyl)piperidin-4-yl)pyrimidine-5-carboxamide | 2.65 | 543.0 |
| A97 | N-(3-chlorobenzyl)-4-(1-(2-(2,6-difluorophenyl)acetyl)piperidin-4-yl)-2-((2-(dimethylamino)ethyl)amino)pyrimidine-5-carboxamide | 2.76 | 571.0 |
| A98 | N-(3-chlorobenzyl)-4-(1-(2-(2,6-difluorophenyl)acetyl)piperidin-4-yl)-2-hydroxypyrimidine-5-carboxamide | 3.52 | 501.1 |

HPLC conditions used to determine retention times: Phenomenex, Gemini, 50×4.6 mm, 5μ column, gradient 10% to 90% $MeCN/H_2O$, in the presence of 0.1% TFA, 5 min gradient time, 6 min total run time at 3.0 mL/min flow rate, λ=254 nM Compound A99—4-(1-(2,6-Difluorophenethyl)piperidin-4-yl)-N-(3,5-dimethylbenzyl)-2-methylpyrimidine-5-carboxamide A99.1: 2-(2,6-Difluorophenyl)ethanol To a stirred solution of 2-(2,6-difluorophenyl)acetic acid (150 mg, 0.871 mmol) in THF (2 mL) at room temperature was added borane dimethyl sulfide complex (1.30 mL, 2M in THF, 2.61 mmol). After stirring for 16 h at 60° C., the mixture was cooled down to room temperature and quenched with MeOH (1 mL). After stirring for 10 min, volatile materials were removed under vacuum and the resulting mixture was purified by silica gel chromatography (Hexane/EtOAc=6:1) to give A99.1 (105 mg, 76%) as a clear oil.

A99.2: 2-(2,6-Difluorophenyl)acetaldehyde

To a stirred solution of A99.1 (40.0 mg, 0.253 mmol) in $CH_2Cl_2$ (2 mL) at room temperature was added Dess-Martin periodinane (161 mg, 0.379 mmol). After stirring for 70 min, water (2 mL) was added and the resulting solution was extracted with EtOAc (4 mL and 2 mL). The combined organic layers were concentrated and purified by silica gel column chromatography (Hexane/EtOAc=5:1) to give A99.2 (22.0 mg, 56%) as a clear oil.

A99.3: 4-(1-(tert-Butoxycarbonyl)piperidin-4-yl)-2-methylpyrimidine-5-carboxylic acid A1.2 was hydrolyzed to A99.3 with the same technique used to hydrolyze A80.3 to A80.4.

A99.4: tert-Butyl 4-(5-(3,5-dimethylbenzylcarbamoyl)-2-methylpyrimidin-4-yl)piperidine-1-carboxylate A99.4 was synthesized from A99.3 and 3,5-dimethylbenzylamine in an identical manner to A1.6.

A99.5: N-(3,5-Dimethlbenzyl)-2-methyl-4-(piperidin-4-yl)pyrimidine-5-carboxamide hydrochloride A99.5 was synthesized from A99.4 in a manner identical to that used to convert A1.2 to A1.3.

Compound A99

To a stirred solution of A99.2 (22.0 mg, 0.141 mmol), A99.5 (63.4 mg, 0.169 mmol) and $CH_2Cl_2$ (2 mL) at room temperature was added $NaBH(OAc)_3$ (60.0 mg, 0.282 mmol). After stirring for 4.5 h at 40° C., aq. sat. $NaHCO_3$ (5 mL) was added and the resulting solution was extracted with EtOAc (5 mL and 2 mL). The combined organic layers were concentrated and purified by silica gel column chromatography (EtOAc) to give Compound A99 (31.0 mg, 46%) as a white powder. $^1$H-NMR (400 MHz, $CDCl_3$): δ 8.54 (s, 1H), 7.15 (m, 1H), 6.97 (s, 3H), 6.85 (t, 2H), 6.02 (t, 1H), 4.56 (d, 2H), 3.10 (m, 3H), 2.89 (m, 2H), 2.69 (s, 3H), 2.58 (m, 2H), 2.32 (s, 6H), 2.08 (m, 4H), 1.76 (m, 2H). MS (EI) for $C_{28}H_{32}F_2N_4O$, found 479.2 (MH+). Analytical HPLC, ret. time=13.060 min, 95% purity.

Compounds A100-A101

Compounds A100 to A101 were prepared from methods analogous to those used to prepare Compound A99 utilizing appropriate reagent replacements.

HPLC conditions used to determine retention times: YMC C18, 5μ 150×4.6 mm column, gradient 10% to 90% MeCN/$H_2O$, in the presence of 0.1% TFA, 25 min gradient time, 27 min total run time at 1.5 mL/min flow rate, λ=254 nM Compound A102—N-(3-Chlorobenzyl)-4-(1-(2-(2,6-difluorophenyl)acetyl)-4-methylpiperidin-4-yl)-2-methylpyrimidine-5-carb oxamide A102.1: tert-Butyl 4-(3-ethoxy-3-oxopropanoyl)-4-methylpiperidine-1-carboxylate To a stirred solution of ethyl N-Boc-4-methylpiperidine-4-carboxylate (1 g, 3.69 mmol) in MeOH (30 mL) was added aq. 1N NaOH (10 mL) and the resulting mixture was stirred at room temperature overnight. The reaction mixture was concentrated in vacuo and the aq. layer was acidified with aq. 1N HCl to pH 4-5 and extracted with $CH_2Cl_2$ (×4). The combined organic layer was dried over sodium sulfate and concentrated in vacuo to give 1-(tert-butoxycarbonyl)-4-methylpiperidine-4-carboxylic acid (905 mg, quant.). Reaction mixture A: to a mixture of N,N'-dimethyldiimidazole (430 mg, 2.41 mmol) in THF (5 mL) was added the 1-(tert-butoxycarbonyl)-4-methylpiperidine-4-carboxylic acid (451 mg, 1.85 mmol) in THF (5 mL) dropwise. The reaction mixture was protected from light and stirred overnight at room temperature. Reaction mixture B: to a stirred mixture of potassium ethyl malonate (504 mg, 2.96 mmol) in EtOAc (15 mL) cooled to 0° C. was added $Et_3N$ (1.05 mL, 7.53 mmol) followed by $MgCl_2$ (342 mg, 3.59 mmol). The reaction mixture was slowly heated to 35° C. and then maintained at 35° C. overnight. To reaction mixture B was added reaction mixture A slowly at room temperature and the resulting mixture was stirred at room temperature overnight. The reaction mixture was diluted with EtOAc, washed with aq. 0.5N HCl, aq. $NaHCO_3$, dried over sodium sulfate, concentrated in vacuo, and the residue was purified by flash chromatography to afford A102.1 (423 mg, 73%).

A102.2: tert-Butyl 4-(3-(dimethylamino)-2-(ethoxycarbonyl)acryloyl)-4-methylpiperidine-1-carboxylate A mixture of A102.1 (423 mg, 1.35 mmol) and DMF/DMA (250 μL, 1.76 mmol) was stirred at 110° C. for 2 h. An additional amount of DMF/DMA (500 μL, 3.52 mmol) was added to the reaction mixture and the resulting mixture was stirred at 110° C. for 2 h. The reaction mixture was concentrated in vacuo to give A102.2, which was used directly for the next step without further purification.

A102.3: Ethyl 4-(1-(tert-butoxycarbonyl)-4-methylpiperidin-4-yl)-2-methylpyrimidine-5-carboxylate To a stirred solution of acetamide-HCl (191 mg, 2.02 mmol) in EtOH (10 mL) was added NaOEt (136 mg, 2.0

| Cpd | Chemical Name | HPLC Retention Time (min) | MS Reported (MH+) |
|---|---|---|---|
| A100 | 4-(1-(2-chlorophenethyl)piperidin-4-yl)-N-(3,5-dimethylbenzyl)-2-methylpyrimidine-5-carboxamide | 12.93 | 477.1 |
| A101 | N-(3,5-dimethylbenzyl)-2-methyl-4-(1-phenethylpiperidin-4-yl)pyrimidine-5-carboxamide | 12.68 | 443.3 | mmol) and the resulting mixture was stirred at room temperature for 20 min. To this suspension was added A102.2 (crude material) in EtOH (5 mL) and the reaction mixture was stirred at reflux for 3 h. The reaction mixture was cooled to room temperature, concentrated in vacuo, and the residue was diluted with water, extracted with $CH_2Cl_2$ (×2), dried over sodium sulfate, concentrated in vacuo, and the residue was purified by flash chromatography to afford A102.3 (369 mg, 75% from A102.1).

A102.4: Ethyl 4-(1-(2-(2,6-difluorophenyl)acetyl)-4-methylpiperidin-4-yl)-2-methylpyrimidine-5-carboxylate To a stirred solution of A102.3 (369 mg, 1.02 mmol) in 1,4-dioxane (6 mL) was added HCl (4 mL, 4M in 1,4-dioxane, 16 mmol) and the resulting mixture was stirred at room temperature overnight. The reaction mixture was concentrated in vacuo and the crude amine residue was used directly for the next step. To a stirred suspension of the crude amine, $Et_3N$ (711 µL, 5.10 mmol), and 2,6-difluorophenylacetic acid (211 mg, 1.23 mmol) was added HATU (465 mg, 1.22 mmol) and the reaction mixture was stirred at room temperature for 1 h. The reaction mixture was partitioned between aq. 1N NaOH and EtOAc and the separated organic layer was washed with brine, dried over sodium sulfate, concentrated in vacuo, and the residue was purified by flash chromatography to give A102.4 (362 mg, 85% from A102.3).

A102.5: 4-(1-(2-(2,6-Difluorophenyl)acetyl)-4-methylpiperidin-4-yl)-2-methylpyrimidine-5-carboxylic acid To a stirred solution of A102.4 (362 mg, 0.87 mmol) in THF (5 mL)/MeOH (10 mL) was added aq. 1N NaOH (4 mL) and the reaction mixture was stirred at 50° C. for 5 h. The reaction mixture was cooled to room temperature, concentrated in vacuo, and the residue was diluted with water, acidified with aq. 1N HCl to pH 3-4, and extracted with $CH_2Cl_2$ (×4). The combined extracts were dried over sodium sulfate and concentrated in vacuo to afford A102.5 (317 mg, 94%).

Compound A102

To a stirred solution of A102.5 (117 mg, 0.30 mmol), 3-chlorobenzylamine (44 µL, 0.36 mmol), and $Et_3N$ (209 µL, 1.50 mmol) in DMF (3 mL) was added HATU (137 mg, 0.36 mmol) and the reaction mixture was stirred at room temperature for 30 min. The reaction mixture was directly purified by preparative reverse phase HPLC to give Compound A102 (84 mg, 55%) as a white powder after lyophilization. Analytical HPLC: retention time=14.852 min, 98%. $^1$H-NMR (400 MHz, $CDCl_3$): δ 8.45 (s, 1H), 7.31-7.17 (m, 5H), 6.89-6.85 (m, 2H), 6.49 (s, 1H), 4.59 (dd, 1H), 4.49 (dd, 1H), 3.76-3.71 (m, 1H), 3.68 (d, 1H), 3.58 (d, 1H), 3.59-3.55 (m, 1H), 3.35-3.29 (m, 1H), 3.18-3.11 (m, 1H), 2.71 (s, 3H), 2.48-2.42 (m, 1H), 2.33-2.27 (m, 1H), 1.75-1.65 (m, 2H), 1.43 (s, 3H). MS (EI) for $C_{27}H_{27}ClF_2N_4O_2$, found 513.0 (MH+).

Compound A103—N-(3-Chlorobenzyl)-4-(1-(2-(2,6-difluorophenyl)acetyl)-4-fluoropiperidin-4-yl)-2-methylpyrimidine-5-carboxamide

A103.1: Ethyl N-Boc-4-fluoropiperidine-4-carboxylate

A stirred solution of lithium diisopropyl amide (LDA) (2.6 mL, 2.0 M in THF/heptane/ethylbenzene, 5.2 mmol) was added ethyl N-Boc-piperidine-4-carboxylate (1.03 g, 4.0 mmol) in THF (5 mL) dropwise over 10 min at 0° C. The reaction mixture was stirred at 0° C. for 30 min and then slowly added to a solution of N-fluorobenzenesulfonimide (1.77 g, 5.6 mmol) in THF (15 mL) at 0° C. The reaction mixture was stirred at 0° C. for 30 min and then at room temperature overnight. The reaction mixture was diluted with aq. $NaHCO_3$ and extracted with $CH_2Cl_2$ (×3). The combined organic layer was dried over sodium sulfate, concentrated in vacuo, and the residue was purified by flash chromatography to afford A103.1 (658 mg, 60%).

A103: N-(3-Chlorobenzyl)-4-(1-(2-(2,6-difluorophenyl)acetyl-4-fluoropiperidin-4-yl)-2-methylpyrimidine-5-carboxamide Compound A103 was synthesized from A103.1 in the same manner that Compound A102 was synthesized from ethyl N-Boc-4-methylpiperidine-4-carboxylate. Analytical HPLC: retention time=13.124 min, 98%. $^1$H-NMR (400 MHz, $CDCl_3$): δ 8.62 (s, 1H), 7.40 (s, 1H), 7.31-7.20 (m, 4H), 6.94-6.88 (m, 2H), 6.09 (t, 1H), 4.66-4.58 (m, 3H), 4.00-3.96 (m, 1H), 3.77 (s, 2H), 3.61-3.53 (m, 1H), 3.07-2.99 (m, 1H), 2.73 (s, 3H), 2.43-2.19 (m, 3H), 2.12-2.06 (m, 1H). MS (EI) for $C_{26}H_{24}ClF_3N_4O_2$, found 517.0 (MH+).

Compounds A104-A105

Compounds A104 to A105 were prepared from methods analogous to those used to prepare Compound A103 utilizing appropriate reagent replacements.

| Cpd | Chemical Name | HPLC Retention Time (min) | MS Reported (MH+) |
|---|---|---|---|
| A104 | 4-(1-(2-(2,6-difluorophenyl)acetyl)-4-fluoropiperidin-4-yl)-2-methyl-N-((6-(trifluoromethyl)pyridin-2-yl)methyl)pyrimidine-5-carboxamide | 12.17 | 552.0 |
| A105 | 4-(1-(2-(2,6-difluorophenyl)acetyl)-4-fluoropiperidin-4-yl)-N-(3,5-dimethylbenzyl)-2-methylpyrimidine-5-carboxamide | 13.99 | 511.1 |

HPLC conditions used to determine retention times: YMC C18, 5µ 150×4.6 mm column, gradient 10% to 90% MeCN/H2O, in the presence of 0.1% TFA, 25 min gradient time, 27 min total run time at 1.5 mL/min flow rate, λ=254 nM

Compound A106—N-(3,5-Dimethylbenzyl)-4-(1-((2-fluorophenyl)carbamoyl)piperidin-4-yl)-2-methylpyrimidine-5-carboxamide

Compound A106

To a stirred solution of A99.5 (100 mg, 0.267 mmol), DIEA (90 µL, 0.53 mmol) and $CH_2Cl_2$ (2 mL) at room temperature was slowly added a solution of 2-fluorophenyl isocyanate (32.9 mg, 0.240 mmol) in $CH_2Cl_2$ (1 mL). After stirring for 1 h, the resulting mixture was filtered through cotton and the collected solid was purified by silica gel column chromatography ($CH_2Cl_2$/MeOH=19/1) to give Compound A106 (72.0 mg, 57%) as a white solid. $^1$H-NMR (400 MHz, $CDCl_3$): δ 8.58 (s, 1H), 8.11 (td, 1H), 7.10 (q, 1H), 7.05 (dd, 1H), 6.97 (s, 3H), 6.96 (m, 1H), 6.64 (d, 1H), 6.16 (t, 1H), 4.56 (d, 2H), 4.19 (d, 2H), 3.42 (tt, 1H), 3.00 (td, 2H), 2.70 (s, 3H), 2.33 (s, 6H), 2.00 (qd, 2H), 1.86 (m, 2H). MS (EI) for $C_{27}H_{30}FN_5O_2$, found 476.2 (MH+). Analytical HPLC, ret. time=16.084 min, 99% purity.

Compound A107—4-(1-((2,6-Difluorophenyl)carbamoyl)piperidin-4-yl)-N-(3,5-dimethylbenzyl)-2-methylpyrimidine-5-carboxamide Compound A107 was synthesized from A99.5 in the same manner as Compound A106. MS (EI) for $C_{27}H_{29}F_2N_5O_2$, found 494.0 (MH+). Analytical HPLC, ret. time=15.368 min, 99% purity.

Compound A108—4-(1-(2-(2,6-Difluorophenyl)acetyl)piperidin-4-yl)-N-(3,5-dimethylbenzyl)-2-methyl-6-(methylamino)pyrimidine-5-carboxamide

A108.1: Diethyl 2-((1-(tert-butoxycarbonyl)piperidin-4-yl)methylene)malonate Diethyl malonate (3.75 g, 23 mmol) and N-Boc piperidine-4-carboxaldehyde (5 g, 23 mmol) were dissolved in iPrOH (30 mL). To this solution were added catalytic amounts of piperidine (70 mg) and AcOH (70 mg). The resulting solution was stirred at room temperature for 48 h. The mixture was then concentrated, and the crude product was used in the next step without further purification.

A108.2: Ethyl 4-(1-(tert-butoxycarbonyl)piperidin-4-yl)-2-methyl-6-oxo-1,6-dihydropyrimidine-5-carboxylate To a flask containing a suspension of acetamidine hydrochloride (2.2 g, 23 mmol) in EtOH (25 mL) was added EtONa (1.6 g, 23 mmol). The resulting mixture was stirred for 15 min at room temperature. To this mixture was added A108.1 as a solution in EtOH (15 mL). The mixture was heated to 70° C. with stirring for 2 h. The solvent was removed under reduced pressure. The residue was dissolved in $CH_2Cl_2$ and washed with brine. Concentration gave crude dihydropyrimidinone which was used as is in the next step by mixing with N-bromosuccinimide (NBS) (1.2 g, 6.6 mmol), freshly ground $K_2CO_3$ (7.6 g, 55 mmol) and benzoyl peroxide (65 mg, 0.27 mmol) in $CCl_4$ (25 mL). The resulting mixture was stirred for 1 h at 85° C. It was then cooled to room temperature. Water was added to dissolve the inorganic salts. The mixture was extracted with EtOAc. The organic layer was washed with brine and dried over sodium sulfate. Concentration gave the crude product, which was further purified by flash column chromatography to yield A108.2.

A108.3: Ethyl 4-(1-(2-(2,6-difluorophenyl)acetyl) piperidin-4-yl)-2-methyl-6-oxo-1,6-dihydropyrimidine-5-carboxylate To a solution of A108.2 (1.1 g, 3 mmol) in EtOH (15 mL) was added 4N HCl in dioxane (2.5 mL). The resulting solution was stirred for 12 h at room temperature. Ether (100 mL) was added. The resulting solid was filtered and dried under vacuum. The crude amine HCl salt was used as is without further purification.

The ethyl 2-methyl-6-oxo-4-(piperidin-4-yl)-1,6-dihydropyrimidine-5-carboxylate hydrochloride obtained in the previous step from the Boc deprotection of A108.2 was mixed with 2,6-difluorophenylacetic acid (619 mg, 3.6 mmol), HOBt (607 mg, 4.5 mmol) and DIEA (3 mL) in $CH_2Cl_2$ (15 mL). To this solution was added EDC (860 g, 4.5 mmol). The resulting reaction mixture was stirred at room temperature for 5 h then diluted with aq. sat. $NaHCO_3$. The resulting mixture was extracted with EtOAc and the organic phase was concentrated. The product was precipitated in ether. Filtration and drying under vacuum gave the desired product.

A108.4: 4-(1-(2-(2,6-Difluorophenyl)acetyl)piperidin-4-yl)-2-methyl-6-(methylamino)pyrimidine-5-carboxylic acid To a solution of A108.3 (200 mg, 0.476 mmol), 1,8-diazabicyclo[5.4.0.]undec-7-ene (DBU) (109 mg, 0.71 mmol) and $MeNH_2$ (0.5 mL, 2.0 M in THF) in $CH_3CN$ (2 mL) was added (benzotriazol-1-yloxy)tris(dimethylamino) phosphonium hexafluorophosphate (BOP) (273 mg, 0.62 mmol). The resulting solution was stirred at room temperature for 3 h. It was then diluted with $CH_2Cl_2$, washed with $Na_2CO_3$, brine, and concentrated. The crude product was purified by flash column chromatography. The resulting pure ethyl 4-(1-(2-(2,6-difluorophenyl)acetyl)piperidin-4-yl)-2-methyl-6-(methylamino)pyrimidine-5-carboxylate was stirred with NaOH (72 mg, 1.8 mmol) in MeOH/water (5 mL/5 mL) at 80° C. for 2 h. The reaction solution was concentrated and the solid was dissolved in water (5 mL) and acidified with conc. HCl. The precipitated product was filtered and dried.

Compound A108

A108.4 (0.35 mmol) was mixed with 3,5-dimethylbenzylamine (60 mg, 0.45 mmol) and DIEA (0.5 mL) in DMF (3 mL). To this solution was added HATU (170 mg, 0.45 mmol). The resulting reaction mixture was stirred at room temperature for 2 h then diluted with aq. sat. $NaHCO_3$. The resulting mixture was extracted with $CH_2Cl_2$ and the organic mixture was dried over sodium sulfate, filtered, and concentrated. The crude mixture was purified by prep HPLC to give Compound A108. $^1$H-NMR (400 MHz, DMSO-d6): δ 8.91 (t, 1H), 7.35 (m, 1H), 7.07 (m, 2H), 6.96 (s, 2H), 6.91 (s, 1H), 6.61 (m, 1H), 4.38 (m, 3H), 4.10 (d, 1H), 3.82 (d, 1H), 3.73 (d, 1H), 3.38 (m, 1H), 2.81 (m, 1H), 2.80 (d, 3H), 2.56 (m, 1H), 2.35 (s, 3H), 2.26 (s, 6H), 1.70 (m, 4H). MS (EI) for $C_{29}H_{33}F_2N_5O_2$, found: 522.1 (MH+). Analytical HPLC, ret. time=18.42 min, 96% purity.

Compound A109—4-{1-[(2,6-Difluorophenyl)
acetyl]piperidin-4-yl}-N-[(3,5-dimethylphenyl)
methyl]-2-methyl-6-(methylamino)pyrimidine-5-
carboxamide A109 was synthesized from A108.4 in the same manner as Compound A108. $^1$H-NMR (400 MHz, DMSO-d6): δ 9.04 (t, 1H), 7.36 (m, 5H), 7.07 (m, 2H), 6.68 (m, 1H), 4.45 (m, 3H), 4.10 (d, 1H), 3.82 (d, 1H), 3.73 (d, 1H), 2.81 (m, 1H), 2.80 (d, 3H), 2.65 (m, 1H), 2.35 (s, 3H), 2.30 (m, 1H), 1.70 (m, 4H). MS (EI) for $C_{27}H_{28}ClF_2N_5O_2$, found: 528.1 (MH+). Analytical HPLC, ret. time=3.23 min, 95% purity.

Compound A110—N-(1-(3-Chlorophenyl)-2-hy-
droxyethyl)-4-(1-(2-(2,6-difluorophenyl)acetyl)pip-
eridin-4-yl)-2-methylpyrimidine-5-carboxamide A110.1: Methyl 2-(3-chlorophenyl)-2-(4-(1-(2-(2,6-
difluorophenyl)acetyl)piperidin-4-yl-2-methylpy-
rimidine-5-carboxamido)acetate A1.5 (200 mg, 0.53 mmol) was mixed with 3-chlorophenylglycine methyl ester hydrochloride (150 mg, 0.63 mmol) and DIEA (0.5 mL) in $CH_2Cl_2$ (3 mL). To this solution was added HATU (240 mg, 0.63 mmol). The resulting mixture was stirred at room temperature for 3 h then diluted with aq. sat. $NaHCO_3$. The mixture was extracted with EtOAc and the organic phase was dried over sodium sulfate, filtered, and concentrated. The crude mixture was purified by flash column chromatography.

Compound A110

To a 0° C. solution of A110.1 (156 mg, 0.26 mmol) in THF (3 mL) was added litium aluminum hydride (LAH) (0.3 mL, 1.0 M in THF). The resulting solution was stirred for 1 h, and quenched with 2 N NaOH solution. The mixture was extracted with EtOAc and the organic phase was dried over sodium sulfate, filtered, and concentrated. The crude product was purified by flash column chromatography to give A110.2. $^1$H-NMR (400 MHz, DMSO-d6): δ 9.09 (d, 1H), 8.66 (s, 1H), 7.46 (m, 1H), 7.37 (m, 4H), 7.07 (m, 2H), 5.08 (m, 2H), 4.42 (m, 1H), 4.13 (m, 1H), 3.83 (m, 2H), 3.68 (t, 2H), 3.41 (m, 1H), 3.10 (m, 1H), 2.64 (s, 3H), 2.56 (m, 1H), 1.70 (m, 4H). MS (EI) for $C_{27}H_{27}ClF_2N_4O_3$, found: 529.0 (MH+). Analytical HPLC, ret. time=3.70 min, 94% purity.

Compound A111—N-(3-Chlorobenzyl)-4-(1-(2-(2,6-
difluorophenyl)acetyl)piperidin-4-yl)-6-methoxy-2-
methylpyrimidine-5-carboxamide A111.1: 4-(1-(2-(2,6-Difluorophenyl)acetyl)piperi-
din-4-yl)-6-methoxy-2-methylpyrimidine-5-carbox-
ylic acid To a solution of A108.3 (100 mg, 0.23 mmol) and DBU (70 mg, 0.46 mmol) in THF (2 mL) was added BOP (140 mg, 0.31 mmol). The resulting solution was stirred at room temperature for 10 min, then $Cs_2CO_3$ (150 mg, 0.46 mmol) and MeOH (1.5 mL) were added. The mixture was stirred at room temperature for an additional 2 h. The crude product was extracted with EtOAc, washed with $Na_2CO_3$, brine, and concentrated. The resulting crude ethyl ester was stirred with NaOH (25 mg, 0.62 mmol) in MeOH/water (2 mL/2 mL) at 80° C. for 2 h. The reaction solution was concentrated and the resulting solid was dissolved in water (5 mL) and acidified with conc. HCl. The precipitated product was filtered and dried to give A111.1.

Compound A111

Crude A111.1 (0.2 mmol) was mixed with 3-chlorobenzylamine (42 mg, 0.3 mmol) and DIEA (0.2 mL) in DMF (2 mL). To this solution was added HATU (114 mg, 0.3 mmol). The resulting reaction mixture was stirred at room temperature for 2 h then diluted with aq. sat. $NaHCO_3$. The resulting mixture was extracted with EtOAc and the organic mixture was dried over sodium sulfate, filtered, and concentrated. The crude mixture was purified by prep HPLC to give Compound A111. $^1$H-NMR (400 MHz, DMSO-d6): δ 9.08 (t, 1H), 7.36 (m, 5H), 7.07 (m, 2H), 4.45 (m, 3H), 4.12 (d, 1H), 3.95 (s, 3H), 3.82 (d, 1H), 3.73 (d, 1H), 3.02 (m, 1H), 2.84 (m, 1H), 2.55 (s, 3H), 2.45 (m, 1H), 1.70 (m, 4H). MS (EI) for $C_{27}H_{27}ClF_2N_4O_3$, found: 529.0 (MH+). Analytical HPLC, ret. time=22.49 min, 92% purity.

Compound A112—4-(1-(2-(2,6-Difluorophenyl)
acetyl)piperidin-4-yl)-N-(3,5-dimethylbenzyl)-2-
methyl-6-(trifluoromethyl)pyrimidine-5-carboxam-
ide A112.1: tert-Butyl 4-(2-(ethoxycarbonyl)-4,4,4-trif-
luoro-3-oxobut-1-enyl)piperidine-1-carboxylate Ethyl 4,4,4-trifluoroacetoacetate (4.3 g, 23 mmol) and N-Boc piperidine-4-carboxaldehyde (5 g, 23 mmol) were dissolved in iPrOH (30 mL). To this solution were added catalytic amounts of piperidine (70 mg) and AcOH (70 mg). The resulting solution was stirred at room temperature for 48 h. The mixture was then concentrated, and the crude product was used in the next step without further purification.

A112.2: Ethyl 4-(1-(tert-butoxycarbonyl)piperidin-
4-yl)-2-methyl-6-(trifluoromethyl)pyrimidine-5-
carboxylate To a flask containing a suspension of acetamidine hydrochloride (2.5 g, 27 mmol) in EtOH (25 mL) was added EtONa (1.9 g, 27 mmol). The resulting mixture was stirred for 15 min at room temperature. To this mixture was added A112.1 as a solution in EtOH (15 mL). The mixture was stirred at room temperature for 12 h and then was concentrated. The residue was dissolved in DMF (20 mL), reacted with pTsOH (8.7 g, 45 mmol) at 110° C. for 2 h. The reaction mixture was cooled to room temperature, basified with 20% NaOH aq. solution until pH 10. The crude product was extracted with $CH_2Cl_2$, dried over sodium sulfate, and concentrated. The residue (4.2 g, 10 mmol) was dissolved in $CH_2Cl_2$ (20 mL), to which were added $NaHCO_3$ (3.1 g, 30 mmol), $Boc_2O$ (3.2 g, 15 mmol) and water (20 mL). The mixture was stirred at room temperature for 12 h, then the organic layer was washed with brine, and concentrated. Flash column chromatography gave the desired dihydropyrimidine which was dissolved in DCE (30 mL), to which was added $MnO_2$ (1.8 g, 21 mmol). The resulting mixture was stirred for 1 h at 85° C., cooled to room temperature and filtered through Celite. The filtrate was washed with brine and dried over sodium sulfate. Concentration gave crude A112.2 which was used in the next step without further purification.

A112.3: Ethyl 4-(1-(2-(2,6-difluorophenyl)acetyl) piperidin-4-yl)-2-methyl-6-(trifluoromethyl)pyrimidine-5-carboxylate To a solution of A112.2 (290 mg, 0.69 mmol) in MeOH (5 mL) was added 4N HCl in dioxane (1 mL). The resulting solution was stirred for 12 h at room temperature. EtOAc (25 mL) was added. The solid was filtered and dried under vacuum. The crude product was used without further purification by mixing with 2,6-difluorophenylacetic acid (180 mg, 1.1 mmol), HATU (418 mg, 1.1 mmol) and DIEA (645 mg, 5 mmol) in THF (5 mL). The resulting reaction mixture was stirred at room temperature for 2 h then diluted with aq. sat. NaHCO$_3$. The resulting mixture was extracted with EtOAc and the organic mixture was dried over sodium sulfate, filtered, and concentrated. The crude product was stirred with NaOH (200 mg, 5 mmol) in MeOH/water (2 mL/1 mL) at 80° C. for 3 h. The solution was concentrated and the solid was dissolved in water (5 mL) and acidified with conc. HCl. The precipitated product was filtered and dried.

Compound A112

A112.3 (80 mg, 0.18 mmol) was mixed with DIEA (0.5 mL) and HATU (100 mg, 0.27 mmol) in THF (3 mL). The formation of the HOAT ester was complete in 3 h. The reaction mixture was diluted with EtOAc, washed with NaHCO$_3$, and concentrated. The crude HOAT ester was reacted with neat 3,5-dimethylbenzylamine (0.5 mL) at room temperature for 12 h. The resulting mixture was extracted with EtOAc and washed with 2 N HCl aq. solution. The organic mixture was dried over sodium sulfate, filtered, and concentrated. The crude mixture was purified by prep HPLC to give Compound A112. MS (EI) for C$_{29}$H$_{29}$F$_5$N$_4$O$_2$, found: 561.0 (MH+). Analytical HPLC, ret. time=4.50 min, 86% purity.

Compound A113—4-(1-(2-(2,6-Difluorophenyl)acetyl)piperidin-4-yl)-N-(3,5-dimethylbenzyl)-N,2-dimethylpyrimidine-5-carboxamide To a stirred solution of A1 (90.0 mg, 0.183 mmol) in DMF (2.0 mL) at room temperature was added NaH (10.9 mg, 60% dispersion in mineral oil, 0.274 mmol). After stirring for 5 min at room temperature, iodomethane (40 μmol, 0.64 mmol) was added. The reaction mixture was stirred for 2 h at room temperature, quenched with aq. sat. NaHCO$_3$ (3 mL) and then extracted with EtOAc (2×3 mL). The combined organic layers were concentrated and purified by silica gel column chromatography (hexane/EtOAc=2:5) to give Compound A113 (45.0 mg, 49%) as a white powder after lyophilization. $^1$H-NMR (400 MHz, CDCl$_3$, rotameric mixture): δ 8.47 and 8.45 (two of s, 1H), 7.23 (m, 1H), 6.99 (s, 2H), 6.90 (m, 2H), 6.67 (s, 1H), 4.73 (m, 2H), 4.35 (s, 1H), 4.09 (d, 1H), 3.75 (s, 2H), 3.25-3.09 (m, 1H), 3.15 and 2.79 (two of s, 3H), 3.02-2.92 (m, 1H), 2.73 and 2.70 (two of s, 3H), 2.68-2.53 (m, 1H), 2.33 and 2.28 (two of s, 6H), 2.05-1.77 (m, 4H). MS (EI) for C$_{29}$H$_{32}$F$_2$N$_4$O$_2$, found 507.2 (MH+). Analytical HPLC, ret. time=18.180 min, 93% purity.

Compound A114—4-(1-(2-(2,6-Difluorophenyl)acetyl)-1,2,3,4-tetrahydropyridin-4-yl)-N-(3,5-dimethylbenzyl)-2-methylpyrimidine-5-carboxamide

A114.1: Ethyl 4-chloro-2-methylpyrimidine-5-carboxylate

A mixture of ethyl 2-methyl-6-oxo-1,6-dihydropyrimidine-5-carboxylate (1.00 g, 5.49 mmol) and phosphorous oxychloride (12 mL) was stirred for 2 h at 90° C. The reaction mixture was concentrated under vacuum, dissolved in MeCN (10 mL), and concentrated again. The resulting material was dissolved in EtOAc (10 mL) and treated with aq. sat. NaHCO$_3$ (10 mL). The aq. solution was separated and further extracted with EtOAc (2×5 mL). The organic layers were immediately washed with aq. sat. NaHCO$_3$ (5 mL), dried over anhydrous magnesium sulfate, concentrated, and purified by silica gel chromatography (hexane/EtOAc=7:1) to provide A114.1 (670 mg, 61%) as a clear oil.

A114.2: Ethyl 4-(1-(tert-butoxycarbonyl)-1,2,3,4-tetrahydropyridin-4-yl)-2-methylpyrimidine-5-carboxylate To a stirred mixture of A114.1 (670 mg, 3.34 mmol), tert-butyl 4-(4,4,5,5-tetramethyl-1,3,2-dioxaborolan-2-yl)-5,6-dihydropyridine-1(2H)-carboxylate (1.34 g, 4.34 mmol) and PdCl$_2$(dppf)$_2$·CH$_2$Cl$_2$ (273 mg, 0.334 mmol) in DMF (10 mL) was added Et$_3$N (1.16 mL, 8.35 mmol) and water (2 mL) in sequence. After stirring for 110 min at 90° C., water (3 mL) and aq. sat. NH$_4$Cl (6 mL) were added and the resulting solution was extracted with EtOAc (4×8 mL). The combined organic layers were concentrated and purified by silica gel chromatography (Hexane/EtOAc=5:1→4:1) to provide A114.2 (980 mg, 85%) as a clear oil. $^1$H-NMR (400 MHz, CDCl$_3$, rotameric mixture): δ 9.02 (s, 1H), 7.05 and 6.95 (two of d, J=8.0 Hz, 1H), 4.93 and 4.84 (two of d, J=8.0 Hz, 1H), 4.50-4.43 (m, 1H), 4.40 (q, J=7.2 Hz, 2H), 4.07-3.93 (m, 1H), 3.57-3.50 (m, 1H), 2.75 (s, 3H), 2.19-2.02 (m, 2H), 1.50 (s, 9H), 1.41 (t, J=7.2 Hz, 3H). MS (EI) for C$_{18}$H$_{25}$N$_3$O$_4$, found 348.1 (MH+).

A114.3: tert-Butyl 4-(5-(3,5-dimethylbenzylcarbamoyl)-2-methylpyrimidin-4-yl)-3,4-dihydropyridine-1(2H)-carboxylate A mixture of A114.2 (248 mg, 0.714 mmol), LiOH (25.7 mg, 1.07 mmol), THF (4 mL) and water (1 mL) was stirred for 80 min at 50° C. The resulting solution was concentrated under vacuum to give the corresponding acid; MS (EI) for C$_{16}$H$_{21}$N$_3$O$_4$, found 320.1 (MH+). To a stirred solution of the resulting carboxylic acid, (3,5-dimethylphenyl)methanamine (106 mg, 0.785 mmol), HATU (407 mg, 1.07 mmol) and DMF (4 mL) at room temperature was added DIEA (0.37 mL, 2.14 mmol). After stirring for 2.5 h, water (4 mL) was added and the resulting solution was extracted with EtOAc (3×4 mL). The combined organic layers were concentrated and purified by silica gel column chromatography (hexane/EtOAc=3:2→4:3) to give A114.3 (210 mg, 67%) as a pale yellow foam. MS (EI) for C$_{25}$H$_{32}$N$_4$O$_3$, found 437.1 (MH+).

Compound A114

A mixture of A114.3 (210 mg, 0.481 mmol) and 4N HCl in 1,4-dioxane (3 mL) was stirred for 1 h at room temperature, and concentrated under vacuum. EtOAc (2 mL) was added and the mixture was concentrated again. To a stirred solution of the resulting residue, 2-(2,6-difluorophenyl)acetic acid (108 mg, 0.625 mmol), HATU (274 mg, 0.722 mmol) and DMF (4 mL) was added DIEA (0.33 mL, 1.9 mmol). After stirring for 4.5 h at room temperature, aq. sat. NaHCO$_3$ (4 mL) and water (1 mL) were added and the resulting solution was extracted with EtOAc (3×4 mL). The combined organic layers were concentrated and purified by silica gel column chromatography (Hexane/EtOAc=2:1).

The isolated material was further purified by prep HPLC to give Compound A114 (25.0 mg, 11%) as a white powder after lyophilization. $^1$H-NMR (400 MHz, CDCl$_3$, rotameric mixture): δ 8.60 and 8.59 (two of s, 1H), 7.24 (m, 1H), 6.96 (s, 3H), 6.93 (dd, 1H), 4.56 (dd, 2H), 4.26-4.07 (m, 2H), 3.85 and 3.82 (two of s, 2H), 3.76 and 3.56 (two of ddd, 1H), 2.74 and 2.73 (two of s, 3H), 2.32 (s, 6H), 2.31-2.04 (m, 2H). MS (EI) for $C_{28}H_{28}F_2N_4O_2$, found 491.0 (MH+). Analytical HPLC, ret. time=18.332 min, 99% purity.

Compound A115—4-(1-(2-(2-Chlorophenyl)-2-oxo-ethyl)piperidin-4-yl)-N-(3,5-dimethylbenzyl)-2-methylpyrimidine-5-carboxamide To a stirred solution of A99.5 (100 mg, 0.267 mmol), 2-bromo-1-(2-chlorophenyl)ethanone (68.6 mg, 0.294 mmol) and CH$_2$Cl$_2$ (2 mL) at room temperature was added DIEA (0.14 mL, 0.80 mmol). After stirring for 70 min, aq. sat. NaHCO$_3$ (3 mL) was added and the resulting solution was extracted with EtOAc (3×3 mL). The combined organic layers were concentrated and purified by silica gel column chromatography (Hexane/EtOAc=1:3→1:4) to give Compound A115 (47 mg, 36%) as a pale yellow powder after lyophilization. $^1$H-NMR (400 MHz, CDCl$_3$): δ 8.53 (s, 1H), 7.38 (m, 4H), 6.96 (s, 3H), 6.05 (t, 1H), 4.55 (d, 2H), 3.76 (s, 2H), 3.13 (tt, 1H), 3.05 (d, 2H), 2.68 (s, 3H), 2.32 (s, 6H), 2.26 (m, 2H), 2.08 (qd, 2H), 1.73 (m, 2H). MS (EI) for $C_{28}H_{31}ClN_4O_2$, found 491.1 (MH+). Analytical HPLC, ret. time=12.464 min, 97% purity.

Compound B1—(1E)-1-(4-{1-[(2,6-Difluorophenyl) acetyl]piperidin-4-yl}-2,6-dimethylpyrimidin-5-yl) ethanone O-[3-(trifluoromethyl)phenyl]

B1.1: 4-(1-(2-(2,6-Difluorophenyl)acetyl)piperidin-4-yl)-2,6-dimethylpyrimidine-5-carboxylic acid To a stirred solution of the methyl/ethyl ester A80.3 (2.1 g, ca 5.0 mmol) in MeOH (30 mL) was added aq. 1N NaOH (20 mL) and the reaction mixture was stirred at room temperature overnight. MeOH was removed in vacuo and the residual aq. layer was acidified with 1N HCl to pH 4-5, and extracted with CH$_2$Cl$_2$ (×5). The combined organic layer was dried over sodium sulfate and concentrated in vacuo to give acid B1.1 (1.88 g, ca. 97%).

B1.2: 4-(1-(2-(2,6-Difluorophenyl)acetyl)piperidin-4-yl)-2,6-dimethylpyrimidine-5-carbaldehyde To a stirred solution of acid B1.1 (195 mg, 0.50 mmol) and Et$_3$N (77 μL, 0.55 mmol) in THF (5 mL) was added ethyl chloroformate (53 μL, 0.55 mmol) at 0° C. After stirring for 1 h at 0° C., the precipitates were filtered and an aq. solution of NaBH$_4$ was added dropwise to the filtrate at 0° C. After stirring for 1.5 h at 0° C., acetone (1 mL) was added to destroy the excess NaBH$_4$ and the resulting mixture was stirred for 30 min. The reaction mixture was diluted with water and extracted with CH$_2$Cl$_2$ (×2). The combined organic layers were dried over sodium sulfate, concentrated in vacuo, and the residue was purified by flash chromatography to afford the corresponding alcohol (104 mg, 55%, 0.28 mmol) which was then dissolved in CH$_2$Cl$_2$ (6 mL) and treated with Dess-Martin periodinane (235 mg, 0.55 mmol) with stirring at room temperature for 2 h. The reaction mixture was diluted with water and the separated aq. layer was extracted with CH$_2$Cl$_2$ (×2). The combined organic layers were dried over sodium sulfate, concentrated in vacuo, and the residue was purified by flash chromatography to give B1.2 (101 mg, 98%).

B1.3: 1-(4-(5-Acetyl-2,6-dimethylpyrimidin-4-yl) piperidin-1-yl)-2-(2,6-difluorophenyl)ethanone To a stirred solution of aldehyde B1.2 (100 mg, 0.27 mmol) in THF (5 mL) was added MeMgBr (0.4 mL, 1.4 M in THF/toluene, 0.56 mmol) and the reaction mixture was stirred at room temperature for 30 min. The reaction mixture was quenched with aq. NH$_4$Cl and extracted with CH$_2$Cl$_2$ (×2). The combined organic layers were dried over sodium sulfate and concentrated in vacuo to give 2-(2,6-difluorophenyl)-1-(4-(5-(1-hydroxyethyl)-2,6-dimethylpyrimidin-4-yl)piperidin-1-yl)ethanone (110 mg, quant., 0.27 mmol), which was directly used for the next step by dissolving it in CH$_2$Cl$_2$ (6 mL) and then adding Dess-Martin periodinane (172 mg, 0.41 mmol). The reaction mixture was stirred at room temperature for 2 h, then diluted with aq. sodium bicarbonate and extracted with CH$_2$Cl$_2$ (×2). The combined organic layers were dried over sodium sulfate, concentrated in vacuo, and the residue was purified by flash chromatography to give ketone B1.3 (91 mg, 88%).

Compound B1.4

A mixture of B1.3 (91 mg, 0.23 mmol) and O-(3-(trifluoromethyl)phenyl)hydroxylamine (82 mg, 0.46 mmol) in EtOH (8 mL) was treated with 2 drops of concentrated HCl and the reaction mixture was stirred at 50° C. for 4 days. 30-40% conversion was observed on LC-MS. The reaction mixture was diluted with aq. sodium bicarbonate and extracted with CH$_2$Cl$_2$ (×3). The combined organic layer was dried over sodium sulfate, concentrated in vacuo, and the residue was purified by flash chromatography to afford B1.4 as an inseparable 3:1 mixture of E/Z isomers as a white powder after lyophilization (19 mg, 15%). Data for major isomer (E): Analytical HPLC: retention time=22.368 min, 98%. $^1$H-NMR (400 MHz, CDCl$_3$): δ 7.48-7.44 (m, 2H), 7.36-7.32 (m, 2H), 7.26-7.19 (m, 1H), 6.92-6.87 (m, 2H), 4.75 (d, 1H), 4.11 (d, 1H), 3.74 (d, 2H), 3.21-3.14 (m, 1H), 2.96-2.87 (m, 1H), 2.80 (s, 3H), 2.68-2.61 (m, 1H), 2.57 (s, 3H), 2.42 (s, 3H), 2.10-1.95 (m, 2H), 1.87-1.75 (m, 2H). MS (EI) for $C_{28}H_{27}F_5N_4O_2$, found 547.1 (MH+).

Compound B2—(1Z)-1-(4-{1-[(2,6-Difluorophenyl) acetyl]piperidin-4-yl}-2,6-dimethylpyrimidin-5-yl) ethanone O-[2-(trifluoromethyl)pyridin-4-yl]oxime Compound B2 was synthesized from B1.3 in the same manner as Compound B1. In the case of Compound B2, a 10:1 mixture of Z/E isomers was recovered. Data for major isomer (Z): Analytical HPLC: retention time=19.692 min, 99%. $^1$H-NMR (400 MHz, CDCl$_3$): δ 8.57 (t, 1H), 7.47 (d, 1H), 7.24-7.13 (m, 2H), 6.92-6.87 (m, 2H), 4.80-4.66 (m, 1H), 4.16-4.03 (m, 1H), 3.75 (s, 1H), 3.72 (d, 1H), 3.24-3.17 (m, 1H), 3.12-3.05 (m, 1H), 2.80 (s, 3H), 2.69-2.63 (m, 1H), 2.45 (s, 3H), 2.38 (s, 3H), 2.18-1.84 (m, 2H), 1.78-1.69 (m, 2H). MS (EI) for $C_{27}H_{26}F_5N_5O_2$, found 548.0 (MH+).

Compound B3—(E)-2-(2,6-Difluorophenyl)-1-(4-(2-methyl-5-(1-(3-(trifluoromethyl)phenoxyimino)ethyl)pyrimidin-4-yl)piperidin-1-yl)ethanone B3.1: 1-(4-(5-Acetyl-2-methylpyrimidin-4-yl)piperidin-1-yl)-2-(2,6-difluorophenyl)ethanone B3.1 was synthesized from A1.5 in the same manner that B1.3 was synthesized from B1.1.

Compound B3

To a stirred solution of B3.1 (112 mg, 0.30 mmol) and O-(3-(trifluoromethyl)phenylhydroxylamine (54 mg, 0.30 mmol) in EtOH (5 mL) was added 2 drops of conc. HCl and the reaction mixture was stirred at room temperature for 4 h. The reaction mixture was diluted with EtOAc, washed with aq. sodium bicarbonate, concentrated in vacuo, and the residue was purified by flash chromatography (hexanes/methyl t-butylether/CH$_2$Cl$_2$=4/3/3) to give Compound B3 (49 mg, 36%) as a white powder after lyophilization. Analytical HPLC: retention time=23.664 min, 98%. $^1$H-NMR (400 MHz, CDCl$_3$): δ 8.57 (s, 1H), 7.49 (s, 1H), 7.45 (t, 1H), 7.36 (dd, 1H), 7.32 (d, 1H), 7.24-7.19 (m, 1H), 6.93-6.86 (m, 2H), 4.75 (d, 1H), 4.12 (d, 1H), 3.75 (d, 2H), 3.31-3.23 (m, 1H), 3.22-3.15 (m, 1H), 2.75 (s, 3H), 2.69-2.61 (m, 1H), 2.48 (s, 3H), 2.14-1.95 (m, 2H), 1.92-1.79 (m, 2H). MS (EI) for C$_{27}$H$_{25}$F$_5$N$_4$O$_2$, found 533.0 (MH+).

Compound B4—(Z)-2-(2,6-Difluorophenyl)-1-(4-(2-methyl-5-(1-(3-(trifluoromethyl)phenoxyimino)ethyl)pyrimidin-4-yl)piperidin-1-yl)ethanone Compound B4 is the Z isomer of Compound B3, recovered as a second compound from the same reaction that generated Compound B3 during the purification process by flash chromatography. Analytical HPLC: retention time=22.856 min, 95%. $^1$H-NMR (400 MHz, CDCl$_3$): δ 8.38 (s, 1H), 7.41-7.38 (m, 2H), 7.29 (d, 1H), 7.24-7.18 (m, 2H), 6.92-6.86 (m, 2H), 4.70 (d, 1H), 4.06 (d, 1H), 3.72*d, 2H), 3.11-3.04 (m, 1H), 2.77 (s, 3H), 2.76-2.70 (m, 1H), 2.60-2.54 (m, 1H), 2.37 (s, 3H), 2.10-1.90 (m, 2H), 1.77-1.67 (m, 2H). MS (EI) for C$_{27}$H$_{25}$F$_5$N$_4$O$_2$, found 533.0 (MH+).

Compounds B5-B22

Compounds B5 to B22 were prepared from methods analogous to those used to prepare Compounds B3 and B4 utilizing appropriate reagent replacements.

| Cpd | Chemical Name | HPLC Retention Time (min) | Mass Reported (MH+) |
|---|---|---|---|
| B5 | (E)-1-(4-(5-(1-((3-chlorophenoxy)imino)ethyl)-2-methylpyrimidin-4-yl)piperidin-1-yl)-2-(2,6-difluorophenyl)ethanone | 22.86 | 499.0 |
| B6 | (Z)-1-(4-(5-(1-((3-chlorophenoxy)imino)ethyl)-2-methylpyrimidin-4-yl)piperidin-1-yl)-2-(2,6-difluorophenyl)ethanone | 4.36* | 499.0 |
| B7 | (E)-2-(2,6-difluorophenyl)-1-(4-(2-methyl-5-(1-((3-(trifluoromethoxy)phenoxy)imino)ethyl)pyrimidin-4-yl)piperidin-1-yl)ethanone | 24.91 | 549.0 |
| B8 | (Z)-2-(2,6-difluorophenyl)-1-(4-(2-methyl-5-(1-((3-(trifluoromethoxy)phenoxy)imino)ethyl)pyrimidin-4-yl)piperidin-1-yl)ethanone | 24.40 | 549.0 |
| B9 | (E)-2-(2,6-difluorophenyl)-1-(4-(5-(1-((3,5-dimethylphenoxy)imino)ethyl)-2-methylpyrimidin-4-yl)piperidin-1-yl)ethanone | 26.69 | 493.0 |
| B10 | (Z)-2-(2,6-difluorophenyl)-1-(4-(5-(1-((3,5-dimethylphenoxy)imino)ethyl)-2-methylpyrimidin-4-yl)piperidin-1-yl)ethanone | 26.35 | 493.0 |
| B11 | (E)-2-(2,6-difluorophenyl)-1-(4-(2-methyl-5-(1-((m-tolyloxy)imino)ethyl)pyrimidin-4-yl)piperidin-1-yl)ethanone | 23.81 | 479.0 |
| B12 | (E)-1-(4-(5-(1-((3-chloro-5-fluorophenoxy)imino)ethyl)-2-methylpyrimidin-4-yl)piperidin-1-yl)-2-(2,6-difluorophenyl)ethanone | 23.26 | 517.0 |
| B13 | (E)-4-(((1-(4-(1-(2-(2,6-difluorophenyl)acetyl)piperidin-4-yl)-2-methylpyrimidin-5-yl)ethylidene)amino)oxy)picolinonitrile | 17.39 | 491.0 |
| B14 | (E)-2-(2,6-difluorophenyl)-1-(4-(2-methyl-5-(1-(((2-(trifluoromethyl)pyridin-4-yl)oxy)imino)ethyl)pyrimidin-4-yl)piperidin-1-yl)ethanone | 19.55 | 534.0 |
| B15 | (E)-1-(4-(5-(1-(((2-chloropyridin-4-yl)oxy)imino)ethyl)-2-methylpyrimidin-4-yl)piperidin-1-yl)-2-(2,6-difluorophenyl)ethanone | 18.01 (Z isomer) 18.62 (E isomer) | 500.0 |
| B16 | (E)-2-(2,6-difluorophenyl)-1-(4-(5-(1-((3-fluorophenoxy)imino)ethyl)-2-methylpyrimidin-4-yl)piperidin-1-yl)ethanone | 23.29 | 483.0 |
| B17 | (E)-2-(2,6-difluorophenyl)-1-(4-(5-(1-((5-fluoro-2-methylphenoxy)imino)ethyl)-2-methylpyrimidin-4-yl)piperidin-1-yl)ethanone | 22.76 | 497.0 |

| Cpd | Chemical Name | HPLC Retention Time (min) | Mass Reported (MH+) |
|---|---|---|---|
| B18 | (E)-2-(2,6-difluorophenyl)-1-(4-(5-(1-((2,5-dimethylphenoxy)imino)ethyl)-2-methylpyrimidin-4-yl)piperidin-1-yl)ethanone | 23.69 | 493.0 |
| B19 | (E)-2-(2,6-difluorophenyl)-1-(4-(2-methyl-5-(1-(((6-(trifluoromethyl)pyridin-2-yl)oxy)imino)ethyl)pyrimidin-4-yl)piperidin-1-yl)ethanone | 20.20 | 534.0 |
| B20 | (E)-2-(2,6-difluorophenyl)-1-(4-(2-methyl-5-(1-(((2-(trifluoromethyl)pyrimidin-4-yl)oxy)imino)ethyl)pyrimidin-4-yl)piperidin-1-yl)ethanone | 18.88 | 535.0 |
| B21 | (E)-2-(2,6-difluorophenyl)-1-(4-(5-(1-((3-methoxyphenoxy)imino)ethyl)-2-methylpyrimidin-4-yl)piperidin-1-yl)ethanone | 22.86 | 495.0 |
| B22 | (E)-2-(2,6-difluorophenyl)-1-(4-(5-(1-((2,3-dimethylphenoxy)imino)ethyl)-2-methylpyrimidin-4-yl)piperidin-1-yl)ethanone | 23.35 | 493.1 |

HPLC Conditions Used to Determine Retention Times:
Unless otherwise noted: YMC C18, 5μ 150×4.6 mm column, gradient 10% to 90% MeCN/H2O, in the presence of 0.1% TFA, 25 min gradient time, 27 min total run time at 1.5 mL/min flow rate, λ=254 nM
* Phenomenex, Gemini, 50×4.6 mm, 5μ column, gradient 10% to 90% MeCN/H2O, in the presence of 0.1% TFA, 5 min gradient time, 6 min total run time at 3.0 mL/min flow rate, λ=254 nM Compound B23—(1Z)-1-(4-{1-[(2,6-Difluorophenyl)acetyl]piperidin-4-yl}-2-methylpyrimidin-5-yl)-2-hydroxyethanone O-[2-(trifluoromethyl)pyridin-4-yl]oxime B23.1: tert-Butyl 4-(5-acetyl-2-methylpyrimidin-4-yl)piperidine-1-carboxylate To a stirred mixture of acid A106.1 (3.07 g, 9.55 mmol), N,O-dimethylhydroxylamine hydrogenchloride (1.12 g, 11.5 mmol), and Et3N (5.32 mL, 38.2 mmol) in dimethylacetamide (DMA) (30 mL) was added HATU (4.36 g, 11.5 mmol) and the reaction mixture was stirred at room temperature for 1 h. The reaction mixture was diluted with EtOAc, washed with aq. sodium bicarbonate, brine, dried over sodium sulfate and concentrated in vacuo to give the corresponding Weinreb amide, which was directly used for the next step. The crude Weinreb amide was dissolved in THF (30 mL) and the resulting solution was treated with MeMgBr (27.3 mL, 1.4 M in THF/toluene, 38.2 mmol) at room temperature. After stirring for 2 h, the reaction mixture was cooled to 0° C., quenched with aq. NH4Cl and extracted with EtOAc (×2). The combined organic layers were dried over sodium sulfate, concentrated in vacuo, and the residue was purified by flash chromatography to give ketone B23.1 (2.76 g, 90% in 2 steps).

B23.2: tert-Butyl 4-(5-(2-acetoxyacetyl)-2-methylpyrimidin-4-yl)piperidine-1-carboxylate To a stirred solution of B23.1 (639 mg, 2.0 mmol) in THF (20 mL) was added lithium bis(trimethylsilyl)amide (LHMDS) (3.0 mL, 1.0 M in THF, 3.0 mmol) at 0° C. and the reaction mixture was stirred for 30 min. To this resulting solution was added TMSCl (383 μL, 3.0 mmol). After stirring for 3 h, the reaction mixture was diluted with aq. sodium bicarbonate and extracted with EtOAc (×2). The combined organic layers were dried over sodium sulfate and concentrated in vacuo to give the corresponding trimethylsilylenol ether, which was directly used for the next step. The crude trimethylsilylenol ether was dissolved in THF (20 mL) and the solution was treated with NaHCO3 (252 mg, 3.0 mmol) followed by NBS (356 mg, 2.0 mmol) at 0° C. The reaction mixture was warmed to room temperature and stirred for 30 min. The reaction mixture was diluted with aq. sodium bicarbonate and extracted with EtOAc (×2). The combined organic layers were dried over sodium sulfate, concentrated in vacuo, and the residue was purified by flash chromatography to afford the corresponding α-bromoketone (661 mg, 83% in 2 steps). To a stirred solution of this α-bromoketone (398 mg, 1.0 mmol) in DMA (5 mL) was added K2CO3 (294 mg, 3.0 mmol) and the reaction mixture was stirred for 1 h. The reaction mixture was diluted with water and extracted with EtOAc (×2). The combined organic layers were washed with brine, dried over sodium sulfate, concentrated in vacuo, and the residue was purified by flash chromatography to give acetate B23.2 (354 mg, 94%).

B23.3: 2-(4-(1-(2-(2,6-Difluorophenyl)acetyl)piperidin-4-yl)-2-methylpyrimidin-5-yl)-2-oxoethyl acetate A solution of B23.2 (354 mg, 0.94 mmol) in 1,4-dioxane (10 mL) was treated with HCl (5 mL, 4 M in 1,4-dioxane, 20 mmol) and the reaction mixture was stirred at room temperature overnight. The reaction mixture was concentrated in vacuo to give the corresponding amine HCl salt, which was directly used for the next step. The crude amine HCl salt was dissolved in DMA (10 mL) and treated with Et3N (655 μL, 4.7 mmol) and 2,6-difluorophenylacetic acid (194 mg, 1.13 mmol) followed by HATU (430 mg, 1.13 mmol). After stirring for 30 min at room temperature, the reaction mixture was diluted with EtOAc, washed with aq. sodium bicarbonate, brine, dried over sodium sulfate, concentrated in vacuo, and the residue was purified by flash chromatography to give B23.3 (338 mg, 83%).

B23.4: 2-(2,6-Difluorophenyl)-1-(4-(5-(2-hydroxy-1-(hydroxyimino)ethyl)-2-methylpyrimidin-4-yl)piperidin-1-yl)ethanone The mixture of B23.3 (338 mg, 0.78 mmol) and hydroxylamine hydrochloride (542 mg, 7.8 mmol) in EtOH (10 mL) was treated with 5 drops of concentrated HCl and the resulting mixture was stirred at room temperature overnight. The reaction mixture was diluted with aq. sodium bicarbonate and extracted with $CH_2Cl_2$ (×5). The combined organic layers were dried over sodium sulfate, concentrated in vacuo, and the residue was purified by flash chromatography to afford oxime B23.4 (244 mg, 70%) along with acetylated oxime (44 mg, 14%). The resulting mixture (89 mg, 0.55 mmol) was dissolved in MeOH (5 mL) and treated with $K_2CO_3$ to hydrolyze the acetylated oxime (138 mg, 1.0 mmol). After stirring for 1 h at room temperature, the reaction mixture was concentrated in vacuo and the residue was directly purified by flash chromatography to give B23.4 (77 mg, 95%).

Compound B23

A mixture of B23.3 (77 mg, 0.19 mmol) and 4-chloro-2-trifluoromethylpyridine (34 mg, 0.19 mmol) in DMA (4 mL) was treated with $K_2CO_3$ (131 mg, 0.95 mmol). After stirring for 24 h at room temperature, additional 4-chloro-2-trifluoromethylpyridine (34 mg, 0.19 mmol) was added to the reaction mixture. After stirring for 48 h at room temperature, the reaction mixture was diluted with water and extracted with EtOAc (×2). The combined organic layer was washed with brine, dried over sodium sulfate, concentrated in vacuo, and the residue was purified by flash chromatography to give Compound B23 (37 mg, 35%) as a white powder after lyophilization. Analytical HPLC: retention time=16.904 min, 99%. $^1$H-NMR (400 MHz, $CDCl_3$): δ 8.69 (br s, 1H), 8.63 (d, 1H), 7.53 (d, 1H), 7.29 (dd, 1H), 7.26-7.19 (m, 1H), 6.93-6.87 (m, 2H), 5.03 (s, 2H), 4.76 (d, 1H), 4.13 (d, 1H), 3.76 (d, 2H), 3.24-3.17 (m, 1H), 3.12-3.05 (m, 1H), 2.84 (s, 3H), 2.70-2.64 (m, 1H), 2.13-1.84 (m, 4H). MS (EI) for $C_{26}H_{24}F_5N_5O_3$, found 549.9 (MH+).

Compound B24—(1Z)-1-(4-{1-[(2,6-Difluorophenyl)acetyl]piperidin-4-yl}-2-methylpyrimidin-5-yl)-2-fluoroethanone O-[2-(trifluoromethyl)pyridin-4-yl] oxime To a stirred solution of B23 (32 mg, 0.058 mmol) and $Et_3N$ (81 μL, 0.58 mmol) in $CH_2Cl_2$ (4 mL) was added diethylaminosulfur trifluoride (DAST) dropwise at room temperature. After stirring for 4 h, the reaction mixture was diluted with aq. sodium bicarbonate and extracted with $CH_2Cl_2$ (×2). The combined organic layers were dried over sodium sulfate, concentrated in vacuo, and the residue was purified by reverse phase HPLC to afford Compound B24 (8.6 mg, 27%) as a white powder after lyophilization. Analytical HPLC: retention time=19.804 min, 99%. $^1$H-NMR (400 MHz, $CDCl_3$): δ 8.65 (d, 1H), 8.58 (s, 1H), 7.53 (d, 1H), 7.30 (dd, 1H), 7.26-7.20 (m, 1H), 6.94-6.87 (m, 2H), 5.77 (d, 2H), 4.77 (d, 1H), 4.14 (d, 1H), 3.76 (d, 2H), 3.24-3.17 (m, 1H), 2.98-2.93 (m, 1H), 2.80 (s, 3H), 2.70-2.63 (m, 1H), 2.16-1.96 (m, 2H), 1.90-1.79 (m, 2H). MS (EI) for $C_{26}H_{23}F_6N_5O_2$, found 552.1 (MH+).

Compounds B25-B28

Compounds B25 to B28 were prepared from methods analogous to those used to prepare Compounds B23 and B24 utilizing appropriate reagent replacements.

| Cpd | Chemical Name | HPLC Retention Time (min) | Mass Reported (MH+) |
|---|---|---|---|
| B25 | (Z)-2-(2,6-difluorophenyl)-1-(4-(5-(2-hydroxy-1-(((2-(trifluoromethyl)pyrimidin-4-yl)oxy)imino)ethyl)-2-methylpyrimidin-4-yl)piperidin-1-yl)ethanone | 16.29 | 551.1 |
| B26 | (E)-2-(2,6-difluorophenyl)-1-(4-(5-(2-hydroxy-1-(((2-(trifluoromethyl)pyrimidin-4-yl)oxy)imino)ethyl)-2-methylpyrimidin-4-yl)piperidin-1-yl)ethanone | 16.14 | 551.1 |
| B27 | (Z)-2-(2,6-difluorophenyl)-1-(4-(5-(2-fluoro-1-(((2-(trifluoromethyl)pyrimidin-4-yl)oxy)imino)ethyl)-2-methylpyrimidin-4-yl)piperidin-1-yl)ethanone | 19.37 | 553.1 |
| B28 | (Z)-2-(2,6-difluorophenyl)-1-(4-(5-(2-hydroxy-1-((3-(trifluoromethyl)phenoxy)imino)ethyl)-2-methylpyrimidin-4-yl)piperidin-1-yl)ethanone | 22.56 | 549.0 |

HPLC conditions used to determine retention times: YMC C18, 5μ 150×4.6 mm column, gradient 10% to 90% MeCN/$H_2O$, in the presence of 0.1% TFA, 25 min gradient time, 27 min total run time at 1.5 mL/min flow rate, λ=254 nM Compound B29—(Z)-2-(2,6-Difluorophenyl)-1-(4-(2-methyl-5-(2,2,2-trifluoro-1-(3-fluorophenoxyimino)ethyl)pyrimidin-4-yl)piperidin-1-yl)ethanone B29.1: 1-(4-(1-(2-(2,6-Difluorophenyl)acetyl)piperidin-4-yl)-2-methylpyrimidin-5-yl)-2,2,2-trifluoroethanone To a stirred solution of A1.4 (530 mg, 1.31 mmol) and trimethyl(trifluoromethyl)silane (280 mg, 1.97 mmol) in toluene (5 mL) at −78° C. was added $Bu_4NF$ (65 μL, 1M in THF, 0.065 mmol). The reaction mixture was warmed slowly to −5° C. for 40 min and then 2N HCl (1.2 mL) was added. After stirring for 1 h at room temperature, EtOAc (5 mL) was added. The organic layer was separated, concentrated, dissolved in THF (5 mL), and transferred to the aq. layer. After stirring for 2 h, water (2 mL) was added and the resulting solution was extracted with EtOAc (3×3 mL). The combined organic layers were concentrated and purified by silica gel column chromatography (Hexane/EtOAc=1:1→1:2) to give B29.1 (205 mg, 37%) as a white foam. MS (EI) for $C_{20}H_{18}F_5N_3O_2$, found 428.0 (MH+).

Compound B29

To a stirred solution of B29.1 (80.0 mg, 0.187 mmol), O-(3-fluorophenyl)hydroxylamine (48.0 mg, 0.374 mmol) and EtOH (1.5 mL) at room temperature was added a catalytic amount of conc HCl. After stirring for 41 h at 80° C., aq. sat. $NaHCO_3$ (2 mL) and water (1 mL) were added and the resulting solution was extracted with EtOAc (3×3 mL). The combined organic layers were concentrated and purified by silica gel column chromatography (hexane/EtOAc=3:1→5:2) to give Compound B29 (8.0 mg, a mixture of E/Z=5:2, 8%) as a pale red powder after lyophilization. $^1$H-NMR (400 MHz, $CDCl_3$, geometric mixture): δ 8.56 and 8.50 (two of s, 1H, 1:2.8), 7.32 (m, 1H), 7.22 (m, 1H), 7.04-6.84 (m, 5H), 4.75 (m, 1H), 4.10 (m, 1H), 3.74 (m, 2H), 3.23-2.47 (m, 3H), 2.81 and 2.79 (two of s, 3H, 2.1:1), 2.12-1.75 (m, 4H). MS (EI) for $C_{26}H_{22}F_6N_4O_2$, found 537.0 (MH+). Analytical HPLC, ret. time=21.632 min (major) and 21.808 min (minor), incomplete separation (gradient 10% to 100% MeCN/H$_2$O), 97% purity.

Compound B30—(E)-4-(1-(2-(2,6-Difluorophenyl) acetyl)piperidin-4-yl)-2-methylpyrimidine-5-carbaldehyde O-3-(trifluoromethyl)phenyl oxime B30.1: 4-(1-(2-(2,6-Difluorophenyl)acetyl)piperidin-4-yl)-2-methylpyrimidine-5-carbaldehyde B30.1 was synthesized from A1.5 in the same manner that B1.2 was synthesized from B1.1

Compound B30

To a stirred solution of B30.1 (40.0 mg, 0.111 mmol), O-(3-(trifluoromethyl)phenyl)hydroxylamine (29.5 mg, 0.167 mmol) and EtOH (1 mL) at room temperature was added a catalytic amount of conc HCl. After stirring for 3 h, aq. sat. NaHCO$_3$ (3 mL) was added and the resulting solution was extracted with EtOAc (3×3 mL). The combined organic layers were concentrated and purified by silica gel column chromatography (hexane/EtOAc=4:3→2:3) to give Compound B30 (39.6 mg, 69%) as a white powder after lyophilization. $^1$H-NMR (400 MHz, CDCl$_3$): δ 8.85 (s, 1H), 8.63 (s, 1H), 7.49 (m, 2H), 7.37 (m, 2H), 7.23 (m, 1H), 6.91 (t, 2H), 4.79 (d, 1H), 4.18 (d, 1H), 3.78 (s, 2H), 3.48 (tt, 1H), 3.29 (td, 1H), 2.78 (m, 1H), 2.77 (s, 3H), 2.10 (qd, 1H), 1.94 (m, 3H). MS (EI) for C$_{26}$H$_{23}$F$_5$N$_4$O$_2$, found 519.0 (MH+). Analytical HPLC, ret. time=23.248 min, 98% purity.

Compound B31—4-{1-[(2,6-Difluorophenyl)acetyl] piperidin-4-yl}-2,6-dimethylpyrimidine-5-carbaldehyde O-[3-(trifluoromethyl)phenyl]oxime To a stirred mixture of aldehyde B1.2 (46 mg, 0.123 mmol) and 3-trifluoromethylphenylhydroxylamine (33 mg, 0.186 mmol) in EtOH (6 mL) was added 2 drops of concentrated HCl and the reaction mixture was stirred at room temperature overnight. The reaction mixture was diluted with aq. sodium bicarbonate and extracted with CH$_2$Cl$_2$ (×3). The combined organic layers were dried over sodium sulfate, concentrated in vacuo, and the residue was purified by flash chromatography to give Compound B31 (41 mg, 63%) as a white powder after lyophilization. Analytical HPLC: retention time=22.624 min, 99%. $^1$H-NMR (400 MHz, CDCl$_3$): δ 8.77 (s, 1H), 7.50-7.46 (m, 2H), 7.36-7.34 (m, 2H), 7.26-7.19 (m, 1H), 6.93-6.87 (m, 2H), 4.77 (d, 1H), 4.15 (d, 1H), 3.76 (d, 2H), 3.46-3.39 (m, 1H), 3.27-3.21 (m, 1H), 2.75-2.68 (m, 1H), 2.71 (s, 3H), 2.66 (s, 3H), 2.15-1.82 (m, 4H). MS (EI) for C$_{27}$H$_{25}$F$_5$N$_4$O$_2$, found 533.0 (MH+).

Compound 32—(1Z)-1-(4-{1-[(2,6-Difluorophenyl) acetyl]piperidin-4-yl}-2-methylpyrimidin-5-yl)-2,2-difluoroethanone O-[2-(trifluoromethyl)pyridin-4-yl] oxime To a stirred solution of B23 (99 mg, 0.18 mmol) in CH$_2$Cl$_2$ (5 mL) was added Dess-Martin periodinane (153 mg, 0.36 mmol) and the reaction mixture was stirred at room temperature for 2 h. The reaction mixture was diluted with aq. sodium bicarbonate and extracted with CH$_2$Cl$_2$ (×3). The combined organic layers were dried over sodium sulfate, concentrated in vacuo, and the residue was purified by flash chromatography to give the corresponding aldehyde, (Z)-2-(4-(1-(2-(2,6-difluorophenyl)acetyl)piperidin-4-yl)-2-methylpyrimidin-5-yl)-2-(2-(trifluoromethyl)pyridin-4-yloxyimino)acetaldehyde (79 mg, 80%). A solution of the aldehyde (44 mg, 0.080 mmol) in CH$_2$Cl$_2$ (5 mL) was treated with DAST (39 mg, 0.24 mmol) and the reaction mixture was stirred at room temperature for 4 h. The reaction mixture was diluted with aq. sodium bicarbonate and extracted with CH$_2$Cl$_2$ (×2). The combined organic layer was dried over sodium sulfate, concentrated in vacuo, and the residue was purified by reverse phase HPLC to afford Compound B32 (21 mg, 46%) as a white powder after lyophilization. Analytical HPLC: retention time=16.772 min, 98%. $^1$H-NMR (400 MHz, CDCl$_3$): δ 8.69 (d, 1H), 8.60 (s, 1H), 7.57 (d, 1H), 7.34 (dd, 1H), 7.26-7.20 (m, 1H), 7.21 (t, 1H), 6.94-6.87 (m, 2H), 4.77 (d, 1H), 4.13 (d, 1H), 3.76 (d, 2H), 3.22-3.15 (m, 1H), 3.01-2.94 (m, 1H), 2.81 (s, 3H), 2.68-2.61 (m, 1H), 2.15-1.96 (m, 2H), 1.88-1.78 (m, 2H). MS (EI) for C$_{26}$H$_{22}$F$_7$N$_5$O$_2$, found 570.1 (MH+).

Compound B33—(E)-4-(1-(2-(2,6-Difluorophenyl) acetyl)-3,3-difluoropiperidin-4-yl)-2-methylpyrimidine-5-carbaldehyde O-3-(trifluoromethyl)phenyl oxime B33.1: 1-Benzyl-3,3-difluoro-4-methylenepiperidine A mixture of methyl triphenylphosphonium bromide (16.6 g, 46.6 mmol), tert-BuOK (4.48 g, 39.9 mmol) and THF (120 mL) was stirred for 30 min at 40° C. The reaction mixture was cooled down to room temperature and 1-benzyl-3,3-difluoropiperidin-4-one (3.00 g, 13.3 mmol, *Bioorganic Med. Chem. Lett.* 2011, 21, 6409-6413) in THF (15 mL) was added. After stirring for 16 h at room temperature, hexane (75 mL) and water (30 mL) were added. The organic layer was separated, concentrated and dissolved in EtOAc/Hexane (1:10, 75 mL). The resulting solution was washed with water (6 mL). Both aq. layers were combined and extracted with EtOAc/Hexane (1:10, 2×30 mL). All organic layers were combined, concentrated and purified by silica gel column chromatography (hexane/EtOAc=25:1) to give B33.1 (2.54 g, 86%) as a clear oil. MS (EI) for C$_{13}$H$_{15}$F$_2$N, found 224.1 (MH+).

B33.2: (1-Benzyl-3,3-difluoropiperidin-4-yl)methanol

To a stirred solution of B33.1 (3.04 g, 13.6 mmol) in THF (50 mL) at room temperature was added BH$_3$.THF (27 mL, 1M in THF, 27 mmol). After stirring for 130 min at 70° C., the reaction mixture was cooled to 0° C. and 2N NaOH (41 mL) and 30% H$_2$O$_2$ (41 mL) were added in sequence. The resulting mixture was stirred for 15 min at room temperature, stirred for 16 h at 40° C., and cooled to room temperature. Water (30 mL) was added and the resulting solution was extracted with EtOAc (4×30 mL). The combined organic layers were concentrated and purified by silica gel column chromatography (Hexane/EtOAc=3:1→7:4) to give B33.2 (2.0 g, 61%) as a clear oil. MS (EI) for C$_{13}$H$_{17}$F$_2$NO, found 242.1 (MH+).

B33.3: 1-Benzyl-3,3-difluoropiperidine-4-carboxylic acid

To a stirred solution of B33.2 (2.0 g, 8.29 mmol) in acetone (30 mL) at 0° C. was added Jones reagent (5.1 mL, 8N, 40.8 mmol). After stirring for 30 min at room temperature, iPrOH (3 mL) and water (24 mL) were added in sequence. The resulting mixture was washed with hexane (2×10 mL). The resulting aq. layer was neutralized with 6N NaOH and extracted with EtOAc (4×15 mL). The combined organic layers were dried over magnesium sulfate and concentrated to give B33.3 (1.57 g, 45%) as a brown oil. MS (EI) for $C_{13}H_{15}F_2NO_2$, found 256.1 (MH+).

B33.4: Ethyl 4-(1-benzyl-3,3-difluoropiperidin-4-yl)-2-methylpyrimidine-5-carboxylate To a stirred solution of B33.3 (750 mg, 2.94 mmol) in THF (6 mL) at 0° C. was slowly added 1,1'-carbonyldiimidazole (CDI) (715 mg, 4.41 mmol) in THF (12 mL) over 30 min. After stirring for 3 h at room temperature, the resulting solution was divided to three equal portions (three portions of the reaction A).

Three same reactions were carried out by the following procedures: To a stirred solution of ethyl potassium malonate (417 mg, 2.45 mmol) in THF (8 mL) at 0° C. were added $Et_3N$ (0.51 mL, 3.7 mmol) and $MgCl_2$ (257 mg, 2.70 mmol). After stirring for 3 h at room temperature, one portion of the reaction A was slowly added for 10 min at 0° C. The resulting mixture was stirred for 30 min at room temperature, stirred for additional 64 h at 30° C., and cooled down to 0° C. Saturated aq. citric acid (8 mL) was added and the resulting solution was extracted with EtOAc (3×10 mL).

The combined organic layers from three reactions were washed with water (10 ml). The aq. layer was extracted with EtOAc (3×5 mL). The combined organic layers were dried over magnesium sulfate, concentrated, and purified by silica gel column chromatography (hexane/EtOAc=4:1→3:1) to give B33.4 (320 mg, crude) as a clear oil. MS (EI) for $C_{17}H_{21}F_2NO_3$, found 326.1 (MH+).

B33.5: Ethyl 4-(1-benzyl-3,3-difluoropiperidin-4-yl)-2-methylpyrimidine-5-carboxylate A mixture of the B33.4 and DMF/DMA (4 mL) was stirred for 5 h at room temperature and then concentrated under vacuum. MS (EI) for $C_{20}H_{26}F_2N_2O_3$, found 381.1 (MH+). To a stirred solution of the resulting residue, acetamidine•HCl (186 mg, 1.97 mmol) and EtOH (8 mL) at 0° C. was added EtONa (0.55 mL, 2.68M in EtOH, 1.48 mmol). After stirring for 1 h at room temperature, aq. sat. $NH_4Cl$ (8 mL) was added at 0° C. and the resulting solution was extracted with EtOAc (3×10 mL). The combined organic layers were concentrated, dissolved in EtOAc (10 mL), and washed with water (1 mL). The aq. layer was extracted with EtOAc (3×2 mL). The combined organic layers were concentrated and purified by silica gel column chromatography (hexane/EtOAc=7:1→5:1) to give B33.5 (180 mg, 16%) as a clear oil. MS (EI) for $C_{20}H_{23}F_2N_3O_2$, found 376.0 (MH+).

B33.6: Ethyl 4-(1-(2-(2,6-Difluorophenyl)acetyl)-3,3-difluoropiperidin-4-yl)-2-methylpyrimidine-5-carboxylate A mixture of B33.5 (30.0 mg, 0.0799 mmol), Pd/C (17 mg, 10 wt. %, 0.016 mmol) and MeOH (2 mL) was stirred for 1 h at room temperature under a balloon of hydrogen. The mixture was filtered through Celite and the filtrate was concentrated. The residue was dissolved in EtOAc (2 mL) and the resulting solution was filtered and concentrated. MS (EI) for $C_{13}H_{17}F_2N_3O_2$, found 286.0 (MH+). To a stirred solution of the resulting residue, 2-(2,6-difluorophenyl)acetic acid (20.7 mg, 0.120 mmol), HATU (61.0 mg, 0.160 mmol) and DMF (0.8 mL) was added DIEA (40 µL, 0.24 mmol). After stirring for 3.5 h at room temperature, aq. sat. $NH_4Cl$ (3 mL) was added and the resulting solution was extracted with EtOAc (3×2 mL). The combined organic layers were concentrated and purified by silica gel column chromatography (hexane/EtOAc=2:1→3:2) to give B33.6 (34 mg, 97%) as a yellow oil. MS (EI) for $C_{21}H_{21}F_4N_3O_3$, found 440.2 (MH+).

B33.7: 4-(1-(2-(2,6-Difluorophenyl)acetyl)-3,3-difluoropiperidin-4-yl)-2-methylpyrimidine-5-carbaldehyde To a stirred solution of B33.6 (30.0 mg, 0.0683 mmol) in THF (1 mL) at 0° C. was added $LiAlH_4$ (50 µL, 1M in THF, 0.055 mmol). After stirring for 1.5 h at 0° C., water (0.01 mL), 15% NaOH (0.01 mL) and water (0.02 mL) were added in sequence at room temperature with vigorous stirring. The resulting mixture was stirred for additional 1.5 h at room temperature, concentrated and purified by silica gel column chromatography (EtOAc/7N $NH_3$ in MeOH=40:1→25:1) to give 1-(3,3-difluoro-4-(5-(hydroxymethyl)-2-methylpyrimidin-4-yl)piperidin-1-yl)-2-(2,6-difluorophenyl)ethanone (11 mg, 41%) as a clear oil. MS (EI) for $C_{19}H_{19}F_4N_3O_2$, found 398.0 (MH+).

To a stirred solution of 1-(3,3-difluoro-4-(5-(hydroxymethyl)-2-methylpyrimidin-4-yl)piperidin-1-yl)-2-(2,6-difluorophenyl)ethanone (11.0 mg, 0.0277 mmol) in $CH_2Cl_2$ (0.5 mL) at room temperature was added Dess-Martin periodinane (23.0 mg, 0.0544 mmol). After stirring for 2 h, water (2 mL) was added and the resulting solution was extracted with EtOAc (3×1.5 mL). The combined organic layers were concentrated and purified by silica gel column chromatography (Hexane/EtOAc=2:3) to give B33.7 (11 mg, quant) as a clear oil. MS (EI) for $C_{19}H_{17}F_4N_3O_2$, found 396.0 (MH+).

Compound B33

To a stirred solution of B33.7 (11.0 mg, 0.0277 mmol), O-(3-(trifluoromethyl)phenyl)hydroxylamine (9.8 mg, 0.055 mmol) and EtOH (1 mL) at room temperature was added a catalytic amount of conc HCl. After stirring for 17 h, aq. sat. $NaHCO_3$ (1 mL) was added and the resulting solution was extracted with EtOAc (2×2 mL). The combined organic layers were concentrated and purified by silica gel column chromatography (hexane/EtOAc=2:1) to give Compound B33 (12 mg, 78%) as a white solid after lyophilization. $^1$H-NMR (400 MHz, $CDCl_3$ 8.98 (d, 1H), 8.65 (d, 1H), 7.48 (m, 2H), 7.38 (m, 2H), 7.26 (m, 1H), 6.92 (t, 2H), 4.65-4.37 (m, 1H), 4.24 (m, 1H), 4.04 (m, 1H), 3.86-3.64 (m, 1H), 3.81 (s, 2H), 3.53 (m, 1H), 2.81 (s, 3H), 2.65-2.39 (m, 1H), 2.08 (m, 1H). MS (EI) for $C_{26}H_{21}F_7N_4O_2$, found 554.9 (MH+). Analytical HPLC, ret. time=21.500 min (gradient 10% to 100% $MeCN/H_2O$), 95% purity.

Compound B34—(E)-1-(3,3-Difluoro-4-(2-methyl-5-(1-(2-(trifluoromethyl)pyridin-4-yloxyimino)ethyl)pyrimidin-4-yl)piperidin-1-yl)-2-(2,6-difluorophenyl)ethanone

B34.1: 4-(1-Benzyl-3,3-difluoropiperidin-4-yl)-2-methylpyrimidine-5-carbaldehyde To a stirred solution of B33.5 (36.0 mg, 0.0959 mmol) in THF (1 mL) at 0° C. was added $LiAlH_4$ (50 µL, 1M in THF, 0.055 mmol). After stirring for 80 min at 0° C., water (0.01 mL) and 15% NaOH (0.01 mL) were added in sequence at room temperature with vigorous stirring. The resulting mixture was stirred for additional 30 min and EtOAc (2 mL) was added. The resulting mixture was filtered through Celite and concentrated to give the alcohol (4-(1-benzyl-3,3-difluoropiperidin-4-yl)-2-methylpyrimidin-5-yl)methanol. MS (EI) for $C_{18}H_{21}F_2N_3O$, found 334.0 (MH+). To a stirred solution of the alcohol in $CH_2Cl_2$ (2 mL) at room temperature was added Dess-Martin periodinane (81.4 mg, 0.192 mmol). After stirring for 1.5 h, water (2 mL) was added and the resulting solution was extracted with EtOAc (4 mL, 3×2 mL). The combined organic layers were concentrated and purified by silica gel column chromatography (hexane/EtOAc=7:3→2:1) to give B34.1 (19 mg, 60%) as a clear oil. MS (EI) for $C_{18}H_{19}F_2N_3O$, found 332.0 (MH+).

B34.2: 1-(4-(1-Benzyl-3,3-difluoropiperidin-4-yl)-2-methylpyrimidin-5-yl)ethanone To a stirred solution of B34.1 (36.0 mg, 0.109 mmol) in THF (1 mL) at 0° C. was added methylmagnesium bromide (0.16 mL, 1.4M in Toluene/THF (3:1), 0.22 mmol). After stirring for 50 min at room temperature, aq. sat. $NH_4Cl$ (3 mL) was added and the resulting solution was extracted with EtOAc (3×2 mL). The combined organic layers were dried over magnesium sulfate and concentrated to give the alcohol 1-(4-(1-benzyl-3,3-difluoropiperidin-4-yl)-2-methylpyrimidin-5-yl)ethanol. MS (EI) for $C_{19}H_{23}F_2N_3O$, found 348.1 (MH+). To a stirred solution of the alcohol in $CH_2Cl_2$ (2 mL) at room temperature was added Dess-Martin periodinane (92.5 mg, 0.218 mmol). After stirring for 70 min, water (3 mL) was added and the resulting solution was extracted with EtOAc (5 mL, 3×2 mL). The combined organic layers were concentrated and purified by silica gel column chromatography (hexane/EtOAc=2:1) to give B34.2 (28 mg, 74%) as a clear oil. MS (EI) for $C_{19}H_{21}F_2N_3O$, found 346.1 (MH+).

B34.3: 1-(4-(5-Acetyl-2-methylpyrimidin-4-yl)-3,3-difluoropiperidin-1-yl)-2-(2,6-difluorophenyl)ethanone A mixture of B34.2 (28.0 mg, 0.0811 mmol), Pd/C (43 mg, 10 wt. %, 0.041 mmol) and MeOH (2 mL) was stirred for 20 h at room temperature under a balloon of hydrogen. The mixture was filtered through Celite and the filtrate was concentrated. The residue was dissolved in MeOH (0.4 mL) and EtOAc (2 mL), and the resulting solution was filtered and concentrated to give the free amine 1-(4-(3,3-difluoropiperidin-4-yl)-2-methylpyrimidin-5-yl)ethanone. MS (EI) for $C_{12}H_{15}F_2N_3O$, found 256.0 (MH+). To a stirred solution of the free amine, 2-(2,6-difluorophenyl)acetic acid (18.1 mg, 0.105 mmol), HATU (46.3 mg, 0.122 mmol) and DMF (0.8 mL) was added DIEA (40 μL, 0.24 mmol). After stirring for 1.5 h at room temperature, water (3 mL) was added and the resulting solution was extracted with EtOAc (3×2 mL). The combined organic layers were concentrated and purified by silica gel column chromatography (hexane/EtOAc=3:5) to give B34.3 (17.5 mg, 53%) as a clear oil. MS (EI) for $C_{20}H_{19}F_4N_3O_2$, found 410.0 (MH+).

B34.4: (E)-1-(3,3-Difluoro-4-(5-(1-(hydroxyimino) ethyl)-2-methylpyrimidin-4-yl)piperidin-1-yl)-2-(2, 6-difluorophenyl)ethanone To a stirred solution of B34.3 (17.0 mg, 0.0415 mmol) in EtOH (0.5 mL) were added hydroxylamine•HCl (8.7 mg, 0.13 mmol) and a catalytic amount of conc HCl. After stirring for 15 h at 50° C., aq. sat. $NaHCO_3$ (2 mL) was added and the resulting solution was extracted with EtOAc (3×2 mL). The combined organic layers were concentrated and purified by silica gel column chromatography (hexane/EtOAc=3:5) to give B34.4 (16 mg, a mixture of E/Z=3.8:1, 91%) as a clear oil. MS (EI) for $C_{20}H_{20}F_4N_4O_2$, found 425.0 (MH+).

Compound B34

To a stirred solution of B34.4 (15.0 mg, a mixture of E/Z=3.8:1, 0.0353 mmol), 4-chloro-2-(trifluoromethyl)pyridine (12.8 mg, 0.0707 mmol) and DMA (0.5 mL) at room temperature was added potassium carbonate (9.8 mg, 0.071 mmol). After stirring for 26 h, water (3 mL) was added and the resulting solution was extracted with EtOAc (4×2 mL). The combined organic layers were concentrated and purified by silica gel column chromatography twice (tBuOMe/$CH_2Cl_2$/Hexane=4:4:3 and Hexane/EtOAc=3:4) to give Compound B34 (5.2 mg, 26%) as a clear oil. $^1$H-NMR (400 MHz, $CDCl_3$): δ 8.65 (d, 1H), 8.62 (d, 1H), 7.53 (d, 1H), 7.28 (m, 1H), 7.24 (m, 1H), 6.91 (t, 2H), 4.46 (m, 1H), 4.17 (m, 1H), 4.03 (m, 1H), 3.86-3.52 (m, 2H), 3.79 (s, 2H), 2.82 (s, 3H), 2.52 (d, 3H), 2.49-2.27 (m, 1H), 2.12 (m, 1H). MS (EI) for $C_{26}H_{22}F_7N_5O_2$, found 569.9 (MH+). Analytical HPLC, ret. time=20.636 min, 95% purity.

Compound B35—(Z)-1-(3,3-Difluoro-4-(5-(2-fluoro-1-(2-(trifluoromethyl)pyrimidin-4-yloxyimino)ethyl)-2-methylpyrimidin-4-yl)piperidin-1-yl)-2-(2,6-difluorophenyl)ethanone B35.1: Ethyl 4-(1-(tert-butoxycarbonyl)-3,3-difluoropiperidin-4-yl)-2-methylpyrimidine-5-carboxylate A mixture of B33.5 (150 mg, 0.399 mmol), Pd/C (128 mg, 10 wt. %, 0.120 mmol) and MeOH (6 mL) was stirred for 70 min at room temperature under a balloon of hydrogen. The mixture was filtered through Celite and the filtrate was concentrated. The residue was dissolved in EtOAc (5 mL), and the resulting solution was filtered and concentrated to give the free amine ethyl 4-(3,3-difluoropiperidin-4-yl)-2-methylpyrimidine-5-carboxylate. MS (EI) for $C_{13}H_{17}F_2N_3O_2$, found 286.0 (MH+). To a stirred solution of the free amine, 1,4-dioxane (3 mL) and water (0.7 mL) at room temperature were added DIEA (0.20 mL, 1.2 mmol) and $Boc_2O$ (130 mg, 0.600 mmol) in sequence. After stirring for 1 h, aq. sat. $NH_4Cl$ (5 mL) was added and the resulting solution was extracted with EtOAc (3×3 mL). The combined organic layers were concentrated and purified by silica gel column chromatography (hexane/EtOAc=6:1→4:1) to give B35.1 (134 mg, 77%) as a clear oil. $^1$H-NMR (400 MHz, $CDCl_3$): δ 9.05 (s, 1H), 4.67 (m, 1H), 4.40 (q, 2H), 4.29 (m, 1H), 4.11 (m, 1H), 3.38 (m, 1H), 3.17 (m, 1H), 2.78 (s, 3H), 2.47 (m, 1H), 1.95 (m, 1H), 1.48 (s, 9H), 1.41 (t, 3H). MS (EI) for $C_{18}H_{25}F_2N_3O_4$, found 386.0 (MH+).

B35.2: tert-Butyl 3,3-difluoro-4-(5-formyl-2-methylpyrimidin-4-yl)piperidine-1-carboxylate To a stirred solution of B35.1 (100 mg, 0.259 mmol) in THF (3 mL) at 0° C. was added $LiAlH_4$ (0.21 mL, 1M in THF, 0.208 mmol). After stirring for 1 h at 0° C., water (0.02 mL), 15% NaOH (0.02 mL) and water (0.04 mL) were added in sequence at room temperature with vigorous stirring. The resulting mixture was stirred for additional 1 h and EtOAc (3 mL) was added. The resulting mixture was filtered through Celite and concentrated to give the alcohol tert-butyl 3,3-difluoro-4-(5-(hydroxymethyl)-2-methylpyrimidin-4-yl)piperidine-1-carboxylate. MS (EI) for $C_{16}H_{23}F_2N_3O_3$, found 344.1 (MH+). To a stirred solution of the alcohol in $CH_2Cl_2$ (3 mL) at room temperature was added Dess-Martin periodinane (220 mg, 0.518 mmol). After stirring for 70 min, water (5 mL) was added and the resulting solution was extracted with EtOAc (10 mL, 2×2 mL). The combined organic layers were concentrated and purified by silica gel column chromatography (Hexane/EtOAc=3:1→4:3) to give B35.2 (40 mg, 45%) as a white solid.

B35.3: tert-Butyl 4-(5-acetyl-2-methylpyrimidin-4-yl)-3,3-difluoropiperidine-1-carboxylate To a stirred solution of B35.2 (40.0 mg, 0.117 mmol) in THF (1 mL) at 0° C. was added methylmagnesium bromide (0.17 mL, 1.4M in Toluene/THF (3:1), 0.23 mmol). After stirring for 1.5 h at room temperature, aq. sat. $NH_4Cl$ (3 mL) was added and the resulting solution was extracted with EtOAc (3×2 mL). The combined organic layers were dried over magnesium sulfate and concentrated to give the alcohol tert-butyl 3,3-difluoro-4-(5-(1-hydroxyethyl)-2-methylpyrimidin-4-yl)piperidine-1-carboxylate. MS (EI) for $C_{17}H_{25}F_2N_3O_3$, found 358.1 (MH+). To a stirred solution of the alcohol in $CH_2Cl_2$ (2 mL) at room temperature was added Dess-Martin periodinane (99.0 mg, 0.234 mmol). After stirring for 1.5 h, water (3 mL) was added and the resulting solution was extracted with EtOAc (5 mL, 2×2 mL). The combined organic layers were concentrated and purified by silica gel column chromatography (hexane/EtOAc=3:2) to give B35.3 (37 mg, 89%) as a clear oil. MS (EI) for $C_{17}H_{23}F_2N_3O_3$, found 356.0 (MH+).

B35.4 tert-Butyl 4-(5-(2-bromoacetyl)-2-methylpyrimidin-4-yl)-3,3-difluoropiperidine-1-carboxylate To a stirred solution of B35.3 (37.0 mg, 0.104 mmol) in THF (1 mL) at 0° C. was added lithium bis(trimethylsilyl)amide (LiHMDS) (0.16 mL, 1M in THF, 0.16 mmol). After stirring for 15 min at 0° C., chlorotrimethylsilane (20 μL, 0.16 mmol) was added. After stirring for 4 h at 0° C., aq. sat. $NaHCO_3$ (3 mL) was added and the resulting solution was extracted with EtOAc (3×2 mL). The combined organic layers were dried over magnesium sulfate and concentrated. To a stirred solution of the resulting residue in THF (1 mL) at 0° C. were added $NaHCO_3$ (13.1 mg, 0.156 mmol) and NBS (18.5 mg, 0.104 mmol) in sequence. After stirring for 40 min at room temperature, aq. sat. $NaHCO_3$ (3 mL) was added at 0° C. and the resulting solution was extracted with EtOAc (3×2 mL). The combined organic layers were concentrated and purified by silica gel column chromatography (hexane/EtOAc=7:3) to give B35.4 (30 mg, 66%) as a clear oil. MS (EI) for $C_{17}H_{22}BrF_2N_3O_3$, found 434.0 (MH+).

B35.5: 2-(4-(1-(2-(2,6-Difluorophenyl)acetyl)-3,3-difluoropiperidin-4-yl)-2-methylpyrimidin-5-yl)-2-oxoethyl acetate A mixture of B35.4 (52.0 mg, 0.120 mmol), potassium acetate (35.3 mg, 0.360 mmol) and DMA (0.8 mL) was stirred for 30 min at room temperature and then purified by silica gel column chromatography (hexane/EtOAc=2:1) to give B35.5 (54 mg, crude) as a pale yellow oil. MS (EI) for $C_{19}H_{25}F_2N_3O_5$, found 414.0 (MH+).

B35.6: 2-(4-(1-(2-(2,6-Difluorophenyl)acetyl)-3,3-difluoropiperidin-4-yl)-2-methylpyrimidin-5-yl)-2-oxoethyl acetate A mixture of B35.5 (27 mg) and 4N HCl in 1,4-dioxane (1 mL) was stirred for 1 h at room temperature and concentrated under vacuum. EtOAc (2 mL) was added and the mixture was concentrated again to give the amine HCl salt, 2-(4-(3,3-difluoropiperidin-4-yl)-2-methylpyrimidin-5-yl)-2-oxoethyl acetate hydrochloride. MS (EI) for $C_{14}H_{17}F_2N_3O_3$, found 314.0 (MH+). To a stirred solution of the amine salt, 2-(2,6-difluorophenyl)acetic acid (13.4 mg, 0.0780 mmol), HATU (34.2 mg, 0.0900 mmol) and DMF (0.6 mL) at room temperature was added DIEA (30 μL, 0.18 mmol). After stirring for 40 min, water (3 mL) was added and the resulting solution was extracted with EtOAc (3×3 mL). The combined organic layers were concentrated and purified by silica gel column chromatography (hexane/EtOAc=1:1→2:3) to give B35.6 (25 mg, 89%) as a clear oil. MS (EI) for $C_{21}H_{21}F_4N_3O_4$, found 468.0 (MH+).

B35.7: (Z)-1-(3,3-Difluoro-4-(5-(2-hydroxy-1-(hydroxyimino)ethyl)-2-methylpyrimidin-4-yl)piperidin-1-yl)-2-(2,6-difluorophenyl)ethanone To a stirred solution of B35.6 (18.0 mg, 0.0385 mmol) in EtOH (1 mL) were added hydroxylamine•HCl (8.0 mg, 0.12 mmol) and a catalytic amount of conc HCl. After stirring for 75 h at 60° C., aq. sat. $NaHCO_3$ (1 mL) and water (1 mL) were added at 0° C., and the resulting solution was extracted with EtOAc (4 mL, 2×2 mL). The combined organic layers were concentrated, dissolved in EtOAc (3 mL) and washed with water (0.5 mL). The aq. layer was extracted with EtOAc (2×1 mL). The combined organic layers were purified by silica gel column chromatography (hexane/EtOAc=1:3→EtOAc) to give B35.7 (10 mg, 59%) as a clear oil. MS (EI) for $C_{20}H_{20}F_4N_4O_3$, found 441.0 (MH+).

B35.8: (Z)-1-(3,3-Difluoro-4-(5-(2-hydroxy-1-(2-(trifluoromethyl)pyrimidin-4-yloxyimino)ethyl)-2-methylpyrimidin-4-yl)piperidin-1-yl)-2-(2,6-difluorophenyl)ethanone To a stirred solution of B35.7 (16.5 mg, 0.0375 mmol), 4-chloro-2-(trifluoromethyl)pyrimidine (20.5 mg, 0.112 mmol) and DMA (1.5 mL) at room temperature was added potassium carbonate (20.7 mg, 0.150 mmol). After stirring for 1 h, the resulting mixture was purified by silica gel column chromatography (hexane/EtOAc=1:1→2:5) to give B35.8 (10 mg, 46%) as a white foam. MS (EI) for $C_{25}H_{21}F_7N_6O_3$, found 587.2 (MH+).

Compound B35

To a stirred solution of B35.8 (10.0 mg, 0.0171 mmol) in $CH_2Cl_2$ (1 mL) at 0° C. was added DAST (8.2 mg, 0.051 mmol). After stirring for 50 min at 0° C., water (2 mL) was added and the resulting solution was extracted with EtOAc (3×2 mL). The combined organic layers were concentrated and purified by silica gel column chromatography (hexane/EtOAc=4:3) to give Compound B35 (6.5 mg, 65%) as a white solid after lyophilization. $^1$H-NMR (400 MHz, $CDCl_3$): δ 8.82 (d, 1H), 8.66 (s, 1H), 7.40 (d, 1H), 7.24 (m, 1H), 6.90 (t, 2H), 5.78 (m, 2H), 4.34 (m, 2H), 3.78 (s, 2H), 3.69 (m, 3H), 2.83 (s, 3H), 2.58-2.34 (m, 1H), 2.11 (m, 1H).

MS (EI) for $C_{25}H_{20}F_8N_6O_2$, found 589.2 (MH+). Analytical HPLC, ret. time=20.084 min, 98% purity.

Compound C1—4-{1-[(2,6-Difluorophenyl)acetyl] piperidin-4-yl}-2,6-dimethyl-5-{3-[3-(trifluoromethyl)phenyl]-1,2,4-oxadiazol-5-yl}pyrimidine C1.1: (Z)—N'-Hydroxy-3-(trifluoromethyl)benzimidamide To a mixture of 3-(trifluoromethyl)benzonitrile (1.80 g, 10.5 mmol) and hydroxylamine hydrochloride (4.39 g, 63.1 mmol) in EtOH (15 mL) was added $Et_3N$ (7.45 g, 73.6 mmol). The resulting white slurry was heated in a sealed tube at 80° C. with stirring for 2.5 h. After cooling to room temperature, the reaction mixture was diluted with EtOAc, and washed with water (3x) and brine, dried (magnesium sulfate), and concentrated in vacuo to give C1.1 as a solid (2.276 g): MS (EI) for $C_8H_7F_3N_2O$, found 205.0 (MH+). The material was used directly for the subsequent reaction without further purification.

Compound C1

To a mixture of A80.4 (120 mg, 0.31 mmol), HATU (141 mg, 0.37 mmol), and DMA (2.1 mL) was added DIEA (80 mg, 0.62 mmol). The resulting mixture was stirred at 35° C. for 5 min, then C1.1 (82 mg, 0.40 mmol) was added. The resulting mixture was stirred at 35° C. for 1 h, followed by heating at 100° C. for an additional 20 h. After cooling to room temperature, the reaction mixture was subjected to a routine aq. workup, and purified by prep HPLC. The fractions containing the desired product were combined and lyophilized to afford Compound C1 as a white solid (21 mg). $^1$H-NMR (400 MHz, $CDCl_3$): δ 8.45 (s, 1H), 8.37 (d, 1H), 7.84 (d, 1H), 7.70 (t, 1H), 7.22 (m, 1H), 6.70 (m, 2H), 4.73 (d, 1H), 4.11 (d, 1H), 3.74 (dd, 2H), 3.15 (t, 1H), 2.93 (m, 1H), 2.78 (s, 3H), 2.62 (m, 1H), 2.56 (s, 3H), 2.10-1.83 (m, 4H). MS (EI) for $C_{28}H_{24}F_5N_5O_2$, found 558.0 (MH+).

Compounds C2-C4

Compounds C2 to C4 were prepared from methods analogous to those used to prepare Compound C1 utilizing appropriate reagent replacements.

| Cpd | Chemical Name | HPLC Retention Time (min) | Mass Reported (MH+) |
|---|---|---|---|
| C2 | 2-(2,6-difluorophenyl)-1-(4-(5-(3-(4-fluorophenyl)-1,2,4-oxadiazol-5-yl)-2,6-dimethylpyrimidin-4-yl)piperidin-1-yl)ethanone | 22.31 | 508.0 |
| C3 | 2-(2,6-difluorophenyl)-1-(4-(5-(3-(4-fluorobenzyl)-1,2,4-oxadiazol-5-yl)-2,6-dimethylpyrimidin-4-yl)piperidin-1-yl)ethanone | 23.58 | 522.0 |
| C4 | 1-(4-(5-(3-(3-chlorophenyl)-1,2,4-oxadiazol-5-yl)-2,6-dimethylpyrimidin-4-yl)piperidin-1-yl)-2-(2,6-difluorophenyl)ethanone | 24.22 | 523.9 |

HPLC conditions used to determine retention times: YMC C18, 5μ 150×4.6 mm column, gradient 10% to 90% MeCN/$H_2O$, in the presence of 0.1% TFA, 25 min gradient time, 27 min total run time at 1.5 mL/min flow rate, λ=254 nM Compound C5—4-{1-[(2,6-Difluorophenyl)acetyl] piperidin-4-yl}-2,6-dimethyl-5-{5-[2-(trifluoromethyl)pyrimidin-4-yl]-1,3,4-oxadiazol-2-yl}pyrimidine C5.1: 2-(Trifluoromethyl)pyrimidine-4-carbohydrazide To a solution of methyl 2-(trifluoromethyl)pyrimidine-4-carboxylate (1.50 g, 7.28 mmol) in 10 mL of anhydrous MeOH was added hydrazine monohydrate (1.09 g, 21.83 mmol). The resulting solution was heated at 50° C. with stirring for 5 min, at which time the reaction was completed. The reaction mixture, as a yellow solution, was reduced to ⅓ of the volume in vacuo. The precipitate thus formed was filtered, washed with MeOH, and dried to give 1.16 g of C5.1 as a yellow crystalline solid. The combined filtrate was concentrated under high vacuum to afford an additional 0.20 g of the hydrazide product as a yellow solid. $^1$H-NMR (400 MHz, $CDCl_3$): δ9.14 (d, 1H), 8.94 (br. s, 1H), 8.27 (d, 1H), 4.16 (d, 2H).

C5.2: N'-(4-(1-(2-(2,6-Difluorophenyl)acetyl)piperidin-4-yl)-2,6-dimethylpyrimidine-5-carbonyl)-2-(trifluoromethyl)pyrimidine-4-carbohydrazide A solution of A80.4 (100 mg, 0.26 mmol), EDC (59 mg, 0.31 mmol), and HOBt (42 mg, 0.31 mmol) in DMA (1.5 mL) was stirred at 35° C. for 1.5 h. C5.1 (69 mg, 33 mmol) was then added to the above solution. The resulting mixture was heated at 50° C. for 24 h. After cooling to room temperature, the mixture was diluted with EtOAc, and washed with water and brine, dried with magnesium sulfate and concentrated in vacuo. The residue was purified by prep HPLC to afford C5.2 (55 mg) as a white solid. $^1$H-NMR (400 MHz, $CDCl_3$): δ 9.65 (br. s, 1H), 9.25 (d, 1H), 8.34 (d, 1H), 8.0 (br. s, 1H), 7.23 (m, 1H), 6.90 (t, 2H), 4.74 (d, 1H), 4.13 (d, 1H), 3.76 (s, 2H), 3.34-3.23 (m, 2H), 2.78 (t, 1H), 2.71 (s, 3H), 2.62 (s, 3H), 2.08-1.82 (m, 4H). MS (EI) for $C_{26}H_{24}F_5N_7O_3$, found 578.1 (MH+).

Compound C5

To a solution of C5.2 (76 mg, 0.13 mmol) in anhydrous MeCN (1.3 mL) was added anhydrous $K_2CO_3$ (55 mg, 0.40 mmol), followed by p-toluenesulfonyl chloride (p-TsCl) (38 mg, 0.20 mmol). The mixture was stirred at 50° C. for 30 min when the reaction was completed. The reaction mixture as a slurry was diluted with water. The organic layer was separated and purified by prep HPLC to give Compound C5 as a white solid (52 mg). $^1$H-NMR (400 MHz, $CDCl_3$): δ 9.22 (d, 1H), 8.48 (d, 1H), 7.23 (m, 1H), 6.90 (m, 2H), 4.73 (d, 1H), 4.11 (d, 1H), 3.75 (dd, 2H), 3.16 (t, 1H), 2.98 (m, 1H), 2.78 (s, 3H), 2.61 (m, 1H), 2.60 (s, 3H), 2.13-1.95 (m, 3H), 1.84 (d, 1H). Analytical HPLC, ret. time=18.83 min, 99% purity. MS (EI) for $C_{26}H_{22}F_5N_7O_2$, found 559.9 (MH+).

Compounds C6-C23

Compounds C6 to C23 were prepared from methods analogous to those used to prepare Compound C5 utilizing appropriate reagent replacements.

| Cpd | Chemical Name | HPLC Retention Time (min) | Mass Reported (MH+) |
|---|---|---|---|
| C6 | 2-(2,6-difluorophenyl)-1-(4-(2,6-dimethyl-5-(5-(6-(trifluoromethyl)pyridin-2-yl)-1,3,4-oxadiazol-2-yl)pyrimidin-4-yl)piperidin-1-yl)ethanone | 15.05 | 559.2 |
| C7 | 2-(2,6-difluorophenyl)-1-(4-(2,6-dimethyl-5-(5-(6-methyl-2-(trifluoromethyl)pyrimidin-4-yl)-1,3,4-oxadiazol-2-yl)pyrimidin-4-yl)piperidin-1-yl)ethanone | 19.60 | 574.2 |
| C8 | 1-(4-(5-(5-(6-(1,1-difluoroethyl)pyridin-2-yl)-1,3,4-oxadiazol-2-yl)-2,6-dimethylpyrimidin-4-yl)piperidin-1-yl)-2-(2,6-difluorophenyl)ethanone | 19.35 | 555.2 |
| C9 | (1-(4-(5-(5-(6-chloropyridin-2-yl)-1,3,4-oxadiazol-2-yl)-2,6-dimethylpyrimidin-4-yl)piperidin-1-yl)-2-(2,6-difluorophenyl)ethanone | 18.04 | 524.9 |
| C10 | 2-(2,6-difluorophenyl)-1-(4-(2,6-dimethyl-5-(5-(3-(trifluoromethoxy)phenyl)-1,3,4-oxadiazol-2-yl)pyrimidin-4-yl)piperidin-1-yl)ethanone | 21.82 | 573.9 |
| C11 | 1-(4-(5-(5-(3-chlorophenyl)-1,3,4-oxadiazol-2-yl)-2,6-dimethylpyrimidin-4-yl)piperidin-1-yl)-2-(2,6-difluorophenyl)ethanone | 20.81 | 523.9 |
| C12 | 2-(2,6-difluorophenyl)-1-(4-(2,6-dimethyl-5-(5-(3-(trifluoromethyl)phenyl)-1,3,4-oxadiazol-2-yl)pyrimidin-4-yl)piperidin-1-yl)ethanone | 21.28 | 558.0 |
| C13 | 2-(2,6-difluorophenyl)-1-(4-(5-(5-(3,5-dimethylphenyl)-1,3,4-oxadiazol-2-yl)-2,6-dimethylpyrimidin-4-yl)piperidin-1-yl)ethanone | 21.73 | 518.0 |
| C14 | 1-(4-(5-(5-(2-chlorophenyl)-1,3,4-oxadiazol-2-yl)-2,6-dimethylpyrimidin-4-yl)piperidin-1-yl)-2-(2,6-difluorophenyl)ethanone | 19.97 | 524.1 |
| C15 | 2-(2,6-difluorophenyl)-1-(4-(2,6-dimethyl-5-(5-(2-(trifluoromethyl)pyridin-4-yl)-1,3,4-oxadiazol-2-yl)pyrimidin-4-yl)piperidin-1-yl)ethanone | 19.39 | 559.0 |
| C16 | 2-(2,6-difluorophenyl)-1-(4-(2,6-dimethyl-5-(5-phenyl-1,3,4-oxadiazol-2-yl)pyrimidin-4-yl)piperidin-1-yl)ethanone | 18.06 | 490.1 |
| C17 | 2-(2,6-difluorophenyl)-1-(4-(5-(5-(2-isopropylpyrimidin-4-yl)-1,3,4-oxadiazol-2-yl)-2,6-dimethylpyrimidin-4-yl)piperidin-1-yl)ethanone | 18.57 | 534.0 |
| C18 | 2-(2,6-difluorophenyl)-1-(4-(2,6-dimethyl-5-(5-(3-(trifluoromethyl)benzyl)-1,3,4-oxadiazol-2-yl)pyrimidin-4-yl)piperidin-1-yl)ethanone | 21.21 | 572.0 |
| C19 | 1-(4-(5-(5-(2-chloro-6-methylpyridin-4-yl)-1,3,4-oxadiazol-2-yl)-2,6-dimethylpyrimidin-4-yl)piperidin-1-yl)-2-(2,6-difluorophenyl)ethanone | 19.20 | 539.0 |
| C20 | 1-(4-(5-(5-(5-chloropyridin-2-yl)-1,3,4-oxadiazol-2-yl)-2,6-dimethylpyrimidin-4-yl)piperidin-1-yl)-2-(2,6-difluorophenyl)ethanone | 18.04 | 525.2 |
| C21 | 1-(4-(5-(5-(4-chloropyridin-2-yl)-1,3,4-oxadiazol-2-yl)-2,6-dimethylpyrimidin-4-yl)piperidin-1-yl)-2-(2,6-difluorophenyl)ethanone | 17.90 | 524.9 |
| C22 | 1-(4-(5-(5-(2-chloropyridin-4-yl)-1,3,4-oxadiazol-2-yl)-2,6-dimethylpyrimidin-4-yl)piperidin-1-yl)-2-(2,6-difluorophenyl)ethanone | 18.04 | 524.9 |
| C23 | 1-(4-(5-(5-(6-chloropyridin-3-yl)-1,3,4-oxadiazol-2-yl)-2,6-dimethylpyrimidin-4-yl)piperidin-1-yl)-2-(2,6-difluorophenyl)ethanone | 17.91 | 524.9 |

HPLC conditions used to determine retention times: YMC C18, 5µ 150×4.6 mm column, gradient 10% to 90% MeCN/H$_2$O, in the presence of 0.1% TFA, 25 min gradient time, 27 min total run time at 1.5 mL/min flow rate, λ=254 nM Compound C24—4-{1-[(2,6-Difluorophenyl)carbonyl]piperidin-4-yl}-2,6-dimethyl-5-{5-[2-(trifluoromethyl)pyrimidin-4-yl]-1,3,4-oxadiazol-2-yl}pyrimidine C24.1: 4-(1-(tert-Butoxycarbonyl)piperidin-4-yl)-2,6-dimethylpyrimidine-5-carboxylic acid The ester of A80.1 was hydrolyzed to C24.1 with the same technique used to hydrolyze A80.3 to A80.4.

C24.2: tert-Butyl 4-(2,6-dimethyl-5-(2-(2-(trifluoromethyl)pyrimidine-4-carbonyl)hydrazinecarbonyl)pyrimidin-4-yl)piperidine-1-carboxylate A solution of C24.1 (500 mg, 1.49 mmol), EDC (329 mg, 1.71 mmol), and HOBt (232 mg, 1.71 mmol) in DMA (10 mL) was stirred at 25° C. for 1.5 h. To the above mixture was added C5.1 (344 mg, 1.67 mmol). The resulting mixture was stirred at 40° C. for 17 h. After cooling to room temperature, the reaction mixture was diluted with EtOAc, washed with water (3×) and brine, dried (magnesium sulfate), and concentrated in vacuo to dryness, yielding a solid (793 mg). LC/MS analysis of the resulting residue showed the presence of C24.2 as a major product. MS (EI) for $C_{23}H_{28}F_3N_7O_4$, found 524.2 (MH+). The crude product was used directly for the next reaction as is.

C24.3: tert-Butyl 4-(2,6-dimethyl-5-(5-(2-(trifluoromethyl)pyrimidin-4-yl)-1,3,4-oxadiazol-2-yl)pyrimidin-4-yl)piperidine-1-carboxylate The entire amount (793 mg) of crude product obtained from the previous step (C24.2) was dissolved in 30 mL of anhydrous MeCN. To this solution was added K$_2$CO$_3$ (850 mg, 4.45 mmol), followed by p-toluenesulfonyl chloride (1236 mg, 4.94 mmol). The mixture was stirred at 50° C. for 1 h. After removal of solvent in vacuo, the crude mixture was diluted with EtOAc, washed with water (3×) and brine, dried (magnesium sulfate), and concentrated in vacuo to dryness, affording C24.3 as a solid (761 mg). MS (EI) for $C_{23}H_{26}F_3N_7O_3$, found 506.2 (MH+). The crude product was used directly for the subsequent reaction.

C24.4: 2-(2,4-Dimethyl-6-(piperidin-4-yl)pyrimidin-5-yl)-5-(2-(trifluoromethyl)pyrimidin-4-yl)-1,3,4-oxadiazole Crude C24.3 (760 mg) obtained above was dissolved in MeCN (4 mL). To this solution was added 4M HCl in dioxane (6 mL), which was allowed to stir at room temperature for 10 min. After removal of solvent in vacuo, the residue was dissolved in water and washed with tert-butyl methyl ether (2×). The aq. layer was cooled to 0° C., and basified to pH 11 by slow addition of 2N NaOH aq. solution, and then extracted with EtOAc (3×). The combined organic extract was washed with brine, dried with magnesium sulfate, and concentrated under high vacuum, to give C24.4 as a solid (310 mg). $^1$H-NMR (400 MHz, CDCl$_3$): δ 9.22 (d, 1H), 8.47 (d, 1H), 3.36 (d, 2H), 2.89 (m, 1H), 2.77 (s, 3H), 2.76 (m, 2H), 2.58 (s, 3H), 2.46 (br. s, 1H), 2.22-2.07 (m, 2H), 1.94-1.91 (m, 2H). MS (EI) for $C_{18}H_{18}F_3N_7O_3$, found 406.2 (MH+).

Compound C24

A solution of 2,6-difluorobenzoic acid (11 mg, 0.07 mmol), EDC (11 mg, 0.06 mmol), and HOBt (8 mg, 0.06 mmol) in DMA (0.6 mL) was stirred at room temperature for 1.5 h. To the mixture was added C24.4 (18 mg, 0.04 mmol). The reaction mixture was stirred at room temperature for 17 h. To the resulting mixture was added 2N NaOH aq. solution (2 drops). The reaction mixture was stirred for 5 min, and neutralized with AcOH. The crude mixture was purified on prep HPLC to give Compound C24 as a solid (8.5 mg). $^1$H-NMR (400 MHz, CDCl$_3$): δ 9.21 (d, 1H), 8.46 (d, 1H), 7.34 (m, 1H), 6.94 (m 2H), 4.89 (d, 1H), 3.63 (d, 1H), 3.12 (m, 1H), 2.99 (m, 1H), 2.81 (m, 1H), m2.77 (s, 3H), 2.59 (s, 3H), 2.15-1.99 (m, 2H), 1.94 (d, 1H), 1.83 (d, 1H). Analytical HPLC, ret. time=18.300 min, 98% purity. MS (EI) for $C_{25}H_{20}F_5N_7O_2$, found: 546.2 (MH+).

Compounds C25-C27

Compounds C25 to C27 were prepared from methods analogous to those used to prepare Compounds C24 utilizing appropriate reagent replacements.

| Cpd | Chemical Name | HPLC Retention Time (min) | Mass Reported (MH+) |
|---|---|---|---|
| C25 | 1-(4-(2,6-dimethyl-5-(5-(2-(trifluoromethyl)pyrimidin-4-yl)-1,3,4-oxadiazol-2-yl)pyrimidin-4-yl)piperidin-1-yl)-2-(2-fluorophenyl)ethanone | 17.93 | 542.2 |
| C26 | 2-(2,6-difluorophenyl)-1-(4-(2,6-dimethyl-5-(5-(2-(trifluoromethyl)pyrimidin-4-yl)-1,3,4-oxadiazol-2-yl)pyrimidin-4-yl)piperidin-1-yl)propan-1-one | 19.23 | 574.2 |
| C27 | (2-chloro-6-fluorophenyl)(4-(2,6-dimethyl-5-(5-(2-(trifluoromethyl)pyrimidin-4-yl)-1,3,4-oxadiazol-2-yl)pyrimidin-4-yl)piperidin-1-yl)methanone | 14.63 | 562.1 |

HPLC conditions used to determine retention times: YMC C18, 5μ 150×4.6 mm column, gradient 10% to 90% MeCN/H$_2$O, in the presence of 0.1% TFA, 25 min gradient time, 27 min total run time at 1.5 mL/min flow rate, λ=254 nM Compound C28—N-(2,6-Difluorophenyl)-4-(2,6-dimethyl-5-{5-[2-(trifluoromethyl)pyrimidin-4-yl]-1,3,4-oxadiazol-2-yl}pyrimidin-4-yl)piperidine-1-carboxamide To a solution of C24.4 (16 mg, 0.04 mmol) in CH$_2$Cl$_2$ was added 1,3-difluoro-2-isocyanatobenzene (9 mg, 0.06 mmol) and a drop of DIEA. The solution was stirred at room temperature for 2 min at which time the reaction was complete. After removal of the solvent in vacuo, the residue was purified on prep. HPLC, affording Compound C28 as a white solid (10 mg). $^1$H-NMR (400 MHz, CDCl$_3$): δ 9.21 (d, 1H), 8.47 (d, 1H), 7.10 (m, 1H), 6.93 (t, 2H), 5.87 (s, 1H), 4.22 (d, 2H), 2.99-2.91 (m, 3H), 2.78 (s, 3H), 2.59 (s, 3H), 2.12 (m, 2H), 1.91 (d, 2H).). Analytical HPLC, ret. time=16.62 min, 98% purity. MS (EI) for $C_{25}H_{21}F_5N_8O_2$, found: 561.2 (NH+)

Compounds C29-C32

Compounds C29 to C32 were prepared from methods analogous to those used to prepare Compound C28 utilizing appropriate reagent replacements.
HPLC conditions used to determine retention times: YMC C18, 5μ 150×4.6 mm column,

| Cpd | Chemical Name | HPLC Retention Time (min) | Mass Reported (MH+) |
|---|---|---|---|
| C29 | N-(2-chlorophenyl)-4-(2,6-dimethyl-5-{5-[2-(trifluoromethyl)pyrimidin-4-yl]-1,3,4-oxadiazol-2-yl}pyrimidin-4-yl)piperidine-1-carboxamide | 14.80 | 559.2 |
| C30 | 4-(2,6-dimethyl-5-{5-[2-(trifluoromethyl)pyrimidin-4-yl]-1,3,4-oxadiazol-2-yl}pyrimidin-4-yl)-N-[2-(trifluoromethyl)phenyl]piperidine-1-carboxamide | 14.00 | 593.1 |
| C31 | N-(2,6-dichlorophenyl)-4-(2,6-dimethyl-5-{5-[2-(trifluoromethyl)pyrimidin-4-yl]-1,3,4-oxadiazol-2-yl}pyrimidin-4-yl)piperidine-1-carboxamide | 14.84 | 593.2 |
| C32 | 4-(2,6-dimethyl-5-{5-[2-(trifluoromethyl)pyrimidin-4-yl]-1,3,4-oxadiazol-2-yl}pyrimidin-4-yl)-N-{2-[(trifluoromethyl)oxy]phenyl}piperidine-1-carboxamide | 20.08 | 609.2 | gradient 10% to 90% MeCN/H$_2$O, in the presence of 0.1% TFA, 25 min gradient time, 27 min total run time at 1.5 mL/min flow rate, λ=254 nM Compound C33—4-{1-[(2,6-Difluorophenyl)sulfonyl]piperidin-4-yl}-2,6-dimethyl-5-{5-[2-(trifluoromethyl)pyrimidin-4-yl]-1,3,4-oxadiazol-2-yl}pyrimidine To a solution of C24.4 (17 mg, 0.04 mmol) in CH$_2$Cl$_2$ (0.5 mL) was added 2,6-difluorobenzene-1-sulfonyl chloride (16 mg, 0.07 mmol), followed by DIEA (9 mg). After stirring at room temperature for 2 min, the reaction mixture was concentrated in vacuo to remove solvent. The residue was dissolved in MeCN and purified on prep HPLC to give Compound C33 as a white solid (9 mg). $^1$H-NMR (400 MHz, CDCl$_3$): δ 9.19 (d, 1H), 8.42 (d, 1H), 7.50 (m, 1H), 7.02 (t, 2H), 4.08 (d, 2H), 2.86 (m, 1H), 2.76 (s, 3H), 2.65 (d, 2H), 2.60 (s, 3H), 2.26-2.16 (m, 2H), 1.92 (d, 2H). Analytical HPLC, ret. time=19.692 min, 99% purity. MS (EI) for $C_{24}H_{20}F_5N_7O_3S$, found: 582.1 (MH+).

Compound C34—4-(1-{[(2-Fluorophenyl)methyl]sulfonyl}piperidin-4-yl)-2,6-dimethyl-5-{5-[2-(trifluoromethyl)pyrimidin-4-yl]-1,3,4-oxadiazol-2-yl}pyrimidine Compound C34 was synthesized in a manner analogous to C33. Analytical HPLC, ret. time=19.628 min. MS (EI) for $C_{25}H_{23}F_4N_7O_3S$, found: 578.2 (MH+).

Compound C35—(R)-2-(2,6-Difluorophenyl)-1-(4-(2,6-dimethyl-5-(5-(2-(trifluoromethyl)pyrimidin-4-yl)-1,3,4-oxadiazol-2-yl)pyrimidin-4-yl)piperidin-1-yl)propan-1-one C35.1: Perfluorophenyl 2-(2,6-difluorophenyl)propanoate To a stirred solution of 2-(2,6-difluorophenyl)propanoic acid (186 mg, 1.00 mmol, *J. Med. Chem.* 2005, 48, 6776.), DCC (248 mg, 1.20 mmol) and CH$_2$Cl$_2$ (4 mL) at room temperature was slowly added a solution of pentafluorophenol (184 mg, 1.00 mmol) in CH$_2$Cl$_2$ (4 mL). After stirring for 18 h, the resulting mixture was filtered through Celite. Water (3 mL) was added to the filtrate and the aq. layer was extracted with EtOAc (2×3 mL). The combined organic layers were concentrated and purified by silica gel column chromatography (CH$_2$Cl$_2$/hexane=1:20) to give C35.1 (300 mg, 85%) as a clear oil.

C35.2: (S)-3-((R)-2-(2,6-Difluorophenyl)propanol)-4-phenyloxazolidin-2-one

To a stirred solution of (S)-4-phenyloxazolidin-2-one (32.6 mg, 0.200 mmol) in THF (1 mL) at −78° C. was added nBuLi (90 μL, 2.5M in Hexane, 0.22 mmol). After stirring for 1 h, a solution of C35.1 (140 mg, 0.400 mmol) in THF (1.5 mL) was slowly added at −78° C. After stirring for 2 h, water (2 mL) was added and the resulting solution was extracted with EtOAc (3×2 mL). The combined organic layers, which contained a diastereomeric mixture with 94% de, were concentrated and purified by silica gel column chromatography (CH$_2$Cl$_2$/hexane=1:5→5:1) to give C35.2 (57 mg, a single diastereomer, 43%) as a white solid. The stereochemistry of C35.2 was predicted by following a method described in *Synlett* 2009, 960. $^1$H-NMR (400 MHz, CDCl$_3$): δ 7.36 (m, 3H), 7.24 (m, 2H), 7.18 (m, 1H), 6.80 (t, 2H), 5.49 (dd, 1H), 4.97 (q, 1H), 4.68 (t, 1H), 4.22 (d, 1H), 1.44 (d, 3H). MS (EI) for C$_{18}$H$_{15}$F$_2$NO$_3$, found 332.1 (MH+).

C35.3: (R)-2-(2,6-Difluorophenyl)propanoic acid

To a stirred solution of C35.2 (25.0 mg, 0.0755 mmol), THF (0.6 mL) and water (0.2 mL) at room temperature were added H$_2$O$_2$ (17 mg, 30 wt. % in H$_2$O, 0.15 mmol) and LiOH (3.6 mg, 0.15 mmol) in sequence. After stirring for 8 h, water (2 mL) was added and the resulting solution was washed with EtOAc (2×2 mL). The aq. layer was acidified with 1N HCl solution and extracted with EtOAc (2×2 mL). The combined organic layers were concentrated and purified by silica gel column chromatography (CH$_2$Cl$_2$/MeOH=40:1→20:1) to give C35.3 (13.5 mg, 96%) as a clear oil.

Compound C35

To a stirred solution of C35.3 (16.0 mg, 0.0860 mmol), C24.4 (24.9 mg, 0.0614 mmol), HATU (46.7 mg, 0.123 mmol) and DMF (0.6 mL) at room temperature was added DIEA (30 μL, 0.18 mmol). After stirring for 1.5 h, water (2 mL) was added and the resulting solution was extracted with EtOAc (3×2 mL). The combined organic layers were concentrated and purified by silica gel column chromatography (hexane/EtOAc=1:1→2:3) to give Compound C35 (15 mg, 43%) as a white solid after lyophilization. $^1$H-NMR (400 MHz, CDCl$_3$, rotameric mixture): δ 9.20 (m, 1H), 8.44 (t, 1H), 7.21 (m, 1H), 6.93 and 6.87 (two of t, 2H), 4.78 (d, 1H), 4.14 (m, 1H), 3.73 (t, 1H), 2.96-2.50 (m, 3H), 2.76 and 2.71 (two of s, 3H), 2.58 and 2.54 (two of s, 3H), 1.98 (m, 1H), 1.81 (m, 2H), 1.51-1.02 (m, 1H), 1.50 (d, 3H). MS (EI) for C$_{27}$H$_{24}$F$_5$N$_7$O$_2$, found 574.2 (MH+). Analytical HPLC, ret. time=19.296 min, 95% purity.

Compound C36—N-(2,6-Difluorophenyl)-4-(2,6-dimethyl-5-(5-(2-(trifluoromethyl)pyrimidin-4-yl)-1,3,4-oxadiazol-2-yl)pyrimidin-4-yl)-N-methylpiperidine-1-carboxamide To a stirred solution of C28 (11.0 mg, 0.0196 mmol), iodomethane (5.6 mg, 0.039 mmol) and THF (0.5 mL) at 0° C. was added NaH (1.2 mg, 60% dispersion in mineral oil, 0.029 mmol). After stirring for 2 h, aq. sat. NH$_4$Cl (1 mL) was added and the resulting solution was extracted with EtOAc (3×1 mL). The combined organic layers were concentrated and purified by silica gel column chromatography (hexane/EtOAc=1:1→1:2) to give Compound C36 (9.0 mg, 80%) as a white solid after lyophilization. $^1$H-NMR (400 MHz, CDCl$_3$): δ 9.20 (d, 1H), 8.44 (d, 1H), 7.19 (m, 1H), 6.97 (t, 2H), 3.81 (d, 2H), 3.12 (s, 3H), 2.74 (s, 3H), 2.73 (m, 1H), 2.60 (td, 2H), 2.54 (s, 3H), 1.71 (qd, 2H), 1.62 (m, 2H) MS (EI) for C$_{26}$H$_{23}$F$_5$N$_8$O$_2$, found 575.2 (MH+). Analytical HPLC, ret. time=18.872 min, 99% purity.

Compound C37—4-{1-[(2,6-Difluorophenyl)acetyl-2-d]piperidin-4-yl}-2-methyl-d$_2$-6-methyl-5-{5-[2-(trifluoromethyl)pyrimidin-4-yl]-1,3,4-oxadiazol-2-yl}pyrimidine To a solution of C5 (12 mg) in anhydrous THF (1.2 mL) under N$_2$ was added NaH (4 mg, 60% in mineral oil) with stirring at room temperature. The mixture was stirred at room temperature for 20 min. To the mixture was added deuterium oxide (3 mL) with stirring. After stirring for 1 h, 2 drops of AcOH were added, the crude mixture was purified on prep HPLC to give Compound C37 (4 mg). $^1$H-NMR (400 MHz, CDCl$_3$); δ 9.23 (d, 1H), 8.48 (d, 1H), 7.23 (m, 1H), 6.90 (t, 2H), 4.74 (d, 1H), 4.11 (d, 1H), 3.74 (m, 1H), 3.16 (t, 1), 2.98 (m, 1H), 2.78 (s, 3H), 2.60 (s, 1H), 2.56 (m, 1H), 2.10-1.95 (m, 3H), 1.84 (d, 1H). Analytical HPLC, ret. time=18.752 min. 97% purity. MS for C$_{26}$H$_{19}$D$_3$F$_5$N$_7$O$_2$, found: 563.0 (MH+).

Compound C38—4-{1-[(2,6-Difluorophenyl)acetyl-2,2-d$_2$]piperidin-4-yl}-2,6-dimethyl-5-{5-[2-(trifluoromethyl)pyrimidin-4-yl]-1,3,4-oxadiazol-2-yl}pyrimidine C38.1: 2-(2,6-Difluorophenyl)acetic-2,2-d$_2$ acid A mixture of 2-(2,6-difluorophenyl)acetic acid (1.00 g, 5.81 mmol), anhydrous K$_2$CO$_3$ (3.21 g, 23.25 mmol) and deuterium oxide (5 mL) was heated at 100° C. with stirring for 24 h. The reaction was cooled to 0° C., acidified to pH 2 with 6N HCl, and then extracted with CH$_2$Cl$_2$. The organic layer was dried over sodium sulfate, and concentrated in vacuo. This process was repeated three more times to give C38.1 as a white solid (0.96 g). $^1$H-NMR (400 MHz, DMSO-d$_6$): δ 12.55 (s, 1H), 7.38 (m. 1H), 7.08 (m, 2H).

Compound C38

A solution of C38.1 (4.5 mg, 0.03 mmol), EDC (4.3 mg, 0.02 mmol) and HOBt (3.0 mg, 0.02 mmol) in DMA (0.5 mL) was stirred at room temperature for 45 min. To the above mixture was added C24.4 (4.5 mg, 0.03 mmol). The resulting mixture was stirred at room temperature for 40 min. The reaction was quenched by adding 2 drops of 2N NaOH aq. solution. The resulting mixture was purified on HPLC to give Compound C38 as a white solid (4 mg). $^1$H-NMR (400 MHz, CDCl$_3$); δ 9.20 (d, 1H), 8.45 (d, 1H), 7.21 (m, 1H), 6.89 (t, 2H), 4.72 (d, 1H), 4.10 (d, 1H), 3.16 (t, 1H), 2.99 (m, 1H), 2.77 (s, 3H), 2.61 (m, 1H), 2.59 (s, 3H), 2.08-1.82 (m, 4H). Analytical HPLC, ret. time=18.72 min, 98% purity. MS (EI) for C$_{26}$H$_{20}$D$_2$F$_5$N$_7$O$_2$, found: 562.2 (MH+).

Compound C39—4-{1-[2-(2,6-Difluorophenyl)ethanethioyl]piperidin-4-yl}-2,6-dimethyl-5-{5-[2-(trifluoromethyl)pyrimidin-4-yl]-1,3,4-thiadiazol-2-yl}pyrimidine To a solution of C5.2 (34 mg, 0.06 mmol) in anhydrous 2-methyltetrahydrofuran (1 mL) was added Lawesson's reagent (21 mg, 0.05 mmol). The mixture was heated in a sealed tube at 100° C. with stirring for 3 days. Upon cooling down to room temperature, the mixture was diluted with water, and extracted with EtOAc. The organic layer was washed with brine, dried (magnesium sulfate), and concentrated in vacuo. The crude product thus obtained was purified by prep. HPLC to give Compound C39 as a solid (22 mg). $^1$H-NMR (400 MHz, CDCl$_3$): δ 9.19 (d, 1H), 8.56 (d, 1H), 7.25 (m, 1H), 6.90 (t, 2H), 5.68 (d, 1H), 4.52 (d, 1H), 4.04 (s, 2H), 3.26 (dt, 1H), 2.99 (dt, 1H), 2.84 (m, 1H), 2.78 (s, 3H), 2.41 (s, 3H), 2.22-2.11 (m, 2H), 1.95-1.86 (m, 2H). Analytical HPLC, ret. time=21.97 min, 99% purity. MS (EI) for $C_{26}H_{22}F_5N_7S_2$, found 591.9 (MH+).

Compound D1—1-(4-(5-(1-(3-Chlorophenylamino)-2-hydroxypropan-2-yl)-2-methylpyrimidin-4-yl)piperidin-1-yl)-2-(2,6-difluorophenyl)ethanone D1.1: tert-Butyl 4-(2-methyl-5-(2-methyloxiran-2-yl)pyrimidin-4-yl)piperidine-1-carboxylate To a mixture of Me$_3$SI (300 mg, 1.5 mmol) in THF (4 mL) was added $^t$BuOK (2 mL, 1.0 M in THF). The resulting mixture was stirred at room temperature for 30 min and B23.1 (320 mg, 1 mmol) was added. Stirring was continued at room temperature for 2 h and then diluted with aq. sat. NaHCO$_3$. The mixture was extracted with EtOAc and the organic mixture was dried over sodium sulfate, filtered, and concentrated. The crude product was used as is in the next step.

D1.2: tert-Butyl 4-(5-(1-(3-chlorophenylamino)-2-hydroxypropan-2-yl)-2-methylpyrimidin-4-yl)piperidine-1-carboxylate A solution of D1.1 (40 mg, 0.12 mmol), 3-chloroaniline (46 mg, 0.36 mmol) and LiCl (21 mg, 0.5 mmol) in EtOH (0.5 mL) was stirred at 80° C. for 5 days. The mixture was diluted with EtOAc, washed with brine, and concentrated. The crude product was purified by flash column chromatography.

Compound D1

To a solution of D1.2 (20 mg, 0.043 mmol) in MeOH (2 mL) was added 4N HCl in dioxane (0.3 mL). The resulting solution was stirred for 12 h at room temperature. EtOAc (25 mL) was added. The mixture was basified with 20% NaOH aq. solution to pH 10. The EtOAc layer was washed with brine, dried over sodium sulfate, and concentrated. The crude amine, 1-(3-chlorophenylamino)-2-(2-methyl-4-(piperidin-4-yl)pyrimidin-5-yl)propan-2-ol, was used in the next step without further purification.

1-(3-Chlorophenoxy)-2-(2-methyl-4-(piperidin-4-yl)pyrimidin-5-yl)propan-2-ol (10 mg, 0.028 mmol) obtained above was mixed with 2,6-difluorophenylacetic acid (10 mg, 0.056 mmol), HATU (15 mg, 0.039 mmol) and DIEA (38 mg, 0.3 mmol) in THF (2 mL). The resulting reaction mixture was stirred at room temperature for 2 h then diluted with aq. sat. NaHCO$_3$. The mixture was extracted with EtOAc and the organic mixture was dried over sodium sulfate, filtered, and concentrated. The crude mixture was purified by prep HPLC to give D1.3. $^1$H-NMR (400 MHz, DMSO-d6): δ 8.58 (d, 1H), 7.36 (m, 1H), 7.04 (m, 3H), 6.70 (d, 1H), 6.60 (d, 1H), 6.50 (d, 1H), 5.78 (m, 1H), 5.54 (s, 1H), 4.45 (d, 1H), 4.13 (d, 1H), 3.82 (m, 4H), 3.23 (m, 1H), 3.08 (m, 1H), 2.62 (m, 1H), 2.51 (s, 3H), 1.75 (m, 4H), 1.68 (s, 3H). MS (EI) for $C_{27}H_{29}ClF_2N_4O_2$, found: 515.0 (MH+). Analytical HPLC, ret. time=3.64 min, 99% purity.

Compounds D2-D10

Compounds D2 to D10 were prepared from methods analogous to those used to Compounds Compound D1 utilizing appropriate reagent replacements.

| Cpd | Chemical Name | HPLC Retention Time (min) | Mass Reported (MH+) |
|---|---|---|---|
| D2 | 2-(2,6-difluorophenyl)-1-(4-(5-(2-hydroxy-1-((6-(trifluoromethyl)pyridin-2-yl)amino)propan-2-yl)-2-methylpyrimidin-4-yl)piperidin-1-yl)ethanone | 15.38 | 550.0 |
| D3 | 2-(2,6-difluorophenyl)-1-(4-(5-(1-((3,5-dimethylphenyl)amino)-2-hydroxypropan-2-yl)-2-methylpyrimidin-4-yl)piperidin-1-yl)ethanone | 3.41* | 509.1 |
| D4 | 2-(2,6-difluorophenyl)-1-(4-(5-(2-hydroxy-1-((3-(trifluoromethyl)phenyl)amino)propan-2-yl)-2-methylpyrimidin-4-yl)piperidin-1-yl)ethanone | 16.96 | 549.0 |
| D5 | 2-(2,6-difluorophenyl)-1-(4-(5-(2-hydroxy-1-((2-(trifluoromethyl)pyridin-4-yl)amino)propan-2-yl)-2-methylpyrimidin-4-yl)piperidin-1-yl)ethanone | 12.88 | 551.0 |
| D6 | 2-(2,6-difluorophenyl)-1-(4-(5-(1-((4,6-dimethylpyridin-2-yl)amino)-2-hydroxypropan-2-yl)-2-methylpyrimidin-4-yl)piperidin-1-yl)ethanone | 10.09 | 510.0 |
| D7 | 1-(4-(5-(1-((2-chloropyridin-4-yl)amino)-2-hydroxypropan-2-yl)-2-methylpyrimidin-4-yl)piperidin-1-yl)-2-(2,6-difluorophenyl)ethanone | 9.19 | 516.0 |
| D8 | 2-(2,6-difluorophenyl)-1-(4-(5-(2-hydroxy-1-((4-(trifluoromethyl)pyridin-2-yl)amino)propan-2-yl)-2-methylpyrimidin-4-yl)piperidin-1-yl)ethanone | 12.72 | 550.0 |
| D9 | 2-(2,6-difluorophenyl)-1-(4-(5-(2-hydroxy-1-((4-methylpyridin-2-yl)amino)propan-2-yl)-2-methylpyrimidin-4-yl)piperidin-1-yl)ethanone | 9.42 | 496.0 |

| Cpd | Chemical Name | HPLC Retention Time (min) | Mass Reported (MH+) |
|---|---|---|---|
| D10 | 2-(2,6-difluorophenyl)-1-(4-(5-(2-hydroxy-1-((1-methyl-1H-pyrazol-3-yl)amino)propan-2-yl)-2-methylpyrimidin-4-yl)piperidin-1-yl)ethanone | 9.60 | 485.2 |

HPLC Conditions Used to Determine Retention Times:
Unless otherwise noted: YMC C18, 5μ 150×4.6 mm column, gradient 10% to 90% MeCN/H2O, in the presence of 0.1% TFA, 25 min gradient time, 27 min total run time at 1.5 mL/min flow rate, λ=254 nM
* Phenomenex, Gemini, 50×4.6 mm, 5μ column, gradient 10% to 90% MeCN/H2O, in the presence of 0.1% TFA, 5 min gradient time, 6 min total run time at 3.0 mL/min flow rate, λ=254 nM Compound D11—2-(2,6-Difluorophenyl)-1-(4-(5-(1-(3,5-dimethylphenoxy)-2-hydroxypropan-2-yl)-2-methylpyrimidin-4-yl)piperidin-1-yl)ethanone D11.1: tert-Butyl 4-(5-(1-(3,5-dimethylphenoxy)-2-hydroxypropan-2-yl)-2-methylpyrimidin-4-yl)piperidine-1-carboxylate To a solution of 3,5-dimethylphenol (244 mg, 2.0 mmol) in DMF (4 mL) was added NaH (120 mg, 3 mmol, 60% in mineral oil). The resulting mixture was stirred at room temperature for 30 min, then D11.1 (1 mmol) was added. The mixture was stirred at 75° C. for 8 h, cooled to room temperature and diluted with aq. sat. NaHCO$_3$. The crude product was extracted with EtOAc, washed with brine, and concentrated. The crude product was purified by flash column chromatography.

Compound D11

To a solution of D11.1 (400 mg, 0.87 mmol) in MeOH (5 mL) was added 4N HCl in dioxane (1 mL). The resulting solution was stirred for 12 h at room temperature. EtOAc (25 mL) was added. The mixture was basified with 20% NaOH aq. solution to pH 10. The EtOAc layer was washed with brine, dried over sodium sulfate, and concentrated. The crude amine was used in the next step without further purification.
1-(3,5-Dimethylphenoxy)-2-(2-methyl-4-(piperidin-4-yl)pyrimidin-5-yl)propan-2-ol (220 mg, 0.61 mmol) obtained above was mixed with 2,6-difluorophenylacetic acid (123 mg, 0.72 mmol), HATU (300 mg, 0.78 mmol) and DIEA (387 mg, 3 mmol) in THF (5 mL). The resulting reaction mixture was stirred at room temperature for 2 h then diluted with aq. sat. NaHCO$_3$. The mixture was extracted with EtOAc and the organic mixture was dried over sodium sulfate, filtered, and concentrated. The crude mixture was purified by prep HPLC to give Compound D11. $^1$H-NMR (400 MHz, DMSO-d6): δ 8.56 (d, 1H), 7.36 (m, 1H), 7.07 (m, 2H), 6.55 (m, 3H), 5.70 (s, 1H), 4.45 (d, 1H), 4.18 (m, 3H), 3.78 (m, 3H), 3.17 (m, 1H), 2.62 (m, 1H), 2.55 (s, 3H), 2.21 (s, 6H), 1.75 (m, 4H), 1.65 (s, 3H). MS (EI) for C$_{29}$H$_{33}$F$_2$N$_3$O$_3$, found: 510.0 (MH+). Analytical HPLC, ret. time=17.17 min, 97% purity.

Compounds D12-D14

Compounds D12 to D14 were prepared from methods analogous to those used to prepare Compound D11 utilizing appropriate reagent replacements.

| Cpd | Chemical Name | HPLC Retention Time (min) | Mass Reported (MH+) |
|---|---|---|---|
| D12 | 1-(4-(5-(1-(3-chlorophenoxy)-2-hydroxypropan-2-yl)-2-methylpyrimidin-4-yl)piperidin-1-yl)-2-(2,6-difluorophenyl)ethanone | 16.49 | 516.0 |
| D13 | 1-(4-(5-(1-((5-chloropyridin-3-yl)oxy)-2-hydroxypropan-2-yl)-2-methylpyrimidin-4-yl)piperidin-1-yl)-2-(2,6-difluorophenyl)ethanone | 3.17* | 517.0 |
| D14 | 2-(2,6-difluorophenyl)-1-(4-(5-(2-hydroxy-1-(pyridin-3-yloxy)propan-2-yl)-2-methylpyrimidin-4-yl)piperidin-1-yl)ethanone | 8.74 | 483.0 |

HPLC Conditions Used to Determine Retention Times:
Unless otherwise noted: YMC C18, 5μ 150×4.6 mm column, gradient 10% to 90% MeCN/H2O, in the presence of 0.1% TFA, 25 min gradient time, 27 min total run time at 1.5 mL/min flow rate, λ=254 nM
* Phenomenex, Gemini, 50×4.6 mm, 5μ column, gradient 10% to 90% MeCN/H2O, in the presence of 0.1% TFA, 5 min gradient time, 6 min total run time at 3.0 mL/min flow rate, λ=254 nM Compound D15—2-(2,6-Difluorophenyl)-1-(4-(5-(4-(3,5-dimethylphenyl)-2-hydroxybutan-2-yl)-2-methylpyrimidin-4-yl)piperidin-1-yl)ethanone D15.1: tert-Butyl 4-(5-(2-bromoacetyl)-2-methylpyrimidin-4-yl)piperidine-1-carboxylate D15.1 was synthesized from B23.1 in the same manner by which B35.4 was synthesized from B35.3.

D15.2: (E)-tert-Butyl 4-(5-(3-(3,5-dimethylphenyl)acryloyl)-2-methylpyrimidin-4-yl)piperidine-1-carboxylate To a stirred solution diethyl phosphite (22.2 mg, 0.161 mmol) in DMF (1 mL) at room temperature was added cesium carbonate (105 mg, 0.322 mmol). After stirring 30 min, D15.1 (53.4 mg, 0.134 mmol) in DMF (1 mL) was added. After stirring 70 min, water (2 mL) was added and the resulting solution was extracted with EtOAc (3×2 mL). The combined organic layers were concentrated to give D15.2 as a brown oil. MS (EI) for C$_{21}$H$_{34}$N$_3$O$_6$P, found 456.0 (MH+).

D15.3: (E)-tert-Butyl 4-(5-(3-(3,5-dimethylphenyl)acryloyl)-2-methylpyrimidin-4-yl)piperidine-1-carboxylate To a stirred solution of D15.2, LiCl (18.2 mg, 0.429 mmol) and MeCN (1 mL) at room temperature were added DIEA (50 μL, 0.27 mmol) and 3,5-dimethylbenzaldehyde (17.8 mg, 0.134 mmol) in MeCN (0.5 mL) in sequence.

After stirring for 24 h at 95° C., water (2 mL) was added and the resulting solution was extracted with EtOAc (2×2 mL). The combined organic layers were concentrated and purified by silica gel column chromatography (hexane/EtOAc=3:1) to give D15.3 (10 mg, 17%) as a pale yellow oil. MS (EI) for $C_{269}H_{33}N_3O_3$, found 436.1 (MH+).

D15.4: tert-Butyl 4-(5-(4-(3,5-dimethylphenyl)-2-hydroxybutan-2-yl)-2-methylpyrimidin-4-yl)piperidine-1-carboxylate A mixture of D15.3 (15.0 mg, 0.0344 mmol), Pd/C (18.0 mg, 10 wt. %, 0.0172 mmol) and MeOH (2 mL) was stirred for 1 h at room temperature under a balloon of hydrogen. The mixture was filtered through Celite and the filtrate was concentrated. The residue was dissolved in EtOAc (1 mL) and the resulting solution was filtered and concentrated to give tert-butyl 4-(5-(3-(3,5-dimethylphenyl)propanoyl)-2-methylpyrimidin-4-yl)piperidine-1-carboxylate (10 mg, 66%) as a clear oil.

To a stirred solution of tert-butyl 4-(5-(3-(3,5-dimethylphenyl)propanoyl)-2-methylpyrimidin-4-yl)piperidine-1-carboxylate (9.0 mg, 0.021 mmol) in THF (0.4 mL) at room temperature was added methylmagnesium bromide (0.12 mL, 1.4M in Toluene/THF (3:1), 0.16 mmol). After stirring for 4 h at 50° C., aq. sat. $NH_4Cl$ (2 mL) was added and the resulting solution was extracted with EtOAc (3×1.5 mL). The combined organic layers were concentrated and purified by silica gel column chromatography (hexane/EtOAc=3: 1→3:4) to give D15.4 (6.0 mg, 64%) as a clear oil. MS (EI) for $C_{27}H_{39}N_3O_3$, found 454.1 (MH+).

Compound D15

A mixture of D15.4 (6.0 mg, 0.0132 mmol) and 4N HCl in 1,4-dioxane (0.3 mL) was stirred for 1 h at room temperature, and concentrated under vacuum. EtOAc (1 mL) was added and the mixture was concentrated again to give the amine HCl salt, 4-(3,5-dimethylphenyl)-2-(2-methyl-4-(piperidin-4-yl)pyrimidin-5-yl)butan-2-ol. MS (EI) for $C_{22}H_{31}N_3O$, found 354.1 (MH+). To a stirred solution of the resulting amine HCl salt, 2-(2,6-difluorophenyl)acetic acid (3.4 mg, 0.020 mmol), HATU (15.0 mg, 0.0396 mmol) and DMF (0.3 mL) at room temperature was added DIEA (10 μL, 0.053 mmol). After stirring for 1 h, water (1 mL) was added and the resulting solution was extracted with EtOAc (3×2 mL). The combined organic layers were concentrated and purified by silica gel column chromatography (hexane/EtOAc=2:5→1:3) to give Compound D15 (4.7 mg, 69%) as a white powder after lyophilization. $^1$H-NMR (400 MHz, $CDCl_3$): δ 8.60 (s, 1H), 7.22 (m, 1H), 6.90 (t, 2H), 6.83 (s, 1H), 6.72 (s, 2H), 4.76 (d, 1H), 4.11 (d, 1H), 3.77 (d, 2H), 3.68 (m, 1H), 3.21 (m, 1H), 2.68 (s, 3H), 2.67 (m, 1H), 2.52 (t, 2H), 2.31-1.97 (m, 4H), 2.27 (s, 6H), 1.72 (s, 3H), 1.71 (m, 2H). MS (EI) for $C_{30}H_{35}F_2N_3O_2$, found 508.1 (MH+). Analytical HPLC, ret. time=16.556 min, 96% purity.

Compound E1—2-(2,6-Difluorophenyl)-1-(4-(5-(2-(3,5-dimethylbenzyloxy)-1-methoxypropan-2-yl)-2-methylpyrimidin-4-yl)piperidin-1-yl)ethanone E1.1: tert-Butyl 4-(5-(2-hydroxy-1-methoxypropan-2-yl)-2-methylpyrimidin-4-yl)piperidine-1-carboxylate To a freshly prepared MeONa (5 mmol) solution in MeOH (5 mL) was added D1.1 (166 mg, 0.5 mmol). The resulting solution was stirred at 60° C. for 12 h and cooled to room temperature. Water was added to quench the reaction. The mixture was extracted with EtOAc and the organic phase was washed with brine, dried over sodium sulfate, and concentrated. The crude product was purified by flash column chromatography.

E1.2: tert-Butyl 4-(5-(2-(3,5-dimethylbenzyloxy)-1-methoxypropan-2-yl)-2-methylpyrimidin-4-yl)piperidine-1-carboxylate To a solution of E1.1 (150 mg, 0.42 mmol), 3,5-dimethylbenzyl bromide (109 mg, 0.55 mmol) and $Bu_4NI$ (30 mg, 0.08 mmol) in THF (5 mL) was added NaH (50 mg, 1.2 mmol, 60% in mineral oil). The resulting mixture was stirred at room temperature for 12 h. Water was added to quench the reaction. The mixture was extracted with EtOAc and the organic mixture was dried over sodium sulfate, filtered, and concentrated. The crude mixture was purified by flash column chromatography.

Compound E1

To a solution of E1.2 (150 mg, 0.31 mmol) in MeOH (2 mL) was added 4N HCl in dioxane (0.5 mL). The resulting solution was stirred for 12 h at room temperature. EtOAc (25 mL) was added. The mixture was basified with 20% NaOH aq. solution to pH 10. The EtOAc layer was washed with brine, dried over sodium sulfate, and concentrated. The crude product was used in the next step without further purification.

5-(2-(3,5-Dimethylbenzyloxy)-1-methoxypropan-2-yl)-2-methyl-4-(piperidin-4-yl)pyrimidine (100 mg, 0.26 mmol) obtained above was mixed with 2,6-difluorophenylacetic acid (54 mg, 0.31 mmol), HATU (128 mg, 0.34 mmol) and DIEA (129 mg, 1 mmol) in THF (2 mL). The resulting reaction mixture was stirred at room temperature for 2 h, then diluted with aq. sat. $NaHCO_3$. The mixture was extracted with EtOAc and the organic mixture was dried over sodium sulfate, filtered, and concentrated. The crude mixture was purified by prep HPLC to give Compound E1. MS (EI) for $C_{31}H_{37}F_2N_3O_3$, found: 538.1 (MH+). Analytical HPLC, ret. time=20.20 min, 97% purity.

Compounds E2-E4

Compounds E2 to E4 were prepared from methods analogous to those used to prepare Compound E1 utilizing appropriate reagent replacements.

| Cpd | Chemical Name | HPLC Retention Time (min) | Mass Reported (MH+) |
|---|---|---|---|
| E2 | 2-(2,6-difluorophenyl)-1-(4-(5-(2-((3,5-dimethylbenzyl)oxy)-1-ethoxypropan-2-yl)-2-methylpyrimidin-4-yl)piperidin-1-yl)ethanone | 21.30 | 552.1 |
| E3 | 2-(2,6-difluorophenyl)-1-(4-(5-(1-(2,3-dihydroxypropoxy)-2-((3,5-dimethylbenzyl)oxy)propan-2-yl)-2-methylpyrimidin-4-yl)piperidin-1-yl)ethanone | 15.14 | 598.1 |
| E4 | 2-(2,6-difluorophenyl)-1-(4-(5-(2-((3,5-dimethylbenzyl)oxy)-1-hydroxypropan-2-yl)-2-methylpyrimidin-4-yl)piperidin-1-yl)ethanone | 3.79* | 524.0 |

HPLC Conditions Used to Determine Retention Times:

Unless otherwise noted: YMC C18, 5μ 150×4.6 mm column, gradient 10% to 90% MeCN/H2O, in the presence of 0.1% TFA, 25 min gradient time, 27 min total run time at 1.5 mL/min flow rate, λ=254 nM

* Phenomenex, Gemini, 50×4.6 mm, 5μ column, gradient 10% to 90% MeCN/H2O, in the presence of 0.1% TFA, 5 min gradient time, 6 min total run time at 3.0 mL/min flow rate, λ=254 nM Compound E5—2-(2,6-Difluorophenyl)-1-(4-(5-(2-(3,5-dimethylbenzyloxy)propan-2-yl)-2-methylpyrimidin-4-yl)piperidin-1-yl)ethanone E5.1: 2-(2,6-Difluorophenyl)-1-(4-(5-(2-hydroxypropan-2-yl)-2-methylpyrimidin-4-yl)piperidin-1-yl)ethanone To a 0° C. solution of B1.3 (280 mg, 0.76 mmol) in THF (1 mL) was added MeMgBr (1 mL, 1.52 mmol, 1.4 M in THF). The reaction was quenched by water after 15 min. The mixture was extracted with EtOAc and the organic mixture was dried over sodium sulfate, filtered, and concentrated. The crude mixture was purified by flash column chromatography to give desired alcohol E5.1.

Compound E5

To a solution of E5.1 (69 mg, 0.18 mmol), 3,5-dimethylbenzyl bromide (46 mg, 0.23 mmol) and Bu$_4$NI (13 mg, 0.036 mmol) in THF (2 mL) was added NaH (22 mg, 0.54 mmol, 60% in mineral oil). The resulting mixture was stirred at room temperature for 12 h. Water was added to quench the reaction. The mixture was extracted with EtOAc and the organic mixture was dried over sodium sulfate, filtered, and concentrated. The crude mixture was purified by HPLC to give Compound E5. MS (EI) for $C_{30}H_{35}F_2N_3O_2$, found: 508.1 (MH+). Analytical HPLC, ret. time=20.40 min, 90% purity.

Compounds E6-E7

Compounds E6 and E7 were prepared from methods analogous to those used to prepare Compound E5 utilizing appropriate reagent replacements.

| Cpd | Chemical Name | HPLC Retention Time (min) | Mass Reported (MH+) |
|---|---|---|---|
| E6 | 1-(4-(5-(2-((3-chlorobenzyl)oxy)propan-2-yl)-2-methylpyrimidin-4-yl)piperidin-1-yl)-2-(2,6-difluorophenyl)ethanone | 19.76 | 514.0 |
| E7 | 1-(4-(5-(2-((6-chloropyridin-2-yl)methoxy)propan-2-yl)-2-methylpyrimidin-4-yl)piperidin-1-yl)-2-(2,6-difluorophenyl)ethanone | 16.58 | 515.0 |

HPLC conditions used to determine retention times: YMC C18, 5μ 150×4.6 mm column, gradient 10% to 90% MeCN/H$_2$O, in the presence of 0.1% TFA, 25 min gradient time, 27 min total run time at 1.5 mL/min flow rate, λ=254 nM Compound E8—2-(2,6-Difluorophenyl)-1-(4-(5-(1-(2,3-dihydroxypropoxy)-2-(3,5-dimethylbenzyloxy)propan-2-yl)-2-methylpyrimidin-4-yl)piperidin-1-yl)ethanone E8.1: tert-Butyl 4-(5-(1-((2,2-dimethyl-1,3-dioxolan-4-yl)methoxy)-2-hydroxypropan-2-yl)-2-methylpyrimidin-4-yl)piperidine-1-carboxylate Sodium (100 mg, 4.3 mmol) was added to ice-water cooled (R)-1,2-isopropylideneglycerol (1.5 mL). The mixture was stirred for 15 min. To the prepared sodium alkoxide solution was added D1.1 (143 mg, 0.43 mmol). The resulting solution was stirred at 65° C. for 12 h. Water was added to the cooled reaction mixture. It was then extracted with EtOAc, washed with NaHCO$_3$, dried over sodium sulfate, and concentrated. The crude product was purified by flash column chromatography.

E8.2: tert-Butyl 4-(5-(1-((2,2-dimethyl-1,3-dioxolan-4-yl)methoxy)-2-(3,5-dimethylbenzyloxy)propan-2-yl)-2-methylpyrimidin-4-yl)piperidine-1-carboxylate To a solution of E8.1 (210 mg, 0.45 mmol), 3,5-dimethylbenzyl bromide (115 mg, 0.57 mmol) and Bu$_4$NI (25 mg, 0.07 mmol) in THF (5 mL) was added NaH (54 mg, 1.35 mmol, 60% in mineral oil). The resulting mixture was stirred at room temperature for 12 h. Water was added to quench the reaction. The mixture was extracted with EtOAc and the organic mixture was dried over sodium sulfate, filtered, and concentrated. The crude mixture was purified by flash column chromatography.

Compound E8

To a solution of E8.2 (230 mg, 0.39 mmol) in MeOH (5 mL) was added 4N HCl in dioxane (1 mL). The resulting solution was stirred for 12 h at room temperature. EtOAc (25 mL) was added. The mixture was basified with 20% NaOH aq. solution to pH 10. The EtOAc layer was washed with brine, dried over sodium sulfate, and concentrated. The resulting crude amine (0.39 mmol) obtained was mixed with 2,6-difluorophenylacetic acid (67 mg, 0.39 mmol), HATU (177 mg, 0.45 mmol) and DIEA (129 mg, 1 mmol) in THF (5 mL). The resulting reaction mixture was stirred at room temperature for 2 h then diluted with aq. sat. NaHCO$_3$. The mixture was extracted with EtOAc and the organic mixture was dried over sodium sulfate, filtered, and concentrated. The crude mixture was purified by prep HPLC to give Compound E8 as a mixture of diastereomers. MS (EI) for $C_{33}H_{41}F_2N_3O_5$, found: 598.0 (MH+). Analytical HPLC, ret. time=15.20 min, 95% purity.

Compound E9—2-(2,6-Difluorophenyl)-1-(4-(5-(1-((R)-2,3-dihydroxypropoxy)-2-(3,5-dimethylbenzyloxy)propan-2-yl)-2-methylpyrimidin-4-yl)piperidin-1-yl)ethanone Compound E9 (as a mixture of diastereomers) was synthesized from D1.1 in the same manner as Compound E8.

MS (EI) for $C_{33}H_{41}F_2N_3O_5$, found: 598.1 (MH+). Analytical HPLC, ret. time=15.14 min, 98% purity.

Compound E10—2-(2,6-Difluorophenyl)-1-(4-(5-((3,5-dimethylbenzyloxy)methyl)-2-methylpyrimidin-4-yl)piperidin-1-yl)ethanone E10.1: 1-(4-(5-(Chloromethyl)-2-methylpyrimidin-4-yl)piperidin-1-yl)-2-(2,6-difluorophenyl)ethanone To a stirred solution of A1.4 (200 mg, 0.496 mmol) in THF (3 mL) at 0° C. was added LiAlH$_4$ (0.40 mL, 1M in THF, 0.396 mmol). After stirring for 2.5 h at 0° C., Et$_2$O (4 mL), water (0.02 mL), 5% NaOH (0.06 mL) and water (0.02 mL) were added in sequence at room temperature with vigorous stirring. The resulting mixture was stirred for additional 2 h at room temperature and then EtOAc (3 mL) was added. The resulting mixture was filtered through Celite, concentrated and purified by silica gel column chromatography (EtOAc/7N NH$_3$ in MeOH=30:1→20:1) to give 2-(2,6-difluorophenyl)-1-(4-(5-(hydroxymethyl)-2-methylpyrimidin-4-yl)piperidin-1-yl)ethanone (95 mg, 53%) as a pale yellow solid. MS (EI) for $C_{19}H_{21}F_2N_3O_2$, found 362.1 (MH+).

To a stirred solution of 2-(2,6-difluorophenyl)-1-(4-(5-(hydroxymethyl)-2-methylpyrimidin-4-yl)piperidin-1-yl)ethanone (20.0 mg, 0.0553 mmol) in CH$_2$Cl$_2$ (1 mL) at room temperature were added Et$_3$N (20 μL, 0.17 mmol), TsCl (13.7 mg, 0.0719 mmol) and N,N-dimethylaminopyridine (DMAP) (0.7 mg, 0.006 mmol) in sequence. After stirring for 5 h, aq. sat. NH$_4$Cl (2 mL) was added and the resulting solution was extracted with EtOAc (2×2 mL). The combined organic layers were concentrated and purified by silica gel column chromatography (hexane/EtOAc=1:2) to give E10.1 (10.0 mg, 48%) as a white solid. MS (EI) for $C_{19}H_{20}ClF_2N_3O$, found 380.0 (MH+).

Compound E10

A mixture of (3,5-dimethylphenyl)methanol (5.4 mg, 0.040 mmol), NaH (1.6 mg, 60% dispersion in mineral oil, 0.40 mmol) and DMF (0.3 mL) was stirred for 10 min at room temperature. A solution of E10.1 (10.0 mg, 0.0263 mmol) in DMF (1 mL) was added. After stirring for 1 h at 50° C., the reaction mixture was quenched with aq. sat. NH$_4$C (1 mL) and then extracted with EtOAc (2×2 mL). The combined organic layers were concentrated and purified by silica gel column chromatography (hexane/EtOAc=2:3) to give Compound E10 (3.1 mg, 25%) as a white solid. $^1$H-NMR (400 MHz, CDCl$_3$): δ 8.48 (s, 1H), 7.23 (m, 1H), 6.97 (m, 3H), 6.91 (t, 2H), 4.73 (d, 1H), 4.51 (s, 2H), 4.50 (d, 2H), 4.11 (d, 1H), 3.76 (s, 2H), 3.16 (td, 1H), 3.07 (tt, 1H), 2.69 (s, 3H), 2.63 (td, 1H), 2.33 (s, 6H), 2.04 (qd, 1H), 1.89 (qd, 1H), 1.75 (m, 2H). MS (EI) for $C_{28}H_{31}F_2N_3O_2$, found 480.1 (MH+). Analytical HPLC, ret. time=18.704 min, 95% purity.

Compound E11—2-(2,6-Difluorophenyl)-1-(4-(5-(1-(3,5-dimethylbenzyloxy)ethyl)-2-methylpyrimidin-4-yl)piperidin-1-yl)ethanone E11.1: 2-(2,6-Difluorophenyl)-1-(4-(5-(1-hydroxyethyl)-2-methylpyrimidin-4-yl)piperidin-1-yl)ethanone To a 0° C. solution of B3.1 (172 mg, 0.45 mmol) in MeOH (3 mL) was added NaBH$_4$ (52 mg, 1.4 mmol). The reaction was quenched by water after 30 min. The mixture was extracted with EtOAc and the organic mixture was dried over sodium sulfate, filtered, and concentrated. The crude mixture was used in the next step without further purification.

Compound E11

To a solution of E11.1 (160 mg, 0.42 mmol), 3,5-dimethylbenzyl bromide (109 mg, 0.55 mmol) and Bu$_4$NI (30 mg, 0.08 mmol) in THF (5 mL) was added NaH (42 mg, 1 mmol, 60% in mineral oil). The resulting mixture was stirred at room temperature for 12 h. Water was added to quench the reaction. The mixture was extracted with EtOAc and the organic mixture was dried over sodium sulfate, filtered, and concentrated. The crude mixture was purified by HPLC to give Compound E11. $^1$H-NMR (400 MHz, DMSO-d6): δ 8.61 (s, 1H), 7.35 (m, 1H), 7.07 (m, 2H), 6.86 (m, 3H), 4.84 (m, 1H), 4.45 (d, 1H), 4.31 (m, 2H), 4.12 (d, 1H), 3.78 (m, 2H), 3.17 (m, 2H), 2.62 (m, 1H), 2.55 (s, 3H), 2.21 (s, 6H), 1.63 (m, 4H), 1.45 (d, 3H). MS (EI) for $C_{29}H_{33}F_2N_3O_2$, found: 494.0 (MH+). Analytical HPLC, ret. time=22.52 min, 90% purity.

Compound F1—2-(2,6-Difluorophenyl)-1-(4-(2-methyl-5-(2-methyl-1-(2-(trifluoromethyl)pyrimidin-4-ylamino)propan-2-yl)pyrimidin-4-yl)piperidin-1-yl)ethanone F1.1: tert-Butyl 4-(5-(cyanomethyl)-2-methylpyrimidin-4-yl)piperidine-1-carboxylate To a −78° C. solution of A1.2 (13 g, 37 mmol) in THF (125 mL) was added dropwise LAH (28 mL, 1 M in THF). The solution was stirred at −78° C. for additional 30 min after the addition. It was then warmed to 0° C. The stirring was continued for 10 min and the reaction was quenched by slow addition of water (1.5 mL), 4 N NaOH (2.5 mL) and water (4.5 mL). The mixture was filtered through Celite, which was washed with EtOAc. Concentration of the EtOAc solution gave the crude alcohol (tert-butyl 4-(5-(hydroxymethyl)-2-methylpyrimidin-4-yl)piperidine-1-carboxylate), which was purified by flash column chromatography.

To a 0° C. solution of tert-butyl 4-(5-(hydroxymethyl)-2-methylpyrimidin-4-yl)piperidine-1-carboxylate (7.15 g, 23 mmol) and Et$_3$N (4.7 g, 46 mmol) in THF (100 mL) was added methanesulfonylchloride (MsCl) (3.14 g, 28 mmol). The mixture was stirred for 30 min after the addition, then quenched with water and extracted with EtOAc. The organic layer was washed with NaHCO$_3$, brine, and dried over sodium sulfate. Concentration gave the crude mesylate (tert-butyl 4-(2-methyl-5-((methylsulfonyloxy)methyl)pyrimidin-4-yl)piperidine-1-carboxylate), which was used in the next step.

A mixture of KCN (1.8 g, 28 mmol) and Bu$_4$NBr (9.0 g, 28 mmol) in DMF (25 mL) was stirred at 40° C. for 3 h. The crude mesylate (~22 mmol) was added as a solution in DMF (15 mL). The reaction mixture was stirred at 40° C. for 2 days, then cooled to room temperature. Water (50 mL) was added and the crude product was extracted with EtOAc. The organic layer was washed with NaHCO$_3$, brine, dried over sodium sulfate, and concentrated. The crude product was purified by flash column chromatography to give F1.1.

F1.2: tert-Butyl 4-(5-(1-amino-2-methylpropan-2-yl)-2-methylpyrimidin-4-yl)piperidine-1-carboxylate To a 0° C. solution of F1.1 (670 mg, 2.1 mmol) and MeI (898 mg, 6.3 mmol) in DMF (10 mL) was added tBuOK (716 mg, 6.3 mmol). The reaction mixture was stirred for 30 min, and quenched with water (10 mL). The mixture was extracted with EtOAc. The organic layer was washed with NaHCO₃, brine, dried over sodium sulfate, and concentrated. The crude product was purified by flash column chromatography to give tert-butyl 4-(5-(2-cyanopropan-2-yl)-2-methylpyrimidin-4-yl)piperidine-1-carboxylate.

To a 250 mL hydrogenation flask were added tert-butyl 4-(5-(2-cyanopropan-2-yl)-2-methylpyrimidin-4-yl)piperidine-1-carboxylate (103 mg, 0.3 mmol), methanolic ammonia (3 N, 20 mL), and Raney nickel (100 mg, Raney 2800 Ni slurry in water). The flask was transferred to a Parr shaker type hydrogenation apparatus, charged with hydrogen (40 psi), and was shaken for 4 h. The catalyst was removed by filtration through Celite (washing with MeOH), and the solution was concentrated in vacuo to afford F1.2.

F1.3: tert-Butyl 4-(2-methyl-5-(2-methyl-1-(2-(trifluoromethyl)pyrimidin-4-ylamino)propan-2-yl)pyrimidin-4-yl)piperidine-1-carboxylate F1.2 (100 mg, 0.28 mmol), 4-chloro-2-(trifluoromethyl)pyrimidine (51 mg, 0.28 mmol) and DIEA (112 mg, 0.86 mmol) were mixed in MeCN (3 mL). The resulting solution was stirred at 50° C. for 12 h. The mixture was concentrated to dryness. The residue was dissolved in EtOAc, washed with NaHCO₃ and brine. Concentration gave crude F1.3, which was used as is in the next step.

F1.4: N-(2-Methyl-2-(2-methyl-4-(piperidin-4-yl)pyrimidin-5-yl)propyl)-2-(trifluoromethyl)pyrimidin-4-amine To a solution of the crude F1.3 in MeOH (2 mL) was added 4N HCl in dioxane (0.3 mL). The resulting solution was stirred for 12 h at room temperature. EtOAc (25 mL) was added. The mixture was basified with 20% NaOH aq. solution to pH 10. The EtOAc layer was washed with brine, dried over sodium sulfate, and concentrated to give F1.4. The crude product was used in the next step without further purification.

Compound F1

F1.4 (100 mg, 0.25 mmol) was mixed with 2,6-difluorophenylacetic acid (52 mg, 0.3 mmol), HATU (114 mg, 0.3 mmol) and DIEA (129 mg, 1 mmol) in THF (2 mL). The resulting reaction mixture was stirred at room temperature for 2 h then diluted with aq. sat. NaHCO₃. The mixture was extracted with EtOAc and the organic mixture was dried over sodium sulfate, filtered, and concentrated. The crude mixture was purified by prep HPLC to give Compound F1. MS (EI) for $C_{27}H_{29}F_5N_6O$, found: 549.0 (MH+). Analytical HPLC, ret. time=3.30 min, 98% purity.

Compound F2-F3

Compounds F2 to F3 were prepared from methods analogous to those used to prepare Compound F1 utilizing appropriate reagent replacements.

| Cpd | Chemical Name | HPLC Retention Time (min) | Mass Reported (MH+) |
|---|---|---|---|
| F2 | 2-(2,6-difluorophenyl)-1-(4-(2-methyl-5-(2-methyl-1-((4-(trifluoromethyl)pyrimidin-2-yl)amino)propan-2-yl)pyrimidin-4-yl)piperidin-1-yl)ethanone | 16.48 | 549.0 |
| F3 | N-[2-(4-{1-[(2,6-difluorophenyl)acetyl]piperidin-4-yl}-2-methylpyrimidin-5-yl)-2-methylpropyl]-6-(trifluoromethyl)pyridin-2-amine | 14.56 | 548.2 |

HPLC conditions used to determine retention times: YMC C18, 5μ 150×4.6 mm column, gradient 10% to 90% MeCN/H₂O, in the presence of 0.1% TFA, 25 min gradient time, 27 min total run time at 1.5 mL/min flow rate, λ=254 nM

Compound F4—Methyl 2-(4-(1-(2-(2,6-difluorophenyl)acetyl)piperidin-4-yl)-2-methylpyrimidin-5-yl)-2-methyl-3-(2-(trifluoromethyl)pyrimidin-4-ylamino)propanoate

F4.1: tert-Butyl 4-(5-(1-cyano-2-methoxy-2-oxoethyl)-2-methylpyrimidin-4-yl)piperidine-1-carboxylate To a solution of F1.1 (570 mg, 1.79 mmol) in dimethylcarbonate (3 mL) was added MeONa (194 mg, 3.6 mmol). The resulting solution was stirred at room temperature for 2 h. The reaction was quenched with water and extracted with EtOAc. The organic phase was dried over sodium sulfate, filtered, and concentrated. The crude product was purified by flash column chromatography to give F4.1.

F4.2: tert-Butyl 4-(5-(2-cyano-1-methoxy-1-oxopropan-2-yl)-2-methylpyrimidin-4-yl)piperidine-1-carboxylate To a solution of F4.1 (370 mg, 1 mmol) and MeI (283 mg, 2 mmol) in DMF (5 mL) was added tBuOK (224 mg, 2 mmol). The reaction mixture was stirred for 12 h, and quenched with water (10 mL). The mixture was extracted with EtOAc. The organic layer was washed with NaHCO₃, brine, dried over sodium sulfate, and concentrated. The crude product was purified by flash column chromatography.

F4.3: tert-Butyl 4-(5-(1-methoxy-2-methyl-1-oxo-3-(2-(trifluoromethyl)pyrimidin-4-ylamino)propan-2-yl)-2-methylpyrimidin-4-yl)piperidine-1-carboxylate To a 250 mL hydrogenation flask were added F4.2 (200 mg, 0.5 mmol), methanolic ammonia (3 N, 10 mL), and Raney nickel (100 mg, Raney 2800 Ni slurry in water). The flask was transferred to a Parr shaker type hydrogenation apparatus, charged with hydrogen (40 psi), and was shaken for 4 h. The catalyst was removed by filtration through Celite (washing with MeOH), and the solution was concentrated in vacuo to afford tert-butyl 4-(5-(3-amino-1-methoxy-2-methyl-1-oxopropan-2-yl)-2-methylpyrimidin-4-yl)piperidine-1-carboxylate.

Tert-butyl 4-(5-(3-amino-1-methoxy-2-methyl-1-oxopropan-2-yl)-2-methylpyrimidin-4-yl)piperidine-1-carboxylate (130 mg, 0.33 mmol), 4-chloro-2-(trifluoromethyl)pyrimidine (73 mg, 0.33 mmol) and DIEA (129 mg, 1 mmol) were mixed in MeCN (3 mL). The resulting solution was stirred at 50° C. for 12 h. The mixture was concentrated to dryness. The residue was dissolved in EtOAc, washed with NaHCO$_3$ and brine. Concentration gave the crude product, which was purified by flash column chromatography to give F4.3.

Compound F4

To a solution of F4.3 (100 mg, 0.18 mmol) in MeOH (2 mL) was added 4N HCl in dioxane (0.3 mL). The resulting solution was stirred for 12 h at room temperature. EtOAc (25 mL) was added. The mixture was basified with 20% NaOH aq. solution to pH 10. The EtOAc layer was washed with brine, dried over sodium sulfate, and concentrated. The crude product was used in the next step without further purification.

Methyl 2-methyl-2-(2-methyl-4-(piperidin-4-yl)pyrimidin-5-yl)-3-(2-(trifluoromethyl)pyrimidin-4-ylamino)propanoate (28 mg, 0.13 mmol) obtained above was mixed with 2,6-difluorophenylacetic acid (28 mg, 0.16 mmol), HATU (60 mg, 0.16 mmol) and DIEA (129 mg, 1 mmol) in THF (2 mL). The resulting reaction mixture was stirred at room temperature for 2 h then diluted with aq. sat. NaHCO$_3$. The mixture was extracted with EtOAc and the organic mixture was dried over sodium sulfate, filtered, and concentrated. The crude mixture was purified by prep HPLC to give Compound F4. MS (EI) for C$_{28}$H$_{29}$F$_5$N$_6$O$_3$, found: 593.2 (MH+). Analytical HPLC, ret. time=12.8 min, 94% purity.

Compound F5—2-(2,6-Difluorophenyl)-1-(4-(5-(1-hydroxy-2-methyl-3-(2-(trifluoromethyl)pyrimidin-4-ylamino)propan-2-yl)-2-methylpyrimidin-4-yl)piperidin-1-yl)ethanone To a 0° C. solution of F4.4 (20 mg, 0.033 mmol) in THF (2 mL) was added LAH (0.033 mL, 2.0 M in THF). The resulting solution was stirred at room temperature for 30 min. The reaction mixture was quenched with aq. 10% NaOH solution, and filtered through Celite. The Celite pad was washed with EtOAc. The EtOAc solution was washed with brine, dried over sodium sulfate, and concentrated. The crude product was purified by prep HPLC to give Compound F5. MS (EI) for C$_{27}$H$_{29}$F$_5$N$_6$O$_2$, found: 565.2 (MH+). Analytical HPLC, ret. time=10.56 min, 93% purity.

Compound F6—2-(2,6-Difluorophenyl)-1-(4-(5-((3,5-dimethylbenzylamino)methyl)-2-methylpyrimidin-4-yl)piperidin-1-yl)ethanone To a stirred solution of E10.1 (9.0 mg, 0.024 mmol), (3,5-dimethylphenyl)methanamine (6.4 mg, 0.047 mmol) and DMF (0.5 mL) at room temperature was added DIEA (10 µL, 0.047 mmol). After stirring for 2 h at 50° C., aq. sat. NaHCO$_3$ (1 mL) and water (1 mL) were added and the resulting solution was extracted with EtOAc (2×2 mL). The combined organic layers were concentrated and purified by silica gel column chromatography (EtOAc→EtOAc/MeOH=30:1) to give Compound F6 (8.5 mg, 75%) as a beige powder after lyophilization. $^1$H-NMR (400 MHz, CDCl$_3$): δ 8.45 (s, 1H), 7.23 (m, 1H), 6.92 (m, 5H), 4.74 (d, 1H), 4.11 (d, 1H), 3.77 (s, 4H), 3.74 (s, 2H), 3.16 (m, 2H), 2.68 (s, 3H), 2.63 (td, 1H), 2.32 (s, 6H), 2.05 (qd, 1H), 1.88 (qd, 1H), 1.75 (m 2H). MS (EI) for C$_{28}$H$_{32}$F$_2$N$_4$O, found 479.1 (MH+). Analytical HPLC, ret. time=12.208 min, 97% purity.

Compound F7—2-(2,6-Difluorophenyl)-1-(4-(5-(1-(3,5-dimethylbenzylamino)-2,2,2-trifluoroethyl)-2-methylpyrimidin-4-yl)piperidin-1-yl)ethanone F7.1: 1-(4-(1-(2-(2,6-Difluorophenyl)acetyl)piperidin-4-yl)-2-methylpyrimidin-5-yl)-2,2,2-trifluoroethanone To a stirred solution of A1.4 (530 mg, 1.31 mmol) and trimethyl(trifluoromethyl)silane (280 mg, 1.97 mmol) in toluene (5 mL) at −78° C. was added Bu$_4$NF (65 µL, 1M in THF, 0.065 mmol). The reaction mixture was warmed slowly to −5° C. for 40 min and then 2N HCl (1.2 mL) was added. After stirring for 1 h at room temperature, EtOAc (5 mL) was added. The organic layer was separated, concentrated, dissolved in THF (5 mL), and transferred to the aq. layer. After stirring for 2 h, water (2 mL) was added and the resulting solution was extracted with EtOAc (3×3 mL). The combined organic layers were concentrated and purified by silica gel column chromatography (hexane/EtOAc=1:1-1:2) to give F7.1 (205 mg, 37%) as a white foam. MS (EI) for C$_{20}$H$_{18}$F$_5$N$_3$O$_2$, found 428.0 (MH+).

F7.2: 2-(2,6-Difluorophenyl)-1-(4-(2-methyl-5-(2,2,2-trifluoro-1-hydroxyethyl)pyrimidin-4-yl)piperidin-1-yl)ethanone To a stirred solution of F7.1 (10.0 mg, 0.0234 mmol) in MeOH (0.5 mL) at room temperature was added NaBH$_4$ (2.7 mg, 0.070 mmol). After stirring for 2 h, aq. sat. NH$_4$Cl (2 mL) was added and the resulting solution was extracted with EtOAc (2×2 mL). The combined organic layers were concentrated and purified by silica gel column chromatography (hexane/EtOAc=3:4) to give F7.2 (9.0 mg, 90%) as a yellow oil. MS (EI) for C$_{20}$H$_{20}$F$_5$N$_3$O$_2$, found 430.0 (MH+).

F7.3: 1-(4-(1-(2-(2,6-Difluorophenyl)acetyl)piperidin-4-yl)-2-methylpyrimidin-5-yl)-2,2,2-trifluoroethyl methanesulfonate To a stirred solution of F7.2 (20.0 mg, 0.0466 mmol) in CH$_2$Cl$_2$ (1 mL) at room temperature were added Et$_3$N (20 µL, 0.14 mmol) and methanesulfonyl chloride (7 µL, 0.09 mmol) in sequence. After stirring for 20 min, aq. sat. NH$_4$Cl (2 mL) was added and the resulting solution was extracted with EtOAc (2×2 mL). The combined organic layers were concentrated and purified by silica gel column chromatography (hexane/EtOAc=4:3→1:1) to give F7.3 (22 mg, 93%) as a clear oil. MS (EI) for C$_{21}$H$_{22}$F$_5$N$_3$O$_4$S, found 507.9 (MH+).

Compound F7

A mixture of F7.3 (19.0 mg, 0.0374 mmol) and (3,5-dimethylphenyl)methanamine (25.0 mg, 0.187 mmol) was stirred for 1 day at room temperature. Aq. sat. NH$_4$Cl (2 mL) was added and the resulting solution was extracted with EtOAc (3×2 mL). The combined organic layers were concentrated and purified by silica gel column chromatography (hexane/EtOAc=2:1→3:2). The isolated material was further purified by prep HPLC to give Compound F7 (8.5 mg, 42%) as a white solid after lyophilization. $^1$H-NMR (400 MHz, CDCl$_3$, rotameric mixture): δ 8.81 and 8.78 (two of s, 1H), 7.24 (m, 1H), 6.91 (m, 3H), 6.82 (m, 2H), 4.67 (two of d, 1H), 4.48 (m, 1H), 4.04 (two of d, 1H), 3.82 (dd, 1H), 3.74 (s, 2H), 3.60 (dd, 1H), 3.13-2.94 (m, 1H), 2.75 (m, 1H), 2.71 (s, 3H), 2.58-2.38 (m, 1H), 2.29 (two of s, 6H), 2.12 (m, 1H), 2.07-1.71 (m, 2H), 1.62 (m, 1H), 1.44-1.28 (m, 1H). MS (EI) for $C_{29}H_{31}F_5N_4O$, found 547.0 (MH+). Analytical HPLC, ret. time=19.952 min (gradient 10% to 100% MeCN/H$_2$O), 98% purity.

Compound F8—N-(2,6-Difluorophenyl)-4-(2-methyl-5-(2-methyl-1-(2-(trifluoromethyl)pyrimidin-4-ylamino)propan-2-yl)pyrimidin-4-yl)piperidine-1-carboxamide F1.4 (80 mg, 0.2 mmol), 2,6-difluorophenyl isocyanate (63 mg, 0.4 mmol) and Et$_3$N (109 mg, 1 mmol) were mixed in acetone (2 mL). The solution was stirred at room temperature for 30 min and diluted with EtOAc (25 mL). The organic phase was washed with NaHCO$_3$, brine, dried over sodium sulfate and concentrated. The crude mixture was purified by prep HPLC to give Compound F8. MS (EI) for $C_{26}H_{28}F_5N_7O$, found: 550.0 (MH+). Analytical HPLC, ret. time=2.98 min, 98% purity.

Compound F9—2-(2,6-Difluorophenyl)-1-(4-(5-(1-(3,5-dimethylbenzylamino)ethyl)-2-methylpyrimidin-4-yl)piperidin-1-yl)ethanone B3.1 (278 mg, 0.77 mmol), 3,5-dimethylbenzylamine (105 mg, 0.77 mmol) and Ti(O$^i$Pr)$_4$ (420 mg, 1.47 mmol) were mixed in THF (2 mL). The resulting mixture was stirred at room temperature for 8 h. NaBH$_4$ (90 mg, 2.4 mmol) and EtOH (0.5 mL) were added. The stirring was continued for additional 4 h. Aq. sat. NaHCO$_3$ was added to quench the reaction. The mixture was extracted with EtOAc and the organic phase was dried over sodium sulfate, filtered, and concentrated. The crude product was purified by prep HPLC to give Compound F9. $^1$H-NMR (400 MHz, DMSO-d6): δ 8.73 (s, 1H), 7.35 (m, 1H), 7.07 (m, 2H), 6.86 (m, 3H), 4.43 (d, 1H), 4.13 (d, 1H), 4.01 (m, 1H), 3.78 (m, 2H), 3.50 (m, 3H), 3.11 (m, 2H), 2.58 (s, 3H), 2.55 (m, 1H), 2.23 (d, 6H), 1.63 (m, 4H), 1.31 (d, 3H). MS (EI) for $C_{29}H_{34}F_2N_4O$, found: 493.1 (MH+). Analytical HPLC, ret. time=2.98 min, 99% purity.

Compound G1—N-(3-Chlorophenyl)-4-(1-(2-(2,6-difluorophenyl)acetyl)piperidin-4-yl)-2-methylpyrimidine-5-carbohydrazide A1.5 (500 mg, 1.32 mmol) was mixed with (3-chlorophenyl)hydrazine (285 mg, 1.59 mmol) and DIEA (1.2 mL) in CH$_2$Cl$_2$ (10 mL). To this solution was added O-(benzotriazol-1-yl)-N,N,N',N'-tetramethyluronium tetrafluoroborate (TBTU) (550 mg, 1.71 mmol). The resulting reaction mixture was stirred at room temperature for 2 h then diluted with aq. sat. NaHCO$_3$. The mixture was extracted with CH$_2$Cl$_2$ and the organic mixture was dried over sodium sulfate, filtered, and concentrated. The crude mixture was purified by flash column chromatography to give Compound G1. MS (EI) for $C_{25}H_{24}ClF_2N_5O_2$, found: 500.1 (MH+). Analytical HPLC, ret. time=18.29 min, 97% purity.

Compounds G2-G4

Compounds G2 to G4 were prepared from methods analogous to those used to prepare Compound G1 utilizing appropriate reagent replacements.

| Cpd | Chemical Name | HPLC Retention Time (min) | Mass Reported (MH+) |
|---|---|---|---|
| G2 | N'-(3-chlorophenyl)-2-cyclopropyl-4-(1-(2-(2,6-difluorophenyl)acetyl)piperidin-4-yl)pyrimidine-5-carbohydrazide | 3.86 | 526.0 |
| G3 | N'-(3-chlorophenyl)-4-(1-(2-(2,6-difluorophenyl)acetyl)piperidin-4-yl)-2-ethylpyrimidine-5-carbohydrazide | 3.70 | 514.0 |
| G4 | N'-(3-chlorophenyl)-4-(1-(2-(2,6-difluorophenyl)acetyl)piperidin-4-yl)-2,6-dimethylpyrimidine-5-carbohydrazide | 3.88 | 514.0 |

HPLC conditions used to determine retention times: Phenomenex, Gemini, 50×4.6 mm, 5 μ column, gradient 10% to 90% MeCN/H2O, in the presence of 0.1% TFA, 5 min gradient time, 6 min total run time at 3.0 mL/min flow rate, λ=254 nM

Compound H1 4-{1-[(2,6-Difluorophenyl)acetyl]piperidin-4-yl}-2-methyl-N-{[3-(trifluoromethyl)phenyl]oxy}pyrimidine-5-carboxamide To a stirred solution of A1.5 (150 mg, 0.40 mmol), O-(3-(trifluoromethyl)phenylhydroxylamine (78 mg, 0.44 mmol) and Et$_3$N (279 μL, 2.0 mmol) in DMF (4 mL) was added HATU (168 mg, 0.44 mmol) and the reaction mixture was stirred at room temperature for 1 h. The reaction mixture was diluted with EtOAc, washed with aq. 1N NaOH and brine, dried over sodium sulfate, and concentrated in vacuo. The residue was purified by flash chromatography to afford Compound H1 (52 mg, 24%) as a white powder after lyophilization. Analytical HPLC: retention time=14.312 min, 99%. $^1$H-NMR (400 MHz, CDCl$_3$): δ 10.40 (br s, 1H), 8.68 (br s, 1H), 7.48-7.44 (m, 1H), 7.36-7.34 (m, 2H), 7.30-7.26 (m, 1H), 7.19-7.12 (m, 1H), 6.86-6.81 (m, 2H), 4.54 (d, 1H), 4.08 (d, 1H), 3.71 (s, 2H), 3.47 (br s, 1H), 3.20 (t, 1H), 2.74 (s, 3H), 2.63 (t, 1H), 2.03-1.90 (m, 2H), 1.84-1.74 (m, 2H). MS (EI) for $C_{26}H_{23}F_5N_4O_3$, found 535.0 (MH+).

Compounds H2-H7

Compounds H2 to H7 were prepared from methods analogous to those used to prepare Compound H1 utilizing appropriate reagent replacements.

| Cpd | Chemical Name | HPLC Retention Time (min) | Mass Reported (MH+) |
|---|---|---|---|
| H2 | 4-(1-(2-(2,6-difluorophenyl)acetyl)piperidin-4-yl)-N-(3,5-dimethylphenoxy)-2-methylpyrimidine-5-carboxamide | 19.68 | 495.0 |
| H3 | N-(3-chlorophenyl)-4-(1-(2-(2,6-difluorophenyl)acetyl)piperidin-4-yl)-2-methylpyrimidine-5-carboxamide | 17.34 | 500.9 |
| H4 | 4-(1-(2-(2,6-difluorophenyl)acetyl)piperidin-4-yl)-2-methyl-N-(3-(trifluoromethoxy)phenoxy)pyrimidine-5-carboxamide | 18.60 | 551.0 |
| H5 | N-(3-chlorophenoxy)-4-(1-(2-(2,6-difluorophenyl)acetyl)piperidin-4-yl)-2,6-dimethylpyrimidine-5-carboxamide | 16.41 | 515.0 |

| Cpd | Chemical Name | HPLC Retention Time (min) | Mass Reported (MH+) |
|---|---|---|---|
| H6 | N-(3-chloro-5-fluorophenoxy)-4-(1-(2-(2,6-difluorophenyl)acetyl)piperidin-4-yl)-2-methylpyrimidine-5-carboxamide | 21.03 | 519.0 |
| H7 | 4-(1-(2-(2,6-difluorophenyl)acetyl)piperidin-4-yl)-2-methyl-N-phenoxypyrimidine-5-carboxamide | 3.87* | 467.0 |

HPLC Conditions Used to Determine Retention Times:
  Unless otherwise noted: YMC C18, 5μ 150×4.6 mm column, gradient 10% to 90% MeCN/H$_2$O, in the presence of 0.1% TFA, 25 min gradient time, 27 min total run time at 1.5 mL/min flow rate, λ=254 nM
  * Phenomenex, Gemini, 50×4.6 mm, 5μ column, gradient 10% to 90% MeCN/H2O, in the presence of 0.1% TFA, 5 min gradient time, 6 min total run time at 3.0 mL/min flow rate, λ=254 nM Compound I1—4-{1-[(2,6-Difluorophenyl)acetyl]piperidin-4-yl}-2-methyl-6-oxo-N-{[6-(trifluoromethyl)pyridin-2-yl]methyl}-1,6-dihydropyrimidine-5-carboxamide I1.1: 4-(1-(2-(2,6-Difluorophenyl)acetyl)piperidin-4-yl)-2-methyl-6-oxo-1,6-dihydropyrimidine-5-carboxylic acid A108.3 (420 mg, 1 mmol) was mixed with NaOH (400 mg, 10 mmol) in MeOH/water (10 mL/5 mL). The resulting mixture was stirred at 85° C. for 2 h. The solution was concentrated, and acidified with conc. HCl. The product was precipitated, filtered, and dried.

Compound I1

To a mixture of I1.1 (85 mg, 0.22 mmol), HATU (107 mg, 0.28 mmol), and CH$_2$Cl$_2$ (1.5 mL) was added DIEA (112 mg, 0.87 mmol). The mixture was stirred at 35° C. for 30 min. To this mixture was added (6-(trifluoromethyl)pyridin-2-yl)methanamine hydrochloride (69 mg, 0.33 m mol). The resulting yellow solution was stirred at 35° C. for 14 h. After removal of solvent in vacuo, the residue was purified on prep HPLC to give 11.2 (64 mg). $^1$H-NMR (400 MHz, DMSO-d$_6$): δ 12.5 (br. s. 1H), 9.22 (t, 1H), 8.10 (t, 1H), 7.82 (d, 1H), 7.78 (d, 1H), 7.33 (m, 1H), 7.05 (t, 2H), 4.57 (d, 2H), 4.40 (d, 1H), 4.10 (d, 1H), 3.74 (dd, 2H), 3.27 (m, 1H), 3.02 (t, 2H), 2.30 (s, 3H), 1.77 (m, 1H), 1.67-1.60 (m, 3H). Analytical HPLC, ret. time=13.72 min, 98% purity. MS (EI) for C$_{26}$H$_{24}$F$_5$N$_5$O$_3$, found 550.0 (MH+).

Compound I2—4-{1-[(2,6-Difluorophenyl)acetyl]piperidin-4-yl}-2-methyl-N-{[2-(trifluoromethyl)pyridin-4-yl]methyl}-6-({[2-(trifluoromethyl)pyridin-4-yl]methyl}amino)pyrimidine-5-carboxamide Compound I2 was recovered as a second product from the reaction that generated Compound I1 (9 mg recovered). $^1$H-NMR (400 MHz, DMSO-d$_6$): δ 9.29 (br. s. 1H), 8.13 (t, 1H), 8.02 (t, 1H), 7.81 (d, 1H), 7.76 (d, 1H), 7.74 (d, 1H), 7.62 (d, 1H), 7.42 (br. s, 1H), 7.33 (m, 1H), 7.05 (t, 2H), 4.74 (s, 2H), 4.66 (d, 2H), 4.40 (d, 1H), 4.11 (d, 1H), 3.74 (dd, 2H), 2.96 (t, 2H), 2.81 (m, 1H), 2.30 (s, 3H), 1.81 (m, 1H), 1.71-1.63 (m, 3H). Analytical HPLC, ret. time=14.38 min, 97% purity. MS (EI) for C$_{33}$H$_{29}$F$_8$N$_7$O$_2$, found 707.9 (MH+).

Compound I3—4-(1-(2-(2,6-Difluorophenyl)acetyl)piperidin-4-yl)-N-(3,5-dimethylbenzyl)-2-methyl-6-oxo-1,6-dihydropyrimidine-5-carboxamide I1.1 (120 mg, 0.31 mmol) was mixed with 3,5-dimethylbenzylamine (67 mg, 0.5 mmol), HATU (130 mg, 0.34 mmol), and DIEA (0.5 mL) in THF (5 mL). The resulting reaction mixture was stirred at room temperature for 2 h then diluted with aq. sat. NaHCO$_3$. The resulting mixture was extracted with CH$_2$Cl$_2$ and the organic mixture was dried over sodium sulfate, filtered, and concentrated. The crude mixture was purified by prep HPLC to give Compound I3. MS (EI) for C$_{28}$H$_{30}$ClF$_2$N$_4$O$_3$, found: 509.0 (MH+). Analytical HPLC, ret. time=17.25 min, 94% purity.

Compounds I4-I5

Compounds I4 and I5 were prepared from methods analogous to those used to prepare Compound I3 utilizing appropriate reagent replacements.

| Cpd | Chemical Name | HPLC Retention Time (min) | Mass Reported (MH+) |
|---|---|---|---|
| I4 | N-(3-chlorobenzyl)-4-(1-(2-(2,6-difluorophenyl)acetyl)piperidin-4-yl)-2-methyl-6-oxo-1,6-dihydropyrimidine-5-carboxamide | 3.41* | 515.0 |
| I5 | 4-(1-(2-(2,6-difluorophenyl)acetyl)piperidin-4-yl)-2-methyl-6-oxo-N-((2-(trifluoromethyl)pyridin-4-yl)methyl)-1,6-dihydropyrimidine-5-carboxamide | 12.99 | 550.0 |

HPLC Conditions Used to Determine Retention Times:
  Unless otherwise noted: YMC C18, 5μ 150×4.6 mm column, gradient 10% to 90% MeCN/H$_2$O, in the presence of 0.1% TFA, 25 min gradient time, 27 min total run time at 1.5 mL/min flow rate, λ=254 nM
  * Phenomenex, Gemini, 50×4.6 mm, 5μ column, gradient 10% to 90% MeCN/H2O, in the presence of 0.1% TFA, 5 min gradient time, 6 min total run time at 3.0 mL/min flow rate, λ=254 nM Compound I6—(E)-4-(1-(2-(2,6-Difluorophenyl)acetyl)piperidin-4-yl)-2-methyl-6-oxo-1,6-dihydropyrimidine-5-carbaldehyde O-3-(trifluoromethyl)phenyl oxime I6.1: 4-(1-(2-(2,6-Difluorophenyl)acetyl)piperidin-4-yl)-2-methyl-6-oxo-1,6-dihydropyrimidine-5-carbaldehyde I6.1 was synthesized from I1.1 in the same manner that B1.2 was synthesized from B1.1

Compound I6

Compound I6 was synthesized from I6.1 in the same manner that B30.2 was synthesized from B30.1. MS (EI) for C$_{26}$H$_{23}$F$_5$N$_4$O$_3$, found: 534.9 (MH+). Analytical HPLC, ret. time=19.74 min, 92% purity.

Compound I7—4-(1-(2-(2,6-Difluorophenyl)acetyl) piperidin-4-yl)-1,2-dimethyl-6-oxo-N-((6-(trifluoromethyl)pyridin-2-yl)methyl)-1,6-dihydropyrimidine-5-carboxamide I7.1: Ethyl 4-(1-(tert-butoxycarbonyl)piperidin-4-yl)-1,2-dimethyl-6-oxo-1,6-dihydropyrimidine-5-carboxylate To a solution of A108.2 (200 mg, 0.55 mmol) in anhydrous ethylene glycol dimethyl ether (3.6 mL) was added NaH (66 mg, 60% suspension in mineral oil, 1.65 mmol) with stirring at room temperature. The resulting suspension was stirred at 45° C. for 15 min. To this mixture was added iodomethane (311 mg, 2.19 mmol). The resulting mixture was stirred at 45° C. for 1 h. After cooling down to 0° C. in an ice bath, the reaction mixture was quenched by addition of sat. NH$_4$Cl solution. The mixture was then diluted with EtOAc, washed with water (3×) and brine, dried over magnesium sulfate, and concentrated in vacuo, affording the crude product of I7.1 (200 mg). $^1$H-NMR (400 MHz, CDCl$_3$): δ 4.39 (q, 2H), 4.19 (br. s 2H), 3.51 (s, 3H), 2.75-2.66 (m 3H), 2.51 (s, 3H), 1.84 (m, 2H), 1.64 (m, 2H), 1.49 (s, 9H), 1.35 (t, 3H). MS (EI) for C$_{19}$H$_{29}$N$_3$O$_5$, found: 380.1 (MH+).

I7.2: 4-(1-(tert-Butoxycarbonyl)piperidin-4-yl)-1,2-dimethyl-6-oxo-1,6-dihydropyrimidine-5-carboxylic acid To a mixture of the crude I7.1 (200 mg) in 1:1 MeOH/water (6 mL) was added NaOH (110 mg). The mixture was stirred at room temperature for 15 h, and then heated 50° C. for an additional 3 h. The mixture was concentrated in vacuo to remove MeOH, and then washed with hexanes (2×). The aq. layer was acidified to pH 2 with 1N hydrochloric acid at 0° C., and then extracted with EtOAc (5×). The combined organic phase was washed with water and brine, dried over magnesium sulfate, and concentrated in vacuo to give the I7.2 as an off-white solid (135 mg). $^1$H-NMR (400 MHz, CDCl$_3$): δ 4.35 (m, 1H), 4.21 (br.s, 2H), 3.63 (s, 3H), 2.86 (m, 2H), 2.64 (s, 3H), 1.80 (m, 2H), 1.80 (m, 2H), 1.48 (s, 9H).

I7.3: tert-Butyl 4-(1,2-dimethyl-6-oxo-5-((6-(trifluoromethyl)pyridin-2-yl)methylcarbamoyl)-1,6-dihydropyrimidin-4-yl)piperidine-1-carboxylate To a mixture of I7.2 (135 mg, 0.38 mmol) and HATU (190 mg, 0.50 mmol) in CH$_2$Cl$_2$ (3.8 mL) was added DIEA (248 mg, 1.92 mmol). The resulting mixture was stirred at 30° C. for 20 min. To the above mixture was added (6-(trifluoromethyl)pyridin-2-yl)methanamine hydrochloride (114 mg, 0.54 mmol). The reaction mixture was stirred at 30° C. for 20 min. The resulting yellow solution was concentrated in vacuo to remove solvent. The residue was dissolved in EtOAc, washed sequentially with 0.2 N HCl aq. solution (2×), 0.2 N NaOH aq. solution (2×), and brine, dried over magnesium sulfate, and concentrated in vacuo to give a crude I7.3 (233 mg). $^1$H-NMR (400 MHz, CDCl$_3$): δ 9.48 (t, 1H), 7.84 (t, 1H), 7.57 (d, 2H), 4.82 (d, 2H), 4.18 (br.s. 2H), 3.98 (m, 1H), 3.56 (s, 3H), 2.80 (m, 2H), 2.57 (s, 3H), 1.84 (m, 2H), 1.68 (m, 2H), 1.47 (s, 9H). The crude product was used directly for the next reaction without further purification.

I7.4: 1,2-Dimethyl-6-oxo-4-(piperidin-4-yl)-N-((6-(trifluoromethyl)pyridin-2-yl)methyl)-1,6-dihydropyrimidine-5-carboxamide hydrochloride To a solution of I7.3 (233 mg) in MeOH (3 mL), was added 4 M HCl in dioxane (5 mL). The mixture was stirred at room temperature for 2.5 h. After removal of solvents in vacuo, the reaction mixture was dissolved in MeCN and concentrated in vacuo. The residue was triturated with tert-butyl methyl ether and the solvent was decanted. The residue was dried under high vacuum to give I7.4 (209 mg), which was used directly for the subsequent reaction. MS (EI) for C$_{19}$H$_{22}$F$_3$N$_5$O$_2$, found: 401.0 (MH+).

Compound I7

To a mixture of 2-(2,6-difluorophenyl)acetic acid (98 mg, 0.57 mmol) and HATU (188 mg, 0.49 mmol) in CH$_2$Cl$_2$ (2 mL) was added DIEA (100 mg). The solution was stirred at room temperature for 20 min. The resulting solution was added into the solution of I7.4 obtained in the previous step (209 mg), DIEA (130 mg) and CH$_2$Cl$_2$ (1 mL). The resulting solution was stirred at room temperature for 15 min. After removal of solvent in vacuo, the reaction mixture was diluted with EtOAc, washed with water (2×) and brine, and concentrated in vacuo. The residue was purified on prep. HPLC to yield Compound I7 as a solid (136 mg). $^1$H-NMR (400 MHz, DMSO-d$_6$): δ 911 (t, 1H), 8.12 (t, 1H), 7.88 (d, 1H), 7.78 (d, 1H), 7.34 (m, 1H), 7.05 (t, 2H), 4.58 (d, 2H), 4.41 (d, 1H), 4.11 (d, 1H), 3.75 (dd, 2H), 3.45 (s, 3H), 3.22 (m, 1H), 3.04 (t, 1H), 2.91 (m, 1H), 2.52 (s, 3H), 1.79 (m, 1H), 1.67-1.60 (m, 3H). Analytical HPLC, ret. time=15.18 min, 98% purity. MS (EI) for C$_{27}$H$_{26}$F$_5$N$_5$O$_3$, found: 564.0 (MH+).

Compound I8—4-(1-(2-(2,6-Difluorophenyl)acetyl) piperidin-4-yl)-1-ethyl-2-methyl-6-oxo-N-((6-(trifluoromethyl)pyridin-2-yl)methyl)-1,6-dihydropyrimidine-5-carboxamide Compound I8 was synthesized with the same method utilized for Compound I7. Analytical HPLC, ret. time=16.228 min. MS (EI) for C$_{28}$H$_{28}$F$_5$N$_5$O$_3$, found: 578.0 (MH+).

Compound J1—(E)-2-(2,6-Difluorophenyl)-1-(4-(5-(3-(3,5-dimethylphenyl)prop-1-enyl)-2-methylpyrimidin-4-yl)piperidin-1-yl)ethanone J1.1: 3,5-Dimethylbenzylphosphonium iodide A mixture of 1-(2-iodoethyl)-3,5-dimethylbenzene (300 mg, 1.15 mmol), triphenylphosphine (452 mg, 1.73 mmol) and MeCN (3 mL) was stirred for 18 h at 85° C. The resulting mixture was concentrated and purified by silica gel column chromatography (CH$_2$Cl$_2$/MeOH=15/1→12/1) to give J1.1 (610 mg, quant) as a white solid. MS (EI) for C$_{28}$H$_{28}$P+, found 395.0 (M+).

Compound J1

To a stirred solution of J1.1 (248 mg, 0.474 mmol) in THF (3 mL) at 0° C. was added nBuLi (0.34 mmol, 2.5M in Hexane, 0.853 mmol). After stirring for 30 min at 0° C., B30.1 (85.0 mg, 0.237 mmol) in THF (1 mL) was added at 0° C. After stirring for 80 min at room temperature, aq. sat. NH$_4$Cl (3 mL) was added and the resulting solution was extracted with EtOAc (3×3 mL). The combined organic layers were concentrated and purified by silica gel column chromatography (hexane/EtOAc=2:1→1:1) to give J1.2 as a white solid. $^1$H-NMR (400 MHz, CDCl$_3$, geometric mixture of E/Z=1.8:1, data for E reported): δ 8.54 (s, 1H), 7.23 (m, 1H), 6.91 (t, 2H), 6.90 (s, 1H), 6.86 (s, 2H), 6.52 (d, J=15.6 Hz, 1H), 6.26 (dt, J=15.6, 6.4 Hz, 1H), 4.73 (d, 1H), 4.15 (d, 1H), 3.77 (s, 2H), 3.53 (d, J=6.4 Hz, 2H), 3.25 (td, 1H), 3.10 (tt, 1H), 2.74 (m, 1H), 2.67 (s, 3H), 2.31 (s, 6H), 2.06 (m, 1H), 1.81 (m, 3H). MS (EI) for C$_{29}$H$_{31}$F$_2$N$_3$O, found 476.1 (MH+). Analytical HPLC, ret. time=21.196 min (E) and 21.468 min (Z), 99% purity.

Compound J2—(Z)-2-(2,6-Difluorophenyl)-1-(4-(5-(3-(3,5-dimethylphenyl)prop-1-enyl)-2-methylpyrimidin-4-yl)piperidin-1-yl)ethanone Compound J2 was an additional isomer recovered from the reaction that generated Compound J1. $^1$H-NMR (400 MHz, CDCl$_3$, geometric mixture of Z/E=9:1, data for Z selected): δ 8.42 (s, 1H), 7.23 (m, 1H), 6.90 (t, 2H), 6.85 (s, 1H), 6.75 (s, 2H), 6.50 (d, J=11.2 Hz, 1H), 6.13 (dt, J=11.2, 7.6 Hz, 1H), 4.73 (d, 1H), 4.12 (d, 1H), 3.76 (s, 2H), 3.36 (d, J=7.6 Hz, 2H), 3.20 (td, 1H), 3.07 (tt, 1H), 2.71 (s, 3H), 2.70 (m, 1H), 2.28 (s, 6H), 2.05 (qd, 1H), 1.81 (m, 3H). MS (EI) for C$_{29}$H$_{31}$F$_2$N$_3$O, found 476.1 (MH+). Analytical HPLC, ret. time=21.248 min (E) and 21.540 min (Z), 90% purity.

Compound J3—2-(2,6-Difluorophenyl)-1-(4-(5-(3-(3,5-dimethylphenyl)propyl)-2-methylpyrimidin-4-yl)piperidin-1-yl)ethanone A mixture of olefin Compounds J1 and J2 (25.0 mg, 0.0526 mmol), Pd/C (28 mg, 10 wt. %, 0.026 mmol) and MeOH (2 mL) was stirred for 1.5 h at room temperature under a balloon of hydrogen. The mixture was filtered through Celite and the filtrate was concentrated. The residue was dissolved in CH$_2$Cl$_2$ (1 mL) and the resulting solution was filtered and concentrated to give J3 (18.0 mg, 72%) as a pale yellow solid after lyophilization. $^1$H-NMR (400 MHz, CDCl$_3$): δ 8.34 (s, 1H), 7.23 (m, 1H), 6.91 (t, 2H), 6.88 (s, 1H), 6.82 (s, 2H), 4.72 (d, 1H), 4.09 (d, 1H), 3.75 (s, 2H), 3.10 (td, 1H), 2.83 (tt, 1H), 2.65 (s, 3H), 2.60 (m, 5H), 2.30 (s, 6H), 2.03 (qd, 1H), 1.87 (m, 3H), 1.65 (m, 2H). MS (EI) for C$_{29}$H$_{33}$F$_2$N$_3$O, found 478.1 (MH+). Analytical HPLC, ret. time=19.088 min, 97% purity.

Compound K1—N-((4-(1-(2-(2,6-Difluorophenyl) acetyl)piperidin-4-yl)-2-methylpyrimidin-5-yl) methyl)-3,5-dimethylbenzamide K1.1: 4-(1-(2-(2,6-Difluorophenyl)acetyl)piperidin-4-yl)-2-methylpyrimidine-5-carboxamide A mixture of A1.4 (300 mg, 0.744 mmol) and NH$_4$OH (4 mL) was stirred for 21 h at 80° C. The resulting solution was cooled to room temperature and extracted with EtOAc (5 mL, 3×3 mL). The combined organic layers were concentrated under vacuum to give K1.1 (83 mg, 30%) as a white foam. MS (EI) for C$_{19}$H$_{20}$F$_2$N$_4$O$_2$, found 375.0 (MH+).

K1.2: 4-(1-(2-(2,6-Difluorophenyl)acetyl)piperidin-4-yl)-2-methylpyrimidine-5-carbonitrile To a stirred solution of K1.1 (75.0 mg, 0.200 mmol), Et$_3$N (0.14 mL, 1.0 mmol) and THF (2 mL) at 0° C. was added trifluoroacetic anhydride (210 mg, 1.00 mmol). After stirring for 10 min at room temperature, the resulting mixture was concentrated, dissolved in water (3 mL), and extracted with EtOAc (2×2 mL). The combined organic layers were concentrated and purified by silica gel column chromatography (hexane/EtOAc=3:2) to give K1.2 (53.0 mg, 74%) as a white solid. MS (EI) for C$_{19}$H$_{18}$F$_2$N$_4$O, found 357.0 (MH+).

K1.3: 1-(4-(5-(Aminomethyl)-2-methylpyrimidin-4-yl)piperidin-1-yl)-2-(2,6-difluorophenyl)ethanone A mixture of K1.2 (53.0 mg, 0.149 mmol), Pd/C (158 mg, 10 wt. %, 0.149 mmol) and NH$_3$ in MeOH (4 mL, 2N) was stirred for 1.5 h at room temperature under a balloon of hydrogen. The mixture was filtered through Celite and the filtrate was concentrated. The residue was dissolved in EtOAc (2.7 mL) and MeOH (0.3 mL), and the resulting solution was filtered and concentrated to give K1.3 (46 mg, 86%) as a white solid. MS (EI) for C$_{19}$H$_{22}$F$_2$N$_4$O, found 361.1 (MH+).

Compound K1

To a stirred solution of K1.3 (12.0 mg, 0.0333 mmol), 3,5-dimethylbenzoic acid (7.3 mg, 0.049 mmol), HATU (23.2 mg, 0.0609 mmol) and DMF (0.5 mL) was added DIEA (20 μL, 0.12 mmol). After stirring for 30 min at room temperature, aq. sat. NaHCO$_3$ (2 mL) and water (1 mL) were added and the resulting solution was extracted with EtOAc (2×2 mL). The combined organic layers were concentrated and purified by silica gel column chromatography (hexane/EtOAc=1:5→1:10) to give Compound K1 (13 mg, 79%) as a white solid after lyophilization. $^1$H-NMR (400 MHz, CDCl$_3$): δ 8.51 (s, 1H), 7.34 (s, 2H), 7.22 (m, 1H), 7.16 (s, 1H), 6.90 (t, 2H), 6.27 (t, 1H), 4.72 (m, 1H), 4.69 (d, 2H), 4.10 (d, 1H), 3.75 (s, 2H), 3.25 (m, 2H), 2.71 (m, 1H), 2.70 (s, 3H), 2.35 (s, 6H), 2.05 (qd, 1H), 1.91 (qd, 1H), 1.78 (m, 1H), 1.69 (m, 1H). MS (EI) for C$_{28}$H$_{30}$F$_2$N$_4$O$_2$, found 493.1 (MH+). Analytical HPLC, ret. time=14.908 min, 95% purity.

Compound L1—N-(3,4-Dichlorobenzyl)-4-(1-(2-(2,6-difluorophenyl)acetyl)piperidin-4-yl)pyrimidine-5-carbothioamide L1.1: tert-Butyl 4-(5-(3,4-dichlorobenzylcarbamoyl) pyrimidin-4-yl)piperidine-1-carboxylate L1.1 was synthesized from A99.3 in an identical manner to that from which A99.4 was synthesized from A99.3.

L1.2: N-(3,4-Dichlorobenzyl)-4-(piperidin-4-yl) pyrimidine-5-carbothioamide

To a solution of L1.1 (525 mg, 1.1 mmol) in 1,4-dioxane (4 mL) was added Lawesson's reagent (547 mg, 1.35 mmol). The resulting mixture was stirred at 100° C. for 5 h, and then cooled to room temperature. To this mixture was added 4 N HCl/dioxane (2 mL) and MeOH (10 mL). The stirring was continued for 2 h. Water (25 mL) was added. The aq. phase was washed with EtOAc, basified with 20% NaOH solution, and extracted with EtOAc. The organic phase was dried over sodium sulfate, filtered, and concentrated. The crude L1.2 was used as is in the next step.

Compound L1

L1.2 (131 mg, 0.34 mmol) was mixed with 2,6-difluorophenylacetic acid (70 mg, 0.41 mmol), HOBt (69 mg, 0.51 mmol) and DIEA (258 mg, 2 mmol) in THF (5 mL). To this solution was added EDC (98 mg, 0.51 mmol). The resulting reaction mixture was stirred at room temperature for 5 h then diluted with aq. sat. NaHCO₃. The resulting mixture was extracted with EtOAc and the organic mixture was dried over sodium sulfate, filtered, and concentrated. The crude product was purified by prep HPLC to give Compound L1. ¹H-NMR (400 MHz, DMSO-d6): δ 11.23 (br s, 1H), 9.13 (s, 1H), 8.61 (s, 1H), 7.70 (m, 2H), 7.45 (m, 1H), 7.35 (m, 1H), 7.07 (m, 2H), 4.98 (m, 2H), 4.45 (d, 1H), 4.15 (d, 1H), 3.83 (d, 1H), 3.75 (d, 1H), 3.05 (m, 2H), 2.46 (m, 1H), 1.70 (m, 4H). MS (EI) for $C_{25}H_{22}Cl_2F_2N_4OS$, found: 535.1 (MH+). Analytical HPLC, ret. time=25.0 min, 93% purity.

Compound M1—2-(3-Chlorophenoxy)-1-(4-(1-(2-(2,6-difluorophenyl)acetyl)piperidin-4-yl)-2-methyl-pyrimidin-5-yl)ethanone M1.1: 2-Bromo-1-(4-(1-(2-(2,6-difluorophenyl) acetyl)piperidin-4-yl)-2-methylpyrimidin-5-yl)etha-none To a solution of B3.1 (100 mg, 0.26 mmol) in AcOH (1 mL) was added 0.3 mL of 33% HBr/AcOH, followed by the addition of Br₂ (0.5 mL, 0.5 M in CHCl₃). The mixture was stirred at room temperature for 30 min. Aq. sat. NaHCO₃ was added to quench the reaction. The mixture was extracted with CH₂Cl₂ and the organic phase was dried over sodium sulfate, filtered, and concentrated. Crude M1.1 was used as is in the next step.

Compound M1

M1.1 (0.2 mmol) was mixed with 3-chlorophenol (51 mg, 0.4 mmol) and K₂CO₃ (60 mg, 0.43 mmol) in acetone (3 mL). The resulting mixture was stirred at 50° C. for 12 h and then water was added. The mixture was extracted with EtOAc and the organic phase was dried over sodium sulfate, filtered, and concentrated. The crude product was purified by flash column chromatography to give Compound M1. ¹H-NMR (400 MHz, DMSO-d6): δ 9.18 (s, 1H), 7.32 (m, 2H), 7.11 (m, 5H), 5.55 (s, 2H), 4.46 (d, 1H), 4.18 (d, 1H), 3.82 (d, 1H), 3.73 (d, 1H), 3.45 (m, 1H), 3.18 (m, 1H), 2.68 (s, 3H), 2.62 (m, 1H), 1.70 (m, 4H). MS (EI) for $C_{26}H_{24}ClF_2N_3O_3$, found: 500.0 (MH+). Analytical HPLC, ret. time=3.48 min, 90% purity.

Common Intermediate CI1: Ethyl 4-(1-(tert-butoxy-carbonyl)piperidin-4-yl)-2-methylpyrimidine-5-car-boxylate CI1.1: tert-Butyl 4-(3-(dimethylamino)-2-(ethoxy-carbonyl)acryloyl)piperidine-1-carboxylate tert-Butyl 4-(3-ethoxy-3-oxopropanoyl)piperidine-1-carboxylate (40 g, 133 mmol) and dimethylformamide dimethylacetal (DMF-DMA) (19 g, 160 mmol) were dissolved in toluene (40 mL). The solution was stirred under reflux for 5 h and cooled to room temperature. The solution was concentrated and used as is in the next reaction.

Common Intermediate CI1

To a suspension of acetamidine hydrochloride (15.1 g, 160 mmol) in EtOH (100 mL) was added EtONa (11 g, 160 mmol). The resulting mixture was stirred for 15 min at room temperature. Crude enamine intermediate CI1.1 was dissolved in EtOH (100 mL) and added to the acetamidine hydrochloride mixture. The mixture was heated to 70° C. with stirring for 2 h. The solvent was removed under reduced pressure. The residue was stirred in EtOAc (500 mL) and filtered. Concentration of the filtrate gave the crude product, which was further purified by flash column chromatography.

Common Intermediate CI2: Methyl/Ethyl 4-(1-(tert-butoxycarbonyl)piperidin-4-yl)-2,6-dimethylpyrimi-dine-5-carboxylate CI2.1: tert-Butyl 4-(2-(ethoxy(or methoxy)carbo-nyl)-3-methoxybut-2-enoyl)piperidine-1-carboxylate tert-Butyl-4-(3-ethoxy-3-oxopropanoyl)piperidine-1-car-boxylate (6.0 g, 20.0 mmol), AcOH (57 μL, 1.0 mmol), trimethyl orthoacetate, (3.0 mL), pyridine (80 μL, 1.0 mmol), and toluene (100 mL) were charged into a 250 mL flask equipped with fractional distillation apparatus. The reaction mixture was stirred at 130° C. (bath temperature) and the solvent distilled at about the boiling point of the MeOH/toluene azeotrope for 48 h. The reaction mixture was cooled to room temperature and concentrated in vacuo to give CI2.1 which was used directly in the next step.

Common Intermediate CI2

To a stirred suspension of acetamidine HCl (2.84 g, 30.0 mmol) in EtOH (60 mL) was added NaOEt (2.05 g, 30.0 mmol) and the reaction mixture was stirred at room temperature for 30 min. To this suspension was added the crude intermediate CI2.1 in EtOH (20 mL) slowly at room temperature and the resulting mixture was stirred at reflux for 5 h. The reaction mixture was cooled down to room temperature, concentrated under reduced pressure, and the residue was partitioned between water and CH₂Cl₂. The separated aq. layer was extracted with CH₂Cl₂ (×2) and the combined organic layers were dried over sodium sulfate, concentrated in vacuo, and purified by flash chromatography to give a mixture of the methyl and ethyl esters of CI2 (2.51 g, ca. 35%).

General Procedure 1: Ester Hydrolysis

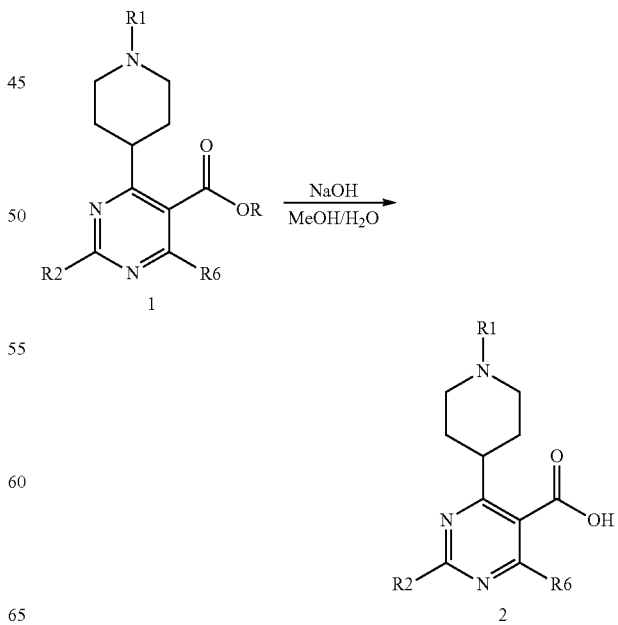

To a stirred solution of ester 1 (5.0 mmol) in MeOH (30 mL) was added aq. 1N NaOH (20 mL) and the reaction mixture was stirred at room temperature overnight. MeOH was removed in vacuo and the residual aq. layer was acidified with 1N HCl to pH 4-5, and extracted with CH$_2$Cl$_2$ (×5). The combined organic layers were dried over sodium sulfate and concentrated in vacuo to give acid 2 (~97% yield). Alternatively, LiOH can be substituted for NaOH using THF as the solvent instead of MeOH. Mild heating can also be used to facilitate the ester hydrolysis.

General Procedure 2: Boc Deprotection

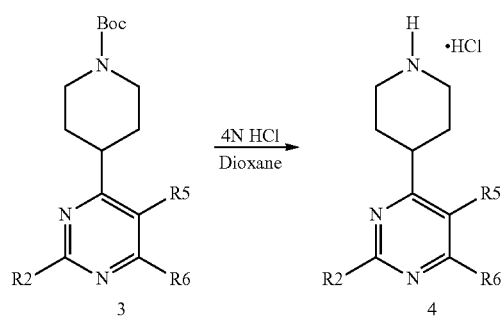

To a solution of 3 (13.7 mmol) in an appropriate solvent such as EtOH, MeOH, DCE or dioxane (20 mL) was added 4N HCl in dioxane (12 mL). The resulting solution was stirred for 12 h at room temperature. Ether (100 mL) was added with stirring. The resulting solid was filtered and dried under vacuum. The crude solid HCl salt 4 was used in the next step without further purification. If no filterable solid formed, the reaction mixture was concentrated in vacuo and the residue was used for the next step without further purification. Alternatively, trifluoroacetic acid can be used instead of 4N HCl in dioxane. The reaction mixture is concentrated in vacuo once Boc deprotection is complete and the crude TFA salt is used for the next step without further purification.

General Procedure 3: Amide Linker Coupling

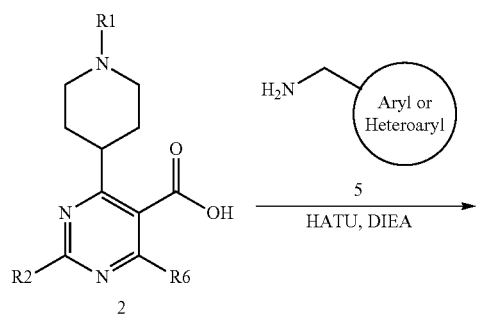

-continued

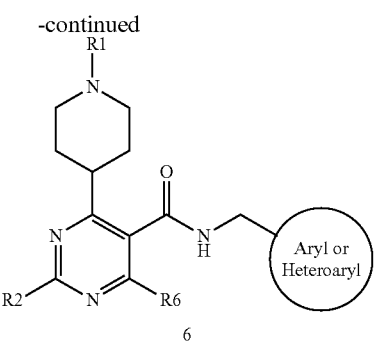

Carboxylic acid 2 (0.39 mmol) was mixed with amine 5 (0.45 mmol) and DIEA (0.5 mL) in THF (3 mL). To this solution was added 2-(1H-7-azabenzotriazol-1-yl)-1,1,3,3-tetramethyluronoium hexafluorphosphate (HATU) (0.58 mmol). The resulting reaction mixture was stirred at room temperature for 2 h then diluted with aq. sat. NaHCO$_3$. The mixture was extracted with CH$_2$Cl$_2$, dried over sodium sulfate, filtered, and concentrated. The crude mixture was purified by flash chromatography or preparative HPLC to give amide 6.

General Procedure 4: Phenylacetamide Formation

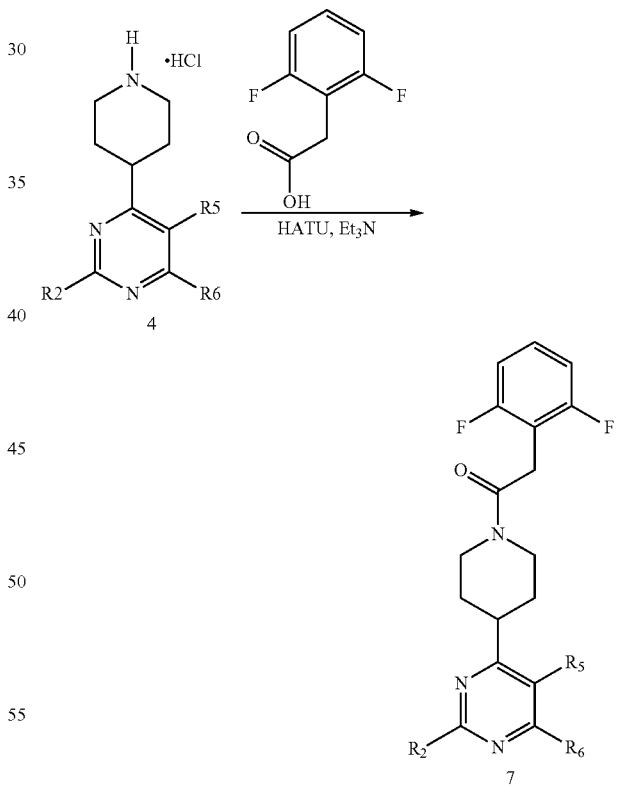

A mixture of amine 4, 2,6-difluorophenylacetic acid (8.31 mmol), Et$_3$N (34.6 mmol) and DMF (20 mL) was treated with HATU (8.31 mmol) and the resulting mixture was stirred at room temperature for 1 h. The reaction mixture was diluted with EtOAc, washed with aq. sodium bicarbonate, brine, dried over sodium sulfate, concentrated in vacuo and the residue purified by flash chromatography to afford phenylacetamide 7 (~81% yield).

General Procedure 5: Phenylurea Formation

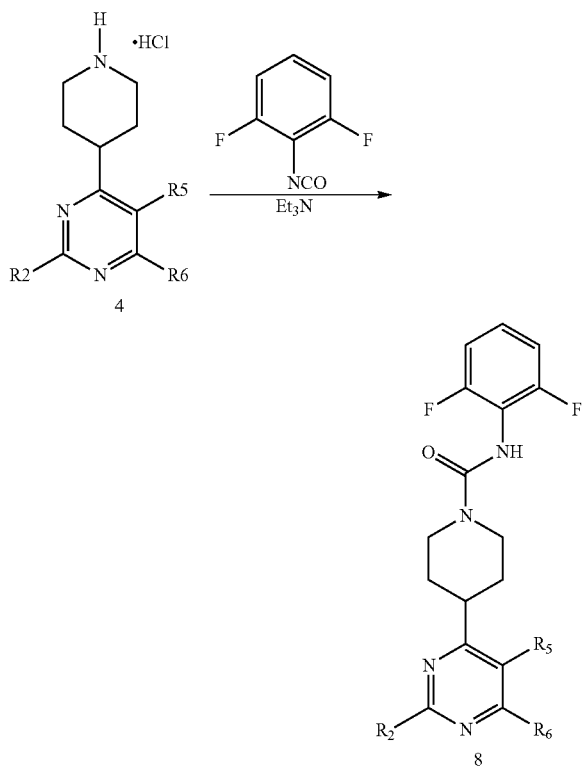

Amine 4 (0.2 mmol), 2,6-difluorophenyl isocyanate (0.4 mmol) and Et$_3$N (1 mmol) were mixed in an appropriate solvent such as CH$_2$Cl$_2$ or acetone (2 mL). The solution was stirred at room temperature for 30 min and diluted with EtOAc (25 mL). The organic phase was washed with NaHCO$_3$, brine, dried over sodium sulfate and concentrated. The crude mixture was purified by flash chromatography or prep HPLC to give phenylurea 8.

General Procedure 6: Oxidation of Methylthio Compounds to Methylsulfonyl Compounds

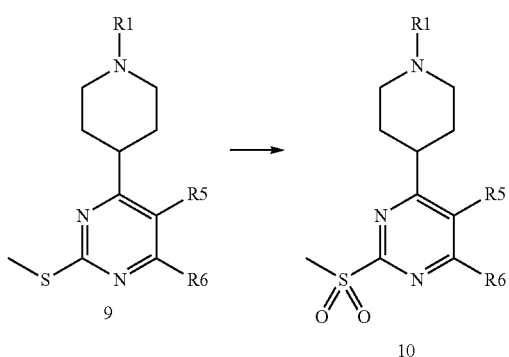

To a 0° C. solution of 9 (0.088 mmol) in CH$_2$Cl$_2$ (3 mL) was added meta-chloroperoxybenzoic acid (mCPBA) (55 mg, 0.22 mmol, ~70%). The resulting mixture was stirred for 2 h while slowly warming to room temperature. Aq. sat. NaHCO$_3$ was added. The mixture was extracted with CH$_2$Cl$_2$ and the organic phase was washed with aq. Na$_2$SO$_3$ solution, dried over sodium sulfate, filtered, and concentrated. The resulting product can be used crude or purified by flash column chromatography.

General Procedure 7: Conversion of 2-(Methylsulfonyl) Pyrimidines to 2-Aminopyrimidines

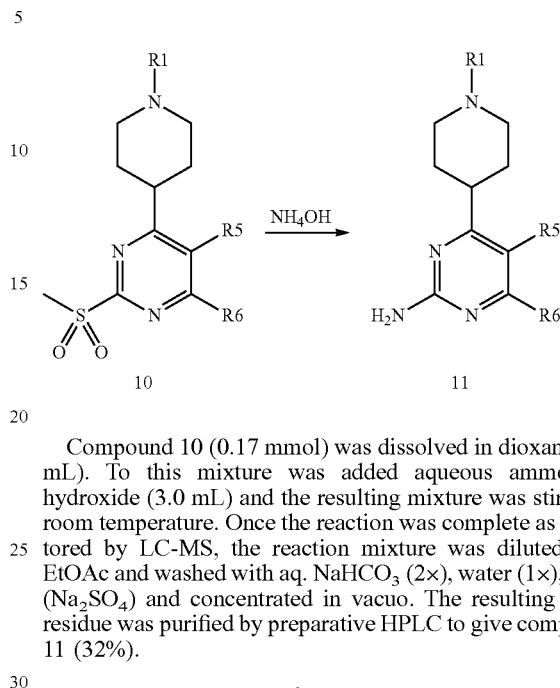

Compound 10 (0.17 mmol) was dissolved in dioxane (3.0 mL). To this mixture was added aqueous ammonium hydroxide (3.0 mL) and the resulting mixture was stirred at room temperature. Once the reaction was complete as monitored by LC-MS, the reaction mixture was diluted with EtOAc and washed with aq. NaHCO$_3$ (2×), water (1×), dried (Na$_2$SO$_4$) and concentrated in vacuo. The resulting crude residue was purified by preparative HPLC to give compound 11 (32%).

Compound A116: 4-{1-[(2,6-Difluorophenyl)(difluoro)acetyl]piperidin-4-yl}-N-[(3,5-dimethylphenyl)methyl]-2-methylpyrimidine-5-carboxamide A116.1: 4-(1-(tert-Butoxycarbonyl)piperidin-4-yl)-2-methylpyrimidine-5-carboxylic acid Intermediate A116.1 was made from the ester hydrolysis of Common Intermediate CI1 using General Procedure 1.

A116.2: tert-Butyl 4-(5-(3,5-dimethylbenzylcarbamoyl)-2-methylpyrimidin-4-yl)piperidine-1-carboxylate Intermediate A116.2 was made from coupling intermediate A116.1 with 3,5-dimethylbenzylamine using General Procedure 3.

A116.3: N-(3,5-Dimethylbenzyl)-2-methyl-4-(piperidin-4-yl)pyrimidine-5-carboxamide hydrochloride salt Intermediate A116.3 was made from the Boc deprotection of intermediate A116.2 using General Procedure 2.

A116.4: 2-(2,6-Difluorophenyl)-2,2-difluoroacetyl chloride

To a solution of 2-(2,6-difluorophenyl)-2,2-difluoroacetic acid (23 mg, 0.13 mmol) and oxalyl chloride (17 mg, 0.13 mmol) in DCM (1 mL) was added 1 drop of DMF with stirring at room temperature for 10 min. The resulting crude reaction solution was used as is in the next reaction.

Compound A116

Intermediate A116.3 (50 mg, 0.12 mmol) was added to the above solution of intermediate A116.4, followed by DIEA (63 mg, 0.49 mmol). The resulting mixture was stirred at RT for 30 min, and then quenched with ice water. The crude mixture was partitioned between EtOAc and saturated aqueous $KHCO_3$. The organic phase was washed with brine, dried over $MgSO_4$, and concentrated. The crude product was purified on prep HPLC to give Compound A116 as a white solid (11 mg). $^1$H-NMR (400 MHz, $CDCl_3$): δ 8.57 (s, 1H), 7.45 (m, 1H), 6.98 (t, 2H), 6.95 (s, 3H), 6.11 (t, 1H), 4.66 (d, 1H), 4.55 (m, 2H), 4.25 (d, 1H), 3.46 (m, 1H), 3.12 (t, 1H), 2.82 (t, 1H), 2.71 (s, 3H), 2.31 (s, 6H), 2.00-1.80 (m, 4H). MS (EI) for $C_{28}H_{28}F_4N_4O_2$, found: 529.2 (MH+). Analytical HPLC, ret. time=15.20 min, 98% purity.

Compound A117: 4-{1-[Difluoro(phenyl)acetyl]piperidin-4-yl}-N-[(3,5-dimethylphenyl)methyl]-2-methylpyrimidine-5-carboxamide Compound A117 was made in a manner similar to Compound A116: $^1$H-NMR (400 MHz, $CDCl_3$): δ 8.55 (s, 1H), 7.58-7.56 (m, 2H), 7.49-7.47 (m, 3H), 6.94-6.93 (m, 3H), 6.13 (t, 1H), 4.71 (d, 1H), 4.52 (d, 2H), 4.01 (d, 1H), 3.39 (m, 1H), 2.92 (m, 1H), 2.76 (t, 1H), 2.69 (s, 3H), 2.29 (s, 6H), 1.96-1.82 (m, 2H), 1.71-1.61 (m, 2H). MS (EI) for $C_{28}H_{30}F_2N_4O_2$, found: 393.2 (MH+). Analytical HPLC, ret. time=14.96 min, 99% purity.

Compound A118: 4-{1-[Difluoro(2-fluorophenyl)acetyl]piperidin-4-yl}-N-[(3,5-dimethylphenyl)methyl]-2-methylpyrimidine-5-carboxamide Compound A118 was made in a manner similar to Compound A116: $^1$H-NMR (400 MHz, $CDCl_3$): δ 8.56 (s, 1H), 7.58 (t, 1H), 7.49 (dd, 1H), 7.25 (m, 1H), 7.16 (t, 1H), 6.95 (s, 3H), 6.12 (t, 1H), 4.67 (d, 1H), 4.54 (m, 2H), 4.25 (d, 1H), 3.44 (m, 1H), 3.09 (m, 1H), 2.80 (t, 1H), 2.71 (s, 3H), 2.31 (s, 6H), 2.00-1.77 (m, 4H). MS (EI) for $C_{28}H_{29}F_3N_4O_2$, found: 511.2 (MH+). Analytical HPLC, ret. time=15.10 min, 99% purity.

Compound A119: 2-Chlorophenyl 4-[5-({[(3,5-dimethylphenyl)methyl]amino}carbonyl)-2-methylpyrimidin-4-yl]piperidine-1-carboxylate To a mixture of intermediate A116.3 (50 mg, 0.12 mmol), diisopropylethylamine (DIEA) (63 mg, 0.49 mmol) and anhydrous THF (1.2 mL) was added 2-chlorophenyl chloroformate (26 mg, 0.13 mmol) at RT and the mixture was stirred at RT for 16 h. The resulting mixture was diluted with EtOAc and the mixture was partitioned between EtOAc and saturated aqueous sodium carbonate solution. The organic phase was separated, washed with brine, dried over $MgSO_4$, filtered, and concentrated in vacuo. The residue was purified on prep. HPLC to afford Compound A119 as a while solid (29 mg). $^1$H-NMR (400 MHz, $CDCl_3$): δ 8.58 (s, 1H), 7.43 (d, 1H), 7.30-7.23 (m, 2H), 7.18-7.14 (t, 1H), 6.97 (s, 3H), 6.16 (t, 1H), 4.56 (m, 2H), 4.48 (d, 1H), 4.33 (d, 1H), 3.4 (m, 1H), 3.11 (t, 1H), 2.94 (t, 1H), 2.72 (s, 3H), 2.33 (s, 6H), 2.10-1.98 (m, 2H), 1.85 (t, 2H). MS (EI) for $C_{27}H_{29}ClN_4O_3$, found: 493.1 (MH+). Analytical HPLC, ret. time=15.77 min, 99% purity.

Compound A120: 2,6-Difluorophenyl 4-[5-({[(3,5-dimethylphenyl)methyl]amino}carbonyl)-2-methylpyrimidin-4-yl]piperidine-1-carboxylate Compound A120 was made in a manner similar to Compound A119: $^1$H-NMR (400 MHz, $CDCl_3$): δ 8.59 (s, 1H), 7.14 (m, 1H), 7.00-6.95 (m, 5H), 6.10 (t, 1H), 4.57 (m, 2H), 4.45 (d, 1H), 4.33 (d, 1H), 3.42 (m, 1H), 3.12 (t, 1H), 2.96 (t, 1H), 2.73 (s, 3H), 2.33 (s, 6H), 2.10-2.00 (m, 2H), 1.86 (t, 2H). MS (EI) for $C_{27}H_{28}F_2N_4O_3$, found: 495.3 (MH+). Analytical HPLC, ret. time=15.88 min, 99% purity.

Compound A121: 4-{1-[(2,6-Difluorophenyl)acetyl]piperidin-4-yl}-2,6-dimethyl-N-{[2-(trifluoromethyl)pyrimidin-4-yl]methyl}pyrimidine-5-carboxamide A121.1: 4-(1-(tert-Butoxycarbonyl)piperidin-4-yl)-2,6-dimethylpyrimidine-5-carboxylic acid Intermediate A121.1 was made from the ester hydrolysis of Common Intermediate CI2 using General Procedure 1.

A121.2: tert-Butyl 4-(2,6-dimethyl-5-((2-(trifluoromethyl)pyrimidin-4-yl)methylcarbamoyl)pyrimidin-4-yl)piperidine-1-carboxylate Intermediate A121.2 was made from coupling intermediate A121.1 with (2-(trifluoromethyl)pyrimidin-4-yl)methanamine using General Procedure 3.

A121.3: 2,4-Dimethyl-6-(piperidin-4-yl)-N-((2-(trifluoromethyl)pyrimidin-4-yl)methyl)pyrimidine-5-carboxamide hydrochloride salt Intermediate A121.3 was made from the Boc deprotection of intermediate A121.2 using General Procedure 2.

Compound A121

Compound A121 was made from intermediate A121.3 and 2,6-difluorophenylacetic acid using General Procedure 4. $^1$H-NMR (400 MHz, $CDCl_3$): δ 8.92 (d, 1H), 7.59 (d, 1H), 7.22 (m, 1H), 6.89 (t, 2H), 6.86 (t, 1H), 4.92 (d, 1H), 4.86 (d, 1H), 4.68 (d, 1H), 4.07 (d, 1H), 3.73 (d, 2H), 3.10 (m, 1H), 2.91 (tt, 1H), 2.69 (s, 3H), 2.58 (td, 1H), 2.50 (s, 3H), 2.04 (qd, 1H), 1.93 (qd, 1H), 1.81 (m, 2H). MS (EI) for $C_{26}H_{25}F_5N_6O_2$, found 549.2 (MH+). Analytical HPLC, ret. time=14.252 min, 96% purity.

Compound A122: 4-(1-{[(2,6-difluorophenyl)amino]carbonyl}piperidin-4-yl)-2,6-dimethyl-N-{[2-(trifluoromethyl)pyrimidin-4-yl]methyl}pyrimidine-5-carboxamide Compound A122 was made from intermediate A121.3 and 2,6-difluorophenyl isocyanate using General Procedure 5. $^1$H-NMR (400 MHz, $CDCl_3$): δ 8.93 (d, 1H), 7.59 (d, 1H), 7.11 (m, 1H), 6.93 (t, 2H), 6.89 (t, 1H), 5.88 (s, 1H), 4.89 (d, 2H), 4.18 (d, 2H), 2.90 (m, 3H), 2.69 (s, 3H), 2.51 (s, 3H), 2.07 (qd, 2H), 1.82 (m, 2H). MS (EI) for $C_{25}H_{24}F_5N_7O_2$, found 550.2 (MH+). Analytical HPLC, ret. time=12.496 min, 97% purity.

Compound A123: 2,6-Difluorophenyl 4-{2,6-dimethyl-5-[({[2-(trifluoromethyl)pyrimidin-4-yl]methyl}amino)carbonyl]pyrimidin-4-yl}piperidine-1-carboxylate Compound A123 was made from intermediate A121.3 and 2,6-difluorophenyl chloroformate (prepared using a general method according to the literature procedure as described in *J. Med. Chem.* 2006, 49, 4981) using a method analogous to that used to convert intermediate A116.3 to Compound A119. $^1$H-NMR (400 MHz, CDCl$_3$): δ 8.94 (d, 1H), 7.60 (d, 1H), 7.14 (m, 1H), 7.00-6.95 (m, 2H), 6.84 (t, 1H), 4.92 (dd, 2H), 4.43 (d, 1H), 4.31 (d, 1H), 3.03 (t, 1H), 2.92-2.84 (m, 2H), 2.71 (s, 3H), 2.51 (s, 3H), 2.13-2.06 (m, 2H), 1.84-1.81 (m, 2H). 1MS (EI) for C$_{25}$H$_{23}$F$_5$N$_6$O$_3$, found: 551.2 (MH+). Analytical HPLC, ret. time=13.21 min, 99% purity.

Compound A124: 2-Fluorophenyl 4-{2,6-dimethyl-5-[({[2-(trifluoromethyl)pyrimidin-4-yl]methyl}amino)carbonyl]pyrimidin-4-yl}piperidine-1-carboxylate Compound A124 was made in a manner similar to Compound A123: $^1$H-NMR (400 MHz, CDCl$_3$): δ 8.94 (d, 1H), 7.60 (d, 1H), 7.22-7.10 (m, 4H), 6.84 (t, 1H), 4.91 (t, 2H), 4.42 (d, 1H), 4.33 (d, 1H), 2.99 (t, 1H), 2.92-2.81 (m, 2H), 2.71 (s, 3H), 2.51 (s, 3H), 2.08 (m, 2H), 1.81 (d, 2H). MS (EI) for C$_{25}$H$_{24}$F$_4$N$_6$O$_3$, found: 533.2 (MH+). Analytical HPLC, ret. time=12.66 min, 99% purity.

Compound A125: Phenyl 4-{2,6-dimethyl-5-[({[2-(trifluoromethyl)pyrimidin-4-yl]methyl}amino)carbonyl]pyrimidin-4-yl}piperidine-1-carboxylate Compound A125 was made in a manner similar to Compound A123: $^1$H-NMR (400 MHz, CDCl$_3$): δ 8.34 (d, 1H), 7.61 (d, 1H), 7.37 (t, 2H), 7.20 (t, 1H), 7.12 (d, 2H), 4.91 (m, 2H), 4.42-4.34 (m, 2H), 2.96-2.80 (m, 3H), 2.71 (s, 3H), 2.52 (s, 3H), 2.10-2.03 (m, 2H), 1.81 (d, 2H). MS (EI) for C$_{25}$H$_{25}$F$_3$N$_6$O$_3$, found: 515.2 (MH+). Analytical HPLC, ret. time=12.34 min, 99% purity.

Compound A126: 2-Fluorophenyl 4-{2-amino-6-methyl-5-[({[2-(trifluoromethyl)pyrimidin-4-yl]methyl}amino)carbonyl]pyrimidin-4-yl}piperidine-1-carboxylate Compound A126 was made in five steps from intermediate C48.2 in the same manner that Compound A123 was made in three steps from intermediate A121.1. 2-Fluorophenyl chloroformate was substituted for 2,6-difluorophenyl chloroformate in the third step and the additional steps of methyl sulfide oxidation (as outlined in General Procedure 6) and conversion of the resulting 2-(methylsulfonyl)pyrimidine to the corresponding 2-aminopyrimidine (as outlined in General Procedure 7) were added to the reaction sequence. $^1$H-NMR (400 MHz, CDCl$_3$): δ 8.92 (d, 1H), 7.59 (d, 1H), 7.15 (m, 4H), 8.86 (t, 1H), 5.13 (s, 2H), 4.86 (dd, 2H), 4.39 (d, 1H), 4.29 (d, 1H), 2.97 (t, 1H), 2.82 (m, 2H), 2.38 (s, 3H), 1.98 (m, 2H), 1.80 (m, 2H). MS (EI) for C$_{24}$H$_{23}$F$_4$N$_7$O$_3$, found 534.2 (MH+). Analytical HPLC, ret. time=10.616 min, 99% purity.

Compound B36: N-(2,6-Difluorophenyl)-4-{2-methyl-5-[(1E)-N-{[2-(trifluoromethyl)pyrimidin-4-yl]oxy}ethanimidoyl]pyrimidin-4-yl}piperidine-1-carboxamide B36.1: tert-Butyl 4-(5-acetyl-2-methylpyrimidin-4-yl)piperidine-1-carboxylate To a stirred mixture of intermediate acid A116.1 (3.07 g, 9.55 mmol), N,O-dimethylhydroxylamine hydrogenchloride (1.12 g, 11.5 mmol), and Et$_3$N (5.32 mL, 38.2 mmol) in dimethylacetamide (DMA) (30 mL) was added HATU (4.36 g, 11.5 mmol) and the reaction mixture was stirred at room temperature for 1 h. The reaction mixture was diluted with EtOAc, washed with aq. sodium bicarbonate, brine, dried over sodium sulfate and concentrated in vacuo to give the corresponding Weinreb amide, which was directly used for the next step. The crude Weinreb amide was dissolved in THF (30 mL) and the resulting solution was treated with MeMgBr (27.3 mL, 1.4 M in THF/toluene, 38.2 mmol) at room temperature. After stirring for 2 h, the reaction mixture was cooled to 0° C., quenched with aq. NH$_4$Cl and extracted with EtOAc (×2). The combined organic layers were dried over sodium sulfate, concentrated in vacuo, and the residue was purified by flash chromatography to give ketone intermediate B36.1 (2.76 g, 90% in 2 steps).

B36.2: tert-Butyl 4-(5-(1-(hydroxyimino)ethyl)-2-methylpyrimidin-4-yl)piperidine-1-carboxylate To a stirred solution of B36.1 (53.0 mg, 0.166 mmol) in ethanol (1 mL) were added hydroxylamine•HCl (34.6 mg, 0.498 mmol) and a catalytic amount of conc HCl. After stirring for 23 h at room temperature, aqueous saturated NaHCO$_3$ (2 mL) was added and the resulting solution was extracted with EtOAc (3×2 mL). The combined organic layers were concentrated and purified by silica gel column chromatography (Hexane/EtOAc=3:2→2:3) to give B36.2 (29 mg, 52%) as a white foam. MS (EI) for C$_{17}$H$_{26}$N$_4$O$_3$, found 335.2 (MH+).

B36.3: tert-Butyl 4-(2-methyl-5-(1-(2-(trifluoromethyl)pyrimidin-4-yloxyimino)ethyl)pyrimidin-4-yl)piperidine-1-carboxylate To a stirred solution of B36.2 (36.6 mg, 0.109 mmol) and 4-chloro-2-(trifluoromethyl)pyrimidine (59.7 mg, 0.327 mmol) in DMA (0.6 mL) at room temperature was added potassium carbonate (60.3 mg, 0.436 mmol). After stirring for 5 h, the mixture was filtered through Celite. The filtrate was concentrated and purified by silica gel column chromatography (Hexane/EtOAc=3:2→4:3) to give B36.3 (50 mg, 95%) as a white foam. MS (EI) for C$_{22}$H$_{27}$F$_3$N$_6$O$_3$, found 481.2 (MH+).

B36.4: 1-(2-Methyl-4-(piperidin-4-yl)pyrimidin-5-yl)ethanone O-2-(trifluoromethyl)pyrimidin-4-yl oxime hydrochloride salt Intermediate B36.4 was made from the Boc deprotection of intermediate B36.3 using General Procedure 2.

Compound B36:

Compound B36 was made from intermediate B36.4 and 2,6-difluorophenyl isocyanate using General Procedure 5. $^1$H-NMR (400 MHz, CDCl$_3$): δ 8.79 (d, 1H), 8.57 (s, 1H), 7.41 (d, 1H), 7.12 (m, 1H), 6.94 (t, 2H), 5.90 (s, 1H), 4.26 (d, 2H), 3.13 (tt, 1H), 3.01 (td, 2H), 2.78 (s, 3H), 2.59 (s, 3H), 2.15 (qd, 2H), 1.85 (m, 2H). MS (EI) for C$_{24}$H$_{22}$F$_5$N$_7$O$_2$, found 536.2 (MH+). Analytical HPLC, ret. time=17.128 min, 99% purity.

Compound B37: N-(2,6-Difluorophenyl)-4-{2-methyl-5-[(1E)-N-{[2-(trifluoromethyl)pyridin-4-yl]oxy}ethanimidoyl]pyrimidin-4-yl}piperidine-1-carboxamide Compound B37 was made in a manner similar to Compound B36: $^1$H-NMR (400 MHz, CDCl$_3$): δ 8.62 (d, 1H), 8.57 (s, 1H), 7.54 (d, 1H), 7.29 (dd, 1H), 7.12 (m, 1H), 6.94 (t, 2H), 5.89 (s, 1H), 4.26 (d, 2H), 3.15 (tt, 1H), 3.00 (td, 2H), 2.77 (s, 3H), 2.52 (s, 3H), 4.16 (qd, 2H), 1.85 (m, 2H). MS (EI) for $C_{25}H_{23}F_5N_6O_2$, found 535.1 (MH+). Analytical HPLC, ret. time=17.632 min, 95% purity.

Compound B38: N-(2,6-Difluorophenyl)-4-{2-methyl-5-[(1E)-N-{[6-(trifluoromethyl)pyridin-2-yl]oxy}ethanimidoyl]pyrimidin-4-yl}piperidine-1-carboxamide Compound B38 was made in a manner similar to Compound B36: $^1$H-NMR (400 MHz, CDCl$_3$): δ 8.57 (s, 1H), 7.90 (t, 1H), 7.45 (t, 2H), 7.11 (m, 1H), 6.93 (t, 2H), 5.88 (s, 1H), 4.24 (d, 2H), 3.23 (tt, 1H), 3.00 (td, 2H), 2.76 (s, 3H), 2.56 (s, 3H), 2.13 (qd, 2H), 1.86 (m, 2H). MS (EI) for $C_{25}H_{23}F_5N_6O_2$, found 535.1 (MH+). Analytical HPLC, ret. time=18.228 min, 97% purity.

Compound B39: N-[2-Fluoro-6-(trifluoromethyl)phenyl]-4-{2-methyl-5-[(1E)-N-{[2-(trifluoromethyl)pyrimidin-4-yl]oxy}ethanimidoyl]pyrimidin-4-yl}piperidine-1-carboxamide Compound B39 was made in a manner similar to Compound B36: $^1$H-NMR (400 MHz, CDCl$_3$): δ 8.79 (d, 1H), 8.57 (s, 1H), 7.45 (m, 1H), 7.40 (d, 1H), 7.33 (m, 2H), 6.08 (s, 1H), 4.20 (d, 2H), 3.15 (tt, 1H), 3.02 (td, 2H), 2.77 (s, 3H), 2.58 (s, 3H), 2.15 (qd, 2H), 1.85 (m, 2H). MS (EI) for $C_{25}H_{22}F_7N_7O_2$, found 586.1 (MH+). Analytical HPLC, ret. time=18.352 min, 98% purity.

Compound B40: 4-{5-[(1E)-N-{[2-chloro-6-(trifluoromethyl)pyridin-4-yl]oxy}ethanimidoyl]-2-methylpyrimidin-4-yl}-N-(2,6-difluorophenyl)piperidine-1-carboxamide Compound B40 was made in a manner similar to Compound B36: $^1$H-NMR (400 MHz, CDCl$_3$): δ 8.56 (s, 1H), 7.44 (d, 1H), 7.36 (d, 1H), 7.12 (m, 1H), 6.94 (t, 2H), 5.90 (s, 1H), 4.26 (d, 2H), 3.11 (m, 1H), 3.01 (t, 2H), 2.77 (s, 3H), 2.51 (s, 3H), 2.21-2.09 (m, 2H), 1.84 (d, 2H). MS (EI) for $C_{25}H_{22}ClF_5N_6O_2$, found: 569.2 (MH+). Analytical HPLC, ret. time=16.3 min, 97% purity.

Compound B41: 4-{5-[(1Z)—N-{[2-chloro-6-(trifluoromethyl)pyridin-4-yl]oxy}ethanimidoyl]-2-methylpyrimidin-4-yl}-N-(2,6-difluorophenyl)piperidine-1-carboxamide Z isomer isolated from the same reaction that formed Compound B40. $^1$H-NMR (400 MHz, CDCl$_3$): δ 8.54 (s, 1H), 7.83 (d, 1H), 7.34 (d, 1H), 7.03 (m, 1H), 6.92-6.82 (m, 2H), 5.82 (s, 1H), 4.14 (d, 2H), 3.42 (m, 1H), 2.67 (s, 3H), 2.06-1.98 (m, 2H), 1.91-1.88 (m, 2H). MS (EI) for $C_{25}H_{22}ClF_5N_6O_2$, found: 569.2 (MH+). Analytical HPLC, ret. time=15.5 min, 86% purity.

Compound B42: N-(2,6-difluorophenyl)-4-{2-methyl-5-[(1E)-N-{[6-methyl-2-(trifluoromethyl)pyrimidin-4-yl]oxy}ethanimidoyl]pyrimidin-4-yl}piperidine-1-carboxamide Compound B42 was made in a manner similar to Compound B36: $^1$H-NMR (400 MHz, CDCl$_3$): δ 8.49 (s, 1H), 7.17 (s, 1H), 7.05 (m, 1H), 6.86 (t, 2H), 5.82 (s, 1H), 4.18 (d, 2H), 3.04 (m, 1H), 2.93 (dd, 2H), 2.69 (s, 3H), 2.54 (s, 3H), 2.49 (s, 3H), 2.12-2.02 (m, 2H), 1.77 (d, 2H). MS (EI) for $C_{25}H_{24}F_5N_7O_2$, found: 550.2 (MH+). Analytical HPLC, ret. time=13.97 min, 98% purity.

Compound B43: N-(2,6-Difluorophenyl)-4-{2-methyl-5-[(1E)-N-{[3-(trifluoromethyl)phenyl]oxy}ethanimidoyl]pyrimidin-4-yl}piperidine-1-carboxamide B43.1: tert-Butyl 4-(2-methyl-5-(1-(3-(trifluoromethyl)phenoxyimino)ethyl)pyrimidin-4-yl)piperidine-1-carboxylate To a stirred solution of B36.1 (63.9 mg, 0.200 mmol) and O-(3-(trifluoromethyl)phenyl)hydroxylamine (53.1 mg, 0.300 mmol) in ethanol (2 mL) at room temperature was added a catalytic amount of conc HCl. After stirring for 1.5 h at 50° C., aqueous saturated NaHCO$_3$ (2 mL) was added and the resulting solution was extracted with EtOAc (3×3 mL). The combined organic layers were concentrated and purified by silica gel column chromatography (Hexane/DCM/EtOAc=3:1:1) to give B8.1 (45 mg, a mixture of E/Z=8.2:1, 47%) as a clear oil.

B43.2: 1-(2-Methyl-4-(piperidin-4-yl)pyrimidin-5-yl)ethanone O-3-(trifluoromethyl)phenyl oxime hydrochloride salt Intermediate B43.2 was made from the Boc deprotection of intermediate B43.1 using General Procedure 2.

Compound B43:

Compound B43 was made from intermediate B43.2 and 2,6-difluorophenyl isocyanate using General Procedure 5. $^1$H-NMR (400 MHz, CDCl$_3$): δ 8.58 (s, 1H), 7.49 (m, 1H), 7.46 (m, 1H), 7.37 (m, 1H), 7.33 (m, 1H), 7.11 (m, 1H), 6.93 (t, 3H), 5.89 (s, 1H), 4.25 (d, 2H), 3.25 (tt, 1H), 3.00 (td, 2H), 2.76 (s, 3H), 2.49 (s, 3H), 2.14 (qd, 2H), 1.87 (m 2H). MS (EI) for $C_{26}H_{24}F_5N_5O_2$, found 534.2 (MH+). Analytical HPLC, ret. time=20.780 min, 99% purity.

Compound B44: N-(2,6-Difluorophenyl)-4-{2-methyl-5-[(1Z)—N-{[3-(trifluoromethyl)phenyl]oxy}ethanimidoyl]pyrimidin-4-yl}piperidine-1-carboxamide Z isomer isolated from the same reaction that formed Compound B43. $^1$H-NMR (400 MHz, CDCl$_3$): δ 8.39 (s, 1H), 7.40 (m, 2H), 7.29 (d, 1H), 7.22 (d, 1H), 7.11 (m, 1H), 6.93 (t, 2H), 5.86 (s, 1H), 4.19 (d, 2H), 2.90 (t, 2H), 2.77 (s, 3H), 2.72 (tt, 1H), 2.38 (s, 3H), 2.10 (qd, 2H), 1.73 (m, 2H). MS (EI) for $C_{26}H_{24}F_5N_5O_2$, found 534.2 (MH+). Analytical HPLC, ret. time=20.168 min, 79% purity (contaminated with B43, Analytical HPLC, ret. time=20.772 min, 21%).

Compound B45: N-[2-fluoro-6-(trifluoromethyl)phenyl]-4-{2-methyl-5-[(1E)-N-{[3-(trifluoromethyl)phenyl]oxy}ethanimidoyl]pyrimidin-4-yl}piperidine-1-carboxamide Compound B45 was made in a manner similar to Compound B43: $^1$H-NMR (400 MHz, CDCl$_3$): δ 8.58 (s, 1H), 7.46 (m, 3H), 7.34 (m, 4H), 6.09 (s, 1H), 4.20 (d, 2H), 3.26 (tt, 1H), 3.01 (td, 2H), 2.76 (s, 3H), 2.49 (s, 3H), 2.14 (qd, 2H), 1.87 (m, 2H). MS (EI) for $C_{27}H_{24}F_7N_5O_2$, found 584.2 (MH+). Analytical HPLC, ret. time=21.900 min, 99% purity.

Compound B46: N-(2,6-Difluorophenyl)-4-{2,6-dimethyl-5-[(E)-({[3-(trifluoromethyl)phenyl]oxy}imino)methyl]pyrimidin-4-yl}piperidine-1-carboxamide B46.1: tert-Butyl 4-(5-(hydroxymethyl)-2,6-dimethylpyrimidin-4-yl)piperidine-1-carboxylate To a stirred solution of Common Intermediate CI2 (140 mg, 0.400 mmol) in THF (3 mL) at 0° C. was added LiAlH$_4$ (0.32 mL, 1M in THF, 0.32 mmol). After stirring for 1 h at room temperature, 3% NaOH (60 mg) was added at 0° C. with vigorous stirring. The resulting mixture was stirred for 1 h at room temperature and EtOAc (2 mL) was added. The resulting mixture was filtered through Celite and concentrated to give crude B46.1 as a pale yellow foam.

B46.2: tert-Butyl 4-(5-formyl-2,6-dimethylpyrimidin-4-yl)piperidine-1-carboxylate To a stirred solution of crude B46.1 in dichloromethane (3 mL) at room temperature was added Dess-Martin periodinane (339 mg, 0.800 mmol). After stirring for 1 h, water (3 mL) was added and the resulting solution was filtered through Celite. Dichloromethane was removed in vacuo and the resulting mixture was extracted with EtOAc (3×3 mL). The combined organic layers were concentrated and purified by silica gel column chromatography (Hexane/EtOAc=2:1) to give B46.2 (80 mg, 63%, 2 steps) as a pale yellow oil.

B46.3: tert-Butyl 4-(2,6-dimethyl-5-((3-(trifluoromethyl)phenoxyimino)methyl)pyrimidin-4-yl)piperidine-1-carboxylate To a stirred solution of B46.2 (31.9 mg, 0.100 mmol), O-(3-(trifluoromethyl)phenyl)hydroxylamine (35.4 mg, 0.200 mmol) and ethanol (1 mL) at room temperature was added a catalytic amount of conc HCl. After stirring for 1 h at room temperature, aqueous saturated NaHCO$_3$ (3 mL) was added and the resulting solution was extracted with EtOAc (2×3 mL). The combined organic layers were concentrated and purified by silica gel column chromatography (Hexane/EtOAc=3:1→5:2) to give B46.3 (31 mg, 65%) as a clear oil.

B46.4: 2,4-Dimethyl-6-(piperidin-4-yl)pyrimidine-5-carbaldehyde O-3-(trifluoromethyl)phenyl oxime hydrochloride salt Intermediate B46.4 was made from the Boc deprotection of intermediate B46.3 using General Procedure 2.

Compound B46:

Compound B46 was made from intermediate B46.4 and 2,6-difluorophenyl isocyanate using General Procedure 5. $^1$H-NMR (400 MHz, CDCl$_3$): δ 8.77 (s, 1H), 7.48 (m, 2H), 7.36 (m, 2H), 7.12 (m, 1H), 6.94 (t, 2H), 5.89 (s, 1H), 4.26 (d, 2H), 3.40 (tt, 1H), 3.06 (td, 2H), 2.71 (s, 3H), 2.66 (s, 3H), 2.12 (qd, 2H), 1.88 (m, 2H). MS (EI) for $C_{26}H_{24}F_5N_5O_2$, found 534.1 (MH+). Analytical HPLC, ret. time=20.524 min, 90% purity.

Compound B47: N-(2,6-Difluorophenyl)-2-methyl-4-{2-methyl-5-[(1E)-N-{[3-(trifluoromethyl)phenyl]oxy}ethanimidoyl]pyrimidin-4-yl}piperidine-1-carboxamide B47.1: Ethyl 4-(1-(tert-butoxycarbonyl)-2-methylpiperidin-4-yl)-2-methylpyrimidine-5-carboxylate To a stirred solution of ethyl 2-methyl-4-(2-methylpiperidin-4-yl)pyrimidine-5-carboxylate (100 mg, 0.380 mmol), 1,4-dioxane (2 mL) and H$_2$O (0.5 mL) were added DIEA (0.20 mL, 1.1 mmol) and di-t-butyl dicarbonate (124 mg, 0.570 mmol) in sequence. After stirring for 1 h at room temperature, aqueous saturated NH$_4$Cl (3 mL) was added and the resulting solution was extracted with EtOAc (3×3 mL). The combined organic layers were concentrated and purified by silica gel column chromatography (Hexane/EtOAc=4:1→3:1) to give intermediate B47.1 (52 mg, one set of two enantiomers, 38%) as a clear oil.

B47.2: tert-Butyl 4-(5-(hydroxymethyl)-2-methylpyrimidin-4-yl)-2-methylpiperidine-1-carboxylate Intermediate B47.2 was synthesized from intermediate B47.1 using a method analogous to the method used to synthesize intermediate B46.1 from Common Intermediate CI2.

B47.3: tert-Butyl 4-(5-formyl-2-methylpyrimidin-4-yl)-2-methylpiperidine-1-carboxylate Intermediate B47.3 was synthesized from intermediate B47.2 using a method analogous to the method used to synthesize intermediate B47.2 from intermediate B47.1.

B47.4: tert-Butyl 4-(5-(1-hydroxyethyl)-2-methylpyrimidin-4-yl)-2-methylpiperidine-1-carboxylate To a stirred solution of intermediate B47.3 (34.0 mg, 0.106 mmol) in THF (1 mL) at 0° C. was added methylmagnesium bromide (0.15 mL, 1.4M in toluene/THF (3:1), 0.21 mmol). After stirring for 1 h at room temperature, aqueous saturated NH$_4$Cl (2 mL) was added and the resulting solution was extracted with EtOAc (3×2 mL). The combined organic layers were dried over MgSO$_4$ and concentrated to give crude intermediate B47.4.

B47.5: tert-Butyl 4-(5-acetyl-2-methylpyrimidin-4-yl)-2-methylpiperidine-1-carboxylate Intermediate B47.5 was synthesized from intermediate B47.4 using a method analogous to the method used to synthesize intermediate B46.2 from intermediate B46.1.

B47.6: tert-Butyl 2-methyl-4-(2-methyl-5-(1-(3-(trifluoromethyl)phenoxyimino)ethyl)pyrimidin-4-yl)piperidine-1-carboxylate Intermediate B47.6 was synthesized from intermediate B47.5 using a method analogous to the method used to synthesize intermediate B43.1 from intermediate B36.1.

B47.7: 1-(2-Methyl-4-(2-methylpiperidin-4-yl)pyrimidin-5-yl)ethanone O-3-(trifluoromethyl)phenyl oxime hydrochloride salt Intermediate B47.7 was made from the Boc deprotection of intermediate B47.6 using General Procedure 2.

Compound B47:

Compound B47 was synthesized from intermediate B47.7 and 2,6-difluorophenyl isocyanate using General Procedure 5. $^1$H-NMR (400 MHz, CDCl$_3$): δ 8.55 (s, 1H), 7.48 (m, 1H), 7.41 (m, 1H), 7.35 (m, 1H), 7.27 (m, 1H), 7.09 (m, 1H), 6.89 (t, 2H), 5.74 (s, 1H), 3.99 (m, 2H), 3.40 (ddd, 1H), 3.27 (m, 1H), 2.76 (s, 3H), 2.46 (s, 3H), 2.13 (m, 2H), 2.01 (m, 2H), 1.34 (d, 3H). MS (EI) for C$_{27}$H$_{26}$F$_5$N$_5$O$_2$, found 548.2 (MH+). Analytical HPLC, ret. time=21.292 min, 90% purity.

Compound B48: (1E)-1-(4-{1-[(2,6-difluorophenyl) acetyl]piperidin-4-yl}-2,6-dimethylpyrimidin-5-yl) butan-1-one O-[3-(trifluoromethyl)phenyl]oxime B48.1: tert-Butyl 4-(5-(1-hydroxyallyl)-2,6-dimethylpyrimidin-4-yl)piperidine-1-carboxylate To a solution of intermediate B46.2 (1.03 g, 3.2 mmol) in dry THF (30 mL) was added vinyl magnesium chloride (5.0 mL, 1.6M in THF, 8 mmol). The resulting mixture was stirred at room temperature and monitored by LC-MS until complete. Upon completion, the reaction mixture was diluted with saturated aqueous NH4Cl and extracted with EtOAc (3×). The combined organic extractions were washed with saturated aqueous NaCl (1×), dried (Na2SO4) and concentrated in vacuo to give intermediate B48.1 which was used as is in subsequent reactions. $^1$H-NMR (400 MHz, CDCl$_3$): δ 6.12 (m, 1H), 5.70 (m, 1H), 5.22 (m, 2H), 4.22 (m, 2H), 3.24 (m, 1H), 2.74 (m, 2H), 2.62 (s, 3H), 2.55 (s, 3H), 2.15 (br s, 1H), 1.90 (m, 2H), 1.60 (m, 2H), 1.47 (s, 9H). MS (EI) for C$_{19}$H$_{29}$N$_3$O$_3$, found: 348.3 (MH+).

B48.2: tert-Butyl 4-(5-acryloyl-2,6-dimethylpyrimidin-4-yl)piperidine-1-carboxylate Intermediate B48.2 was synthesized from intermediate B48.1 using a method analogous to the method used to synthesize intermediate B46.2 from intermediate B46.1. Crude material was purified by flash chromatography to give intermediate B48.2 (959 mg, 90% yield).

B48.3: tert-Butyl 4-(5-butyryl-2,6-dimethylpyrimidin-4-yl)piperidine-1-carboxylate To a solution of intermediate B48.2 (959 mg, 2.8 mmol) in dry THF (30 mL) was added MeMgBr (5.5 mL, 1.4M in 1:3 THF:Toluene, 7.7 mmol). The resulting mixture was stirred at room temperature for 1 hour, at which time, it was diluted with saturated aqueous NH$_4$Cl and extracted with EtOAc (3×). The combined organic extractions were washed with saturated aqueous NaCl (1×), dried (Na$_2$SO$_4$) and concentrated in vacuo. The resulting residue was purified by flash chromatography (18% EtOAc, 80% heptanes, 2% 7N NH$_3$ in MeOH) to give intermediate B48.3 (643 mg, 64% yield). $^1$H-NMR (400 MHz, CDCl$_3$): δ 4.22 (m, 2H), 2.71 (m, 4H), 2.66 (s, 3H), 2.50 (m, 1H), 2.38 (s, 3H), 1.92 (m, 2H), 1.78 (m, 2H), 1.65 (m, 2H), 1.47 (s, 9H) 1.02 (t, 3H). MS (EI) for C$_{20}$H$_{31}$N$_3$O$_3$, found: 362.3 (MH+).

B48.4: 1-(2,4-Dimethyl-6-(piperidin-4-yl)pyrimidin-5-yl)butan-1-one hydrochloride salt Intermediate B48.4 was made from the Boc deprotection of intermediate B48.3 using General Procedure 2.

B48.5: 1-(4-(1-(2-(2,6-Difluorophenyl)acetyl)piperidin-4-yl)-2,6-dimethylpyrimidin-5-yl)butan-1-one Intermediate B48.5 was made from intermediate B48.4 and 2,6-difluorophenylacetic acid using General Procedure 4.

Compound B48:

Compound B48 was synthesized from intermediate B48.5 using a method analogous to the method used to synthesize intermediate B43.1 from intermediate B36.1. H-NMR (400 MHz, CDCl$_3$): δ 7.43 (m, 2H), 7.37-7.17 (m, 3H), 6.88 (m, 2H), 4.75 (m, 1H), 4.10 (m, 1H), 3.73 (m, 2H), 3.14 (m, 1H), 2.85 (m, 2H), 2.70 (s, 3H), 2.68-2.48 (comp m, 2H), 2.47 (s, 3H), 1.75 (m, 2H), 1.50 (m, 4H), 1.03 (t, 3H). MS (EI) for C$_{30}$H$_{31}$F$_5$N$_4$O$_2$, found: 575.3 (MH+). Analytical HPLC, ret. time=25.00 min, 80% purity.

Compound B49: (1Z)-1-(4-{1-[(2,6-difluorophenyl) acetyl]piperidin-4-yl}-2,6-dimethylpyrimidin-5-yl) butan-1-one O-[3-(trifluoromethyl)phenyl]oxime Z isomer isolated from the same reaction that formed Compound B48. $^1$H-NMR (400 MHz, CDCl$_3$): δ 7.37 (m, 2H), 7.30-7.15 (m, 3H), 6.88 (m, 2H), 4.70 (dd, 1H), 4.07 (dd, 1H), 3.72 (m, 2H), 3.12 (dt, 1H), 2.71 (s, 3H), 2.65 (m, 2H), 2.56 (m, 2H), 2.38 (s, 3H), 2.15 (m, (1H), 1.90 (m, 1H), 1.73 (m, 4H), 1.09 (t, 3H). MS (EI) for C$_{30}$H$_{31}$F$_5$N$_4$O2, found: 575.3 (MH+). Analytical HPLC, ret. time=24.74 min, 98% purity.

Compound B50: N-(2,6-Difluorophenyl)-4-{2-(methylthio)-5-[(1E)-N-{[3-(trifluoromethyl)phenyl] oxy}ethanimidoyl]pyrimidin-4-yl}piperidine-1-carboxamide B50.1: Ethyl 4-(1-(tert-butoxycarbonyl)piperidin-4-yl)-2-(methylthio)pyrimidine-5-carboxylate To a suspension of S-methyl thiourea sulfate (5.5 g, 39 mmol) in EtOH (50 mL) was added EtONa (2.7 g, 39 mmol). The resulting mixture was stirred for 15 min at room temperature. Common Intermediate CI1.1 in EtOH (30 mL) was added. The mixture was heated at 70° C. with stirring for 2 h. The solvent was removed under reduced pressure. The residue was stirred in EtOAc (500 mL) and filtered. Concentration of the filtrate gave the crude product, which was further purified by flash column chromatography.

B50.2: 4-(1-(tert-Butoxycarbonyl)piperidin-4-yl)-2-(methylthio)pyrimidine-5-carboxylic acid Intermediate B50.2 was made from the ester hydrolysis of intermediate B50.1 using General Procedure 1.

B50.3: tert-Butyl 4-(5-acetyl-2-(methlythio)pyrimidin-4-yl)piperidine-1-carboxylate Intermediate B50.3 was synthesized from intermediate B50.2 using a method analogous to the method used to synthesize intermediate B36.1 from intermediate A116.1.

B50.4: 1-(2-(Methylthio)-4-(piperidin-4-yl)pyrimidin-5-yl)ethanone hydrochloride salt Intermediate B50.4 was made from the Boc deprotection of intermediate B50.3 using General Procedure 2.

B50.5: 4-(5-Acetyl-2-(methlythio)pyrimidin-4-yl)-N-(2,6-difluorophenyl)piperidine-1-carboxamide Intermediate B50.5 was made from intermediate B50.4 and 2,6-difluorophenyl isocyanate using General Procedure 5.

Compound B50:

Compound B50 was made from intermediate B50.5 using a method analogous to the method used to synthesize intermediate B43.1 from intermediate B116.1. $^1$H NMR (400 MHz, CDCl$_3$) δ 8.47 (s, 1H), 7.51-7.43 (m, 2H), 7.39-7.30 (m, 2H), 7.17-7.06 (m, 1H), 6.94 (t, 2H), 5.89 (s, 1H), 4.24 (d, 2H), 3.29 (t, 1H), 2.99 (t, 2H), 2.61 (s, 3H), 2.48 (s, 3H), 2.12 (td, 2H), 1.90 (d, 2H). MS (EI) for C$_{26}$H$_{24}$F$_5$N$_5$O$_2$S, found: 566.2 (MH+). Analytical HPLC, ret. time=23.54 min, 98% purity.

Compound B51: 4-{2-Amino-5-[(1E)-N-{[3-(trifluoromethyl)phenyl]oxy}ethanimidoyl]pyrimidin-4-yl}-N-(2,6-difluorophenyl)piperidine-1-carboxamide

B51.1: N-(2,6-Difluorophenyl)-4-(2-(methylsulfonyl)-5-(1-(3-(trifluoromethyl)phenoxyimino)ethyl)pyrimidin-4-yl)piperidine-1-carboxamide Intermediate B51.1 was synthesized from Compound B50 using General Procedure 6.

Compound B51:

Compound B51 was synthesized from intermediate B51.1 using General Procedure 7. $^1$H NMR (400 MHz, CDCl$_3$) δ 8.28 (s, 1H), 7.46 (dd, 2H), 7.33 (dd, 2H), 7.11 (t, 1H), 6.94 (t, 2H), 5.89 (s, 1H), 5.19 (s, 2H), 4.23 (d, 2H), 3.25 (s, 1H), 2.97 (t, 2H), 2.44 (s, 3H), 2.05 (dd, 2H), 1.86 (dd, 2H). MS (EI) for C$_{25}$H$_{23}$F$_5$N$_6$O$_2$, found: 535.2 (MH+). Analytical HPLC, ret. time=17.42 min, 98% purity.

Compound B52: N-(2,6-Difluorophenyl)-4-{2-(methylthio)-5-[(1E)-N-{[2-(trifluoromethyl)pyridin-4-yl]oxy}ethanimidoyl]pyrimidin-4-yl}piperidine-1-carboxamide

B52.1: N-(2,6-Difluorophenyl)-4-(5-(1-(hydroxyimino)ethyl)-2-(methylthio)pyrimidin-4-yl)piperidine-1-carboxamide Intermediate B52.1 was made from intermediate B50.5 using a method analogous to the method used to synthesize intermediate B116.2 from intermediate B116.1.

Compound B52:

To a solution of intermediate B52.1 in diemthylacetamide (2 mL) was added sodium hydride (40 mg, 1.20 mmol, 60% in mineral oil) at 0° C. The reaction mixture was allowed to warm up to room temperature for 15 min. To this heterogeneous mixture was added 4-chloro-2-(trifluoromethyl)pyridine (119 mg, 0.66 mmol) and stirred for 1 h. The reaction mixture was quenched with water at 0° C. and partitioned with EtOAc. The organic layer was washed with brine, dried over MgSO$_4$ and concentrated. The resulting crude material was purified by flash column chromatography to give a (E/Z) mixture of Compound B52 (210 mg, 68%, E/Z=4.5:1). $^1$H NMR (400 MHz, CDCl$_3$) δ 8.63 (d, 1H), 8.47 (s, 1H), 7.54 (t, 1H), 7.32-7.26 (m, 1H), 7.17-7.07 (m, 1H), 6.99-6.90 (m, 2H), 5.91 (s, 1H), 4.26 (d, 2H), 3.20 (dd, 1H), 3.06-2.94 (dt, 2H), 2.62 (s, 3H), 2.51 (s, 3H), 2.21-2.07 (m, 2H), 1.88 (m, 2H). MS (EI) for C$_{25}$H$_{23}$F$_5$N$_6$O$_2$S, found: 567.2 (MH+). Analytical HPLC, ret. time=20.80 min, 99% purity.

Compound B53: 4-{2-amino-5-[(1E)-N-{[2-(trifluoromethyl)pyridin-4-yl]oxy}ethanimidoyl]pyrimidin-4-yl}-N-(2,6-difluorophenyl)piperidine-1-carboxamide

B53.1: N-(2,6-Difluorophenyl)-4-(2-(methylsulfonyl)-5-(1-(2-(trifluoromethyl)pyridin-4-yloxyimino)ethyl)pyrimidin-4-yl)piperidine-1-carboxamide Intermediate B53.1 was synthesized from Compound B52 using General Procedure 6.

Compound B53:

Compound B53 was synthesized from intermediate B53.1 using General Procedure 7. $^1$H NMR (400 MHz, CDCl$_3$) δ 8.61 (d, 1H), 8.27 (s, 1H), 7.54 (d, 1H), 7.28 (dd, 1H), 7.12 (tt, 1H), 6.99-6.87 (m, 2H), 5.95 (s, 1H), 5.37 (s, 2H), 4.24 (dd, 2H), 3.16 (tt, 1H), 3.04-2.89 (m, 2H), 2.47 (s, 3H), 2.06 (m, 2H), 1.84 (d, 2H). MS (EI) for C$_{24}$H$_{22}$F$_5$N$_7$O$_2$, found: 373.2 (not shown MH+). Analytical HPLC, ret. time=11.66 min, 99% purity.

Compound B54: 4-{2-Amino-5-[(1E)-N-{[2-(trifluoromethyl)pyrimidin-4-yl]oxy}ethanimidoyl]pyrimidin-4-yl}-N-(2,6-difluorophenyl)piperidine-1-carboxamide Compound B54 was made in a manner similar to Compounds B52 and B53: $^1$H NMR (400 MHz, CDCl$_3$) δ 8.78 (d, 1H), 8.27 (s, 1H), 7.41 (d, 1H), 7.17-7.07 (m, 1H), 6.98-6.87 (m, 2H), 5.91 (s, 1H), 5.32 (d, 2H), 4.24 (d, 2H), 3.14 (m, 1H), 2.98 (dd, 2H), 2.54 (s, 3H), 2.10-1.97 (m, 2H), 1.93-1.77 (m, 2H). MS (EI) for C$_{23}$H$_{21}$F$_5$N$_8$O$_2$, found: 537.2 (MH+). Analytical HPLC, ret. time=11.24 min, 99% purity.

Compound B55: 4-{2-Amino-5-[(1E)-N-{[2-chloro-6-(trifluoromethyl)pyridin-4-yl]oxy}ethanimidoyl]pyrimidin-4-yl}-N-(2,6-difluorophenyl)piperidine-1-carboxamide Compound B55 was made in a manner similar to Compounds B52 and B53: $^1$H NMR (400 MHz, CDCl$_3$) δ 8.25 (s, 1H), 7.44 (d, 1H), 7.36 (d, 1H), 7.19-7.05 (m, 1H), 6.94 (t, 2H), 5.95 (s, 1H), 5.47 (d, 2H), 4.25 (d, 2H), 3.21-3.06 (m, 1H), 2.96 (dt, 2H), 2.48 (d, 3H), 2.14-1.97 (m, 2H), 1.83 (d, 2H). MS (EI) for C$_{24}$H$_{21}$ClF$_5$N$_7$O$_2$, found: 570.1 (MH+). Analytical HPLC, ret. time=13.94 min, 99% purity.

Compound B56: 4-(2-Amino-5-{(1E)-N-[(2,6-difluoropyridin-4-yl)oxy]ethanimidoyl}pyrimidin-4-yl)-N-(2,6-difluorophenyl)piperidine-1-carboxamide Compound B56 was made in a manner similar to Compounds B52 and B53: $^1$H NMR (400 MHz, CDCl$_3$) δ 8.26 (s, 1H), 7.18-7.07 (m, 1H), 6.94 (t, 2H), 6.63 (s, 2H), 5.91 (s, 1H), 5.25 (s, 2H), 4.25 (d, 2H), 3.12 (dd, 1H), 2.99 (t, 2H), 2.46 (d, 3H), 2.06 (ddd, 2H), 1.83 (d, 2H). MS (EI) for C$_{23}$H$_{21}$F$_4$N$_7$O$_2$, found: 504.2 (MH+). Analytical HPLC, ret. time=11.12 min, 99% purity.

Compound B57: 4-(2-Amino-5-{(1Z)—N-[(2,6-difluoropyridin-4-yl)oxy]ethanimidoyl}pyrimidin-4-yl)-N-(2,6-difluorophenyl)piperidine-1-carboxamide Z isomer isolated from the same reaction that formed Compound B56. $^1$H NMR (400 MHz, CDCl$_3$) δ 8.28 (bs, 1H), 7.19-7.05 (m, 1H), 6.94 (t, 2H), 6.82 (dd, 1H), 6.40 (d, 1H), 5.90 (s, 1H), 5.23 (s, 2H), 4.24 (d, 2H), 3.20 (t, 1H), 3.00 (t, 2H), 2.47 (s, 3H), 2.11-1.96 (m, 2H), 1.84 (m, 2H). MS (EI) for C$_{23}$H$_{21}$F$_4$N$_7$O$_2$, found: 504.2 (MH+). Analytical HPLC, ret. time=11.04 min, 99% purity.

Compound B58: 4-[5-{(1E)-N-[(2-Chloropyridin-4-yl)oxy]ethanimidoyl}-2-(methylthio)pyrimidin-4-yl]-N-(2,6-difluorophenyl)piperidine-1-carboxamide B58.1: 2-(2-Chloropyridin-4-yloxy)isoindoline-1,3-dione To a solution of N-hydroxyphthalimide (1.34 g, 8.21 mmol), copper acetate (1.49 g, 8.21 mmol), 2-chloro-4-pyridnylboronic acid (2.58 g, 16.4 mmol) in dichloroethane (30 mL) was added pyridine (0.73 mL, 9.035 mmol) at room temperature. The resulting mixture was stirred for 18 h and diluted with DCM. The precipitate was filtered over Celite, and the filtrate concentrated. The residue was purified by flash column chromatography to give intermediate B58.1 (538 mg, 23.9%); $^1$H NMR (400 MHz, CDCl$_3$-d) δ 8.34 (d, 1H), 8.02-7.94 (m, 2H), 7.93-7.85 (m, 2H), 7.07 (d, 1H), 7.03 (dd, 1H).

B58.2: O-(2-Chloropyridin-4-yl)hydroxylamine

A mixture of intermediate B58.1 (520 mg, 1.89 mmol) and hydrazine hydrate (0.28 mL, 5.68 mmol) was stirred in MeOH-DCM (1:1) for 18 h. The reaction mixture was diluted with DCM and partitioned with saturated aqueous NaHCO$_3$. The resulting solution was extracted with DCM (3×50 mL). The combined organic layers were washed with brine, dried over MgSO$_4$, concentrated in vacuo and purified by flash column chromatography to give intermediate B58.2 (66 mg, 23.8%); MS (EI) for C$_5$H$_5$ClN$_2$O, found 144.01 (MH$^+$).

B58.3: tert-Butyl 4-(5-(1-(2-chloropyridin-4-yloxyimino)ethyl)-2-(methylthio)pyrimidin-4-yl)piperidine-1-carboxylate Intermediate B58.3 was synthesized from intermediate B50.3 and intermediate B58.2 using a method analogous to the method that was used to synthesize intermediate B43.1 from intermediate B36.1.

B58.4: 1-(2-(Methylthio)-4-(piperidin-4-yl)pyrimidin-5-yl)ethanone O-2-chloropyridin-4-yl oxime hydrochloride salt Intermediate B58.4 was made from the Boc deprotection of intermediate B58.3 using General Procedure 2.

Compound B58:

Compound B58 was made from intermediate B58.4 and 2,6-difluorophenyl isocyanate using General Procedure 5. $^1$H NMR (400 MHz, CDCl$_3$) δ 8.46 (s, 1H), 8.29 (d, 1H), 7.21 (d, 1H), 7.12 (d, 1H), 7.04 (dd, 1H), 6.94 (t, 2H), 5.91 (s, 1H), 4.27 (d, 2H), 3.21 (t, 1H), 3.02 (t, 2H), 2.62 (s, 3H), 2.48 (s, 3H), 2.21-2.06 (m, 2H), 1.88 (m, 2H). MS (EI) for C$_{24}$H$_{23}$ClF$_2$N$_6$O$_2$S, found: 533.2 (MH+). Analytical HPLC, ret. time=19.62 min, 98% purity.

Compound B59: 4-(2-Amino-5-{(1E)-N-[(2-chloropyridin-4-yl)oxy]ethanimidoyl}pyrimidin-4-yl)-N-(2,6-difluorophenyl)piperidine-1-carboxamide B59.1: 4-(5-(1-(2-Chloropyridin-4-yloxyimino)ethyl)-2-(methylsulfonyl)pyrimidin-4-yl)-N-(2,6-difluorophenyl)piperidine-1-carboxamide Intermediate B59.1 was synthesized from Compound B58 using General Procedure 6.

Compound B59:

Compound B59 was synthesized from intermediate B59.1 using General Procedure 7. $^1$H NMR (400 MHz, CDCl$_3$) δ 8.27 (d, 2H), 7.21 (d, 1H), 7.11 (dd, 1H), 7.03 (dd, 1H), 6.94 (t, 2H), 5.90 (s, 1H), 5.29 (s, 2H), 4.25 (d, 2H), 3.17 (t, 1H), 3.00 (t, 2H), 2.44 (s, 3H), 2.14-1.98 (m, 2H), 1.85 (dd, 2H). MS (EI) for C$_{23}$H$_{22}$ClF$_2$N$_7$O$_2$, found: 502.2 (MH+). Analytical HPLC, ret. time=13.48 min, 99% purity.

Compound B60: N-(2,6-Difluorophenyl)-4-{2-(ethylamino)-5-[(1E)-N-{[2-(trifluoromethyl)pyridin-4-yl]oxy}ethanimidoyl]pyrimidin-4-yl}piperidine-1-carboxamide To a solution of intermediate B53.1 (a mixture of E and Z isomers) (70 mg, 0.12 mmol) in dioxane (2 mL) was added ethylamine in THF (0.18 mL, 0.35 mmol) at room temperature and the resulting mixture was stirred for 2 h. The reaction mixture was then concentrated in vacuo and purified by preparative HPLC to give Compound B60 (20.7 mg, 31.4%). $^1$H NMR (400 MHz, CDCl$_3$) δ 8.61 (d, 1H), 8.21 (bs, 1H), 7.54 (d, 1H), 7.31-7.27 (m, 1H), 7.17-7.06 (m, 1H), 6.99-6.87 (m, 2H), 6.34 (bs, 1H), 5.99 (s, 1H), 4.24 (d, 2H), 3.57-3.44 (m, 2H), 3.20 (t, 1H), 2.98 (t, 2H), 2.46 (s, 3H), 2.17-1.98 (m, 2H), 1.86 (d, 2H), 1.27 (t, 3H). MS (EI) for C$_{26}$H$_{26}$F$_5$N$_7$O$_2$, found: 564.2 (MH+). Analytical HPLC, ret. time=18.62 min, 96% purity.

Compound B61: N-(2,6-Difluorophenyl)-4-{2-(dimethylamino)-5-[(1E)-N-{[2-(trifluoromethyl)pyridin-4-yl]oxy}ethanimidoyl]pyrimidin-4-yl}piperidine-1-carboxamide Compound B61 was made in a manner similar to Compound B60: $^1$H NMR (400 MHz, CDCl$_3$) δ 8.60 (d, 1H), 8.31 (s, 1H), 7.54 (t, 1H), 7.30-7.26 (m, 1H), 7.17-7.07 (m, 1H), 6.94 (t, 2H), 5.91 (s, 1H), 4.23 (d, 2H), 3.23 (m, 2H, 6H), 3.00 (t, 2H), 2.46 (s, 3H), 2.10 (qd, 2H), 1.88 (d, 2H). MS (EI) for C$_{26}$H$_{26}$F$_5$N$_7$O$_2$, found: 564.2 (MH+). Analytical HPLC, ret. time=19.33 min, 98% purity.

Compound C40: 4-(2,6-Dimethyl-5-{5-[2-(trifluoromethyl)pyrimidin-4-yl]-1,3,4-oxadiazol-2-yl}pyrimidin-4-yl)-N-[2-fluoro-6-(trifluoromethyl)phenyl]piperidine-1-carboxamide C40.1: 2-(Trifluoromethyl)pyrimidine-4-carbohydrazide To a solution of methyl 2-(trifluoromethyl)pyrimidine-4-carboxylate (1.50 g, 7.28 mmol) in 10 mL of anhydrous MeOH was added hydrazine monohydrate (1.09 g, 21.83 mmol). The resulting solution was heated at 50° C. with stirring for 5 min, at which time the reaction was completed. The reaction mixture, as a yellow solution, was reduced to ⅓ of the volume in vacuo. The precipitate thus formed was filtered, washed with MeOH, and dried to give 1.16 g of intermediate C40.1 as a yellow crystalline solid. The combined filtrate was concentrated under high vacuum to afford an additional 0.20 g of the hydrazide product as a yellow solid. $^1$H-NMR (400 MHz, CDCl$_3$): δ 9.14 (d, 1H), 8.94 (br. s, 1H), 8.27 (d, 1H), 4.16 (d, 2H).

C40.2: tert-Butyl 4-(2,6-dimethyl-5-(2-(2-(trifluoromethyl)pyrimidine-4-carbonyl)hydrazinecarbonyl)pyrimidin-4-yl)piperidine-1-carboxylate A solution of intermediate A121.1 (500 mg, 1.49 mmol), EDC (329 mg, 1.71 mmol), and HOBt (232 mg, 1.71 mmol) in DMA (10 mL) was stirred at 25° C. for 1.5 h. To this mixture was added intermediate C40.1 (344 mg, 1.67 mmol). The resulting mixture was stirred at 40° C. for 17 h. After cooling to room temperature, the reaction mixture was diluted with EtOAc, washed with water (3×) and brine, dried (magnesium sulfate), and concentrated in vacuo to dryness, yielding a solid (793 mg). LC/MS analysis of the resulting residue showed the presence of intermediate C40.2 as the major product. MS (EI) for $C_{23}H_{28}F_3N_7O_4$, found 524.2 (MH+). The crude product was used directly in the next reaction.

C40.3: tert-Butyl 4-(2,6-dimethyl-5-(5-(2-(trifluoromethyl)pyrimidin-4-yl)-1,3,4-oxadiazol-2-yl)pyrimidin-4-yl)piperidine-1-carboxylate The entire amount (793 mg) of crude product obtained from the previous step (intermediate C40.2) was dissolved in 30 mL of anhydrous MeCN. To this solution was added K$_2$CO$_3$ (850 mg, 4.45 mmol), followed by p-toluenesulfonyl chloride (1236 mg, 4.94 mmol). The mixture was stirred at 50° C. for 1 h. After removal of solvent in vacuo, the crude mixture was diluted with EtOAc, washed with water (3×) and brine, dried (magnesium sulfate), and concentrated in vacuo to dryness, affording intermediate C40.3 as a solid (761 mg). MS (EI) for $C_{23}H_{26}F_3N_7O_3$, found 506.2 (MH+). The crude product was used directly for the subsequent reaction.

C40.4: 2-(2,4-Dimethyl-6-(piperidin-4-yl)pyrimidin-5-yl)-5-(2-(trifluoromethyl)pyrimidin-4-yl)-1,3,4-oxadiazole hydrochloride salt Intermediate C40.4 was made from the Boc deprotection of intermediate C40.3 using General Procedure 2.

Compound C40:

Compound C40 was made from intermediate C40.4 and 1-fluoro-2-isocyanato-3-(trifluoromethyl)benzene using General Procedure 5. $^1$H-NMR (400 MHz, CDCl$_3$): δ 9.22 (d, 1H), 8.48 (d, 1H), 7.44 (m, 1H), 7.34 (m, 2H), 6.08 (s, 1H), 4.18 (d, 2H), 2.97 (m, 3H), 2.79 (s, 3H), 2.60 (s, 3H), 2.12 (qd, 2H), 1.91 (m, 3H). MS (EI) for $C_{26}H_{21}F_7N_7O_2$, found 611.2 (MH+). Analytical HPLC, ret. time=17.144 min, 99% purity.

Compound C41: 4-{1-[(2-Chlorophenyl)acetyl]piperidin-4-yl}-2,6-dimethyl-5-{5-[2-(trifluoromethyl)pyrimidin-4-yl]-1,3,4-oxadiazol-2-yl}pyrimidine Compound C41 was made from intermediate C40.3 and 2-chlorophenylacetic acid using General Procedure 4. $^1$H-NMR (400 MHz, CDCl$_3$): δ 9.21 (d, H), 8.46 (d, 1H), 7.38 (dd, 1H), 7.32 (dd, 1H), 7.26-7.19 (m, 2H), 4.77 (d, 1H), 3.85 (s, 2H), 3.04 (m, 1H), 2.94 (m, 1H), 2.76 (s, 3H), 2.60 (m, 1H), 2.58 (s, 3H), 2.02-1.91 (m, 2H), 1.86-1.83 (m, 2H). MS (EI) for $C_{26}H_{23}ClF_3N_7O_2$, found: 558.2 (MH+). Analytical HPLC, ret. time=19.3 min, 98% purity.

Compound C42: 4-{1-[(3-Chloropyridin-2-yl)acetyl]piperidin-4-yl}-2,6-dimethyl-5-{5-[2-(trifluoromethyl)pyrimidin-4-yl]-1,3,4-oxadiazol-2-yl}pyrimidine Compound C42 was made in a manner similar to Compound C41: $^1$H-NMR (400 MHz, CDCl$_3$): δ 9.21 (d, 1H), 8.47-8.45 (m, 2H), 7.68 (dd, 1H), 7.17 (dd, 1H), 4.76 (d, 1H), 4.08 (dd, 2H), 3.99 (d, 1H), 3.10 (m, H), 2.96 (m, 1H), 2.77 (s, 3H), 2.61 (m, 1H), 2.58 (s, 3H), 2.07-1.95 (m, 2H), 1.90-1.81 (m, 2H). MS (EI) for $C_{25}H_{22}ClF_3N_8O_2$, found: 599.2 (MH+). Analytical HPLC, ret. time=14.6 min, 98% purity.

Compound C43: 4-{1-[(2,6-difluorophenyl)(difluoro)acetyl]piperidin-4-yl}-2,6-dimethyl-5-{5-[2-(trifluoromethyl)pyrimidin-4-yl]-1,3,4-oxadiazol-2-yl}pyrimidine Compound C43 was made from intermediate C40.3 and intermediate A116.4 using a method analogous to the method that was used to synthesize Compound A116 from intermediate A116.3 and intermediate A116.4. $^1$H-NMR (400 MHz, CDCl$_3$): δ 9.22 (d, 1H), 8.47 (d, 1H), 7.44 (m, 1H), 6.98 (t, 2H), 4.68 (d, 1H), 3.09 (t, 1H), 3.00 (m, 1H), 2.78 (s, 3H), 2.77 (t, 1H), 2.60 (s, 3H), 2.12-2.00 (m, 2H), 1.93-1.88 (m, 2H). MS (EI) for $C_{26}H_{20}F_7N_7O_2$, found: 596.1 (MH+). Analytical HPLC, ret. time=16.10 min, 98% purity.

Compound C44: 4-{1-[Difluoro(2-fluorophenyl)acetyl]piperidin-4-yl}-2,6-dimethyl-5-{5-[2-(trifluoromethyl)pyrimidin-4-yl]-1,3,4-oxadiazol-2-yl}pyrimidine Compound C44 was made in a manner similar to Compound C43: $^1$H-NMR (400 MHz, CDCl$_3$): δ 9.15 (d, 1H), 8.40 (d, 1H), 7.52 (t, 1H), 7.42 (m, 1H), 7.16 (m, 1H), 7.09 (t, 1H), 4.63 (d, 1H), 4.22 (d, 1H), 3.02-2.90 (m, 2H), 2.71 (s, 3H), 2.68 (t, 1H), 2.53 (s, 3H), 2.03-1.77 (m, 4H). MS (EI) for $C_{26}H_{21}F_6N_7O_2$, found: 578.1 (MH+). Analytical HPLC, ret. time=16.02 min, 98% purity.

Compound C45: 2-Chlorophenyl 4-(2,6-dimethyl-5-{5-[2-(trifluoromethyl)pyrimidin-4-yl]-1,3,4-oxadiazol-2-yl}pyrimidin-4-yl)piperidine-1-carboxylate Compound C45 was made from intermediate C40.3 and 2-chlorophenyl chloroformate using a method analogous to the method that was used to synthesize Compound A119 from intermediate A116.3 and 2-chlorophenyl chloroformate. $^1$H-NMR (400 MHz, CDCl$_3$): δ 9.22 (d, 1H), 8.48 (d, 1H), 7.42 (dd, 1H), 7.30-7.23 (m, 2H), 7.16 (m, 1H), 4.50 (d, 1H), 4.36 (d, 1H), 3.05 (t, 1H), 2.97 (m, 1H), 2.88 (t, 1H), 2.79 (s, 3H), 2.60 (s, 3H), 2.20-2.10 (m, 2H), 1.91 (m, 2H). MS (EI) for $C_{25}H_{21}ClF_3N_7O_3$, found: 560.2 (MH+). Analytical HPLC, ret. time=16.70 min, 92% purity.

Compound C46: N-(2,6-Difluorophenyl)-4-(2,6-dimethyl-5-{5-[2-(trifluoromethyl)pyrimidin-4-yl]-1,3,4-oxadiazol-2-yl}pyrimidin-4-yl)piperidine-1-carbothioamide Compound C46 was made from intermediate C40.4 and 2,6-difluorophenyl isothiocyanate using General Procedure 5. $^1$H-NMR (400 MHz, CDCl$_3$): δ 9.23 (d, 1H), 8.48 (d, 1H), 7.24 (m, 1H), 6.98 (t, 2H), 6.50 (s, 1H), 4.83 (d, 2H), 3.22 (td, 2H), 3.08 (tt, 1H), 2.79 (s, 3H), 2.61 (s, 3H), 2.22 (qd, 2H), 1.98 (m, 2H). MS (EI) for $C_{25}H_{21}F_5N_8OS$, found 577.2 (MH+). Analytical HPLC, ret. time=18.948 min, 96% purity.

Compound C47: 4-(2,6-Dimethyl-5-{5-[2-(trifluoromethyl)pyrimidin-4-yl]-1,3,4-oxadiazol-2-yl}pyrimidin-4-yl)-N-[2-(trifluoromethyl)phenyl]piperidine-1-carbothioamide Compound C47 was made in a manner similar to Compound C46: $^1$H-NMR (400 MHz, CDCl$_3$): δ 9.22 (d, 1H), 8.46 (d, 1H), 7.65 (d, 1H), 7.54 (m, 2H), 7.29 (m, 2H), 7.18 (s, 1H), 4.70 (d, 2H), 3.11 (td, 2H), 3.07 (tt, 1H), 2.78 (s, 3H), 2.61 (s, 3H), 2.18 (qd, 2H), 1.92 (m, 2H). MS (EI) for $C_{26}H_{22}F_6N_8OS$, found 609.2 (MH+). Analytical HPLC, ret. time=20.068 min, 91% purity.

Compound C48: 4-(2-Amino-6-methyl-5-{5-[2-(trifluoromethyl)pyrimidin-4-yl]-1,3,4-oxadiazol-2-yl}pyrimidin-4-yl)-N-(2,6-difluorophenyl)piperidine-1-carboxamide

C48.1: Methyl/Ethyl 4-(1-(tert-butoxycarbonyl)piperidin-4-yl)-6-methyl-2-(methylthio)pyrimidine-5-carboxylate To a suspension of S-methyl thiourea sulfate (1.15 g, 8.3 mmol) in EtOH (10 mL) was added EtONa (640 mg, 9.2 mmol). The resulting mixture was stirred for 15 min at room temperature. Common Intermediate CI2.1 (1.9 g, 4.9 mmol) in EtOH (15 mL) was added. The mixture was heated at 70° C. with stirring. The reaction was monitored by LC-MS. Once complete, the solvent was removed under reduced pressure. The resulting residue was stirred in EtOAc and any insoluble material was filtered. Concentration of the filtrate gave the crude product, which was further purified by flash column chromatography to give intermediate C48.1 (623 mg, 30%).

C48.2: 4-(1-(tert-Butoxycarbonyl)piperidin-4-yl)-6-methyl-2-(methylthio)pyrimidine-5-carboxylic acid Intermediate C48.2 was made from the ester hydrolysis of intermediate C48.1 using General Procedure 1. $^1$H-NMR (400 MHz, DMSO-d$_6$): δ 14.0 (br. s, 1H), 3.96 (m, 2H), 2.97 (m, 1H), 2.77 (m, 2H), 2.50 (s, 3H, overlap with DMSO-d$_6$), 2.41 (s, 3H), 1.68-1.60 (m, 4H), 1.41 (s, 9H). MS (EI) for $C_{17}H_{25}N_3O_4S$, found: 368.2 (MH+).

C48.3: tert-Butyl 4-(6-methyl-2-(methylthio)-5-(2-(2-(trifluoromethyl)pyrimidine-4-carbonyl)hydrazinecarbonyl)pyrimidin-4-yl)piperidine-1-carboxylate Intermediate C48.3 was made from intermediate C48.2 and intermediate C40.1 using a method analogous to the method that was used to synthesize intermediate C40.2 from intermediate A121.1 and intermediate C40.1. MS (EI) for $C_{23}H_{28}F_3N_7O_4S$, found: 556.2 (MH+).

C48.4: tert-Butyl 4-(6-methyl-2-(methlythio)-5-(5-(2-(trifluoromethyl)pyrimidin-4-yl)-1,3,4-oxadiazol-2-yl)pyrimidin-4-yl)piperidine-1-carboxylate compound with 1,3-difluorobenzene (1:1)

Intermediate C48.4 was made from intermediate C48.3 using a method analogous to the method that was used to synthesize intermediate C40.3 from intermediate C40.2. $^1$H-NMR (400 MHz, CDCl$_3$): δ 9.21 (d, 1H), 8.46 (d, 1H), 4.22 (m, 2H), 2.90 (m, 1H), 2.70 (m, 2H), 2.62 (s, 3H), 2.57 (s, 3H), 1.98-1.92 (m, 2H), 1.82 (d, 2H), 1.47 (s, 9H). MS (EI) for $C_{23}H_{26}F_3N_7O_3S$, found: 538.2 (MH+).

C48.5: 2-(4-Methyl-2-(methylthio)-6-(piperidin-4-yl)pyrimidin-5-yl)-5-(2-(trifluoromethyl)pyrimidin-4-yl)-1,3,4-oxadiazole hydrochloride salt Intermediate C48.5 was made from the Boc deprotection of intermediate C48.4 using General Procedure 2.

C48.6: N-(2,6-Difluorophenyl)-4-(6-methyl-2-(methylthio)-5-(5-(2-(trifluoromethyl)pyrimidin-4-yl)-1,3,4-oxadiazol-2-yl)pyrimidin-4-yl)piperidine-1-carboxamide Intermediate C48.6 was made from intermediate C48.5 and 2,6-difluorophenyl isocyanate using General Procedure 5.

C48.7: N-(2,6-Difluorophenyl)-4-(6-methyl-2-(methylsulfonyl)-5-(5-(2-(trifluoromethyl)pyrimidin-4-yl)-1,3,4-oxadiazol-2-yl)pyrimidin-4-yl)piperidine-1-carboxamide Intermediate C48.7 was synthesized from intermediate C48.6 using General Procedure 6.

Compound C48:

Compound C48 was synthesized from intermediate C48.7 using General Procedure 7. $^1$H-NMR (400 MHz, CDCl$_3$): δ 9.22 (dd, 1H), 8.46 (dd, 1H), 7.12 (m, 1H), 6.92 (m, 3H), 5.93 (br s, 2H), 4.28 (d, 2H), 2.93 (m, 3H), 2.48 (s, 3H), 2.02 (m, 2H), 1.88 (m, 2H). MS (EI) for $C_{24}H_{20}F_5N_9O_2$, found: 562.2 (MH+). Analytical HPLC, ret. time=14.58 min, 99% purity.

Compound C49: 4-(2-Amino-6-methyl-5-{5-[2-(trifluoromethyl)pyrimidin-4-yl]-1,3,4-oxadiazol-2-yl}pyrimidin-4-yl)-N-[2-fluoro-6-(trifluoromethyl)phenyl]piperidine-1-carboxamide Compound C49 was made in a manner similar to Compound C48: $^1$H-NMR (400 MHz, CDCl$_3$): δ 9.20 (d, 1H), 8.46 (d, 1H), 7.44 (m, 1H), 7.32 (m, 2H), 6.08 (s, 1H), 5.41 (s, 2H), 4.17 (m, 2H), 2.96 (m, 3H), 2.50 (s, 3H), 2.03 (m, 2H), 1.91 (m, 2H). MS (EI) for $C_{25}H_{20}F_7N_9O_2$, found: 612.1 (MH+). Analytical HPLC, ret. time=15.87 min, 99% purity.

Compound C50: 2,6-Difluorophenyl 4-(2-amino-6-methyl-5-{5-[2-(trifluoromethyl)pyrimidin-4-yl]-1,3,4-oxadiazol-2-yl}pyrimidin-4-yl)piperidine-1-carboxylate C50.1: tert-Butyl 4-(6-methyl-2-(methylsulfonyl)-5-(5-(2-(trifluoromethyl)pyrimidin-4-yl)-1,3,4-oxadiazol-2-yl)pyrimidin-4-yl)piperidine-1-carboxylate Intermediate C50.1 was made from intermediate C48.4 using General Procedure 6. MS (EI, Neg.) for $C_{23}H_{26}F_3N_7O_5S$, found: 567.7 [(M-H)⁻].

C50.2: tert-Butyl 4-(2-amino-6-methyl-5-(5-(2-(trifluoromethyl)pyrimidin-4-yl)-1,3,4-oxadiazol-2-yl)pyrimidin-4-yl)piperidine-1-carboxylate Intermediate C50.2 was made from intermediate C50.1 using General Procedure 7. $^1$H-NMR (400 MHz, CDCl$_3$): δ 9.19 (d, 1H), 8.44 (d, 1H), 5.29 (br. s, 2H), 4.20 (m, 2H), 2.83 (m, 1H), 2.69 (m, 2H), 2.47 (s, 3H), 1.90-1.77 (m, 4H), 1.47 (s, 9H). MS (EI) for $C_{22}H_{25}F_3N_8O_3$, found: 507.2 (MH+).

C50.3: 4-Methyl-6-(piperidin-4-yl)-5-(5-(2-(trifluoromethyl)pyrimidin-4-yl)-1,3,4-oxadiazol-2-yl)pyrimidin-2-amine dihydrochloride salt Intermediate C50.3 was made from the Boc deprotection of intermediate C50.2 using General Procedure 2, and obtained as a light yellow solid. $^1$H-NMR (400 MHz, DMSO-d$_6$): δ 9.38 (d, 1H), 8.78 (br. s, 1H), 8.56 (d, 1H), 8.53 (br. s, 1H), 7.34 (br. s, 2H), 4.82 (br. s, 1H), 3.31 (d, 2H), 3.02 (m, 1H), 2.87 (m, 2H), 2.38 (s, 3H), 2.03-1.91 (m, 4H). MS (EI) for $C_{17}H_{17}F_3N_8O$, found: 407.2 (MH+).

Compound C50:

Compound C50 was made from intermediate C50.3 and 2,6-difluorophenyl chloroformate (prepared using a general method according to the literature procedure as described in *J. Med. Chem.* 2006, 49, 4981) using a method analogous to the method that was used to synthesize Compound A119 from intermediate A116.3. $^1$H-NMR (400 MHz, CDCl$_3$): δ 9.20 (d, 1H), 8.45 (d, 1H), 7.14 (m, 1H), 6.99-6.94 (m, 2), 5.71 (br s, 2H), 4.44 (d, 1H), 4.32 (d, 1H), 3.06 (t, 1H), 2.97 (m, 1H), 2.89 (t, 1H), 2.49 (s, 3H), 2.03 (m, 2H), 1.90 (t, 2H). MS (EI) for $C_{24}H_{19}F_5N_8O_3$, found: 563.2 (MH+). Analytical HPLC, ret. time=14.56 min, 98% purity.

Compounds C51-C57 were made from intermediate C50.3 and the corresponding substituted phenyl chloroformates (either purchased from commercial sources, or prepared using a general method according to the literature procedure as described in. *J. Med. Chem.* 2006, 49, 4981) in a manner similar to Compound C50:

Compound C51: 2-Chlorophenyl 4-(2-amino-6-methyl-5-{5-[2-(trifluoromethyl)pyrimidin-4-yl]-1,3,4-oxadiazol-2-yl}pyrimidin-4-yl)piperidine-1-carboxylate $^1$H-NMR (400 MHz, CDCl$_3$): δ 9.20 (d, 1H), 8.45 (d, 1H), 7.42 (d, 1H), 7.30-7.22 (m, 2H), 7.16 (t, 1H), 5.34 (s, 2H), 4.49 (d, 1H), 4.35 (d, 1H), 3.08-2.95 (m, 2H), 2.87 (t, 1H), 2.50 (s, 3H), 2.10-1.98 (m, 2H), 1.95-1.85 (m, 2H). MS (EI) for $C_{24}H_{20}ClF_3N_8O_3$, found: 561.2 (MH+). Analytical HPLC, ret. time=14.72 min, 99% purity.

Compound C52: 2-Fluorophenyl 4-(2-amino-6-methyl-5-{5-[2-(trifluoromethyl)pyrimidin-4-yl]-1,3,4-oxadiazol-2-yl}pyrimidin-4-yl)piperidine-1-carboxylate $^1$H-NMR (400 MHz, CDCl3): δ 9.20 (d, 1H), 8.45 (d, 1H), 7.21-7.10 (m, 4H), 5.37 (s, 2H), 4.44 (d, 1H), 4.34 (d, 1H), 3.06-2.94 (m, 2H), 2.87 (t, 1H), 2.49 (s, 3H), 2.07-1.95 (m, 2H), 1.90 (t, 2H). MS (EI) for $C_{24}H_{20}F_4N_8O_3$, found: 545.2 (MH+). Analytical HPLC, ret. time=14.18 min, 98% purity.

Compound C53: 4-Fluorophenyl 4-(2-amino-6-methyl-5-{5-[2-(trifluoromethyl)pyrimidin-4-yl]-1,3,4-oxadiazol-2-yl}pyrimidin-4-yl)piperidine-1-carboxylate $^1$H-NMR (400 MHz, CDCl3): δ 9.20 (d, 1H), 8.45 (d, 1H), 7.10-7.02 (m, 4H), 5.52 (s, 2H), 4.37 (dd, 2H), 3.02-2.94 (m, 2H), 2.84 (t, 1H), 2.49 (s, 3H), 2.05-1.85 (m, 4H). MS (EI) for $C_{24}H_{20}F_4N_8O_3$, found: 545.2 (MH+). Analytical HPLC, ret. time=14.28 min, 97% purity.

Compound C54: 2,5-Difluorophenyl 4-(2-amino-6-methyl-5-{5-[2-(trifluoromethyl)pyrimidin-4-yl]-1,3,4-oxadiazol-2-yl}pyrimidin-4-yl)piperidine-1-carboxylate $^1$H-NMR (400 MHz, CDCl$_3$): 9.20 (d, 1H), 8.46 (d, 1H), 7.09 (m, 1H), 6.98 (m, 1H), 6.89 (m, 1H), 5.39 (s, 2H), 4.37 (dd, 2H), 3.06-2.95 (m, 2H), 2.88 (t, 1H), 2.50 (s, 3H), 2.08-1.98 (m, 2H), 1.91 (t, 2H). MS (EI) for $C_{24}H_{19}F_5N_8O_3$, found: 563.2 (MH+). Analytical HPLC, ret. time=14.92 min, 99% purity.

Compound C55: 3-Fluorophenyl 4-(2-amino-6-methyl-5-{5-[2-(trifluoromethyl)pyrimidin-4-yl]-1,3,4-oxadiazol-2-yl}pyrimidin-4-yl)piperidine-1-carboxylate $^1$H-NMR (400 MHz, CDCl$_3$): δ 9.20 (d, 1H), 8.46 (d, 1H), 7.32 (m, 1H), 6.95-6.89 (m, 3H), 5.46 (s, 2H), 4.37 (dd, 2H), 3.03-2.94 (m, 2H), 2.85 (t, 1H), 2.50 (s, 3H), 2.06-1.87 (m, 4H). MS (EI) for $C_{24}H_{20}F_4N_8O_3$, found: 545.2 (MH+). Analytical HPLC, ret. time=14.54 min, 99% purity.

Compound C56: 2,4-Difluorophenyl 4-(2-amino-6-methyl-5-{5-[2-(trifluoromethyl)pyrimidin-4-yl]-1,3,4-oxadiazol-2-yl}pyrimidin-4-yl)piperidine-1-carboxylate $^1$H-NMR (400 MHz, CDCl$_3$): δ 9.20 (d, 1H), 8.45 (d, 1H), 7.16 (m, 1H), 6.94-6.84 (m, 2H), 5.44 (s, 2H), 4.37 (dd, 2H), 3.06-2.93 (m, 2H), 2.89 (t, 1H), 2.50 (s, 3H), 2.07-1.97 (m, 2H), 1.90 (t, 2H). MS (EI) for $C_{24}H_{19}F_5N_8O_3$, found: 563.2 (MH+). Analytical HPLC, ret. time=14.90 min, 99% purity.

Compound C57: 2-(methyloxy)phenyl 4-(2-amino-6-methyl-5-{5-[2-(trifluoromethyl)pyrimidin-4-yl]-1,3,4-oxadiazol-2-yl}pyrimidin-4-yl)piperidine-1-carboxylate $^1$H-NMR (400 MHz, CDCl$_3$): δ 9.20 (d, 1H), 8.46 (d, 1H), 7.18 (t, 1H), 7.09 (d, 1H), 6.97-6.92 (m, 2H), 5.34 (s, 2H), 4.45 (d, 1H), 4.34 (d, 1H), 3.86 (s, 3H), 3.05-2.93 (m, 2H), 2.85 (m, 1H), 2.49 (s, 3H), 2.09-1.98 (m, 2H), 1.90-1.85 (m, 2H). MS (EI) for $C_{25}H_{23}F_3N_8O_4$, found: 557.2 (MH+). Analytical HPLC, ret. time=13.96 min, 98% purity.

Compound C58: N-(2,6-Difluorophenyl)-4-[6-methyl-2-(methylthio)-5-{5-[6-(trifluoromethyl)pyridin-2-yl]-1,3,4-oxadiazol-2-yl}pyrimidin-4-yl]piperidine-1-carboxamide C58.1: 6-(Trifluoromethyl)picolinohydrazide Intermediate C58.1 was made from methyl 6-(trifluoromethyl)picolinate using a method analogous to the method that was used to synthesize intermediate C40.1 from methyl 2-(trifluoromethyl)pyrimidine-4-carboxylate.

C58.2: tert-Butyl 4-(6-methyl-2-(methylthio)-5-(2-(6-(trifluoromethyl)picolinoyl)hydrazinecarbonyl)pyrimidin-4-yl)piperidine-1-carboxylate Intermediate C58.2 was made from intermediate C48.2 and intermediate C58.1 using a method analogous to the method that was used to synthesize intermediate C40.2 from intermediate A121.1 and intermediate C40.1.

C58.3: tert-Butyl 4-(6-methyl-2-(methylthio)-5-(5-(6-(trifluoromethyl)pyridin-2-yl)-1,3,4-oxadiazol-2-yl)pyrimidin-4-yl)piperidine-1-carboxylate Intermediate C58.3 was made from intermediate C58.2 using a method analogous to the method used to synthesize intermediate C40.3 from intermediate C40.2.

C58.4: 2-(4-Methyl-2-(methylthio)-6-(piperidin-4-yl)pyrimidin-5-yl)-5-(6-(trifluoromethyl)pyridin-2-yl)-1,3,4-oxadiazole hydrochloride salt Intermediate C58.4 was made from the Boc deprotection of intermediate C58.3 using General Procedure 2.

Compound C58:

Compound C58 was made from intermediate C58.4 and 2,6-difluorophenyl isocyanate using General Procedure 5. $^1$H-NMR (400 MHz, CDCl$_3$): δ 8.54 (d, 1H), 8.16 (t, 1H), 7.90 (d, 1H), 7.11 (m, 1H), 6.93 (t, 2H), 5.88 (s, 1H), 4.22 (d, 1H), 3.06-2.94 (m, 3H), 2.64 (s, 3H), 2.60 (s, 3H), 2.16-2.06 (m, 2H), 1.95 (d, 2H). MS (EI) for $C_{26}H_{22}F_5N_7O_2S$, found: 591.9 (MH+). Analytical HPLC, ret. time=20.76 min, 99% purity.

Compound C59: 4-(2-Amino-6-methyl-5-{5-[6-(trifluoromethyl)pyridin-2-yl]-1,3,4-oxadiazol-2-yl}pyrimidin-4-yl)-N-(2,6-difluorophenyl)piperidine-1-carboxamide C59.1: N-(2,6-Difluorophenyl)-4-(6-methyl-2-(methylsulfonyl)-5-(5-(6-(trifluoromethyl)pyridin-2-yl)-1,3,4-oxadiazol-2-yl)pyrimidin-4-yl)piperidine-1-carboxamide Intermediate C59.1 was synthesized from Compound C58 using General Procedure 6.

Compound C59:

Intermediate C59.1 (25 mg, 0.04 mmol) was dissolved in 4 mL of 7 N ammonium in MeOH solution and the resulting mixture was stirred at 30° C. for 10 min. After removal of solvent in vacuo, the crude mixture was purified on prep HPLC to give Compound C59. $^1$H-NMR (400 MHz, CDCl$_3$): δ 8.46 (d, 1H), 8.07 (t, 1H), 7.81 (d, 1H), 7.03 (m, 1H), 6.86 (t, 2H), 5.80 (s, 1H), 5.27 (s, 2H), 4.13 (d, 2H), 2.91-2.85 (m, 3H), 2.42 (s, 3H), 2.00-1.90 (m 2H), 1.85 (d, 2H). MS (EI) for $C_{25}H_{21}F_5N_8O_2$, found: 560.9 (MH+). Analytical HPLC, ret. time=15.37 min, 98% purity.

Compound C60: N-(2,6-Difluorophenyl)-4-[6-methyl-2-(methyloxy)-5-{5-[6-(trifluoromethyl)pyridin-2-yl]-1,3,4-oxadiazol-2-yl}pyrimidin-4-yl]piperidine-1-carboxamide Compound C60 was recovered as a side product from the reaction that generated Compound C59. $^1$H-NMR (400 MHz, CDCl$_3$): δ 8.48 (d, 2H), 8.09 (t, 1H), 7.83 (d, 1H), 7.04 (m, 1H), 6.86 (t, 2H), 5.80 (s, 1H), 4.15 (d, 2H), 4.04 (s, 3H), 2.99-2.88 (m, 3H), 2.53 (s, 3H), 2.10-1.99 (m, 2H), 1.89 (d, 2H). MS (EI) for $C_{26}H_{22}F_5N_7O_3$, found: 575.9 (MH+). Analytical HPLC, ret. time=18.80 min, 99% purity.

Compound C61: N-(2,6-Difluorophenyl)-4-[6-methyl-2-(methyloxy)-5-{5-[2-(trifluoromethyl)pyrimidin-4-yl]-1,3,4-oxadiazol-2-yl}pyrimidin-4-yl]piperidine-1-carboxamide Compound C61 was made in a manner similar to Compound C60: $^1$H-NMR (400 MHz, CDCl$_3$): δ 9.21 (d, 1H), 8.47 (d, 1H), 7.11 (m, 1H), 6.93 (m, 2H), 5.90 (br s, 1H), 4.23 (m, 2H), 4.11 (s, 3H) 3.00 (m, 3H), 2.60 (s, 3H), 2.12 (m, 2H), 1.94 (m, 2H). MS (EI) for $C_{25}H_{21}F_5N_8O_3$, found: 577.2 (MH+). Analytical HPLC, ret. time=17.84 min, 99% purity.

Compound C62: 4-{1-[(2,6-difluorophenyl)acetyl]piperidin-4-yl}-2-methyl-5-{5-[2-(trifluoromethyl)pyrimidin-4-yl]-1,3,4-oxadiazol-2-yl}pyrimidine C62.1: Methyl 2-methyl-4-(piperidin-4-yl)pyrimidine-5-carboxylate Intermediate C62.1 was made from the Boc deprotection of Common Intermediate CI1 using General Procedure 2.

C62.2: Methyl 4-(1-(2-(2,6-difluorophenyl)acetyl)piperidin-4-yl)-2-methylpyrimidine-5-carboxylate Intermediate C62.2 was synthesized from intermediate C62.1 and 2,6-difluorophenylacetic acid using General Procedure 4.

C62.3: 4-(1-(2-(2,6-Difluorophenyl)acetyl)piperidin-4-yl)-2-methylpyrimidine-5-carboxylic acid Intermediate C62.3 was made from intermediate C62.2 using General Procedure 1.

C62.4: N-(4-(1-(2-(2,6-Difluorophenyl)acetyl)piperidin-4-yl)-2-methylpyrimidine-5-carbonyl)-2-(trifluoromethyl)pyrimidine-4-carbohydrazide Intermediate C62.4 was made from intermediate C62.3 and intermediate C40.1 using a method analogous to the method that was used to synthesize intermediate C40.2 from intermediate A121.1 and intermediate C40.1.

Compound C62

Compound C62 was synthesized from intermediate C62.4 using a method analogous to the method used to synthesize intermediate C40.3 from intermediate C40.2. $^1$H-NMR (400 MHz, CDCl$_3$): δ 9.31 (s, 1H), 9.21 (d, 1H), 8.45 (d, 1H), 7.24 (m, 1H), 6.91 (t, 2H), 4.82 (d, 1H), 4.18 (d, 1H), 4.00 (tt, 1H), 3.79 (s, 2H), 3.37 (td, 1H), 2.84 (s, 3H), 2.83 (m, 1H), 2.03 (m, 4H). MS (EI) for C$_{25}$H$_{20}$F$_5$N$_7$O$_2$, found 546.1 (MH+). Analytical HPLC, ret. time=18.784 min, 99% purity.

Compound C63: N-(2,6-difluorophenyl)-4-(2,6-dimethyl-5-{3-[3-(trifluoromethyl)phenyl]-1,2,4-oxadiazol-5-yl}pyrimidin-4-yl)piperidine-1-carboxamide C63.1: tert-Butyl 4-(2,6-dimethyl-5-((3-(trifluoromethyl)benzimidamidooxy)carbonyl)pyrimidin-4-yl)piperidine-1-carboxylate To a mixture of 3-(trifluoromethyl)benzonitrile (1.00 g, 5.84 mmol) and hydroxylamine hydrochloride (2.44 g, 35 mmol) in anhydrous ethanol (8.3 mL) was added triethylamine (4.14 g, 41 mmol). The resulting mixture was heated at 80° C. with stirring in a sealed tube for 20 min. After cooling to RT, the mixture was diluted with EtOAc, washed with water (3×) and brine, dried over MgSO$_4$, and concentrated in vacuo to give (Z)—N'-hydroxy-3-(trifluoromethyl)benzimidamide as an off-white solid (1.18 g): $^1$H-NMR (400 MHz, DMSO-d$_3$): δ 9.86 (s, 1H), 7.98 (s, 1H), 7.96 (d, 1H), 7.72 (d, 1H), 7.60 (t, 1H), 6.01 (s, 2H). MS (EI) for C8H7F3N2O, found: 205.1 (MH+). A mixture of intermediate A121.1 (300 mg, 0.89 mmol), HATU (408 mg, 1.07 mmol), DIEA (230 mg, 1.79 mmol) and DCM (7 mL) was heated at 35° C. with stirring for 40 min. To the mixture was added (Z)—N'-hydroxy-3-(trifluoromethyl)benzimidamide (237 mg, 1.16 mmol) and the resulting mixture was heated at 35° C. for 30 min. After removal of DCM in vacuo, the resulting mixture was partitioned between EtOAc and water. The organic phase was separated, washed with water (3×) and brine, dried over MgSO$_4$ and concentrated in vacuo to afford intermediate C63.1 (515 mg) as a light orange solid: MS (EI) for C$_{25}$H$_{30}$F$_3$N$_5$O$_4$, found: 522.2 (MH+). The crude product was used directly in the next reaction without further purification.

C63.2: tert-Butyl 4-(2,6-dimethyl-5-(3-(3-(trifluoromethyl)phenyl)-1,2,4-oxadiazol-5-yl)pyrimidin-4-yl)piperidine-1-carboxylate To crude intermediate C63.1 obtained above was added glacial acetic acid (10 ml). The mixture was heated at 95° C. with stirring for 2.5 days. The resulting crude reaction solution was used as is in the next reaction.

C63.3: 5-(2,4-Dimethyl-6-(piperidin-4-yl)pyrimidin-5-yl)-3-(3-(trifluoromethyl)phenyl)-1,2,4-oxadiazole TFA salt TFA (2 mL) was added to the crude reaction solution of intermediate C63.2 generated above. The resulting mixture was heated at 80-90° C. for an additional 2 h. The crude mixture was cooled to RT, diluted with water, and washed with t-butylethyl ether. The aqueous phase was basified with 0.5 N NaOH, and then extracted with EtOAc (3×). The organic phase was washed with water and brine, dried over MgSO4 and concentrated to give intermediate C63.3 (46 mg). MS (EI) for C20H20F3N5O, found: 404.2 (MH+). The compound was used for the next step without further purification.

Compound C63:

Compound C63 was made from intermediate C63.3 and 2,6-difluorophenyl isocyanate using General Procedure 5. $^1$H-NMR (400 MHz, CDCl$_3$): δ 8.44 (s, 1H), 8.36 (d, 1H), 7.83 (d, 1H), 7.70 (t, 1H), 7.10 (m, 1H), 6.93 (m, 2H), 5.97 (s, 1H), 4.22 (d, 2H), 2.95 (m, 2H), 2.89 (m, 1H), 2.77 (s, 3H), 2.56 (s, 3H), 2.10 (m, 2H), 1.88 (d, 2H). MS (EI) for C$_{27}$H$_{23}$F$_5$N$_6$O$_2$, found: 559.2 (MH+). Analytical HPLC, ret. time=21.5 min, 99% purity.

Compound C64: 4-(2,6-Dimethyl-5-{3-[3-(trifluoromethyl)phenyl]-1,2,4-oxadiazol-5-yl}pyrimidin-4-yl)-N-[2-fluoro-6-(trifluoromethyl)phenyl]piperidine-1-carboxamide Compound C64 was made in a manner similar to Compound C63: $^1$H-NMR (400 MHz, DMSO-d$_6$): δ 8.41 (d, 1H), 8.33 (s, 1H), 8.18 (s, 1H), 8.04 (d, 1H), 7.89 (t, 1H), 7.60-7.49 (m, 3H), 4.12 (d, 2H), 3.35 (s, 3H), 3.03 (m, 1H), 2.82 (t, 2H), 2.67 (s, 3H), 1.83-1.72 (m, 2H). MS (EI) for C$_{28}$H$_{23}$F$_7$N$_6$O$_2$, found: 609.1 (MH+). Analytical HPLC, ret. time=4.57 min over a 6 min-run, 99% purity.

Compound C65: 4-{1-[(2,6-Difluorophenyl)carbonyl]piperidin-4-yl}-2,6-dimethyl-5-{3-[3-(trifluoromethyl)phenyl]-1,2,4-oxadiazol-5-yl}pyrimidine Compound C65 was synthesized from intermediate C63.3 and 2,6-difluorobenzoic acid using General Procedure 4. $^1$H-NMR (400 MHz, DMSO-d6): δ 8.42 (d, 1H), 8.34 (s, 1H), 8.05 (d, 1H), 7.90 (t, 1H), 7.55 (m, 1H), 7.26-7.18 (m, 2H), 4.20 (d, 1H), 3.43 (m, 1H), 3.38 (s, 3H), 3.16 (m, 2H), 2.86 (m, 1H), 2.69 (s, 3H), 1.92 (m, 1H), 1.83-1.76 (m, 3H). MS (EI) for C$_{27}$H$_{22}$F$_5$N$_5$O$_2$, found: 544.1 (MH+). Analytical HPLC, ret. time=23.6 min, 98% purity.

Compound C66: 5-[5-(3-Chlorophenyl)-1,3-oxazol-2-yl]-4-{1-[(2,6-difluorophenyl)acetyl]piperidin-4-yl}-2,6-dimethylpyrimidine C66.1: tert-butyl 4-(5-(2-(3-chlorophenyl)-2-oxoethylcarbamoyl)-2,6-dimethylpyrimidin-4-yl)piperidine-1-carboxylate Intermediate C66.1 was made from intermediate A121.1 and 2-amino-1-(3-chlorophenyl)ethanone•HCl using General Procedure 3.

C66.2: N-(2-(3-Chlorophenyl)-2-oxoethyl)-2,4-dimethyl-6-(piperidin-4-yl)pyrimidine-5-carboxamide hydrochloride salt Intermediate C66.2 was made by the Boc-deprotection of intermediate C66.1 using General Procedure 2.

C66.3: N-(2-(3-Chlorophenyl)-2-oxoethyl)-4-(1-(2-(2,6-difluorophenyl)acetyl)piperidin-4-yl)-2,6-dimethylpyrimidine-5-carboxamide Intermediate C66.3 was made from intermediate C66.2 and 2,6-difluorophenylacetic acid using General Procedure 4.

Compound C66:

A mixture of C66.3 (14 mg, 0.026 mmol) and POCl$_3$ (0.5 mL) was stirred for 6.5 h at 95° C. After evaporating POCl$_3$ in vacuo, the resulting residue was dissolved in EtOAc (2 mL) and treated with aqueous saturated NaHCO$_3$ (2 mL). The aqueous layer was further extracted with EtOAc (2×2 mL). The combined organic layers were concentrated and purified by silica gel column chromatography (Hexane/EtOAc=4:3→1:1) to give Compound C66 (4.3 mg, 32%) as a clear oil. $^1$H-NMR (400 MHz, CDCl$_3$): δ 7.66 (s, 1H), 7.57 (s, 1H), 7.56 (d, 1H), 7.41 (t, 1H), 7.36 (m, 1H), 7.22 (m, 1H), 6.89 (t, 2H), 4.71 (d, 1H), 4.09 (d, 1H), 3.74 (d, 2H), 3.13 (t, 1H), 3.04 (tt, 1H), 2.75 (s, 3H), 2.60 (td, 1H), 2.53 (s, 3H), 2.06 (qd, 1H), 1.89 (m, 3H). MS (EI) for C$_{28}$H$_{25}$ClF$_2$N$_4$O$_2$, found 523.2 (MH+). Analytical HPLC, ret. time=22.116 min, 96% purity.

Compound C67: 4-{5-[5-(3-Chlorophenyl)-1,3-oxazol-2-yl]-2,6-dimethylpyrimidin-4-yl}-N-(2,6-difluorophenyl)piperidine-1-carboxamide C67.1: N-(2-(3-Chlorophenyl)-2-oxoethyl)-4-(1-(2,6-difluorophenylcarbamoyl)piperidin-4-yl)-2,6-dimethylpyrimidine-5-carboxamide Intermediate C67.1 was made from intermediate C67.2 and 2,6-difluorophenyl isocyanate using General Procedure 5.

Compound C67:

Compound C67 was made from intermediate C67.1 using a method analogous to the cyclization of intermediate C66.3 to make Compound C66. $^1$H-NMR (400 MHz, CDCl$_3$): δ 7.66 (t, 1H), 7.58 (s, 1H), 7.56 (m, 1H), 7.41 (t, 1H), 7.36 (m, 1H), 7.10 (m, 1H), 6.93 (t, 2H), 5.86 (s, 1H), 4.21 (d, 2H), 3.01 (tt, 1H), 2.95 (td, 2H), 2.75 (s, 3H), 2.53 (s, 3H), 2.08 (qd, 2H), 1.86 (m, 2H). MS (EI) for C$_{27}$H$_{24}$ClF$_2$N$_5$O$_2$, found 524.1 (MH+). Analytical HPLC, ret. time=19.588 min, 99% purity.

Compound C68: N-(2,6-Difluorophenyl)-4-(2,6-dimethyl-5-{5-[2-(trifluoromethyl)pyrimidin-4-yl]-1,3-oxazol-2-yl}pyrimidin-4-yl)piperidine-1-carboxamide C68.1: 2-Azido-1-(2-(trifluoromethyl)pyrimidin-4-yl)ethanone 2-Bromo-1-(2-(trifluoromethyl)pyrimidin-4-yl)ethanone was prepared from 4-chloro-2-(trifluoromethyl)pyrimidine by the same method used in the synthesis of 2-bromo-1-(2-chloropyrimidin-4-yl)ethanone (*Bioorganic Med. Chem. Lett.* 2011, 21, 3818-3822). To a stirred solution of 2-bromo-1-(2-(trifluoromethyl)pyrimidin-4-yl)ethanone (270 mg, 1.00 mmol) in THF (4 mL) at 0° C. were added sodium azide (98.0 mg, 1.50 mmol) and H$_2$O (0.2 mL) in sequence and the mixture was stirred for 20 min at 0° C. The resulting crude reaction solution was used as is in the next reaction.

C68.2: 2-Azido-1-(2-(trifluoromethyl)pyrimidin-4-yl)ethanol

To the crude reaction solution of intermediate C68.1 was added NaBH$_4$ (57 mg, 1.5 mmol). After stirring for 20 min at room temperature, aqueous saturated NH$_4$Cl (4 mL) was added and the resulting solution was extracted with EtOAc (3×2 mL). The combined organic layers were concentrated and purified by silica gel column chromatography (Hexane/EtOAc=5:2) to give intermediate C68.2 (116 mg, 50%).

C68.3: 2-Amino-1-(2-(trifluoromethyl)pyrimidin-4-yl)ethanol

A mixture of intermediate C68.2 (116 mg, 0.498 mmol), palladium on activated carbon (53 mg, 10 wt. %, 0.050 mmol) and MeOH (5 mL) was stirred for 1 h at room temperature under hydrogen atmosphere using a balloon. The mixture was filtered through Celite and the filtrate was concentrated. The residue was dissolved in EtOAc (3 mL), and the resulting solution was filtered and concentrated to give a crude intermediate C68.3. MS (EI) for C$_7$H$_8$F$_3$N$_3$O, found 207.1 (MH+).

C68.4: Methyl/Ethyl 2,4-dimethyl-6-(piperidin-4-yl)pyrimidine-5-carboxylate hydrochloride salt Intermediate C68.4 was made from the Boc-deprotection of Common Intermediate CI2 using General Procedure 2.

C68.5: Methyl/Ethyl 4-(1-(2,6-difluorophenylcarbamoyl)piperidin-4-yl)-2,6-dimethylpyrimidine-5-carboxylate Intermediate C68.5 was made from intermediate C68.4 and 2,6-difluorophenyl isocyanate using General Procedure 5.

C68.6: 4-(1-(2,6-Difluorophenylcarbamoyl)piperidin-4-yl)-2,6-dimethylpyrimidine-5-carboxylic acid Intermediate C68.6 was made from the ester hydrolysis of intermediate C68.5 using General Procedure 1.

C68.7: 4-(1-(2,6-Difluorophenylcarbamoyl)piperidin-4-yl)-N-(2-hydroxy-2-(2-(trifluoromethyl)pyrimidin-4-yl)ethyl)-2,6-dimethylpyrimidine-5-carboxamide Intermediate C68.7 was made from the coupling of intermediate C68.6 and intermediate C68.3 using General Procedure 3.

C68.8: 4-(1-(2,6-Difluorophenylcarbamoyl)piperidin-4-yl)-2,6-dimethyl-N-(2-oxo-2-(2-(trifluoromethyl)pyrimidin-4-yl)ethyl)pyrimidine-5-carboxamide Intermediate C68.8 was made from intermediate C68.7 using a method analogous to the oxidation of intermediate B46.1 to intermediate B46.2.

Compound C68:

Compound C68 was made from intermediate C68.8 using a method analogous to the cyclization of intermediate C66.3 to form Compound C66. $^1$H-NMR (400 MHz, CDCl$_3$): δ 8.99 (d, 1H), 8.24 (s, 1H), 7.72 (d, 1H), 7.12 (m, 1H), 6.93 (t, 2H), 5.87 (s, 1H), 4.21 (d, 2H), 2.97 (m, 3H), 2.77 (s, 3H), 2.53 (s, 3H), 2.09 (qd, 2H), 1.86 (m, 2H). MS (EI) for C$_{26}$H$_{22}$F$_5$N$_7$O$_2$, found 560.2 (MH+). Analytical HPLC, ret. time=17.628 min, 99% purity.

Compound C69: 4-(2-amino-6-methyl-5-{5-[2-(trifluoromethyl)pyrimidin-4-yl]-1,3-oxazol-2-yl}pyrimidin-4-yl)-N-(2,6-difluorophenyl)piperidine-1-carboxamide C69.1: tert-Butyl 4-(5-(2-hydroxy-2-(2-(trifluoromethyl)pyrimidin-4-yl)ethylcarbamoyl)-6-methyl-2-(methylthio)pyrimidin-4-yl)piperidine-1-carboxylate Intermediate C69.1 was made by coupling intermediate C48.2 with C68.3 using General Procedure 3.

C69.2: N-(2-Hydroxy-2-(2-(trifluoromethyl)pyrimidin-4-yl)ethyl)-4-methyl-2-(methylthio)-6-(piperidin-4-yl)pyrimidine-5-carboxamide TFA salt Intermediate C69.2 was made from the Boc deprotection of intermediate C69.1 using General Procedure 2.

C69.3: 4-(1-(2,6-Difluorophenylcarbamoyl)piperidin-4-yl)-N-(2-hydroxy-2-(2-(trifluoromethyl)pyrimidin-4-yl)ethyl)-6-methyl-2-(methylthio)pyrimidine-5-carboxamide Intermediate C69.3 was made from intermediate C69.2 and 2,6-difluorophenyl isocyanate using General Procedure 5.

C69.4: 4-(1-(2,6-Difluorophenylcarbamoyl)piperidin-4-yl)-6-methyl-2-(methylthio)-N-(2-oxo-2-(2-(trifluoromethyl)pyrimidin-4-yl)ethyl)pyrimidine-5-carboxamide Intermediate C69.4 was made from intermediate C69.3 using a method analogous to the oxidation of intermediate B46.1 to intermediate B46.2.

C69.5: N-(2,6-Difluorophenyl)-4-(6-methyl-2-(methylthio)-5-(5-(2-(trifluoromethyl)pyrimidin-4-yl)oxazol-2-yl)pyrimidin-4-yl)piperidine-1-carboxamide Intermediate C69.5 was made from intermediate C69.4 using a method analogous to the cyclization of intermediate C66.3 to form Compound C66.

C69.6: N-(2,6-Difluorophenyl)-4-(6-methyl-2-(methylsulfonyl)-5-(5-(2-(trifluoromethyl)pyrimidin-4-yl)oxazol-2-yl)pyrimidin-4-yl)piperidine-1-carboxamide Intermediate C69.6 was made from intermediate C69.5 using General Procedure 6.

Compound C69:

To a stirred solution of intermediate C69.6 (4.6 mg, 0.0074 mmol) in 2-propanol (1.5 mL) at −78° C. was bubbled ammonia gas for 5 min. The mixture was sealed and stirred for 1 h at room temperature. The resulting solution was concentrated in vacuo and purified by preparative HPLC to give Compound C69 (3.0 mg, 72%) as a white solid after lyophilization. $^1$H-NMR (400 MHz, CDCl$_3$, DMSO-d6): δ 9.00 (d, 1H), 8.21 (s, 1H), 7.80 (d, 1H), 7.59 (s, 1H), 7.14 (m, 1H), 6.92 (t, 2H), 6.27 (br s, 2H), 4.30 (d, 2H), 2.85 (m, 3H), 2.42 (s, 3H), 1.96 (qd, 2H), 1.82 (m, 2H). MS (EI) for $C_{25}H_{21}F_5N_8O_2$, found 561.1 (MH+). Analytical HPLC, ret. time=11.360 min, 99% purity.

Compound C70: 4-(2-Amino-6-methyl-5-{2-[2-(trifluoromethyl)pyrimidin-4-yl]-1,3-oxazol-5-yl}pyrimidin-4-yl)-N-(2,6-difluorophenyl)piperidine-1-carboxamide C70.1: tert-Butyl 4-(2-acetyl-3-oxobut-1-enyl)piperidine-1-carboxylate To a mixture of acetylacetone (2 g, 20 mmol) and N-boc-4-piperidinecarboxaldehyde (4.3 g, 20 mmol) in isopropanol (30 mL) were added acetic acid (60 mg) and piperidine (60 mg). The mixture was stirred at rt for 48 h. Isopropanol was removed. The residue was dissolved in EtOAc, washed with saturated NaHCO$_3$, brine, and dried over anhydrous Na$_2$SO$_4$. Removal of EtOAc gave the crude intermediate C70.1. It was used in the next step without further purification.

C70.2: tert-Butyl 4-(5-acetyl-6-methyl-2-(methylthio)pyrimidin-4-yl)piperidine-1-carboxylate To a solution of intermediate C70.1 (460 mg, 1.56 mmol) in DMF (3 mL) were added S-methylisothiourea hemisulfate (260 mg, 1.87 mmol) and NaHCO$_3$ (524 mg, 6.2 mmol). The resulting mixture was stirred at 70° C. for 4 h. The reaction mixture was cooled to rt, extracted with EtOAc, and dried over anhydrous Na$_2$SO$_4$. EtOAc was removed, and the crude dihydropyrimidine product was dissolved in DCE (10 mL). To this solution was added MnO$_2$ (1.1 g, 12.5 mmol). The mixture was stirred at 85° C. for 30 min. It was then cooled to rt, filtered through Celite, and concentrated. Purification by flash column chromatography gave intermediate C70.2.

C70.3: tert-Butyl 4-(5-(2-bromoacetyl)-6-methyl-2-(methylthio)pyrimidin-4-yl)piperidine-1-carboxylate To a stirred solution of C70.2 (365 mg, 1.00 mmol) in THF (4 mL) at 0° C. was added LiHMDS (1.5 mL, 1M in THF, 1.5 mmol). After stirring for 15 min at 0° C., chlorotrimethylsilane (0.19 mL, 1.5 mmol) was added. After stirring for 3 h at 0° C., aqueous saturated NaHCO$_3$ (5 mL) was added and the resulting solution was extracted with EtOAc (3×3 mL). The combined organic layers were dried over MgSO$_4$ and concentrated. To a stirred solution of the residue in THF (4 mL) at 0° C. were added NaHCO$_3$ (126 mg, 1.50 mmol) and NBS (106 mg, 0.596 mmol) in sequence. After stirring for 1 h at room temperature, aqueous saturated NaHCO$_3$ (5 mL) was added and the resulting solution was extracted with EtOAc (3×3 mL). The combined organic layers were concentrated and purified by silica gel column chromatography (Hexane/EtOAc=6:1→4:1→5:2) to give intermediate C70.3 (240 mg, 54%) as a pale brown oil. MS (EI) for $C_{18}H_{26}BrN_3O_3S$, found 446.1 (MH+).

C70.4: tert-Butyl 4-(5-(2-azidoacetyl)-6-methyl-2-(methylthio)pyrimidin-4-yl)piperidine-1-carboxylate A mixture of intermediate C70.3 (200 mg, 0.451 mmol), sodium azide (58.6 mg, 0.902 mmol) and acetone (4 mL) was stirred for 3.5 h at room temperature. Aqueous saturated NH$_4$Cl (3 mL) was added and the resulting solution was extracted with EtOAc (2×3 mL). The combined organic layers were concentrated and purified by silica gel column chromatography (Hexane/EtOAc=3:1) to give intermediate C70.4 (157 mg, 86%) as a pale brown solid. MS (EI) for $C_{18}H_{26}N_6O_3S$, found 407.2 (MH+).

C70.5: tert-Butyl 4-(5-(2-aminoacetyl)-6-methyl-2-(methylthio)pyrimidin-4-yl)piperidine-1-carboxylate Intermediate C70.5 was made from intermediate C70.4 in EtOAc using a method analogous to the conversion of intermediate C68.2 to intermediate C68.3.

C70.6: tert-Butyl 4-(6-methyl-2-(methylthio)-5-(2-(2-(trifluoromethyl)pyrimidine-4-carboxamido)acetyl)pyrimidin-4-yl)piperidine-1-carboxylate Intermediate C70.6 was made from intermediate C70.5 and 2-(trifluoromethyl)pyrimidine-4-carboxylic acid using standard amide coupling techniques analogous to those used in General Procedure 3.

C70.7: N-(2-(4-Methyl-2-(methylthio)-6-(piperidin-4-yl)pyrimidin-5-yl)-2-oxoethyl)-2-(trifluoromethyl)pyrimidine-4-carboxamide TFA salt Intermediate C70.7 was made from the Boc deprotection of intermediate C70.6 using General Procedure 2.

C70.8: N-(2-(4-(1-(2,6-Difluorophenylcarbamoyl)piperidin-4-yl)-6-methyl-2-(methylthi)pyrimidin-5-yl)-2-oxoethyl)-2-(trifluoromethyl)pyrimidine-4-carboxamide Intermediate C70.8 was made from intermediate C70.7 and 2,6-difluorophenyl isocyanate using General Procedure 5.

C70.9: N-(2,6-Difluorophenyl)-4-(6-methyl-2-(methylthio)-5-(2-(2-(trifluoromethyl)pyrimidin-4-yl)oxazol-5-yl)pyrimidin-4-yl)piperidine-1-carboxamide Intermediate C70.9 was made from intermediate C70.8 using a method analogous to the cyclization of intermediate C66.3 to form Compound C66.

C70.10: N-(2,6-Difluorophenyl)-4-(6-methyl-2-(methylsulfonyl)-5-(2-(2-(trifluoromethyl)pyrimidin-4-yl)oxazol-5-yl)pyrimidin-4-yl)piperidine-1-carboxamide Intermediate C70.10 was made from intermediate C70.9 using General Procedure 6.

Compound C70:

Compound C70 was made from intermediate C70.10 using a method analogous to that used to convert intermediate C69.6 to Compound C69. $^1$H-NMR (400 MHz, CDCl$_3$): δ 9.09 (d, 1H), 8.27 (d, 1H), 7.38 (s, 1H), 7.11 (m, 1H), 6.93 (t, 2H), 5.87 (s, 1H), 5.43 (br s, 2H), 4.20 (d, 2H), 2.89 (td, 2H), 2.71 (tt, 1H), 2.36 (s, 3H), 2.02 (qd, 2H), 1.84 (m, 2H). MS (EI) for $C_{25}H_{21}F_5N_8O_2$, found 561.1 (MH+). Analytical HPLC, ret. time=10.088 min, 95% purity.

Compound C71: 4-(2-Amino-6-methyl-5-{5-[2-(trifluoromethyl)pyrimidin-4-yl]-1,3,4-oxadiazol-2-yl}pyrimidin-4-yl)-N-(2-chlorophenyl)piperidine-1-carboxamide Compound C71 was made in three steps from intermediate C48.5 in the same manner that Compound C48 was made in three steps from intermediate C48.5, substituting 2-chlorophenyl isocyanate for 2,6-difluorophenyl isocyanate in the first step. $^1$H-NMR (400 MHz, CDCl$_3$): δ 9.20 (d, 1H), 8.45 (d, 1H), 8.21 (dd, 1H), 7.34 (dd, 1H), 7.25 (m, 1H), 7.07 (s, 1H), 6.95 (dt, 1H), 5.34 (s, 2H), 4.22 (d, 2H), 3.01-2.93 (m, 3H), 2.50 (s, 3H), 2.06-1.91 (m, 4H). MS (EI) for $C_{24}H_{21}ClF_3N_9O_2$, found: 560.2 (MH+). Analytical HPLC, ret. time=16.54 min, 98% purity.

Compound D16: N-(2,6-Difluorophenyl)-4-[5-(1-hydroxy-1-methyl-2-{[6-(trifluoromethyl)pyridin-2-yl]amino}ethyl)-2-methylpyrimidin-4-yl]piperidine-1-carboxamide D16.1: tert-Butyl 4-(5-(2-hydroxybut-3-en-2-yl)-2-methylpyrimidin-4-yl)piperidine-1-carboxylate To a 0° C. solution of vinyl magnesium chloride in THF (1 mL, 1.6 M in THF) was added dropwise a solution of intermediate B36.1 (346 mg, 1.1 mmol) in PhMe (2 mL). The reaction mixture was stirred at 0° C. for 10 min, and then was quenched by slow addition of ice-water. The mixture was extracted with EtOAc, washed with brine, and dried over anhydrous Na$_2$SO$_4$. After removal of the solvents, the residue was purified by flash column chromatography to give intermediate D16.1 (180 mg, 48%).

D16.2: tert-Butyl 4-(5-(2-hydroxy-1-oxopropan-2-yl)-2-methylpyrimidin-4-yl)piperidine-1-carboxylate Ozone was bubbled through a −78° C. solution of intermediate D16.1 (180 mg, 0.57 mmol) in DCM/MeOH (5 mL/11 mL) until the blue color persisted. Nitrogen was then bubbled through the mixture to remove excess ozone. To this solution was added dimethylsulfide (160 mg, 2.5 mmol). The mixture was allowed to warm to rt gradually. Removal of the solvents gave the crude aldehyde, which was used in the next step without further purification.

D16.3: tert-Butyl 4-(5-(2-hydroxy-1-(6-(trifluoromethyl)pyridin-2-ylamino)propan-2-yl)-2-methylpyrimidin-4-yl)piperidine-1-carboxylate Crude intermediate D16.2 (140 mg, 0.4 mmol) was dissolved in AcOH (0.8 mL). The solution was stirred for 1 h at rt. Then NaBH$_4$ (10 mg) was added. The stirring was continued for 1 h. EtOAc was added. The organic phase was washed with saturated NaHCO$_3$, brine, and dried over anhydrous Na$_2$SO$_4$. After removal of the solvents, the residue was purified by flash column chromatography to give intermediate D16.3 (118 mg, 59%).

D16.4: 2-(2-Methyl-4-(piperidin-4-yl)pyrimidin-5-yl)-1-(6-(trifluoromethyl)pyridin-2-ylamino)propan-2-ol hydrochloride salt Intermediate D16.4 was made from the Boc deprotection of intermediate D16.3 using General Procedure 2.

Compound D16:

Compound D16 was made from intermediate D16.4 and 2,6-difluorophenyl isocyanate using General Procedure 5. $^1$H NMR (400 MHz, DMSO-d6) δ 8.62 (s, 1H), 8.22 (s, 1H), 7.51 (t, 1H), 7.24 (m, 1H), 7.06 (m, 3H), 6.86 (d, 1H), 6.81 (d, 1H), 5.71 (s, 1H), 4.41 (m, 2H), 3.55 (m, 3H), 2.85 (m, 2H), 2.51 (s, 3H), 1.70 (m, 4H). MS (EI) for $C_{26}H_{27}F_5N_6O_2$, found: 551.2 (MH+). Analytical HPLC, ret. time=11.08 min, 98% purity.

Compound D17: N-(2,6-Difluorophenyl)-4-[5-(1-hydroxy-1-methyl-2-{[2-(trifluoromethyl)pyrimidin-4-yl]amino}ethyl)-2-methylpyrimidin-4-yl]piperidine-1-carboxamide D17.1: tert-Butyl 4-(2-methyl-5-(2-methyloxiran-2-yl)pyrimidin-4-yl)piperidine-1-carboxylate To a mixture of $Me_3SI$ (300 mg, 1.5 mmol) in THF (4 mL) was added $^tBuOK$ (2 mL, 1.0 M in THF). The resulting mixture was stirred at room temperature for 30 min and B1.1 (320 mg, 1 mmol) was added. Stirring was continued at room temperature for 2 h and then the reaction mixture was diluted with aq. sat. $NaHCO_3$. The mixture was extracted with EtOAc and the organic mixture was dried over sodium sulfate, filtered, and concentrated. The crude product was used as is in the next step.

D17.2: tert-Butyl 4-(5-(1-amino-2-hydroxypropan-2-yl)-2-methylpyrimidin-4-yl)piperidine-1-carboxylate Intermediate D17.1 (668 mg, 2.0 mmol) and ammonium hydroxide (28%, 7 mL) were dissolved in 1,4-dioxane (7 mL). The mixture was warmed to 60° C. with stirring in a sealed tube for 72 h. After the mixture was cooled to RT, EtOAc was added to extract the product. The organic layer was washed with water and dried over anhydrous $Na_2SO_4$. Removal of the solvents gave crude intermediate D17.2, which was used in the next step without further purification.

D17.3: tert-Butyl 4-(5-(2-hydroxy-1-(2-(trifluoromethyl)pyrimidin-4-ylamino)propan-2-yl)-2-methyl-pyrimidin-4-yl)piperidine-1-carboxylate To a solution of the crude intermediate D17.2 (133 mg, 0.38 mmol) prepared above in acetonitrile (2 mL) were added 2-chloro-6-trifluoromethylpyrimidine (69 mg, 0.38 mmol), and DIEA (147 mg, 1.14 mmol). The mixture was stirred at 50° C. for 12 h. After the mixture was cooled to rt, EtOAc was added to extract the product. The organic layer was washed with water and dried over anhydrous $Na_2SO_4$. Removal of the solvents gave crude intermediate D17.3, which was used in the next step without further purification.

D17.4: 2-(2-Methyl-4-(piperidin-4-yl)pyrimidin-5-yl)-1-(2-(trifluoromethyl)pyrimidin-4-ylamino)propan-2-ol hydrochloride salt Intermediate D17.4 was made from the Boc deprotection of intermediate D17.3 using General Procedure 2.

Compound D17:

Compound D17 was made from intermediate D17.4 and 2,6-difluorophenyl isocyanate using General Procedure 5. $^1$H NMR (400 MHz, DMSO-d6) δ 8.61 (s, 1H), 8.24 (s, 1H), 8.09 (d, 1H), 7.97 (m, 1H), 7.24 (m, 1H), 7.09 (m, 2H), 6.74 (d, 1H), 5.76 (s, 1H), 4.18 (m, 2H), 3.55 (m, 3H), 2.85 (m, 2H), 2.51 (s, 3H), 1.70 (m, 4H). MS (EI) for $C_{25}H_{26}F_5N_7O_2$, found: 552.2 (MH+). Analytical HPLC, ret. time=11.50 min, 96% purity.

Compound D18: N-[2-Fluoro-6-(trifluoromethyl)phenyl]-4-[5-(1-hydroxy-1-methyl-2-{[2-(trifluoromethyl)pyrimidin-4-yl]amino}ethyl)-2-methylpyrimidin-4-yl]piperidine-1-carboxamide Compound D18 was made in a manner similar to Compound D17: $^1$H-NMR (400 MHz, CDCl$_3$): δ 8.64 (s, 1H), 8.23 (d, 1H), 7.45 (m, 1H), 7.44-7.31 (m, 2H), 6.45 (d, 1H), 6.14 (s, 1H), 5.86 (t, 1H), 4.18 (t, 2H), 3.92 (br. s, 1H), 3.88 (m, 2H), 3.62 (m, 1H), 3.14-2.30 (m, 2H), 2.67 (s, 3H), 2.22-2.13 (m, 2H), 1.79-1.71 (m, 2H), 1.67 (s, 3H). MS (EI) for $C_{26}H_{26}F_7N_7O_2$, found: 602.2 (MH+). Analytical HPLC, ret. time=11.4 min, 95% purity.

Compound D19: N-(2,6-Difluorophenyl)-4-[5-(1-hydroxy-1-methyl-2-{methyl[2-(trifluoromethyl)pyrimidin-4-yl]amino}ethyl)-2-methylpyrimidin-4-yl]piperidine-1-carboxamide D19.1: tert-Butyl 4-(5-(2-hydroxy-1-(methylamino)propan-2-yl)-2-methylpyrimidin-4-yl)piperidine-1-carboxylate Intermediate D19.1 was made from intermediate D17.1 using a method analogous to the method that was used to convert intermediate D17.1 to intermediate D17.2.

D19.2: tert-Butyl 4-(5-(2-hydroxy-1-(methyl(2-(trifluoromethyl)pyrimidin-4-yl)amino)propan-2-yl)-2-methylpyrimidin-4-yl)piperidine-1-carboxylate Intermediate D19.2 was made from intermediate D19.1 using a method analogous to the method that was used to convert intermediate D17.2 to intermediate D17.3.

D194.3: 1-(Methyl(2-(trifluoromethyl)pyrimidin-4-yl)amino)-2-(2-methyl-4-(piperidin-4-yl)pyrimidin-5-yl)propan-2-ol hydrochloride salt Intermediate D19.3 was made from the Boc deprotection of intermediate D19.2 using General Procedure 2.

Compound D19:

Compound D19 was made from intermediate D19.3 and 2,6-difluorophenyl isocyanate using General Procedure 5. $^1$H NMR (400 MHz, DMSO-d6) δ 8.67 (m, 1H), 8.33 (m, 1H), 8.03 (m, 1H), 7.26 (m, 1H), 7.11 (m, 2H), 6.74 (m, 1H), 5.76 (s, 1H), 4.16 (m, 2H), 3.63 (s, 3H), 3.55 (m, 3H), 2.85 (m, 2H), 2.53 (s, 3H), 1.70 (m, 4H), 1.54 (s, 3H). MS (EI) for $C_{26}H_{28}F_5N_7O_2$, found: 566.2 (MH+). Analytical HPLC, ret. time=12.44 min, 91% purity.

Compound D20: 2-(4-{1-[(2,6-Difluorophenyl)acetyl]piperidin-4-yl}-2-methylpyrimidin-5-yl)-1-{methyl[2-(trifluoromethyl)pyrimidin-4-yl]amino}propan-2-ol Compound D20 was made from intermediate D19.3 and 2,6-difluorophenylacetic acid using General Procedure 4. $^1$H NMR (400 MHz, DMSO-d6) δ 8.67 (m, 1H), 8.33 (m, 1H), 7.34 (m, 1H), 7.05 (m, 2H), 6.90 (m, 1H), 5.73 (s, 1H), 4.47 (m, 2H), 4.16 (m, 2H), 3.63 (s, 3H), 3.55 (m, 3H), 2.85 (m, 2H), 2.53 (s, 3H), 1.70 (m, 4H), 1.54 (s, 3H). MS (EI) for $C_{27}H_{29}F_5N_6O_2$, found: 565.2 (MH+). Analytical HPLC, ret. time=14.42 min, 95% purity.

Compound D21: N-(2,6-Difluorophenyl)-4-[5-(1-hydroxy-1-methyl-2-{[4-(trifluoromethyl)pyrimidin-2-yl]amino}ethyl)-2-methylpyrimidin-4-yl]piperidine-1-carboxamide D21.1: tert-Butyl 4-(5-(2-hydroxy-1-(4-(trifluoromethyl)pyrimidin-2-ylamino)propan-2-yl)-2-methylpyrimidin-4-yl)piperidine-1-carboxylate Intermediate D21.1 was made from intermediate D17.2 and 2-chloro-4-(trifluoromethyl)pyrimidine using a method analogous to that used to convert intermediate D17.2 to intermediate D17.3.

D21.2: 2-(2-Methyl-4-(piperidin-4-yl)pyrimidin-5-yl)-1-(4-(trifluoromethyl)pyrimidin-2-ylamino)propan-2-ol hydrochloride salt Intermediate D21.2 was made from the Boc deprotection of intermediate D21.1 using General Procedure 2.

Compound D21:

Compound D21 was made from intermediate D21.2 and 2,6-difluorophenyl isocyanate using General Procedure 5. $^1$H NMR (400 MHz, DMSO-d6) δ 8.50 (m, 2H), 8.23 (s, 1H), 7.58 (m, 1H), 7.24 (m, 1H), 7.09 (m, 2H), 6.92 (d, 1H), 5.64 (s, 1H), 4.16 (m, 2H), 3.55 (m, 3H), 2.85 (m, 2H), 2.53 (s, 3H), 1.70 (m, 4H), 1.54 (s, 3H). MS (EI) for $C_{25}H_{26}F_5N_7O_2$, found: 552.1 (MH+). Analytical HPLC, ret. time=12.47 min, 94% purity.

Compound D22: N-[2-Fluoro-6-(trifluoromethyl)phenyl]-4-[5-(1-hydroxy-1-methyl-2-{[4-(trifluoromethyl)pyrimidin-2-yl]amino}ethyl)-2-methylpyrimidin-4-yl]piperidine-1-carboxamide Compound D22 was made in a manner similar to Compound D21: $^1$H-NMR (400 MHz, CDCl$_3$): δ 8.66 (s, 1H), 8.51 (d, 1H), 7.45 (d, 1H), 7.38-7.31 (m, 2H), 6.93 (d, 1H), 6.12 (s, 1H), 5.85 (br. s, 1H), 4.20 (m, 2H), 3.91 (d, 2H), 3.66 (m, 1H), 3.11-2.98 (m, 2H), 2.67 (s, 3H), 2.23-2.10 (m, 2H), 1.81-1.73 (m, 2H), 1.70 s, 3H). MS (EI) for $C_{26}H_{26}F_7N_7O_2$, found: 602.2 (MH+). Analytical HPLC, ret. time=13.7 min, 99% purity.

Compound D23: 2-(4-{1-[(2,6-Difluorophenyl)acetyl]piperidin-4-yl}-2-methylpyrimidin-5-yl)-1-{[4-(trifluoromethyl)pyrimidin-2-yl]amino}propan-2-ol Compound D23 was made from intermediate D21.2 and 2,6-difluorophenylacetic acid using General Procedure 4. $^1$H NMR (400 MHz, DMSO-d6) δ 8.50 (m, 2H), 7.58 (m, 1H), 7.34 (m, 1H), 7.03 (m, 2H), 6.91 (m, 1H), 5.64 (s, 1H), 4.47 (m, 2H), 4.16 (m, 2H), 3.55 (m, 3H), 2.85 (m, 2H), 2.53 (s, 3H), 1.70 (m, 4H), 1.54 (s, 3H). MS (EI) for $C_{26}H_{27}F_5N_6O_2$, found: 551.2 (MH+). Analytical HPLC, ret. time=14.19 min, 97% purity.

Compound D24: 2-(4-{1-[(2,6-difluorophenyl)acetyl]piperidin-4-yl}-2-methylpyrimidin-5-yl)-1-{[6-(trifluoromethyl)pyridin-2-yl]oxy}propan-2-ol D24.1: tert-Butyl 4-(5-(2-bromoacetyl)-2-methylpyrimidin-4-yl)piperidine-1-carboxylate Intermediate D24.1 was made from intermediate B36.1 using a method analogous to that used to convert intermediate C70.2 to intermediate C70.3.

D24.2: tert-Butyl 4-(2-methyl-5-(2-(6-(trifluoromethyl)pyridin-2-yloxy)acetyl)pyrimidin-4-yl)piperidine-1-carboxylate Crude intermediate D24.1 (1.4 g, 3.5 mmol) was mixed with 2-hydroxy-6-trifluoromethylpyridine (700 mg, 3.85 mmol) in acetone (15 mL). To this mixture was added $K_2CO_3$ (1.0 g, 7.2 mmol). The resulting mixture was stirred for 3 h. EtOAc was added to extract the product. The organic phase was washed with saturated $NaHCO_3$, brine, and dried over anhydrous $Na_2SO_4$. After removal of the solvents, the residue was purified by flash column chromatography to give intermediate D24.2 (810 mg, 48%).

D24.3: tert-Butyl 4-(5-(2-hydroxy-1-(6-(trifluoromethyl)pyridin-2-yloxy)propan-2-yl)-2-methylpyrimidin-4-yl)piperidine-1-carboxylate To a 0° C. solution of methyl magnesium bromide in THF (0.3 mL, 1.4 M in THF, 0.42 mmol) was added dropwise a solution of intermediate D24.2 (50 mg, 0.1 mmol) in PhMe (1 mL). The reaction mixture was stirred at 0° C. for 10 min, and then was quenched by slow addition of ice-water. The mixture was extracted with EtOAc, washed with brine, and dried over anhydrous $Na_2SO_4$. After removal of the solvents, the residue was purified by flash column chromatography to give intermediate D24.3 (30 mg, 60%).

D24.4: 2-(2-Methyl-4-(piperidin-4-yl)pyrimidin-5-yl)-1-(6-(trifluoromethyl)pyridin-2-yloxy)propan-2-ol hydrochloride salt Intermediate D24.4 was made from the Boc deprotection of intermediate D24.3 using General Procedure 2.

Compound D24:

Compound D24 was made from intermediate D24.4 and 2,6-difluorophenylacetic acid using General Procedure 4. $^1$H NMR (400 MHz, DMSO-d6) δ 8.64 (s, 1H), 7.95 (t, 1H), 7.48 (d, 1H), 7.35 (m, 1H), 7.09 (m, 3H), 5.77 (s, 1H), 4.57 (m, 2H), 4.48 (m, 1H), 4.16 (m, 1H), 3.80 (m, 3H), 3.20 (m, 1H), 2.65 (m, 1H), 2.55 (s, 3H), 1.90 (m, 1H), 1.65 (m, 3H), 1.68 (s, 3H). MS (EI) for $C_{27}H_{27}F_5N_4O_3$, found: 551.2 (MH+). Analytical HPLC, ret. time=16.67 min, 99% purity.

Compound D25: N-(2,6-difluorophenyl)-4-[5-(1-hydroxy-1-methyl-2-{[6-(trifluoromethyl)pyridin-2-yl]oxy}ethyl)-2-methylpyrimidin-4-yl]piperidine-1-carboxamide Compound D25 was made from intermediate C24.4 and 2,6-difluorophenyl isocyanate using General Procedure 5. H NMR (400 MHz, DMSO-d6) δ 8.63 (s, 1H), 8.21 (s, 1H), 7.95 (t, 1H), 7.49 (d, 1H), 7.27 (m, 1H), 7.09 (m, 3H), 5.77 (s, 1H), 4.57 (m, 2H), 4.21 (m, 2H), 3.82 (m, 1H), 2.90 (m, 2H), 2.55 (s, 3H), 1.70 (m, 4H), 1.66 (s, 3H). MS (EI) for C$_{26}$H$_{26}$F$_5$N$_5$O$_3$, found: 552.2 (MH+). Analytical HPLC, ret. time=14.26 min, 95% purity.

Compound D26: N-(2,6-Difluorophenyl)-4-[5-(1-hydroxy-1-methyl-2-{[6-(trifluoromethyl)pyridin-2-yl]oxy}ethyl)-2-(methylthio)pyrimidin-4-yl]piperidine-1-carboxamide D26.1: tert-Butyl 4-(5-(2-bromoacetyl)-2-(methylthio)pyrimidin-4-yl)piperidine-1-carboxylate Intermediate D26.1 was synthesized from intermediate B50.3 using a method analogous to the method used to convert intermediate C70.2 to intermediate C70.3.

D26.2: tert-Butyl 4-(2-(methylthio)-5-(2-(6-(trifluoromethyl)pyridin-2-yloxy)acetyl)pyrimidin-4-yl)piperidine-1-carboxylate Intermediate D26.2 was synthesized from intermediate D26.1 and 6-(trifluoromethyl)pyridin-2-ol using a method analogous to that used to synthesize intermediate D24.2 from intermediate D24.1.

D26.3: tert-Butyl 4-(5-(2-hydroxy-1-(6-(trifluoromethyl)pyridin-2-yloxy)propan-2-yl)-2-(methylthio)pyrimidin-4-yl)piperidine-1-carboxylate Intermediate D26.3 was synthesized from intermediate D26.2 using a method analogous to that used to convert intermediate D24.2 to intermediate D24.3.

D26.4: 2-(2-(Methylthio)-4-(piperidin-4-yl)pyrimidin-5-yl)-1-(6-(trifluoromethyl)pyridin-2-yloxy)propan-2-ol hydrochloride salt Intermediate D26.4 was synthesized from the Boc deprotection of intermediate D26.3 using General Procedure 2.

Compound D26:

Compound D26 was made from intermediate D26.4 and 2,6-difluorophenyl isocyanate using General Procedure 5. $^1$H-NMR (400 MHz, CDCl$_3$): δ 8.52 (s, 1H), 7.78 (t, 1H), 7.35 (d, 1H), 7.12 (m, 1H), 6.94 (m, 3H), 5.92 (s, 1H), 4.80 (d, 1H), 4.60 (d, 1H), 4.24 (d, 2H), 3.89 (s, 1H), 3.70 (tt, 1H), 3.05 (qd, 2H), 2.14 (m, 2H), 1.81 (m, 2H), 1.71 (s, 3H). MS (EI) for C$_{26}$H$_{26}$F$_5$N$_5$O$_3$S, found 584.2 (MH+). Analytical HPLC, ret. time=19.552 min, 95% purity.

Compound D27: 4-[2-Amino-5-(1-hydroxy-1-methyl-2-{[6-(trifluoromethyl)pyridin-2-yl]oxy}ethyl)pyrimidin-4-yl]-N-(2,6-difluorophenyl)piperidine-1-carboxamide D27.1: N-(2,6-Difluorophenyl)-4-(5-(2-hydroxy-1-(6-(trifluoromethyl)pyridin-2-yloxy)propan-2-yl)-2-(methylsulfonyl)pyrimidin-4-yl)piperidine-1-carboxamide Intermediate D27.1 was synthesized from Compound D26 using General Procedure 6.

Compound D27:

Compound D27 was synthesized from intermediate D27.1 using a method analogous to that used to convert intermediate C69.6 to Compound C69. $^1$H-NMR (400 MHz, CDCl$_3$): δ 8.29 (s, 1H), 7.77 (t, 1H), 7.33 (d, 1H), 7.11 (m, 1H), 6.95 (m, 3H), 5.91 (s, 1H), 4.93 (s, 2H), 4.77 (d, 1H), 4.52 (d, 1H), 4.23 (d, 2H), 3.64 (tt, 1H), 3.57 (s, 1H), 3.03 (qd, 2H), 2.07 (m, 2H), 1.78 (m, 2H), 1.69 (s, 3H). MS (EI) for C$_{25}$H$_{25}$F$_5$N$_6$O$_3$, found 553.1 (MH+). Analytical HPLC, ret. time=12.596 min, 95% purity.

Compound D28: N-(2,6-Difluorophenyl)-4-[5-(1-hydroxy-1-methyl-2-{[2-(trifluoromethyl)pyrimidin-4-yl]oxy}ethyl)-2-(methylthio)pyrimidin-4-yl]piperidine-1-carboxamide D28.1: tert-Butyl 4-(2-(methylthio)-5-(2-(2-(trifluoromethyl)pyrimidin-4-yloxy)acetyl)pyrimidin-4-yl)piperidine-1-carboxylate Intermediate D28.1 was synthesized from intermediate D26.1 and 2-(trifluoromethyl)pyrimidin-4-ol using a method analogous to that used to synthesize intermediate D24.2 from intermediate D24.1.

D28.2: tert-Butyl 4-(5-(2-hydroxy-1-(2-(trifluoromethyl)pyrimidin-4-yloxy)propan-2-yl)-2-(methylthio)pyrimidin-4-yl)piperidine-1-carboxylate Intermediate D28.2 was synthesized from intermediate D28.1 using a method analogous to that used to convert intermediate D24.2 to intermediate D24.3.

D28.3: 2-(2-(Methylthio)-4-(piperidin-4-yl)pyrimidin-5-yl)-1-(2-(trifluoromethyl)pyrimidin-4-yloxy)propan-2-ol hydrochloride salt Intermediate D28.3 was synthesized from the Boc deprotection of intermediate D28.2 using General Procedure 2.

Compound D28:

Compound D28 was made from intermediate D28.3 and 2,6-difluorophenyl isocyanate using General Procedure 5. $^1$H-NMR (400 MHz, CDCl$_3$): δ 8.64 (d, 1H), 8.47 (s, 1H), 7.13 (m, 1H), 6.95 (m, 3H), 5.93 (s, 1H), 4.84 (d, 1H), 4.66 (d, 1H), 4.25 (d, 2H), 3.71 (m, 1H), 3.06 (t, 2H), 2.95 (s, 1H), 2.57 (s, 3H), 2.15 (m, 2H), 1.80 (m, 2H), 1.76 (s, 3H). MS (EI) for C$_{25}$H$_{25}$F$_5$N$_6$O$_3$S, found 585.2 (MH+). Analytical HPLC, ret. time=14.052 min, 95% purity.

Compound D29: 4-[2-Amino-5-(1-hydroxy-1-methyl-2-{[2-(trifluoromethyl)pyrimidin-4-yl]oxy}ethyl)pyrimidin-4-yl]-N-(2,6-difluorophenyl)piperidine-1-carboxamide D29.1: N-(2,6-Difluorophenyl)-4-(5-(2-hydroxy-1-(2-(trifluoromethyl)pyrimidin-4-yloxy)propan-2-yl)-2-(methylsulfonyl)pyrimidin-4-yl)piperidine-1-carboxamide Intermediate D29.1 was synthesized from Compound D28 using General Procedure 6.

Compound D29:

Compound D29 was synthesized from intermediate D29.1 using a method analogous to that used to convert intermediate C69.6 to Compound C69. $^1$H NMR (400 MHz, CDCl$_3$) δ 8.63 (d, 1H), 8.24 (s, 1H), 7.11 (m, 1H), 6.95 (m, 3H), 5.91

(s, 1H), 5.04 (s, 2H), 4.81 (d, 1H), 4.59 (d, 1H), 4.24 (d, 2H), 3.64 (m, 1H), 3.04 (t, 2H), 2.72 (bs, 1H), 2.21 (dd, 2H), 1.75 (s, 3H), 1.74 (m, 2H). MS (EI) for $C_{24}H_{24}F_5N_7O_3$, found: 554.2 (MH+). Analytical HPLC, ret. time=11.54 min, 99% purity.

Compound D30: 2-(2-Amino-4-{1-[(2,6-difluorophenyl)acetyl]piperidin-4-yl}pyrimidin-5-yl)-1-{[2-(trifluoromethyl)pyrimidin-4-yl]oxy}propan-2-ol D30.1: 2-(2,6-Difluorophenyl)-1-(4-(5-(2-hydroxy-1-(2-(trifluoromethyl)pyrimidin-4-yloxy)propan-2-yl)-2-(methylthio)pyrimidin-4-yl)piperidin-1-yl)ethanone Compound D30.1 was made from intermediate D28.3 and 2,6-difluorophenylacetic acid using General Procedure 4.

D30.2: 2-(2,6-Difluorophenyl)-1-(4-(5-(2-hydroxy-1-(2-(trifluoromethyl)pyrimidin-4-yloxy)propan-2-yl)-2-(methylsulfonyl)pyrimidin-4-yl)piperidin-1-yl)ethanone Intermediate D30.2 was synthesized from intermediate D30.1 using General Procedure 6.

Compound D30:

Compound D30 was synthesized from intermediate D30.2 using a method analogous to that used to convert intermediate C69.6 to Compound C69. $^1$H NMR (400 MHz, CDCl$_3$) δ 8.63 (d, 1H), 8.24 (bs, 1H), 7.22 (td, 1H), 6.98-6.84 (m, 3H), 5.04 (s, 2H), 4.79 (dt, 2H), 4.59 (d, 1H), 4.11 (d, 1H), 3.77 (s, 2H), 3.66 (d, 1H), 3.23 (t, 1H), 2.79-2.60 (m, 2H), 2.01 (ddd, 4H), 1.76 (s, 3H), 1.72 (d, 4H). MS (EI) for $C_{25}H_{25}F_5N_6O_3$, found: 553.1 (MH+). Analytical HPLC, ret. time=9.80 min, 98% purity.

Compound D31: 4-[2-(Acetylamino)-5-(1-hydroxy-1-methyl-2-{[2-(trifluoromethyl)pyrimidin-4-yl]oxy}ethyl)pyrimidin-4-yl]-N-(2,6-difluorophenyl)piperidine-1-carboxamide To a solution of Compound D29 (33.1 mg, 0.06 mmol) in pyridine (2 mL) was slowly added acetyl chloride (23.4 mg, 0.30 mmol) at 0° C. The resulting white mixture was stirred for a half hour at 0° C. Upon completion of the reaction, the mixture was quenched with ice and extracted with ethyl acetate (3×10 mL). The combined organic extracts were dried over magnesium sulfate and concentrated in vacuo. The crude product was purified by preparative HPLC to give Compound D31; $^1$H NMR (400 MHz, CDCl$_3$) δ 8.64 (d, 1H), 8.54 (s, 1H), 7.93 (s, 1H), 7.13 (t, 1H), 6.94 (dd, 3H), 5.91 (s, 1H), 4.83 (d, 1H), 4.68 (d, 1H), 4.25 (d, 2H), 3.75 (s, 1H), 3.06 (t, 2H), 2.88 (s, 1H), 2.54 (s, 3H), 2.15-1.99 (m, 2H), 1.81 (m, 2H), 1.77 (s, 3H). MS (EI) for $C_{26}H_{26}F_5N_7O_4$, found: 596.2 (MH+). Analytical HPLC, ret. time=13.76 min, 99% purity.

Compound D32: 4-[2-(Acetylamino)-5-(1-hydroxy-1-methyl-2-{[6-(trifluoromethyl)pyridin-2-yl]oxy}ethyl)pyrimidin-4-yl]-N-(2,6-difluorophenyl)piperidine-1-carboxamide Compound D32 was made in a manner similar to Compound D31: $^1$H NMR (400 MHz, CDCl3) δ 8.59 (s, 1H), 7.94 (s, 1H), 7.79 (t, 1H), 7.35 (d, 1H), 7.16-7.07 (m, 1H), 6.99-6.90 (m, 3H), 5.92 (s, 1H), 4.80 (d, 1H), 4.61 (d, 1H), 4.24 (d, 2H), 3.85 (s, 1H), 3.76 (dd, 1H), 3.13-2.98 (m, 2H), 2.54 (s, 3H), 2.12-1.97 (m, 2H), 1.89-1.75 (m, 2H), 1.73 (s, 3H). MS (EI) for $C_{27}H_{27}F_5N_6O_4$, found: 595.1 (MH+). Analytical HPLC, ret. time=11.59 min, 99% purity.

Compound D33: N-[4-{1-[(2,6-Difluorophenyl)acetyl]piperidin-4-yl}-5-(1-hydroxy-1-methyl-2-{[2-(trifluoromethyl)pyrimidin-4-yl]oxy}ethyl)pyrimidin-2-yl]acetamide Compound D33 was made in a manner similar to Compound D31: $^1$H-NMR (400 MHz, CDCl$_3$): δ 8.64 (d, 1H), 8.56 (br s, 1H), 8.23 (br s, 1H), 7.23 (m, 1H), 6.92 (m, 3H), 4.80 (m, 2H), 4.68 (d, 1H), 4.13 (d, 1H), 3.77 (comp m, 3H), 3.27 (t, 1H), 3.12 (br s, 1H), 2.70 (t, 1H), 2.51 (s, 3H), 2065-1.68 (comp m, 7H). MS (EI) for $C_{27}H_{27}F_5N_6O_4$, found: 595.1 (MH+). Analytical HPLC, ret. time=11.47 min, 96% purity.

Compound D34: 4-[2-(Cyclopropylamino)-5-(1-hydroxy-1-methyl-2-{[2-(trifluoromethyl)pyrimidin-4-yl]oxy}ethyl)pyrimidin-4-yl]-N-(2,6-difluorophenyl)piperidine-1-carboxamide Compound D34 was synthesized from intermediate D29.1 and cyclopropylamine using a method analogous to the conversion of intermediate B53.1 to Compound B60. $^1$H NMR (400 MHz, CDCl$_3$) δ 8.63 (d, 1H), 8.28 (s, 1H), 7.17-7.06 (m, 1H), 6.94 (t, 3H), 5.91 (s, 1H), 5.38 (s, 1H), 4.81 (d, 1H), 4.57 (d, 1H), 4.23 (d, 2H), 3.64 (d, 1H), 3.05 (t, 2H), 2.72 (t, 2H), 2.69 (bs, 1H), 2.08 (m, 2H), 1.85-1.66 (m, 2H), 1.77 (s, 3H), 0.83 (m, 2H), 0.54 (m, 2H). MS (EI) for $C_{27}H_{28}F_5N_7O_3$, found: 594.2 (MH+). Analytical HPLC, ret. time=12.48 min, 97% purity.

Compound D35: N-(2,6-Difluorophenyl)-4-[2-(ethylamino)-5-(1-hydroxy-1-methyl-2-{[2-(trifluoromethyl)pyrimidin-4-yl]oxy}ethyl)pyrimidin-4-yl]piperidine-1-carboxamide Compound D35 was made in a manner similar to Compound D34: $^1$H-NMR (400 MHz, CDCl$_3$, DMSO-d6): δ 8.62 (d, 1H), 8.23 (br s, 1H), 7.32 (s, 1H), 6.97 (d, 1H), 6.94 (t, 2H), 5.61 (br s, 1H), 4.70 (d, 1H), 4.61 (d, 1H), 4.34 (d, 2H), 3.80 (m, 1H), 3.58 (m, 2H), 3.00 (m, 2H), 2.01 (m, 2H), 1.80 (m, 2H), 1.72 (s, 3H), 1.30 (t, 3H). MS (EI) for $C_{26}H_{28}F_5N_7O_3$, found 582.2 (MH+). Analytical HPLC, ret. time=13.528 min, 95% purity.

Compound D36: N-(2,6-Difluorophenyl)-4-[5-(1-hydroxy-1-methyl-2-{[2-(trifluoromethyl)pyrimidin-4-yl]oxy}ethyl)-2-(methylamino)pyrimidin-4-yl]piperidine-1-carboxamide Compound D36 was made in a manner similar to Compound D34: $^1$H-NMR (400 MHz, CDCl$_3$): δ 8.62 (d, 1H), 8.23 (s, 1H), 7.12 (m, 1H), 6.94 (t, 2H), 6.95 (d, 1H), 5.92 (s, 1H), 5.03 (m, 1H), 4.81 (d, 1H), 4.56 (d, 1H), 4.23 (d, 2H), 3.64 (tt, 1H), 3.05 (tt, 2H), 3.00 (d, 3H), 2.66 (s, 1H), 2.11 (m, 2H), 1.78 (m, 2H), 1.72 (s, 3H). MS (EI) for $C_{25}H_{26}F_5N_7O_3$, found 568.2 (MH+). Analytical HPLC, ret. time=12.940 min, 97% purity.

Compound D37: 4-[2-({[2,4-Bis(methyloxy)phenyl]methyl}amino)-5-(1-hydroxy-1-methyl-2-{[2-(trifluoromethyl)pyrimidin-4-yl]oxy}ethyl)pyrimidin-4-yl]-N-(2,6-difluorophenyl)piperidine-1-carboxamide Compound D37 was made in a manner similar to Compound D34: $^1$H NMR (400 MHz, CDCl$_3$) δ 8.62 (d, 1H), 8.19 (s, 1H), 7.25 (m, 1H), 7.10 (m, 1H), 6.99-6.88 (m, 3H), 6.50-6.40 (m, 2H), 5.93 (s, 1H), 5.69-5.51 (m, 1H), 4.80 (d, 1H), 4.60-4.48 (m, 3H), 4.25 (d, 2H), 3.85 (s, 3H), 3.79 (s, 3H), 3.62 (m, 1H), 3.05 (m, 2H), 2.12 (m, 2H), 1.76 (m, 2H), 1.70 (s, 3H). MS (EI) for $C_{33}H_{34}F_5N_7O_5$, found: 704.2 (MH+). Analytical HPLC, ret. time=14.58 min, 95% purity.

Compound M2: N-(2,6-Difluorophenyl)-4-[2-(methylthio)-5-({[2-(trifluoromethyl)pyrimidin-4-yl]oxy}acetyl)pyrimidin-4-yl]piperidine-1-carboxamide M2.1: 1-(2-(Methylthio)-4-(piperidin-4-yl)pyrimidin-5-yl)-2-(2-(trifluoromethyl)pyrimidin-4-yloxy)ethanone hydrochloride salt Intermediate M2.1 was made from the Boc deprotection of intermediate D28.1 using General Procedure 2.

Compound M2:

Compound M2 was made from intermediate M2.1 and 2,6-difluorophenyl isocyanate using General Procedure 5. $^1$H NMR (400 MHz, CDCl$_3$) δ 8.85 (s, 1H), 8.69 (d, 1H), 7.17-7.05 (m, 2H), 6.93 (t, 2H), 5.88 (s, 1H), 5.52 (s, 2H), 4.21 (d, 2H), 3.50 (t, 1H), 3.02 (t, 2H), 2.63 (s, 3H), 2.09-1.93 (m, 2H), 1.85 (d, 2H). MS (EI) for $C_{24}H_{21}F_5N_6O_3S$, found: 569.1 (MH+). Analytical HPLC, ret. time=19.42 min, 99% purity.

Compound D38: N-(2,6-Difluorophenyl)-4-[2-(dimethylamino)-5-(1-hydroxy-1-methyl-2-{[2-(trifluoromethyl)pyrimidin-4-yl]oxy}ethyl)pyrimidin-4-yl]piperidine-1-carboxamide D38.1: N-(2,6-Difluorophenyl)-4-(2-(methylsulfonyl)-5-(2-(2-(trifluoromethyl)pyrimidin-4-yloxy)acetyl)pyrimidin-4-yl)piperidine-1-carboxamide Intermediate D38.1 was made from Compound M2 using General Procedure 6.

D38.2: N-(2,6-Difluorophenyl)-4-(2-(dimethylamino)-5-(2-(2-(trifluoromethyl)pyrimidin-4-yloxy)acetyl)pyrimidin-4-yl)piperidine-1-carboxamide Intermediate D38.2 was made from intermediate D38.1 and dimethylamine using a method analogous to the conversion of intermediate B53.1 to Compound B60.

Compound D38:

Compound D38 was made from intermediate D38.2 using a method analogous to the synthesis of intermediate D24.3 from D24.2. $^1$H NMR (400 MHz, CDCl$_3$) δ 8.61 (d, 1H), 8.26 (s, 1H), 7.16-7.07 (m, 1H), 6.93 (dd, 3H), 5.91 (s, 1H), 4.81 (d, 1H), 4.55 (d, 1H), 4.23 (d, 2H), 3.64 (t, 1H), 3.18 (s, 6H), 3.06 (t, 2H), 2.55 (s, 1H), 2.22-1.98 (m, 3H), 1.77 (m, 2H), 1.71 (s, 3H). MS (EI) for $C_{26}H_{28}F_5N_7O_3$, found: 582.2 (MH+). Analytical HPLC, ret. time=12.53 min, 97% purity.

Compound D39: 4-{2-[(2,2-Difluoroethyl)amino]-5-(1-hydroxy-1-methyl-2-{[2-(trifluoromethyl)pyrimidin-4-yl]oxy}ethyl)pyrimidin-4-yl}-N-(2,6-difluorophenyl)piperidine-1-carboxamide Compound D39 was made in a manner similar to Compound D39: $^1$H NMR (400 MHz, CDCl$_3$) δ 8.63 (d, 1H), 8.26 (s, 1H), 7.12 (tt, 1H), 6.99-6.88 (m, 3H), 6.08-5.80 (tt, 1H), 5.93 (s, 1H), 5.45 (bs, 1H), 4.79 (d, 1H), 4.60 (d, 1H), 4.23 (d, 2H), 3.92-3.76 (m, 2H), 3.73-3.60 (m, 1H), 3.04 (t, 2H), 2.70 (bs, 1H), 2.17-1.97 (m, 2H), 1.83-1.74 (m, 2H), 1.73 (s, 3H). MS (EI) for $C_{26}H_{26}F_7N_7O_3$, found: 617.9 (MH+). Analytical HPLC, ret. time=14.76 min, 99% purity.

Compound D40: N-(2,6-Difluorophenyl)-4-{5-(1-hydroxy-1-methyl-2-{[2-(trifluoromethyl)pyrimidin-4-yl]oxy}ethyl)-2-[(1-methylethyl)oxy]pyrimidin-4-yl}piperidine-1-carboxamide A solution of intermediate D29.1 (45.3 mg, 0.07 mmol) in isopropyl alcohol (3 mL) was treated with sodium (~7 mg). The resulting mixture was monitored by LC/MS and quenched with an ice upon completion in 15 min at room temperature. The mixture was diluted with water (5 mL) and extracted with ethyl acetate (3×10 mL). The combined organic layers were dried over magnesium sulfate and concentrated in vacuo. The crude product was purified by prep HPLC to give Compound D40; $^1$H NMR (400 MHz, CDCl$_3$) δ 8.63 (d, 1H), 8.46 (s, 1H), 7.17-7.06 (m, 1H), 7.01-6.88 (m, 3H), 5.89 (s, 1H), 5.39-5.31 (m, 1H), 5.28 (dt, 1H), 4.82 (d, 1H), 4.65 (d, 1H), 4.26 (d, 2H), 3.71 (dd, 1H), 3.06 (t, 2H), 2.80 (bs, 1H), 2.30-2.09 (m, 2H), 2.06-1.97 (m, 2H), 1.82 (d, 2H), 1.76 (s, 3H), 1.40 (d, 6H). MS (EI) for $C_{27}H_{29}F_5N_6O_4$, found: 597.2 (MH+). Analytical HPLC, ret. time=17.84 min, 99% purity.

Compound D41: 4-{2-[(2,2-Difluoroethyl)oxy]-5-(1-hydroxy-1-methyl-2-{[2-(trifluoromethyl)pyrimidin-4-yl]oxy}ethyl)pyrimidin-4-yl}-N-(2,6-difluorophenyl)piperidine-1-carboxamide Compound D41 was made from intermediate D29.1 in a manner similar to Compound D40: $^1$H NMR (400 MHz, CDCl$_3$) δ 8.64 (d, 1H), 8.52 (s, 1H), 7.16-7.07 (m, 1H), 6.99-6.90 (m, 3H), 6.29-6.01 (tt, 1H), 5.91 (s, 1H), 4.82 (d, 1H), 4.68 (d, 1H), 4.60 (td, 2H), 4.26 (d, 2H), 3.75 (t, 1H), 3.06 (t, 2H), 2.24-1.95 (m, 2H), 1.87-1.78 (m, 2H), 1.77 (s, 3H). MS (EI) for $C_{26}H_{25}F_7N_6O_4$, found: 619.2 (MH+). Analytical HPLC, ret. time=17.78 min, 99% purity.

Compound D42: N-(2,6-Difluorophenyl)-4-[2-{[2-fluoro-1-(fluoromethyl)ethyl]oxy}-5-(1-hydroxy-1-methyl-2-{[2-(trifluoromethyl)pyrimidin-4-yl]oxy}ethyl)pyrimidin-4-yl]piperidine-1-carboxamide Compound D41 was made from intermediate D29.1 in a manner similar to Compound D40: $^1$H NMR (400 MHz, CDCl$_3$) δ 8.65 (d, 1H), 8.52 (s, 1H), 7.12 (t, 1H), 7.00-6.90 (m, 3H), 5.89 (s, 1H), 5.58 (t, 1H), 4.87-4.80 (m, 3H), 4.70 (dd, 2H), 4.26 (d, 2H), 3.74 (s, 1H), 3.06 (t, 2H), 2.09 (d, 2H), 2.04 (m, 1H), 1.81 (m, 2H), 1.77 (s, 3H). MS (EI) for $C_{27}H_{27}F_7N_6O_4$, found: 633.2 (MH+). Analytical HPLC, ret. time=17.62 min, 99% purity.

Compound D43: N-(2,6-Difluorophenyl)-4-{2-[(2-fluoroethyl)oxy]-5-(1-hydroxy-1-methyl-2-{[2-(trifluoromethyl)pyrimidin-4-yl]oxy}ethyl)pyrimidin-4-yl}piperidine-1-carboxamide Compound D41 was made from intermediate D29.1 in a manner similar to Compound D40: $^1$H NMR (400 MHz, CDCl$_3$) δ 8.64 (d, 1H), 8.50 (s, 1H), 7.17-7.08 (m 1H), 6.99-6.88 (m, 3H), 5.90 (s, 1H), 4.84 (dd, 2H), 4.75-4.70 (m, 1H), 4.70-4.65 (m, 2H), 4.63-4.59 (m, 1H), 4.26 (d, 2H), 3.73 (t, 1H), 3.06 (t, 2H), 2.22-2.06 (m, 3H), 1.79 (d, 2H), 1.77 (s, 3H). MS (EI) for $C_{26}H_{26}F_6N_6O_4$, found: 601.2 (MH+). Analytical HPLC, ret. time=16.38 min, 99% purity.

Compound D44: N-(2,6-Difluorophenyl)-4-[5-(1-hydroxy-1-methyl-2-{[2-(trifluoromethyl)pyrimidin-4-yl]oxy}ethyl)-2-(methyloxy)pyrimidin-4-yl]piperidine-1-carboxamide Compound D41 was made from intermediate D29.1 in a manner similar to Compound D40: $^1$H NMR (400 MHz, CDCl$_3$) δ 8.64 (d, 1H), 8.48 (s, 1H), 7.17-7.07 (m, 1H), 6.94 (dd, 3H), 5.91 (s, 1H), 4.84 (d, 1H), 4.66 (d, 1H), 4.26 (d, 2H), 4.01 (s, 3H), 3.72 (t, 1H), 3.06 (t, 2H), 2.25-2.07 (m, 2H), 1.76 (s, 3H). MS (EI) for $C_{25}H_{25}F_5N_6O_4$, found: 569.2 (MH+). Analytical HPLC, ret. time=17.16 min, 99% purity.

Compound D45: N-(2,6-Difluorophenyl)-4-[5-(1-hydroxy-1-methyl-2-{[6-(trifluoromethyl)pyridin-2-yl]oxy}ethyl)-2-(methyloxy)pyrimidin-4-yl]piperidine-1-carboxamide Compound D41 was made from intermediate D12.1 in a manner similar to Compound D40: $^1$H NMR (400 MHz, CDCl$_3$) δ 8.53 (s, 1H), 7.78 (t, 1H), 7.34 (d, 1H), 7.17-7.06 (m, 1H), 6.98-6.89 (m, 3H), 5.89 (s, 1H), 4.79 (d, 1H), 4.59 (d, 1H), 4.25 (d, 2H), 4.00 (s, 3H), 3.83-3.62 (m, 2H), 3.04 (tt, 2H), 2.22-2.08 (m, 3H), 1.82 (dd, 2H), 1.72 (s, 3H). MS (EI) for $C_{26}H_{26}F_5N_5O_4$, found: 568.2 (MH+). Analytical HPLC, ret. time=14.05 min, 99% purity.

Compound M3: 2,6-Difluorophenyl 4-[2-amino-5-({[2-(trifluoromethyl)pyrimidin-4-yl]oxy}acetyl)pyrimidin-4-yl]piperidine-1-carboxylate M3.1: 2,6-Difluorophenyl 4-(2-(methylthio)-5-(2-(2-(trifluoromethyl)pyrimidin-4-yloxy)acetyl)pyrimidin-4-yl)piperidine-1-carboxylate Intermediate M3.1 was synthesized from intermediate M2.1 and 2,6-difluorophenyl chloroformate using a method analogous to that used to make Compound A119 from intermediate A116.3 and 2-chlorophenyl chloroformate.

M3.2: 2,6-Difluorophenyl 4-(2-(methylsulfonyl)-5-(2-(2-(trifluoromethyl)pyrimidin-4-yloxy)acetyl)pyrimidin-4-yl)piperidine-1-carboxylate Intermediate M3.2 was made from intermediate M3.1 using General Procedure 6.

Compound M3:

Compound M3 was made from intermediate M3.2 using General Procedure 7. $^1$H NMR (400 MHz, CDCl$_3$) δ δ 8.75 (s, 1H), 8.67 (d, 1H), 7.19-7.07 (m, 2H), 6.96 (t, 2H), 5.52 (dd, 4H), 4.41 (d, 1H), 4.30 (d, 1H), 3.61 (ddd, 1H), 3.11 (t, 1H), 2.96 (t, 1H), 1.88 (m, 4H). MS (EI) for $C_{23}H_{19}F_5N_6O_4$, found: 539.2 (MH+). Analytical HPLC, ret. time=14.79 min, 99% purity.

Compound D46: 2,6-Difluorophenyl 4-[2-amino-5-(1-hydroxy-1-methyl-2-{[2-(trifluoromethyl)pyrimidin-4-yl]oxy}ethyl)pyrimidin-4-yl]piperidine-1-carboxylate Compound D46 was made from Compound M3 using a method analogous to that used to convert intermediate D24.2 to intermediate D24.3. $^1$H NMR (400 MHz, CDCl$_3$) δ 8.63 (d, 1H), 8.23 (s, 1H), 7.14 (dq, 1H), 6.97 (dd, 3H), 5.15 (s, 2H), 4.80 (d, 1H), 4.60 (d, 1H), 4.46 (d, 1H), 4.35 (d, 1H), 3.64 (t, 1H), 3.13 (t, 1H), 2.98 (t, 1H), 2.70 (bs, 1H), 2.10 (m, 2H), 1.85-1.71 (m, 2H), 1.76 (s, 3H). MS (EI) for $C_{24}H_{23}F_5N_6O_4$, found: 555.2 (MH+). Analytical HPLC, ret. time=15.62 min, 97% purity.

Compound D47: N-(2,6-Difluorophenyl)-4-(5-{1-hydroxy-1-methyl-2-[6-(trifluoromethyl)pyridin-2-yl]ethyl}-2-methylpyrimidin-4-yl)piperidine-1-carboxamide D47.1: tert-Butyl 4-(5-(2-hydroxy-1-(6-(trifluoromethyl)pyridin-2-yl)propan-2-yl)-2-methylpyrimidin-4-yl)piperidine-1-carboxylate To a −78° C. solution of 2-methyl-6-trifluoromethylpyridine (320 mg, 2.0 mmol) in THF (6 mL) was added nBuLi (0.8 mL, 2.5 M in hexanes, 2.0 mmol). The resulting solution was stirred at −78° C. for 1 h. A solution of intermediate B36.1 (128 mg, 0.4 mmol) in THF (1 mL) was added. The mixture was stirred for 2 h and was allowed to warm to rt gradually. Water was added slowly to quench the reaction. EtOAc was added to extract the product. The organic phase was washed with saturated NaHCO$_3$, brine, and dried over anhydrous Na$_2$SO$_4$. After removal of the solvents, the residue was purified by flash column chromatography to give intermediate D47.1 (30 mg, 16%).

D47.2: 2-(2-Methyl-4-(piperidin-4-yl)pyrimidin-5-yl)-1-(6-(trifluoromethyl)pyridin-2-yl)propan-2-ol hydrochloride salt Intermediate D47.2 was made from the Boc deprotection of intermediate D47.1 using General Procedure 2.

Compound D47:

Compound D47 was synthesized from intermediate D47.2 and 2,6-difluorophenyl isocyanate using General Procedure 5. $^1$H NMR (400 MHz, DMSO-d6) δ 8.26 (s, 1H), 8.21 (st, 1H), 7.91 (t, 1H), 7.60 (d, 1H), 7.52 (d, 1H), 7.24 (m, 1H), 7.08 (m, 2H), 5.76 (s, 1H), 4.25 (m, 2H), 3.50 (m, 3H), 2.85 (m, 2H), 2.45 (s, 3H), 1.80 (m, 4H), 1.62 (s, 3H). MS (EI) for $C_{26}H_{26}F_5N_5O_2$, found: 536.2 (MH+). Analytical HPLC, ret. time=13.30 min, 100% purity.

Compound D48: 2,6-Difluorophenyl 4-[2-amino-5-(1-hydroxy-1-methyl-2-{[6-(trifluoromethyl)pyridin-2-yl]oxy}ethyl)pyrimidin-4-yl]piperidine-1-carboxylate Compound D48 was made in five steps from intermediate D26.2 in the same manner that Compound D46 was made in five steps from intermediate D28.1. $^1$H NMR (400 MHz, CDCl$_3$) δ 8.60 (d, 1H), 8.13 (s, 1H), 7.25 (d, 1H), 7.15 (m, 1H), 6.98 (m, 3H), 5.11 (s, 2H), 4.47 (dd, 1H), 4.37 (d, 1H), 4.36 (dd, 1H), 4.12 (d, 1H), 3.69 (t, 1H), 3.13 (t, 1H), 2.97 (t, 1H), 2.57 (bs, 1H), 3.22 (m, 2H), 1.90 (m, 2H), 1.89 (s, 3H). MS (EI) for C$_{25}$H$_{24}$F$_5$N$_5$O$_4$, found: 554.2 (MH+). Analytical HPLC, ret. time=11.25 min, 94% purity.

Compound D49: 2-Fluorophenyl 4-[2-amino-5-(1-hydroxy-1-methyl-2-{[2-(trifluoromethyl)pyrimidin-4-yl]oxy}ethyl)pyrimidin-4-yl]piperidine-1-carboxylate Compound D49 was made in four steps from intermediate M2.1 in the same manner that Compound D46 was made in four steps from intermediate M2.1, substituting 2,6-difluorophenyl chloroformate with 2-fluorophenyl chloroformate in the first step. $^1$H NMR (400 MHz, CDCl$_3$) δ 8.63 (d, 1H), 8.26 (bs, 1H), 7.18 (m, 4H), 6.95 (d, 1H), 5.01 (s, 2H), 4.81 (d, 1H), 4.60 (d, 1H), 4.42 (dd, 2H), 3.64 (m, 1H), 3.11 (s, 1H), 2.95 (s, 1H), 2.72 (s, 1H), 2.09 (m, 2H), 1.74 (s, 3H), 1.73 (m, 2H). MS (EI) for C$_{24}$H$_{24}$F$_4$N$_6$O$_4$, found: 537.2 (MH+). Analytical HPLC, ret. time=13.66 min, 99% purity.

Compound D50: 4-Fluorophenyl 4-[2-amino-5-(1-hydroxy-1-methyl-2-{[2-(trifluoromethyl)pyrimidin-4-yl]oxy}ethyl)pyrimidin-4-yl]piperidine-1-carboxylate Compound D50 was made in four steps from intermediate M2.1 in the same manner that Compound D46 was made in four steps from intermediate M2.1, substituting 2,6-difluorophenyl chloroformate with 4-fluorophenyl chloroformate in the first step. $^1$H NMR (400 MHz, CDCl$_3$) δ 8.64 (d, 1H), 8.24 (s, 1H), 7.14-7.01 (m, 4H), 6.95 (d, 1H), 5.17 (bs, 2H), 4.81 (d, 1H), 4.61 (d, 1H), 4.40 (t, 2H), 3.64 (t, 1H), 3.07 (t, 1H), 2.92 (t, 1H), 2.74 (bs, 1H), 2.15-1.94 (m, 2H), 1.81 (m, 2H), 1.73 (s, 3H). MS (EI) for C$_{24}$H$_{24}$F$_4$N$_6$O$_4$, found: 537.2 (MH+). Analytical HPLC, ret. time=13.72 min, 98% purity.

Compound E12: N-(2,6-Difluorophenyl)-4-[5-(1-fluoro-1-methyl-2-{[6-(trifluoromethyl)pyridin-2-yl]oxy}ethyl)-2-methylpyrimidin-4-yl]piperidine-1-carboxamide E12.1: tert-Butyl 4-(5-(2-fluoro-1-(6-(trifluoromethyl)pyridin-2-yloxy)propan-2-yl)-2-methylpyrimidin-4-yl)piperidine-1-carboxylate To a solution of intermediate D24.3 (37 mg, 0.07) in DCM (1 mL) at 0° C. was added DAST (30 mg, 0.19 mmol) with stirring. The solution was warmed to RT. After 25 min, the reaction mixture was quenched with saturated aqueous NaHCO$_3$ solution, and diluted with EtOAc. The organic phase was separated, washed with brine, dried (MgSO$_4$), and concentrated. The crude product was purified on prep HPLC to give intermediate E12.1 (16 mg). $^1$H-NMR (400 MHz, CDCl$_3$): δ 8.54 (d, 1H), 7.72 (t, 1H), 7.28 (d, 1H), 6.91 (d, 1H), 4.76 (dd, 2H), 4.23 (m, 2H), 3.29 (m, 1H), 2.79 (m, 2H), 2.67 (s, 3H), 2.04 (m, 1H), 1.92 (m, 1H), 1.86 (d, 3H), 1.65 (m, 2H), 1.47 (s, 9H). MS (EI) for C$_{24}$H$_{30}$F$_4$N$_4$O$_3$, found: 499.3 (MH+).

E12.2: 5-(2-Fluoro-1-(6-(trifluoromethyl)pyridin-2-yloxy)propan-2-yl)-2-methyl-4-(piperidin-4-yl)pyrimidine hydrochloride salt Intermediate E12.2 was made from the Boc deprotection of intermediate E12.1 using General Procedure 2.

Compound E12:

Compound E12 was made from intermediate E12.2 and 2,6-difluorophenyl isocyanate using General Procedure 5. $^1$H-NMR (400 MHz, CDCl$_3$): δ 8.55 (d, 1H), 7.74 (dd, 1H), 7.30 (d, 1H), 7.13-7.10 (m, 1H), 6.95-6.92 (m, 3H), 5.92 (s, 1H), 4.76 (m, 2H), 4.25 (m, 2H), 3.43 (m, 1H), 3.06 (m, 2H), 2.69 (s, 3H), 2.21-2.09 (m, 2H), 1.89 (d, 3H), 1.81-1.75 (m, 2H). MS (EI) for C$_{26}$H$_{25}$F$_6$N$_5$O$_2$, found: 554.2 (MH+). Analytical HPLC, ret. time=18.8 min, 91% purity.

Compound E13: 4-[5-(1-Fluoro-1-methyl-2-{[6-(trifluoromethyl)pyridin-2-yl]oxy}ethyl)-2-methylpyrimidin-4-yl]-N-[2-fluoro-6-(trifluoromethyl)phenyl]piperidine-1-carboxamide Compound E13 was made in a manner similar to Compound E12: $^1$H-NMR (400 MHz, CDCl$_3$): δ 8.55 (d, 1H), 7.74 (dd, 1H), 7.44 (d, 1H), 7.37-7.30 (m, 3H), 6.93 (d, 1H), 6.10 (s, 1H), 4.77 (m, 2H), 4.20 (m, 2H), 3.43 (m, 1H), 3.08 (m, 2H), 2.69 (s, 3H), 2.23 (m, 1H), 2.09 (m, 1H), 1.89 (d, 3H), 1.81 (m, 2H). MS (EI) for C$_{27}$H$_{25}$F$_8$N$_5$O$_2$, found: 604.2 (MH+). Analytical HPLC, ret. time=19.9 min, 92% purity.

Compound E14: 4-{1-[(2,6-Difluorophenyl)acetyl]piperidin-4-yl}-5-{2-[(3,5-dimethylphenyl)oxy]-1-fluoro-1-methylethyl}-2-methylpyrimidine E14.1: tert-Butyl 4-(5-(1-(3,5-dimethylphenoxy)-2-hydroxypropan-2-yl)-2-methylpyrimidin-4-yl)piperidine-1-carboxylate To a solution of 3,5-dimethylphenol (244 mg, 2.0 mmol) in DMF (4 mL) was added NaH (120 mg, 3 mmol, 60% in mineral oil). The resulting mixture was stirred at room temperature for 30 min, then D2.1 (1 mmol) was added. The mixture was stirred at 75° C. for 8 h, cooled to room temperature and diluted with aq. sat. NaHCO$_3$. The crude product was extracted with EtOAc, washed with brine, and concentrated. The crude product was purified by flash column chromatography.

E14.2: 1-(3,5-Dimethylphenoxy)-2-(2-methyl-4-(piperidin-4-yl)pyrimidin-5-yl)propan-2-ol hydrochloride salt Intermediate E14.2 was made from the Boc deprotection of intermediate E14.1 using General Procedure 2.

E14.3: 2-(2,6-Difluorophenyl)-1-(4-(5-(1-(3,5-dimethylphenoxy)-2-hydroxypropan-2-yl)-2-methylpyrimidin-4-yl)piperidin-1-yl)ethanone Intermediate E14.3 was made from intermediate E14.2 and 2,6-difluorophenylacetic acid using General Procedure 4. $^1$H-NMR (400 MHz, DMSO-d6): δ 8.56 (d, 1H), 7.36 (m, 1H), 7.07 (m, 2H), 6.55 (m, 3H), 5.70 (s, 1H), 4.45 (d, 1H), 4.18 (m, 3H), 3.78 (m, 3H), 3.17 (m, 1H), 2.62 (m, 1H), 2.55 (s, 3H), 2.21 (s, 6H), 1.75 (m, 4H), 1.65 (s, 3H). MS (EI) for C$_{29}$H$_{33}$F$_2$N$_3$O$_3$, found: 510.0 (MH+). Analytical HPLC, ret. time=17.17 min, 97% purity.

Compound E14:

Compound E14 was made from intermediate E14.3 using a method analogous to that used to convert intermediate D24.3 to intermediate E12.1. $^1$H-NMR (400 MHz, CDCl$_3$):

δ 8.52 (s, 1H), 7.22 (m, 1H), 6.90 (dd, 2H), 6.04 (s, 1H), 6.50 (s, 2H), 4.77 (m, 1H), 4.25 (m, 1H), 4.11 (m, 1H), 3.77 (s, 2H), 3.47 (m, 1H), 3.21 (m, 1H), 2.69 (s, 3H), 2.27 (s, 6H), 2.17-2.00 (m, 2H), 1.90 (d, 3H), 1.80-1.72 (m, 2H). MS (EI) for $C_{29}H_{32}F_3N_3O_2$, found: 512.3 (MH+). Analytical HPLC, ret. time=22.1 min, 85% purity.

The following compound was made from Compound D17 in a manner similar to the way Compound E14 was made from intermediate E14.3:

Compound E15: N-(2,6-Difluorophenyl)-4-[5-(1-fluoro-1-methyl-2-{[2-(trifluoromethyl)pyrimidin-4-yl]amino}ethyl)-2-methylpyrimidin-4-yl]piperidine-1-carboxamide Compound E15 was made from intermediate D17 in a manner similar to the way Compound E14 was made from intermediate E14.3: $^1$H-NMR (400 MHz, CDCl$_3$): δ 8.64 (br. s, 1H), 8.30 (s, 1H), 7.13 (m, 1H), 6.70-6.93 (m, 2H), 6.54 (br. s, 1H), 5.91 (s, 1H), 5.44 (br. s, 1H), 4.37-4.23 (m, 4H), 3.99 (m, 1H), 3.30 (m, 1H), 3.16-3.02 (m, 2H), 2.74 (s, 3H), 2.19 (m, 2H), 1.83-1.75 (m, 5H). MS (EI) for $C_{25}H_{25}F_6N_7O$, found: 554.2 (MH+). Analytical HPLC, ret. time=15.3 min, 98% purity.

Compound M4: N-(2,6-Difluorophenyl)-4-[2-methyl-5-({[6-(trifluoromethyl)pyridin-2-yl]oxy}acetyl)pyrimidin-4-yl]piperidine-1-carboxamide M4.1: 1-(2-Methyl-4-(piperidin-4-yl)pyrimidin-5-yl)-2-(6-(trifluoromethyl)pyridin-2-yloxy)ethanone hydrochloride salt Intermediate M4.1 was made from the Boc deprotection of intermediate D24.2 using General Procedure 2.

Compound M4:

Compound M4 was made from intermediate M4.1 and 2,6-difluorophenyl isocyanate using General Procedure 5. $^1$H-NMR (400 MHz, CDCl$_3$): δ 8.99 (s, 1H), 7.80 (dd, 1H), 7.32 (d, 1H), 7.12-7.05 (m, 2H), 6.93 (m, 2H), 5.89 (s, 1H), 5.41 (s, 2H), 4.19 (d, 1H), 3.39 (m, 1H), 3.02 (m, 1H), 2.07-1.97 (m, 2H), 1.81 (d, 2H). MS (EI) for $C_{25}H_{22}F_5N_5O_3$, found: 536.2 (MH+). Analytical HPLC, ret. time=18.0 min, 98% purity.

Compound N1: N-(2,6-Difluorophenyl)-4-[5-(1-hydroxy-2-{[6-(trifluoromethyl)pyridin-2-yl]oxy}ethyl)-2-methylpyrimidin-4-yl]piperidine-1-carboxamide To a solution of Compound M4 (60 mg, 0.12 mmol) in MeOH (1 mL) were added NH$_4$OAc (270 mg, 3.5 mmol) and Na(CN)BH$_3$ (20 mg, 0.32 mmol). The mixture was stirred at rt for 48 h. MeOH was removed. The residue was extracted with EtOAc. The organic phase was washed with saturated NaHCO$_3$, brine, and dried over anhydrous Na$_2$SO$_4$. After removal of the solvents, the residue was purified by preparative HPLC to give Compound N1 (23 mg, 35%). $^1$H NMR (400 MHz, DMSO-d6) δ 8.72 (s, 1H), 8.23 (s, 1H), 7.97 (t, 1H), 7.50 (d, 1H), 7.25 (m, 1H), 7.11 (m, 3H), 5.90 (m, 1H), 5.34 (m, 1H), 4.47 (m, 2H), 4.20 (d, 1H), 3.22 (m, 1H), 2.82 (m, 2H), 2.57 (s, 3H), 1.62 (m, 4H). MS (EI) for $C_{25}H_{24}F_5N_5O_3$, found: 538.2 (MH+). Analytical HPLC, ret. time=14.93 min, 97.8% purity.

Compound M5: 1-(2-Amino-4-{1-[(2,6-difluorophenyl)acetyl]piperidin-4-yl}pyrimidin-5-yl)-2-{[2-(trifluoromethyl)pyrimidin-4-yl]oxy}ethanone M5.1: 2-(2,6-Difluorophenyl)-1-(4-(2-(methylthio)-5-(2-(2-(trifluoromethyl)pyrimidin-4-yloxy)acetyl)pyrimidin-4-yl)piperidin-1-yl)ethanone Intermediate M5.1 was made from intermediate M2.1 and 2,6-difluorophenylacetic acid using General Procedure 4.

M5.2: 2-(2,6-Difluorophenyl)-1-(4-(2-(methylsulfonyl)-5-(2-(2-(trifluoromethyl)pyrimidin-4-yloxy)acetyl)pyrimidin-4-yl)piperidin-1-yl)ethanone Intermediate M5.2 was made from intermediate M5.1 using General Procedure 6.

Compound M5:

Compound M5 was synthesized from intermediate M5.2 using General Procedure 7. $^1$H NMR (400 MHz, CDCl$_3$) δ 8.73 (s, 1H), 8.66 (d, 1H), 7.21 (td, 1H), 7.10 (d, 1H), 6.94-6.84 (m, 2H), 5.51 (q, 4H), 4.70 (d, 1H), 4.05 (d, 1H), 3.73 (s, 2H), 3.68-3.56 (m, 1H), 3.20 (t, 1H), 2.66 (dd, 1H), 2.11 (s, 1H), 1.89-1.72 (m, 4H). MS (EI) for $C_{24}H_{21}F_5N_6O_3$, found: 537.1 (MH+). Analytical HPLC, ret. time=12.62 min, 99% purity.

Compound M6: 4-[2-Amino-5-({[2-(trifluoromethyl)pyrimidin-4-yl]oxy}acetyl)pyrimidin-4-yl]-N-(2,6-difluorophenyl)piperidine-1-carboxamide Compound M6 was synthesized from intermediate D38.1 using General Procedure 7. $^1$H NMR (400 MHz, CDCl$_3$) δ 8.74 (s, 1H), 8.67 (d, 1H), 7.14-7.05 (m, 2H), 6.97-6.89 (m, 2H), 5.87 (s, 1H), 5.52 (m, 4H), 4.19 (d, 2H), 3.67-3.53 (m, 1H), 3.00 (dd, 2H), 1.98-1.74 (m, 4H). MS (EI) for $C_{23}H_{20}F_5N_7O_3$, found: 538.1 (MH+). Analytical HPLC, ret. time=15.76 min, 97% purity.

Compound M7: N-(2,6-Difluorophenyl)-4-{2-[(2-fluoroethyl)amino]-5-({[2-(trifluoromethyl)pyrimidin-4-yl]oxy}acetyl)pyrimidin-4-yl}piperidine-1-carboxamide Compound M7 was synthesized from intermediate D38.1 using a method analogous to that used to convert intermediate B53.1 to Compound B60.1H NMR (400 MHz, CDCl$_3$) δ 8.73 (s, 1H), 8.66 (d, 1H), 7.10 (d, 2H), 6.93 (t, 2H), 5.87 (s, 1H), 5.85 (s, 1H), 5.52 (s, 2H), 4.69 (t, 1H), 4.58 (t, 1H), 4.18 (d, 2H), 3.95-3.77 (m, 2H), 3.65 (bs, 1H), 3.02 (t, 2H), 1.83 (m, 4H). MS (EI) for $C_{25}H_{23}F_6N_7O_3$, found: 584.1 (MH+). Analytical HPLC, ret. time=17.30 min, 98% purity.

Compound N2: 4-[2-Amino-5-(1-hydroxy-2-{[2-(trifluoromethyl)pyrimidin-4-yl]oxy}ethyl)pyrimidin-4-yl]-N-(2,6-difluorophenyl)piperidine-1-carboxamide To a solution of Compound M6 (55.9 mg, 0.104 mmol) in MeOH (2 mL) was added NaBH$_4$ (12 mg, 0.312 mmol) at 0° C. The reaction mixture was stirred at 0° C. for 15 min. The mixture was monitored by LC/MS and quenched with water at 0° C. upon completion. The resulting mixture was diluted with EtOAc, washed with water, brine, dried over magnesium sulfate and concentrated in vacuo to give a crude product, which was purified by preparative HPLC to give Compound N2 (17 mg, 30.3%). $^1$H NMR (400 MHz, CDCl$_3$) δ 8.64 (d, 1H), 8.41 (s, 1H), 7.12 (dt, 1H), 7.03-6.89 (m, 3H), 5.90 (s, 1H), 5.32 (dd, 1H), 5.15 (s, 2H), 4.69 (dd, 1H), 4.51 (dd, 1H), 4.23 (d, 2H), 3.07 (dt, 3H), 2.19-1.96 (m, 2H), 1.87-1.69 (m, 2H). MS (EI) for C$_{23}$H$_{22}$F$_5$N$_7$O$_3$, found: 540.2 (MH+). Analytical HPLC, ret. time=11.30 min, 99% purity.

Compound N3: 4-[2-Amino-5-(1-hydroxy-2-{[6-(trifluoromethyl)pyridin-2-yl]oxy}ethyl)pyrimidin-4-yl]-N-(2,6-difluorophenyl)piperidine-1-carboxamide N3.1: 1-(2-(Methylthio)-4-(piperidin-4-yl)pyrimidin-5-yl)-2-(6-(trifluoromethyl)pyridin-2-yloxy)ethanone hydrochloride salt Intermediate N3.1 was made from the Boc deprotection of intermediate D26.2 using General Procedure 2.

N3.2: N-(2,6-Difluorophenyl)-4-(2-(methylthio)-5-(2-(6-(trifluoromethyl)pyridin-2-yloxy)acetyl)pyrimidin-4-yl)piperidine-1-carboxamide Intermediate N3.2 was made from intermediate N3.1 and 2,6-difluorophenyl isocyanate using General Procedure 5.

N3.3: N-(2,6-Difluorophenyl)-4-(2-(methylsulfonyl)-5-(2-(6-(trifluoromethyl)pyridin-2-yloxy)acetyl)pyrimidin-4-yl)piperidine-1-carboxamide Intermediate N3.3 was made from intermediate N3.2 using General Procedure 6.

N3.4: 4-(2-Amino-5-(2-(6-(trifluoromethyl)pyridin-2-yloxy)acetyl)pyrimidin-4-yl)-N-(2,6-difluorophenyl)piperidine-1-carboxamide Intermediate N3.4 was made from intermediate N3.3 using General Procedure 7.

Compound N3:

Compound N3 was made from intermediate N3.4 using a method analogous to that used to convert Compound M6 to compound N2. $^1$H NMR (400 MHz, CDCl$_3$) δ 8.43 (s, 1H), 7.80 (t, 1H), 7.35 (d, 1H), 7.15-7.06 (m, 1H), 7.01 (t, 1H), 6.98-6.89 (m, 2H), 5.89 (s, 1H), 5.32 (dd, 1H), 5.03 (s, 2H), 4.63 (dd, 1H), 4.42 (dd, 1H), 4.22 (d, 2H), 3.07 (m, 3H), 2.16-1.94 (m, 2H), 1.86-1.70 (m, 2H). MS (EI) for C$_{24}$H$_{23}$F$_5$N$_6$O$_3$, found: 539.2 (MH+). Analytical HPLC, ret. time=9.76 min, 99% purity.

Compound N4: N-(2,6-Difluorophenyl)-4-[5-(1-hydroxy-2-{[6-(trifluoromethyl)pyridin-2-yl]oxy}ethyl)-2-(methyloxy)pyrimidin-4-yl]piperidine-1-carboxamide N4.1: N-(2,6-Difluorophenyl)-4-(2-methoxy-5-(2-(6-(trifluoromethyl)pyridin-2-yloxy)acetyl)pyrimidin-4-yl)piperidine-1-carboxamide Intermediate N4.1 was made from intermediate N3.3 using a method analogous to that used to convert intermediate D29.1 to Compound D40.

Compound N4:

Compound N4 was made from intermediate N4.1 using a method analogous to that used to convert Compound M6 to compound N2. $^1$H NMR (400 MHz, CDCl$_3$) δ 8.67 (s, 1H), 7.81 (t, 1H), 7.36 (d, 1H), 7.12 (s, 1H), 7.05-6.98 (m, 1H), 6.94 (t, 2H), 5.88 (s, 1H), 5.39 (dd, 1H), 4.67 (dd, 1H), 4.44 (dd, 1H), 4.23 (m, 2H), 4.03 (s, 3H), 3.26 (d, 1H), 3.20 (m, 1H), 3.06 (m, 2H), 2.05 (m, 2H), 1.82 (m, 2H). MS (EI) for C$_{25}$H$_{24}$F$_5$N$_5$O$_4$, found: 554.1 (MH+). Analytical HPLC, ret. time=18.02 min, 99% purity.

Compound M8: N-(2,6-Difluorophenyl)-4-[2,6-dimethyl-5-({[2-(trifluoromethyl)pyrimidin-4-yl]oxy}acetyl)pyrimidin-4-yl]piperidine-1-carboxamide M8.1: tert-Butyl 4-(5-(1-hydroxyethyl)-2,6-dimethylpyrimidin-4-yl)piperidine-1-carboxylate To a solution of intermediate B46.2 (870 mg, 2.7 mmol) in dry THF (25 mL) was added MeMgBr (5.0 mL, 1.4M in 1:3 THF:Toluene, 7.0 mmol). The resulting mixture was stirred at room temperature and monitored by LC-MS until complete. Upon completion, the reaction mixture was diluted with saturated aqueous NH$_4$Cl and extracted with EtOAc (3×). The combined organic extractions were washed with saturated aqueous NaCl (1×), dried (Na$_2$SO$_4$) and concentrated in vacuo to give intermediate M8.1 which was used as is in subsequent reactions. MS (EI) for C$_{18}$H$_{29}$N$_3$O$_3$, found: 336.3 (MH+).

F9.2: tert-Butyl 4-(5-acetyl-2,6-dimethylpyrimidin-4-yl)piperidine-1-carboxylate Intermediate M8.2 was made from intermediate M8.1 using a method analogous to the oxidation of intermediate B46.1 to intermediate B46.2.

M8.3: tert-Butyl 4-(5-(2-bromoacetyl)-2,6-dimethylpyrimidin-4-yl)piperidine-1-carboxylate Intermediate M8.3 was made from intermediate M8.2 using a method analogous to the conversion of intermediate C70.2 to intermediate C70.3.

M8.4: tert-Butyl 4-(2,6-dimethyl-5-(2-(2-(trifluoromethyl)pyrimidin-4-yloxy)acetyl)pyrimidin-4-yl)piperidine-1-carboxylate Intermediate M8.4 was made from intermediate M8.3 and 2-(trifluoromethyl)pyrimidin-4-ol using a method analogous to the synthesis of intermediate D24.2 from intermediate D24.1.

M8.5: 1-(2,4-Dimethyl-6-(piperidin-4-yl)pyrimidin-5-yl)-2-(2-(trifluoromethylpyrimidin-4-yloxy)ethanone hydrochloride salt Intermediate M8.5 was made from the Boc deprotection of intermediate M8.4 using General Procedure 2.

Compound M8:

Compound M8 was made from intermediate M8.5 and 2,6-difluorophenyl isocyanate using General Procedure 5. $^1$H-NMR (400 MHz, CDCl$_3$): δ 8.71 (d, 1H), 7.12 (m, 2H), 6.94 (m, 2H), 5.90 (s, 1H), 5.42 (s, 2H), 4.23 (m, 2H), 3.05

(m, 2H), 2.74 (m, 1H), 2.71 (s, 3H), 2.58 (s, 3H), 2.13 (m, 2H), 1.80 (m, 2H). MS (EI) for $C_{25}H_{23}F_5N_6O_3$, found: 551.2 (MH+). Analytical HPLC, ret. time=17.00 min, 98% purity.

Compound N5: N-(2,6-Difluorophenyl)-4-[5-(1-hydroxy-2-{[2-(trifluoromethyl)pyrimidin-4-yl]oxy}ethyl)-2,6-dimethylpyrimidin-4-yl]piperidine-1-carboxamide Compound N5 was made from Compound M8 using a method analogous to that used to convert Compound M6 to compound N2. $^1$H-NMR (400 MHz, CDCl$_3$): δ 8.64 (d, 1H), 7.11 (m, 1H), 6.98 (d, 1H) 6.93 (m, 2H), 5.95 (s, 1H), 5.28 (m, 1H), 4.70 (m, 2H), 4.20 (m, 2H), 3.53 (m, 1H), 3.28 (m, 1H), 3.03 (m, 2H), 2.64 (s, 3H), 2.63 (s, 3H), 2.18 (m, 1H), 2.03 (m, 1H), 1.85-1.65 (m, 2H). MS (EI) for $C_{25}H_{25}F_5N_6O_3$, found: 553.2 (MH+). Analytical HPLC, ret. time=12.22 min, 99% purity.

Compound M9: N-(2,6-Difluorophenyl)-4-[5-(1-hydroxy-2-{[2-(trifluoromethyl)pyrimidin-4-yl]oxy}ethyl)-2,6-dimethylpyrimidin-4-yl]piperidine-1-carboxamide M9.1: tert-Butyl 4-(2,6-dimethyl-5-(2-(6-(trifluoromethyl)pyridin-2-yloxy)acetyl)pyrimidin-4-yl)piperidine-1-carboxylate Intermediate M9.1 was made from intermediate M8.3 using a method analogous to the synthesis of intermediate D24.2 from intermediate D24.1.

M9.2: 1-(2,4-Dimethyl-6-(piperidin-4-yl)pyrimidin-5-yl)-2-(6-(trifluoromethyl)pyridin-2-yloxy)ethanone hydrochloride salt Intermediate M9.2 was made from the Boc deprotection of intermediate M9.1 using General Procedure 2.

Compound M9:

Compound M9 was made from intermediate M9.2 and 2,6-difluorophenyl isocyanate using General Procedure 5. 1H-NMR (400 MHz, CDCl$_3$): δ 7.83 (t, 1H), 7.37 (d, 1H), 7.11 (m, 2H), 6.94 (m, 2H), 5.90 (s, 1H), 5.38 (s, 2H), 4.21 (m, 2H), 3.03 (m, 2H), 2.77 (m, 1H), 2.70 (s, 3H), 2.57 (s, 3H), 2.11 (m, 2H), 1.78 (m, 2H). MS (EI) for $C_{26}H_{24}F_5N_5O_3$, found: 550.2 (MH+). Analytical HPLC, ret. time=14.57 min, 99% purity.

Compound N6: N-(2,6-Difluorophenyl)-4-[5-(1-hydroxy-2-{[6-(trifluoromethyl)pyridin-2-yl]oxy}ethyl)-2,6-dimethylpyrimidin-4-yl]piperidine-1-carboxamide Compound N6 was made from Compound M4 using a method analogous to that used to convert Compound M6 to compound N2. $^1$H-NMR (400 MHz, CDCl$_3$): δ 7.83 (t, 1H), 7.36 (d, 1H), 7.11 (m, 1H), 7.05 (d, 1H), 6.94 (m, 2H), 5.93 (s, 1H), 5.60 (dd, 1H), 4.70 (dd, 1H), 4.60 (dd, 1H), 4.24 (m, 2H), 3.55 (m, 1H), 3.38 (m, 1H), 3.03 (m, 2H), 2.65 (s, 3H), 2.64 (s, 3H), 2.25-2.00 (m, 2H), 1.87-1.70 (m, 2H). MS (EI) for $C_{26}H_{26}F_5N_5O_3$, found: 552.2 (MH+). Analytical HPLC, ret. time=10.43 min, 99% purity.

Compound M10: 4-[2-Amino-6-methyl-5-({[2-(trifluoromethyl)pyrimidin-4-yl]oxy}acetyl)pyrimidin-4-yl]-N-(2,6-difluorophenyl)piperidine-1-carboxamide M10.1: tert-Butyl 4-(6-methyl-2-(methylthio)-5-(2-(2-(trifluoromethyl)pyrimidin-4-yloxy)acetyl)pyrimidin-4-yl)piperidine-1-carboxylate Intermediate M10.1 was made from intermediate C70.3 and 2-(trifluoromethyl)pyrimidin-4-ol using a method analogous to the synthesis of intermediate D24.2 from intermediate D24.1.

M10.2: 1-(4-Methyl-2-(methlythio)-6-(piperidin-4-yl)pyrimidin-5-yl)-2-(2-(trifluoromethyl)pyrimidin-4-yloxy)ethanone hydrochloride salt Intermediate M10.2 was made from the Boc deprotection of intermediate M10.1 using General Procedure 2.

M10.3: N-(2,6-Difluorophenyl)-4-(6-methyl-2-(methylthio)-5-(2-(2-(trifluoromethyl)pyrimidin-4-yloxy)acetyl)pyrimidin-4-yl)piperidine-1-carboxamide Intermediate M10.3 was made from intermediate M10.2 and 2,6-difluorophenyl isocyanate using General Procedure 5.

M10.4: N-(2,6-Difluorophenyl)-4-(6-methyl-2-(methylsulfonyl)-5-(2-(2-(trifluoromethyl)pyrimidin-4-yloxy)acetyl)pyrimidin-4-yl)piperidine-1-carboxamide Intermediate M10.4 was made from intermediate M10.3 using General Procedure 6.

Compound M10:

Compound M10 was made from intermediate M10.4 using General Procedure 7. $^1$H-NMR (400 MHz, CDCl$_3$): δ 8.68 (d, 1H), 7.09 (m, 2H), 6.93 (m, 2H), 5.84 (s, 1H), 5.39 (s, 2H), 5.20 (br s, 2H), 4.20 (m, 2H), 3.01 (m, 2H), 2.69 (m, 1H), 2.46 (s, 3H), 2.05 (m, 2H), 1.89 (m, 2H). MS (EI) for $C_{24}H_{22}F_5N_7O_3$, found: 552.2 (MH+). Analytical HPLC, ret. time=14.44 min, 97% purity.

Compound N7: 4-[2-amino-5-(1-hydroxy-2-{[2-(trifluoromethyl)pyrimidin-4-yl]oxy}ethyl)-6-methylpyrimidin-4-yl]-N-(2,6-difluorophenyl)piperidine-1-carboxamide Compound N7 was made from Compound M10 using a method analogous to that used to convert Compound M6 to compound N2. $^1$H NMR (400 MHz, CDCl$_3$) δ 8.64 (d, 1H), 7.15-7.07 (m, 1H), 6.99 (d, 1H), 6.93 (t, 2H), 5.90 (s, 1H), 5.50 (dd, 1H), 5.01 (s, 2H), 4.73 (dd, 1H), 4.63 (dd, 1H), 4.22 (t, 2H), 3.41 (t, 1H), 3.03 (td, 2H), 2.59 (bs, 1H), 2.51 (s, 3H), 2.17-1.93 (m, 4H), 1.75 (m, 4H). MS (EI) for $C_{24}H_{24}F_5N_7O_3$, found: 554.2 (MH+). Analytical HPLC, ret. time=12.37 min, 99% purity.

Compound N8: N-(2,6-Difluorophenyl)-4-[5-(1-hydroxy-2-{[2-(trifluoromethyl)pyrimidin-4-yl]oxy}ethyl)-6-methyl-2-(methyloxy)pyrimidin-4-yl]piperidine-1-carboxamide N8.1: N-(2,6-Difluorophenyl)-4-(2-methoxy-6-methyl-5-(2-(2-(trifluoromethyl)pyrimidin-4-yloxy)acetyl)pyrimidin-4-yl)piperidine-1-carboxamide Intermediate N8.1 was made from intermediate M10.4 using a method analogous to that used to convert intermediate D29.1 to Compound D40.

Compound N8:

Compound N8 was made from intermediate N8.1 using a method analogous to that used to convert Compound M6 to compound N2. $^1$H NMR (400 MHz, CDCl$_3$) δ 8.65 (d, 1H), 7.15-7.07 (m, 1H), 6.99 (d, 1H), 6.98-6.89 (m, 2H), 5.89 (s, 1H), 5.58 (d, 1H), 4.75 (dd, 1H), 4.66 (dd, 1H), 4.24 (td, 2H), 4.00 (s, 3H), 3.51 (t, 1H), 3.15-2.96 (m, 2H), 2.66 (s, 1H), 2.62 (s, 3H), 2.20 (dt, 1H), 2.08 (dt, 1H), 1.84 (d, 1H), 1.76 (d, 1H). MS (EI) for $C_{25}H_{25}F_5N_6O_4$, found: 569.2 (MH+). Analytical HPLC, ret. time=15.82 min, 97% purity.

Compound M11: 4-[2-Amino-6-methyl-5-({[6-(trifluoromethyl)pyridin-2-yl]oxy}acetyl)pyrimidin-4-yl]-N-(2,6-difluorophenyl)piperidine-1-carboxamide M11.1: tert-Butyl 4-(6-methyl-2-(methylthio)-5-(2-(6-(trifluoromethyl)pyridin-2-yloxy)acetyl)pyrimidin-4-yl)piperidine-1-carboxylate Intermediate M11.1 was made from intermediate C70.3 using a method analogous to the synthesis of intermediate D24.2 from intermediate D24.1.

M11.2: 1-(4-Methyl-2-(methylthio)-6-(piperidin-4-yl)pyrimidin-5-yl)-2-(6-(trifluoromethyl)pyridin-2-yloxy)ethanone hydrochloride salt Intermediate M11.2 was made from the Boc deprotection of intermediate M11.1 using General Procedure 2.

M11.3: N-(2,6-Difluorophenyl)-4-(6-methyl-2-(methylthio)-5-(2-(6-(trifluoromethyl)pyridin-2-yloxy)acetyl)pyrimidin-4-yl)piperidine-1-carboxamide Intermediate M11.3 was made from intermediate M11.2 and 2,6-difluorophenyl isocyanate using General Procedure 5.

M11.4: N-(2,6-Difluorophenyl)-4-(6-methyl-2-(methylsulfonyl)-5-(2-(6-(trifluoromethyl)pyridin-2-yloxy)acetyl)pyrimidin-4-yl)piperidine-1-carboxamide Intermediate M11.4 was made from intermediate M11.3 using General Procedure 6.

Compound M11:

Compound M11 was made from intermediate M11.4 using General Procedure 7. $^1$H-NMR (400 MHz, CDCl$_3$): δ 7.81 (t, 1H), 7.34 (d, 1H), 7.10 (m, 2H), 6.93 (m, 2H), 5.88 (s, 1H), 5.32 (s, 2H), 5.25 (m, 2H), 4.19 (m, 2H), 3.01 (m, 2H), 2.72 (m, 1H), 2.47 (s, 3H), 2.00 (m, 2H), 1.79 (m, 2H). MS (EI) for $C_{25}H_{23}F_5N_6O_3$, found: 551.2 (MH+). Analytical HPLC, ret. time=15.71 min, 99% purity.

Compound M12: 4-[2-(Acetylamino)-6-methyl-5-({[6-(trifluoromethyl)pyridin-2-yl]oxy}acetyl)pyrimidin-4-yl]-N-(2,6-difluorophenyl)piperidine-1-carboxamide Compound M12 was made from Compound M11 using a method analogous to that used to convert Compound D30 to Compound D31. $^1$H NMR (400 MHz, CDCl$_3$) δ 7.93 (s, 1H), 7.82 (t, 1H), 7.37 (d, 1H), 7.16-7.06 (m, 2H), 6.98-6.89 (m, 2H), 5.89 (s, 1H), 5.34 (s, 2H), 4.20 (d, 2H), 3.03 (t, 2H), 2.80 (dd, 1H), 2.58 (d, 6H), 2.01 (qd, 2H), 1.80 (d, 2H). MS (EI) for $C_{27}H_{25}F_5N_6O_4$, found: 593.1 (MH+). Analytical HPLC, ret. time=13.72 min, 99% purity.

Compound N9: 4-[2-Amino-5-(1-hydroxy-2-{[6-(trifluoromethyl)pyridin-2-yl]oxy}ethyl)-6-methylpyrimidin-4-yl]-N-(2,6-difluorophenyl)piperidine-1-carboxamide Compound N9 was made from Compound M11 using a method analogous to that used to convert Compound M6 to compound N2. $^1$H-NMR (400 MHz, CDCl$_3$): δ 7.73 (t, 1H), 7.28 (d, 1H), 7.03 (m, 1H), 6.96 (d, 1H), 6.86 (t, 2H), 5.81 (s, 1H), 5.43 (dd, 1H), 4.86 (s, 2H), 4.61 (dd, 1H), 4.49 (dd, 1H), 4.15 (t, 2H), 3.37 (m, 1H), 3.00-2.90 (m, 2H), 2.45 (s, 3H), 2.05-1.88 (m, 2H), 1.76-1.64 (m, 2H). MS (EI) for $C_{25}H_{25}F_5N_6O_3$, found: 553.2 (MH+). Analytical HPLC, ret. time=13.39 min, 98% purity.

Compound N10: 4-[2-(Acetylamino)-5-(1-hydroxy-2-{1-[6-(trifluoromethyl)pyridin-2-yl]oxy}ethyl)-6-methylpyrimidin-4-yl]-N-(2,6-difluorophenyl)piperidine-1-carboxamide Compound N10 was made from Compound N10 using a method analogous to that used to convert Compound D30 to Compound D31. $^1$H NMR (400 MHz, CDCl$_3$) δ 7.82 (dd, 2H), 7.37 (d, 1H), 7.16-7.07 (m, 1H), 7.04 (d, 1H), 6.94 (t, 2H), 5.92 (s, 1H), 5.56 (d, 1H), 4.64 (ddd, 2H), 4.23 (t, 2H), 3.57 (t, 1H), 3.27 (s, 1H), 3.12-2.95 (m, 2H), 2.61 (d, 6H), 2.17-1.91 (m, 2H), 1.87 (d, 1H), 1.75 (d, 1H). MS (EI) for $C_{27}H_{27}F_5N_6O_4$, found: 595.1 (MH+). Analytical HPLC, ret. time=11.56 min, 99% purity.

Compound N11: 1-[2-(Acetylamino)-4-(1-{[(2,6-difluorophenyl)amino]carbonyl}piperidin-4-yl)-6-methylpyrimidin-5-yl]-2-{[6-(trifluoromethyl)pyridin-2-yl]oxy}ethyl acetate Compound N11 was isolated as a side product generated from the reaction that made Compound N10. $^1$H NMR (400 MHz, CDCl$_3$) δ 7.85 (s, 1H), 7.77 (t, 1H), 7.33 (d, 1H), 7.18-7.07 (m, 1H), 6.94 (t, 3H), 6.56 (dd, 1H), 5.92 (s, 1H), 4.77 (ddd, 2H), 4.26 (dd, 2H), 3.45 (m, 1H), 3.08 (dt, 2H), 2.69 (s, 3H), 2.59 (s, 3H), 2.02 (s, 3H), 2.13-1.94 (m, 2H), 1.87 (d, 1H), 1.72-1.63 (m, 1H). MS (EI) for $C_{29}H_{29}F_5N_6O_5$, found: 637.1 (MH+). Analytical HPLC, ret. time=18.27 min, 95% purity.

Compound N12: 4-[2-amino-5-(1-hydroxy-2-{[2-(trifluoromethyl)pyrimidin-4-yl]amino}ethyl)pyrimidin-4-yl]-N-(2,6-difluorophenyl)piperidine-1-carboxamide

N12.1: tert-Butyl 4-(5-(2-azidoacetyl)-2-(methylthio)pyrimidin-4-yl)piperidine-1-carboxylate Intermediate N12.1 was synthesized from intermediate D26.1 using a method analogous to the conversion of intermediate C70.3 to intermediate C70.4.

N12.2: tert-Butyl 4-(5-(2-azido-1-hydroxyethyl)-2-(methylthio)pyrimidin-4-yl)piperidine-1-carboxylate Intermediate N12.2 was synthesized from intermediate N12.1 using a method analogous to the conversion of Compound M6 to compound N2.

N12.3: tert-Butyl 4-(5-(2-amino-1-hydroxyethyl)-2-(methylthio)pyrimidin-4-yl)piperidine-1-carboxylate Intermediate N12.3 was synthesized from intermediate N12.2 using a method analogous to that used to convert intermediate C68.2 to intermediate C68.3.

N12.4: tert-Butyl 4-(5-(1-hydroxy-2-(2-(trifluoromethyl)pyrimidin-4-ylamino)ethyl)-2-(methylthio)pyrimidin-4-yl)piperidine-1-carboxylate Intermediate N12.4 was synthesized from intermediate N12.3 using a method analogous to that used to synthesize intermediate D17.3 from intermediate D17.2.

N12.5: tert-Butyl 4-(5-(1-hydroxy-2-(2-(trifluoromethyl)pyrimidin-4-ylamino)ethyl)-2-(methylsulfonyl)pyrimidin-4-yl)piperidine-1-carboxylate Intermediate N12.5 was made from intermediate N12.4 using General Procedure 6.

N12.6: tert-Butyl 4-(2-amino-5-(1-hydroxy-2-(2-(trifluoromethyl)pyrimidin-4-ylamino)ethyl)pyrimidin-4-yl)piperidine-1-carboxylate To a 48 mL sealed-tube were added intermediate N12.5 (80.0 mg, 0.146 mmol), dioxane (4 mL) and conc. ammonium hydroxide (2 mL) at room temperature. The tube was sealed and heated at 100° C. overnight. After completion, the reaction mixture was diluted with 10 mL of water and extracted with EtOAc (3×10 mL). The combined organic layers were dried over anhydrous magnesium sulfate and concentrated in vacuo to give the desired crude intermediate N12.6 (50 mg, 71%); MS (EI) for $C_{21}H_{28}F_3N_7O_3$, found 484.2 (MH+).

N12.7: 1-(2-Amino-4-(piperidin-4-yl)pyrimidin-5-yl)-2-(2-(trifluoromethyl)pyrimidin-4-ylamino)ethanol hydrochloride salt Intermediate N12.7 was synthesized from the Boc deprotection of intermediate N12.6 using General Procedure 2.

Compound N12:

Compound N12 was synthesized from intermediate N12.7 and 2,6-difluorophenyl isocyanate using General Procedure 5. $^1$H NMR (400 MHz, CDCl$_3$) δ 8.39 (s, 1H), 8.28 (d, 1H), 7.11 (dd, 1H), 6.96 (dd, 2H), 6.52 (d, 1H), 5.92 (s, 1H), 5.70 (bs, 1H), 5.17 (d, 1H), 5.04 (s, 2H), 4.21 (m, 2H), 4.04-3.86 (bs, 1H), 3.44 (s, 1H), 3.14-2.96 (m, 3H), 2.17-1.93 (m, 2H), 1.75 (d, 2H). MS (EI) for $C_{23}H_{23}F_5N_8O_2$, found: 539.2 (MH+). Analytical HPLC, ret. time=7.82 min, 99% purity.

Compound M13: 1-(2-Amino-4-{1-[(2,6-difluorophenyl)carbonyl]piperidin-4-yl}pyrimidin-5-yl)-2-{[2-(trifluoromethyl)pyrimidin-4-yl]oxy}ethanone Compound M13 was made in three steps from intermediate M2.1 in the same manner that Compound M5 was made in three steps from intermediate M2.1, substituting 2,6-difluorobenzoic acid for 2-(2,6-difluorophenyl)acetic acid in the first step. $^1$H NMR (400 MHz, CDCl$_3$) δ 8.73 (s, 1H), 8.66 (d, 1H), 7.33 (m, 2H), 7.10 (d, 1H), 6.95 (m, 2H), 5.50 (m, 4H), 4.88 (dd, 1H), 3.60 (m, 2H), 3.16 (dt, 1H), 2.87 (m, 1H), 1.88 (m, 2H), 1.73 (m, 2H). MS (EI) for $C_{23}H_{19}F_5N_6O_3$, found: 523.2 (MH+). Analytical HPLC, ret. time=12.50 min, 98% purity.

Compound N13: 2,6-Difluorophenyl 4-[2-amino-5-(1-hydroxy-2-{[2-(trifluoromethyl)pyrimidin-4-yl]oxy}ethyl)pyrimidin-4-yl]piperidine-1-carboxylate Compound N13 was made in four steps from intermediate M2.1 in the same manner that Compound N2 was made in four steps from intermediate M2.1, substituting 2,6-difluorophenyl chloroformate for 2,6-difluorophenyl isocyanate in the first step and using standard reaction conditions typical with chloroformates such as those elaborated on in the synthesis of Compound A119 from intermediate A116.3. $^1$H NMR (400 MHz, CDCl$_3$) δ 8.65 (d, 1H), 8.42 (s, 1H), 7.15 (dq, 1H), 7.03-6.92 (m, 3H), 5.33 (d, 1H), 5.08 (s, 2H), 4.69 (d, 1H), 4.56-4.41 (m, 2H), 4.36 (bs, 1H), 3.10 (m, 3H), 2.61 (s, 1H), 2.19-1.96 (m, 2H), 1.86-1.71 (m, 2H). MS (EI) for $C_{23}H_{21}F_5N_6O_4$, found: 541.2 (MH+). Analytical HPLC, ret. time=13.72 min, 99% purity.

Compound M14: 2-Fluorophenyl 4-[2-amino-5-({[6-(trifluoromethyl)pyridin-2-yl]oxy}acetyl)pyrimidin-4-yl]piperidine-1-carboxylate Compound M14 was made in three steps from intermediate N3.1 in the same manner that intermediate N3.4 was made in three steps from intermediate N3.1, substituting 2-fluorophenyl chloroformate for 2,6-difluorophenyl isocyanate in the first step and using standard reaction conditions typical with chloroformates such as those elaborated on in the synthesis of Compound A119 from intermediate A116.3. $^1$H NMR (400 MHz, CDCl$_3$) δ 8.74 (s, 1H), 8.59 (d, 1H), 7.24-7.09 (m, 5H), 7.01-6.95 (m, 1H), 5.56 (s, 2H), 5.24 (s, 2H), 4.43 (d, 1H), 4.34 (d, 1H), 3.77-3.65 (m, 1H), 3.12 (t, 1H), 2.97 (t, 1H), 1.91 (dd, 2H), 1.80 (d, 2H). MS (EI) for $C_{24}H_{21}F_4N_5O_4$, found: 520.2 (MH+). Analytical HPLC, ret. time=18.06 min, 95% purity.

Compound N14: N-(2,6-Difluorophenyl)-4-[5-(1,1-difluoro-2-{[6-(trifluoromethyl)pyridin-2-yl]oxy}ethyl)-2-methylpyrimidin-4-yl]piperidine-1-carboxamide

N14.1: tert-Butyl 4-(5-(1,1-difluoro-2-(6-(trifluoromethyl)pyridin-2-yloxy)ethyl)-2-methylpyrimidin-4-yl)piperidine-1-carboxylate To a stirred solution of tert-butyl intermediate D24.2 (50 mg, 0.10 mmol) in DCM (1 mL) was added bis(2-methoxyethyl)aminosulfur trifluoride (92 mg, 0.42 mmol). The reaction mixture was heated at 65° C. in a sealed tube with stirring for 21 h. The resulting mixture was cooled to 0° C. and partitioned between EtOAc and saturated aqueous NaHCO$_3$. The aqueous layer was extracted with EtOAc. The combined organic portions were washed with brine, dried (MgSO$_4$), filtered, and concentrated in vacuo. The residue was purified on prep. HPLC to give intermediate N14.1 (24 mg). $^1$H-NMR (400 MHz, CDCl$_3$): δ 8.69 (s, 1H), 7.75 (t, 1H), 7.32 (d, 1H), 6.93 (d, 1H), 4.89 (t, 2H), 4.23 (m, 2H), 3.18 (m, 1H), 2.80 (m, 2H), 2.70 (s, 3H), 1.98 (m, 2H), 1.68 (m, 2H), 1.47 (s, 9H). MS (EI) for C$_{23}$H$_{27}$F$_5$N$_4$O$_3$, found: 503.2 (MH+).

N14.2: 5-(1,1-Difluoro-2-(6-(trifluoromethyl)pyridin-2-yloxy)ethyl)-2-methyl-4-(piperidin-4-yl)pyrimidine hydrochloride salt Intermediate N14.2 was synthesized from the Boc deprotection of intermediate N14.1 using General Procedure 2.

Compound N14:

Compound N14 was synthesized from intermediate N14.2 and 2,6-difluorophenyl isocyanate using General Procedure 5. $^1$H-NMR (400 MHz, CDCl$_3$): δ 8.72 (s, 1H), 7.77 (dd, 1H), 7.34 (d, 1H), 7.11 (m, 1H), 6.96-6.92 (m, 3H), 5.90 (s, 1H), 4.92 (t, 2H), 4.25 (d, 2H), 3.30 (m, 1H), 3.07 (t, 2H), 2.73 (s, 3H), 2.18-2.09 (m, 2H), 1.78 (d, 2H). MS (EI) for C$_{25}$H$_{22}$F$_7$N$_5$O$_2$, found: 558.2 (MH+). Analytical HPLC, ret. time=19.9 min, 97% purity.

Compound N15: 4-[5-(1,1-Difluoro-2-{[6-(trifluoromethyl)pyridin-2-yl]oxy}ethyl)-2-methylpyrimidin-4-yl]-N-[2-fluoro-6-(trifluoromethyl)phenyl]piperidine-1-carboxamide Compound N15 was made in a manner similar to Compound N14. $^1$H-NMR (400 MHz, CDCl$_3$): δ 8.72 (s, 1H), 7.77 (dd, 1H), 7.44 (d, 1H), 7.37-7.30 (m, 3H), 6.95 (d, 1H), 6.10 (s, 1H), 4.92 (dd, 2H), 4.21 (d, 2H), 3.31 (m, 1H), 3.08 (m, 2H), 2.73 (s, 3H), 2.19-2.09 (m, 2H), 1.79 (d, 2H). MS (EI) for C$_{26}$H$_{22}$F$_9$N$_5$O$_2$, found: 608.2 (MH+). Analytical HPLC, ret. time=21.2 min, 98% purity.

Compound N16: 4-[2-Amino-5-(1,1-difluoro-2-{[6-(trifluoromethyl)pyridin-2-yl]oxy}ethyl)pyrimidin-4-yl]-N-(2,6-difluorophenyl)piperidine-1-carboxamide N16.1: tert-Butyl 4-(5-(1,1-difluoro-2-(6-(trifluoromethyl)pyridin-2-yloxy)ethyl)-2-(methylthio)pyrimidin-4-yl)piperidine-1-carboxylate Intermediate N16.1 was synthesized from intermediate D26.2 using a method analogous to that used to synthesize intermediate N14.1 from intermediate D24.2.

N16.2: 5-(1,1-Difluoro-2-(6-(trifluoromethyl)pyridin-2-yloxy)ethyl)-2-(methylthio-4-(piperidin-4-yl)pyrimidine hydrochloride salt Intermediate N16.2 was synthesized from the Boc deprotection of intermediate N16.1 using General Procedure 2.

N16.3: 4-(5-(1,1-Difluoro-2-(6-(trifluoromethyl)pyridin-2-yloxy)ethyl)-2-(methylthio)pyrimidin-4-yl)-N-(2,6-difluorophenyl)piperidine-1-carboxamide Intermediate N16.3 was synthesized from intermediate N16.2 and 2,6-difluorophenyl isocyanate using General Procedure 5.

N16.4: 4-(5-(1,1-Difluoro-2-(6-(trifluoromethyl)pyridin-2-yloxy)ethyl)-2-(methylsulfonyl)pyrimidin-4-yl)-N-(2,6-difluorophenyl)piperidine-1-carboxamide Intermediate N16.4 was synthesized from intermediate N16.3 using General Procedure 6.

Compound N16:

Compound N16 was synthesized from intermediate N16.4 using a method analogous to that used to convert intermediate C69.6 to Compound C69. $^1$H-NMR (400 MHz, CDCl$_3$): δ 8.39 (s, 1H), 7.78 (t, 2H), 7.34 (d, 1H), 7.12 (m, 1H), 6.98 (d, 1H), 6.94 (t, 2H), 5.91 (s, 1H), 5.19 (s, 2H), 4.88 (t, 2H), 4.24 (d, 2H), 3.20 (tt, 1H), 3.05 (td, 2H), 2.04 (qd, 2H), 1.79 (m, 2H). MS (EI) for C$_{24}$H$_{21}$F$_7$N$_6$O$_2$, found 559.0 (MH+). Analytical HPLC, ret. time=19.772 min, 95% purity.

Compound N17: 4-[2-Amino-5-(1,1-difluoro-2-{[2-(trifluoromethyl)pyrimidin-4-yl]oxy}ethyl)pyrimidin-4-yl]-N-(2,6-difluorophenyl)piperidine-1-carboxamide N17.1: tert-Butyl 4-(5-(1,1-difluoro-2-(2-(trifluoromethyl)pyrimidin-4-yloxy)ethyl)-2-(methylthio)pyrimidin-4-yl)piperidine-1-carboxylate Intermediate N17.1 was synthesized from intermediate D28.1 using a method analogous to that used to synthesize intermediate N14.1 from intermediate D24.2.

N17.2: 5-(1,1-Difluoro-2-(2-(trifluoromethyl)pyrimidin-4-yloxy)ethyl)-2-(methylthio)-4-(piperidin-4-yl)pyrimidine hydrochloride salt Intermediate N17.2 was synthesized from the Boc deprotection of intermediate N17.1 using General Procedure 2.

N17.3: 4-(5-(1,1-Difluoro-2-(2-(trifluoromethylpyrimidin-4-yloxy)ethyl)-2-(methylthio)pyrimidin-4-yl)-N-(2,6-difluorophenyl)piperidine-1-carboxamide Intermediate N17.3 was synthesized from intermediate N17.2 and 2,6-difluorophenyl isocyanate using General Procedure 5.

N17.4: 4-(5-(1,1-Difluoro-2-(2-(trifluoromethyl)pyrimidin-4-yloxy)ethyl)-2-(methylsulfonyl)pyrimidin-4-yl)-N-(2,6-difluorophenyl)piperidine-1-carboxamide Intermediate N17.4 was synthesized from intermediate N17.3 using General Procedure 6.

Compound N17:

Compound N17 was synthesized from intermediate N17.4 using a method analogous to that used to convert intermediate C69.6 to Compound C69. $^1$H-NMR (400 MHz, CDCl$_3$): δ 8.67 (d, 1H), 8.38 (s, 1H), 7.12 (m, 1H), 7.00 (d, 1H), 6.95 (t, 2H), 5.91 (s, 1H), 5.23 (s, 2H), 4.94 (t, 2H), 4.25 (d, 2H), 3.15 (tt, 1H), 3.05 (td, 2H), 2.06 (qd, 2H), 1.79 (m, 2H). MS (EI) for C$_{23}$H$_{20}$F$_7$N$_7$O$_2$, found 560.2 (MH+). Analytical HPLC, ret. time=16.280 min, 99% purity.

Compound N18: N-(2,6-Difluorophenyl)-4-[5-(1,1-difluoro-2-{[2-(trifluoromethyl)pyrimidin-4-yl]amino}ethyl)-2-methylpyrimidin-4-yl]piperidine-1-carboxamide N18.1: tert-Butyl 4-(5-(2-azidoacetyl)-2-methylpyrimidin-4-yl)piperidine-1-carboxylate Intermediate N18.1 was synthesized from intermediate D24.1 using a method analogous to that used for the conversion of intermediate C70.3 to intermediate C70.4.

N18.2: tert-Butyl 4-(5-(2-azido-1,1-difluoroethyl)-2-methylpyrimidin-4-yl)piperidine-1-carboxylate Intermediate N18.2 was made from intermediate N18.1 using a method analogous to that used to convert intermediate D24.2 to intermediate N14.1

N18.3: tert-Butyl 4-(5-(2-amino-1,1-difluoroethyl)-2-methylpyrimidin-4-yl)piperidine-1-carboxylate To a solution of intermediate N18.2 (56 mg, 0.15 mmol) in THF-H$_2$O (2 mL/0.1 mL) was added Ph$_3$P (43 mg, 0.16 mmol). The mixture was stirred at 60° C. for 4 h, and then cooled to rt. The crude reaction solution was used as is in the next reaction.

N18.4: tert-Butyl 4-(5-(1,1-difluoro-2-(2-(trifluoromethyl)pyrimidin-4-ylamino)ethyl)-2-methylpyrimidin-4-yl)piperidine-1-carboxylate To the crude reaction solution of intermediate N18.3 were added 4-chloro-2-trifluoromethylpyrimidine (55 mg, 0.30 mmol) and excess triethylamine. The reaction mixture was stirred at 60° C. for 24 h and cooled to rt. EtOAc was added to extract the product. The organic phase was washed with saturated NaHCO$_3$, brine, and dried over anhydrous Na$_2$SO$_4$. After removal of the solvents, the residue was purified by flash column chromatography to give intermediate N18.4 (50 mg, 66%).

N18.5: N-(2,2-Difluoro-2-(2-methyl-4-(piperidin-4-yl)pyrimidin-5-yl)ethyl)-2-(trifluoromethyl)pyrimidin-4-amine hydrochloride salt Intermediate N18.5 was made from the Boc deprotection of intermediate N18.4 using General Procedure 2.

Compound N18:

Compound N18 was made from intermediate N18.5 and 2,6-difluorophenyl isocyanate using General Procedure 5. $^1$H NMR (400 MHz, DMSO-d6) δ 8.67 (s, 1H), 8.59 (m, 1H), 8.29 (m, 2H), 7.28 (m, 1H), 7.11 (m, 2H), 6.81 (m, 1H), 4.24 (m, 2H), 3.60 (m, 2H), 3.45 (m, 1H), 2.80 (m, 1H), 2.62 (s, 3H), 1.62 (m, 5H). MS (EI) for C$_{24}$H$_{22}$F$_7$N$_7$O, found: 558.2 (MH+). Analytical HPLC, ret. time=16.06 min, 99.7% purity.

Compound N19: N-[2-(4-{1-[(2,6-Difluorophenyl)acetyl]piperidin-4-yl}-2-methylpyrimidin-5-yl)-2,2-difluoroethyl]-2-(trifluoromethyl)pyrimidin-4-amine Compound N19 was made from intermediate N18.5 and 2,6-difluorophenylacetic acid using General Procedure 4. $^1$H NMR (400 MHz, DMSO-d6) δ 8.63 (s, 1H), 8.58 (m, 1H), 7.34 (m, 1H), 7.28 (m, 1H), 7.09 (m, 2H), 6.76 (m, 1H), 4.40 (m, 2H), 4.24 (m, 2H), 3.60 (m, 2H), 3.45 (m, 1H), 2.80 (m, 1H), 2.60 (s, 3H), 1.62 (m, 5H). MS (EI) for C$_{25}$H$_{23}$F$_7$N$_6$O, found: 557.2 (MH+). Analytical HPLC, ret. time=18.17 min, 99.7% purity.

Compound N20: N-(2,6-Difluorophenyl)-4-[5-(1,1-difluoro-2-{[4-(trifluoromethyl)pyrimidin-2-yl]amino}ethyl)-2-methylpyrimidin-4-yl]piperidine-1-carboxamide N20.1: tert-Butyl 4-(5-(1,1-difluoro-2-(4-(trifluoromethyl)pyrimidin-2-ylamino)ethyl)-2-methylpyrimidin-4-yl)piperidine-1-carboxylate Intermediate N20.1 was made from intermediate N18.3 and 2-chloro-4-(trifluoromethyl)pyrimidine using a method analogous to that used to synthesize intermediate N18.4 from intermediate N18.3

N20.2: N-(2,2-Difluoro-2-(2-methyl-4-(piperidin-4-yl)pyrimidin-5-yl)ethyl)-4-(trifluoromethyl)pyrimidin-2-amine hydrochloride salt Intermediate N20.2 was made from the Boc deprotection of intermediate N20.1 using General Procedure 2.

Compound N20:

Compound N20 was made from intermediate N20.2 and 2,6-difluorophenyl isocyanate using General Procedure 5. $^1$H NMR (400 MHz, DMSO-d6) δ 8.67 (s, 1H), 8.59 (m, 1H), 8.29 (m, 2H), 7.26 (m, 1H), 7.08 (m, 2H), 7.02 (m, 1H), 4.24 (m, 2H), 3.60 (m, 2H), 3.45 (m, 1H), 2.80 (m, 1H), 2.58 (s, 3H), 1.62 (m, 5H). MS (EI) for C$_{24}$H$_{22}$F$_7$N$_7$O, found: 558.2 (MH+). Analytical HPLC, ret. time=16.75 min, 95% purity.

Compound N21: N-[2-(4-{1-[(2,6-Difluorophenyl)acetyl]piperidin-4-yl}-2-methylpyrimidin-5-yl)-2,2-difluoroethyl]-4-(trifluoromethyl)pyrimidin-2-amine Compound N21 was made from intermediate N20.2 and 2,6-difluorophenylacetic acid using General Procedure 4. $^1$H NMR (400 MHz, DMSO-d6) δ 8.65 (s, 1H), 8.59 (m, 1H), 8.48 (m, 1H), 7.36 (m, 1H), 7.08 (m, 3H), 4.50 (m, 1H), 4.24 (m, 3H), 3.80 (m, 2H), 3.45 (m, 1H), 2.80 (m, 1H), 2.58 (s, 3H), 1.62 (m, 5H). MS (EI) for C$_{25}$H$_{23}$F$_7$N$_6$O, found: 557.2 (MH+). Analytical HPLC, ret. time=19.74 min, 98% purity.

Compound N22: N-(2,6-Difluorophenyl)-4-[5-(1-fluoro-2-{[6-(trifluoromethyl)pyridin-2-yl]oxy}ethyl)-2-methylpyrimidin-4-yl]piperidine-1-carboxamide N22.1: tert-Butyl 4-(5-(1-hydroxy-2-(6-(trifluoromethyl)pyridin-2-yloxy)ethyl)-2-methylpyrimidin-4-yl)piperidine-1-carboxylate Intermediate N22.1 was synthesized from intermediate D24.2 using a method analogous to the reduction of Compound M6 to Compound N2.

N22.2: tert-Butyl 4-(5-(1-fluoro-2-(6-(trifluoromethyl)pyridin-2-yloxy)ethyl)-2-methylpyrimidin-4-yl)piperidine-1-carboxylate To a stirred solution of intermediate N22.1 (41 mg, 0.08 mmol) at 0° C. was added DAST (34 mg, 0.21 mmol). The mixture was stirred at 0° C. for 30 min and then partitioned between EtOAc and saturated aqueous $NaHCO_3$. The aqueous layer was extracted with EtOAc. The combined organic portions were washed with brine, dried ($MgSO_4$), filtered, and concentrated in vacuo to give a crude intermediate N22.2. The crude product was used directly in the next reaction without further purification. MS (EI) for $C_{23}H_{28}F_4N_4O_3$, found: 485.2 (MH+).

N22.3: 5-(1-Fluoro-2-(6-(trifluoromethyl)pyridin-2-yloxy)ethyl)-2-methyl-4-(piperidin-4-yl)pyrimidine hydrochloride salt Intermediate N22.3 was made from the Boc deprotection of intermediate N22.2 using General Procedure 2.

Compound N22:

Compound N22 was synthesized from intermediate N22.3 and 2,6-difluorophenyl isocyanate using General Procedure 5. $^1$H-NMR (400 MHz, $CDCl_3$): δ 8.55 (s, 1H), 7.65 (t, 1H), 7.20 (d, 1H), 6.98 (m, 1H), 6.88 (d, 1H), 6.83-6.78 (m 2H), 6.00 (ddd, 1H), 5.76 (s, 1H), 4.70-4.47 (m, 2H), 4.11 (d, 2H), 3.03-2.90 (m 3H), 2.58 (s, 3H), 2.13-1.88 (m, 2H), 1.65 (m, 2H). MS (EI) for $C_{25}H_{23}F_6N_5O_2$, found: 540.2 (MH+). Analytical HPLC, ret. time=14.7 min, 98% purity.

Compound N23: 4-[5-(1-Amino-2-{[6-(trifluoromethyl)pyridin-2-yl]oxy}ethyl)-2-methylpyrimidin-4-yl]-N-(2,6-difluorophenyl)piperidine-1-carboxamide Compound N23 was recovered from the same procedure that was used to generated Compound N. $^1$H NMR (400 MHz, DMSO-d6) δ 8.77 (s, 1H), 8.21 (s, 1H), 7.94 (t, 1H), 7.47 (d, 1H), 7.25 (m, 1H), 7.08 (m, 3H), 4.61 (m, 1H), 4.40 (m, 2H), 4.18 (m, 2H), 3.45 (m, 3H), 2.85 (m, 2H), 2.55 (s, 3H), 1.62 (m, 4H). MS (EI) for $C_{25}H_{25}F_5N_6O_2$, found: 537.2 (MH+). Analytical HPLC, ret. time=12.47 min, 99% purity.

Compound N24: 4-[2-Amino-5-(1-amino-2-{[6-(trifluoromethyl)pyridin-2-yl]oxy}ethyl)pyrimidin-4-yl]-N-(2,6-difluorophenyl)piperidine-1-carboxamide Compound N24 was made from intermediate N3.4 in a manner similar to the way Compound N23 was made from Compound M4. $^1$H-NMR (400 MHz, $CDCl_3$): δ 8.50 (s, 1H), 7.76 (t, 1H), 7.31 (d, 1H), 7.12 (m, 1H), 6.95 (m, 3H), 5.93 (br s, 1H), 5.03 (br s, 2H), 4.69 (dd, 1H), 4.58 (dd, 1H), 4.22 (m, 3H), 3.18 (m, 1H), 3.03 (t, 2H), 2.18-1.82 (comp m, 4H), 1.76 (m, 2H). MS (EI) for $C_{24}H_{24}F_5N_7O_2$, found: 538.1 (MH+). Analytical HPLC, ret. time=8.54 min, 98% purity.

Compound N25: 4-[5-(1-Amino-2-{[2-(trifluoromethyl)pyrimidin-4-yl]oxy}ethyl)-2-methylpyrimidin-4-yl]-N-(2,6-difluorophenyl)piperidine-1-carboxamide

N25.1: tert-Butyl 4-(2-methyl-5-(2-(2-(trifluoromethyl)pyrimidin-4-yloxy)acetyl)pyrimidin-4-yl)piperidine-1-carboxylate Intermediate N25.1 was synthesized from intermediate D24.1 and 2-(trifluoromethyl)pyrimidin-4-ol using a method analogous to the method used to synthesize intermediate D24.2 from intermediate D24.1 and 6-(trifluoromethyl)pyridin-2-ol.

N25.2: 1-(2-Methyl-4-(piperidin-4-yl)pyrimidin-5-yl)-2-(2-(trifluoromethyl)pyrimidin-4-yloxy)ethanone hydrochloride salt Intermediate N25.2 was synthesized from the Boc deprotection of intermediate N25.1 using General Procedure 2.

N25.3: N-(2,6-Difluorophenyl)-4-(2-methyl-5-(2-(2-(trifluoromethyl)pyrimidin-4-yloxy)acetyl)pyrimidin-4-yl)piperidine-1-carboxamide Intermediate N25.3 was made from intermediate N25.2 and 2,6-difluorophenyl isocyanate using General Procedure 5.

Compound N25:

Compound N25 was synthesized from intermediate N25.3 using a method analogous to that used to synthesize Compound N23 from Compound M4. $^1$H-NMR (400 MHz, DMSO-d6): δ 8.77 (d, 1H), 8.57 (s, 1H), 8.26 (s, 1H), 8.21 (d, 1H), 7.27 (m, 1H), 7.11 (m, 2H), 6.83 (d, 1H), 5.45 (m, 1H), 5.28 (m, 1H), 4.24 (m, 2H), 3.72 (m, 2H), 3.38 (m, 1H), 2.91 (m, 2H), 2.55 (s, 3H), 1.86 (m, 2H), 1.70 (m, 2H). MS (EI) for $C_{24}H_{24}F_5N_7O_2$, found: 538.2 (MH+). Analytical HPLC, ret. time=9.30 min, 88% purity.

Compound N26: N-(2,6-difluorophenyl)-4-{5-[(1Z)—N-hydroxy-2-{[6-(trifluoromethyl)pyridin-2-yl]oxy}ethanimidoyl]-2-methylpyrimidin-4-yl}piperidine-1-carboxamide Compound M4 (32 mg, 0.06 mmol) was dissolved in EtOH (2 mL). Hydroxylamine hydrochloride (15 mg) was added. The reaction mixture was stirred at 40° C. for 12 h. EtOH was removed. The residue was purified by preparative HPLC to give a 5.6:1 mixture of the desired oximes. Data for the major isomer: $^1$H NMR (400 MHz, DMSO-d6) δ 12.04 (s, 1H), 8.45 (s, 1H), 8.24 (s, 1H), 7.88 (t, 1H), 7.47 (d, 1H), 7.25 (m, 1H), 7.11 (m, 2H), 6.96 (d, 1H), 5.60 (s, 1H), 4.16 (m, 2H), 3.45 (m, 2H), 3.08 (m, 1H), 2.82 (m, 2H), 2.52 (s, 3H), 1.72 (m, 2H), 1.50 (m, 2H). MS (EI) for $C_{25}H_{23}F_5N_6O_3$, found: 551.2 (MH+). Analytical HPLC, ret. time=16.34 min, 5.6:1 mixture, 99% purity.

Compound N27: 4-{2-Amino-5-[1-(methylamino)-2-{[6-(trifluoromethyl)pyridin-2-yl]oxy}ethyl]pyrimidin-4-yl}-N-(2,6-difluorophenyl)piperidine-1-carboxamide To a solution of intermediate N3.4 (60 mg, 0.11 mmol) in 2M methylamine in MeOH (1.5 mL, 3.0 mmol methylamine) was added AcOH (50 μL) and $Na(CN)BH_3$ (21 mg, 0.33 mmol). The resulting mixture was heated with stirring to 45° C. overnight, followed by the addition of additional aliquots of $Na(CN)BH_3$ (21 mg), 2M methylamine in MeOH (1.0 mL), and AcOH (50 μL) and heating in a sealed tube at 60° C. for several days. The reaction mixture was allowed to cool to room temperature, diluted with EtOAc and washed with saturated aqueous $NaHCO_3$ (3×), saturated aqueous NaCl (1×) dried ($Na_2SO_4$) and concentrated in vacuo. The resulting residue was purified by preparative HPLC to give Compound N27 (10 mg, 16% yield). $^1$H-NMR (400 MHz, CDCl₃): δ 8.53 (br s, 1H), 7.76 (t, 1H), 7.32 (d, 1H), 7.12 (m, 1H), 7.00 (d, 1H), 6.94 (t, 2H), 5.93 (br s, 1H), 5.21 (br s, 2H), 4.63 (m, 1H), 4.37 (m, 2H), 4.22 (m, 2H), 3.17 (m, 1H), 3.05 (m, 2H), 2.39 (s, 3H), 2.25-1.92 (m, 3H), 1.74 (m, 2H). MS (EI) for $C_{25}H_{26}F_5N_7O_2$, found: 552.2 (MH+). Analytical HPLC, ret. time=8.65 min, 92% purity.

Compound N28: 4-[5-(1-[(1-Acetylpiperidin-4-yl)amino]-2-{[6-(trifluoromethyl)pyridin-2-yl]oxy}ethyl)-2-methylpyrimidin-4-yl]-N-(2,6-difluorophenyl)piperidine-1-carboxamide N28.1: tert-Butyl 4-(1-(4-(1-(2,6-difluorophenylcarbamoyl)piperidin-4-yl)-2-methylpyrimidin-5-yl)-2-(6-trifluoromethyl)pyridin-2-yloxy)ethylamino)piperidine-1-carboxylate To a solution of intermediate N3.4 (106 mg, 0.20 mmol) in MeOH (3.0 mL) was added tert-butyl 4-aminopiperidine-1-carboxylate (1.16 g, 6.8 mmol), AcOH (150 μL) and Na(CN)BH₃ (120 mg, 1.9 mmol). The resulting mixture was heated with stirring to 60° C. in a sealed tube for several days. The reaction mixture was allowed to cool to room temperature, diluted with EtOAc and washed with saturated aqueous NaHCO₃ (3×), water (1×), aqueous 10% citric acid (3×), saturated aqueous NaCl (1×) dried (Na₂SO₄) and concentrated in vacuo to give crude intermediate N28.1 which was used as is in the next reaction. MS (EI) for $C_{35}H_{42}F_5N_7O_4$, found: 720.3 (MH+).

N28.2: N-(2,6-difluorophenyl)-4-(2-methyl-5-(1-(piperidin-4-ylamino)-2-(6-(trifluoromethyl)pyridin-2-yloxy)ethyl)pyrimidin-4-yl)piperidine-1-carboxamide hydrochloride salt Intermediate N28.2 was made from the Boc deprotection of intermediate N28.1 using General Procedure 2.

Compound N28:

Compound N28 was made from intermediate N28.2 using a method analogous to that used to convert Compound D29 to Compound D31. ¹H-NMR (400 MHz, CDCl₃): δ 8.85 (br s, 1H), 7.78 (t, 1H), 7.35 (d, 1H), 7.12 (m, 1H), 6.94 (m, 3H), 5.93 (br s, 1H), 4.74 (m, 1H), 4.56 (m, 1H), 4.39 (m, 1H), 4.22 (m, 2H), 3.80-3.55 (m, 2H), 3.27 (m, 1H), 3.05 (m, 2H), 2.70 (s, 3H), 2.60 (m, 2H), 2.22 (m, 1H), 2.07 (s, 3H), 1.80-1.10 (comp m, 9H). MS (EI) for $C_{32}H_{36}F_5N_7O_3$, found: 662.3 (MH+). Analytical HPLC, ret. time=9.85 min, 95% purity.

Compound N29: 2-Fluorophenyl 4-[2-amino-5-(1-amino-2-{[6-(trifluoromethyl)pyridin-2-yl]oxy}ethyl)pyrimidin-4-yl]piperidine-1-carboxylate Compound N29 was made in four steps from intermediate N29.1 in the same manner that Compound N24 was made in four steps from intermediate N3.1, substituting 2-fluorophenyl chloroformate for 2,6-difluorophenyl isocyanate in the first step and using standard reaction conditions typical with chloroformates such as those elaborated on in the synthesis of Compound A119 from intermediate A116.3. ¹H NMR (400 MHz, CDCl₃) δ 8.22 (d, 1H), 8.20 (bs, 1H), 7.25-7.08 (m, 4H), 6.74 (d, 1H), 6.45 (s, 1H), 5.45 (s, 1H), 5.24 (s, 2H), 4.72 (d, 1H), 4.57-4.31 (td, 2H), 3.96 (d, 1H), 3.76 (d, 1H), 3.01 (ddd, 3H), 1.83 (s, 2H), 1.65 (d, 1H). MS (EI) for $C_{24}H_{24}F_4N_6O_3$, found: 521.2 (MH+). Analytical HPLC, ret. time=10.70 min, 98% purity.

Compound N30: N-(2,6-Difluorophenyl)-4-{5-[1,3-dihydroxy-1-({[6-(trifluoromethyl)pyridin-2-yl]oxy}methyl)propyl]-2-methylpyrimidin-4-yl}piperidine-1-carboxamide N30.1: tert-Butyl 4-(5-(2-hydroxy-1-(6-(trifluoromethyl)pyridin-2-yloxy)pent-4-en-2-yl)-2-methylpyrimidin-4-yl)piperidine-1-carboxylate To a 0° C. solution of intermediate D24.2 (450 mg, 0.93 mmol) in THF (3 mL) was added dropwise allyl magnesium bromide (2.8 mL, 1.0 M in diethyl ether). The reaction mixture was stirred at 0° C. for 10 min, and then was quenched by slow addition of ice-water. The mixture was extracted with EtOAc, washed with brine, and dried over anhydrous Na₂SO₄. After removal of the solvents, the residue was purified by flash column chromatography to give intermediate N30.1 (290 mg, 60%).

N30.2: tert-Butyl 4-(5-(2,4-dihydroxy-1-(6-(trifluoromethyl)pyridin-2-yloxy)butan-2-yl)-2-methylpyrimidin-4-yl)piperidine-1-carboxylate Ozone was bubbled though a −78° C. solution of the intermediate N30.1 prepared above (33 mg, 0.063 mmol) in DCM/MeOH (5 mL/2 mL) until the blue color persisted. Nitrogen was then bubbled through the mixture to remove excess ozone. To this solution was added NaBH₄ (10 mg, 0.26 mmol). The mixture was allowed to warm to rt gradually. Removal of the solvents gave crude intermediate N30.2, which was used in the next step without further purification.

N30.3: 3-(2-Methyl-4-(piperidin-4-yl)pyrimidin-5-yl)-4-(6-(trifluoromethyl)pyridin-2-yloxy)butane-1,3-diol hydrochloride salt Intermediate N30.3 was made from the Boc deprotection of intermediate N30.2 using General Procedure 2.

Compound N30:

Compound N30 was made from intermediate N30.3 and 2,6-difluorophenyl isocyanate using General Procedure 5. ¹H NMR (400 MHz, DMSO-d6) δ 8.66 (s, 1H), 8.22 (s, 1H), 7.95 (t, 1H), 7.48 (m, 1H), 7.26 (m, 1H), 7.08 (m, 3H), 5.74 (s, 1H), 4.65 (m, 3H), 4.12 (m, 2H), 3.60 (m, 1H), 3.52 (m, 1H), 2.89 (m, 2H), 2.57 (s, 3H), 2.20 (m, 2H), 1.82 (m, 3H), 1.68 (d, 1H), 1.55 (d, 1H). MS (EI) for $C_{27}H_{28}F_5N_5O_4$, found: 582.2 (MH+). Analytical HPLC, ret. time=14.88 min, 88% purity.

Compound N31: 4-(5-(4-Amino-2-hydroxy-1-(6-(trifluoromethyl)pyridin-2-yloxy)butan-2-yl)-2-methylpyrimidin-4-yl)-N-(2,6-difluorophenyl)piperidine-1-carboxamide N31.1: tert-Butyl 4-(5-(4-azido-2-hydroxy-1-(6-(trifluoromethyl)pyridin-2-yloxy)butan-2-yl)-2-methylpyrimidin-4-yl)piperidine-1-carboxylate To a solution of intermediate N30.2 (80 mg, 0.15 mmol) in DCM (2 mL) were added pyridine (120 mg, 1.5 mmol)

and tosyl chloride (43 mg, 0.23 mmol). The reaction mixture was stirred at rt for 12 h. Saturated NaHCO$_3$ was added to quench the reaction. The mixture was diluted with DCM, washed with saturated NaHCO$_3$, and dried over anhydrous Na$_2$SO$_4$. The solvents were removed under reduced pressure. The residue was dissolved in DMF (0.6 mL) to which was added NaN$_3$ (65 mg, 1 mmol). The mixture was stirred at 55° C. for 24 h. The mixture was extracted with EtOAc, washed with brine and dried over anhydrous Na$_2$SO$_4$. Removal of the solvents gave the crude intermediate N31.1 which was used in the next step without further purification.

N31.2: 4-Azido-2-(2-methyl-4-(piperidin-4-yl)pyrimidin-5-yl)-1-(6-(trifluoromethyl)pyridin-2-yloxy)butan-2-ol Intermediate N31.2 was made from the Boc deprotection of intermediate N31.1 using General Procedure 2.

N31.3: 4-(5-(4-Azido-2-hydroxy-1-(6-(trifluoromethyl)pyridin-2-yloxy)butan-2-yl)-2-methylpyrimidin-4-yl)-N-(2,6-difluorophenyl)piperidine-1-carboxamide Intermediate N31.3 was made from intermediate N31.2 and 2,6-difluorophenyl isocyanate using General Procedure 5.

Compound N31:

Compound N31 was made from intermediate N31.3 using a method analogous to that used to convert intermediate N18.2 to intermediate N18.3. $^1$H NMR (400 MHz, DMSO-d6) δ 8.69 (s, 1H), 8.21 (s, 1H), 7.94 (t, 1H), 7.48 (d, 1H), 7.26 (m, 1H), 7.08 (m, 3H), 4.58 (s, 2H), 4.18 (m, 2H), 3.75 (m, 1H), 2.90 (m, 2H), 2.78 (m, 1H), 2.63 (m, 1H), 2.56 (s, 3H), 2.14 (m, 2H), 1.86 (m, 4H), 1.62 (m, 2H), 1.55 (d, 1H). MS (EI) for C$_{27}$H$_{29}$F$_5$N$_6$O$_3$, found: 581.2 (MH+). Analytical HPLC, ret. time=11.91 min, 94% purity.

Compound N32: N-(2,6-Difluorophenyl)-4-{5-[1,2-dihydroxy-1-({[6-(trifluoromethyl)pyridin-2-yl]oxy}methyl)ethyl]-2-methylpyrimidin-4-yl}piperidine-1-carboxamide N32.1: tert-Butyl 4-(2-methyl-5-(3-(6-(trifluoromethyl)pyridin-2-yloxy)prop-1-en-2-yl)pyrimidin-4-yl)piperidine-1-carboxylate To a 0° C. suspension of methyltriphenylphosphonium bromide (1.1 g, 2.86 mmol) in THF (12 mL) was added KO$^t$Bu (2.86 mL, 2.86 mmol, 1.0 M in THF). The ice bath was removed and mixture was stirred at rt for 30 min. The mixture was cooled to 0° C. and a solution of intermediate D24.2 (920 mg, 1.91 mmol) in THF (1 mL) was added. Then the reaction mixture was stirred at rt for 12 h. Water was added to quench the reaction. The mixture was extracted with EtOAc, washed with brine, and dried over anhydrous Na$_2$SO$_4$. Further purification by flash column chromatography gave intermediate N32.1 (550 mg, 60%).

N32.2: tert-Butyl 4-(5-(1,2-dihydroxy-3-(6-(trifluoromethyl)pyridin-2-yloxy)propan-2-yl)-2-methylpyrimidin-4-yl)piperidine-1-carboxylate To a solution of intermediate N32.1 (100 mg, 0.21 mmol) in acetone/H$_2$O/tBuOH (1 mL/0.2 mL/0.2 mL) were added NMO (50 mg, 0.42 mmol) and OsO$_4$ (0.12 mL, 2.5% w/w solution in tBuOH). The reaction was stirred at rt for 48 h. The solvent was removed under reduced pressure, and the residue was extracted with EtOAc (10 mL) and washed with 5% aq HCl and saturated Na$_2$S$_2$O$_3$ solution. The organic layer was dried over anhydrous Na$_2$SO$_4$. Further purification by flash column chromatography gave intermediate N32.2 (80 mg, 78%).

N32.3: 2-(2-Methyl-4-(piperidin-4-yl)pyrimidin-5-yl)-3-(6-(trifluoromethyl)pyridin-2-yloxy)propane-1,2-diol hydrochloride salt Intermediate N32.3 was made from the Boc deprotection of intermediate N32.2 using General Procedure 2.

Compound N32:

Compound N32 was made from intermediate N32.3 and 2,6-difluorophenyl isocyanate using General Procedure 5. $^1$H NMR (400 MHz, DMSO-d6) δ 8.58 (s, 1H), 8.24 (s, 1H), 7.95 (t, 1H), 7.49 (d, 1H), 7.27 (m, 1H), 7.10 (m, 3H), 5.73 (s, 1H), 5.19 (s, 1H), 4.84 (d, 1H), 4.57 (d, 1H), 4.20 (t, 1H), 3.82 (m, 3H), 2.83 (m, 2H), 2.57 (s, 3H), 1.80 (m, 4H). MS (EI) for C$_{26}$H$_{26}$F$_5$N$_5$O$_4$, found: 568.2 (MH+). Analytical HPLC, ret. time=10.48 min, 98% purity.

Compound N33: 4-{5-[2-Azido-1-hydroxy-1-({[6-(trifluoromethyl)pyridin-2-yl]oxy}methyl)ethyl]-2-methylpyrimidin-4-yl}-N-(2,6-difluorophenyl)piperidine-1-carboxamide N33.1: tert-Butyl 4-(5-(1-azido-2-hydroxy-3-(6-(trifluoromethyl)pyridin-2-yloxy)propan-2-yl)-2-methylpyrimidin-4-yl)piperidine-1-carboxylate Intermediate N33.1 was made from intermediate N32.2 using a method analogous to that used to make N31.1 from N30.2

N33.2: 1-Azido-2-(2-methyl-4-(piperidin-4-yl)pyrimidin-5-yl)-3-(6-(trifluoromethyl)pyridin-2-yloxy)propan-2-ol hydrochloride salt Intermediate N33.2 was made from the Boc deprotection of intermediate N33.1 using General Procedure 2.

Compound N33:

Compound N33 was made from intermediate N33.2 and 2,6-difluorophenyl isocyanate using General Procedure 5. $^1$H NMR (400 MHz, DMSO-d6) δ 8.63 (s, 1H), 8.21 (s, 1H), 7.96 (t, 1H), 7.51 (d, 1H), 7.27 (m, 1H), 7.11 (m, 3H), 6.33 (s, 1H), 4.65 (q, 2H), 4.19 (m, 2H), 3.90 (m, 2H), 3.76 (m, 1H), 2.90 (m, 2H), 2.56 (s, 3H), 1.83 (m, 2H), 1.66 (m, 2H). MS (EI) for C$_{26}$H$_{25}$F$_5$N$_8$O$_3$, found: 593.2 (MH+). Analytical HPLC, ret. time=17.09 min, 92% purity.

Compound N34: 4-{5-[2-Amino-1-hydroxy-1-({[6-(trifluoromethyl)pyridin-2-yl]oxy}methyl)ethyl]-2-methylpyrimidin-4-yl}-N-(2,6-difluorophenyl)piperidine-1-carboxamide Compound N34 was made from Compound N33 using a method analogous to that used to convert intermediate N18.2 to intermediate N18.3. $^1$H NMR (400 MHz, CDCl$_3$) δ 8.59 (s, 1H), 7.73 (t, 1H), 7.25 (m, 2H), 7.09 (m, 1H), 6.90

(m, 3H), 5.92 (s, 1H), 4.75 (m, 1H), 4.60 (m, 1H), 4.25 (m, 2H), 3.60 (m, 1H), 3.38 (m, 1H), 3.15 (m, 1H), 3.05 (m, 2H), 2.60 (s, 3H), 2.12 (m, 2H), 1.86 (m, 4H). MS (EI) for $C_{26}H_{27}F_5N_6O_3$, found: 567.2 (MH+). Analytical HPLC, ret. time=12.21 min, 95% purity.

Compound N35: 1-Amino-2-(4-{1-[(2,6-difluorophenyl)acetyl]piperidin-4-yl}-2-methylpyrimidin-5-yl)-3-{[6-(trifluoromethyl)pyridin-2-yl]oxy}propan-2-ol N35.1: 1-(4-(5-(1-Azido-2-hydroxy-3-(6-(trifluoromethyl)pyridin-2-yl)propan-2-yl)-2-methylpyrimidin-4-yl)piperidin-1-yl)-2-(2,6-difluorophenyl)ethanone Intermediate N35.1 was made from intermediate N33.2 and 2,6-difluorophenylacetic acid using General Procedure 4.

Compound N35:

Compound N35 was made from intermediate N35.1 using a method analogous to the conversion of intermediate C68.2 to intermediate C68.3. $^1$H-NMR (400 MHz, CDCl$_3$, DMSO-d6): δ 8.66 (d, 1H), 7.79 (t, 1H), 7.34 (d, 1H), 7.24 (m, 1H), 6.99 (d, 1H), 6.91 (t, 2H), 4.74 (m, 1H), 4.70 (t, 2H), 4.12 (d, 1H), 3.78 (s, 2H), 3.66 (m, 1H), 3.48 (m, 1H), 3.29 (m, 2H), 2.73 (t, 2H), 2.66 (s, 3H), 2.04 (m, 2H), 1.79 (m, 2H). MS (EI) for $C_{27}H_{28}F_5N_5O_3$. found 566.1 (MH+). Analytical HPLC, ret. time=10.216 min, 95% purity.

Compound N36: N-(2,6-Difluorophenyl)-4-{5-[2-{[(ethylamino)carbonyl]amino}-1-hydroxy-1-({[6-(trifluoromethyl)pyridin-2-yl]oxy}methyl)ethyl]-2-methylpyrimidin-4-yl}piperidine-1-carboxamide N36.1: tert-Butyl 4-(5-(1-amino-2-hydroxy-3-(6-(trifluoromethyl)pyridin-2-yloxy)propan-2-yl)-2-methylpyrimidin-4-yl)piperidine-1-carboxylate Intermediate N36.1 was made from intermediate N33.1 using a method analogous to that used to convert intermediate N35.1 to Compound N35.

N36.2: tert-Butyl 4-(5-(1-(3-ethylureido)-2-hydroxy-3-(6-(trifluoromethyl)pyridin-2-yloxy)propan-2-yl)-2-methylpyrimidin-4-yl)piperidine-1-carboxylate Intermediate N36.2 was made from intermediate N36.1 and ethyl isocyanate using General Procedure 5. MS (EI) for $C_{27}H_{37}F_3N_6O_5$, found 583.3 (MH+).

N36.3: 1-Ethyl-3-(2-hydroxy-2-(2-methyl-4-(piperidin-4-yl)pyrimidin-5-yl)-3-(6-(trifluoromethyl)pyridin-2-yloxy)propyl)urea TFA salt Intermediate N36.3 was made from the Boc deprotection of intermediate N36.2 using General Procedure 2.

Compound N36:

Compound N36 was made from intermediate N36.3 and 2,6-difluorophenyl isocyanate using General Procedure 5. $^1$H-NMR (400 MHz, CDCl$_3$): δ 8.58 (s, 1H), 7.74 (t, 1H), 7.31 (d, 1H), 7.11 (m, 1H), 6.94 (t, 2H), 6.89 (d, 1H), 6.24 (s, 1H), 5.93 (s, 1H), 5.21 (t, 1H), 4.91 (d, 1H), 4.65 (d, 1H), 4.50 (t, 1H), 4.23 (t, 1H), 3.76 (d, 2H), 3.75 (m, 1H), 3.21 (m, 2H), 3.09 (qd, 2H), 2.65 (s, 3H), 2.12 (m, 2H), 1.83 (m, 2H), 1.13 (t, 3H). MS (EI) for $C_{29}H_{32}F_5N_7O_4$, found 638.3 (MH+). Analytical HPLC, ret. time=13.672 min, 99% purity.

Compound N37: 4-{5-[2-(Acetylamino)-1-hydroxy-1-({[6-(trifluoromethyl)pyridin-2-yl]oxy}methyl)ethyl]-2-methylpyrimidin-4-yl}-N-(2,6-difluorophenyl)piperidine-1-carboxamide N37.1: tert-Butyl 4-(5-(1-acetamido-2-hydroxy-3-(6-(trifluoromethyl)pyridin-2-yloxy)propan-2-yl)-2-methylpyrimidin-4-yl)piperidine-1-carboxylate To a stirred solution of N36.1 (6.5 mg, 0.013 mmol) in dichloromethane (0.3 mL) were added Et$_3$N (3.9 mg, 0.039 mmol) and acetic anhydride (2.0 mg, 0.020 mmol) in sequence. After stirring for 40 min at room temperature, aqueous saturated NH$_4$Cl (3 mL) was added and the resulting solution was extracted with EtOAc (2×1 mL). The combined organic layers were dried over MgSO$_4$ and concentrated to give a crude intermediate N36.1. MS (EI) for $C_{26}H_{34}F_3N_5O_5$, found 554.3 (MH+).

N37.2: N-(2-Hydroxy-2-(2-methyl-4-(piperidin-4-yl)pyrimidin-5-yl)-3-(6-(trifluoromethyl)pyridin-2-yloxy)propyl)acetamide TFA salt Intermediate N37.2 was made from the Boc deprotection of intermediate N37.1 using General Procedure 2.

Compound N37:

Compound N37 was made from intermediate N37.2 and 2,6-difluorophenyl isocyanate using General Procedure 5. $^1$H-NMR (400 MHz, CDCl$_3$): δ 8.62 (s, 1H), 7.76 (t, 1H), 7.34 (d, 1H), 7.11 (m, 1H), 6.94 (t, 2H), 6.90 (d, 1H), 6.33 (t, 1H), 5.92 (s, 1H), 5.74 (s, 1H), 4.93 (d, 1H), 4.70 (d, 1H), 4.26 (m, 2H), 3.86 (m, 1H), 3.76 (m, 1H), 3.63 (tt, 1H), 3.10 (qd, 2H), 2.65 (s, 3H), 2.15 (m, 2H), 2.03 (s, 3H), 1.85 (m, 2H). MS (EI) for $C_{28}H_{29}F_5N_6O_4$, found 609.2 (MH+). Analytical HPLC, ret. time=10.628 min, 99% purity.

Compound N38: 4-{5-[2-{[2-(Acetylamino)ethyl]amino}-1-hydroxy-1-({[6-(trifluoromethyl)pyridin-2-yl]oxy}methyl)ethyl]-2-methylpyrimidin-4-yl}-N-(2,6-difluorophenyl)piperidine-1-carboxamide N38.1: N-(2,6-Difluorophenyl)-4-(5-(2-hydroxy-1-oxo-3-(6-(trifluoromethyl)pyridin-2-yloxy)propan-2-yl)-2-methylpyrimidin-4-yl)piperidine-1-carboxamide Intermediate N38.1 was synthesized by the oxidation of Compound N32 using a method analogous to that used to oxidize intermediate B46.1 to intermediate B46.2.

Compound N38:

To a stirred solution of crude intermediate N38.1 (5.7 mg, 0.010 mmol), N-(2-aminoethyl)acetamide (1.7 mg, 90%, 0.015 mmol) and dichloromethane (0.5 mL) at room temperature was added NaBH(OAc)$_3$ (6.4 mg, 0.030 mmol). After stirring for 40 min at 95° C., the resulting solution was purified by preparative HPLC to give Compound N38 (2.2 mg, 34%, 2 steps) as a white solid after lyophilization.

$^1$H-NMR (400 MHz, CDCl$_3$): δ 8.59 (s, 1H), 7.75 (t, 1H), 7.31 (d, 1H), 7.11 (m, 1H), 6.94 (t, 2H), 6.92 (d, 1H), 5.93 (s, 1H), 5.74 (t, 1H), 4.75 (d, 1H), 4.61 (d, 1H), 4.24 (d, 2H), 3.71 (tt, 1H), 3.35 (q, 2H), 3.27 (d, 1H), 3.07 (td, 2H), 3.06 (d, 1H), 2.80 (m, 2H), 2.67 (s, 3H), 2.12 (m, 2H), 1.98 (s, 3H), 1.78 (m, 2H). MS (EI) for C$_{30}$H$_{34}$F$_5$N$_7$O$_4$, found 652.3 (MH+). Analytical HPLC, ret. time=11.496 min, 98% purity.

Compound N39: 4-{5-[2-(4-Acetylpiperazin-1-yl)-1-hydroxy-1-({[6-(trifluoromethyl)pyridin-2-yl]oxy}methyl)ethyl]-2-methylpyrimidin-4-yl}-N-(2,6-difluorophenyl)piperidine-1-carboxamide Compound N39 was made in a manner similar to Compound N38: $^1$H-NMR (400 MHz, CDCl$_3$): δ 8.70 (s, 1H), 7.74 (t, 1H), 7.30 (d, 1H), 7.12 (m, 1H), 6.94 (t, 2H), 6.91 (d, 1H), 5.91 (s, 1H), 4.98 (br s, 1H), 4.74 (d, 1H), 4.59 (d, 1H), 4.25 (t, 2H), 3.60 (m, 3H), 3.43 (m, 2H), 3.13 (d, 1H), 3.04 (t, 2H), 2.92 (d, 1H), 2.67 (s, 3H), 2.54 (m, 4H), 2.14 (m, 2H), 2.06 (s, 3H), 1.75 (m, 2H). MS (EI) for C$_{32}$H$_{36}$F$_5$N$_7$O$_4$, found 678.3 (MH+). Analytical HPLC, ret. time=11.540 min, 98% purity.

Compound N40: 4-(5-{2-[(1-Acetylpyrrolidin-3-yl)amino]-1-hydroxy-1-({[6-(trifluoromethyl)pyridin-2-yl]oxy}methyl)ethyl}-2-methylpyrimidin-4-yl)-N-(2,6-difluorophenyl)piperidine-1-carboxamide Compound N40 was made in a manner similar to Compound N38: $^1$H-NMR (400 MHz, CDCl$_3$, a mixture of four stereomers): δ 8.55 and 8.53 (s, 1H), 7.76 (m, 1H), 7.32 (m, 1H), 7.12 (m, 1H), 6.93 (m, 3H), 5.98 (m, 1H), 4.77 (m, 1H), 4.55 (m, 1H), 4.25 (m, 2H), 3.76-3.55 (m, 3H), 3.52-3.18 (m, 4H), 3.12-2.93 (m, 3H), 2.68 (s, 3H), 2.23-2.06 (m, 3H), 2.05 and 2.03 (s, 3H), 1.85 (m, 2H), 1.70 (m, 2H). MS (EI) for C$_{32}$H$_{36}$F$_5$N$_7$O$_4$, found 678.3 (MH+). Analytical HPLC, ret. time=11.120 min, 98% purity.

Compound N41: 4-(5-{2-[(N-Acetyl-beta-alanyl)amino]-1-hydroxy-1-({[6-(trifluoromethyl)pyridin-2-yl]oxy}methyl)ethyl}-2-methylpyrimidin-4-yl)-N-(2,6-difluorophenyl)piperidine-1-carboxamide Compound N41 was made from Compound N34 and 3-acetamidopropanoic acid using standard amide coupling procedures such as those elaborated on in General Procedure 3. $^1$H-NMR (400 MHz, CDCl$_3$): δ 8.62 (s, 1H), 7.77 (t, 1H), 7.35 (d, 1H), 7.12 (m, 1H), 6.95 (t, 2H), 6.92 (d, 1H), 6.67 (t, 1H), 6.13 (t, 1H), 5.93 (s, 1H), 5.59 (s, 1H), 4.85 (d, 1H), 4.70 (d, 1H), 4.27 (m, 2H), 3.85 (m, 2H), 3.65 (t, 1H), 3.50 (m, 2H), 3.11 (m, 2H), 2.66 (s, 3H), 2.45 (t, 2H), 2.16 (m, 2H), 1.92 (s, 3H), 1.85 (m, 2H). MS (EI) for C$_{31}$H$_{34}$F$_5$N$_7$O$_5$, found 680.3 (MH+). Analytical HPLC, ret. time=10.416 min, 95% purity.

Compound N42: N-(2,6-Difluorophenyl)-4-(5-{1-hydroxy-2-[(3-hydroxypropanoyl)amino]-1-({[6-(trifluoromethyl)pyridin-2-yl]oxy}methyl)ethyl}-2-methylpyrimidin-4-yl)piperidine-1-carboxamide Compound N42 was made in a manner similar to Compound N41. $^1$H-NMR (400 MHz, CDCl$_3$): δ 8.64 (s, 1H), 7.70 (t, 1H), 7.34 (d, 1H), 7.12 (m, 1H), 6.95 (t, 2H), 6.91 (d, 1H), 6.65 (t, 1H), 5.93 (s, 1H), 4.90 (d, 1H), 4.74 (d, 1H), 4.26 (m, 2H), 3.89 (d, 1H), 3.87 (t, 2H), 3.80 (d, 1H), 3.62 (tt, 1H), 3.11 (m, 2H), 2.65 (s, 3H), 2.47 (t, 2H), 2.15 (m, 2H), 1.85 (m, 2H). MS (EI) for C$_{29}$H$_{31}$F$_5$N$_6$O$_5$, found 639.2 (MH+). Analytical HPLC, ret. time=10.520 min, 91% purity.

Compound N43: 2-Fluorophenyl 4-{5-[2-(acetylamino)-1-hydroxy-1-({[6-(trifluoromethyl)pyridin-2-yl]oxy}methyl)ethyl]-2-methylpyrimidin-4-yl}piperidine-1-carboxylate Compound N43 was made from intermediate N37.2 and 2-fluorophenyl chloroformate using a method analogous to that used to make Compound A119 from intermediate A116.3 and 2-chlorophenyl chloroformate. $^1$H-NMR (400 MHz, CDCl$_3$, rotameric mixture): δ 8.64 and 8.61 (two of s, 1H), 7.77 (t, 1H), 7.35 (d, 1H), 7.18 (m, 4H), 6.90 (d, 1H), 6.34 (m, 1H), 5.84 and 5.72 (two of s, 1H), 4.95 (d, 1H), 4.71 and 4.68 (two of d, 1H), 4.48 (m, 1H), 4.40 (m, 1H), 3.88 (m, 1H), 3.75 (m, 1H), 3.65 (m, 1H), 3.18 (q, 1H), 3.02 (t, 1H), 2.67 (s, 3H), 2.16 (m, 2H), 2.04 (s, 3H), 1.89 (m, 1H), 1.80 (m, 1H). MS (EI) for C$_{28}$H$_{29}$F$_4$N$_5$O$_5$, found 592.2 (MH+). Analytical HPLC, ret. time=13.408 min, 99% purity.

Compound N44: 2-[4-(1-{[(2,6-Difluorophenyl)amino]carbonyl}piperidin-4-yl)-2-methylpyrimidin-5-yl]-2-hydroxy-3-{[6-(trifluoromethyl)pyridin-2-yl]oxy}propanoic acid To a stirred solution of crude intermediate N38.1 (16.5 mg, 0.029 mmol) and 2-methyl-2-butene (50 μL) in t-BuOH (0.3 mL) at room temperature was added a mixture of NaH$_2$PO$_4$.2H$_2$O (23 mg, 0.15 mmol), NaClO$_2$ (13 mg, 0.15 mmol) and H$_2$O (0.3 mL). After stirring for 15 min at room temperature, the resulting solution was purified by preparative HPLC to give Compound N44 (8.5 mg, 50%, 2 steps) as a white solid after lyophilization. $^1$H-NMR (400 MHz, MeOH-d4): δ 8.66 (s, 1H), 7.88 (t, 1H), 7.40 (d, 1H), 7.25 (m, 1H), 7.07 (d, 1H), 7.00 (t, 2H), 5.49 (s, 1H), 5.07 (d, 1H), 4.86 (d, 1H), 4.28 (t, 2H), 3.66 (t, 1H), 3.02 (q, 2H), 2.65 (s, 3H), 1.98 (m, 2H), 1.85 (m, 1H), 1.69 (m, 1H). MS (EI) for C$_{26}$H$_{24}$F$_5$N$_5$O$_5$, found 582.2 (MH+). Analytical HPLC, ret. time=11.244 min, 95% purity.

Compound N45: N-(2,6-Difluorophenyl)-4-{5-[1-hydroxy-2-(methylamino)-2-oxo-1-({[6-(trifluoromethyl)pyridin-2-yl]oxy}methyl)ethyl]-2-methylpyrimidin-4-yl}piperidine-1-carboxamide Compound N45 was made from Compound N44 and methylamine using standard amide coupling procedures such as those elaborated on in General Procedure 3. $^1$H-NMR (400 MHz, CDCl$_3$): δ 8.76 (s, 1H), 7.83 (t, 1H), 7.39 (d, 1H), 7.11 (m, 1H), 7.03 (m, 2H), 6.94 (t, 2H), 6.25 (s, 1H), 5.90 (s, 1H), 5.16 (d, 1H), 4.97 (d, 1H), 4.24 (m, 2H), 3.53 (m, 1H), 3.01 (m, 2H), 2.89 (d, 3H), 2.67 (s, 3H), 2.08 (m, 2H), 1.75 (m, 2H). MS (EI) for C$_{27}$H$_{27}$F$_5$N$_6$O$_4$, found 595.2 (MH+). Analytical HPLC, ret. time=11.260 min, 95% purity.

Compound N46: 4-Fluorophenyl 4-{5-[2-(acetylamino)-1-hydroxy-1-({[6-(trifluoromethyl)pyridin-2-yl]oxy}methyl)ethyl]-2-methylpyrimidin-4-yl}piperidine-1-carboxylate Compound N46 was made from intermediate N37.2 in the same manner that Compound N43 was from intermediate N37.2, substituting 4-fluorophenyl chloroformate for 2-fluorophenyl chloroformate. $^1$H-NMR (400 MHz, CDCl$_3$, rotameric mixture): δ 8.64 and 8.61 (two of s, 1H), 7.77 (t, 1H), 7.35 (d, 1H), 7.08 (m, 4H), 6.90 (d, 1H), 6.37 (m, 1H), 5.86 and 5.72 (two of s, 1H), 4.94 (d, 1H), 4.71 and 4.68 (two of d, 1H), 4.43 (m, 2H), 3.87 (m, 1H), 3.75 (m, 1H), 3.64 (m, 1H), 3.14 (q, 1H), 2.99 (t, 1H), 2.66 (s, 3H), 2.12 (m, 2H), 2.04 (s, 3H), 1.88 (m, 1H), 1.79 (m, 1H). MS (EI) for $C_{28}H_{29}F_4N_5O_5$, found 592.2 (MH+). Analytical HPLC, ret. time=13.416 min, 96% purity.

Compound N47: 2,6-Difluorophenyl 4-{5-[2-(acetylamino)-1-hydroxy-1-({[6-(trifluoromethyl)pyridin-2-yl]oxy}methyl)ethyl]-2-methylpyrimidin-4-yl}piperidine-1-carboxylate Compound N47 was made from intermediate N37.2 in the same manner that Compound N43 was from intermediate N37.2, substituting 2,6-difluorophenyl chloroformate for 2-fluorophenyl chloroformate. $^1$H-NMR (400 MHz, CDCl$_3$, rotameric mixture): δ 8.63 and 8.61 (two of s, 1H), 7.77 (t, 1H), 7.34 (d, 1H), 7.14 (m, 1H), 6.97 (t, 2H), 6.90 (d, 1H), 6.37 (m, 1H), 5.84 and 5.73 (two of s, 1H), 4.94 (d, 1H), 4.71 and 4.68 (two of d, 1H), 4.49 (m, 1H), 4.38 (m, 1H), 3.88 (m, 1H), 3.74 (m, 1H), 3.65 (m, 1H), 3.21 (q, 1H), 3.05 (t, 1H), 2.66 (s, 3H), 2.16 (m, 2H), 2.04 (s, 3H), 1.89 (m, 1H), 1.80 (m, 1H). MS (EI) for $C_{28}H_{28}F_5N_5O_5$, found 610.2 (MH+). Analytical HPLC, ret. time=16.840 min, 98% purity.

Compound N48: 4-[5-(1-Amino-1-cyano-2-{[6-(trifluoromethyl)pyridin-2-yl]oxy}ethyl)-2-methylpyrimidin-4-yl]-N-(2,6-difluorophenyl)piperidine-1-carboxamide N48.1: tert-Butyl 4-(5-(1-amino-1-cyano-2-(6-(trifluoromethyl)pyridin-2-yloxy)ethyl)-2-methylpyrimidin-4-yl)piperidine-1-carboxylate To a mixture of intermediate D24.2 (115 mg, 0.24 mmol) and NH$_3$/MeOH (0.4 mL, 7 N) was added Ti(O$^i$Pr)$_4$ (68 mg, 0.24 mmol). The mixture was stirred at rt for 4 h, and then was added TMSCN (100 mg, 1.0 mmol). The mixture was stirred at rt for 72 h. The reaction was diluted with EtOAc, and filtered through the Celite. The filtrate was concentrated and purified by flash column chromatography to intermediate N48.1 (60 mg, 49%).

N48.2: 2-Amino-2-(2-methyl-4-(piperidin-4-yl)pyrimidin-5-yl)-3-(6-(trifluoromethyl)pyridin-2-yloxy)propanenitrile hydrochloride salt Intermediate N48.2 was made from the Boc deprotection of intermediate N48.1 using General Procedure 2.

Compound N48:

Compound N48 was made from intermediate N48.2 and 2,6-difluorophenyl isocyanate using General Procedure 5. $^1$H NMR (400 MHz, DMSO-d6) δ 8.85 (s, 1H), 8.27 (s, 1H), 8.03 (t, 1H), 7.57 (d, 1H), 7.27 (m, 1H), 7.21 (d, 1H), 7.12 (m, 2H), 4.85 (d, 1H), 4.68 (d, 1H), 4.24 (m, 2H), 3.90 (m, 1H), 3.51 (s, 2H), 2.88 (m, 2H), 2.61 (s, 3H), 1.70 (m, 4H). MS (EI) for $C_{26}H_{24}F_5N_7O_2$, found: 562.2 (MH+). Analytical HPLC, ret. time=20.08 min, 95% purity.

Compound N49: 4-{5-[1,2-Diamino-2-oxo-1-({[6-(trifluoromethyl)pyridin-2-yl]oxy}methyl)ethyl]-2-methylpyrimidin-4-yl}-N-(2,6-difluorophenyl)piperidine-1-carboxamide To a solution of Compound N48 (28 mg, 0.05 mmol) in THF/H$_2$O (1 mL/0.5 mL) was added LiOH H$_2$O (20 mg, 0.47 mmol). The mixture was stirred at rt for 72 h. The reaction progress was monitored by LC-MS. After the starting material was consumed, EtOAc was added to extract the product. The organic layer was washed with water, dried over anhydrous Na$_2$SO$_4$. Removal of the solvents gave the crude amide. Further purification by HPLC gave the desired product. $^1$H NMR (400 MHz, DMSO-d6) δ 8.59 (s, 1H), 8.24 (s, 1H), 7.99 (t, 1H), 7.54 (m, 2H), 7.41 (m, 1H), 7.26 (m, 1H), 7.13 (m, 3H), 4.72 (m, 2H), 4.20 (m, 2H), 3.53 (m, 1H), 2.65 (m, 1H), 2.55 (s, 3H), 1.65 (m, 4H). MS (EI) for $C_{26}H_{26}F_5N_7O_3$, found: 580.2 (MH+). Analytical HPLC, ret. time=11.32 min, 99% purity.

Compound N50: 5-(4-{1-[(2,6-Difluorophenyl)acetyl]piperidin-4-yl}-2-methylpyrimidin-5-yl)-5-methyl-3-[2-(trifluoromethyl)pyrimidin-4-yl]-1,3-oxazolidin-2-one N50.1: tert-Butyl 4-(2-methyl-5-(5-methyl-2-oxooxazolidin-5-yl)pyrimidin-4-yl)piperidine-1-carboxylate To a stirred solution of intermediate D17.2 (30 mg, 0.086 mmol), DIEA (33 mg, 0.257 mmol) and DCM (1 mL) was added triphosgene (10 mg, 0.034 mmol). The mixture was stirred at RT for 10 min. Saturated NaHCO3 was added and the mixture was stirred for 15 min. The reaction mixture was diluted with DCM and worked up, and purified on prep HPLC to give intermediate N50.1 (23 mg): MS (EI) for C19H28N4O4, found: 377.2. Analytical HPLC, ret. time=12.32 min, 97% purity.

N50.2: tert-Butyl 4-(2-methyl-5-(5-methyl-2-oxo-3-(2-(trifluoromethyl)pyrimidin-4-yl)oxazolidin-5-yl)pyrimidin-4-yl)piperidine-1-carboxylate To solution of intermediate N50.1 (23 mg, 0.061 mmol) in DMAC was added NaH (60% in mineral oil, 24 mg) at RT with stirring. The resulting suspension was stirred at RT for 10 min, and cooled to 0° C., to which was added 4-chloro-2-(trifluoromethyl)pyrimidine (17 mg, 0.091 mmol). The reaction mixture was stirred at 0° C. for 30 min, and then saturated NH4Cl solution was added at 0° C. with stirring. The resulting mixture was diluted with MeOH and water, and then filtered. The filtrate was concentrated in vacuo. The residue was purified on prep HPLC to give intermediate N50.2 (23 mg) as a white solid. $^1$H-NMR (400 MHz, CDCl$_3$): δ 8.78 (d, 1H), 8.74 (br. s, 1H), 8.38 (d, 1H), 4.89 (d, 1H), 4.45 (d, 1H), 4.33 (br. s, 2H), 2.88-2.72 (m, 3H), 2.71 (s, 3H), 2.12-2.01 (m 2H), 1.95 (s, 3H), 1.78-1.66 (m, 3H), 1.50 (s, 9H). MS (EI) for $C_{24}H_{29}F_3N_6O_4$, found: 523.3 (MH+). Analytical HPLC, ret. time=20.76 min, 98% purity.

N50.3: 5-Methyl-5-(2-methyl-4-(piperidin-4-yl)pyrimidin-5-yl)-3-(2-(trifluoromethyl)pyrimidin-4-yl)oxazolidin-2-one hydrochloride salt Intermediate N50.3 was made from the Boc deprotection of intermediate N50.2 using General Procedure 2.

Compound N50:

Compound N50 was made from intermediate N50.3 and 2,6-difluorophenylacetic acid using General Procedure 4. $^1$H-NMR (400 MHz, CDCl$_3$): δ 8.79 (d, 1H), 8.73 (br. s 1H), 8.38 (m, 1H), 7.24 (m, 1H), 6.96-6.90 (m, 2H), 4.84 (m, 1H), 4.60 (d, 2H), 4.48 (m, 1H), 4.20 (m, 1), 3.80 (m, 2H), 3.30

(t, 1H), 3.00 (m, 1H), 2.75 (m, 1H), 2.71 (s, 3H), 2.23-2.07 (m, 2H), 1.96 (s, 3H), 1.85-1.78 (m, 2H). MS (EI) for $C_{27}H_{25}F_5N_6O_3$, found: 577.2 (MH+). Analytical HPLC, ret. time=18.5 min, 96% purity.

Compound N51: N-(2,6-Difluorophenyl)-4-{2-methyl-5-[2-({[6-(trifluoromethyl)pyridin-2-yl]oxy}methyl)oxetan-2-yl]pyrimidin-4-yl}piperidine-1-carboxamide N51.1: tert-Butyl 4-(2-methyl-5-(2-((6-(trifluoromethyl)pyridin-2-yloxy)methyl)oxetan-2-yl)pyrimidin-4-yl)piperidine-1-carboxylate To a 0° C. solution of intermediate N51.2 (134 mg, 0.25 mmol) and Et$_3$N (80 mg, 0.76 mmol) in DCM (5 mL) was added MsCl (34 mg, 0.3 mmol). The mixture was stirred at rt for 1 h. THF was added (8 mL), followed by the addition of KO$^t$Bu (1.5 mL, 1 M in THF). The resulting solution was stirred at rt for 1 h. The mixture was diluted with DCM, washed with saturated NaHCO$_3$, brine, and dried over anhydrous Na$_2$SO$_4$. Further purification by flash column chromatography gave intermediate N51.1 (102 mg, 80%).

N51.2: 4-Chloro-2-(2-methyl-4-(piperidin-4-yl)pyrimidin-5-yl)-1-(6-(trifluoromethyl)pyridin-2-yloxy)butan-2-ol Intermediate N51.2 was made from the Boc deprotection of intermediate N51.1 using General Procedure 2.

N51.3: 4-(5-(4-Chloro-2-hydroxy-1-(6-(trifluoromethyl)pyridin-2-yloxy)butan-2-yl)-2-methylpyrimidin-4-yl)-N-(2,6-difluorophenyl)piperidine-1-carboxamide Intermediate N51.3 was made from intermediate N51.2 and 2,6-difluorophenyl isocyanate using General Procedure 5.

Compound N51:

To a solution intermediate N51.3 (40 mg, 0.07 mmol) in THF (5 mL) was added KO$^t$Bu (0.5 mL, 1 M in THF, 0.5 mmol). The mixture was stirred at rt for 2.5 h. EtOAc was added, the organic layer was washed with brine and dried over anhydrous Na$_2$SO$_4$. Further purification by flash column chromatography gave Compound N51 (7 mg, 17%). $^1$H NMR (400 MHz, DMSO-d6) δ 8.60 (s, 1H), 8.26 (s, 1H), 7.99 (t, 1H), 7.51 (d, 1H), 7.26 (m, 1H), 7.18 (d, 1H), 7.11 (m, 2H), 4.74 (d, 1H), 4.69 (m, 1H), 4.61 (d, 1H), 4.46 (m, 1H), 4.18 (m, 2H), 3.27 (m, 2H), 2.88 (m, 3H), 2.59 (s, 3H), 1.90 (m, 1H), 1.72 (m, 2H), 1.62 (d, 1H). MS (EI) for $C_{27}H_{26}F_5N_5O_3$, found: 564.1 (MH+). Analytical HPLC, ret. time=13.42 min, 95% purity.

Compound N52: N-(2,6-Difluorophenyl)-4-{2-methyl-5-[2-oxo-5-({[6-(trifluoromethyl)pyridin-2-yl]oxy}methyl)-1,3-oxazolidin-5-yl]pyrimidin-4-yl}piperidine-1-carboxamide N52.1: tert-Butyl 4-(2-methyl-5-(2-oxo-5-((6-(trifluoromethyl)pyridin-2-yloxy)methyl)oxazolidin-5-yl)pyrimidin-4-yl)piperidine-1-carboxylate Intermediate N52.1 was synthesized from intermediate N36.1 using a method analogous to that used to synthesize intermediate N50.1 from intermediate D17.2.

N52.2: 5-(2-Methyl-4-(piperidin-4-yl)pyrimidin-5-yl)-5-((6-(trifluoromethyl)pyridin-2-yloxy)methyl) oxazolidin-2-one TFA salt Intermediate N52.2 was made from the Boc Deprotection of intermediate N52.1 using General Procedure 2.

Compound N52:

Compound N52 was synthesized from intermediate N52.2 and 2,6-difluorophenyl isocyanate using General Procedure 5. $^1$H-NMR (400 MHz, CDCl$_3$): δ 8.8.74 (s, 1H), 7.79 (t, 1H), 7.35 (d, 1H), 7.13 (m, 1H), 7.00 (d, 1H), 6.95 (t, 2H), 5.92 (s, 1H), 5.09 (s, 1H), 4.96 (d, 1H), 4.59 (d, 1H), 4.33 (d, 1H), 4.32 (d, 1H), 4.22 (d, 1H), 3.82 (d, 1H), 3.14 (td, 1H), 3.02 (t, 2H), 2.72 (s, 3H), 2.28 (qd, 1H), 2.15 (qd, 1H), 1.84 (m, 1H), 1.74 (m, 1H). MS (EI) for $C_{27}H_{25}F_5N_6O_4$, found 593.1 (MH+). Analytical HPLC, ret. time=12.308 min, 99% purity.

Example 2 General RORγ SPA Binding Assay

The binding of potential ligands to RORγ is measured by competition with [$^3$H]25-hydroxycholesterol using a scintillation proximity assay (SPA) binding assay. The ligand binding domain of human RORγ (A262-S507) with an N-terminal His tag is expressed in *E. coli* and purified using nickel affinity chromatography. 50 nM RORγ (A262-S507) is incubated with test compound at varying concentrations for 15 min at room temperature in PBS buffer containing 0.5% fatty acid free BSA. O1 nM of [$^3$H]25-hydroxycholesterol is then added, and the reaction is incubated for 15 min. 4 mg/mL of Ysi Copper HIS-TAG SPA Beads (Perkin Elmer) are added, and the mixture is incubated for 30 min. The reaction is read on a MicroBeta Trilux scintillation plate reader (Perkin Elmer). IC$_{50}$ values are determined from the percentage inhibition of [$^3$H]25-hydroxycholesterol binding.

IC$_{50}$ values of the compounds of Tables 1-14 in the RORγ binding assay are provided in the Table, below.

| Compound | IC$_{50}$ (nM) |
|---|---|
| A1 | 4.7 |
| A2 | 6.8 |
| A3 | 7.2 |
| A4 | 7.8 |
| A5 | 8.9 |
| A6 | 26.4 |
| A7 | 28.1 |
| A8 | 29.4 |
| A9 | 31.6 |
| A10 | 33.1 |
| A11 | 49 |
| A12 | 50 |
| A13 | 52 |
| A14 | 66 |
| A15 | 70 |
| A16 | 89 |
| A17 | 93 |
| A18 | 124 |
| A19 | 155 |
| A20 | 158 |
| A21 | 209 |
| A22 | 235 |
| A23 | 254 |
| A24 | 215 |
| A25 | 267 |
| A26 | 446 |
| A27 | 719.7 |
| A28 | 1034.6 |
| A29 | 1087.9 |
| A30 | 1445.6 |

-continued

| Compound | IC$_{50}$ (nM) |
|---|---|
| A31 | 1630.4 |
| A32 | 1690 |
| A33 | 1952.8 |
| A34 | 2687.4 |
| A35 | 2966.3 |
| A36 | 3327.1 |
| A37 | 4200 |
| A38 | 5306.4 |
| A39 | 5453.1 |
| A40 | 5.8 |
| A41 | 4.8 |
| A42 | 5.1 |
| A43 | 5.4 |
| A44 | 5.7 |
| A45 | 6 |
| A46 | 6.1 |
| A47 | 6.3 |
| A48 | 6.7 |
| A49 | 6.8 |
| A50 | 7.1 |
| A51 | 7.2 |
| A52 | 7.5 |
| A53 | 8.1 |
| A54 | 13.9 |
| A55 | 19.2 |
| A56 | 19.3 |
| A57 | 21.8 |
| A58 | 24.3 |
| A59 | 25.5 |
| A60 | 35 |
| A61 | 38.2 |
| A62 | 43.4 |
| A63 | 63 |
| A64 | 64 |
| A65 | 69 |
| A66 | 72 |
| A67 | 85 |
| A68 | 95 |
| A69 | 144 |
| A70 | 213 |
| A71 | 242 |
| A72 | 317 |
| A73 | 426 |
| A74 | 618.9 |
| A75 | 750.3 |
| A76 | 1123.5 |
| A77 | 1337.5 |
| A78 | 1794.6 |
| A79 | 5263 |
| A80 | 9.8 |
| A81 | 5.2 |
| A82 | 6.2 |
| A83 | 45.8 |
| A84 | 1652.7 |
| A85 | 43.8 |
| A86 | 7 |
| A87 | 1.7 |
| A88 | 5.4 |
| A89 | 5.8 |
| A90 | 6.3 |
| A91 | 6.7 |
| A92 | 10 |
| A93 | 16 |
| A94 | 25.4 |
| A95 | 175 |
| A96 | 202 |
| A97 | 290 |
| A98 | 398 |
| A99 | 58 |
| A100 | 433 |
| A101 | 634.2 |
| A102 | 1729.5 |
| A103 | 3.4 |
| A104 | 231 |
| A105 | 551.5 |
| A106 | 270 |

-continued

| Compound | IC$_{50}$ (nM) |
|---|---|
| A107 | 12.1 |
| A108 | 21.7 |
| A109 | 7.3 |
| A110 | 1438.6 |
| A111 | 9.8 |
| A112 | 33.6 |
| A113 | 338 |
| A114 | 3 |
| A115 | 342 |
| A116 | 37.1 |
| A117 | 252.9 |
| A118 | 51.6 |
| A119 | 6.2 |
| A120 | 6 |
| A121 | 58.4 |
| A122 | 116.4 |
| A123 | 5.4 |
| A124 | 11.4 |
| A125 | 11.6 |
| A126 | 15.2 |
| B1 | 54 |
| B2 | 444 |
| B3 | 3.1 |
| B4 | 137 |
| B5 | 2.5 |
| B6 | 1933.7 |
| B7 | 10.6 |
| B8 | 1504.4 |
| B9 | 2.7 |
| B10 | 1668.9 |
| B11 | 1.7 |
| B12 | 2.2 |
| B13 | 4.7 |
| B14 | 4.8 |
| B15 | 5.1 |
| B16 | 5.9 |
| B17 | 9.3 |
| B18 | 11.2 |
| B19 | 13.9 |
| B20 | 15.8 |
| B21 | 23.7 |
| B22 | 84 |
| B23 | 8.4 |
| B24 | 8.7 |
| B25 | 11.2 |
| B26 | 95 |
| B27 | 35.8 |
| B28 | 696.3 |
| B29 | 3721.6 |
| B30 | 9.7 |
| B31 | 3.4 |
| B32 | 15.3 |
| B33 | 36.7 |
| B34 | 12.5 |
| B35 | 14.2 |
| B36 | 157.9 |
| B37 | 67.6 |
| B38 | 169 |
| B39 | 93.3 |
| B40 | 21.4 |
| B41 | 12.6 |
| B42 | 150.5 |
| B43 | 13.5 |
| B44 | 84.9 |
| B45 | 8 |
| B46 | 105.9 |
| B47 | 76.4 |
| B48 | 240.9 |
| B49 | 1970.5 |
| B50 | 445 |
| B51 | 8.6 |
| B52 | 334 |
| B53 | 35.1 |
| B54 | 167.7 |
| B55 | 5.8 |
| B56 | 31.8 |

| Compound | IC$_{50}$ (nM) |
|---|---|
| B57 | 92.7 |
| B58 | 4093.7 |
| B59 | 49.1 |
| B60 | 114.9 |
| B61 | 366.7 |
| C1 | 114 |
| C2 | 337 |
| C3 | 605.9 |
| C4 | 619.7 |
| C5 | 6.3 |
| C6 | 5.2 |
| C7 | 218 |
| C8 | 6.9 |
| C9 | 7.8 |
| C10 | 12.3 |
| C11 | 15.5 |
| C12 | 18.9 |
| C13 | 19.4 |
| C14 | 26.3 |
| C15 | 102 |
| C16 | 110 |
| C17 | 161 |
| C18 | 201 |
| C19 | 269 |
| C20 | 656.6 |
| C21 | 3009.4 |
| C22 | 3960.4 |
| C23 | 5294.8 |
| C24 | 276.9 |
| C25 | 23.1 |
| C26 | 234.7 |
| C27 | 460.8 |
| C28 | 65.2 |
| C29 | 157.6 |
| C30 | 49.7 |
| C31 | 49.6 |
| C32 | 159 |
| C33 | 843.9 |
| C34 | 87.1 |
| C35 | 608.3 |
| C36 | 154.7 |
| C37 | 22.1 |
| C38 | 8.0 |
| C39 | 4519.9 |
| C40 | 47.5 |
| C41 | 20.5 |
| C42 | 240.4 |
| C43 | 11.2 |
| C44 | 3.2 |
| C45 | 42.8 |
| C46 | 123.1 |
| C47 | 80.6 |
| C48 | 63.9 |
| C49 | 23.3 |
| C50 | 6.1 |
| C51 | 10.5 |
| C52 | 8.7 |
| C53 | 37.3 |
| C54 | 21.1 |
| C55 | 19.2 |
| C56 | 24.7 |
| C57 | 23.6 |
| C58 | 14.1 |
| C59 | 27.9 |
| C60 | 203.6 |
| C61 | 1138.3 |
| C62 | 157 |
| C63 | 280.9 |
| C64 | 182.6 |
| C65 | 2727.6 |
| C66 | 65.9 |
| C67 | 110.7 |
| C68 | 102.3 |
| C69 | 30.8 |
| C70 | 108.3 |
| C71 | 30.2 |
| D1 | 2.6 |
| D2 | 3.9 |
| D3 | 5 |
| D4 | 6.1 |
| D5 | 8.4 |
| D6 | 23.3 |
| D7 | 80 |
| D8 | 105 |
| D9 | 118 |
| D10 | 4378 |
| D11 | 14.5 |
| D12 | 6.2 |
| D13 | 8.9 |
| D14 | 481 |
| D15 | 33.9 |
| D16 | 12.3 |
| D17 | 88.8 |
| D18 | 111.6 |
| D19 | 196.4 |
| D20 | 72.8 |
| D21 | 47.7 |
| D22 | 76.1 |
| D23 | 18.5 |
| D24 | 5 |
| D25 | 8.7 |
| D26 | 12.6 |
| D27 | 3.6 |
| D28 | 14.7 |
| D29 | 14.4 |
| D30 | 4.3 |
| D31 | 118.9 |
| D32 | 13.9 |
| D33 | 14 |
| D34 | 15 |
| D35 | 14.8 |
| D36 | 15.8 |
| D37 | 112.3 |
| D38 | 25.9 |
| D39 | 5.1 |
| D40 | 29.6 |
| D41 | 100.8 |
| D42 | 348 |
| D43 | 22 |
| D44 | 4.6 |
| D45 | 3.4 |
| D46 | 6.3 |
| D47 | 52.9 |
| D48 | 30.3 |
| D49 | 7.2 |
| D50 | 15 |
| E1 | 6.3 |
| E2 | 5.3 |
| E3 | 6.2 |
| E4 | 16.7 |
| E5 | 10.6 |
| E6 | 45.7 |
| E7 | 63 |
| E8 | 4.1 |
| E9 | 6.2 |
| E10 | 79 |
| E11 | 19.2 |
| E12 | 11 |
| E13 | 13.2 |
| E14 | 28 |
| E15 | 56.5 |
| F1 | 76 |
| F2 | 26 |
| F3 | 3.3 |
| F4 | 195.2 |
| F5 | 101.3 |
| F6 | 44.2 |
| F7 | 9.8 |
| F8 | 1340.8 |
| F9 | 29.9 |
| G1 | 9.6 |
| G2 | 4.6 |

| Compound | IC$_{50}$ (nM) |
|---|---|
| G3 | 8.1 |
| G4 | 12.1 |
| H1 | 327 |
| H2 | 49 |
| H3 | 84 |
| H4 | 294 |
| H5 | 503 |
| H6 | 1633 |
| H7 | 1749 |
| I1 | 40.3 |
| I2 | 71 |
| I3 | 10.7 |
| I4 | 10.9 |
| I5 | 69.3 |
| I6 | 60.9 |
| I7 | 653.9 |
| I8 | 2289.6 |
| J1 | 46 |
| J2 | 28 |
| J3 | 7.7 |
| K1 | 4109 |
| L1 | 81 |
| M1 | 26 |
| M2 | 18.6 |
| M3 | 19.1 |
| M4 | 6.5 |
| M5 | 16.3 |
| M6 | 12.2 |
| M7 | 158.8 |
| M8 | 1.7 |
| M9 | 2 |
| M10 | 5.3 |
| M11 | 2.8 |
| M12 | 6.2 |
| M13 | 343.7 |
| M14 | 485 |
| N1 | 6.6 |
| N2 | 19.5 |
| N3 | 2.3 |
| N4 | 12.1 |
| N5 | 8.4 |
| N6 | 4 |
| N7 | 16.9 |
| N8 | 4.8 |
| N9 | 4.2 |
| N10 | 20.9 |
| N11 | 37 |
| N12 | 69.5 |
| N13 | 6.8 |
| N14 | 4.1 |
| N15 | 10.9 |
| N16 | 1.9 |
| N17 | 6.2 |
| N18 | 16.2 |
| N19 | 6.5 |
| N20 | 21.2 |
| N21 | 14.2 |
| N22 | 7 |
| N23 | 12.3 |
| N24 | 9.3 |
| N25 | 544.4 |
| N26 | 140.7 |
| N27 | 18.2 |
| N28 | 71 |
| N29 | 10000 |
| N30 | 10.9 |
| N31 | 620 |
| N32 | 5.7 |
| N33 | 2.9 |
| N34 | 12.8 |
| N35 | 5.5 |
| N36 | 47.8 |
| N37 | 36.9 |
| N38 | 57.9 |
| N39 | 84.1 |
| N40 | 133.8 |

| Compound | IC$_{50}$ (nM) |
|---|---|
| N41 | 150.2 |
| N42 | 182.7 |
| N43 | 9.2 |
| N44 | 898.8 |
| N45 | 81.9 |
| N46 | 39 |
| N47 | 3.6 |
| N48 | 5.6 |
| N49 | 176 |
| N50 | 289.7 |
| N51 | 4.9 |
| N52 | 13.8 |

We claim:

1. A compound having the structural formula

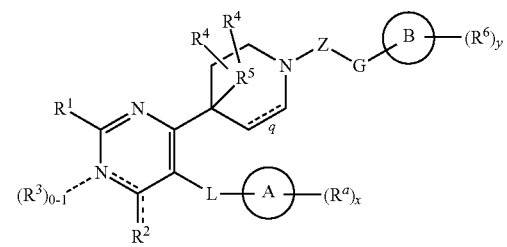

or a stereoisomeric form thereof, or an N-oxide thereof, or a pharmaceutically acceptable salt thereof, wherein $R^1$ is selected from the group consisting of —H, -halogen, —CN, —NO$_2$, —OH, —O—(C$_1$-C$_4$)alkyl, —O—(C$_1$-C$_4$)fluoroalkyl, —SH, —S—(C$_1$-C$_4$)alkyl, —NH$_2$, —NH—(C$_1$-C$_4$)alkyl, —NH—(C$_1$-C$_4$)fluoroalkyl, —N((C$_1$-C$_4$)alkyl)$_2$, —N((C$_1$-C$_4$)fluoroalkyl)$_2$, —NH—(C$_3$-C$_6$)cycloalkyl, —O—C(O)—(C$_1$-C$_4$)alkyl, —S—C(O)—(C$_1$-C$_4$)alkyl, —NH—C(O)—(C$_1$-C$_4$)alkyl, —N((C$_1$-C$_4$)alkyl)-C(O)—(C$_1$-C$_4$)alkyl, —S(O)$_{1-2}$H, —S(O)$_{1-2}$(C$_1$-C$_4$)alkyl, —S(O)$_{1-2}$OH, —S(O)$_{1-2}$O(C$_1$-C$_4$)alkyl, —S(O)$_{1-2}$NH$_2$, —S(O)$_{1-2}$NH(C$_1$-C$_4$)alkyl, —S(O)$_{1-2}$N((C$_1$-C$_4$)alkyl)$_2$, —(C$_1$-C$_6$)alkyl, —(C$_1$-C$_6$)fluoroalkyl, —(C$_3$-C$_6$)cycloalkyl, —(C$_3$-C$_6$)heterocycloalkyl, —C(O)OH, —C(O)—(C$_1$-C$_4$)alkyl, —C(O)NH$_2$, —C(O)NH(C$_1$-C$_4$)alkyl, —C(O)N((C$_1$-C$_4$)alkyl)$_2$, —NH—CH$_2$-phenyl and phenyl, wherein each phenyl is optionally substituted by 1, 2 or 3 substituents selected from -halogen, —CN, —NO$_2$, —O—R$^{30}$, —N(R$^{31}$)$_2$ and —S(R$^{30}$), in which each R$^{30}$ is independently selected from the group consisting of —H, —CH$_3$, —CH$_2$CH$_3$ and —CF$_3$, and each R$^{31}$ is independently selected from the group consisting of —H, —CH$_3$ and —CH$_2$CH$_3$;

the

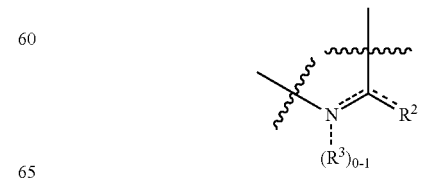

moiety has the structure (a)

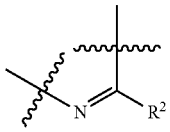

in which R² is selected from the group consisting of —H, -halogen, —CN, —NO₂, —N₃, —OH, —O—(C₁-C₄)alkyl, —O—(C₁-C₄)fluoroalkyl, —SH, —S—(C₁-C₄)alkyl, —NH₂, —NH—(C₁-C₄)alkyl, —N((C₁-C₄)alkyl)₂, —O—C(O)—(C₁-C₄)alkyl, —S—C(O)—(C₁-C₄)alkyl, —NH—C(O)—(C₁-C₄)alkyl, —N((C₁-C₄)alkyl)-C(O)—(C₁-C₄)alkyl, —S(O)₁₋₂H, —S(O)₁₋₂(C₁-C₄)alkyl, —S(O)₁₋₂OH, —S(O)₁₋₂O(C₁-C₄)alkyl, —S(O)₁₋₂NH₂, —S(O)₁₋₂NH(C₁-C₄)alkyl, —S(O)₁₋₂N((C₁-C₄)alkyl)₂, —(C₁-C₆)alkyl, —(C₁-C₆)fluoroalkyl, —(C₃-C₆)cycloalkyl, —(C₃-C₆)heterocycloalkyl, —C(O)OH, —C(O)—(C₁-C₄)alkyl, —C(O)NH₂, —C(O)NH(C₁-C₄)alkyl and —C(O)N((C₁-C₄)alkyl)₂, and when L is —C(O)—NH—CH₂—, R² is optionally the same

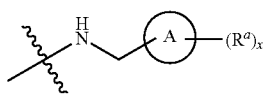

as defined below; or (b)

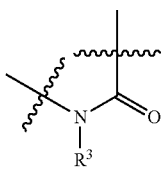

in which R³ is —H, —(C₁-C₄)alkyl or —(C₁-C₄)fluoroalkyl;
each R⁴ is independently —H, —CH₃ or —F;
R⁵ is —H, —F or —CH₃;
the bond denoted by "q" is a single bond or a double bond;
Z is —C(O)—, —C(S)—, —S(O)₂— or —CH₂—;
G is a single bond, —CH₂—, —CHD-, —CD₂-, —CHF—, —CF₂—, —CH(R¹⁴)—, —C(R¹⁴)₂—, (C₃-C₅)cycloalkan-1,1-diyl, —NH—, —O— or —N(R¹⁴)— in which each R¹⁴ is independently methyl, ethyl, isopropyl or n-propyl;
the ring system denoted by "B" is phenyl, pyridyl, naphthyl, thiazolyl or pyrimidinyl;
y is 1, 2, or 3;
each R⁶ is independently -halogen, —O—(C₁-C₄)fluoroalkyl, or —(C₁-C₆)fluoroalkyl;
L is selected from the group consisting of —C(O)—NH—CH₂—, —C(O)—NH₂—CH₂—CH₂—O—, —C(O)—NH—CH—(CO₂R¹⁵)—, —C(O)—NH—CH(R¹⁵)—; C(O)—NH—CH(CH₂OH)—,

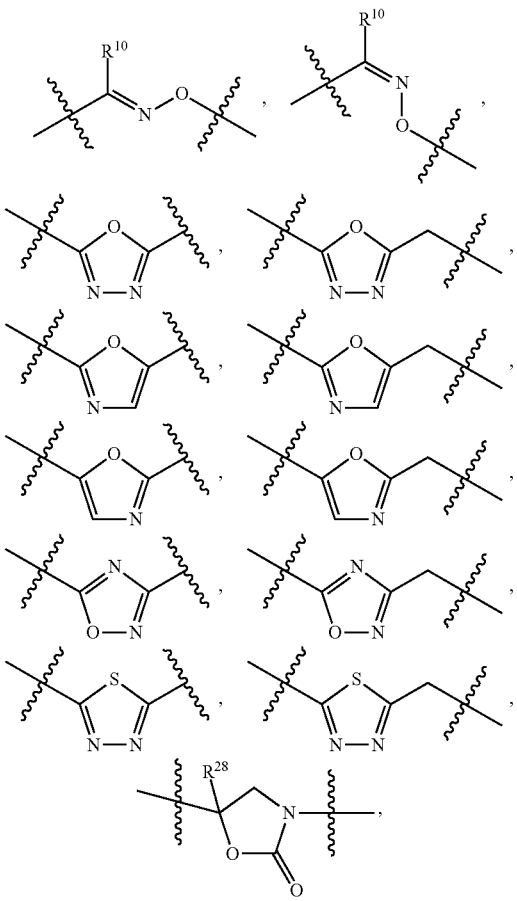

—C(OR²²)(R¹⁶)—CH₂—NH—, —C(OR²²)(R¹⁶)—CH₂—N(C₁-C₄)alkyl-, —C(OR²²)(R¹⁶)—CH₂—O—, —C(OR²²)(R²⁴)—CH₂—O—, —C(OR²²)(R²⁵)—CH₂—O—, —C(OR²²)(R¹⁶)—CH₂—CH₂—, —CH(NH₂)—CH₂—O—, —CH(NH(R²³))—CH₂—O—, —C(NH2)(R²⁷)—CH₂—O—, —C(=NHOH)—CH₂—O—, —C(OR²²)(R²⁶)—CH₂—O—, —C(R¹¹)(R¹⁶)—CH₂—O—CH₂—, —C(R¹²)(R¹³)—CH₂—NH—CH₂—, —C(R¹²)(R¹³)—CH₂—NH—, —C(R¹²)(R¹³)—CH₂—O—, —C(R¹²)(R¹³)—CH₂—, —C(R¹²)(R¹³)—CH₂—S(O)₀₋₂—, —C(O)—NH—NH—, —C(O)—NH—O—, —CH₂—CH₂—CH₂—, —C(O)—CH₂—O—, —C(O)—CH₂—NH—, —CH=CH—CH₂—, —C(S)—NH—CH₂, and —CH₂—CH=CH—, in which
R¹⁰ is —H, —R¹⁵, —CH₂OH or —CH₂F,
R¹¹ is —H, —R¹⁵, —CH₂OH, —CH₂OCH₃ or —CH₂—O—CH₂—CH(OH)—CH₂OH,
R¹² is —H, —F, or —R¹⁵,
R¹³ is —H, —F, —R¹⁵, —CF₃, CH₂OH or CO₂R¹⁵, or
R¹² and R¹³ come together to form a 4-6 membered heterocycloalkyl;
R²² is H or —C(O)(C₁-C₄)alkyl;
R²⁴ is (C₁-C₄)alkyl, —C(O)(C₁-C₄)alkyl, —C(O)—NH—(C₁-C₄)alkyl, —(C₁-C₄)alkyl-NH—C(O)(C₁-C₄)alkyl, —C(O)—(C₁-C₄)alkyl-NH—C(O)—(C₁-C₄)alkyl, —C(O)—(C₁-C₄)alkyl-OH, piperidinyl, piperazinyl or pyrrolidinyl optionally substituted at a nitrogen position with —C(O)(C₁-C₄)alkyl or (C₁-C₄)alkyl $R^{25}$ is piperidinyl, piperazinyl or pyrrolidinyl optionally substituted at a nitrogen position with —C(O)($C_1$-$C_4$)alkyl or ($C_1$-$C_4$)alkyl;

$R^{26}$ is —COOH, —COO($C_1$-$C_4$)alkyl, —CN, —$CONH_2$, $CONH(C_1$-$C_4$)alkyl, —($C_1$-$C_4$)alkyl, —($C_1$-$C_4$)alkyl-OH, —($C_1$-$C_4$)alkyl-$NH_2$, —($C_1$-$C_4$)alkyl-$N_3$, —($C_1$-$C_4$)alkyl-$NHR^{24}$, or —$CH_2$—$R^{23}$ in which $R^{23}$ is piperazinyl, piperidinyl or pyrrolidinyl optionally substituted at a nitrogen position with —C(O)($C_1$-$C_4$)alkyl or ($C_1$-$C_4$)alkyl;

$R^{27}$ is —CN, —$CONH_2$, —$CONH(C_1$-$C_4$)alkyl, —($C_1$-$C_4$)alkyl, —($C_1$-$C_4$)alkyl-OH, —($C_1$-$C_4$)alkyl-$NH_2$, —($C_1$-$C_4$)alkyl-$N_3$, —($C_1$-$C_4$)alkyl-$NHR^{24}$, —$CH_2$—$R^{23}$ in which $R^{23}$ is piperazinyl, piperidinyl or pyrrolidinyl optionally substituted at a nitrogen position with —C(O)($C_1$-$C_4$)alkyl or ($C_1$-$C_4$)alkyl; $R^{28}$ is H or ($C_1$-$C_4$)alkyl wherein each $R^{15}$ is independently methyl, ethyl, isopropyl or n-propyl, and each $R^{16}$ is independently —H, methyl, ethyl, isopropyl or n-propyl;

the ring system denoted by "A" is phenyl, pyridyl, pyrimidyl, thiazolyl, pyrazolyl or pyrazinyl;

x is 0, 1, 2 or 3; and each $R^a$ is independently —H, -halogen, —CN, —$NO_2$, —$N_3$, —OH, —O—($C_1$-$C_4$)alkyl, —O—($C_1$-$C_4$)fluoroalkyl, —SH, —S—($C_1$-$C_4$)alkyl, —$NH_2$, —NH—($C_1$-$C_4$)alkyl, —N(($C_1$-$C_4$)alkyl)$_2$, —O—C(O)—($C_1$-$C_4$)alkyl, —S—C(O)—($C_1$-$C_4$)alkyl, —NH—C(O)—($C_1$-$C_4$)alkyl, —N(($C_1$-$C_4$)alkyl)-C(O)—($C_1$-$C_4$)alkyl, —S(O)$_{1-2}$H, —S(O)$_{1-2}$($C_1$-$C_4$)alkyl, —S(O)$_{1-2}$OH, —S(O)$_{1-2}$O($C_1$-$C_4$)alkyl, S(O)$_{1-2}$$NH_2$, —S(O)$_{1-2}$NH($C_1$-$C_4$)alkyl, —S(O)$_{1-2}$N(($C_1$-$C_4$)alkyl)$_2$, —($C_1$-$C_6$)alkyl, —($C_1$-$C_6$)fluoroalkyl, —($C_3$-$C_6$)cycloalkyl, —($C_3$-$C_6$)heterocycloalkyl, —C(O)OH, —C(O)—($C_1$-$C_4$)alkyl, —C(O)$NH_2$, —C(O)NH($C_1$-$C_4$)alkyl or —C(O)N(($C_1$-$C_4$)alkyl)$_2$, in which each alkyl is optionally substituted with one or more substituents selected from the group consisting of -D, -halogen, —CN, —$NO_2$, —O—$R^{20}$, —N($R^{21}$)$_2$ and —S($R^{20}$), in which each $R^{20}$ is independently selected from the group consisting of —H, —$CH_3$, —$CH_2CH_3$ and —CF3, and each $R^{21}$ is independently selected from the group consisting of —H, —$CH_3$ and —$CH_2CH_3$.

2. The compound, stereoisomeric form, N-oxide, or pharmaceutically acceptable salt according to claim 1, having the formula

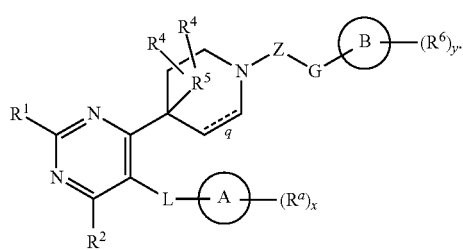

3. The compound, stereoisomeric form, N-oxide, or pharmaceutically acceptable salt according to claim 1, wherein $R^1$ is —H, —($C_1$-$C_2$)alkyl, -cyclopropyl, —O—($C_1$-$C_3$)alkyl, —S—($C_1$-$C_2$)alkyl, —$NH_2$, —NH—($C_1$-$C_3$)alkyl or —N(($C_1$-$C_2$)alkyl)$_2$.

4. The compound, stereoisomeric form, N-oxide, or pharmaceutically acceptable salt according to claim 1, wherein $R^2$ is —H, —($C_1$-$C_2$)alkyl, —($C_1$-$C_2$)fluoroalkyl, —($C_3$-$C_4$)cycloalkyl, —O—($C_1$-$C_2$)alkyl, —S—($C_1$-$C_2$)alkyl, —NH—($C_1$-$C_2$)alkyl or —N(($C_1$-$C_2$)alkyl)$_2$.

5. The compound, stereoisomeric form, N-oxide, or pharmaceutically acceptable salt according to claim 1, wherein the bond denoted by "q" is a single bond, both $R^4$ are H, and $R^5$ is H; the bond denoted by "q" is a double bond, both $R^4$ are H, and $R^5$ is H; the bond denoted by "q" is a single bond, both $R^4$ are H, and $R^5$ is F; or the bond denoted by "q" is a single bond, both $R^4$ are F, and $R^5$ is H.

6. The compound, stereoisomeric form, N-oxide, or pharmaceutically acceptable salt according to claim 1, wherein G is —$CH_2$—.

7. The compound, stereoisomeric form, N-oxide, or pharmaceutically acceptable salt according to claim 1, wherein L is —C(O)—NH—$CH_2$—, —C(O)—NH—CHD- or —C(O)—NH—$CD_2$-.

8. The compound, stereoisomeric form, N-oxide, or pharmaceutically acceptable salt according to claim 1, wherein L is

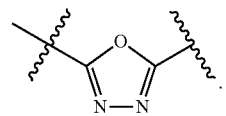 [SMILES: *c1nnc(*)o1]

9. The compound, stereoisomeric form, N-oxide, or pharmaceutically acceptable salt according to claim 1, wherein the ring system denoted by "A" is phenyl.

10. The compound, stereoisomeric form, N-oxide, or pharmaceutically acceptable salt according to claim 1, wherein the ring system denoted by "A" is pyridyl or pyrimidyl.

11. The compound, stereoisomeric form, N-oxide, or pharmaceutically acceptable salt according to claim 1, wherein each $R^a$ is independently -halogen, —($C_1$-$C_2$)alkyl, —($C_1$-$C_2$)fluoroalkyl, —O—($C_1$-$C_2$)alkyl, —O—($C_1$-$C_2$)fluoroalkyl, —CN or —$NO_2$.

12. The compound according to claim 1, having the structural formula

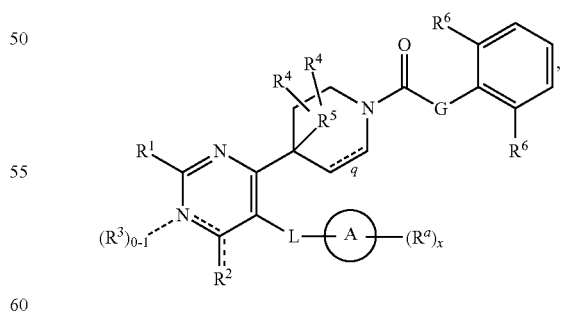

or a stereoisomeric form thereof, or a N-oxides thereof, or a pharmaceutically acceptable salt thereof, wherein $R^1$ is selected from the group consisting of —H, —($C_1$-$C_4$)alkyl, —($C_1$-$C_4$)fluoroalkyl, —($C_3$-$C_5$)cycloalkyl, —OH, —O—($C_1$-$C_4$)alkyl, —SH, —S—($C_1$-$C_4$)alkyl, —$NH_2$, —NH—($C_1$-$C_4$)alkyl and —N(($C_1$-$C_4$)alkyl)$_2$;

the

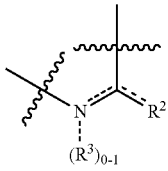

moiety has the structure (a)

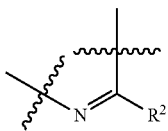

in which $R^2$ is selected from the group consisting of —H, —($C_1$-$C_4$)alkyl, —($C_1$-$C_4$)fluoroalkyl, —OH, —O—($C_1$-$C_6$)alkyl, —$NH_2$, —NH—($C_1$-$C_4$)alkyl and —N(($C_1$-$C_4$)alkyl)$_2$, or (b)

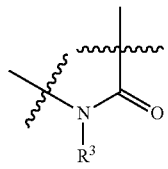

in which $R^3$ is —H;
each $R^4$ is independently H or F;
$R^5$ is —H, —$CH_3$, or —F;
the bond denoted by "q" is a single bond or a double bond;
G is a single bond, —$CH_2$—, —CHD-, —$CD_2$- or —NH—; and
each $R^6$ is independently —H, -halogen, —($C_1$-$C_4$ fluoroalkyl) or —O—($C_1$-$C_4$ fluoroalkyl), provided that at least one $R^6$ is not —H, L is selected from the group consisting of —C(O)—NH—$CH_2$—,

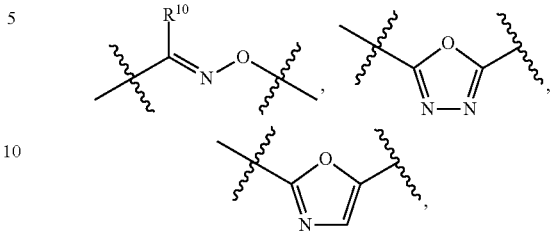

—C(OH)($CH_3$)—$CH_2$—NH—, —C(OH)($CH_3$)—$CH_2$—O—, —C($R^{11}$)($CH_3$)—$CH_2$—O—$CH_2$—, —C($R^{12}$)($R^{13}$)—$CH_2$—NH—$CH_2$—, —C($R^{12}$)($R^{13}$)—$CH_2$—NH—, —C($R^{12}$)($R^{13}$)—$CH_2$—O—, —C($R^{12}$)($R^{13}$)—$CH_2$—S(O)$_{0-2}$—, and —C(O)—NH—NH—, in which
$R^{10}$ is —H, —$CH_3$, —$CH_2$OH or —$CH_2$F,
$R^{11}$ is —H, —$CH_3$, —$CH_2$OH, —$CH_2$O$CH_3$ or —$CH_2$—O—$CH_2$—CH(OH)—$CH_2$OH,
$R^{12}$ is —H, —F, or —$CH_3$, and
$R^{13}$ is —H, —F, —$CH_3$ or —$CF_3$;
the ring system denoted by "A" is phenyl, pyridyl or pyrimidyl;
x is 1, 2 or 3; and
each $R^a$ is independently -halogen, —($C_1$-$C_4$)alkyl, —($C_1$-$C_4$)fluoroalkyl, —O—($C_1$-$C_4$)alkyl, —O—($C_1$-$C_4$)fluoroalkyl, —CN or —$NO_2$,
in which
each alkyl is optionally substituted with one or more substituents selected from the group consisting of -D, -halogen, —CN, —$NO_2$, —O—$R^{20}$, —N($R^{21}$)$_2$ and —S($R^{20}$), in which each $R^{20}$ is independently selected from the group consisting of —H, —$CH_3$, —$CH_2$$CH_3$ and —$CF_3$, and each $R^{21}$ is independently selected from the group consisting of —H, —$CH_3$ and —$CH_2$$CH_3$.

13. A pharmaceutical composition comprising a compound, stereoisomeric form, N-oxide, or pharmaceutically acceptable salt according to claim 1 and a pharmaceutically acceptable carrier, excipient or diluent.

* * * * *